United States Patent [19]
Ogawa et al.

[11] Patent Number: 5,652,247
[45] Date of Patent: Jul. 29, 1997

[54] CARBOSTYRIL DERIVATIVES

[75] Inventors: Hidenori Ogawa, Tokushima; Hisashi Miyamoto, Tokushima-ken; Kazumi Kondo, Naruto; Hiroshi Yamashita, Tokushima-ken; Kenji Nakaya, Tokushima; Michiaki Tominaga, Tokushima-ken; Yoichi Yabuuchi, Tokushima, all of Japan

[73] Assignee: Otsuka Pharmaceutical Co., Ltd., Tokyo, Japan

[21] Appl. No.: 359,081

[22] Filed: Dec. 14, 1994

Related U.S. Application Data

[60] Continuation of Ser. No. 846,941, Mar. 6, 1992, abandoned, which is a division of Ser. No. 762,736, Sep. 18, 1991, Pat. No. 5,225,402, which is a continuation of Ser. No. 478,181, Feb. 9, 1990, abandoned.

[30] Foreign Application Priority Data

| Feb. 10, 1989 | [JP] | Japan | 1-31580 |
| Apr. 21, 1989 | [JP] | Japan | 1-102699 |
| Jul. 13, 1989 | [JP] | Japan | 1-181440 |
| Sep. 7, 1989 | [JP] | Japan | 1-232333 |

[51] Int. Cl.$^6$ ............... A61K 31/47; A61K 31/495; C07D 215/16; C07D 215/36
[52] U.S. Cl. ............... 514/314; 514/312; 514/228.2; 514/253; 514/235.2; 546/157; 546/158; 544/56; 544/62; 544/128
[58] Field of Search ............... 514/314, 312, 514/253, 228.2; 546/157, 158; 544/56, 62, 128

[56] References Cited

U.S. PATENT DOCUMENTS

| 4,692,522 | 9/1987 | Parsons et al. | 540/523 |
| 4,894,084 | 1/1990 | Theodoridis | 546/155 |
| 4,895,841 | 1/1990 | Sugimoto et al. | 514/212 |
| 5,100,901 | 3/1992 | Sugimoto et al. | 514/319 |
| 5,225,402 | 7/1993 | Ogawa | 544/235 |

FOREIGN PATENT DOCUMENTS

| 44-24596 | 10/1969 | Japan . | |
| 51-118773 | 10/1976 | Japan | C07D 216/22 |
| 59-70671 | 4/1984 | Japan | C07D 215/22 |
| 1502312 | 3/1978 | United Kingdom . | |
| WO9107401 | 5/1991 | WIPO . | |

OTHER PUBLICATIONS

Sayed, et al. Chemical Abstracts, vol. 108, 1988 Abstract 112151e.
Srivastava et al., Chem. Abs., vol. 114 143242p 1991.
J. Med. Chem., 24(7), 777–782 (1981).
Chemical Abstracts, vol. 81, p. 450 (Abstract No. 77786r), 1974.
Chemical Abstracts, vol. 102, p. 17 (Abstract No. 143336z), 1985.
Journal of Medicinal Chemistry, vol. 24, No. 7, Jul. 1981, pp. 777–782.
Chemical Abstracts, vol. 108, p. 13 (Abstract No. 112151e), 1988.

Primary Examiner—Mukund J. Shah
Assistant Examiner—Pavanaram K. Sripada
Attorney, Agent, or Firm—Sughrue, Mion, Zinn, Macpeak & Seas

[57] ABSTRACT

Novel carbostyril derivatives of the formula:

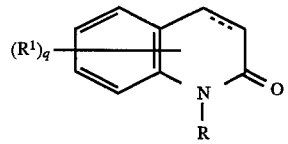

wherein $R^1$ is H, $NO_2$, alkoxy, alkoxycarbonyl, alkyl, halogen, optionally substituted amino, OH, CN, COOH, alkanoyloxy, hydrazinocarbonyl; q is 1 to 3, and R is a group of the formula:

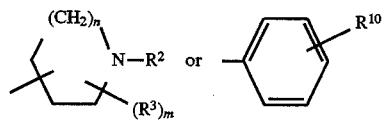

[wherein $R^2$ is H, alkoxycarbonyl, optionally substituted phenoxycarbonyl, phenylalkenyl-CO—, optionally substituted phenylalkanoyl, alkanoyl, alkenyl-CO—, optionally substituted phenyl-$SO_2$—, —$CONR^8R^9$, optionally substituted heterocyclic group-CO—, naphthyl-CO—, thienylalkanoyl, tricyclo[3.3.1.1] alkanoyl,

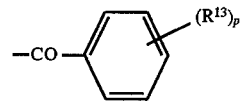

($R^{13}$ is OH, optionally substituted alkoxy, —$NR^{32}R^{33}$, —O—A—(E)$_r$—$NR^4R^5$, —(B)$_r$—$NR^6R^7$, etc.), n is 1 or 2, m is 0 or 1 to 3, $R^3$ is alkyl, $R^{10}$ is —(CO)$_r$—$NR^{11}R^{12}$], and the bond between 3- and 4-position of carbostyril nucleus is single or double bond, which have excellent vasopressin antagonistic activities and are useful as vasodilator, hypotensive agent, water diuretics, platelet agglutination inhibitor, and a vasopressin antagonistic composition containing the compound as the active ingredient.

10 Claims, No Drawings

CARBOSTYRIL DERIVATIVES

This is a continuation of application Ser. No. 07/846,941, filed Mar. 6, 1992, now abandoned, which is a divisional of application Ser. No. 07/762,736, filed Sep. 18, 1991 now U.S. Pat. No. 5,225,402, which is a continuation of application Ser. No. 07/478,181, filed Feb. 9, 1990 now abandoned.

This invention relates to novel carbostyril derivatives which have excellent vasopressin antagonistic activities and are useful as vasodilator, hypotensive agent, water diuretics, platelet agglutination inhibitor.

The carbostyril derivatives of this invention have the following formula:

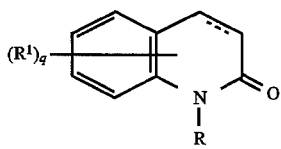
(1)

wherein $R^1$ is hydrogen atom; nitro; a lower alkoxy; a lower alkoxycarbonyl; a lower alkyl; a halogen atom; an amino having optionally one or two substituents selected from a lower alkanoyl, a lower alkyl, benozyl and a phenyl(lower)alkoxycarbonyl; hydroxy; cyano; carboxy; a lower alkanoyloxy; or hydrazinocarbonyl, q is an integer of 1 to 3 and R is a group of the formula:

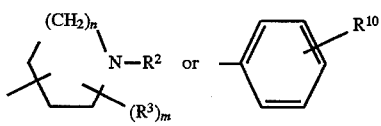

wherein $R^2$ is hydrogen atom; a lower alkoxycarbonyl; a phenoxycarbonyl which phenyl ring may optionally be substituted by one to three substituents selected from nitro and an amino having optionally one or two substituents selected from a lower alkanoyl, a lower alkyl and benzoyl; a phenyl(lower)alkenylcarbonyl; a phenyl(lower)alkanoyl which lower alkanoyl moiety may optionally be substituted by an amino having optionally a lower alkoxycarbonyl substituent; an alkanoyl; an alkenylcarbonyl; a phenylsulfonyl which phenyl ring may optionally be substituted by a lower alkoxy; a group of the formula:

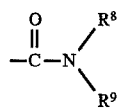

(wherein $R^8$ and $R^9$ are the same or different and are each hydrogen atom or a phenyl which may optionally have one to three substituents selected from a lower alkoxy, a lower alkyl, a halogen atom, an amino having optionally one or two substituents selected from a lower alkyl and a lower alkanoyl, and nitro); a heterocyclic group-substituted carbonyl which heterocyclic group may optionally have one to three substituents selected from a phenyl(lower)alkoxycarbonyl, a phenyl(lower)alkoxy, oxo, a lower alkyl, and a lower alkylenedioxy); a group of the formula:

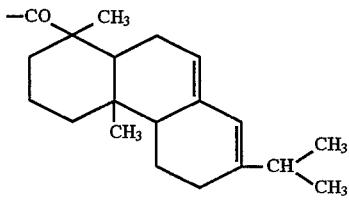

naphthylcarbonyl; thienyl(lower)alkanoyl; tricyclo[3.3.1.1]decanyl(lower)alkanoyl; tricyclo[3.3.1.1]decanylcarbonyl; or a group of the formula:

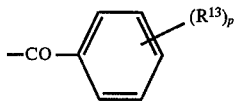

(wherein p is 0 or an integer of 1 to 3, and $R^{13}$ is hydroxy; an alkoxy; an alkoxy which has one or two substituents selected from hydroxy, a lower alkanoyloxy, a tri(lower)alkylammonium, a lower alkoxy, and a group of the formula:

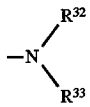

[wherein $R^{32}$ and $R^{33}$ are the same or different and are each hydrogen atom, a lower alkyl, a hydroxy-substituted lower alkyl, a lower alkanoyl, a tetrahydropyranyl(lower)alkyl, phenyl, a phenyl(lower)alkyl (wherein the alkyl moiety may optionally be substituted by hydroxy and the phenyl ring may optionally be substituted by a lower alkoxy), or a pyridyl(lower)alkyl; or $R^{32}$ and $R^{33}$ may bind with the nitrogen atom to which they bond to form a 5- or 6-membered, saturated heterocyclic group which may be intervened or not with nitrogen, oxygen or sulfur atom (wherein the heterocyclic group may optionally be substituted by a member selected from carbamoyl, a lower alkyl, a phenyl(lower)alkyl, phenyl and a hydroxy-substituted lower alkyl)]; a carboxy-substituted alkoxy; a halogen-substituted lower alkoxy; a lower alkoxycarbonyl-substituted alkoxy; a lower alkanoyloxy-substituted lower alkoxy; a lower alkenyloxy-substituted lower alkoxy; a lower alkoxy(lower)alkoxy; a lower alkylsulfonyloxy-substituted lower alkoxy; a benzoyloxy-substituted lower alkoxy; tricyclo[3.3.1.1]decanyl-substituted lower alkoxy; a lower alkoxy(lower)alkoxy which is substituted by one or two substituents selected from hydroxy and an amino being optionally substituted by a lower alkyl; a morpholinyl-substituted lower alkoxy which may optionally be substituted by a lower alkyl or oxo; a benzimidazolylthio-substituted lower alkoxy; a benzimidazolylsulfinyl-substituted lower alkoxy; a group of the formula:

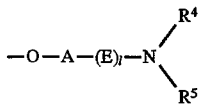

(wherein A is an alkylene, l is an integer of 0 or 1, E is —CO— or —OCO—, $R^4$ and $R^5$ are the same or different and are each hydrogen atom; a lower alkyl which may optionally be substituted by hydroxy or cyano; a lower alkenyl; a lower alkynyl; a phenyl(lower)alkyl; a lower alkanoyl which may optionally have one to three substituents of a halogen atom; a benzoyl which phenyl ring may optionally be substituted by a member selected from nitro and an amino having optionally one or two substituents selected from a lower alkyl, a lower alkanoyl and a phenyl (lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a pyrrolidinyl-substituted carbonyl which pyrrolidinyl ring may optionally be substituted by a phenyl(lower) alkoxycarbonyl; an amino-substituted lower alkanoyl wherein the lower alkanoyl moiety may optionally be substituted by a member selected from phenyl(lower) alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a phenyl(lower)alkyl having optionally a lower alkoxy substituent on the phenyl ring, a lower alkylsulfonyl, a lower alkanoyl, or a phenyl (lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by a lower alkyl group, nitro or an amino having optionally one or two substituents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally substituted by a lower alkyl or a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholinyl wherein the heterocyclic group have optionally a substituent selected from a lower alkyl and phenyl; a piperidinyl-substituted carbonyl which may optionally be substituted by a lower alkanoyl; a lower alkanoyloxy(lower)alkyl; a pyridyl-substituted lower alkyl; or an amino acid residue which can form an amido group with its amino group, or $R^4$ and $R^5$ may bind together with the nitrogen atom to which they bond to form a 5- or 6-membered, saturated or unsaturated heterocyclic group which may be intervened or not with nitrogen, oxygen or sulfur atom, wherein the heterocyclic group may optionally be substituted by a member selected from a phenyl having optionally a subsituent selected from a lower alkoxy and a halogen atom, oxo, hydroxy, a lower alkenyl, carboxy, a phenyl(lower)alkyl having optionally a hydroxy substituent on the lower alkyl moiety, a lower alkanoyl, a lower alkyl having optionally a hydroxy substituent, benzoyl, an amido having optionally a lower alkyl substituent, anilinocarbonyl, a benzoyl(lower)alkyl, a lower alkylsulfonyl, piperidinyl, pyrimidinyl, pyridyl, and a lower alkoxycarbonyl); a carbamoyloxy-substituted lower alkoxy; a lower alkylthio-substituted lower alkoxy; a lower alkylsulfonyl-substituted lower alkoxy; a lower alkylsulfinyl-substituted lower alkoxy; an alkenyloxy; phenoxy; a lower alkanoyloxy; a lower alkylsulfonyloxy; a lower alkynyloxy; a phenyl (lower)alkoxy; a cycloalkyl; a cycloalkyloxy; a cycloalkenyloxy; imidazo-[4,5-c]pyridylcarbonyl(lower)alkoxy; a group of the formula:

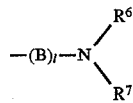

(wherein l is as defined above, B is a lower alkylene or a group of —CO—, and $R^6$ and $R^7$ are the same or different and are each hydrogen atom, a lower alkyl, a lower alkanoyl having optionally one to three halogen substituents, a carboxy(lower)alkyl, a lower alkoxycarbonyl, a lower alkoxycarbonyl(lower)alkyl, a lower alkenyl, an amido-substituted lower alkyl having optionally a lower alkyl substituent, or a phenyl(lower)alkoxycarbonyl, or $R^6$ and $R^7$ may bind together with nitrogen atom to which they bond to form a 5- or 6-membered, saturated or unsaturated heterocyclic group which may be intervened or not with nitrogen, oxygen or sulfur atom, wherein the heterocyclic group may optionally have a substituent selected from a lower alkoxycarbonyl, a lower alkyl, a lower alkylthio, or oxo); nitro; a halogen atom; a lower alkylsulfonyl; a lower alkyl which may optionally have one to three substituents selected from a halogen atom, hydroxy, phenyl and a lower alkoxy; a cyano-substituted lower alkoxy; an oxilanyl-substituted lower alkoxy; a phthalimido-substituted alkoxy; an amidino-substituted lower alkoxy, a pyrrolyl-substituted lower alkoxy; cyano; a lower alkoxycarbonyl; amidino; carbamoyl; carboxy; a lower alkanoyl; benzoyl; a lower alkoxycarbonyl(lower)alkyl; a carboxy(lower)alkyl; a lower alkoxy(lower)alkyl; a lower alkanoyloxy(lower)alkyl; hydroxyimino-substituted lower alkyl; phenyl; a lower alkylthio; a lower alkylsulfinyl; a lower alkenyl having optionally a hydroxy substituent; a lower alkylenedioxy, a lower alkylsilyl; a pyrimidylthio-substituted lower alkoxy; a pyrimidylsulfinyl-substituted lower alkoxy; a pyrmidylsufonyl-substituted lower alkoxy; an imidazolylthio-substituted lower alkoxy which may optionally have a lower alkyl substituent; an imidazolylsulfonyl-substituted lower alkoxy which may optionally have a lower alkyl substituent; an ammonium-lower alkoxy having three substituents selected from lower alkyl, lower alkenyl and oxo; a phenylthio-substituted lower alkoxy which phenyl ring may optionally have a substituent selected from nitro and amino; a phenylsulfonyl-substituted lower alkoxy which phenyl ring may optionally have a substituent selected from nitro and an amino having optionally one or two substituents selected from a lower alkanoyl and lower alkyl; a pyridylthio-substituted lower alkoxy; or a pyridylsuflonyl-substituted lower alkoxy which pyridyl ring may optionally be substituted by oxo), n is an integer of 1 or 2, m is 0 or an integer of 1 to 3, $R^3$ is a lower alkyl, $R^{10}$ is a group of the formula:

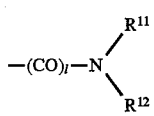

(wherein l is as defined above and $R^{11}$ and $R^{12}$ are the same or different and are each hydrogen atom, a lower alkyl, a phenyl(lower)alkyl, a lower alkenyl, a benzoyl which may optionally have a lower alkoxy substituent, tricyclo[3.3.1.1] decanyl, a phenyl which may optionally have a lower alkoxy substituent, or a cycloalkyl, or $R^{11}$ and $R^{12}$ may bind together with nitrogen atom to which they bond to form a saturated or unsaturated heterocyclic group which may be intervened or not with nitrogen, oxygen or sulfur atom, wherein the heterocyclic group may optionally have a substituent selected from a benzoyl, a lower alkanoyl, a phenyl (lower)alkyl and a phenyl which may optionally be substituted by a lower alkoxy and a lower alkanoyl), the bond between 3- and 4-positions of the carbostyril ring is single bond or double bond, provided that when $R^1$ is hydrogen atom and the l in the formula:

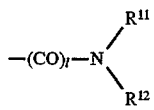

is 0, $R^{11}$ and $R^{12}$ are not simultaneously hydrogen atom.

The carbostyril derivatives of the formula (1) and their salts have excellent vasopressin antagonistic activities and vasodilating activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor and are used for the prophylaxis and treatment of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formula (1) includes specifically the following groups.

The "lower alkoxy" includes a straight chain or branched chain alkoxy group having 1 to 12 carbon atoms, for example, methoxy, ethoxy, propoxy, isopropoxy, butoxy, tert-butoxy, pentyloxy, hexyloxy, heptyloxy, octyloxy, nonyloxy, decyloxy, undecyloxy, dodecyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "halogen atom" includes fluorine atom, chlorine atom, bromine atom and iodine atome.

The "amino having optionally one or two substituents selected from a lower alkanoyl, a lower alkyl and benzoyl" includes an amino having one or two substituents selected from a straight chain or branched chain alkyl group having 1 to 6 carbon atoms, a straight chain or branched chain alkanoyl group having 1 to 6 carbon atoms and benzoyl group, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, benzoylamino, N-methyl-N-benzoylamino, N-ethyl-N-benzoylamino, and the like.

The "amino having optionally one or two substituents selected from a lower alkanoyl and a lower alkyl" includes an amino having one or two substituents selected from a straight chain or branched chain alkyl group having 1 to 6 carbon atoms and a straight chain or branched chain alkanoyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, and the like.

The "phenyl(lower)alkyl" includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, and the like.

The "amino having optionally one or two substituents selected from a lower alkyl, phenyl and a phenyl(lower) alkyl" includes an amino having one or two substituents selected from a straight chain or branched chain alkyl group having 1 to 6 carbon atoms, phenyl and a phenylalkyl wherein the alkyl moiety is a straight chain or branched chain alkyl group having 1 to 6 carbon atoms, for example, amino, phenylamino, diphenylamino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-phenylamino, N-ethyl-N-phenylamino, N-benzylamino, N-(2-phenylethyl)amino, N-(1-phenylethyl)amino, N-(3-phenylpropyl)amino, N-(4-phenylbutyl)amino, N-(5-phenylpentyl)amino, N-(6-phenylhexyl)amino, N-(1,1-dimethyl-2-phenylethyl)amino, N-(2-methyl-3-phenylpropyl)amino, N-methyl-N-benzylamino, N-ethyl-N-benzylamino, N-phenyl-N-benzylamino, and the like.

The "alkoxy which has one or two substituents selected from hydroxy, a lower alkanoyloxy, a tri(lower) alkylammonium, a lower alkoxy, and a group of the formula:

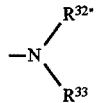

includes an alkoxy group having 1 to 10 carbon atoms which has one or two substituents selected from hydroxy, a straight chain or branched chain alkanoyloxy having 1 to 6 carbon atoms, a trialkylammonium group wherein the alkyl moiety is a straight chain or branched chain alkyl group having 1 to 6 carbon atoms, a straight chain or branched chain alkoxy group having 1 to 6 carbon atoms, and a group of the formula:

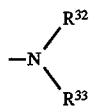

[wherein $R^{32}$ and $R^{33}$ are the same or different and are each hydrogen atom, a straight chain or branched chain alkyl group having 1 to 6 carbon atoms, a hydroxy-substituted straight chain or branched chain alkyl group having 1 to 6 carbon atoms, a straight chain or branched chain alkanoyl group having 1 to 6 carbon atoms, a tetrahydropyranylalkyl group (wherein the alkyl moiety is straight chain or branched chain alkyl group having 1 to 6 carbon atoms, phenyl, a phenylalkyl wherein the alkyl moiety is straight chain or branched chain alkyl group having 1 to 6 carbon atoms which may optionally be substituted by hydroxy and the phenyl ring may optionally be substituted by one to three of straight chain or branched chain alkoxy group having 1 to 6 carbon atoms), or a pyridylalkyl wherein the alkyl moiety is straight chain or branched chain alkyl group having 1 to 6 carbon atoms, or $R^{32}$ and $R^{33}$ may bind with the nitrogen atom to which they bond to form a 5- or 6-membered, saturated heterocyclic group which may be intervened or not with nitrogen, oxygen or sulfur atom (wherein the heterocyclic group may optionally be substituted by one to three substituents selected from carbamoyl, a straight chain or branched chain alkyl group having 1 to 6 carbon atoms, a phenylalkyl group wherein the alkyl moiety is a straight chain or branched chain alkyl group having 1 to 6 carbon atoms, phenyl and a hydroxy-substituted alkyl group wherein the alkyl moiety is a straight chain or branched chain alkyl group having 1 to 6 carbon atoms], for example, hydroxymethoxy, 2-hydroxyethoxy, 1-hydroxyethoxy, 3-hydroxypropoxy, 2,3-dihydroxypropoxy, 4-hydroxybutoxy, 3,4-dihydroxybutoxy, 1,1-dimethyl-2-hydroxyethoxy, 5,6-dihydroxyhexyloxy, 5-hydroxypentyloxy, 6-hydroxyhexyloxy, 7-hydroxyheptyloxy, 8-hydroxyoctyloxy, 9-hydroxynonyloxy, 10-hydroxydecyloxy, 6-(3,4-dimethoxybenzylamino)-5-hydroxyhexyloxy, 6-(3-methoxybenzylamino)-5-hydroxyhexyloxy, 6-[2-(2-pyridyl)ethylamino]-5-hydroxyhexyloxy, 6-[N-methyl-N-(2-pyridylethyl)amino]-5-hydroxyhexyloxy, 6-{N-ethyl-N-[2-(2-pyridyl)ethylamino]-5-hydroxyhexyloxy, 6-[N-ethyl-N-(4-pyridylmethyl)amino]-5-hydroxyhexyloxy, 6-(3-pyridylmethylamino)-5-hydroxyhexyloxy, 6-(2-pyridylmethylamino)-5-hydroxyhexyloxy, 6-(diethylmethylammonium)-5-methoxyhexyloxy, 4-(trimethylammonium)-3-hydroxyhexyloxy, 5-(dipropylethylammonium)-4-acetyloxypentyloxy, 7-(2-ethoxybenzylamino)-6-acetyloxyheptyloxy, 8-(3,4,5-trimethoxybenzylamino)-7-ethoxyoctyloxy, 5-[3-(2-pyridyl)propyl]-4-acetyloxypentyloxy, 7-[4-(3-pyridyl)butyl]-6-propoxyheptyloxy, 2-methyl-3-hydroxypropoxy, aminomethoxy, 1-aminoethoxy, 2-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, ethylaminomethoxy, propylaminomethoxy, isopropylaminomethoxy, butylaminomethoxy, tert-butylaminomethoxy, pentylaminomethoxy, hexylaminomethoxy, dimethylaminomethoxy, diethylaminomethoxy, dibutylaminomethoxy, dipentylaminomethoxy, dihexylaminomethoxy, N-methyl-N-ethylaminomethoxy, N-methyl-N-propylaminomethoxy, N-methyl-N-butylaminomethoxy, N-methyl-N-hexylaminomethoxy, 1-methylaminoethoxy, 2-ethylaminoethoxy, 3-propylaminopropoxy, 4-butylaminobutoxy, 1,1-dimethyl-2-pentylaminoethoxy, 5-hexylaminopentyloxy, 6-dimethylaminohexyloxy, 7-methylaminoheptyloxy, 8-dimethylaminooctyloxy, 4-dimethylaminobutoxy, 2-diethylaminoethoxy, 1-(N-methyl-N-hexylamino)ethoxy, 3-dihexylaminopropoxy, 6-diethylaminohexyloxy, 4-dibutylaminobutoxy, 9-(N-methyl-N-propylamino)nonyloxy, 2-(N-methyl-N-pentylamino)ethoxy, 7-hydroxy-8-dimethylaminooctyloxy, 2-hydroxy-3-diethylaminopropoxy, 7-hydroxy-8-diethylaminooctyloxy, 2-hydroxy-3-(N-phenyl-N-benzylamino)propoxy, 7-hydroxy-8-ethylaminooctyloxy, 3-hydroxy-4-methylaminobutoxy, 5-hydroxy-6-diethylaminohexyloxy, 3-hydroxy-4-phenylaminobutoxy, 8-hydroxy-9-dimethylaminononyloxy, 4-hydroxy-5-dimethylaminopentyloxy, 9-hydroxy-10-diethylaminodecyloxy, 4-hydroxy-5-methylaminopentyloxy, 4-hydroxy-5-diethylaminopentyloxy, phenylaminomethoxy, diphetnylaminomethoxy, benzylaminomethoxy, 5-hydroxy-6-benzylaminohexyloxy, 5-hydroxy-6-[N-methyl-N-(2-phenylethyl)amino]hexyloxy, 5-hydroxy-6-ethylaminohexyloxy, 5-hydroxy-6-isopropylaminohexyloxy, 5-hydroxy-6-(N-methyl-N-benzylamino)hexyloxy, 5-hydroxy-6-aminohexyloxy, (N-methyl-N-benzylamino)methoxy, (N-ethyl-N-benzylamino)methoxy, (N-phenyl-N-benzylamino)methoxy, 2-(phenylamino)ethoxy, 3-(2-phentylethylamino)propoxy, 4-(3-phenylpropylamino)butoxy, 1,1-dimethyl-2-(4-phenylbutylamino)ethoxy, 5-(5-phenylpentylamino)pentyloxy, 6-(6-phenylhexylamino)hexyloxy, 7-hydroxy-8-(N-phenyl-N-benzylamino)octyloxy, 8-hydroxy-9-[N-(2-phenylethyl)amino]nonyloxy, 9-hydroxy-10-(N-ethyl-N-benzylamino)decyloxy, acetyloxymethoxy, 2-propionyloxyethoxy, 1-butyryloxyethoxy, 3-acetyloxypropoxy, 4-isobutyryloxybutoxy, 5-pentanoyloxypentyloxy, 6-tert-butylcarbonyloxyhexyloxy, 1,1-dimethyl-2-hexanoyloxyethoxy, 2-methyl-3-acetyloxypropoxy, 7-acetyloxyheptyloxy, 8-acetyloxyoctyloxy, 9-acetyloxynonyloxy, 10-acetyloxydecyloxy, (hydroxymethyl)aminomethoxy, 1-[N,N-di-(2-hydroxyethyl)amino]ethoxy, 2-(3-hydroxypropyl)aminoethoxy, 3-(4-hydroxybutyl)aminopropoxy, 4-(5-hydroxypentyl)aminobutoxy, 5-(6-hydroxyhexyl)aminopentyloxy, 6-[N-(2-hydroxyethyl)-N-methylamino]hexyloxy, 5-hydroxy-6-[N-(2-hydroxyethyl)-N-methylamino]hexyloxy, 5-hydroxy-6-[N,N-di(2-hydroxyethyl)amino]hexyloxy, 6-hydroxy-7-[N-(2-hydroxyethyl)-N-benzylamino]heptyloxy, 7-hydroxy-8-[N-(3-hydroxypropyl)-N-phenylamino]octyloxy, 7-hydroxy-9-{N-(4-hydroxybutyl)-N-[(tetrahydropyranyl-2-yl)methyl]amino}nonyloxy, 8-hydroxy-10-[N-(2-hydroxyethyl)-N-acetylamino]decyloxy, acetylaminomethoxy, 2-(formylamino)ethoxy, 1-(propionylamino)ethoxy, 3-(butyrylamino)propoxy, 4-(isobutyrylamino)butyloxy, 5-(pentanoylamino)pentyloxy, 6-(hexanoylamino)hexyloxy, 5-acetyloxy-6-acetylaminohexyloxy, 5-hydroxy-6-acetylaminohexyloxy, 6-hydroxy-7-(N-methyl-N-acetylamino)heptyloxy, 7-hydroxy-8-(N-benzyl-N-acetylamino)octyloxy, 8-hydroxy-9-(N-phenyl-N-acetylamino)nonyloxy, 9-acetyloxy-10-[N-(tetrahydropyran-2-yl)methyl-N-acetylamino]decyloxy, (tetrahydropyran-2-yl)methylaminomethoxy, 2-[(tetrahydropyran-3-yl)methylamino]ethoxy, 1-[(tetrahydropyran-4-yl)methylamino]ethoxy, 3-[2-(tetrahydropyran-2-yl)ethylamino]propoxy, 4-[3-(tetrahydropyran-2-yl)propylamino]butoxy, 5-[4-(tetrahydropyran-2-yl)butylamino]pentyloxy, 5-hydroxy-6-[N-ethyl-N-(tetrahydropyran-2-yl)methylamino]hexyloxy, 6-hydroxy-7-{N-phenyl-N-[5-(tetrahydropyran-2-yl)pentylamino}heptyloxy, 7-hydroxy-8-{N-benzyl-N-[6-(tetrahydropyran-2-yl)hexylamino}octyloxy, (2-hydroxy-2-phenylethyl)aminomethoxy, 2-[(3-hydroxy-3-phenylpropyl)amino]ethoxy, 3-[(2-hydroxy-4-phenylbutyl)amino]propoxy, 4-[(6-hydroxy-6-phenylhexyl)amino]butoxy, 5-[(2-hydroxy-2-phenylethyl)amino]pentyloxy, 5-hydroxy-6-[(2-hydroxy-2-phenylethyl)amino]hexyloxy, 6-hydroxy-7-

[N-(2-hydroxy-2-phenylethyl)-N-methylamino]heptyloxy, 7-hydroxy-8-[N-(2-hydroxy-2-phenylethyl)-N-phenylamino]octyloxy, 8-hydroxy-9-[N-(2-hydroxy-2-phenylethyl)-N-benzylamino]nonyloxy, 9-hydroxy-10-[N-(2-hydroxy-2-phenylethyl)-N-acetylamino]decyloxy, (piperazin-1-yl)methoxy, 2-(pyrrolidin-1-yl)ethoxy, 3-(piperidin-1-yl)propoxy, 4-morpholinobutoxy, 5-thiomorpholinopentyloxy, 6-(piperazin-1-yl)hexyloxy, 5-hydroxy-6-(4-benzyl-1-piperazinyl)hexyloxy, 5-hydroxy-6-(1-piperazinyl)hexyloxy, 5-hydroxy-6-(4-methyl-1-piperazinyl)hexyloxy, 4-hydroxy-5-(1-pyrrolidinyl)pentyloxy, 4-hydroxy-5-(1-piperidinyl)pentyloxy, 4-hydroxy-5-morpholinopentyloxy, 5-hydroxy-6-(1-pyrrolidinyl)hexyloxy, 5-hydroxy-6-(1-piperidinyl)hexyloxy, 5-hydroxy-6-(4-phenyl-1-piperazinyl)hexyloxy, 5-hydroxy-6-(2-carbamoyl-1-pyrrolidinyl)hexyloxy, 7-hydroxy-8-(1-pyrrolidinyl)octyloxy, 5-hydroxy-6-(2-hydroxymethyl-1-pyrrolidinyl)hexyloxy, 7-(2-carbamoylmorpholino)-6-hydroxyheptyloxy, 8-hydroxy-9-(4-benzyl-1-piperazinyl)nonyloxy, 4-(3-carbamoyl-1-piperidinyl)-3-hydroxybutoxy, 9-hydroxy-10-(4-ethyl-1-piperazinyl)decyloxy, 6-(4-carbamoyl-1-piperazinyl)-5-hydroxyhexyloxy, and the like.

The "carboxy-substituted alkoxy" includes a carboxy-substituted alkoxy group wherein the alkoxy moiety is a straight chain or branched chain alkoxy group having 1 to 12 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, 7-carboxyheptyloxy, 8-carboxyoctyloxy, 9-carboxynonyloxy, 10-carboxydecyloxy, 11-carboxyundecyloxy, 12-carboxydodecyloxy, and the like.

The "lower alkoxycarbonyl-substituted alkoxy" includes an alkoxycarbonyl-substituted straight chain or branched chain alkoxy group having 1 to 12 carbon atoms wherein the alkoxycarbonyl moiety is a straight chain or branched chain alkoxycarbonyl group having 1 to 6 carbon atoms, for example, methoxycarbonylmethoxy, 3-methoxycarbonylpropoxy, ethoxycarboxymethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy, 7-methoxycarbonylheptyloxy, 8-ethoxycarbonyloctyloxy, 9-propoxycarbonylnonyloxy, 10-butoxycarbonyldecyloxy, 11-methoxycarbonylundecyloxy, 12-ethoxycarbonyldodecyloxy, and the like.

The "lower alkanoyloxy-substituted lower alkoxy" includes a straight chain or branched chain alkoxy group having 1 to 6 carbon atoms which is substituted by a straight chain or branched chain alkanoyloxy group having 2 to 6 carbon atoms, for example, acetyloxymethoxy, 2-propionyloxyethoxy, 1-butyryloxyethoxy, 3-acetyloxypropoxy, 4-isobutyryloxybutoxy, 5-pentanoyloxypentyloxy, 6-tert-butylcarbonyloxyhexyloxy, 1,1-dimethyl-2-hexanoyloxyethoxy, 2-methyl-3-acetyloxypropoxy, and the like.

The "lower alkenyloxy-substituted lower alkoxy" includes a straight chain or branched chain alkoxy group having 1 to 6 carbon atoms which is substituted by a straight chain or branched chain alkanyloxy group having 2 to 6 carbon atoms, for example, vinyloxymethoxy, 2-allyloxyethoxy, 1-(2-butenyloxy)ethoxy, 3-allyloxypropoxy, 4-(3-butenyloxy)butoxy, 5-(1-methylallyloxy)pentyloxy, 6-(2-pentenyloxy)hexyloxy, 1,1-dimethyl-2-(2-hexenyloxy)ethoxy, 2-methyl-3-allyloxypropoxy, and the like.

The "lower alkoxy(lower)alkoxy" includes a straight chain or branched chain alkoxy group having 1 to 6 carbon atoms which is substituted by a straight chain or branched chain alkoxy group having 1 to 6 carbon atoms, for example, methoxymethoxy, 3-methoxypropoxy, 4-ethoxybutoxy, 6-propoxyhexyloxy, 5-isopropoxypentyloxy, 1,1-dimethyl-2-butoxyethoxy, 2-methyl-3-tert-butoxypropoxy, 2-pentyloxyethoxy, hexyloxymethoxy, and the like.

The "lower alkylsulfonyloxy-substituted lower alkoxy" includes a straight chain or branched chain alkoxy group having 1 to 6 carbon atoms which is substituted by a straight chain or branched chain alkylsulfonyloxy group having 1 to 6 carbon atoms, for example, methylsulfonyloxymethoxy, 3-methylsulfonyloxypropoxy, 4-ethylsulfonyloxybutoxy, 2-methylsulfoyloxyethoxy, 6-propylsulfonyloxyhexyloxy, 5-isopropylsulfonyloxypentyloxy, 1,1-dimethyl-2-butylsulfoyloxyethoxy, 2-methyl-3-methlsulfonyloxypropoxy, and the like.

The "benzoyloxy-substituted lower alkoxy" includes a benzoyloxyalkoxy group wherein the alkoxy moiety is a straight chain or branched chain alkoxy group having 1 to 6 carbon atoms, for example, benzoyloxymethoxy, 2-benzoyloxyethoxy, 1-benzoyloxyethoxy, 3-benzoyloxypropoxy, 4-benzoyloxybutoxy, 6-benzoyloxyhexyloxy, 5-benzoyloxypentyloxy, 1,1-dimethyl-2-benzoyloxyethoxy, 2-methyl-3-benzoyloxypropoxy, and the like.

The "tricyclo[3.3.1.1]decanyl-substituted lower alkoxy" includes a tricyclo[3.3.1.1]decanyl-substituted straight chain or branched chain alkoxy group having 1 to 6 carbon atoms, for example, tricyclo[3.3.1.1]decanylmethoxy, 2-tricyclo[3.3.1.1]decanylethoxy, 1-tricyclo[3.3.1.1]decanylethoxy, 3-tricyclo[3.3.1.1]decanylpropoxy, 4-tricyclo[3.3.1.1]decanylbutoxy, 5-tricyclo[3.3.1.1]decanylpentyloxy, 6-tricyclo[3.3.1.1]decanylhexyloxy, 1,1-dimethyl-2-tricyclo[3.3.1.1]decanylethoxy, 2-methyl-3-tricyclo[3.3.1.1]decanylpropoxy, and the like.

The "lower alkylene" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyl" includes a straight chain or branched chain alkanoyl group having 1 to 6 carbon atoms, for example, formyl, acetyl, propionyl, butyryl, isobutyryl, pentanoyl, tert-butylcarbonyl, hexanolyl, and the like.

The "amino having optionally one or two substituents selected from a lower alkyl, a lower alkanoyl and a phenyl (lower)alkoxycarbonyl" includes an amino having one or two substituents selected from a straight chain or branched chain alkyl group having 1 to 6 carbon atoms, a straight chain or branched chain alkanoyl group having 1 to 6 carbon atoms and a phenylalkoxycarbonyl group wherein the alkoxy moiety is a straight chain or branched chain alkoxy group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-benzyloxycarbonylamino, N-(2-phenylethoxycarbonyl) amino, N-(1-phenylethoxycarbonyl)amino, N-(3-phenylpropoxycarbonyl)amino, N-(4-phenylbutoxycarbonyl)amino, N-(5-phenylpentyloxycarbonyl)amino, N-(6-phenylhexyloxycarbonyl)amino, N-(1,1-dimethyl-2-phenylethoxycarbonyl)amino, N-(2-methyl-3-phenylpropoxycarbonyl)amino, N-methyl-N-benzyloxycarbonylamino, N-ethyl-N-benzyloxycarbonylamino, acetylamino, formylamino, propionylamino, butyrylamino, isobutyrylamino, pentanoylamino, tert-butylcarbonylamino, hexanoylamino, N-methyl-N-acetylamino, N-ethyl-N-acetylamino, N-benzyloxycarbonyl-N-acetylamino, and the like.

The "benzoyl which phenyl ring may optionally has a substituent selected from nitro and an amino having optionally one or two substituents selected from a lower alkyl, a lower alkanoyl and a phenyl(lower)alkoxycarbonyl" includes a benzoyl group which phenyl ring may optionally have one to three substituents selected from nitro and an amino having one or two substituents selected from a straight chain or branched chain alkyl group having 1 to 6 carbon atoms, a straight chain or branched chain alkanoyl group having 1 to 6 carbon atoms and a phenylalkoxycarbonyl group wherein the alkoxy moiety is a straight chain or branched chain alkoxy group having 1 to 6 carbon atoms, for example, benzoyl, 2-aminobenzoyl, 4-aminobenzoyl, 4-methylaminobenzoyl, 3-ethylaminobenzoyl, 2-(N-methyl-N-ethylamino)benzoyl, 3-(N-methyl-N-hexylamino)benzoyl, 4-dimethylaminobenzoyl, 4-dipentylaminobenzoyl, 2-isopropylaminobenzoyl, 3-butylaminobenzoyl, 4-(N-methyl-N-benzyloxycarbonylamino)benzoyl, 2-[N-(2-phenylethoxycarbonyl)amino]benzoyl, 2,3-bis(dimethylamino)benzoyl, 3,4-bis(methylamino)benzoyl, 3,4,5-tri(methylamino)benzoyl, 2,6-di(N-methyl-N-benzyloxycarbonylamino)benzoyl, 3-[N-(3-phenylpropoxycarbonyl)amino]benzoyl, 4-[N-(5-phenylpentyloxycarbonyl)amino]benzoyl, 2-[N-(6-phenylhexyloxycarbonyl)amino]benzoyl, 3-[N-(4-phenylbutoxycarbonyl)amino]benzoyl, 4-acetylaminobenzoyl, 3-(N-methyl-N-acetylamino)benzoyl, 2-(N-benzyloxycarbonyl-N-acetylamino)benzoyl, 4-nitrobenzoyl, 4-nitro-3-methylaminobenzoyl, 2,4-dinitrobenzoyl, 2,4,6-trinitrobenzoyl, and the like.

The "lower alkoxycarbonyl" includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

The "lower alkoxycarbonyl(lower)alkyl" includes a straight chain or branched chain alkoxycarbonylalkyl group having 1 to 6 carbon atoms in the alkoxy moiety wherein the alkyl moiety is a straight chain or branched chain alkyl group having 1 to 6 carbon atoms, for example, methoxycarbonylmethyl, 3-methoxycarbonylpropyl, ethoxycarbonylmethyl, 4-ethoxycarbonylbutyl, 1-ethoxycarbonylethyl, 1-methoxycarbonylethyl, 6-propoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The "amido having optionally a lower alkyl substituent" includes an amido having one or two substituents of a straight chain or branched chain alkyl group having 1 to 6 carbon atoms, for example, carbamoyl, methylamido, ethylamido, propylamido, isopropylamido, butylamido, tert-butylamido, pentylamido, hexylamido, dimethylamido, diethylamido, dipropylamido, dibutylamido, dipentylamido, dihexylamido, N-methyl-N-ethylamido, N-ethyl-N-propylamido, N-methyl-N-butylamido, N-methyl-N-hexylamido, and the like.

The "lower alkylsulfonyl" includes a straight chain or branched chain alkylsulfonyl group having 1 to 6 carbon atoms, for example, methylsulfonyl, ethylsulfonyl, isopropylsulfonyl, butylsulfonyl, tert-butylsulfonyl, pentylsulfonyl, hexylsulfonyl, and the like.

The "5- or 6-membered, saturated or unsaturated heterocyclic group which is formed by binding the groups $R^4$ and $R^5$ together with the nitrogen atom to which they bond and may be intervened or not with nitrogen, oxygen or sulfur atom" includes, for example, pyrrolidinyl, piperidinyl, piperazinyl, morpholino, thiomorpholino, pyrrolyl, pyrazolyl, imidazolyl, imidazolidinyl, 1,2,4-triazolyl, 1,2,3,4-tetrazolyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, and the like.

The "phenyl which may optionally have a substituent selected from a lower alkoxy and a halogen atom" includes a phenyl group which may optionally have one to three substituents selected from a straight chain or branched chain alkoxy group having 1 to 6 carbon atoms and a halogen atom, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, and the like.

The "heterocyclic group which may optionally be substituted by a member selected from a phenyl having optionally a subsitutent selected from a lower alkoxy and a halogen atom, oxo, hydroxy, a lower alkenyl, carboxy, a phenyl (lower)alkyl having optionally a hydroxy substituent on the lower alkyl moiety, a lower alkanoyl, a lower alkyl having optionally a hydroxy substituent, benzoyl, an amido having optionally a lower alkyl substituent, anilinocarbonyl, a benzoyl(lower)alkyl, a lower alkylsulfonyl, piperidinyl, pyrimidinyl, pyridyl, and a lower alkoxycarbonyl" includes the above-mentioned heterocyclic group which may optionally be substituted by one to three substituents selected from a phenyl having optionally one to three subsitutents selected from a straight chain or branched chain alkoxy group having 1 to 6 carbon atoms and a halogen atom, an oxo group, a hydroxy group, a straight chain or branched chain alkenyl group having 2 to 6 carbon atoms, carboxy, a phenylalkyl wherein the alkyl moiety is a straight chain or branched chain alkyl group having 1 to 6 carbon atoms and having optionally a hydroxy substituent, a straight chain or branched chain alkanoyl group having 1 to 6 carbon atoms, a straight chain or branched chain alkyl group having 1 to 6 carbon atoms and having optionally one to three hydroxy substituents, benzoyl, an amido group having optionally one or two substituents of a straight chain or branched chain alkyl group having 1 to 6 carbon atoms, anilinocarbonyl, a benzoylalkyl group wherein the alkyl moiety is a straight chain or branched chain alkyl group having 1 to 6 carbon atoms, a straight chain or branched chain alkylsulfonyl group having 1 to 6 carbon atoms in the alkyl moiety, piperidinyl, pyrimidinyl, pyridyl, and a straight chain or branched chain alkoxycarbonyl group having 1 to 6 carbon atoms, for example, 4-phenylpiperazinyl, 4-(4-methoxyphenyl)piperazinyl, 4-(4-chlorophenyl)piperazinyl, 3-(2-ethoxyphenyl)pyrrolidinyl, 2-(4-isopropoxyphenyl) pyrrolidinyl, 4-(4-pentyloxyphenyl)piperidinyl, 3-(4-hexyloxyphenyl)piperidinyl, 3-(2,3-dimethoxyphenyl) morpholino, 2-(2-methoxyphenyl)morpholino, 3-(3-ethoxyphenyl)thiomorpholino, 2-(3,4,5-trimethoxyphenyl) thiomorpholino, 4-(3,4-dimethoxyphenyl)piperazinyl, 4-(3,4,5-trimethoxyphenyl)piperazinyl, 3-(2-fluorophenyl) pyrrolidinyl, 2-(3-bromophenyl)pyrrolidinyl, 4-(3-iodophenyl)piperidinyl, 3-(4-bromophenyl)piperidinyl, 2-(3,4-dichlorophenyl)morpholino, 3-(3-chlorophenyl) morpholino, 3-(2-bromophenyl)thiomorpholino, 2-(4-fluorophenyl)thiomorpholino, 4-(3,4,5-trichlorophenyl) piperazinyl, 4-(2,6-dichlorophenyl)piperazinyl, 4-benzylpiperazinyl, 3-(2-phenylethyl)pyrrolidinyl, 2-(3-phenylpropyl)pyrrolidinyl, 4-(4-phenylbutyl)piperidinyl, 3-(5-phenylpentyl)morpholino, 2-(6-phenylhexyl) thiomorpholino, 4-(2-phenyl-2-hydroxyethyl)piperazinyl, 3-(1-hydroxy-1-phenylmethyl)pyrrolidinyl, 2-(3-hydroxy-3-phenylpropyl)pyrrolidinyl, 4-(2-hydroxy-4-phenylbutyl) piperidinyl, 2-(5-hydroxy-5-phenylpentyl)thiomorpholino, 3-(6-hydroxy-6-phenylhexyl)morpholino, 4-acetylpiperazinyl, 3-formylpyrrolidinyl, 2-propionylpyrrolidinyl, 4-butyrylpiperidinyl, 3-pentanoylthiomorpholino, 2-hexanoylmorpholino, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 2-hexylthiomorpholino, 4-benzoylpiperazinyl, 3-benzoylpyrrolidinyl, 3-benzoylmorpholino, 2-benzoylthiomorpholino, 3-benzoylpiperidinyl, 4-anilinocarbonylpiperazinyl, 2-anilinocarbonylpyrrolidinyl, 3-anilinocarbonylpiperidinyl, 2-anilinocarbonylmorpholino, 3-anilinocarbonylthiomorpholino, 4-(benzoylmethyl) piperazinyl, 3-(1-benzoylethyl)pyrrolidinyl, 2-(3-benzoylpropyl)pyrrolidinyl, 4-(4-benzoylbutyl)piperidinyl, 3-(5-benzoylpentyl)morpholino, 2-(6-benzoylhexyl) thiomorpholino, 3-methyl-4-benzoylpiperazinyl, 3-ethyl-4-acetylpiperidinyl, 3-methyl-4-benzylpyrrolidinyl, 3-propyl-4-anilinocarbonylpyrrolidinyl, 3-methyl-5-(benzoylmethyl) morpholino, 3-methyl-5-(2-phenyl-2-hydroxyethyl) thiomorpholino, 4-methylsulfonylpiperazinyl, 4-methoxycarbonylpiperazinyl, 3-ethylsulfonylpyrrolidinyl, 3-ethoxycarbonylpyrrolidinyl, 4-propylsulfonylpiperidinyl, 3-propoxycarbonylpiperidinyl, 3-butylsulfonylmorpholino, 2-pentyloxycarbonylmorpholino, 2-hexylsulfonylthiomorpholino, 3-hexyloxycarbonylthiomorpholino, 4-allylpiperazinyl, 4-ethoxycarbonylpiperidinyl, 4-carboxypiperidinyl, 4-dimethylamidopiperidinyl, 4-carbamoylpiperidinyl, 4-(1-piperidinyl)piperidinyl, 3-hydroxypiperidinyl, 2-carbamoylpyrrolidinyl, 2-hydroxymethylpiperidinyl, 2-hydroxymethylpyrrolidinyl, 3-hydroxymethylpiperidinyl, 3-hydroxypyrrolidinyl, 4-(2-hydroxyethyl)piperidinyl, 2-methoxycarbonylpyrrolidinyl, 2-(2-hydroxyethyl) piperidinyl, (2-pyrimidyl)piperazinyl, (2-pyridyl) piperazinyl, 2-methylimidazolyl, 3-methyl-1,2,4-triazolyl, 5-methyl-1,2,3,4-tetrazolyl, 4-hydroxymethylimidazolyl, 3-allyl-1,2,4-triazolyl, 5-phenyl-1,2,3,4-tetrazolyl, 3-carboxypyrrolyl, 2-hydroxyoxazolidinyl, 2-carbamoylthiazolidinyl, 4-oxothiomorpholino, 4,4-dioxothiomorpholino, and the like.

The "phenyl(lower)alkyl having optionally a hydroxy-substituent on the alkyl moiety and having optionally a lower alkoxy substituent on the phenyl ring" includes a phenylalkyl group wherein the alkyl moiety is a straight chain or branched chain alkyl group having 1 to 6 carbon atoms and having optionally a hydroxy-substituent and the phenyl ring has optionally one to three substituents of a straight chain or branched chain alkoxy group having 1 to 6 carbon atoms, for example, in addition to the above-mentioned phenyl(lower)alkyl groups, 1-hydroxy-1-phenylmethyl, 1-phenyl-2-hydroxyethyl, 2-phenyl-2-hydroxyethyl, 3-hydroxy-3-phenylpropyl, 2-hydroxy-4-phenylbutyl, 6-hydroxy-6-phenylhexyl, 3,4-dimethoxybenzyl, 3-methoxybenzyl, 1-(2-methoxyphenyl) ethyl, 2-(4-methoxyphenyl)ethyl, 3-(2-ethoxyphenyl) propyl, 4-(3-ethoxyphenyl)butyl, 5-(4-ethoxyphenyl)pentyl, 6-(4-isopropoxyphenyl)hexyl, 1,1-dimethyl-2-(4-pentyloxyphenyl)ethyl, 2-methyl-3-(4-hexyloxyphenyl) propyl, 3-ethoxy-4-methoxybenzyl, 2,3-dimethoxybenzyl, 3,4-diethoxybenzyl, 3,4,5-trimethoxybenzyl, 1-hydroxy-1-(3-methoxyphenyl)methyl, 1-(2,5-dimethoxyphenyl)-2-hydroxyethyl, 2-(2,6-dimethoxyphenyl)-2-hydroxyethyl, 5-hydroxy-5-(3,4-dipentyloxyphenyl)pentyl, and the like.

The "benzoyl(lower)alkyl" includes a benzoylalkyl group wherein the alkyl moiety is a straight chain or branched chain alkyl group having 1 to 6 carbon atoms, for example, benzoylmethyl, 1-benzoylethyl, 2-benzoylethyl, 3-benzoylpropyl, 4-benzoylbutyl, 5-benzoylpentyl, 6-benzoylhexyl, 1,1-dimethyl-2-benzoylethyl, 2-methyl-3-benzoylpropyl, and the like.

The "carbamoyloxy-substituted lower alkoxy" includes a carbamoyloxy-substituted alkoxy group wherein the alkoxy moiety is a straight chain or branched chain alkoxy group having 1 to 6 carbon atoms, for example, carbamoyloxymethoxy, 2-carbamoyloxyethoxy, 1-carbamoyloxyethoxy, 3-carbamoyloxypropoxy, 4-carbamoyloxybutoxy, 5-carbamoyloxypentyloxy, 6-carbamoyloxyhexyloxy, 1,1-dimethyl-2-carbamoyloxyethoxy, 2-methyl-3-carbamoyloxypropoxy, and the like.

The "lower alkylthio-substituted alkoxy" includes a alkylthio-substituted straight chain or branched chain alkoxy group having 1 to 6 carbon atoms wherein the alkylthio moiety is a straight chain or branched chain alkylthio group having 1 to 6 carbon atoms, for example, methylthiomethoxy, 3-ethylthiopropoxy, 4-methylthiobutoxy, 2-methylthioethoxy, 6-propylthiohexyloxy, 5-isopropylthiopentyloxy, 1,1-dimethyl-2-butylthioethoxy, 2-methyl-3-methylthiopropoxy, and the like.

The "lower alkylsulfonyl-substituted lower alkoxy" includes a straight chain or branched chain alkoxy group having 1 to 6 carbon atoms which is substituted by a straight chain or branched chain alkylsulfonyl group having 1 to 6 carbon atoms, for example, methylsulfonylmethoxy, 3-ethylsulfonylpropoxy, 4-methylsulfonylbutoxy, 2-methylsulfoylethoxy, 6-propylsulfonylhexyloxy, 5-isopropylsulfonylpentyloxy, 1,1-dimethyl-2-butylsulfoylethoxy, 2-methyl-3-methylsulfonylpropoxy, and the like.

The "lower alkylsulfinyl-substituted lower alkoxy" includes a straight chain or branched chain alkoxy group having 1 to 6 carbon atoms which is substituted by a straight chain or branched chain alkylsulfinyl group having 1 to 6 carbon atoms, for example, methylsulfinylmethoxy, 3-ethylsulfinylpropoxy, 4-methylsulfinylbutoxy, 2-methylsulfinylethoxy, 6-propylsulfinylhexyloxy, 5-isopropylsulfinylpentyloxy, 1,1-dimethyl-2-butylsulfinylethoxy, 2-methyl-3-methylsulfinylpropoxy, and the like.

The "lower alkenyloxy" includes a straight chain or branched chain alkenyl group having 2 to 12 carbon atoms and containing one to three double bonds, for example, vinyloxy, allyloxy, 3-methyl-2-butenyloxy, 2-butenyloxy, 3-butenyloxy, 1-methylallyloxy, 2-pentenyloxy, 2-hexenyloxy, 1-heptenyloxy, 1-octenyloxy, 1-nonenyloxy, 1-decenyloxy, 1-undecenyloxy, 1-dodecenyloxy, 2-heptenyloxy, 3-heptenyloxy, 2-methyl-4-heptenyloxy, 2-methyl-5-heptenyloxy, 4-methyl-2-heptenyloxy, 3-methyl-1-heptenyloxy, 1,3-heptadienyloxy, 1,4-heptadienyloxy, 1,5-heptadienyloxy, 1,6-heptadienyloxy, 2,4-heptadienyloxy, 2-methyl-2,4-heptadienyloxy, 2,6-dimethyl-2,4-heptadienyloxy, 2,5-dimethyl-1,3-heptadienyloxy, 2,4,6-trimethyl-2,4-heptadienyloxy, 2-octenyloxy, 3-octenyloxy, 4-octenyloxy, 2-methyl-5-octenyloxy, 2-methyl-6-octenyloxy, 2-methyl-7-octenyloxy, 1,3-octadienyloxy, 1,4-octadienyloxy, 1,5-octadienyloxy, 1,6-octadienyloxy, 1,7-octadienyloxy, 2,4-octadienyloxy, 3,7-octadienyloxy, 4,8-dimethyl-3,7-octadienyloxy, 2,4,6-trimethyl-3,7-octadienyloxy, 3,4-dimethyl-2,5-octadienyloxy, 3,7-dimethyl-2,6-octadienyloxy, 4,8-dimethyl-2,6-octadienyloxy, 2-nonenyloxy, 3-nonenyloxy, 4-nonenyloxy, 2-methyl-5-nonenyloxy, 2-methyl-6-nonenyloxy, 2-methyl-7-nonenyloxy, 2-methyl-8-nonenyloxy, 1,3-nonadienyloxy, 1,4-nonadienyloxy, 1,5-nonadienyloxy, 1,6-nonadienyloxy, 1,7-nonadienyloxy, 1,8-nonadienyloxy, 2,4-nonadienyloxy, 3,7-nonadienyloxy, 4,8-dimethyl-3,7-nonadienyloxy, 2,4,6-trimethyl-3,7-nonadienyloxy, 3,4-dimethyl-2,5-nonadienyloxy, 4,8-dimethyl-2,6-nonadienyloxy, 2-decenyloxy, 3-decenyloxy, 4-decenyloxy, 5-decenyloxy, 2-methyl-6-decenyloxy, 3-methyl-7-decenyloxy, 4-methyl-8-decenyloxy, 5-methyl-9-decenyloxy, 1,3-decadienyloxy, 1,4-decadienyloxy, 1,5-decadienyloxy, 1,6-decadienyloxy, 1,7-decadienyloxy, 1,8-decadienyloxy, 1,9-decadienyloxy, 2-methyl-2,4-decadienyloxy, 3-methyl-2,5-decadienyloxy, 4,8-dimethyl-2,6-decadienyloxy, 2,4,6-trimethyl-3,7-decadienyloxy, 2,9-dimethyl-3,7-decadienyloxy, 2-undecenyloxy, 3-undecenyloxy, 4-undecenyloxy, 5-undecenyloxy, 2-methyl-6-undecenyloxy, 3-methyl-7-undecenyloxy, 4-methyl-8-undecenyloxy, 5-methyl-9-undecenyloxy, 2-methyl-10-undecenyloxy, 1,3-undecadienyloxy, 1,4-undecadienyloxy, 1,5-undecadienyloxy, 1,6-undecadienyloxy, 1,7-undecadienyloxy, 1,8-undecadienyloxy, 1,9-undecadienyloxy, 1,10-undecadienyloxy, 2-methyl-2,4-undecadienyloxy, 3-methyl-2,5-undecadienyloxy, 4,8-dimethyl-2,6-undecadienyloxy, 2,4,6-trimethyl-3,8-undecadienyloxy, 2,9-dimethyl-3,8-undecadienyloxy, 2-dodecenyloxy, 3-dodecenyloxy, 4-dodecenyloxy, 5-dodecenyloxy, 6-dodecenyloxy, 2-methyl-7-dodecenyloxy, 3-methyl-8-dodecenyloxy, 4-methyl-9-dodecenyloxy, 5-methyl-10-dodecenyloxy, 6-methyl-11-dodecenyloxy, 2-methyl-2,4-dodecadienyloxy, 3-methyl-2,5-dodecadienyloxy, 4,8-dimethyl-2,6-dodecadienyloxy, 2,4,6-trimethyl-2,7-dodecadienyloxy, 2,10-dimethyl-2,8-dodecadienyloxy, 2,5-dimethyl-3,7-dodecadienyloxy, 4,8,12-trimethyl-3,7,11-dodecatrienyloxy, 1,3,5-heptatrienyloxy, 2,4,6-octatrienyloxy, 1,3,6-nonatrienyloxy, 2,6,8-dodecatrienyloxy, 1,5,7-undecatrienyloxy, and the like.

The "lower alkanoyloxy" includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, and the like.

The "lower alkylsulfonyloxy" includes a straight chain or branched chain alkylsulfonyloxy group having 1 to 6 carbon atoms, for example, methylsulfonyloxy, ethylsulfonyloxy, isopropylsulfonyloxy, butylsulfoyloxy, tert-butylsulfonyloxy, pentylsulfonyloxy, hexylsulfonyloxy, and the like.

The "lower alkynyloxy" includes a straight chain or branched chain alkynyloxy group having 2 to 6 carbon atoms, for example, ethynyloxy, 2-propynyloxy, 2-butynyloxy, 3-butynyloxy, 1-methyl-2-propynyloxy, 2-pentynyloxy, 2-hexynyloxy, and the like.

The "phenyl(lower)alkoxy" includes a phenylalkoxy group wherein the alkoxy moiety is a straight chain or branched chain alkoxy group having 1 to 6 carbon atoms, for example, benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, and the like.

The "cycloalkyloxy" includes a cycloalkyloxy group having 3 to 8 carbon atoms, for example, cyclopropyloxy, cyclopentyloxy, cyclohexyloxy, cycloheptyloxy, cyclooctyloxy, and the like.

The "cycloalkenyloxy" includes a cycloalkenyloxy group having 3 to 8 carbon atoms, for example, cyclopropenyloxy, cyclobutenyloxy, cyclopentenyloxy, cyclohexenyloxy, cycloheptenyloxy, cyclooctenyloxy, and the like.

The "lower alkanoyl which may optionally have one to three substituents of a halogen atom" includes a straight chain or branched chain alkanoyl group having 1 to 6 carbon atoms which may optionally have one to three substituents of a halogen atom, for example, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichlopropionyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkylthio" includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The "5- or 6-membered, saturated or unsaturated heterocyclic group which is formed by binding $R^6$ and $R^7$ together with the nitrogen atom to which they bond and may be intervened or not with nitrogen, oxygen or sulfur atom" includes, for example, pyrrolidinyl, piperidinyl, piperazinyl, morpholino, thiomorpholino, pyrrolyl, pyrazolyl, imidazolyl, imidazolidinyl, pyrrolyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, and the like.

The "heterocyclic group having a substituent selected from a lower alkoxycarbonyl, lower alkyl, lower alkylthio or oxo" includes the above heterocyclic groups which have a substituent selected from a straight chain or branched chain alkoxycarbonyl group having 1 to 6 carbon atoms, a straight chain or branched chain alkyl group having 1 to 6 carbon atoms, a straight chain or branched chain alkylthio group having 1 to 6 carbon atoms, and an oxo group, for example, 4-tert-butoxycarbonylpiperazinyl, 4-methylpiperazinyl, 2-ethylthioimidazolyl, 2-oxopyrrolidinyl, 2-oxo-oxazolidinyl, 3-oxopiperazinyl, 4-methoxycarbonylpiperazinyl, 3-ethoxycarbonylpiperidinyl, 2-propoxycarbonylpyrrolidinyl, 3-pentyloxycarbonylthiomorpholino, 2-hexyloxycarbonylthiomorpholino, 3-ethoxycarbonylpyrrolyl, 3-methoxycarbonylimidazolyl, 3-ethylpiperidinyl, 3-propylpyrrolidinyl, 3-butylpyrrolyl, 2-pentylimidazolyl, 3-hexylmorpholino, 2-methylthiomorpholino, 2-methyloxazolidinyl, 2-ethylthiazolinyl, 3-methylisoxazolinyl, 2-methylthioimidazolyl, 2-propylthioimidazolinyl, 2-butylthioimidazolidinyl, 3-pentylthiopyrrolyl, 3-hexylthiopyrrolinyl, 3-methylthiopyrrolidinyl, 3-ethylthiomorpholino, 2-methylthiomorpholino, 2-methylthioisoxazalidinyl, and the like.

The "lower alkyl which may optionally have one to three substituents selected from a halogen atom, hydroxy, phenyl and a lower alkoxy" includes a straight chain or branched chain alkyl group having 1 to 6 carbon atoms which may optionally have one to three substituents selected from a halogen atom, hydroxy, phenyl and a straight chain or branched chain alkoxy group having 1 to 6 carbon atoms, for example, in addition to the above-mentioned lower alkyl groups, hydroxymethyl, 2-hydroxyethyl, 1-hydroxyethyl, 3-hydroxypropyl, 2,3-dihyroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, benzyl, 1-phenylethyl, 2-phenylethyl, 3-phenylpropyl, 4-phenylbutyl, 1,1-dimethyl-2-phenylethyl, 5-phenylpentyl,-6-phenylhexyl, 2-methyl-3-phenylpropyl, methoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, hexyloxymethyl, dimethoxymethyl, 2,3-dimethoxyethyl, 6,6,5-trimethoxyhexyl, 1-hydroxy-1-phenylmethyl, 1-hydroxy-2-phenylethyl, 1-hydroxy-3-phenylpropyl, 1-methoxy-1-phenylmethyl, and the like.

The "cyano-substituted lower alkoxy" includes a straight chain or branched chain alkoxy group having 1 to 6 carbon atoms which is substituted by cyano group, for example, cyanomethoxy, 2-cyanoethoxy, 1-cyanoethoxy, 3-cyanopropoxy, 4-cyanobutoxy, 5-cyanopentyloxy, 6-cyanohexyloxy, 1,1-dimethyl-2-caynoethoxy, 2-methyl-3-cyanopropoxy, and the like.

The "oxilanyl-substituted lower alkoxy" includes a straight chain or branched chain alkoxy group having 1 to 6 carbon atoms which is substituted by oxilanyl group, for example, glycidoxy, 2-oxilanylethoxy, 1-oxilanylethoxy, 3-oxilanylpropoxy, 4-oxilanylbutoxy, 5-oxilanylpentyloxy, 6-oxilanylhexyloxy, 1,1-dimethyl-2-oxilanylethoxy, 2-methyl-3-oxilanylpropoxy, and the like.

The "phthalimido-substituted alkoxy" includes a straight chain or branched chain alkoxy group having 1 to 12 carbon atoms which is substituted by phthalimido group, for example, phthalimidomethoxy, 2-phthalimidoethoxy, 1-phthalimidoethoxy, 3-phthalimidopropoxy, 4-phthalimidobutoxy, 5-phthalimidopentyloxy, 6-phthalimidohexyloxy, 1,1-dimethyl-2-phthalimidoethoxy, 2-methyl-3-phthalimidopropoxy, 7-phthalimidoheptyloxy, 8-phthalimidooctyloxy, 9-phthalimidononyloxy, 10-phthalimidodecyloxy, 11-phthalimidoundecyloxy, 12-phthalimidododecyloxy, and the like.

The "pyrrolyl-substituted lower alkoxy" includes a straight chain or branched chain alkoxy group having 1 to 6 carbon atoms which is substituted by pyrrolyl group, for example, (1-pyrrolyl)methoxy, 2-(2-pyrrolyl)ethoxy, 1-(3-pyrrolyl)ethoxy, 3-(1-pyrrolyl)propoxy, 4-(1-pyrrolyl)butoxy, 5-(2-pyrrolyl)pentyloxy, 6-(3-pyrrolyl)hexyloxy, 1,1-dimethyl-2-(1-pyrrolyl)ethoxy, 2-methyl-3-(1-pyrrolyl)propoxy, and the like.

The "amidino-substituted lower alkoxy" includes a straight chain or branched chain alkoxy group having 1 to 6 carbon atoms which is substituted by amidino group, for example, amidinomethoxy, 2-amidinoethoxy, 1-amidinoethoxy, 3-amidinopropoxy, 4-amidinobutoxy, 5-amidinopentyloxy, 6-amidinohexyloxy, 1,1-dimethyl-2-amidinoethoxy, 2-methyl-3-amidinopropoxy, and the like.

The "lower alkanoyloxy(lower)alkyl" includes a straight chain or branched chain alkyl group having 1 to 6 carbon atoms which is substituted by a straight chain or branched chain alkanoyloxy group having 2 to 6 carbon atoms, for example, acetyloxymethyl, 2-propionyloxyethyl, 1-butyryloxyethyl, 3-acetyloxypropyl, 4-isobutyryloxybutyl, 5-pentanoyloxypentyl, 6-tert-butylcarbonyloxyhexyl, 1,1-dimethyl-2-hexanoyloxyethyl, 2-methyl-3-acetyloxypropyl, and the like.

The "lower alkylsulfinyl" includes a straight chain or branched chain alkylsulfinyl group having 1 to 6 carbon atoms, for example, methylsulfinyl, ethylsulfinyl, isopropylsulfinyl, butylsulfiyl, tert-butylsulfinyl, pentylsulfinyl, hexylsulfinyl, and the like.

The "lower alkenyl having optionally a hydroxy-substituent" include a straight chain or branched chain alkenyl group having 2 to 6 carbon atoms and having optionally a hydroxy-substituent, for example, in addition to the above-mentioned alkenyl groups, 1-hydroxyallyl, 4-hydroxy-1-butenyl, 4-hydroxy-2-butenyl, 2-hydroxy-3-butenyl, 5-hydroxy-2-pentenyl, 6-hydroxy-2-hexenyl, and the like.

The "lower alkylenedioxy" includes a straight chain or branched chain alkylenedioxy group having 1 to 4 carbon atoms, for example, methylenedioxy, ethylenedioxy, trimethylenedioxy, tetramethylenedioxy, and the like.

The lower alkylsilyl includes a silyl group having one to three substituents of a straight chain or branched chain alkyl group having 1 to 6 carbon atoms, for example, methylsilyl, ethylsilyl, propylsilyl, isopropylsilyl, butylsilyl, tert-butylsilyl, pentylsilyl, hexylsilyl, dimethylsilyl, trimethylsilyl, dimethyl-tert-butylsilyl, and the like.

The "amino which may optionally substituted by a lower alkanoyl" includes an amino which may optionally substituted by a straight chain or branched chain alkanoyl group having 1 to 6 carbon atoms, for example, amino, formylamino, acetylamino, propionylamino, butyrylamino, isobutyrylamino, pentanoylamino, tert-butylcarbonylamino, hexanoylamino, and the like.

The "phenoxycarbonyl which may optionally have one to three substituents selected from nitro and an amino having optionally one or two substituents selected from a lower alkanoyl, lower alkyl and benzoyl" includes a phenoxycarbonyl group which may optionally have one to three substituents selected from nitro group and an amino group having optionally one or two substituents selected from a straight chain or branched chain alkanoyl group having 1 to 6 carbon atoms, a straight chain or branched chain alkyl group having 1 to 6 carbon atoms and benzoyl group, for example, phenoxycarbonyl, 2-nitrophenoxycarbonyl, 3-nitrophenoxycarbonyl, 4-nitrophenoxycarbonyl, 3,4-dinitrophenoxycarbonyl, 2,5-dinitrophenoxycarbonyl, 2,6-dinitrophenoxycarbonyl, 3,4,5-trinitrophenoxycarbonyl, 2-aminophenoxycarbonyl, 3-aminophenoxycarbonyl, 4-aminophenoxycarbonyl, 3-acetylaminophenoxycarbonyl, 4-formylaminophenoxycarbonyl, 4-isobutyrylaminophenoxycarbonyl, 2-pentanoylaminophenoxycarbonyl, 3-hexanoylaminophenoxycarbonyl, 3,4-diacetylaminophenoxycarbonyl, 3,4-diaminophenoxycarbonyl, 2,6-diaminophenoxycarbonyl, 2,5-diaminophenoxycarbonyl, 2,4,6-triaminophenoxycarbonyl, 4-acetylaminophenoxycarbonyl, 4-dimethylaminophenoxycarbonyl, 4-benzoylaminophenoxycarbonyl, 3-(N-methyl-N-benzoylamino)phenoxycarbonyl, 2-(N-ethyl-N-acetylamino)phenoxycarbonyl, and the like.

The "phenyl(lower)alkenylcarbonyl" includes a phenylalkenylcarbonyl group wherein the alkenylcarbonyl moiety is a straight chain or branched chain alkenylcarbonyl group having 3 to 6 carbon atoms, for example, cinnamoyl, 4-phenyl-3-butenoyl, 4-phenyl-2-butenoyl, 5-phenyl-4-pentenoyl, 5-phenyl-3-pentenoyl, 5-phenyl-2-pentenoyl, 6-phenyl-5-hexenoyl, 6-phenyl-4-hexenoyl, 6-phenyl-3-hexenoyl, 6-phenyl-2-hexenoyl, 2-methyl-4-phenyl-3-butenoyl, and the like.

The "amino having optionally a lower alkoxycarbonyl substituent" includes an amino being optionally substituted by a straight chain or branched chain alkoxycarbonyl group having 1 to 6 carbon atoms, for example, amino, methoxycarbonylamino, ethoxycarbonylamino, propoxycarbonylamino, isopropoxycarbonylamino, butoxycarbonylamino, tert-butoxycarbonylamino, pentyloxycarbonylamino, hexyloxycarbonylamino, and the like.

The "phenyl(lower)alkanoyl wherein the lower alkanoyl moiety may optionally be substituted by an amino having optionally a lower alkoxycarbonyl substituent" includes a phenylalkanoyl wherein the alkanoyl moiety is a straight chain or branched chain alkanoyl group having 2 to 6 carbon atoms and may optionally be substituted by an amino group which may optionally be substituted by a straight chain or branched chain alkoxycarbonyl group having 1 to 6 carbon atoms, for example, phenylacetyl, 3-phenylpropionyl, 2-phenylpropionyl, 4-phenylbutyryl, 2,2-dimethyl-3-phenylpropionyl, 5-phenylpentanoyl, 6-phenylhexanoyl, 3-methyl-4-phenylbutyryl, 2-amino-4-phenylacetyl, 2-tert-butoxycarbonylamino-2-phenylacetyl, 2-methoxycarbonylamino-2-phenylacetyl, 2-ethoxycarbonylamino-3-phenylpropionyl, 2-propoxycarbonylamino-4-phenylbutyryl, 2-pentyloxycarbonylamino-5-phenylpentanoyl, 2-hexyloxycarbonylamino-6-phenylhexanoyl, and the like.

The "alkanoyl" includes a straight chain or branched chain alkanoyl group having 1 to 12 carbon atoms, for example, in addition to the above-mentioned lower alkanoyl groups, heptanoyl, octanoyl, nonanoyl, decanoyl, undecanoyl, dodecanoyl, neopentanoyl, and the like.

The "alkenylcarbonyl" includes a straight chain or branched chain alkenylcarbonyl group having 2 to 12 carbon atoms and having one to three double bonds, for example, vinylcarbonyl, acrylcarbonyl, 3-methyl-2-butenylcarbonyl, 2-butenylcarbonyl, 1-methylallylcarbonyl, 2-pentenylcarbonyl, 2-hexenylcarbonyl, 1-heptenylcarbonyl, 1-octenylcarbonyl, 1-nonenylcarbonyl, 1-decenylcarbonyl, 1-undecenylcarbonyl, 1-dodecenylcarbonyl, 2-heptenylcarbonyl, 3-heptenylcarbonyl, 2-methyl-4-heptenylcarbonyl, 2-methyl-5-heptenylcarbonyl, 4-methyl-2-heptenylcarbonyl, 3-methyl-1-heptenylcarbonyl, 1,3-heptadienylcarbonyl, 1,4-heptadienylcarbonyl, 1,5-heptadienylcarbonyl, 1,6-heptadienylcarbonyl, 2,4-heptadienylcarbonyl, 2-methyl-2,4-heptadienylcarbonyl, 2,6-dimethyl-2,4-heptadienylcarbonyl, 2,6-dimethyl-1,5-heptadienylcarbonyl, 2,5-dimethyl-1,3-heptadienylcarbonyl, 2,4,6-trimethyl-2,4-heptadienylcarbonyl, 2-octenylcarbonyl, 3-octenylcarbonyl, 4-octenylcarbonyl, 2-methyl-5-octenylcarbonyl, 2-methyl-6-octenylcarbonyl, 2-methyl-7-octenylcarbonyl, 1,3-octadienylcarbonyl, 1,4-octadienylcarbonyl, 1,5-octadienylcarbonyl, 1,6-octadienylcarbonyl, 1,7-octadienylcarbonyl, 2,4-octadienylcarbonyl, 3,7-octadienylcarbonyl, 4,8-dimethyl-3,7-octadienylcarbonyl, 2,4,6-trimethyl-3,7-octadienylcarbonyl, 3,4-dimethyl-2,5-octadienylcarbonyl, 4,8-dimethyl-2,6-octadienylcarbonyl, 2-nonenylcarbonyl, 3-nonenylcarbonyl, 4-nonenylcarbonyl, 2-methyl-5-nonenylcarbonyl, 2-methyl-6-nonenylcarbonyl, 2-methyl-7-nonenylcarbonyl, 2-methyl-8-nonenylcarbonyl, 1,3-nonadienylcarbonyl, 1,4-nonadienylcarbonyl, 1,5-nonadienylcarbonyl, 1,6-nonadienylcarbonyl, 1,7-nonadienylcarbonyl, 1,8-nonadienylcarbonyl, 2,4-nonadienylcarbonyl, 3,7-nonadienylcarbonyl, 4,8-dimethyl-3,7-nonadienylcarbonyl, 2,4,6-trimethyl-3,7-nonadienylcarbonyl, 3,4-dimethyl-2,5-nonadienylcarbonyl, 4,8-dimethyl-2,6-nonadienylcarbonyl, 2-decenylcarbonyl, 3-decenylcarbonyl, 4-decenylcarbonyl, 5-decenylcarbonyl, 2-methyl-6-decenylcarbonyl, 3-methyl-7-decenylcarbonyl, 4-methyl-8-decenylcarbonyl, 5-methyl-9-decenylcarbonyl, 1,3-decadienylcarbonyl, 1,4-decadienylcarbonyl, 1,5-decadienylcarbonyl, 1,6-decadienylcarbonyl, 1,7-decadienylcarbonyl, 1,8-decadienylcarbonyl, 1,9-decadienylcarbonyl, 2-methyl-2,4-decadienylcarbonyl, 3-methyl-2,5-decadienylcarbonyl, 4,8-dimethyl-2,6-decadienylcarbonyl, 2,4,6-trimethyl-3,7-decadienylcarbonyl, 2,9-dimethyl-3,7-decadienylcarbonyl, 2-undecenylcarbonyl, 3-undecenylcarbonyl, 4-undecenylcarbonyl, 5-undecenylcarbonyl, 2-methyl-6-undecenylcarbonyl, 3-methyl-7-undecenylcarbonyl, 4-methyl-8-undecenylcarbonyl, 5-methyl-9-undecenylcarbonyl, 2-methyl-10-undecenylcarbonyl, 1,3-undecadienylcarbonyl, 1,4-undecadienylcarbonyl, 1,5-undecadienylcarbonyl, 1,6-undecadienylcarbonyl, 1,7-undecadienylcarbonyl, 1,8-undecadienylcarbonyl, 1,9-undecadienylcarbonyl, 1,10-undecadienylcarbonyl, 2-methyl-2,4-undecadienylcarbonyl, 3-methyl-2,5-undecadienylcarbonyl, 4,8-dimethyl-2,6-undecadienylcarbonyl, 2,4,6-trimethyl-3,8-undecadienylcarbonyl, 2,9-dimethyl-3,8-undecadienylcarbonyl, 2-dodecenylcarbonyl, 3-dodecenylcarbonyl, 4-dodecenylcarbonyl, 5-dodecenylcarbonyl, 6-dodecenylcarbonyl, 2-methyl-7-dodecenylcarbonyl, 3-methyl-8-dodecenylcarbonyl, 4-methyl-9-dodecenylcarbonyl, 5-methyl-10-dodecenylcarbonyl, 6-methyl-11-dodecenylcarbonyl, 2-methyl-2,4-dodecadienylcarbonyl, 3-methyl-2,5-dodecadienylcarbonyl, 4,8-dimethyl-2,6-dodecadienylcarbonyl, 2,4,6-trimethyl-2,7-dodecadienylcarbonyl, 2,10-dimethyl-2,8-dodecadienylcarbonyl, 2,5-dimethyl-3,7- dodecadienylcarbonyl, 4,8,12-trimethyl-3,7,11-dodecatrienylcarbonyl, 1,3,5-heptatrienylcarbonyl, 2,4,6-octatrienylcarbonyl, 1,3,6-nonatrienylcarbonyl, 2,6,8-dodecatrienylcarbonyl, 1,5,7-undecatrienylcarbonyl, and the like.

The "phenylsulfonyl which phenyl ring may optionally have a lower alkoxy substituent" includes a phenylsulfonyl group which phenyl ring may optionally have one to three substituents of a straight chain or branched chain alkoxy group having 1 to 6 carbon atoms, for example, phenylsulfonyl, 2-methoxyphenylsulfonyl, 3-methoxyphenylsulfonyl, 4-methoxyphenylsulfonyl, 2-ethoxyphenylsulfonyl, 3-ethoxyphenylsulfonyl, 4-ethoxyphenylsulfonyl, 4-isopropoxyphenylsulfonyl, 4-pentyloxyphenylsulfonyl, 4-hexyloxyphenylsulfonyl, 3,4-dimethoxyphenylsulfonyl, 3-ethoxy-4-methoxyphenylsulfonyl, 2,3-dimethoxyphenylsulfonyl, 3,4-diethoxyphenylsulfonyl, 2,5-dimethoxyphenylsulfonyl, 2,6-dimethoxyphenylsulfonyl, 3,5-dimethoxyphenylsulfonyl, 3,4-dipentyloxyphenylsulfonyl, 3,4,5-trimethoxyphenylsulfonyl, and the like.

The "phenyl which may optionally have one to three substituents selected from a lower alkoxy, a lower alkyl, a halogen atom, an amino having optionally one or two substituents selected from a lower alkyl and a lower alkanoyl, and nitro" includes a phenyl group which may optionally have one to three substituents selected from a straight chain or branched chain alkoxy group having 1 to 6 carbon atoms, a straight chain or branched chain alkyl group having 1 to 6 carbon atoms, a halogen atom, an amino group having optionally one or two substituents selected from straight chain or branched chain alkyl group having 1 to 6 carbon atoms and a straight chain or branched chain alkanoyl group having 1 to 6 carbon atoms, and a nitro group, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,5-dimethylphenyl, 2,6-dimethylphenyl, 3,4,5-trimethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-nitrophenyl, 3-nitrophenyl, 4-nitrophenyl, 3,4-dinitrophenyl, 2,5-dinitrophenyl, 2,6-dinitrophenyl, 3,4,5-trinitrophenyl, 2-aminophenyl, 3-aminophenyl, 4-aminophenyl, 3-(N-acetylamino)phenyl, 4-(N-formylamino)phenyl, 4-(N-isobutyrylamino)phenyl, 2-(N-pentanoylamino)phenyl, 3,4-diaminophenyl, 3,4-di(N-acetylamino)phenyl, 3,4,5-triaminophenyl, 2,6-diaminophenyl, 2,5-diaminophenyl, 3,5-di-t-butyl-4-hydroxyphenyl, 3-hydroxy-4-pentyloxyphenyl, 2-hydroxy-5-t-butylphenyl, 3,5-dichloro-4-aminophenyl, 3-amino-4-hydroxyphenyl, 3-acetylamino-4-methoxyphenyl, 3-nitro-4-acetylaminophenyl, 3-nitro-4-chlorophenyl, 3-chloro-4-methylphenyl, 3-methoxy-4-methyl-5-iodophenyl, 3,4-dimethoxy-5-bromophenyl, 3,5-diiodo-4-methoxyphenyl, 4-dimethylaminophenyl, 3-methylaminophenyl, 2-butylaminophenyl, 4-diethylaminophenyl, 3-dipropylaminophenyl, 2-(N-methyl-N-hexaylamino)phenyl, 4-(N-methyl-N-acetylamino)phenyl, 2,4-dimethylaminophenyl, and the like.

The "heterocyclic group-substituted carbonyl" includes a 5- to 10-membered, monocyclic or dicyclic heterocyclic groups containing one or two hetero atoms selected from nitrogen atom, oxygen atom and/or sulfur atom, for example, 2-pyrrolidinylcarbonyl, 3-pyrrolidinylcarbonyl, 1-piperidinylcarbonyl, 1-piperazinylcarbonyl, morpholinocarbonyl, thiomopholinocarbonyl, 2-tetrahydrofurylcarbonyl, 2-thienylcarbonyl, 3-thienylcarbonyl, 2-pyrrolylcarbonyl, 3-pyrrolylcarbonyl, 2-furoyl, 3-furoyl, 2-pyridylcarbonyl, 3-pyridylcarbonyl, 4-pyridylcarbonyl, 3-pyridazylcarbonyl, 2-thiazolylcarbonyl, 2-oxazolylcarbonyl, 2-imidazolylcarbonyl, 4-pyridazylcarbonyl, 5-pyridazylcarbonyl, 6-pyridazylcarbonyl, 2-pyrimidylcarbonyl, 4-pyrimidylcarbonyl, 5-pyrimidylcarbonyl, 6-pyrimidylcarbonyl, 2-pyradylcarbonyl, 3-pyradylcarbonyl, 6-quinolylcarbonyl, 5-indolylcarbonyl, 6-isoquinolylcarbonyl, 4-cinnolylcarbonyl, 3-quinoxalylcarbonyl, 4-phthalazylcarbonyl, 3-benzo[b]furanylcarbonyl, 5-benzo[b]thiophenylcarbonyl, 2-oxo-6-quinolylcarbonyl, 2-oxo-4-quinolylcarbonyl, and the like.

The above "heterocyclic group-substituted carbonyl which has one to three substitutents selected from a phenyl (lower)alkoxycarbonyl, a phenyl(lower)alkoxy, oxo, a lower alkyl and a lower alkylenedioxy" includes the above-mentioned heterocyclic group-substituted carbonyl groups which have one to three substituents selected from a phenylalkoxycarbonyl group wherein the alkoxycarbonyl moiety is a straight chain or branched chain alkoxycarbonyl group having 1 to 6 carbon atoms, a phenylalkoxy group wherein the alkoxy moiety is a straight chain or branched chain alkoxy group having 1 to 6 carbon atoms, an oxo group, a straight chain or branched chain alkyl group having 1 to 6 carbon atoms, and a straight chain or branched chain alkylenedioxy group having 1 to 4 carbon atoms, for example, 1-benzyloxycarbonyl-2-pyrrolidinylcarbonyl, 3-benzyloxycarbonyl-4,5-(1,1-dimethylmethylene)-2-tetrahydrofurylcarbonyl, 4-(2-phenylethoxycarbonyl)-1-piperazinylcarbonyl, 3-methyl-2-thienylcarbonyl, 3-ethyl-2-pyrrolylcarbonyl, 3-propyl-2-furoyl, 4-butyl-2-oxo-6-quinolylcarbonyl, 6-pentyl-2-oxo-4-quinolylcarbonyl, 5-hexyl-2-pyrazylcarbonyl, 1,3-dioxo-2-methyl-6-quinazolylcarbonyl, 4,5-methylenedioxy-3-indolylcarbonyl, 3-(3-phenylpropoxy)morpholinocarbonyl, and the like.

The "thienyl(lower)alkanoyl" includes a thienylalkanoyl wherein the alkanoyl moiety is a straight chain or branched chain alkanoyl group having 2 to 6 carbon atoms, for example, 2-(2-thienyl)acetyl, 3-(3-thienyl)propionyl, 2-(3-thienyl)propionyl, 4-(2-thienyl)butyryl, 2,2-dimethyl-3-(3-thienyl)propionyl, 5-(2-thienyl)pentanoyl, 6-(3-thienyl)hexanoyl, 3-methyl-4-(2-thienyl)butyryl, and the like.

The "tricyclo[3.3.1.1]decanyl(lower)alkanoyl" includes a tricyclo[3.3.1.1]decanylalkanoyl wherein the alkanoyl moiety is a straight chain or branched chain alkanoyl group having 2 to 6 carbon atoms, for example, 2-tricyclo[3.3.1.1]decanylacetyl, 3-tricyclo[3.3.1.1]decanylpropionyl, 2-tricyclo[3.3.1.1]decanylpropionyl, 4-tricyclo[3.3.1.1]decanylbutyryl, 2,2,-dimethyl-3-tricyclo[3.3.1.1]decanylpropionyl, 5-tricyclo[3.3.1.1]decanylpentanoyl, 6-tricyclo[3.3.1.1]decanylhexanoyl, 3-methyl-4-tricyclo[3.3.1.1]decanylbutyryl, and the like.

The "benzoyl which phenyl ring may optionally have a lower alkoxy substituent" includes a benzoyl which may optionally have one to three substituents of a straight chain or branched chain alkoxy group having 1 to 6 carbon atoms, for example, benzoyl, 2-methoxybenzoyl, 3-methoxybenzoyl, 4-methoxybenzoyl, 2-ethoxybenzoyl, 3-ethoxybenzoyl, 4-butoxybenzoyl, 4-isopropoxybenzoyl, 4-pentyloxybenzoyl, 4-hexyloxybenzoyl, 3,4-dimethoxybenzoyl, 3-ethoxy-4-methoxybenzoyl, 2,3-dimethoxybenzoyl, 2,4-dimethoxybenzoyl, 3,4-diethoxybenzoyl, 2,5-dimethoxybenzoyl, 2,6-dimethoxybenzoyl, 3,5-dimethoxybenzoyl, 3,4-dipentyloxybenzoyl, 2-methoxy-4-methoxybenzoyl, 2,4,6-trimethoxybenzoyl, 3,4,5-trimethoxybenzoyl, and the like.

The "phenyl which may optionally have a lower alkoxy substituent" includes a phenyl group which may optionally have one to three substituents of a straight chain or branched chain alkoxy group having 1 to 6 carbon atoms, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, and the like.

The "cycloalkyl" includes a cycloalkyl having 3 to 8 carbon atoms, for example, cyclopropyl, cyclobutyl, cyclopentyl, cyclohexyl, cycloheptyl, cyclooctyl, and the like.

The "saturated or unsaturated heterocyclic group which is formed by binding the groups $R^{11}$ and $R^{12}$ together with the nitrogen atom to which they bond and may be intervened or not with nitrogen, oxygen or sulfur atom" includes, a 5- to 10-membered, saturated or unsaturated, monocyclic or dicyclic heterocyclic group, for example, pyrrolidinyl, piperidinyl, piperazinyl, morpholino, thiomorpholino, pyrrolyl, imidazolyl, pyrazolyl, imidazolidinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, 1,2,3,4-tetrahydroquinolyl, 1,2-dihydroquinolyl, indolyl, isoindolyl, 1,2-dihydroisoquinolyl, 1,2,3,4-tetrahydroisoquinolyl, 1H-indazolyl, 1,2-dihyroquinazolyl, 1,2-dihydrocinnolyl, 1,2-dihydroquinoxalyl, 1,2,3,4-tetrahydroquinazolyl, 1,2,3,4-tetrahydrocinnolyl, 1,2,3,4-tetrahydroquinoxalyl, and the like.

The "phenyl which may optionally have a substituent selected from a lower alkoxy and a lower alkanoyl" includes a phenyl group which may optionally have one to three substituents selected from a straight chain or branched chain alkoxy group having 1 to 6 carbon atoms and a straight chain or branched chain alkanoyl group having 1 to 6 carbon atoms, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 3-methoxy-4-acetylphenyl, 2-acetylphenyl, 3-acetylphenyl, 4-acetylphenyl, 2-formylphenyl, 3-propionylphenyl, 4-isobutyrylphenyl, 2-pentanoylphenyl, 3-hexanoylphenyl, 3,4-diacetylphenyl, 2,5-diacetylphenyl, 3,4,5-triacetylphenyl, and the like.

The "heterocyclic group which may optionally be substituted by a member selected from benzoyl, a lower alkanoyl, a phenyl(lower)alkyl, and a phenyl having optionally a substituent selected from a lower alkoxy and a lower alkanoyl" includes the above heterocyclic groups which may optionally have a substituent selected from benzoyl group, a straight chain or branched chain alkanoyl group having 1 to 6 carbon atoms, a phenylalkyl group wherein the alkyl moiety is a straight chain or branched chain alkyl group having 1 to 6 carbon atoms, and a phenyl group having optionally one to three substituents selected from a straight chain or branched chain alkoxy group having 1 to 6 carbon atoms and a straight chain or branched chain alkanoyl group having 1 to 6 carbon atoms, for example, 3-benzoyl-1-pyrrolidinyl, 4-benzoyl-1-piperidinyl, 4-benzoyl-1-piperazinyl, 4-benzyl-1-piperazinyl, 3-(2-phenylethyl)morpholino, 3-(3-phenylpropyl)thiomorpholino, 3-(4-phenylbutyl)-1-pyrrolyl, 4-acetyl-1-piperidinyl, 4-acetyl-1-piperazinyl, 4-formyl-1-piperazinyl, 2-(5-phenylpentyl)-1-imidazolyl, 3-(6-phenylpentyl)-1-pyrazolyl, 4-(4-methoxyphenyl)-1-piperazinyl, 4-(4-acetylphenyl)-1-piperazinyl, 4-(3-ethoxyphenyl)-1-piperazinyl, 4-(3-propionylphenyl)-1-piperazinyl, 5-benzyl-1,2,3,4-tetrahydroquinolin-1-yl, 6-(4-butyrylphenyl)-1,2,3,4-tetrahydroisoquinolin-2-yl, 4-(2-propoxyphenyl)-1-indolyl, 5-(3-pentanoylphenyl)-1H-indazol-1-yl, 6-(3-butoxyphenyl)-1,2-dihydroquinazolin-1-yl, 7-(4-hexanoylphenyl)-1,2-dihydrocinnolin-2-yl, 6-(4-hexyloxyphenyl)-1,2,3,4-tetrahydroquinoxalin-1-yl, and the like.

The "alkylene" includes a straight chain or branched chain alkylene group having 1 to 12 carbon atoms, for example, in addition to the above-mentioned alkylene groups, heptamethylene, octamethylene, nonamethylene, decamethylene, undecamethylene, dodecamethylene, and the like.

The "lower alkoxycarbonyl(lower)alkyl wherein the alkyl moiety may optionally be substituted by hydroxy or an amino having optionally a phenyl(lower)alkoxycarbonyl substituent" includes a straight chain or branched chain alkoxycarbonylalkyl group having 1 to 6 carbon atoms in the alkoxy moiety, wherein the alkyl moiety is straight chain or branched chain alkyl group having 1 to 6 carbon atoms and has optionaly a substituent selected from a hydroxy group and an amino group having optionally a substituent of a phenylalkoxycarbonyl group wherein the alkoxycarbonyl moiety is a straight chain or branched chain alkoxycarbonyl group having 1 to 6 carbon atoms, for example, 1-hydroxy-1-methoxycarbonylmethyl, 1-methoxycarbonyl-2-hydroxyethyl, 3-hydroxy-3-methoxycarbonylpropyl, 2-hydroxy-4-ethoxycarbonylbutyl, 2-hydroxy-6-propoxycarbonylhexyl, 2-hydroxy-2-pentyloxycarbonylethyl, 1-hydroxy-1-hexyloxycarbonylmethyl, 5-benzyloxycarbonyl-1-methoxycarbonylpentyl, 5-amino-1-methoxycarbonylpentyl, 3-(2-phenylethoxycarbonylamino)-1-ethoxycarbonylpropyl, 4-amino-1-butyloxycarbonylbutyl, and the like.

The "amino-substituted lower alkanoyl wherein the lower alkanoyl moiety may optionally be substituted by a member selected from a phenyl(lower)alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a phenyl(lower)alkyl having optionally a lower alkoxy substituent on the phenyl ring, a lower alkylsulfonyl, a lower alkanoyl, or a phenyl(lower) alkoxycarbonyl" includes an amino-substituted straight chain or branched chain alkanoyl group having 2 to 6 carbon atoms, wherein the alkanoyl moiety may optionally be substituted by a member selected from phenylalkoxycarbonylamino wherein the alkoxycarbonyl moiety is a straight chain or branched chain alkoxycarbonyl group having 1 to 6 carbon atoms, a hydroxy group, a phenyl group having optionally one to three hydroxy-substitutents, a carbamoyl group, an imidazolyl group or a straight chain or branched chain alkylthio group having 1 to 6 carbon atoms, and the amino group may optionally have a substituent selected from a straight chain or branched chain alkyl group having 1 to 6 carbon atoms and having optionally one to three hydroxy-substitutents, a straight chain or branched chain alkenyl group having 2 to 6 carbon atoms, a phenylalkyl group wherein the alkyl moiety is a straight chain or branched chain alkyl group having 1 to 6 carbon atoms and the phenyl ring has optionally one to three substituents of a straight chain or branched chain alkoxy group having 1 to 6 carbon atoms, a straight chain or branched chain alkylsulfonyl group having 1 to 6 carbon atoms, a straight chain or branched chain alkanoyl group having 1 to 6 carbon atoms, or a phenylalkoxycarbonyl wherein the alkoxycarbonyl moiety is a straight chain or branched chain alkoxycarbonyl group having 1 to 6 carbon atoms, for example, aminoacetyl, 3-formylaminopropionyl, acetylaminoacetyl, 2-propionylaminopropionyl, 4-butyrylaminobutyryl, 2,2-dimethyl-3-isobutyrylaminopropionyl, 5-pentanoylaminopentanoyl, 6-tert-butylcarbonylaminohexanoyl, 3-methyl-4-hexanoylaminobutyryl, 4-methylthio-2-acetylaminobutyryl, 3-(imidazol-4-yl)-2-acetylaminopropionyl, 2-acetylaminopropionyl, 3-(4-hydroxyphenyl)-2-benzyloxycarbonylaminopropionyl, 4-carbomyl-2-acetylaminobutyryl, 2-acetylaminoisopentanoyl, 5-ethylthio-2-acetylaminopentanoyl, 4-(imidazol-2-yl)-2-propionylaminobutyryl, 6-(2-hydroxyphenyl)-2-butyrylaminohexanoyl, 3-carbamoyl-2-benzyloxycarbonylaminopropionyl, 5-carbamoyl-2-(2-phenylethoxycarbonylamino)pentanoyl, 3-(2,4-dihydroxyphenyl)-2-(3-phenylpropoxycarbonylamino) propionyl, 2,5-dibenzyloxycarbonylaminohexanoyl, 3-(4-hydroxyphenyl)-2-aminopropionyl, dimethylaminoacetyl, 3-hydroxy-2-benzyloxycarbonylaminopropionyl, 2-benzyloxycarbonylaminopropionyl, 2-aminopropionyl, 2-aminoisopentanoyl, 2-aminobutyryl, 4-benzyloxycarbonylaminobutyryl, diethylaminoacetyl, 4-acetylaminobutyryl, 4-dimethylaminobutyryl, 2-hdyroxyacetyl, ethylaminoacetyl, allylaminoacetyl, benzylaminoacetyl, isopropylaminoacetyl, (N-methyl-N-benzylamino)acetyl, [N-methyl-N-(2-hydroxyethyl)amino] acetyl, [N-methyl-N-(4-ethoxybenzyl)amino]acetyl, 2-benzyloxycarbonylaminoacetyl, methylsulfonylaminoacetyl, (3-methoxybenzyl) aminoacetyl, (N-methyl-N-acetylamino)acetyl, 5-(N-methyl-N-allylamino)pentanoyl, 6-[N-allyl-N-(3,4-dimethoxybenzyl)amino]hexanoyl, and the like.

The "amido-substituted lower alkyl wherein the lower alkyl moiety have optionally a substituent selected from a phenyl having optionally a hydroxy substituent, imidazolyl, carbamoyl or a lower alkylthio, and the amido group may optionally have a lower alkyl substituent" includes an amido-substituted straight chain or branched chain alkyl group having 1 to 6 carbon atoms wherein the alkyl moiety have optionally a substituent selected from a phenyl having optionally one to three hydroxy-substitutents, an imidazolyl group, a carbamoyl group or a straight chain or branched chain alkylthio group having 1 to 6 carbon atoms, and the amido group may optionally have one or two substituents of a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,2-dimethyl-2-carbamoylethyl, 2-methyl-3-carbamoylpropyl, methylamidomethyl, 1-ethylamidoethyl, 2-propylamidoethyl, 3-isopropylamidopropyl, 4-butylamidobutyl, 5-pentylamidopentyl, 6-hexylamidohexyl, dimethylamidomethyl, (N-ethyl-N-propylamido)methyl, 2-(N-methyl-N-hexylamido)ethyl, 2-(4-hydroxyphenyl)carbamoylethyl, 1-carbamoylisobutyl, 2-(imidazol-4-yl)-1-carbamoylethyl, 1,3-dicarbamoylpropyl, 3-methylthio-1-carbamoylpropyl, 3-(2-hydroxyphenyl)-1-methylamidopropyl, 4-(2,6-dihydroxyphenyl)-1-(N-methyl-N-hexylamido)butyl, 3-(imidazol-2-yl)-1-propylamidopropyl, 1,4-dicarbamoylbutyl, 2-ethylthio-1-butylamidobutyl, 4-pentylthio-1-hexylamidobutyl, and the like.

The "carboxy(lower)alkyl" includes a carboxyalkyl group wherein the alkyl moietyl is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "lower alkoxy(lower)alkyl" includes a straight chain or branched chain alkoxyalkyl group having 1 to 6 carbon atoms in the alkoxy moiety wherein the alkyl moiety is a straight chain or branched chain alkyl group having 1 to 6 carbon atoms, for example, methoxymethyl, 2-ethoxyethyl, 1-methoxyethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, hexyloxymethyl, and the like.

The "amino acid residue which is able to form an amido bond with the amino group to which $R^4$ and $R^5$ bind" includes, for example, alanine residue, $N^2$-arginine residue, $N^5$-arginine residue, $N^6$-arginine residue, $N^4$-asparagine residue, aspattic acid residue, $N^5$-glutamine residue, cysteine residue, glutamic acid residue, glycine residue, histidine residue, isoleucine residue, leucine residue, $N^2$-lysine residue, $N^6$-lysine residue, methionine residue, phenylalanine residue, proline residue, serine residue, threonine residue, tryptophane residue, tyrosine residue, valine residue, and the like.

The "hydroxyimino-substituted lower alkyl" includes a hydroxyimino-substituted straight chain or branched chain alkyl group having 1 to 6 carbon atoms, for example, hydroxyiminomethyl, 1-hydroxyiminoethyl, 2-hydroxyiminoethyl, 3-hydroxyiminopropyl, 4-hydroxyiminobutyl, 5-hydroxyiminopentyl, 6-hydroxyiminohexyl, 1,1-dimethyl-2-hydroxyiminoethyl, 2-methyl-3-hydroxyiminopropyl, and the like.

The "halogen-substituted lower alkoxy" includes a straight chain or branched chain alkoxy group having 1 to 6 carbon atoms which is substituted by one, to three halogen atoms, for example, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, and the like.

The "phenyl(lower)alkoxycarbonyl" includes a phenylalkoxycarbonyl wherein the alkoxycarbonyl moiety is a straight chain or branched chain alkoxycarbonyl group having 1 to 6 carbon atoms, for example, benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, and the like.

The "lower alkoxy(lower)alkoxy which is substituted by one or two substituents selected from hydroxy and an amino being optionally substituted by a lower alkyl" includes an alkoxy-alkoxy group wherein both alkoxy moiety are each a straight chain or branched chain alkoxy group having 1 to 6 carbon atoms which is substituted by one or two substituents selected from hydroxy and an amino being optionally substituted by a straight chain or branched chain alkyl group having 1 to 6 carbon atoms, for example, hydroxymethoxymethoxy, 3-(2-hydroxyethoxy)propoxy, 4-(1-hydroxyethoxy)butoxy, 6-(3-hydroxypropoxy) hexyloxy, 5-(2,3-dihydroxypropoxy)pentyloxy, 1,1-dimethyl-2-(4-hydroxybutoxy)ethoxy, 2-methyl-3-(3,4-dihydroxybutoxy)propoxy, 2-(1,1-dimethyl-2-hydroxyethoxy)ethoxy, (5-hydroxypentyloxy)methoxy, (6-hydroxyhexyloxy)methoxy, (2-methyl-3-hydroxypropoxy)methoxy, aminomethoxymethoxy, 2-(1-aminoethoxy)ethoxy, 1-(2-aminoethoxy)ethoxy, 3-(3-aminopropoxy)propoxy, 4-(4-aminobutoxy)butoxy, 5-(5-aminopentyloxy)pentyloxy, 6-(6-aminohexyloxy)hexyloxy, (1,1-dimethyl-2-aminoethoxy)methoxy, (2-methyl-3-aminopropoxy)methoxy, 1,1-dimethyl-2-(methylaminomethoxy)ethoxy, 2-methyl-3-(ethylaminomethoxy)propoxy, propylaminomethoxymethoxy, 1-(isopropylaminomethoxy)ethoxy, 2-(butylaminomethoxy)ethoxy, 3-(tert-butylaminomethoxy)propoxy, 4-(pentylaminomethoxy)butoxy, 5-(hexylaminomethoxy)pentyloxy, 6-(dimethylaminomethoxy)hexyloxy, 1,1-dimethyl-2-(diethylaminomethoxy)ethoxy, 2-methyl-3-(dipropylaminomethoxy)propoxy, dibutylaminomethoxymethoxy, 1-(dipentylaminomethoxy)ethoxy, 2-(dihexylaminomethoxy)ethoxy, 3-(N-methyl-N-ethylaminomethoxy)propoxy, 4-(N-methyl-N-propylaminomethoxy)butoxy, 5-(N-methyl-N-butylaminomethoxy)pentyloxy, 6-(N-methyl-N-hexylaminomethoxy)hexyloxy, (1-methylaminoethoxy)methoxy, 1-(2-ethylaminoethoxy)ethoxy, 2-(3-propylaminopropoxy)ethoxy, 3-(4-butylaminobutoxy)propoxy, 4-(1,1-dimethyl-2-pentylaminoethoxy)butoxy, 5-(5-hexylaminopentyloxy)pentyloxy, 6-(6-dimethylaminohexyloxy)hexyloxy, 3-(2-diethylaminoethoxy)propoxy, 4-[1-(N-methyl-N-hexylamino)ethoxy]butoxy, 5-(3-dihexylaminopropoxy)pentyloxy, 6-(4-dibutylaminobutoxy)hexyloxy, 3-[2-(N-methyl-N-pentylamino)ethoxy]propoxy, 5-(2-hydroxy-3-dimethylaminopropoxy)pentyloxy, 5-(2-hydroxy-3-diethylaminopropoxy)pentyloxy, 3-(2-hydroxy-3-diethylaminopropoxy)propoxy, 4-(3-hydroxy-4-methylaminobutoxy)butoxy, 5-(4-hydroxy-5-dimethylaminopentyloxy)pentyloxy, 6-(4-hydroxy-5-methylaminopentyloxy)hexyloxy, and the like.

The "morpholinyl-substituted lower alkoxy which may optionally have a substituent selected from a lower alkyl and oxo" includes a morpholinyl-substituted straight chain or branched chain alkoxy group having 1 to 6 carbon atoms which may optionally have one or two substituents selected from a straight chain or branched chain alkyl group having 1 to 6 carbon atoms, and an oxo group, for example, (2-morpholinyl)methoxy, 2-(3-morpholinyl)ethoxy, 1-(3-morpholinyl)ethoxy, 3-(2-morpholinyl)propoxy, 4-(3-morpholinyl)butoxy, 5-(2-morpholinyl)pentyloxy, 6-(3-morpholinyl)hexyloxy, 1,1-dimethyl-2-(3-morpholinyl)ethoxy, 2-methyl-3-(2-morpholinyl)propoxy, 6-(1-methyl-5-oxo-3-morpholinyl)hexyloxy, (1-ethyl-2-morpholinyl)methoxy, 2-(2-oxo-3-morpholinyl)ethoxy, 1-(2-propyl-3-morpholinyl)ethoxy, 3-(3-butyl-2-morpholinyl)propoxy, 4-(5-pentyl-3-morpholinyl)butoxy, 5-(6-hexyl-2-morpholinyl)pentyloxy, 3-(5-oxo-1-propyl-2-morpholinyl)propoxy, 4-(2-oxo-1-butyl-3-morpholinyl)butoxy, 5-(3-oxo-1-pentyl-6-morpholinyl)pentyloxy, 6-(2-oxo-1-hexyl-5-morpholinyl)hexyloxy, and the like.

The "benzimidazolylthio-substituted lower alkoxy" includes a benzimidazolylthio-substituted straight chain or branched chain alkoxy group having 1 to 6 carbon atoms, for example, (benzimidazol-2-yl)thiomethoxy, 1-(benzimidazol-4-yl)thioethoxy, 2-(benzimidazol-5-yl)thioethoxy, 3-(benzimidazol-6-yl)thiopropoxy, 4-(benzimidazol-2-yl)thiobutoxy, 5-(benzimidazol-7-yl)thiopentyloxy, 6-(benzimidazol-2-yl)thiohexyloxy, 1,1-dimethyl-2-(benzimidazol-2-yl)thioethoxy, 2-methyl-3-(benzimidazol-2-yl)thiopropoxy, and the like.

The "benzimidazolylsulfinyl-substituted lower alkoxy" includes a benzimidazolylsulfinyl-substituted straight chain or branched chain alkoxy group having 1 to 6 carbon atoms, for example, (benzimidazol-2-yl)sulfinylmethoxy, 1-(benzimidazol-4-yl)sulfinylethoxy, 3-(benzimidazol-6-yl)sulfinylpropoxy, 4-(benzimidazol-2-yl)sulfinylbutoxy, 5-(benzimidazol-7-yl)sulfinylpentyloxy, 6-(benzimidazol-2-yl)sulfinylhexyloxy, 1,1-dimethyl-2-(benzimidazol-2-yl)sulfinylethoxy, 2-methyl-3-(benzimidazol-2-yl)sulfinylpropoxy, and the like.

The "tetrahydropyranyl-substituted lower alkyl" includes a tetrahydropyranyl-substituted straight chain or branched chain alkyl group having 1 to 6 carbon atoms, for example, (2-, 3- or 4-tetrahydropyranyl)methyl, 2-(2-, 3- or 4-tetrahydropyranyl)ethyl, 1-(2-, 3- or 4-tetrahydropyranyl)ethyl, 3-(2-, 3- or 4-tetrahydropyranyl)propyl, 4-(2-, 3- or 4-tetrahydropyranyl)butyl, 5-(2-, 3- or 4-tetrahydropyranyl)pentyl, 6-(2-, 3- or 4-tetrahydropyranyl)hexyl, 1,1-dimethyl-2-(2-, 3- or 4-tetrahydropyranyl)ethyl, 2-methyl-3-(2-, 3- or 4-tetrahydropyranyl)propyl, and the like.

The "5- or 6-membered saturated heterocyclic group which is formed by binding $R^{32}$ and $R^{33}$ together with the nitrogen atom to which they bond with being intervened or not with nitrogen, oxygen or sulfur atom" includes, for example, pyrrolidinyl, piperidinyl, piperazinyl, morpholino, thiomorpholino, and the like.

The "heterocyclic group having a substituent selected from carbamoyl, a lower alkyl, a phenyl(lower)alkyl, phenyl and a hydroxy-substituted lower alkyl" includes the above-mentioned heterocyclic groups which have one to three substituents selected from a carbamoyl group, a straight chain or branched chain alkyl group having 1 to 6 carbon atoms, a phenylalkyl group wherein the alkyl moiety is a straight chain or branched chain alkyl group having 1 to 6 carbon atoms, a phenyl group and a hydroxy-substituted straight chain or branched chain alkyl group having 1 to 6 carbon atoms, for example, 4-phenylpiperazinyl, 2-phenylpyrrolidinyl, 4-phenylpiperidinyl, 3-phenylmorpholino, 3-phenylthiomorpholino, 4-benzylpiperazinyl, 3-(2-phenylethyl)pyrrolidinyl, 2-(3-phenylpropyl)pyrrolidinyl, 4-(4-phenylbutyl)piperidinyl, 3-(5-phenylpentyl)morpholino, 2-(6-phenylhexyl)thiomorpholino, 4-methylpiperazinyl, 3,4- dimethylpiperazinyl, 3-ethylpyrrolidinyl, 2-propylpyrrolidinyl, 3,4,5-trimethylpiperidinyl, 4-butylpiperidinyl, 3-pentylmorpholino, 2-hexylthiomorpholino, 4-ethylpiperazinyl, 3-methyl-4-phenylpiperazinyl, 3-ethyl-4-benzylpiperidinyl, 3-methyl-4-benzylpyrrolidinyl, 3-methyl-5-phenylmorpholino, 3-methyl-5-(2-hydroxyethyl)thiomorpholino, 4-(2-hydroxyethyl)piperazinyl, 2-(hydroxymethyl)pyrrolidinyl, 4-(4-hydroxybutyl)piperidinyl, 2-(5-hydroxypentyl)thiomorpholino, 3-(6-hydroxyhexyl)morpholino, 2-methyl-4-(2-hydroxyethyl)pyrrolidinyl, 2-carbamoylpyrrolidinyl, 3-carbamoylpyrrolidinyl, 4-carbamoylpiperazinyl, 3-carbamoylpiperazinyl, 2-carbamoylpiperazinyl, 4-carbamoylpiperidinyl, 3-carbamoylpiperidinyl, 2-2ylpiperidinyl, 3-carbamoylmorpholino, 2-carbamoylthiomorpholino, 2-methyl-3-carbamoylpyrrolidinyl, 3-methyl-4-carbamoylpiperidinyl, 2,6-dimethyl-4-carbamoylpiperazinyl, and the like.

The "amino having optionally a phenyl(lower)alkoxycarbonyl substituent" includes an amino group which may optionally have a substituent of a phenylalkoxycarbonyl group wherein the alkoxycarbonyl moiety is a straight chain or branched chain alkoxycarbonyl group having 1 to 6 carbon atoms, for example, amino, benzyloxycarbonylamino, (2-phenylethoxycarbonyl)amino, (1-phenylethoxycarbonyl)amino, (3-phenylpropoxycarbonyl)amino, (4-phenylbutoxycarbonyl)amino, (5-phenylpentyloxycarbonyl)amino, (6-phenylhexyloxycarbonyl)amino, (1,1-dimethyl-2-phenylethoxycarbonyl)amino, (2-methyl-3-phenylpropoxycarbonyl)amino, and the like.

The "phenyl having optionally hydroxy substituent" includes a phenyl group having optionally one to three hydroxy-substituents, for example, phenyl, 4-hydroxyphenyl, 3-hydroxyphenyl, 2-hydroxyphenyl, 2,4-dihydroxyphenyl, 3,4-dihydroxyphenyl, 2,3,4-trihydroxyphenyl, and the like.

The "phenylsulfonyl which phenyl ring may optionally have a substituent selected from a lower alkyl, nitro, and an amino having optionally one or two substituents selected from a lower alkanoyl and lower alkyl" includes a phenylsulfonyl group which phenyl ring may optionally have one to three substitutents selected from a straight chain or branched chain alkyl group having 1 to 6 carbon atoms, a nitro group, an amino group having optionally one or two substituents selected from a straight chain or branched chain alkanoyl group having 1 to 6 carbon atoms and a straight chain or branched chain alkyl group having 1 to 6 carbon atoms, for example, phenylsulfonyl, 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 4-isopropylphenylsulfonyl, 4-butylphenylsulfonyl, 2-pentylphenylsulfonyl, 3-hexylphenylsulfonyl, 2,4-dimethylphenylsulfonyl, 3,4-diethylphenylsulfonyl, 3,4,5-trimethylphenylsulfonyl, 4-aminophenylsulfonyl, 3-aminophenylsulfonyl, 2-aminophenylsulfonyl, 3,4-diaminophenylsulfonyl, 2,5-diaminophenylsulfonyl, 2,4,6-triaminophenylsulfonyl, 4-nitrophenylsulfonyl, 3-nitrophenylsulfonyl, 2-nitrophenylsulfonyl, 2,3-dinitrophenylsulfonyl, 2,6-dinitrophenylsulfonyl, 2,4,6-trinitrophenylsulfonyl, 4-acetylaminophenylsulfonyl, 4-dimethylaminophenylsulfonyl, 3-(N-methyl-N-acetylamino)phenylsulfonyl, 2-methyl-4-aminophenylsulfonyl, 3-nitro-4-methylphenylsulfonyl, 2-ethylaminophenylsulfonyl, 2-methyl-3-diethylaminophenylsulfonyl, and the like.

The "amino-substituted lower alkyl which may optionally have a substituent selected from a lower alkyl and a lower alkanoyl" include a straight chain or branched chain alkyl group having 1 to 6 carbon atoms which is substituted by an amino group having optionally one or two substituents selected from a straight chain or branched chain alkyl group having 1 to 6 carbon atoms and a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, 2-(acetylamino)ethyl, 3-(acetylamino)propyl, formylaminomethyl, 1-(propionylamino)ethyl, 4-(butyrylamino)butyl, 5-(pentanoylamino)pentyl, 5-(hexanoylamino)hexyl, 2-(N-methyl-N-acetylamino)ethyl, 1-(N-ethyl-N-acetylamino)ethyl, and the like.

The "piperidinyl having optionally a phenyl(lower)alkyl substituent" includes a piperidinyl which has optionally a substituent of a phenylalkyl group wherein the alkyl moiety is a straight chain or branched chain alkyl group having 1 to 6 carbon atoms, for example, 4-piperidinyl, 3-piperidinyl, 2-piperidinyl, 1-benzyl-4-piperidinyl, 1-(2-phenylethyl)-3-piperidinyl, 2-(3-phenylpropyl)-5-piperidinyl, 3-(4-phenylbutyl)-6-piperidinyl, 4-(5-phenylpentyl)-3-piperidinyl, 5-(6-phenylhexyl)-4-piperidinyl, 2-benzyl-4-piperidinyl, 1-(3-phenylpropyl)-4-piperidinyl, and the like.

The "imidazo[4,5-c]pyridylcarbonyl(lower)alkoxy" includes an imidazo[4,5-c]pyridylcarbonylalkoxy group wherein the alkoxy moiety is a straight chain or branched chain alkoxy group having 1 to 6 carbon atoms, for example, (imidazo[4,5-c]pyridin-2-yl)carbonylmethoxy, 2-(imidazo[4,5-c]pyridin-2-yl)carbonylethoxy, 1-(imidazo[4,5-c]pyridin-4-yl)carbonylethoxy, 3-(imidazo[4,5-c]pyridin-5-yl)carbonylpropoxy, 4-(imidazo[4,5-c]pyridin-7-yl)carbonylbutoxy, 5-(imidazo[4,5-c]pyridin-2-yl)carbonylpentyloxy, 6-(imidazo[4,5-c]pyridin-2-yl)carbonylhexyloxy, 1,1-dimethyl-2-(imidazo[4,5-c]pyridin-2-yl)carbonylethoxy, 2-methyl-3-(imidazo[4,5-c]pyridin-2-yl)carbonylpropoxy, and the like.

The "tri(lower alkyl)ammonium" includes an ammonium group having three of a straight chain or branched chain alkyl group having 1 to 6 carbon atoms, for example, trimethylammonium, triethylammonium, tripropylammonium, triisopropylammonium, tributylammonium, tri(tert-butyl)ammonium, tripentylammonium, trihexylammonium, dimethylethylammonium, diethylpropylammonium, dimethylbutylammonium, diethylmethylammonium, dimethylhexylammonium, dipropylmethylammonium, dibutylethylammonium, methylethylpropylammonium, methylbutylpentylammonium, and the like.

The "pyridyl(lower)alkyl" include a pyridylalkyl group wherein the alkyl moiety is a straight chain or branched chain alkyl group having 1 to 6 carbon atoms, for example, (2-pyridyl)methyl, (3-pyridyl)methyl, (4-pyridyl)methyl, 2-(2-pyridyl)ethyl, 1-(3-pyridyl)ethyl, 3-(4-pyridyl)propyl, 4-(2-pyridyl)butyl, 5-(3-pyridyl)pentyl, 6-(4-pyridyl)hexyl, 1,1-dimethyl-2-(2-pyridyl)ethyl, 2-methyl-3-(3-pyridyl)propyl, and the like.

The "lower alkyl which may optionally have a substituent selected from hydroxy and cyano" includes a straight chain or branched chain alkyl group having 1 to 6 carbon atoms which may optionally have one to three substituents selected from a hydroxy group and a cyano group, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 2,3-dihydroxyethyl, 3,4-dihydroxybutyl, 5,6-dihydroxyhexyl, cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl, and the like.

The "lower alkynyl" includes a straight chain or branched chain alkynyl group having 2 to 6 carbon atoms, for example, ethynyl, 2-propynyl, 2-butynyl, 3-butynyl, 1-methyl-2-propynyl, 2-pentynyl, 2-hexynyl, and the like.

The "pyrrolidinylcarbonyl which may optionally be substituted by a phenyl(lower)alkoxycarbonyl on the pyrrolidine group" includes a pyrrolidinylcarbonyl which may optionally be substituted by a phenylalkoxycarbonyl group wherein the alkoxy moiety is a straight chain or branched chain alkoxy group having 1 to 6 carbon atoms, for example, 1-benzyloxycarbonyl-2-pyrrolidinylcarbonyl, 2-pyrrolidinylcarbonyl, 1-pyrrolidinylcarbonyl, 3-pyrrolidinylcarbonyl, 1-(2-phenylethoxycarbonyl)-2-pyrrolidinylcarbonyl, 2-(1-phenylethoxycarbonyl)-1-pyrrolidinylcarbonyl, 3-(3-phenylpropoxycarbonyl)-2-pyrrolidinylcarbonyl, 1-(4-phenylbutoxycarbonyl)-2-pyrrolidinylcarbonyl, 2-(5-phenylpentyloxycarbonyl)-1-pyrrolidinylcarbonyl, 2-(6-phenylhexyloxycarbonyl)-3-pyrrolidinylcarbonyl, and the like.

The "phenyl(lower)alkoxycarbonylamino" includes a phenylalkoxycarbonylamino wherein the alkoxycarbonyl moiety is a straight chain or branched chain alkoxycarbonyl group having 1 to 6 carbon atoms, for example, N-benzyloxycarbonylamino, N-(2-phenylethoxycarbonyl)amino, N-(1-phenylethoxycarbonyl)amino, N-(3-phenylpropoxycarbonyl)amino, N-(4-phenylbutoxycarbonyl)amino, N-(5-phenylpentyloxycarbonyl)amino, N-(6-phenylhexyloxycarbonyl)amino, N-(1,1-dimethyl-2-phenylethoxycarbonyl)amino, N-(2-methyl-3-phenylpropoxycarbonyl)amino, and the like.

The "lower alkyl having optionally a hydroxy-substituent" includes a straight chain or branched chain alkyl group having 1 to 6 carbon atoms which has optionally one to three hydroxy-substituents, for example, in addition to the above-mentioned lower alkyl groups, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 3,4-dihydroxybutyl, 5,6-dihydroxyhexyl, and the like.

The "hydroxy-substituted lower alkanoyl" includes a hydroxy-substituted straight chain or branched chain alkanoyl group having 2 to 6 carbon atoms, for example, 2-hydroxyacetyl, 3-hydroxypropionyl, 2-hydroxypropionyl, 4-hydroxybutyryl, 2,2-dimethyl-3-hydroxypropionyl, 5-hydroxypentanoyl, 6-hydroxyhexanoyl, 3-methyl-4-hydroxybutyryl, and the like.

The "lower alkanoyloxy(lower)alkanoyl" includes an alkanoyloxyalkanoyl wherein both alkanoyl moieties are a straight chain or branched chain alkanoyl group having 2 to 6 carbon atoms, for example, 2-acetyloxyacetyl, 3-propionyloxypropionyl, 2-butyryloxypropionyl, 4-pentanoyloxybutyryl, 2,2-dimethyl-3-hexanoyloxypropionyl, 5-acetyloxypentanoyl, 6-propionyloxyhexanoyl, and the like.

The "phenyl(lower)alkyl which phenyl ring may optionally have a lower alkoxy substituent" includes a phenylalkyl group wherein the alkyl moiety is a straight chain or branched chain alkyl group having 1 to 6 carbon atoms and the phenyl ring has optionally one to three substituents of a straight chain or branched chain alkoxy group having 1 to 6 carbon atoms, for example, in addition to the above-mentioned phenyl(lower)alkyl groups, 2-methoxybenzyl, 3-methoxybenzyl, 2-(4-methoxyphenyl)ethyl, 1-(2-ethoxyphenyl)ethyl, 3-(4-isopropoxyphenyl)propyl, 4-(3-pentyloxyphenyl)butyl, 5-(4-hexyloxyphenyl)pentyl, 6-(2-butyloxyphenyl)hexyl, 3,4-dimethoxybenzyl, 3-ethoxy-4-methoxybenzyl, 2,3-dimethoxybenzyl, 2,6-dimethoxybenzyl, 3,4,5-trimethoxybenzyl, and the like.

The "cycloalkenylcarbonyl" includes a cycloalkenylcarbonyl group having 3 to 8 carbon atoms, for example, cyclopropenylcarbonyl, cyclobutenylcarbonyl, cyclopentenylcarbonyl, cyclohexenylcarbonyl, cycloheptenylcarbonyl, cyclooctenylcarbonyl, and the like.

The "pyrimidylthio-substituted lower alkoxy" includes a pyrimidylthio-substituted straight chain or branched chain alkoxy group having 1 to 6 carbon atoms, for example, (2-pyrimidyl)thiomethoxy, 2-(4-pyrimidyl)thioethoxy, 1-(5-pyrimidyl)thioethoxy, 3-(6-pyrimidyl)thiopropoxy, 4-(4-pyrimidyl)thiobutoxy, 5-(2-pyrimidyl)thiopentyloxy, 6-(5-pyrimidyl)thiohexyloxy, 1,1-dimethyl-2-(2-pyrimidyl)thioethoxy, 2-methyl-3-(2-pyrimidyl)thiopropoxy, and the like.

The "pyrimidylsulfinyl-substituted lower alkoxy" includes a pyrimidylsulfinyl-substituted straight chain or branched chain alkoxy group having 1 to 6 carbon atoms, for example, (2-pyrimidyl)sulfinylmethoxy, 2-(4-pyrimidyl)sulfinylethoxy, 1-(5-pyrimidyl)sulfinylethoxy, 3-(6-pyrimidyl)sulfinylpropoxy, 4-(4-pyrimidyl)sulfinylbutoxy, 5-(2-pyrimidyl)sulfinylpentyloxy, 6-(5-pyrimidyl)sulfinylhexyloxy, 1,1-dimethyl-2-(2-pyrimidyl)sulfinylethoxy, 2-methyl-3-(2-pyrimidyl)sulfinylpropoxy, and the like.

The "pyrimidylsulfonyl-substituted lower alkoxy" includes a pyrimidylsulfonyl-substituted straight chain or branched chain alkoxy group having 1 to 6 carbon atoms, for example, (2-pyrimidyl)sulfonylmethoxy, 2-(4-pyrimidyl)sulfonylethoxy, 1-(5-pyrimidyl)sulfonylethoxy, 3-(6-pyrimidyl)sulfonylpropoxy, 4-(4-pyrimidyl)sulfonylbutoxy, 5-(2-pyrimidyl)sulfonylpentyloxy, 6-(5-pyrimidyl)sulfonylhexyloxy, 1,1-dimethyl-2-(2-pyrimidyl)sulfonylethoxy, 2-methyl-3-(2-pyrimidyl)sulfonylpropoxy, and the like.

The "imidazolylthio-substituted lower alkoxy which may optionally have a lower alkyl substituent" includes a imidazolylthio-substituted straight chain or branched chain alkoxy group having 1 to 6 carbon atoms which may optionally have a substituent of a straight chain or branched chain alkyl group having 1 to 6 carbon atoms on the imidazolyl group, for example, (2-imidazolyl)thiomethoxy, 2-(4-imidazolyl)thioethoxy, 1-(5-imidazolyl)thioethoxy, 3-(2-imidazolyl)thiopropoxy, 4-(4-imidazolyl)thiobutoxy, 5-(2-imidazolyl)thiopentyloxy, 6-(5-imidazolyl)thiohexyloxy, 1,1-dimethyl-2-(2-imidazolyl)thioethoxy, 2-methyl-3-(2-imidazolyl)thiopropoxy, (4-methyl-2-imidazolyl)thiomethoxy, 2-(5-ethyl-4-imidazolyl)thioethoxy, 1-(4-propyl-5-imidazolyl)thioethoxy, 3-(1-butyl-2-imidazolyl)thiopropoxy, 4-(2-pentyl-4-imidazolyl)thiobutoxy, 5-(1-methyl-2-imidazolyl)thiopentyloxy, 6-(1-hexyl-5-imidazolyl)thiohexyloxy, 1,1-dimethyl-2-(1-ethyl-2-imidazolyl)thioethoxy, 2-methyl-3-(1-propyl-2-imidazolyl)thiopropoxy, and the like.

The "imidazolylsulfonyl-substituted lower alkoxy which may optionally have a lower alkyl substituent" includes a imidazolylsulfonyl-substituted straight chain or branched chain alkoxy group having 1 to 6 carbon atoms which may optionally have a substituent of a straight chain or branched chain alkyl group having 1 to 6 carbon atoms on the imidazolyl group, for example, (2-imidazolyl)sulfonylmethoxy, 2-(4-imidazolyl)sulfonylethoxy, 1-(5-imidazolyl)sulfonylethoxy, 3-(2-imidazolyl)sulfonylpropoxy, 4-(4-imidazolyl)sulfonylbutoxy, 5-(2-imidazolyl)sulfonylpentyloxy, 6-(5-imidazolyl)sulfonylhexyloxy, 1,1-dimethyl-2-(2-imidazolyl)sulfonylethoxy, 2-methyl-3-(2-imidazolyl)sulfonylpropoxy, (4-methyl-2-imidazolyl)sulfonylmethoxy, 2-(5-ethyl-4-imidazolyl)sulfonylethoxy, 1-(4-propyl-5-imidazolyl)sulfonylethoxy, 3-(1-butyl-2-imidazolyl)sulfonylpropoxy, 4-(2-pentyl-4-imidazolyl)sulfonylbutoxy, 5-(1-methyl-2-imidazolyl)sulfonylpentyloxy, 6-(1-hexyl-5-imidazolyl)sulfonylhexyloxy, 1,1-dimethyl-2-(1-ethyl-2-imidazolyl)sulfonylethoxy, 2-methyl-3-(1-propyl-2-imidazolyl)sulfonylpropoxy, and the like.

The "ammonium-substituted lower alkoxy having three substituents selected from a lower alkyl, a lower alkenyl and oxo" includes an ammonium-substituted straight chain or branched chain alkoxy group having 1 to 6 carbon atoms, which have three substituents selected from a straight chain or branched chain alkyl group having 1 to 6 carbon atoms, a straight chain or branched chain alkenyl group having 2 to 6 carbon atoms, and an oxo group, for example, trimethylammoniummethoxy, 2-(triethylammonium)ethoxy, 1-(tripropylammonium)ethoxy, 3-(tributylammonium)propoxy, 4-(tripentylammonium)butoxy, 5-(triethylammonium)pentyloxy, 6-(trihexylammonium)hexyloxy, 1,1-dimethyl-2-(triallylammonium)ethoxy, 2-methyl-3-(tributenylammonium)propoxy, tri(1-methylallyl)ammonium-methoxy, 2-[tri(2-pentenyl)ammonium]ethoxy, 1-[tri(2-hexenyl)ammonium]ethoxy, 3-(N-allyl-N,N-dimethylammonium)propoxy, 4-(N,N-diallyl-N-methylammonium)butoxy, 5-(N-allyl-N-methylamino)pentyloxy N-oxide, 6-(N-allyl-N-ethylamino)hexyloxy N-oxide, 5-(N-allyl-N-methyl-N-ethylammonium)pentyloxy, and the like.

The "phenylthio(lower)alkoxy which phenyl ring may optionally have a substituent selected from nitro and an amino" includes a phenylthioalkoxy wherein the alkoxy moiety is a straight chain or branched chain alkoxy group having 1 to 6 carbon atoms, and the phenyl ring may optionally have one to three substituents selected from a nitro group and an amino group, for example, phenylthiomethoxy, 2-phenylthioethoxy, 1-phenylthioethoxy, 3-phenylthiopropoxy, 4-phenylthiobutoxy, 5-phenylthiopentyloxy, 6-phenylthiohexyloxy, 1,1-dimethyl-2-phenylthioethoxy, 2-methyl-3-phenylthiopropoxy, (2-nitrophenyl)thiomethoxy, 2-(3-nitrophenyl)thioethoxy, 1-(4-nitrophenyl)thioethoxy, 3-(2,3-dinitrophenyl)thiopropoxy, 4-(3,4-dinitrophenyl)thiobutoxy, 5-(4-nitrophenyl)thiopentyloxy, 6-(2,6-dinitrophenyl)thiohexyloxy, 1,1-dimethyl-2-(2,4,6-trinitrophenyl)thioethoxy, 2-methyl-3-(4-nitrophenyl)thiopropoxy, (2-aminophenyl)thiomethoxy, 2-(3-aminophenyl)thioethoxy, 1-(4-aminophenyl)thioethoxy, 3-(2,3-diaminophenyl)thiopropoxy, 4-(3,4-diaminophenyl)thiobutoxy, 5-(4-aminophenyl)thiopentyloxy, 6-(2,6-diaminophenyl)thiohexyloxy, 1,1-dimethyl-2-(2,4,6-triaminophenyl)thioethoxy, 2-methyl-3-(4-aminophenyl)thiopropoxy, and the like.

The "phenylsulfonyl(lower)alkoxy which phenyl ring may optionally have a substituent selected from nitro and an amino having optionally one or two substituents selected from a lower alkanoyl and a lower alkyl" includes a phenylsulfonylalkoxy wherein the alkoxy moiety is a straight chain or branched chain alkoxy group having 1 to 6 carbon atoms, and the phenyl ring may optionally have one to three substituents selected from a nitro group and an amino group having optionally one or two substituents selected from a straight chain or branched chain alkyl group having 1 to 6 carbon atoms and a straight chain or branched chain alkanoyl group having 1 to 6 carbon atoms, for example, phenylsulfonylmethoxy, 2-phenylsulfonylethoxy, 1-phenylsulfonylethoxy, 3-phenylsulfonylpropoxy, 4-phenylsulfonylbutoxy, 5-phenylsulfonylpentyloxy, 6-phenylsulfonylhexyloxy, 1,1-dimethyl-2-phenylsulfonylethoxy, 2-methyl-3-phenylsulfonylpropoxy, (2-aminophenyl)sulfonylmethoxy, 5-(4-aminophenyl)sulfonylpentyloxy, 2-(4-methylaminophenyl)sulfonylethoxy, 1-(3-ethylaminophenyl)sulfonylethoxy, 3-[2-(N-methyl-N-ethylamino)phenyl]sulfonylpropoxy, 4-[3-(N-methyl-N-hexylamino)phenyl]sulfonylbutoxy, 5-(4-dimethylaminophenyl)sulfonylpentyloxy, 4-dipentylaminophenylsulfonylmethoxy, 2-(2-isopropylaminophenyl)sulfonylethoxy, 1-(3-butylaminophenyl)sulfonylethoxy, 5-(2,4-diaminophenyl)sulfonylpentyloxy, 3-[2,3-bis(dimethylamino)phenyl]sulfonylpropoxy, 4-[3,4-bis(methylamino)phenyl]sulfonylbutoxy, 5-(2,4,6-triaminophenyl)sulfonylpentyloxy, 6-[3,4,5-tri(methylamino)phenyl]sulfonylhexyloxy, 5-(4-acetylaminophenyl)sulfonylpentyloxy, 3-[4-(N-methyl-N-acetylamino)phenyl]sulfonylpropoxy, 5-(4-nitrophenyl)sulfonylpentyloxy, 2-(4-nitro-3-methylaminophenyl)sulfonylethoxy, 3-(2,4-dinitrophenyl)sulfonylpropoxy, 4-(2,4,6-trinitrophenyl)sulfonylbutoxy, and the like.

The "pyridylthio-substituted lower alkoxy" includes a pyridylthio-substituted straight chain or branched chain alkoxy group having 1 to 6 carbon atoms, for example, (2-pyridyl)thiomethoxy, 2-(3-pyridyl)thioethoxy, 1-(4-pyridyl)thioethoxy, 3-(3-pyridyl)thiopropoxy, 4-(4-pyridyl)thiobutoxy, 5-(2-pyridyl)thiopentyloxy, 5-(4-pyridyl)thiopentyloxy, 6-(3-pyridyl)thiohexyloxy, 1,1-dimethyl-2-(2-pyridyl)thioethoxy, 2-methyl-3-(4-pyridyl)thiopropoxy, and the like.

The "pyridylsulfonyl-substituted lower alkoxy which may optionally have an oxo subsituent on the pyridyl ring" includes a pyridylsulfonyl-substituted straight chain or branched chain alkoxy group having 1 to 6 carbon atoms which may optionally have an oxo substituent on the pyridyl ring, for example, (2-pyridyl)sulfonylmethoxy, 2-(3-pyridyl)sulfonylethoxy, 1-(4-pyridyl)sulfonylethoxy, 3-(3-pyridyl)sulfonylpropoxy, 4-(4-pyridyl)sulfonylbutoxy, 5-(2-pyridyl)sulfonylpentyloxy, 5-(4-pyridyl)sulfonylpentyloxy, 6-(3-pyridyl)sulfonylhexyloxy, 1,1-dimethyl-2-(2-pyridyl)sulfonylethoxy, 2-methyl-3-(4-pyridyl)sulfonylpropoxy, 5-(1-oxido-4-pyridyl)sulfonylpentyloxy, (4-oxo-2-pyridyl)sulfonylmethoxy, 2-(1-oxido-3-pyridyl)sulfonylethoxy, 1-(2-oxo-4-pyridyl)sulfonylethoxy, 3-(2-oxo-3-pyridyl)sulfonylpropoxy, 4-(3-oxo-4-pyridyl)sulfonylbutoxy, 5-(1-oxido-2-pyridyl)sulfonylpentyloxy, 6-(1-oxido-3-pyridyl)sulfonylhexyloxy, and the like.

The "cycloalkylcarbonyl having optionally one to three substituents selected from hydroxy and a lower alkanoyloxy" includes a cycloalkylcarbonyl having 3 to 8 carbon atoms which has optionally one to three substituents selected from a hydroxy group and a straight chain or branched chain alkanoyloxy group having 2 to 6 carbon atoms, for example, cyclopropylcarbonyl, cyclobutylcarbonyl, cyclopentylcarbonyl, cyclohexylcarbonyl, cycloheptylcarbonyl, cyclooctylcarbonyl, 2-hydroxycyclopropylcarbonyl, 3-hydroxycyclobutylcarbonyl, 2-hydroxycyclopentylcarbonyl, 3-hydroxycyclopentylcarbonyl, 2,4-dihydroxycyclopentylcarbonyl, 2-hydroxycyclohexylcarbonyl, 3-hydroxycyclohexylcarbonyl, 4-hydroxycyclohexylcarbonyl, 3,4-dihydroxycyclohexylcarbonyl, 2,4-dihydroxycyclohexylcarbonyl, 2,5-dihydroxycyclohexylcarbonyl, 3,4,5-trihydroxycyclohexylcarbonyl, 3-hydroxycycloheptylcarbonyl, 3,4-dihydroxycycloheptylcarbonyl, 2,3,4-trihydroxycycloheptylcarbonyl, 4-hydroxycyclooctylcarbonyl, 4,5-dihydroxycyclooctylcarbonyl, 4,5,6-trihydroxycyclooctylcarbonyl, 2-acetyloxycyclopropylcarbonyl, 3-propionyloxycyclobutylcarbonyl, 2-butyryloxycyclopentylcarbonyl, 3-pentanoyloxycyclopentylcarbonyl, 2,4-dihexanoyloxycyclopentylcarbonyl, 2-acetyloxycyclohexylcarbonyl, 3-propionyloxycyclohexylcarbonyl, 4-butyryloxycyclohexylcarbonyl, 3,4-diacetyloxycyclohexylcarbonyl, 2,4-diacetyloxycyclohexylcarbonyl, 2,5-diacetyloxycyclohexylcarbonyl, 3,4,5-triacetyloxycyclohexylcarbonyl, 3,4-diacetyloxy-5-hyroxycyclohexylcarbonyl, 3-pentanoyloxycycloheptylcarbonyl, 3,4-diacetyloxycycloheptylcarbonyl, 2,3,4-tripropionyloxycycloheptylcarbonyl, 4-hexanoyloxycyclooctylcarbonyl, 4,5-dibutyryloxycyclooctylcarbonyl, 4,5,6-triacetyloxycyclooctylcarbonyl, and the like.

The "tetrahydroypyranyl(lower)alkyl which tetrahydroxypyranyl ring may optionally have one to four substituents selected from hydroxy and a lower alkoxy" includes a tetrahydropyranylalkyl wherein the alkyl moiety is a straight chain or branched chain alkyl group having 1 to 6 carbon atoms, and the tetrahydropyranyl ring may optionally have one to four substituents selected from a hydroxy group and a straight chain or branched chain alkoxy group having 1 to 6 carbon atoms, for example, (2-tetrahydropyranyl)methyl, 2-(3-tetrahydropyranyl)ethyl, 1-(4-tetrahydropyranyl)ethyl, 3-(2-tetrahydropyranyl)propyl, 4-(3-tetrahydropyranyl)butyl, 5-(4-tetrahydropyranyl)pentyl, 6-(2-tetrahydropyranyl)hexyl, 1,1-dimethyl-2-(3-tetrahydropyranyl)ethyl, 2-methyl-3-(4-tetrahydropyranyl)propyl, (3-hydroxy-2-tetrahydropyranyl)methyl, 2-(2,4-dihydroxy-3-tetrahydropyranyl)ethyl, 1-(2,3,5-trihydroxy-4-tetrahydropyranyl)ethyl, 3-(6-methoxy-2-tetrahydropyranyl)propyl, 4-(4-ethoxy-3-tetrahydropyranyl)butyl, 5-(4,6-dimethoxy-4-tetrahydropyranyl)pentyl, 6-(4,5,6-trimethoxy-2-tetrahydropyranyl)hexyl, 1,1-dimethyl-2-(2-propoxy-3-tetrahydropyranyl)ethyl, 2-methyl-3-(6-butoxy-4-tetrahydropyranyl)propyl, (6-pentyloxy-2-tetrahydropyranyl)methyl, 2-(4-hexyloxy-3-tetrahydropyranyl)ethyl, 2-(3,4,5-trihydroxy-6-methoxy-2-tetrahydropyranyl)methyl, 1-(3,4,5,6-tetrahydroxy-2-tetrahydropyranyl)ethyl, 3-(3,4,5,6-tetramethoxy-2-tetrahydropyranyl)propyl, and the like.

The "lower alkanoyl substituted by a 5- or 6-membered saturated heterocyclic group selected from pyrrolidinyl, piperazinyl, piperidinyl, and morpholinyl" includes a straight chain or branched chain alkanoyl group having 2 to 6 carbon atoms which is substituted by a 5- or 6-membered saturated heterocyclic group selected from pyrrolidinyl, piperazinyl, piperidinyl, and morpholinyl, for example, 2-(1-pyrrolidinyl)acetyl, 3-(2-pyrrolidinyl)propionyl, 2-(3-pyrrolidinyl)propionyl, 4-(1-pyrrolidinyl)butyryl, 2,2-dimethyl-3-(2-pyrrolidinyl)propionyl, 5-(3-pyrrolidinyl)pentanoyl, 6-(1-pyrrolidinyl)hexanoyl, 2-(1-piperazinyl)acetyl, 3-(2-piperazinyl)propionyl, 2-(3-piperazinyl)propionyl, 4-(1-piperazinyl)butyryl, 2,2-dimethyl-3-(2-piperazinyl)propionyl, 5-(3-piperazinyl)pentanoyl, 6-(1-piperazinyl)hexanoyl, 2-(1-piperidinyl)acetyl, 3-(2-piperidinyl)propionyl, 2-(3-piperidinyl)propionyl, 4-(4-piperidinyl)butyryl, 2,2-dimethyl-3-(1-piperidinyl)propionyl, 5-(2-piperidinyl)pentanoyl, 6-(3-piperidinyl)hexanoyl, 2-(1-morpholinyl)acetyl, 3-(2-morpholinyl)propionyl, 2-(3-morpholinyl)propionyl, 4-(1-morpholinyl)butyryl, 2,2-dimethyl-3-(2-morpholinyl)propionyl, 5-(3-morpholinyl)pentanoyl, 6-(1-morpholinyl)hexanoyl, and the like.

The above "heterocyclic group-substituted lower alkanoyl which has a substituent selected from a lower alkyl and phenyl" includes the above heterocyclic group-substituted straight chain or branched chain alkanoyl group having 2 to 6 carbon atoms, which has one to three substituents selected from a straight chain or branched chain alkyl group having 1 to 6 carbon atoms, and a phenyl group, for example, 2-(2-methyl-1-pyrrolidinyl)acetyl, 3-(1-ethyl-2-pyrrolidinyl)propionyl, 2-(1-propyl-3-pyrrolidinyl)propionyl, 4-(3-butyl-1-pyrrolidinyl)butyryl, 2,2-dimethyl-3-(4-pentyl-2-pyrrolidinyl)propionyl, 5-(1-hexyl-3-pyrrolidinyl)pentanoyl, 6-(2,3-dimethyl-1-pyrrolidinyl)hexanoyl, 2-(2,3,4-trimethyl-1-pyrrolidinyl)acetyl, 3-(1-phenyl-2-pyrrolidinyl)propionyl, 2-(1-methyl-2-phenyl-3-pyrrolidinyl)propionyl, 2-(4-methyl-1-piperazinyl)acetyl, 2-(4-phenyl-1-piperazinyl)acetyl, 3-(4-ethyl-2-piperazinyl)propionyl, 2-(4-propyl-3-piperazinyl)propionyl, 4-(4-butyl-1-piperazinyl)butyryl, 2,2-dimethyl-3-(4-pentyl-2-piperazinyl)propionyl, 5-(4-hexyl-3-piperazinyl)pentanoyl, 6-(2,4-dimethyl-1-piperazinyl)hexanoyl, 2-(3,4,5-trimethyl-1-piperazinyl)acetyl, 2-(4-phenyl-3-methyl-1-piperazinyl)acetyl, 2-(4-methyl-1-piperidinyl)acetyl, 3-(1-ethyl-2-piperidinyl)propionyl, 2-(1-propyl-3-piperidinyl)propionyl, 4-(1-butyl-4-piperidinyl)butyryl, 2,2-dimethyl-3-(4-pentyl-1-piperidinyl)propionyl, 5-(1-hexyl-2-piperidinyl)pentanoyl, 6-(1-phenyl-3-piperidinyl)hexanoyl, 2-(2,5-dimethyl-4-phenyl-1-piperidinyl)acetyl, 2-(2,3,4-trimethyl-1-piperidinyl)acetyl, 2-(1,2-dimethyl-4-piperidinyl)acetyl, 2-(3-methyl-1-morpholinyl)acetyl, 3-(1-ethyl-2-morpholinyl)propionyl, 2-(1-propyl-3-morpholinyl)propionyl, 4-(2-butyl-1-morpholinyl)butyryl, 2,2-dimethyl-3-(1-pentyl-2-morpholinyl)propionyl, 5-(2-hexyl-3-morpholinyl)pentanoyl, 6-(3,5-dimethyl-1-morpholinyl)hexanoyl, 2-(2,3,5-trimethyl-1-morpholinyl)acetyl, 2-(3-phenyl-1-morpholinyl)acetyl, 2-(2-methyl-3-phenyl-1-morpholinyl)acetyl, and the like.

The "piperidinylcarbonyl which may optionally have a lower alkanoyl substituent" includes a piperidinylcarbonyl which may optionally have a substituent of a straight chain or branched chain alkanoyl group having 1 to 6 carbon atoms, for example, (1-piperidinyl)carbonyl, (2-piperidinyl)carbonyl, (3-piperidinyl)carbonyl, (4-piperidinyl)carbonyl, (1-acetyl-4-piperidinyl)carbonyl, (4-formyl-1-piperidinyl)carbonyl, (3-propionyl-2-piperidinyl)carbonyl, (1-butyryl-4-piperidinyl)carbonyl, (1-pentanoyl-4-piperidinyl)carbonyl, (1-hexanoyl-4-piperidinyl)carbonyl, and the like.

The carbostyril derivatives of the present invention can be prepared by various processes, for example, by the processes shown in the following reaction schemes.

[Reaction Scheme-1]

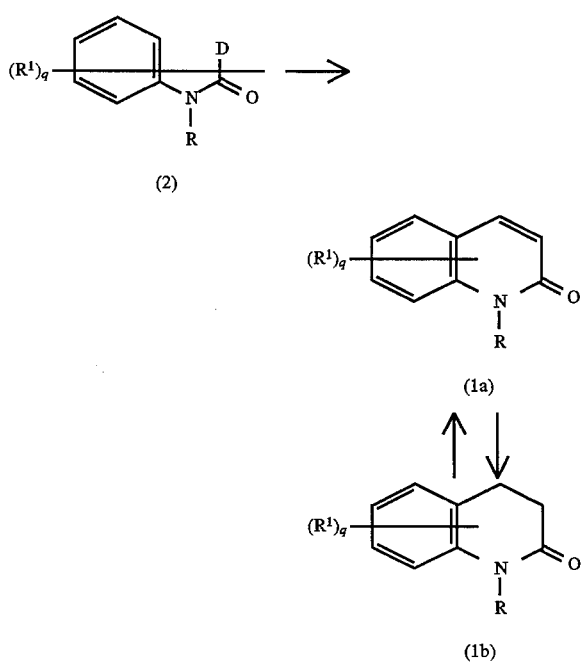

wherein R, q and $R^1$ are the same as defined above, and D is a group of the formula: —CH=CHR$^{14}$ ($R^{14}$ is a lower alkoxy, phenyl or a halogen atom), a group of the formula:

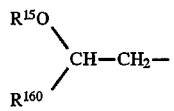

($R^{15}$ and $R^{16}$ are each a lower alkyl), or a group of the formula: —C≡CH, and the D group may optionally be substituted by the group $R^1$.

The cyclization reaction of the compound of the formula (2) is carried out in an appropriate solvent or without solvent in the presence of an acid. The acid includes any conventional inorganic acids and organic acids, for example, inorganic acids (e.g. hydrochloric acid, hydrobromic acid, sulfuric acid, etc.), Lewis acids (e.g. aluminum chloride, boron trifluoride, titanium tetrachloride, etc.), organic acids (e.g. formic acid, acetic acid, ethanesulfonic acid, p-toluenesulfonic acid, etc.), phosphorus pentoxide, polyphosphoric acid, among which hydrochloric acid, hydrobromic acid and sulfuric acid are preferable. The acid is usually used in at least equivalent amount, preferably in an amount of 10 to 50 times by weight, as much as the amount of the compound (2). The solvent includes any conventional inert solvents, for example, water, lower alcohols (e.g. methanol, ethanol, propanol, etc.), ethers (e.g. dioxane, tetrahydrofuran, etc.), aromatic hydrocarbons (e.g. benzene, chlorobenzene, toluene, etc.), halogenated hydrocarbonss (e.g. methylene chloride, chloroform, carbon tetrachloride, etc.), acetone, dimethylsulfoxide, dimethylformamide, hexamethylphosphoric triamide, and the like. The reaction is usually carried out at a temperature of from about 0° to about 200° C., preferably from room temperature to about 150° C., for about 5 minutes to 6 hours.

The reduction of the compound of the formula (1a) is usually carried out under conventional conditions for the usual catalytic reduction. The catalyst includes metals such as palladium, palladium-carbon, platinum, Raney nickel, etc. The solvent used therein includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.). The reduction reaction can be carried out at atmospheric pressure or under pressure, usually under atmospheric pressure to 20 kg/cm$^2$, preferably atmospheric pressure to 10 kg/cm$^2$. The reaction temperature is usually in the range of from about 0° C. to about 150° C., prefarably from room temperature to about 100° C.

The dehydration reaction of the compound of the formula (1b) is usually carried out in an appropriate solvent with an oxidizing agent. The oxidizing agent includes, for example, benzoquinones (e.g. 2,3-dichloro-5,6-dicyanobenzoquinone, chloranil (=2,3,5,6-tetrachlorobenzoquinone), etc.), halogenating agents (e.g. N-bromosuccinimide, N-chlorosuccinimide, bromine, etc.), hydrogenating catalysts (e.g. selenium oxide, palladium-carbon, palladium black, palladium oxide, Raney nickel, etc.). When a halogenating agent is used, it is usually used in an amount of 1 to 5 moles, peferably 1 to 2 moles, to 1 mole of the compound (1b). When a hydrogenating catalyst is used, it is used in a catalytic amount as usual. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar solvents (e.g. acetic acid, etc.), aprotic polar solvents (e.g. dimethylformamide, dimethylsulfoxide, hexamethylphosphoric triamide, etc.). The reaction is usually carried out at a temperature of from room temperature to about 300° C., peferably from room temperature to about 200° C., for 1 to 40 hours.

[Reaction Scheme-2]

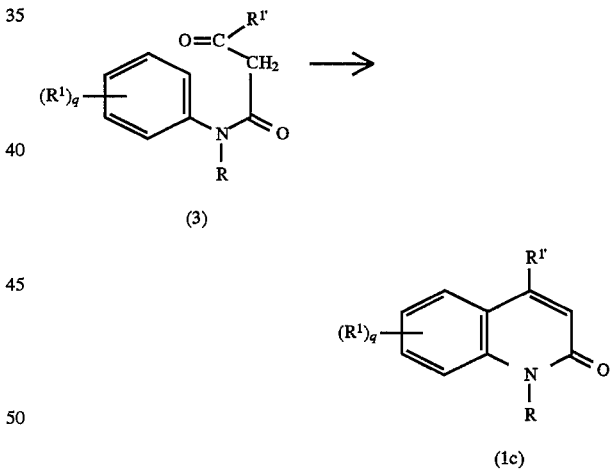

wherein $R^1$, q and R are the same as defined above, and $R^{1'}$ is hydrogen atom or a lower alkyl, provided that when $R^{1'}$ is a lower alkyl, q is 1 or 2.

The cyclization reaction of the compound (3) is carried out in an appropriate solvent in the presence of a condensation agent. The concensation agent includes, for example, Lewis acids, such as phosphorus pentoxide, hydrogen fluoride, sulfuric acid, polyphosphoric acid, aluminum chloride, zinc chloride, etc. The solvent includes, for example, halogenated hydrocarbons (e.g. chloroform, dichloromethane, 1,2-dichloroethane, etc.), ethers (e.g. diethyl ether, dioxane, etc.), aromatic hydrocarbons (e.g. nitrobenzene, chlorobenzene, etc.). The condensation agent is usually used in an amount of about 1 to 10 moles, peferably about 3 to 6 moles, to 1 mole of the compound (3).

The reaction is usually carried out at a temperature of about 50° C. to about 250° C., peferably about 70° C. to about 200° C., for about 20 minutes to about 6 hours.

[Reaction Scheme-3]

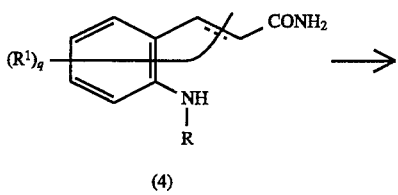

(4)

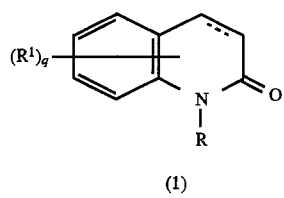

(1)

wherein R, $R^1$, q, and the bond between 3- and 4-positions of the carbonstyril nucleus are the same as defined above.

The cyclization reaction of the compound (4) is carried out in an appropriate solvent or without using a solvent in the presence of an acid. The acid includes, for example, inorganic acids (e.g. hydrochloric acid, sulfuric acid, hydrobromic acid, nitric acid, polyphosphoric acid, etc.), organic acids (e.g. p-toluenesulfonic acid, ethanesulfonic acid, trifluoroacetic acid, etc.). The solvent includes any conventional solvents unless they affect on the reaction, for example, water, lower alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, diphenyl ether, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The reaction is usually carried out at a temperature of from about –20° C. to about 150° C., preferably from about 0° C. to about 150° C., for about 5 minutes to about 30 hours.

[Reaction Scheme-4]

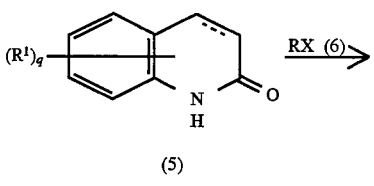

(5)

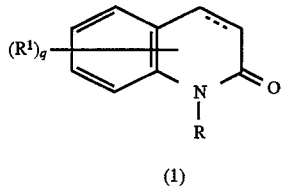

(1)

wherein R, $R^1$, q and the bond between 3- and 4-positions of the carbostyril nucleus are the same as defined above.

The reaction of the compound of the fomrula (5) and the compound of the formula (6) is usually carried out in an appropriate inert solvent in the presence or absence of a basic compound. The inert solvent includes, for example, aromatic hydrocarbons (e.g. benzene, toluene, xylene, etc.), alcohols (e.g. methanol, ethanol, propanol, butanol, 3-methoxy-1-butanol, ethylcellosolve, methylcellosolve, etc.), pyridine, acetone, N-methylpyrrolidone, dimethylsulfoxide, dimethylformamide, hexamethylphosphoric triamide, etc. The basic compound includes, for example, sodium carbonate, potassium carbonate, sodium hydrogen carbonate, potassium hydrogen carbonate, sodium hydroxide, potassium hydroxide, sodium hydride, potassium hydride, triethylamine, etc.

The amounts of the compound (5) and the compound (6) are not critical, but the compound (6) is usually used at least in equimolar amount, preferably in an amount of 1 to 5 moles to 1 mole of the compound (5). The reaction is usually carried out at a temperature of from room temperature to about 200° C., preferably about 100° C. to about 180° C., for about 3 to 30 hours. In the above reaction, a copper powder may also be used as a catalyst, by which the reaction can proceed advantageously.

[Reaction Scheme-5]

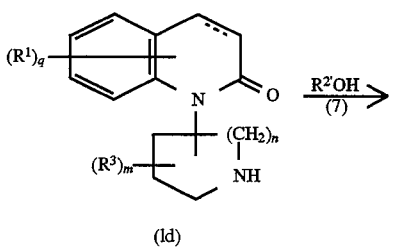

(1d)

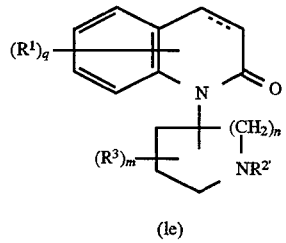

(1e)

wherein $R^1$, q, $R^3$, m, n and the bond between 3- and 4-positions of the carbostyril nucleus are the same as defined above, and $R^{2'}$ is the same groups as $R^2$ other than hydrogen atom and a group of the formula:

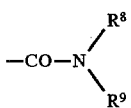

($R^8$ and $R^9$ are the same as defined above).

The process of Reaction Scheme-5 is carried out by reacting a carbostyril derivative of the formula (1d) and a carboxylic acid compound of the formula (7) by a conventional amido bond producing reaction. The amido bond producing reaction can be carried out under the conditions for the conventional amido bond producing reaction, for example, (a) a mixed acid anhydride process, i.e. a process of reacting the carboxylic acid compound (7) with an alkylhalocarboxylic acid to form a mixed acid anhydride and reacting the resultant with the amine compound (1d), (b) an activated ester process, i.e. a process of converting the carboxylic acid compound (7) into an activated ester, such as p-nitrophenyl ester, N-hydroxysuccinimide ester, 1-hydroxybenzotriazole ester, etc., and reacting the resultant with the amine compound (1d), (c) a carbodiimide process, i.e. a process of condensing the carboxylic acid compound (7) and the amine compound (1d) in the presence of an activating agent such as dicyclohexylcarbodiimide, carbonyldiimidazole, etc., (d) other processes, i.e. a process of converting the carboxylic acid compound (7) into a carboxylic anhydride by treating it with a dehydrating agent such as acetic anhydride, and reacting the resultant with the amine compound (1d); a process of reacting an ester of the carboxylic acid compound (7) with a lower alcohol and the amine compound (1d) at a high temperature under high pressure; a process of reacting an acid halide compound of the carboxylic acid compound (7), i.e. a carboxylic acid halide, with the amine compound (1d), and the like.

The mixed acid anhydride used in the above mixed acid anhydride process is obtained by the known Schötten-Baumann reaction, and the reaction product is used without isolation from the reaction mixture for the reaction with the amine compound (1d) to give the desired compound of the formula (1e). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about –20° C. to about 100° C., preferably from about 0° C. to about 50° C., for about 5 minutes to about 10 hours, preferably about 5 minutes to about 2 hours.

The reaction of the thus obtained mixed acid anhydride with the amine compound (1d) is usually carried out at a temperature of from about –20° C. to about 150° C., preferably about 10° C. to about 50° C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (7), the alkylhalocarboxylic acid and the amine (1d) are usually used in each equimolar amount, but preferably, the alkylhalocarboxylic acid and the carboxylic acid compound (7) are used each in an amount of about 1 to 1.5 mole to 1 mole of the amine (1d).

Among the above other processes (d), in case of the process of reacting the carboxylic acid halide with the amine compound (1d), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride, etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, and the like. The amount of the amine compound (1d) and the carboxylic acid halide is not critical, but the carboxylic acid halide is usually used at least in equimolar amount, preferably about 1 to 5 moles to 1 mole of the amine compound (1d). The reaction is usually carried out at a temperature of from about –20° C. to about 180° C., preferably from about 0° C. to about 150° C., for about 5 minutes to about 30 hours.

The amido bond producing reaction in the above Reaction Scheme-5 may also be carried out by reacting the carboxylic acid compound (7) and the amine (1d) in the presence of a condensation agent such as triphenylphosphine, diphenylphosphinyl chloride, phenyl-N-phenylphosphoramide chloridate, diethyl chlorophosphate, diethyl cyanophosphate, bis(2-oxo-3-oxazolidinyl)phosphinic chloride, etc. The reaction is usually carried out in the presence of the solvent and basic compound as used in the above reaction of the carboxylic acid halide and the amine (1d) at a temperature of from about –20° C. to about 150° C., preferably about 0° C. to about 100° C., for about 5 minutes to about 30 hours. The condensation agent and the carboxylic acid compound (7) are used at least in equimolar amount, preferably about 1 to 2 moles, to 1 mole of the amine (1d).

[Reaction Scheme-6]

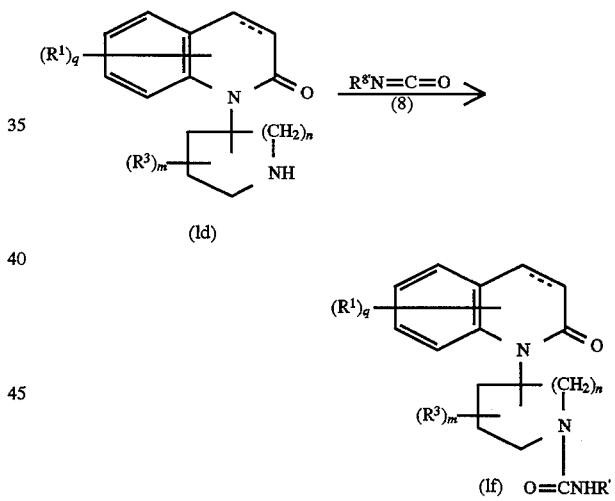

wherein $R^1$, q, $R^3$, m, n and the bond between 3- and 4-positions of the carbostyril nucleus are the same as defined above, and $R^{8'}$ is the same as $R^8$ other than hydrogen atom.

The reaction of the compound (1d) and the compound (8) can be carried out in the presence or preferably absence of a basic compound in an appropriate solvent or without solvent. The solvent and the basic compound used therein are the same as the solvent and basic compound as used in the reaction of the carboxylic acid halide and the amine (1d) of the above Reaction Scheme-5. The compound (8) is usually used in an amount of about 1 to 5 moles, preferably about 1 to 3 moles, to 1 mole of the compound (1d). The reaction is usually carried out at a temperature of about 0° to 200° C., peferably from room temperature to about 150° C., for about 5 minutes to about 30 hours. In the above reaction, a boron compound (e.g. borone trifluoride etherate, etc.) may be added to the reaction system.

[Reaction Scheme-7]

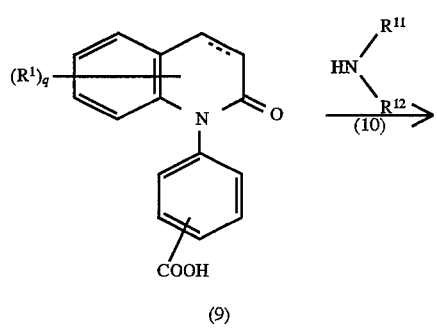

(9)

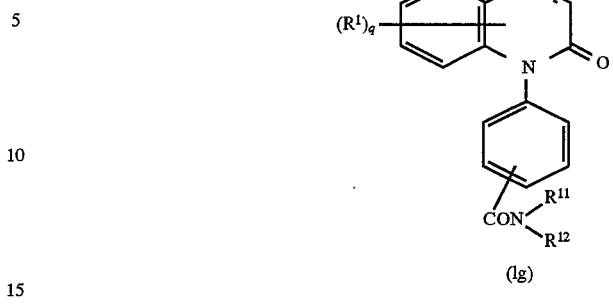

(1g)

wherein $R^1$, q, $R^{11}$, $R^{12}$ and the bond between 3- and 4-positions of the carbostyril nucleus are the same as defined above.

The reaction of the compound (9) and the compound (10) is carried out under the same conditions as used in the reaction of the compound (1d) and the compound (7) in the above Reaction Scheme-5.

[Reaction Scheme-8]

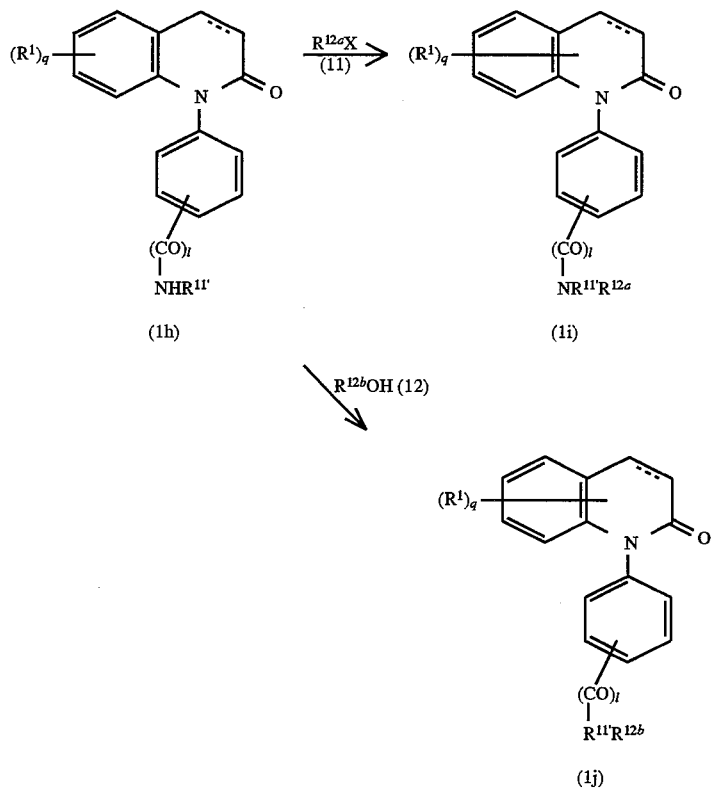

wherein $R^1$, q, X, l and the bond between 3- and 4-positions of carbostyril nucleus are the same as defined above, and $R^{11'}$ is hydrogen atom, a lower alkyl, a phenyl(lower)alkyl, a lower alkenyl, a benzoyl which may optionally have a lower alkoxy substituent, tricyclo[3.3.1.1]decanyl, a phenyl which may optionally have a lower alkoxy substituent, or a cycloalkyl, $R^{12a}$ is a lower alkyl, a phenyl(lower)alkyl, a lower alkenyl, tricyclo[3.3.1.1]decanyl, a phenyl which may optionally have a lower alkoxy substituent, or a cycloalkyl, and $R^{12b}$ is a benzoyl which may optionally have a lower alkoxy substituent.

The reaction of the compound (1h) and the compound (11) is usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), acetic acid, ethyl acetate, acetone, acetonitrile, dimethylsulfoxide, dimethylformamide, hexamethylphosphoric triamide, and the like. The basic compound includes, for example, carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, ethyldiisopropylamine, dimethylaminopyridine, triethylamine, 1,5-diazabicyclo[4.3.0]nonene-(5) (DBN), 1,8-diazabicyclo[5.4.0]undecene-7 (DBU), 1,4-diazabicyclo[2.2.2]octane (DABCO), etc.). The amount of the compound (1h) and the compound (11) is not critical, but the compound (11) is usually used at least in equivalent amount, preferably 1 to 5 moles, to 1 mole of the compound (1h). The reaction is usually carried out at a temperature of from about 0° C. to about 200° C., preferably from about 0° C. to about 170° C., for about 30 minutes to about 30 hours.

The reaction of the compound (1h) and the compound (12) is carried out under the same coniditons in the reaction of the compound (1d) and the compound (7) in the above Reaction Scheme-5.

In case of the compound of the formula (1) wherein $R^{11}$ and $R^{12}$ combine together with the nitrogen atom to which they bond to form a saturated or unsatrated heterocyclic group which may be intervened or not with nitrogen, oxygen or sulfur atom and said heterocyclic group contains a secondary amino group, the compound can be converted into a compound where said heterocyclic group is substituted on said secondary amino group by a substituent selected from a phenyl(lower)alkyl and a phenyl having optionally a substituent selected from a lower alkoxy and a lower alkanoyl by treating it in the same manner as in the reaction of the compound (1h) and the compound (11) in the above Reaction Scheme-8.

Besides, said compound can also be converted into a compound where the heterocyclic group is substitued on said secondary amine by a substituent selected from benzoyl and a lower alkanoyl by treating it in the same manner as in the reaction of the compound (1h) and the compound (12) in the above Reaction Scheme-8.

[Reaction Scheme-9A]

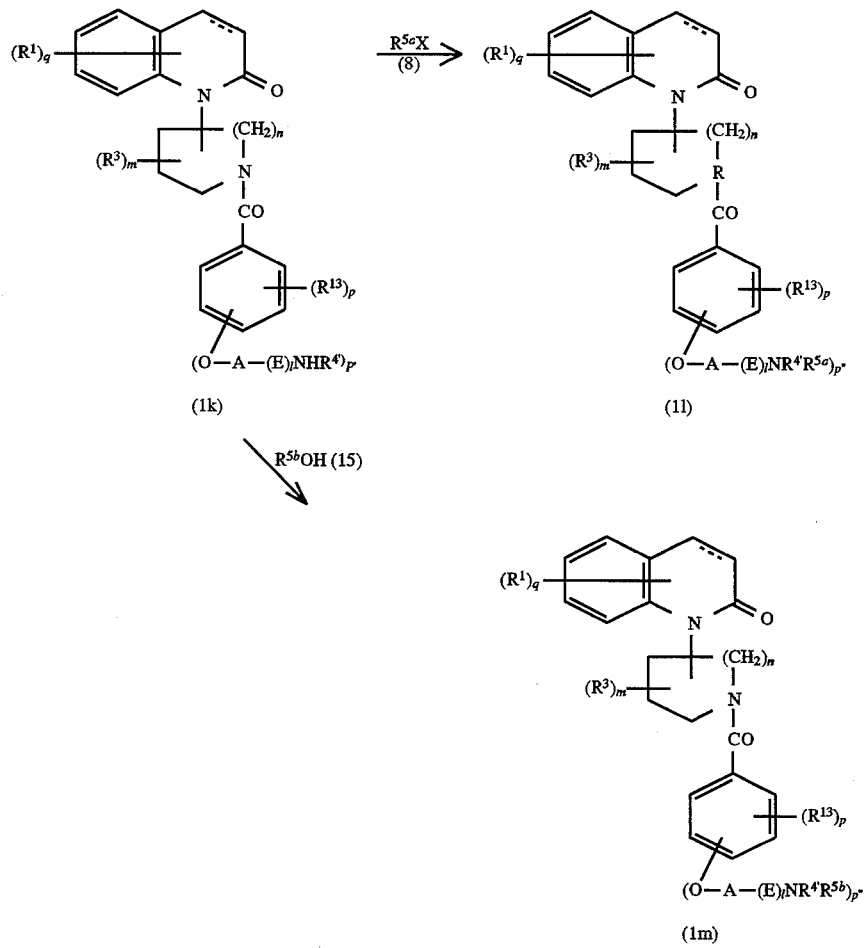

wherein $R^1$, q, $R^3$, m, n, $R^{13}$, p, X, A, E, l, and the bond between 3- and 4-positions of the carbostyril nucleus are the same as defined above, and $R^{4'}$ is hydrogen atom; a lower alkyl which may optionally be substituted by hydroxy or cyano; a lower alkenyl; a lower alkynyl; a phenyl(lower)alkyl; a lower alkanoyl which may optionally have one to three substitutents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl (lower)alkoxycarbonyl substituent; an amido having optionally a lower alkyl substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a phenyl (lower)alkyl having optionally a lower alkoxy substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by nitro or an amino having optionally one or two substitutents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have substituent selected from a lower alkyl and a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholino wherein the heterocyclic group may optionally have substituent selected from a lower alkyl and phenyl; a piperidinyl-substituted carbonyl which may optionally be substituted by a lower alkanoyl; a lower alkanoyloxy(lower) alkyl; a pyridyl-substituted lower alkyl; or an amino acid residue which can form an amido group with its amino group, $R^{5a}$ is a lower alkyl which may optionally be substituted by hydroxy or cyano; a lower alkenyl; a lower alkynyl; a phenyl(lower)alkyl; phenyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a lower alkylsulfonyl; a phenylsulfonyl which phenyl ring may optionally be substituted by nitro or an amino having optionally one or two substitutents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have a substituent selected from a lower alkyl and a lower alkanoyl; anilinocarbonyl; a piperidinyl which may optionally be substituted by a phenyl(lower)alkyl; a cycloalkyl, a tetrahydropyranyl-substituted lower alkyl wherein the tetrahydropyranyl ring may optionally have one to four substituents selected from hydroxy and a lower alkoxy; a lower alkanoyloxy(lower)alkyl; or a pyridyl-substituted lower alkyl, $R^{5b}$ is a lower alkanoyl which may optionally have one to three substitutents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; a lower alkoxycarbonyl; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower) alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a lower alkanoyl, or a phenyl(lower)alkoxycarbonyl; a hydroxy-substituted lower alkanoyl; a lower alkanoyloxy(lower)alkanoyl; a cycloalkenylcarbonyl; a cycloalkylcarbonyl which may optionally have one to three substituents selected from hydroxy and a lower alkanoyloxy; a lower alkanoyl which is substituted by a 5- or 6-membered saturated heterocyclic group selected from pyrrolidinyl, piperazinyl, piperidinyl and morpholino wherein the heterocyclic group may optionally be substituted by a lower alkyl or phenyl; a piperidinyl-substituted carbonyl which may optionally be substituted by a lower alkanoyl; or an amino acid residue which can form an amido group with its amino group, p' and p" are each an integer of 1 to 3, provided that p+p' and p+p" are each an integer not more than 3.

[Reaction Scheme-9B]

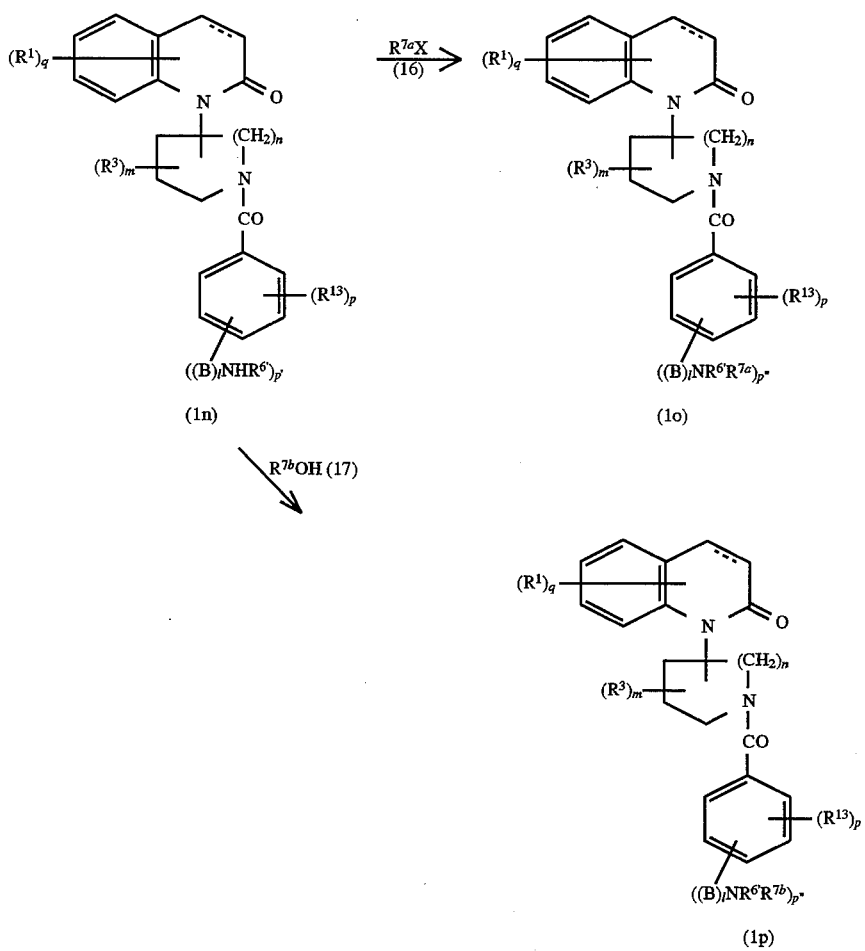

wherein $R^1$, q, $R^3$, m, n, $R^{13}$, p, X, B, l, and the bond between 3- and 4-positions of the carbostyril nucleus are the same as defined above, and $R^{6'}$ is hydrogen atom, a lower alkyl, a lower alkanoyl having optionally one to three halogen substituents, a lower alkoxycarbonyl, a carboxy (lower)alkyl, a lower alkoxycarbonyl(lower)alkyl, a lower alkenyl, an amido-substituted lower alkyl having optionally a lower alkyl substituent, or a phenyl(lower)alkoxycarbonyl, $R^{7a}$ is a lower alkyl, a lower alakoxycarbonyl(lower)alkyl, carboxy(lower)alkyl, a lower alkenyl, or an amido-substituted lower alkyl having optionally a lower alkyl substituent, $R^{7b}$ is a lower alkanoyl having optionally one to three halogen substitituents, a lower alkoxycarbonyl, or a phenyl(lower)alkoxycarbonyl, p' and p" are each an integer of 1 to 3, provided that p+p' and p+p" are each an integer not more than 3.

The reaction of the compound (1k) and the compound (14) in the Reaction Scheme-9A and the reaction of the compound (1n) and the compound (16) in the Reaction Scheme-9B can be carried out under the same conditions as in the reaction of the compound (1h) and the compound (12) in the above Reaction Scheme-8.

Besides, the compound (1m) wherein $R^{5b}$ is a lower alkanoyl or the compound (1p) wherein $R^{7b}$ is a lower alkanoyl having optionally one to three substituents of a halogen atom can also be obtained by reacting the compound (1k) or the compound (1n) with an alkanoylating agent of the formula: $(R^{5b'})_2O$ or $(R^{7b'})_2O$ (wherein $R^{5b'}$ is a lower alkanoyl, and $R^{7b'}$ is a lower alkanoyl having optionally one to three substituents of a halogen atom) in an appropriate solvent or without solvent in the presence or absence, peferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, etc. The basic compound includes, for example, tertiary amines (e.g. triethylamine, pyridine, etc.), sodium hydroxide, potassium hydroxide, sodium hydride, and the like. The above reaction can also be carried out in a solvent such as acetic acid in the presence of a mineral acid (e.g. sulfuric acid, etc.). The alkanoylating agent is usually used in an equimolar amount or more, preferably 1 to 10 moles, to 1 mole of the staring compound, and the reaction is usually carried out at a temperature of about 0° C. to about 200° C., preferably from about 0° C. to about 150° C., for about 0.5 to 15 hours.

Moreover, the compound (1l) wherein $R^{5a}$ is a lower alkyl or a phenyl(lower)alkyl) and the compound (1o) wherein $R^{7a}$ is a lower alkyl can also be obtained by reacting the compound (1k) or the compound (1n) with a compound of the formula: $R^{18}$—CO—$R^{19}$ (18) (wherein $R^{18}$ and $R^{19}$ are each hydrogen atom, phenyl, or a lower alkyl), respectively. In case of the compound (1n), however, the compound to be reacted should be the compound (18) wherein $R^{18}$ and $R^{19}$ are other than phenyl. The reaction is usually carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium boro hydride, sodium cyanoboro hydride, lithium aluminum hydride, etc.), catalystic reducing agents (e.g. palladium black, palladium-carbon, platinum oxide, platinum black, Raney nickel, etc.). When formic acid is used as the reducing agent, the reaction is usually carried out at a temperature of from room temperature to about 200° C., peferably about 50° C. to about 150° C., for about 1 to 10 hours. The formic acid is usually used in a large excess amount to the compound (1k) or the compound (1n).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (1k) or the compound (1n). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40% by weight, preferably about 1 to 20% by weight, of the amount of the compound (1k) or the compound (1n). The compound (18) is usually used at least in equivalent amount, preferably equivalent to a large excess amount, to the compound (1k) or the compound (1n).

In case of the compound of the formula (1) wherein $R^6$ and $R^7$ combine together with the nitrogen atom to which they bond to form a 5- or 6-membered, saturated or unsatrated heterocyclic group which may be intervened or not with nitrogen, oxygen or sulfur atom and said heterocyclic group contains a secondary amino group, and/or $R^4$ and $R^5$ combine together with the nitrogen atom to which they bond to form a 5- or 6-membered, saturated heterocyclic group which may be intervened or not with nitrogen, oxygen or sulfur atom and said heterocyclic group contains a secondary amino group, the compound can be converted into a compound where said heterocyclic groups are substituted on said secondary amino group by a substituent selected from a lower alkyl (in case of forming a heterocyclic group by $R^6$ and $R^7$) or a phenyl having optionally a substituent selected from a halogen atom and a lower alkoxy (in case of forming a heterocyclic group by $R^4$ and $R^5$) by treating it in the same manner as in the reaction of the compound (1k) and the compound (14) in the above Reaction Scheme-9A.

Besides, said compound (where $R^6$ and $R^7$ form a heterocyclic group) can also be converted into a compound where the heterocyclic group is substitued on said secondary amino group by a substituent selected from a lower alkoxycarbonyl by treating it in the same manner as in the reaction of the compound (1k) and the compound (15) in the above Reaction Scheme-9A.

[Reaction Scheme-10A]

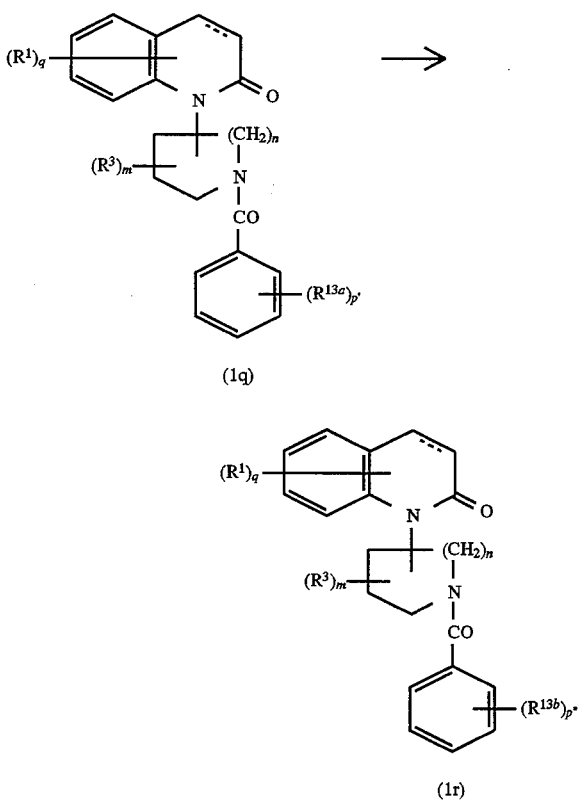

wherein $R^1$, q, $R^3$, m, n, p', p", and the bond between 3- and 4-positions of the carbostyril nucleus are the same as defined above, and $R^{13a}$ is the same groups as $R^{13}$ provided that at least one of the $R^{13a}$ is cyano, and $R^{13b}$ is the same groups as $R^{13}$ provided that at least one of the $R^{13b}$ is amidino.

[Reaction Scheme-10B]

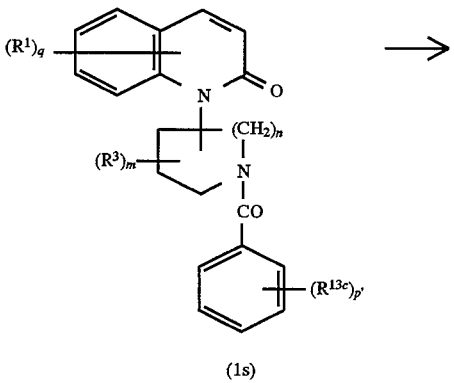

-continued
[Reaction Scheme-10B]

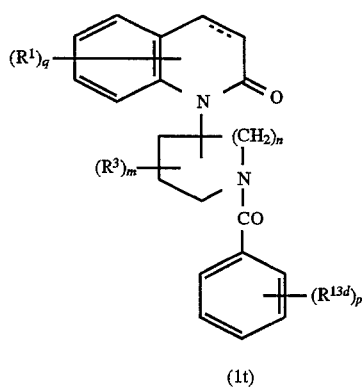

(1t)

wherein $R^1$, q, $R^3$, m, n, p', p", and the bond between 3- and 4-positions of the carbostyril nucleus are the same as defined above, and $R^{13c}$ is the same groups as $R^{13}$ provided that at least one of the $R^{13c}$ is a cyano-substituted lower alkoxy, and $R^{13d}$ is the same groups as $R^{13}$ provided that at least one of the $R^{13d}$ is an amidino-substituted lower alkoxy.

The reaction of converting the compound (1q) to the compound (1r) in the above Reaction Scheme-10A and of converting the compound (1s) to the compound (1t) in the above Reaction Scheme-10B is carried out by reacting the compound (1q) and the compound (1s) with various alcohols, phenols, and thiols, respectively in an appropriate solvent or without solvent in the co-presence of a basic compound and hydrogen chloride, followed by reacting the resultant imidate compound with aqueous ammonia in an appropriate solvent. The solvent used in the reaction for obtaining an imidate compound includes, for example, halogenated hydrocarbons (e.g. dichloromethane, chloroform, etc.), aromatic hydrocarbons (e.g. benzene, toluene, etc.), and the like. The alcohols used therein include, preferably lower alcohols such as methanol, ethanol, etc. These alcohols are usually used in an amount of 1 mole or more, peferably 1 to 2 moles, to 1 mole of the starting compound. The basic compound includes, preferably metal alcoholates such as sodium methylate, sodium ethylate, etc., particularly preferably the alcoholates with the same alcohols as above. The reaction for forming imidate compound is usually carried out at a temperature of about −10° C. to about 50° C., preferably about 0° C. to room temperature, for about 1 to 200 hours. The imidate compound thus obtained can be used in the subsequent reaction without being isolated from the reaction mixture.

The solvent used in the reaction of converting the imidate compound to the desired amidine compound includes, for example, water soluble solvents such as lower alcohols (e.g. methanol, ethanol, isopropanol, etc.), acetone, dimethylformamide, acetonitrile, and the like. The aqueous ammonium used in the reaction is usally used in an amount of 1 mole or more, preferably 5 to 50 moles, to 1 mole of the imidate compound. The reaction is usually carried out at a temperature of about 0° C. to about 100° C., preferably 0° C. to room temperature, for about 10 minutes to about 15 hours. In the above reaction of converting the imidate compound to the amidine compound, there may occasionally be produced a compound where $R^{13d}$ is the same groups as $R^{13}$ provided that at least one of the $R^{13d}$ is a carbamoyl-substituted lower alkoxy, or $R^{13b}$ is the same groups as $R^{13}$ provided that at least one of $R^{13b}$ is a carbamoyl group, but these compounds can easily be separated from the reaction system.

[Reaction Scheme-11]

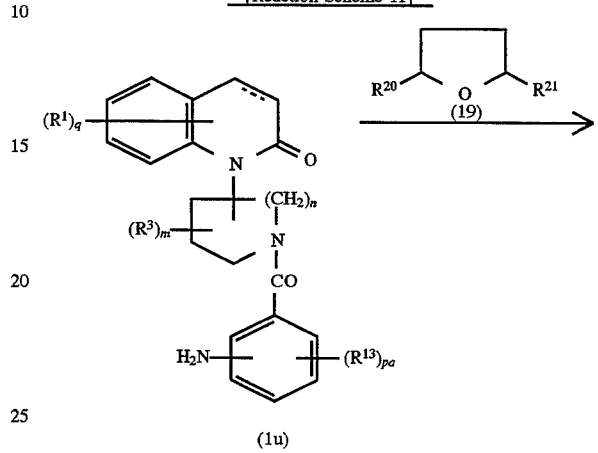

(1u)

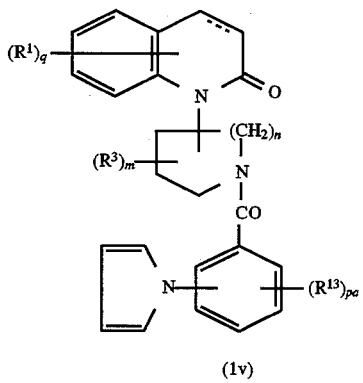

(1v)

wherein $R^1$, q, $R^3$, m, n, $R^{13}$, and the bond between 3- and 4-positions of the carbostyril nucleus are the same as defined above, and $R^{20}$ and $R^{21}$ are each lower alkoxy, and pa is 0 or an integer of 1 to 2.

The reaction of the compound (1u) and the compound (19) can be carried out in an appropriate solvent in the presence of an acid. The solvent includes, for example, water, lower alcohols (e.g. methanol, ethanol, isopropanol, etc.), ketones (e.g. acetone, methyl ethyl keton, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.). The reaction is usually carried out at a temperature of from room temperature to about 200° C., preferably from room temperature to about 150° C., for about 0.5 to 5 hours The compound (19) is usually used in an amount of at least 1 mole, preferably 1 to 2 moles, to 1 mole of the compound (1u).

[Reaction Scheme-12A]

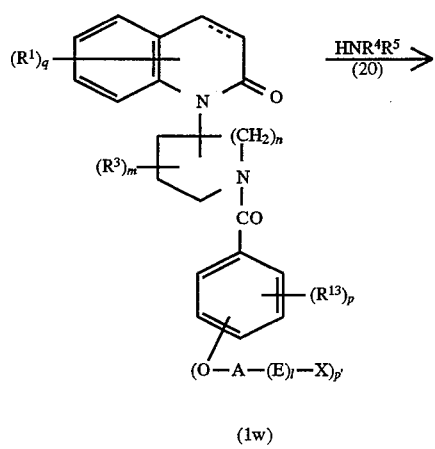

(1w)

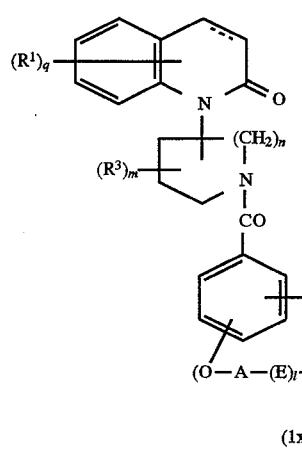

(1x)

wherein $R^1$, q, $R^3$, m, n, $R^4$, $R^5$, $R^{13}$, p, p', p'', X, A, E, l, and the bond between 3- and 4-positions of the carbostyril nucleus are the same as defined above.

[Reaction Scheme-12B]

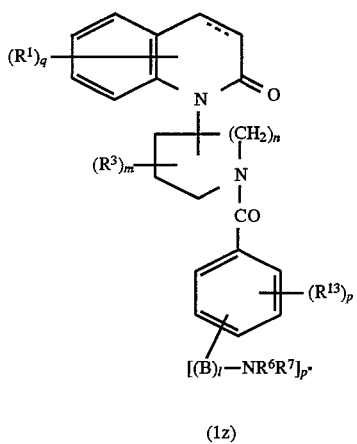

(1y)

-continued
[Reaction Scheme-12B]

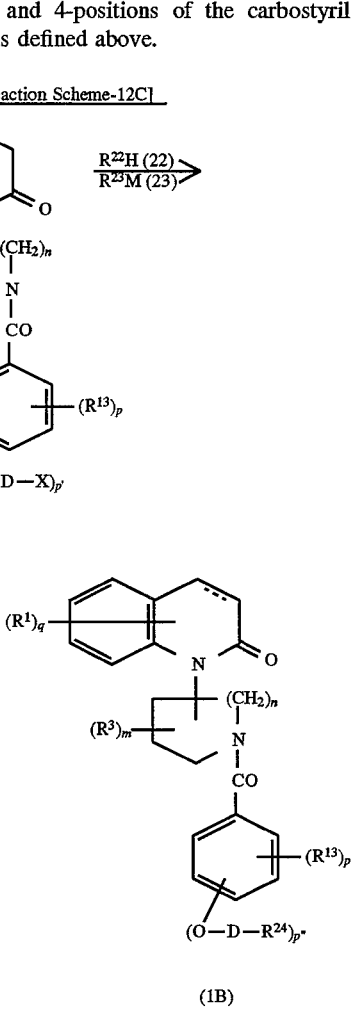

(1z)

wherein $R^1$, q, $R^3$, m, n, $R^6$, $R^7$, $R^{13}$, p, p', p'', X, B, l, and the bond between 3- and 4-positions of the carbostyril nucleus are the same as defined above.

[Reaction Scheme-12C]

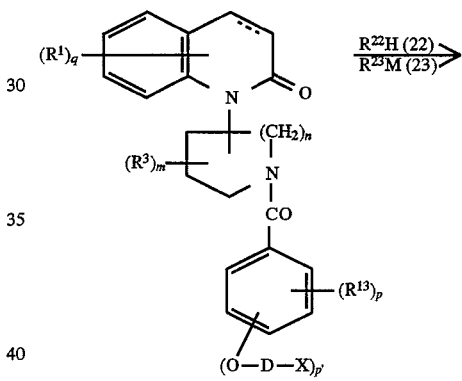

(1A)

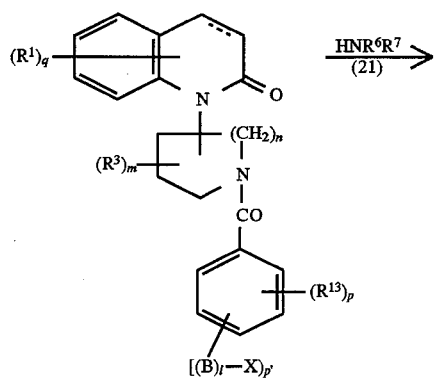

(1B)

wherein $R^1$, q, $R^3$, m, n, $R^{13}$, p, p', p'', X, and the bond between 3- and 4-positions of the carbostyril nucleus are the same as defined above, and D is a lower alkylene, $R^{22}$ is a group of the formula:

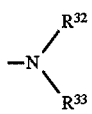

($R^{32}$ and $R^{33}$ are the same as defined above), benzoyloxy, a lower alkylsulfonyloxy, a lower alkanoyloxy, a lower alkylthio, benzimidazolylthio, pyrimidylthio, an imidazolylthio having optionally a lower alkyl substituent, a phenylthio having optionally a substituent selected from nitro and amino on the phenyl ring, pyridylthio, or pyrrolyl, $R^{23}$ is hydroxy, a lower alkoxy, benzoyloxy, a lower alkylsulfonyloxy, a lower alkanoyloxy, or a lower alkoxy having one or two substituents selected from cyano, hydroxy and an amino having optionally a lower alkyl substituent, $R^{24}$ is the same as the above $R^{22}$ or $R^{23}$, and M is an alkali metal (e.g. potassium, sodium, etc.).

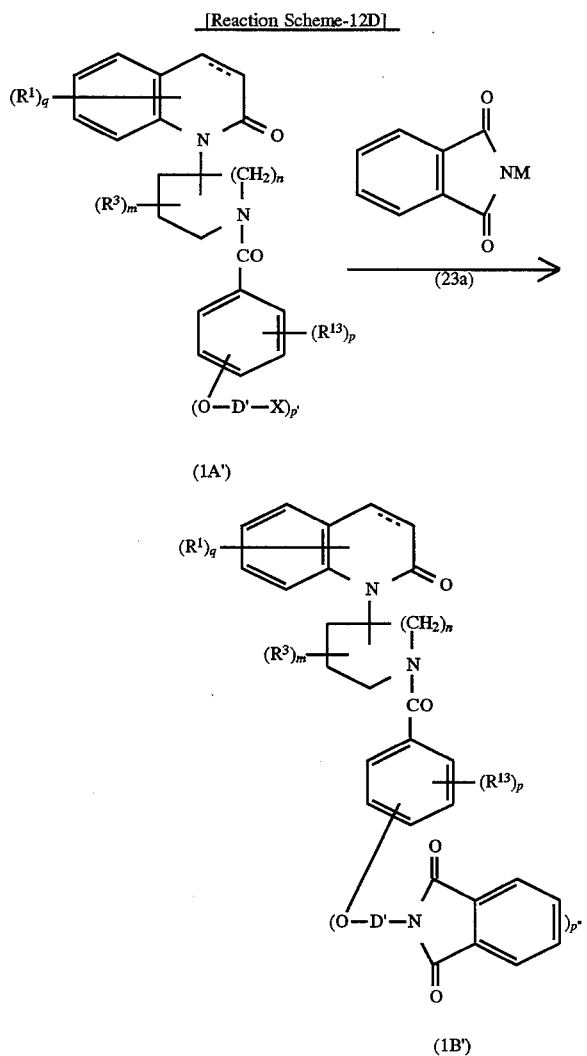

wherein $R^1$, q, $R^3$, m, n, $R^{13}$, p, p', p", X, M and the bond between 3- and 4-positions of the carbostyril nucleus are the same as defined above, and D' is a lower alkylene.

The reaction of the compound (1w) and the compound (20) in Reaction Scheme-12A, of the compound (1y) and the compound (21) in Reaction Scheme-12B, of the compound (1A) and the compound (22) or (23) in Reaction Scheme-12C, and of the compound (1A') and teh compound (23a) in Reaction Scheme-12D is carried out under the same conditions as in the reaction of the compound (1h) and the compound (11) in the above Reaction Scheme-8.

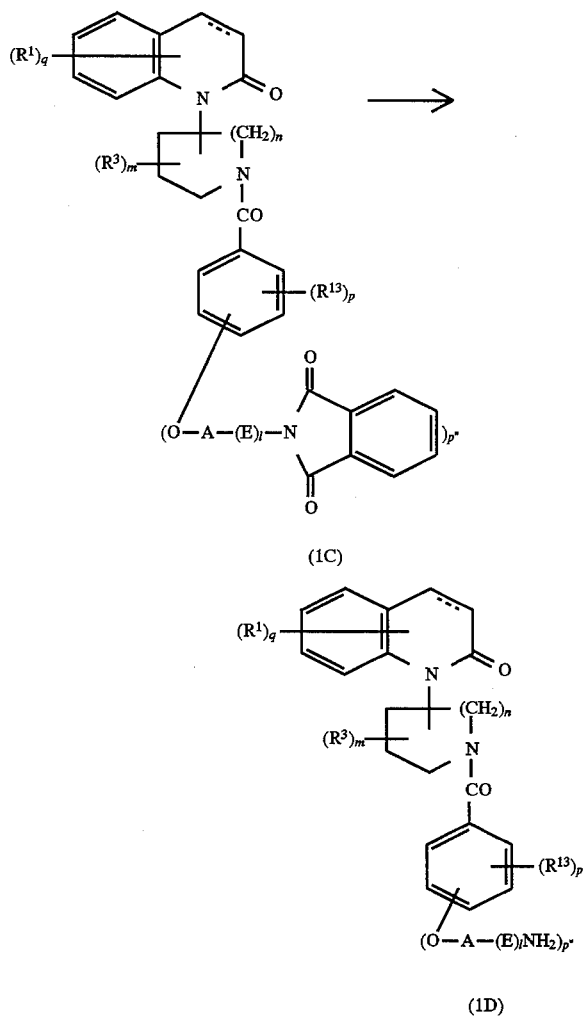

wherein $R^1$, q, $R^3$, m, n, $R^{13}$, p, p', p", A, E, l, and the bond between 3- and 4-positions of the carbostyril nucleus are the same as defined above.

The reaction of converting the compound (1C) into the compound (1D) can be carried out by reacting the compound (1C) with hydrazine in an appropriate solvent or by hydrolyzing the compound (1C). The solvent used in the reaction with hydrazine includes the same solvent as used in the reaction of the compound (1h) and the compound (11) in the above Reaction Scheme-8. The reaction is usually carried out at a temperature of from room temperature to about 120° C., preferably about 0° C. to about 100° C., for about 0.5 to 5 hours. Hydrazine is usually used in an amount of at least 1 mole, preferably about 1 to 5 moles, to 1 mole of the compound (1C). The hydrolysis is carried out under the same conditions as in the hydrolysis of the compound (1) wherein $R^4$ or $R^5$ is a lower alkoxycarbonyl as described hereinafter.

[Reaction Scheme-14]

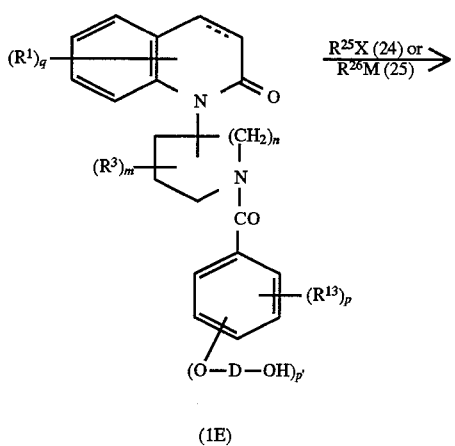

(1E)

wherein $R^1$, q, $R^3$, m, n, $R^{13}$, p, p', p", X, D, M, and the bond between 3- and 4-positions of the carbostyril nucleus are the same as defined above, and $R^{25}$ is a lower alkanoyl, a lower alkenyl, a lower alkyl, a lower alkylsulfonyl, a lower alkyl having one or two substituents selected from hydroxy and an amino having optionally a lower alkyl substituent, or benzoyl, $R^{26}$ is a group of —OCN, and $R^{27}$ is the same groups as the above $R^{25}$ or a carbamoyl.

The reaction of the compound (1E) and the compound (24) is carried out under the same conditions as in the reaction of the compound (1h) and the compound (11) in the above Reaction Scheme-8. In said reaction, an alkali metal halide (e.g. sodium iodide, potassium iodide, etc.) may be added to the reaction system.

The reaction of the compound (1E) and the compound (25) is carried out in an appropriate solvent in the presence of an acid. The solvent includes the same solvents as used in the reaction of the compound (1h) and the compound (11) in the above Reaction Scheme-8. In addition thereto, there may also be used halogenated hydrocarbons (e.g. methylene chloride, chloroform, carbon tetrachloride, etc.). The acid includes, for example, mineral acids (e.g. hydrochloric acid, sulfuric acid, hydrobromic acid, etc.) and organic acids (e.g. formic acid, acetic acid, trifluroacetic acid, aromatic sulfonic acids, etc.). The reaction is usually carried out at a temperature of about 0° C. to about 150° C., preferably, from room temperature to about 100° C., for about 1 to 15 hours. The compound (25) is usually used in an amount of 1 to 5 moles, preferably 1 to 3 moles, to 1 mole of the compound (1E).

[Reaction Scheme-15]

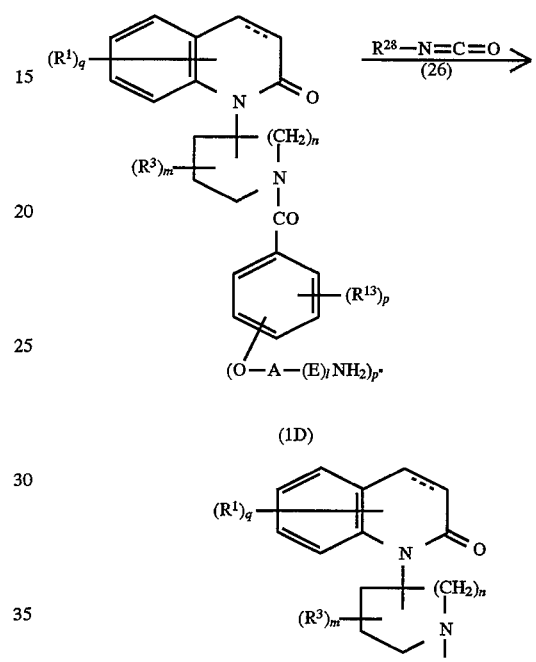

wherein $R^1$, q, $R^3$, m, n, $R^{13}$, p, p', p", A, E, l, and the bond between 3- and 4-positions of the carbostyril nucleus are the same as defined above, and $R^{28}$ is hydrogen atom, phenyl or a lower alkyl.

The reaction of the compound (1D) and the compound (26) is carried out under the same conditions as in the reaction of the compound (1d) and the compound (8) in the above Reaction Scheme-6.

[Reaction Scheme-16]

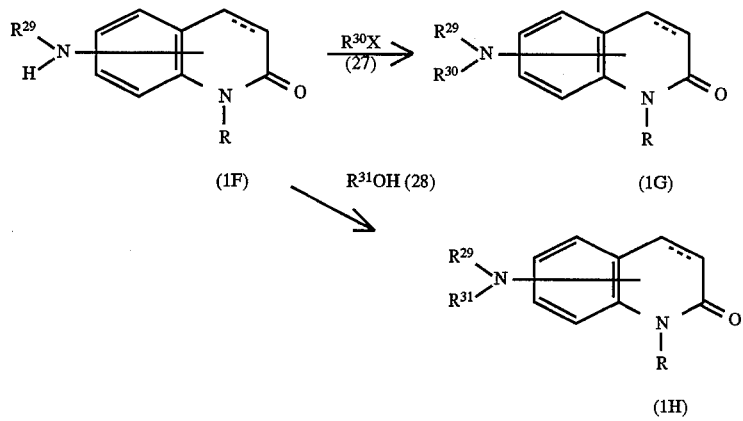

wherein R, X, and the bond between 3- and 4-positions of the carbostyril nucleus are the same as defined above, and $R^{29}$ is hydrogen atom, a lower alkanoyl, a lower alkyl or benzoyl, $R^{30}$ is a lower alkyl, and $R^{31}$ is a lower alkanoyl or benzoyl.

The reaction of the compound (1F) and the compound (27) is carried out under the same conditions as in the reaction of the compound (1k) and the compound (14) in the above Reaction Scheme-9A.

The reaction of the compound (1F) and the compound (28) is carried out under the same conditions as in the reaction of the compound (1k) and the compound (15) in the above Reaction Scheme-9A.

[Reaction Scheme-17]

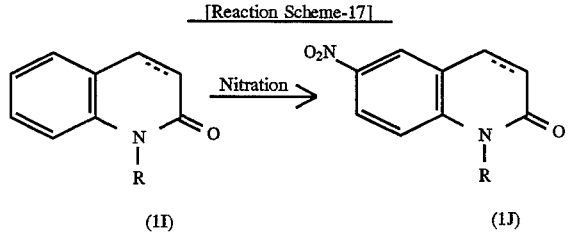

wherein R and the bond between 3- and 4-positions of the carbostyril nucleus are the same as defined above.

The nitration of the compound (1I) can be carried our under the same conditions as used in the conventional nitration reaction of an aromatic compound. That is, it can be carried out by using a nitrating agent in an appropriate inert solvent or without solvent. The inert solvent includes, for example, acetic acid, acetic anhydride, conc. sulfuric acid, and the like. The nitrating agent includes, for example, fuming nitric acid, conc. nitric acid, mixed acid (e.g. a mixture of nitric acid with sulfuric acid, fuming sulfuric acid, phosphoric acid, or acetic anhydride), a mixture of an alkali metal nitrate (e.g. potassium nitrate, sodium nitrate, etc.) with sulfuric acid, and the like. The nitrating agent is used in an equimolar amount or more, usually in an excess amount, to the amount of the starting compound. The reaction is advantageously carried out at a temperature of about 0° C. to room temperature for about 0.5 to 4 hours.

[Reaction Scheme-18]

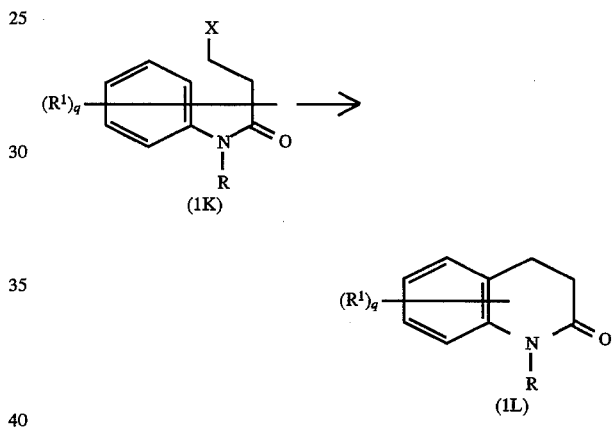

wherein $R^1$, q, R, and X are the same as defined above.

The cyclization reaction of the compound (1K) is so-called Friedel Craft reaction and is usually carried out in an appropriate solvent in the presence of a Lewis acid. The solvent includes any conventional solvent which is usually used in this kind of reaction, for example, carbon disulfide, nitrobenzene, chlorobenzene, dichloromethane, dichloroethane, trichloroethane, tetrachloroethane, and the like. The Lewis acid includes any conventional acid, for example, aluminum chloride, zinc chloride, iron chloride, tin chloride, boron tribromide, boron trifluoride, conc. sulfuric acid, and the like. The amount of Lewis acid is not critical but is usually in the range of about 2 to 6 moles, preferably about 3 to 4 moles, to 1 mole of the compound (1K). The reaction temperature is usually in the range of about 20° C. to 200° C., preferably 40° C. to 180° C. The reaction period of time may vary depending on the kinds of the starting compound, catalyst and reaction temperature, etc., but is usually in the range of about 0.5 to 6 hours. Besides, sodium chloride may be added to the reaction system in order to proceed the reaction advantageously.

[Reaction Scheme-19]

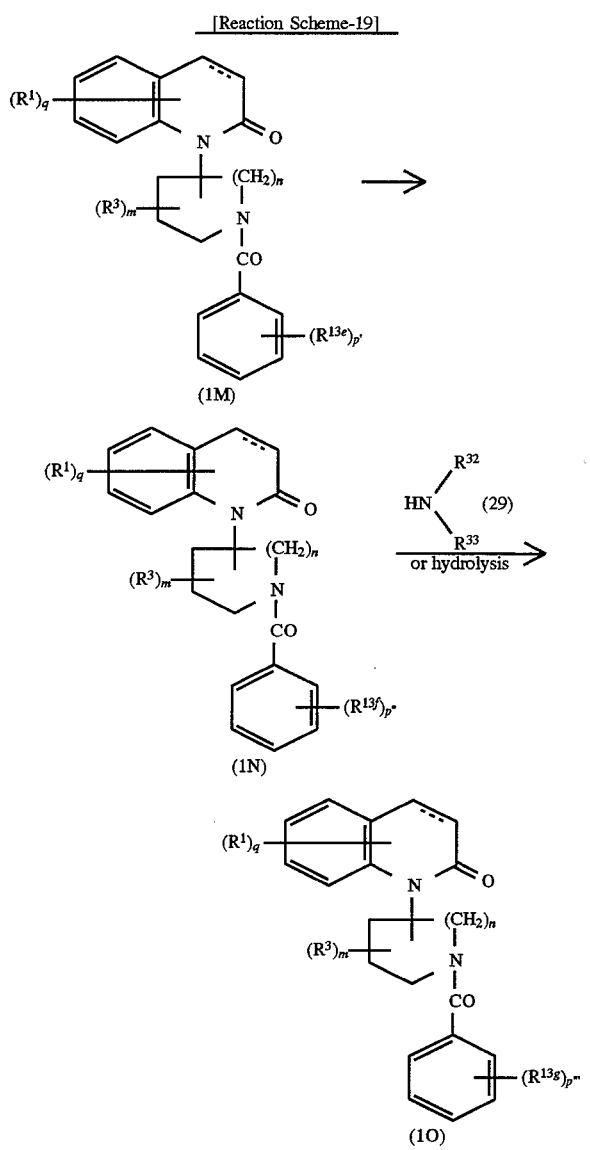

wherein $R^1$, q, $R^3$, m, n, p', p", and the bond between 3- and 4-positions of the carbostyril nucleus are the same as defined above, and $R^{13e}$ is the same groups as $R^{13}$ provided that at least one of the $R^{13e}$ is a lower alkenyloxy, $R^{13f}$ is the same groups as $R^{13}$ provided that at least one of the $R^{13f}$ is an oxilanyl-substituted lower alkoxy, $R^{13g}$ is the same groups as $R^{13}$ provided that at least one of the $R^{13g}$ is a lower alkoxy having a substituent selected from hydroxy and a group of the formula:

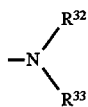

($R^{32}$ and $R^{33}$ are as defined above), and p'" is an integer of 1 to 3.

The reaction of converting the compound (M) into the compound (N) is carried out under the same conditions as in the reaction of oxidizing lower alkylthio into lower alkylsulfonyl as mentioned above. The reaction of the compound (1N) and the compound (29) is carried out under the same conditions as in the reaction of the compound (1h) and the compound (11) in the above Reaction Scheme-8. Besides, the hydrolysis of the compound (1N) can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

[Reaction Scheme-20]

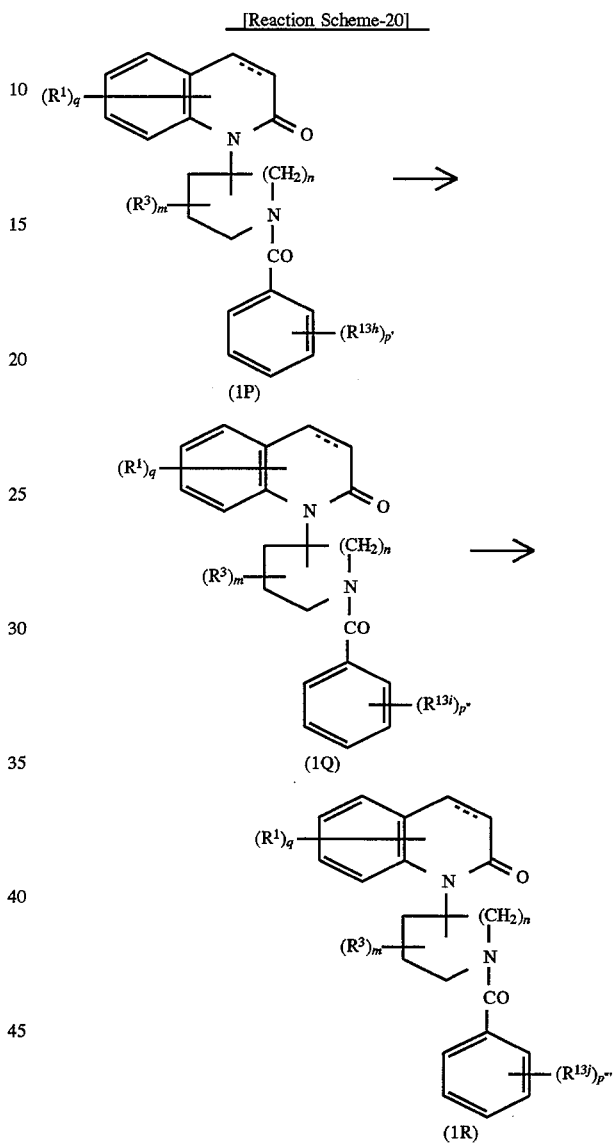

wherein $R^1$, q, $R^3$, m, n, p', p", p'", and the bond between 3- and 4-positions of the carbostyril nucleus are the same as defined above, and $R^{13h}$ is the same groups as $R^{13}$ provided that at least one of the $R^{13h}$ is a lower alkanoyl, $R^{13i}$ is the same groups as $R^{13}$ provided that at least one of the $R^{13i}$ is a lower alkenyl having optionally a substituent selected from a lower alkoxycarbonyl, carboxyl or hydroxy, $R^{13j}$ is the same groups as $R^{13}$ provided that at least one of the $R^{13j}$ is a lower alkyl having optionally a substituent selected from a lower alkoxycarbonyl, carboxyl and hydroxy.

The reaction of converting the compound (1P) into the compound (1Q) is carried out in an appropriate solvent in the presence of a Wittig reagent and a basic compound. The Wittig reagent includes, for example, a phosphoric compound of the formula:

 (A)

wherein $R^{34}$ is phenyl, $R^{35}$ is a lower alkyl having optionally a substituent selected from a lower alkoxycarbonyl, carboxyl and hydroxy, and X is a halogen atom, and a phosphoric compound of the formula:

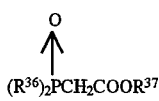   (B)

wherein $R^{36}$ is a lower alkoxy, and $R^{37}$ is a lower alkyl.

The basic compound includes inorganic bases (e.g. metallic sodium, metallic potassium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about −80° C. to about 150° C., preferably about −80° C. to about 120° C., for about 0.5 to 15 hours.

The reaction of converting the compound (1Q) into the compound (1R) is carried out under the same conditions as in the catalytic hydrogenation as described herebefore.

The starting compound (2) can be prepared, for example, by the processes as shown in the following Reaction Schemes-21 and -22.

[Reaction Scheme-21]

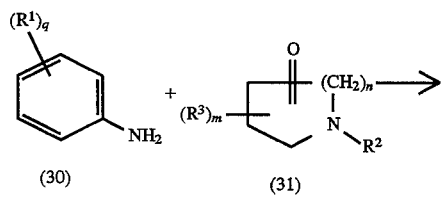

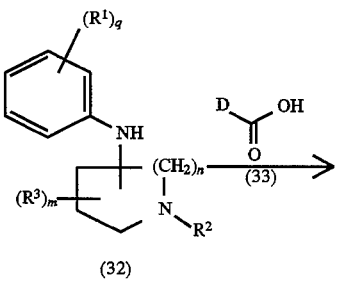

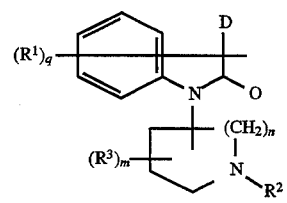

wherein $R^1$, q, $R^2$, $R^3$, m, n and D are the same as defined above, provided that the group $R^1$ may substitute on either of the benzene ring or the group D of the compound (2a).

The reaction of the compound (30) and the compound (31) is carried out under the same conditions as in the reaction of the compound (1k) and the compound (18) in the above Reaction Scheme-9A.

The reaction of the compound (32) and the compound (33) is carried out under the same conditions as in the reaction of the compound (1d) and the compound (7) in the above Reaction Scheme-5.

[Reaction Scheme-22]

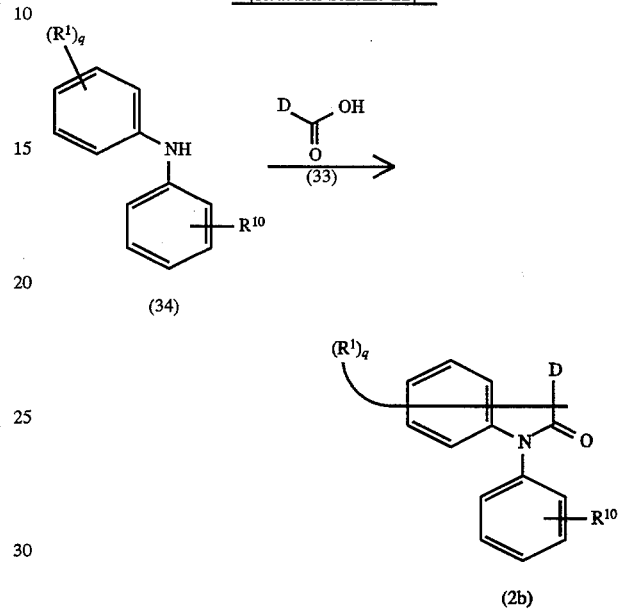

wherein $R^1$, q, $R^{10}$, and D are the same as defined above, provided that the group $R^1$ may substitute on either of the benzene ring or the group D of the compound (2b).

The reaction of the compound (34) and the compound (33) is carried out under the same conditions as the above reaction of the compound (32) and the compound (33).

The starting compound (3) can be prepared, for example, by the process of the following Reaction Scheme-23.

[Reaction Scheme-23]

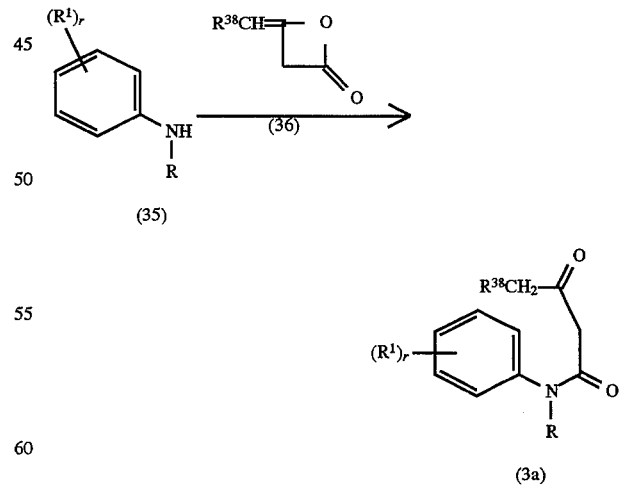

wherein $R^1$ and R are the same as defined above, $R^{38}$ is hydrogen atom or a lower alkyl, and r is 1 or 2.

The reaction of the compound (35) and the compound (36) is carried out in a solvent as used in the reaction of the compound (1E) and the compound (25) in the above Reaction Scheme-14. The compound (36) is usually used in an amount of at least 1 mole, preferably 1 to 2 moles, to 1 mole of the compound (35). The reaction is usually carried out at a temperature of 0° C. to 150° C., preferably from room temperature to about 100° C., for about 0.5 to 5 hours.

The starting compound (4) can be prepared, for example, by the process of the following Reaction Scheme-24.

[Reaction Scheme-24]

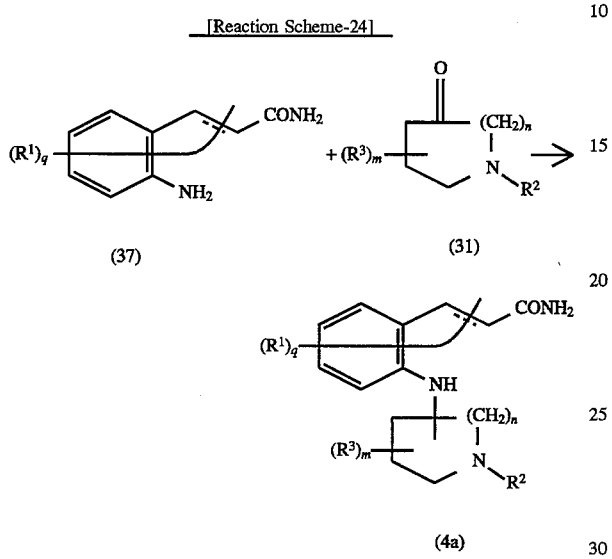

wherein $R^1$, q, $R^2$, $R^3$, m, and n are the same as defined above.

The reaction of the compound (37) and the compound (31) is carried out under the same conditions as in the reaction of the compound (30) and the compound (31) in the above Reaction Scheme-21.

The staring compound (1K) can be prepared, for example, by the process of the following Reaction Scheme-25.

[Reaction Scheme-25]

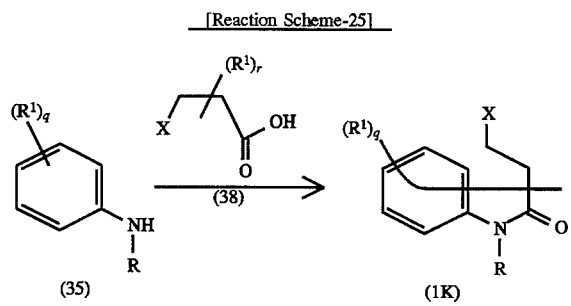

wherein $R^1$, q, r, R and X are as defined above, provided that the total of q and r is not more than 3.

The reaction of the compound (35) and the compound (38) is carried out under the same conditions as in the reaction of the compound (32) and the compound (33) in the above Reaction Scheme-21.

[Reaction Scheme-26]

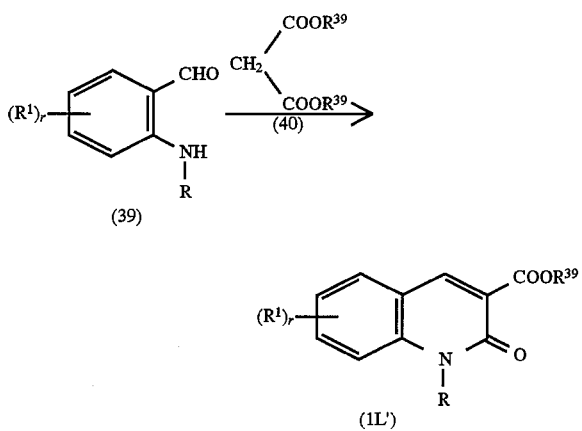

wherein $R^1$, r and R are as defined above, and $R^{39}$ is a lower alkyl.

The reaction of the compound (39) and the compound (40) is carried out in an appropriate solvent in the presence of a basic compound. The basic compound includes, inorganic bases (e.g. sodium hydroxide, potassium hydroxide, sodium hydrogen carbonate, potassium hydrogen carbonate, potassium carbonate, sodium carbonate, sodium hydride, etc.), alkali metal alcoholates (e.g. sodium methylate, sodium ethylate, etc.), and organic bases (e.g. triethylamine, pyridine, α-picoline, N,N-dimethylaniline, N-methylmorpholine, piperidine, pyrrolidine, etc.). The solvent includes, for example, ethers (e.g. dioxane, tetrahydrofuran, monoglyme, diglyme, etc.), aromatic hydrocarbons (e.g. benzene, toluene, xylene, etc.), lower alcohols (e.g. methanol, ethanol, isopropanol, etc.), polar solvents (e.g. dimethylsulfoxide, dimethylformamide, etc.), and the like. The reaction is usually carried out at a temperature of from room temperature to 150° C., preferably from 60° C. to 120° C., for about 1 to 24 hours. The compound (40) is usually used in an equimolar to large excess amount, preferably 1 to 5 moles to 1 mole of the compound (39). A lower alkane (e.g. acetic acid, etc.) or molecular sieves may be added to the reaction system to proceed the reaction advantageously.

The compound (39) can be prepared, for example, by the process of the following reaction scheme.

[Reaction Scheme-27]

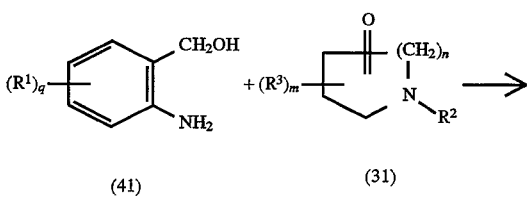

-continued
[Reaction Scheme-27]

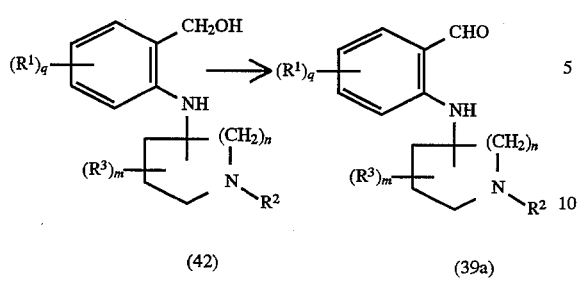

wherein R¹, q, R², R³, m and n are as defined above.

The reaction of the compound (41) and the compound (31) is carried out under the same conditions as in the reaction of the compound (30) and the compound (31) in the above Reaction Scheme-21.

The reaction of converting the compound (42) into the compound (39a) is carried out in an appropriate solvent or without solvent in the presence of an oxidizing agent. The solvent includes the above-mentioned aromatic hydrocarbons, lower alcohols, halogenated hydrocarbons, ethers, polar solvents (e.g. dimethylsulfoxide, dimethylformamide, hexamethylphosphoric triamide, etc.). The oxidizing agent includes acetic anhydride-dimethylsulfoxide, phosphorus pentoxide-dimethylsulfoxide, sulfur trioxide.pyridine complex-dimethylsulfoxide, dicyclohexylcarbodiimide-dimethylsulfoxide, oxalyl chloride-dimethylsulfoxide, chromic acid, chromic acid complexes (e.g. chromic acid-pyridine complex, chromic acid-2-pyridine complex, etc.), manganese dioxide, and the like. When oxayl chloride-dimethylsulfoxide is used as the oxidizing agent, there may be added to the reaction system the basic compound as used in the reaction of the compound (1d) and the carboxylic halide in the above Reaction Scheme-5. The reaction is usually carried out at a temperature of 0° C. to 150° C., preferably from room temperature to about 100° C., for about 1 to 30 hours. The oxidizing agent is usually used in an amount of 1 to 20 moles, preferably 1 to 15 moles, to 1 mole of the compound (42).

[Reaction Scheme-28]

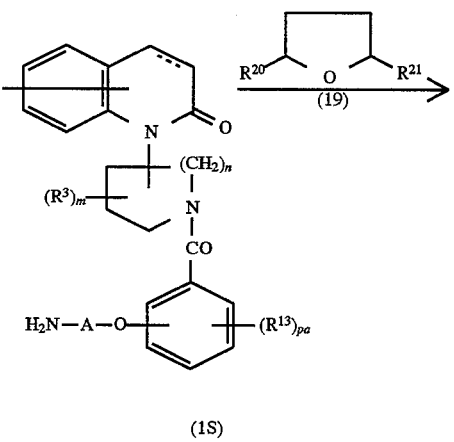

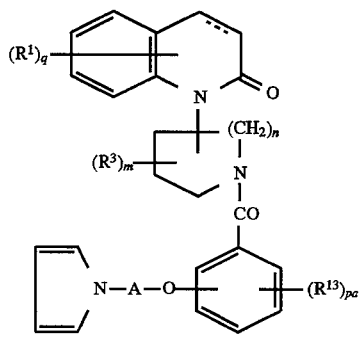

wherein R¹, q, R³, m, n, R¹³, pa, A, R²⁰, R²¹ and the bond between 3- and 4-positions of the carbostyril nucleus are the same as defined above.

The reaction of the compound (1S) and the compound (19) is carried out under the same conditions as in the reaction of the compound (1u) and the compound (19) in the above Reaction Scheme-11.

[Reaction Scheme-29]

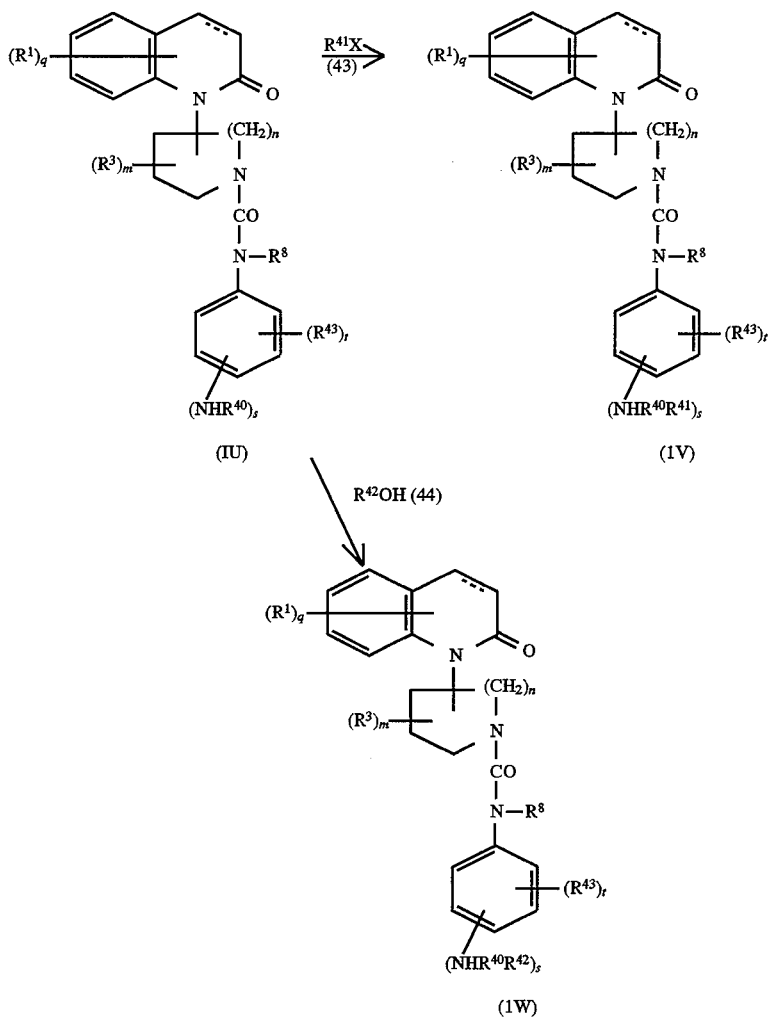

wherein $R^1$, q, $R^3$, m, n, $R^8$, X, and the bond between 3- and 4-positions of the carbostyril nucleus are the same as defined above, and $R^{40}$ is hydrogen atom, a lower alkyl or a lower alkanoyl, $R^{41}$ is a lower alkyl, $R^{42}$ is a lower alkanoyl, $R^{43}$ is a lower alkoxy, a halogen atom, an amino having optionally one or two substituents selected from a lower alkyl and a lower alkanoyl, or nitro, t is 0, 1 or 2, s is an integer of 1 to 3, provided that total of t and s is not more than 3.

The reaction of the compound (1U) and the compound (43) is carried out under the same conditions as in the reaction of the compound (1k) and the compound (14) in the above Reaction Scheme-9A.

The reaction of the compound (1U) and the compound (44) is carried out under the same conditions as in the reaction of the compound (1k) and the compound (15) in the above Reaction Scheme-9A.

[Reaction Scheme-30]

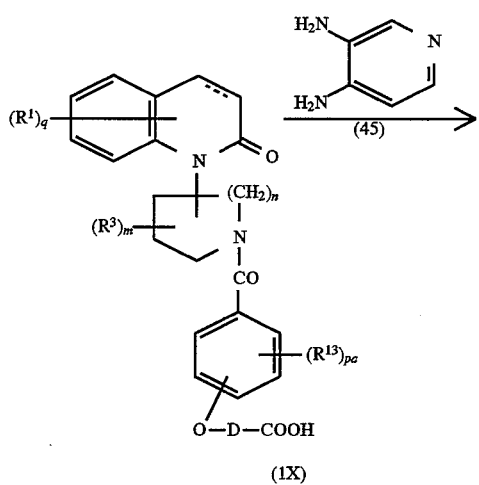

73
-continued
[Reaction Scheme-30]

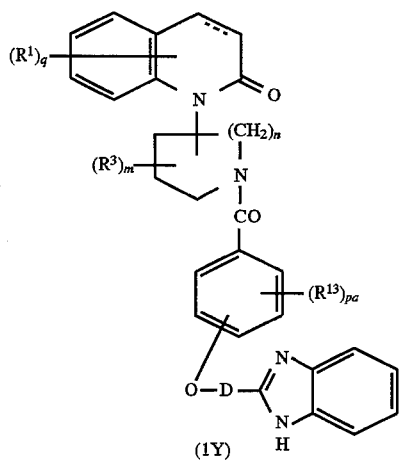

74 wherein $R^1$, q, $R^3$, m, n, $R^{13}$, pa, D, and the bond between 3- and 4-positions of the carbostyril nucleus are the same as defined above.

The reaction of the compound (1X) and the compound (45) is carried out in an appropriate solvent or withtout solvent in the presence of an acid. The acid includes, for example, inorganic acids (e.g. hydrochloric acid, sulfuric acid, hydrobromic acid, nitric acid, phosphorus pentoxide, polyphosphoric acid, etc,), and organic acids (e.g. p-toluenesulfonic acid, ethanesulfonic acid, methanesulfonic acid, trifluoroacetic acid, etc.), or a mixture of these acids. The solvent includes the same solvents as used in the cyclization reaction of the compound (4) in the above Reaction Scheme-3. The compound (45) is usually used in an amount of at least 1 mole, preferably 1 to 1.5 mole, to 1 mole of the compound (1x). The reaction is usually carried out at a temperature of from room temperature to about 200° C., preferably from room temperature to about 150° C., for about 1 to 5 hours.

[Reaction Scheme-31]

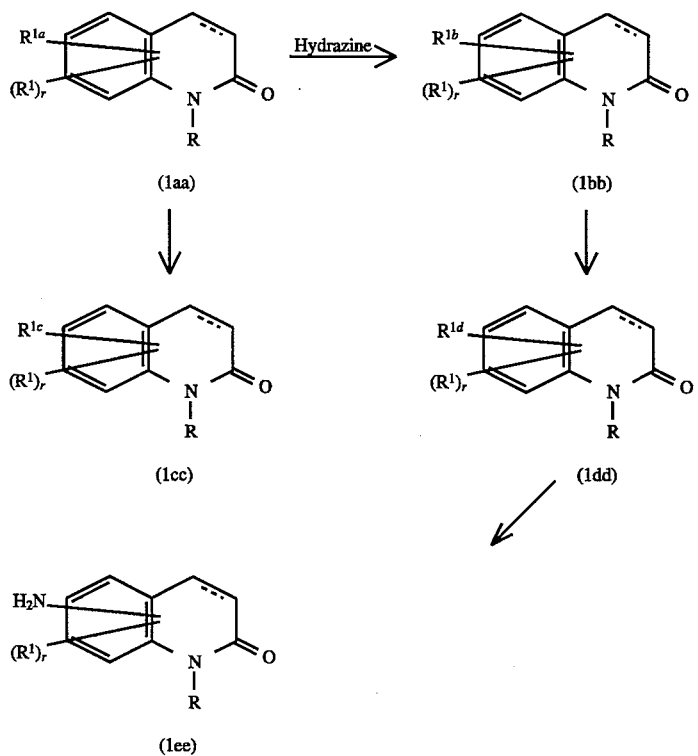

wherein R, R¹ and the bond between 3- and 4-positions of the carbostyril nucleus are the same as defined above, and $R^{1a}$ is a lower alkoxycarbonyl, $R^{1b}$ is hydrazinocarbonyl, $R^{1c}$ is carboxyl, $R^{1d}$ is a phenyl(lower)alkoxycarbonyl-substituted amino, and r is 1 or 2.

The reaction of the compound (1aa) and hydrazine is carried out in an appropriate solvent. The solvent includes the same solvents as used in the reaction of the compound (1d) and the halide (7) in the above Reaction Scheme-5. Hydrazine is used in a large excess amount, preferably in 8 to 20 moles to 1 mole of the compound (1aa). The reaction is usually carried out at a temperature of from room temperature to about 150° C., preferably from room temperature to about 100° C., for about 1 to 10 hours.

The reaction of converting the compound (1aa) into the compound (1cc) is carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

The reaction of converting the compound (1bb) into the compound (1dd) is carried out by reacting the compound (1bb) with a metal nitrite (e.g. sodium nitrite, potassium nitrite, etc.) in an appropriate solvent in the presence of an acid, followed by reacting the resultant with a phenyl lower alcohol (e.g. benzyl alcohol, α-phenethyl alcohol, β-phenethyl alcohol, etc.). The acid used therein includes, for example, hydrochloric acid, hyrobromic acid, sulfuric acid, tetrafluoroboric acid, hexafluorophosphoric acid, and the like. The solvent used in the reaction with a metal nitrite includes, for example, water, dichloromethane, chloroform, carbon tetrachloride or a mixture of these solvents. The reaction is usually carried out at a temperature of about –20° C. to about 10° C., preferably about –5° C. to about 5° C., for about 5 minutes to about one hour. The nitrite is usually used in an amount of at least 1 mole, preferably 1 to 1.5 mole, to 1 mole of the compound (1bb). The solvent used in the reaction with a phenyl lower alcohol includes, for example, aromatic hydrocarbons (e.g. benzene, toluene, xylene, etc.), ketones (e.g. acetone, methyl ethyl ketone, etc.), ethers (e.g. dioxane, tetrahydrofuran, diethyl ether, ethylene glycol dimethyl ether, etc.), and the like. The reaction is carried out at a temperature of from room temperature to about 200° C., preferably from room temperature to about 150° C., for about 0.5 to 10 hour. The phenyl lower alcohol is usually used in an amount of at least 1 mole, preferably 1 to 2 moles, to 1 mole of the compound (1bb).

The reaction of converting the compound (1dd) into the compound (1ee) is carried out under the same conditions as in the reduction reaction of the compound (1) wherein $R^2$ is a heterocyclic group-substituted carbonyl having a phenyl (lower)alkoxycarbonyl on at least one nitrogen atom thereof as described hereinafter.

[Reaction Scheme-32]

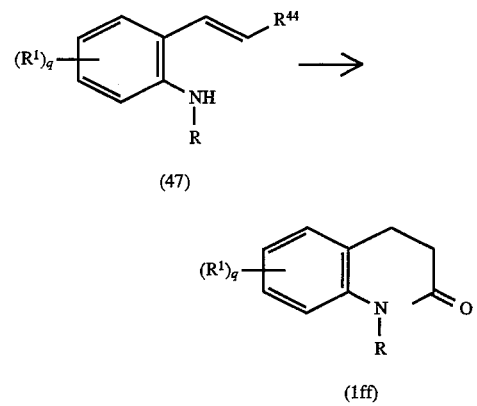

wherein $R^1$, q, R, $R^{34}$, and X are the same as defined above, and $R^{44}$ is a lower alkoxycarbonyl.

The reaction of the compound (39) and the compound (46) is carried out under the same conditions as in the reaction of converting the compound (1P) into the compound (1Q) in the above Reaction Scheme-20.

The cyclization reaction of the compound (47) is carried out in the presence of a catalytic reducing agent and in the presence or absence of a basic compound or an acid, preferably in the presence of an acid, in an appropriate solvent. The basic compound includes, for example, organic bases (e.g. triethylamine, trimethylamine, pyridine, dimethylaniline, N-methylmorpholine, DBN, DBU, DABCO, etc.), and inorganic bases (e.g. potassium carbonate, sodium carbonate, sodium hydroxide, potassium hydroxide, sodium hydride, potassium hydride, potassium hydrogen carbonate, sodium hydrogen carbonate, etc.), and the acid includes, for example, inorganic acids (e.g. hydrochloric acid, sulfuric acid, phosphoric acid, etc.), organic acids (e.g. acetic acid, etc.), or a mixture of these acids. The solvent includes, for example, water, alcohols (e.g. methanol, ethanol, propanol, butanol, 3-emthoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. tetrahydrofuran, diethyl ether, dimethoxyethane, etc.), esters (e.g. methyl acetate, ethyl acetate, etc.), N,N-dimethylformamide, dimethylsulfoxide, hexamethylphosphoric triamide, or a mixture of these solvents. The catalytic reducing agent includes the same catalysts as used in the reduction reaction of the compound (1a) in the above Reaction Scheme-1. The reaction is usually carried out under atmospheric pressure to about 20 kg/cm², preferably atmospheric pressure to about 10 kg/cm², at a temperature of about 0° C. to about 200° C., preferably from room temperature to about 150° C., for about 1 to 10 hours. The catalytic reducing agent is preferably used in an amount of 0.02 to 1 part by weight to 1 part of the compound (47).

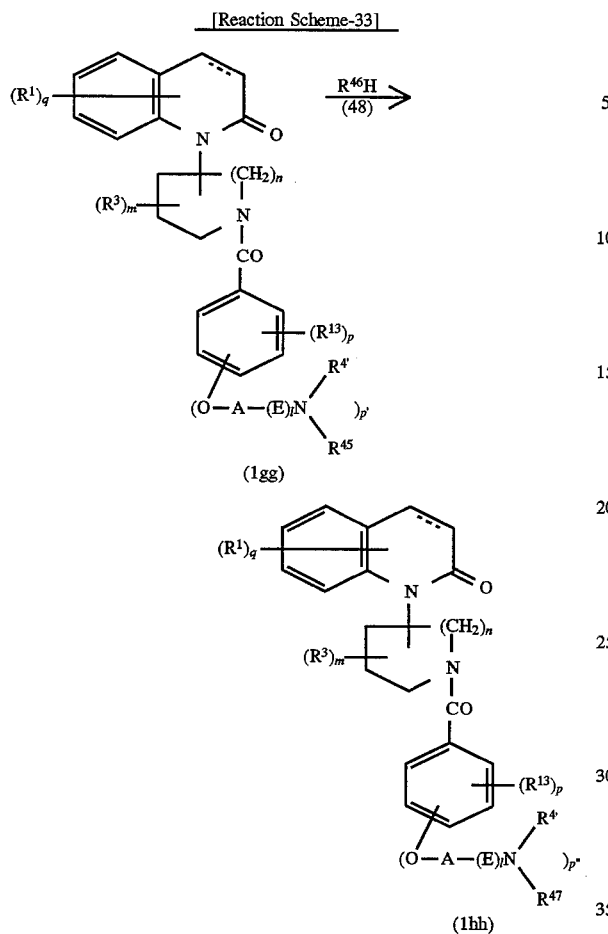

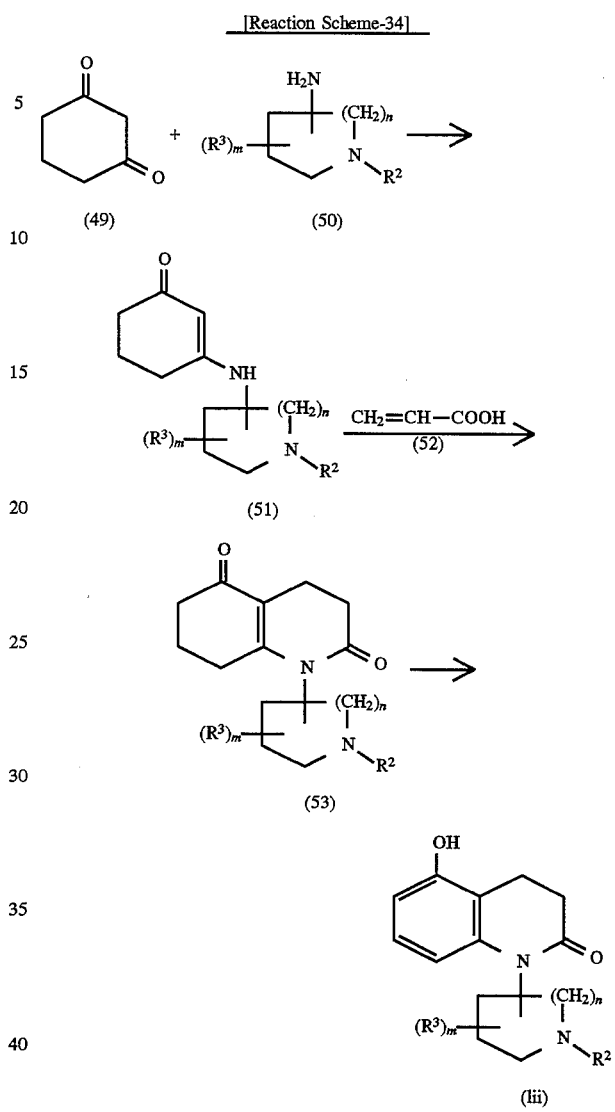

wherein $R^1$, q, $R^3$, m, n, $R^{13}$, $R^{4'}$, p', p", A, E, l, and the bond between 3- and 4-positions of the carbostyril nucleus are the same as defined above, and $R^{45}$ is a lower alkanoyl which has one halogen substituent and may optionally have a further substituent selected from a phenyl(lower) alkoxycarbonylamino, hydroxy, a phenyl having optionally a hydroxy substituent, carbamoyl, imidazolyl and a lower alkylthio, $R^{46}$ is an amino which may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower) alkoxycarbonyl, and $R^{47}$ is an amino-substituted lower alkanoyl wherein the lower alkanoyl moiety may optionally have a substituent selected from a phenyl(lower) alkoxycarbonylamino, hydroxy, a phenyl having optionally a hydroxy substituent, carbamoyl, imidazolyl, and a lower alkylthio, and the amino group may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower) alkoxycarbonyl.

The reaction of the compound (1gg) and the compound (48) is carried out under the same conditions as in the reaction of the compound (1h) and the compound (11) in the above Reaction Scheme-8.

wherein $R^2$, $R^3$, m, and n are the same as defined above.

The reaction of the compound (49) and the compound (50) is carried out by heating them in an appropriate solvent. The solvent includes, for example, alcohols (e.g. methanol, ethanol, isopropanol, etc.), acetonitrile, ethers (e.g. dioxane, diethyl ether, diglyme, tetrahydrofuran, etc.), aromatic hydrocarbons (e.g. benzene, toluene, xylene, etc.), or a mixture of these solvents. The reaction is usually carried out at a temperature of from room temperature to about 200° C., preferably about 50° C. to about 150° C., for about 1 to 10 hours. The compound (50) is usually used in an amount of at least 1 mole, preferably 1 to 1.5 mole, to 1 mole of the compound (49).

The reaction of the compound (51) and the compound (52) is usually carried out without using any solvent at a temperature of about 50° C. to about 200° C., preferably from about 50° C. to about 150° C., for about 1 to 10 hours.

The reaction of converting the compound (53) into the compound (1bb) is carried out in an appropriate solvent in the presence of a halogenating agent and a basic compound. The solvent includes, for example, halogenated hydrocarbons (e.g. dichloromethane, dichloroethane, chloroform, carbon tetrachloride, etc.), alcohols (e.g. methanol, ethanol, propanol, etc.), and the like. The halogenating agent includes N-halogenated succinimides (e.g. N-bromosuccinimide, N-chlorosuccinimide, etc.), halogen molecules (e.g. bromine, chlorine, etc.), N-bromoacetamide, pyrrolidinium bormide perbromide, and the like. The basic compound includes the compounds as used in the reaction of the compound (1h) and the compound (11) in the above Reaction Scheme-8. The reaction is usually carried out at a temperature of about 0° C. to about 150° C., preferably from room temperature to about 100° C., for about 1 to 10 hours. The halogenating agent is usually used in an amount of at least 1 mole, preferably 1 to 3 moles, to 1 mole of the compound (53).

[Reaction Scheme-35]

(1jj)

(1kk)

(1ll)

wherein $R^1$, r, $R^2$, $R^3$, m, n, X, and the bond between 3- and 4-positions of the carbostyril nucleus are the same as defined above, and $R^{48}$ is a lower alkyl, and $R^{49}$ is a lower alkanoyl.

The reaction of the compound (1jj) and the compound (54) is carried out under the same conditions as in the reaction of the compound (1h) and the compound (11) in the above Reaction Scheme-8.

The reaction of the compound (1jj) and the compound (55) is carried out under the same conditions as in the reaction of the compound (1h) and the compound (12), wherein a carboxylic halide is used, in the above Reaction Scheme-8, and the reaction of the compound (1jj) and the compound (56) is carried out under the same conditions as in the reaction of the compound (1k) and the compound of the formula: $(R^{5b'})_2O$ in the above Reaction Scheme-9A.

[Reaction Scheme-36]

(57) + (58) →

-continued
[Reaction Scheme-36]

(59)

-continued
[Reaction Scheme-36]

(42)

wherein $R^1$, q, n, R and X are as defined above.

The reaction of the compound (57) and the compound (58) is carried out under the same conditions as in the reaction of the compound (5) and the compound (6) in the above Reaction Scheme-4. In this reaction, copper monoxide may be added to the reaction system in order to proceed the reaction advantageously.

The reaction of converting the compound (59) into the compound (42) can be carried out under the same conditions as used in the reduction reaction of the compound (1) wherein $R^{13}$ is a lower alkanoyl or benzoyl as described hereinafter.

In case of the compounds of the formula (1) wherein (a) $R^2$ is a phenyl(lower)alkanoyl wherein the lower alkanoyl moiety is substituted by an amino having a lower alkoxycarbonyl substituent, (b) $R^4$ or $R^5$ is a lower alkoxycarbonyl, (c) $R^6$ or $R^7$ is a lower alkoxycarbonyl, or (d) $R^6$ and $R^7$ form a heterocyclic group which has a lower alkoxycarbonyl substituent on at least one nitrogen atom of the heterocyclic group, these compound can be subjected to hydrolysis to obtain the corresponding compounds of the formula (1) wherein (a) $R^2$ is a phenyl(lower)alkanoyl wherein the lower alkanoyl moiety is substituted by an amino, (b) $R^4$ or $R^5$ is hydrogen atom, (c) $R^6$ or $R^7$ is hydrogen atom, or (d) $R^6$ and $R^7$ form a heterocyclic group where at least one nitrogen has no substituent, respectively.

The hydrolysis can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydoxides (e.g. sodium hydroxide, potassium hydroxide, calcium hydroxide, etc.), and the like. The reaction is usually carried out at a temperature of from room temperature to about 200° C., preferably from room temperature to about 150° C., for about 0.5 to 25 hours.

In the case of the compounds of the formula (1) wherein $R^2$ is a heterocyclic group-substituted carbonyl which has a phenyl(lower)alkoxycarbonyl on at least one nitrogen atom thereof; $R^{13}$ is a benzoyl which is substituted by at least one amino group having at least one phenyl(lower)alkoxycarbonyl substituent on the phenyl ring; $R^4$ or $R^5$ is a pyrrolidinylcarbonyl having at least one phenyl(lower)alkoxycarbonyl substituent on the nitrogen atom of the pyrrolidine ring, or an amino-substituted lower alkanoyl wherein the amino has at least one phenyl(lower)alkoxycarbonyl susbtituent and the lower alkanoyl moiety may optionally have a substituent; or $R^6$ or $R^7$ is a phenyl (lower)alkoxycarbonyl, these compounds can be subjected to a reduction reaction to obtain the corresponding compounds of the formula (1) wherein $R^2$ is a heterocyclic group-substituted carbonyl wherein at least one nitrogen has hydrogen substituent; $R^{13}$ is a benzoyl which has at least one amino group having no phenyl(lower)alkoxycarbonyl substituent; $R^4$ or $R^5$ is a pyrrolidinylcarbonyl having no substituent on the nitrogen atom thereof or an amino-substituted lower alkanoyl having no substituent on the amino group thereof; or $R^6$ or $R^7$ is hydrogen atom. The reduction is carried out by catalytic reduction in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 100° C., preferably from about 0° C. to about 80° C., under atmospheric pressure to 10 atm., for about 0.5 to 20 hours.

The compound of the formula (1) wherein $R^{13}$ is a phenyl(lower)alkoxy can be converted into the corresponding compound (1) wherein $R^{13}$ is hydroxy by reduction thereof. The reduction can be carried out under the same conditions as in the reduction of the compound (1) wherein $R^2$ is a heterocyclic group-substituted carbonyl having a phenyl(lower)alkoxycarbonyl substituent on at least one nitrogen atom as described above.

In the case of the compounds of the formula (1) wherein $R^1$ is nitro; $R^2$ is a phenoxycarbonyl having at least one nitro substituent; $R^8$ or $R^9$ is a phenyl having at least one nitro substituent; $R^{13}$ is nitro, a phenylthio-substituted lower alkoxy having at least one nitro substituent on the phenyl ring, or a phenylsulfonyl-substituted lower alkoxy having at least one nitro substituent on the phenyl ring; or $R^4$ or $R^5$ is a benzoyl having at least one nitro susbtituent, or a phenylsulfonyl having at least one nitro substituent on the phenyl ring, these compounds can be subjected to a reduction reaction to obtain the corresponding compounds of the formula (1) wherein $R^1$ is amino; $R^2$ is a phenoxycarbonyl having at least one amino substituent; $R^8$ or $R^9$ is a phenyl having at least one amino substituent; $R^{13}$ is amino, or a phenylthio-substituted lower alkoxy having at least one amino substituent on the phenyl ring, or a phenylsulfonyl-substituted lower alkoxy having at least one amino substituent on the phenyl ring; or $R^4$ or $R^5$ is a benzoyl having at least one amino substituent, or a phenylsulfonyl having at least one amino substituent on the phenyl ring.

The reduction reaction can be carried out, for example, (1) by reducing them in an appropriate solvent with a catalytic reducing agent, or (2) by reducing them in an appropriate inert solvent with a reducing agent, such as a combination of a metal or metal salt and an acid, or a metal or metal salt and an alkali metal hydroxide, sulfide, ammonium salt, and the like.

In the case of reduction using a catalytic reducing agent (1), the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), and the like. The catalytic reducing agent includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 150° C., preferably from about 0° C. to about 100° C., under atmospheric hydrogen pressure to 10 atm., for about 0.5 to 10 hours.

In the case of the reduction (2), the reducing agent includes a combination of iron, zinc, tin or stannous chloride with a mineral acid (e.g. hydrochloric acid, sulfuric acid, etc.), or of iron, ferrous sulfate, zinc or tin with an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example, water, acetic acid, methanol, ethanol, dioxane, and the like. The conditions of the reduction reaction are determined depending on the kinds of the reducing agent, for example, in case of a combination of stannous chloride and hydrochloric acid, it is advantageously carried out at a temperature of about 0° C. to room temperature for about 0.5 to 10 hours. The reducing agent is usually used in an amount of at least 1 mole, preferably 1 to 5 moles, to 1 mole of the starting compound.

The compound of the formula (1) wherein $R^{13}$ is a lower alkanoyl or benzoyl can be converted into the corresponding compound (1) wherein $R^{13}$ is a lower alkyl substituted by hydroxy and/or phenyl by reduction thereof. The reduction reaction can advantageously be carried out by using a hydrogenating reducing agent. The hydrogenating reducing agent includes, for example, lithium aluminum hydride, sodium boro hydride, diborane, and the like. The reducing agent is usually used in an amount of at least 1 mole, preferably 1 to 15 moles, to 1 mole of the starting compound. The reduction reaction is usually carried out in an appropriate solvent such as water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about $-60°$ C. to about $150°$ C., preferably about $-30°$ C. to about $100°$ C., for about 10 minutes to about 5 hours. In case of using lithium aluminum hydride or diborane as the reducing agent, it is preferable to proceed the reaction in an anhydrous solvent such as tetrahydrofuran, diethyl ether, diisopropyl ether, diglyme, or the like.

The compound of the formula (1) wherein $R^{13}$ is hydroxy can be converted into the corresponding compound (1) wherein $R^{13}$ is a group of the formula: —$OR^{17}$ (wherein $R^{17}$ is as defined below) by reacting it with a compound of the formula:

wherein $R^{17}$ is a carboxy-substituted alkyl, a lower alkoxycarbonyl-substituted alkyl, a lower alkanoyloxy-substituted lower alkyl, a lower alkenyloxy-substituted lower alkyl, a lower alkoxy(lower)alkyl, an alkyl, a lower alkyl having one or two substituents selected from hydroxy, a lower alkanoyloxy, a tri(lower)alkylammonium, a lower alkoxy, or a group of the formula:

(wherein $R^{32}$ and $R^{33}$ are as defined above), a halogen-substituted lower alkyl, a lower alkylsulfonyloxy-substituted lower alkyl, a benzoyloxy-substituted lower alkyl, a tricyclo[3.3.1.1]decanyl-substituted lower alkyl, a group of the formula:

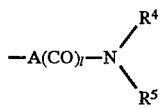

(wherein A, l, $R^4$ and $R^5$ are as defined above), a carbamoyloxy-substituted lower alkyl, a lower alkylthio-substituted lower alkyl, a lower alkylsulfonyl-substituted lower alkyl, a lower alkylsulfinyl-substituted lower alkyl, an alkenyl, a lower alkanoyl, a lower alkylsulfonyl, a lower alkynyl, a phenyl(lower)alkyl, a cycloalkyl, a cycloalkenyl, a cyano-susbtituted lower alkyl, an oxilanyl-substituted lower alkyl, a phthalimido-substituted alkyl, a pyrrolyl-substituted lower alkyl, an amidino-substituted lower alkyl, a lower alkoxy(lower)alkyl having one or two substituents selected from hydroxy and an amino having optionally a lower alkyl-substituent, a morpholino-substituted lower alkyl which may optionally have a substituent selected from a lower alkyl and oxo, a benzimidazolylthio-substituted lower alkyl, a benzimidazolylsulfinyl-substituted lower alkyl, an imidazo[4,5-c]pyridylcarbonyl-substituted lower alkyl, a pyrimidylthio-substituted lower alkyl, a pyrimidylsulfinyl-substituted lower alkyl, a pyrimidylsulfonyl-substituted lower alkyl, an imidazolylthio-substituted lower alkyl which may optionally have a lower alkyl substituent on the imidazole ring, an imidazolylsulfonyl-substituted lower alkyl which may optionally have a lower alkyl substituent on the imidazole ring, a phenylthio-substituted lower alkyl which may optionally have a substituent selected from nitro and amino on the phenyl ring, a phenylsulfonyl-substituted lower alkyl which may optionally have a substituent selected from nitro and an amino having optionally one or two subsitutents selected from a lower alkanoyl and a lower alkyl on the phenyl ring, a pyridylthio-substituted lower alkyl, a pyridylsulfonyl-substituted lower alkyl having optionally an oxo substituent on the pyridine ring, and X is as defined above.

The above reaction is carried out under the same conditions as in the reaction of the compound (1h) and the compound (11) in the above Reaction Scheme-8. Besides, an alkali metal halide (e.g. sodium iodide, potassium iodide, etc.) may be added to the reaction system.

The compounds of the formula (1) wherein $R^{13}$ is a lower alkylthio, a lower alkylthio-susbtituted lower alkoxy, a benzimidazolylthio-substituted lower alkoxy, a pyrimidylthio-substituted lower alkoxy, an imidazolylthio-substituted lower alkoxy having optionally a lower alkyl substituent on the imidazole ring, a phenylthio-substituted lower alkoxy which may optionally have a substituent selected from nitro and amino on the phenyl ring, or a pyridylthio-substituted lower alkoxy can be converted into the corresponding compounds of the formula (1) wherein $R^{13}$ is a lower alkylsulfinyl or a lower alkylsulfonyl; or a lower alkylsulfinyl-substituted lower alkoxy or a lower alkylsulfonyl-substituted lower alkoxy; a benzimidazolylsulfinyl-substituted lower alkoxy; a pyrimidylsulfinyl-substituted lower alkoxy or a pyrimidylsulfonyl-substituted lower alkoxyl; an imidazolylsulfonyl-substituted lower alkoxy which may optionally have a lower alkyl substituent on the imidazole ring; a phenylsulfonyl-substituted lower alkoxy which may optionally have a substituent selected from nitro and amino on the phenyl ring; or pyridylsulfonyl-substituted lower alkoxy, by oxidation thereof.

The oxidation of converting the lower alkylthio into the lower alkylsulfinyl; the oxidation of converting the lower alkylsulfinyl into the lower alkylsulfonyl; the oxidation of converting the lower alkylthio-substituted lower alkoxy into the lower alkylsulfinyl-substituted lower alkoxy; the oxidation of converting the lower alkylsulfinyl-substituted lower alkoxy into the lower alkylsulfonyl-substituted lower alkoxy; the oxidation of converting the pyrimidylthio-substituted lower alkoxy into the pyridylsulfinyl-substituted lower alkoxy; and the oxiation of converting the pyrimidylsulfinyl-substituted lower alkoxy into the pyrimidylsulfonyl-substituted lower alkoxy are carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. Besides, in cases of the oxidation of converting the lower alkylthio into the lower alkylsulfonyl; the oxidation of converting the lower alkylthio-substituted lower alkoxy into the lower alkylsulfonyl-substituted lower alkoxy; the oxidation of converting the pyrimidylthio-substituted lower alkoxy into the pyrimidylsulfonyl-substituted lower alkoxy; the oxidation of converting the imidazolylthio-substituted lower alkoxy having optionally a lower alkyl substituent on the imidazole ring into the imidazolylsulfonyl-substituted lower alkoxy having optionally a lower alkyl substituent on the imidazole ring; the oxiation of converting the phenylthio-substituted lower alkoxy which may optionally have a substituent selected from nitro and amino on the phenyl ring into the phenylsulfonyl-substituted lower alkoxy which may optionally have a substituent selected from nitro and amino on the phenyl ring; and the oxidation of converting the pyridylthio-substituted lower alkoxy into the pyridylsulfonyl-substituted lower alkoxy, the oxidizing agent is usually used at least 2 moles, preferably 2 to 4 moles, to 1 mole of the starting compound. The above reaction is usually carried out at a temperature of about 0° C. to about 40° C., preferably from about 0° C. to room temperature, for about 1 to 15 hours. In the above reaction, in case of the compound wherein $R^{13}$ is a pyridylthio-substituted lower alkoxy, the pyridyl group may occasionally also be oxidized to give the corresponding pyridine N-oxide compound.

The compound of the formula (1) wherein $R^{13}$ is a lower alkenyl, an alkenyloxy or a cycloalkenyloxy can be converted into the corresponding compound (1) wherein $R^{13}$ is a lower alkyl, an alkoxy or a cycloalkyloxy by reduction thereof. The reduction reaction is carried out under the same conditions as in the above-mentioned reaction of converting the compound (1) wherein $R^6$ or $R^7$ is a phenyl(lower)alkoxycarbonyl into the compound (1) wherein $R^6$ or $R^7$ is hydrogen atom.

The compound of the formula (1) wherein $R^{13}$ is a lower alkanoyl can be converted into the corresponding compound (1) wherein $R^{13}$ is a hydroxyimino-substituted lower alkyl by reacting it with hydroxylamine. The reaction is carried out in an inert solvent in the presence or absence of a basic compound. The basic compound includes, for example, inorganic basic compounds (e.g. sodium hydroxide, potassium hyroxide, sodium carbonate, potassium carbonate, etc.), lower alkanic acid alkali metal salts (e.g. sodium acetate, etc.), organic bases (e.g. piperidine, pyridine, 4-dimethylaminopyridine, triethylamine, DBN, DBU, DABCO, etc.), and the like. The solvent includes any solvent which does not affect on the reaction, for example, water, lower alcohols (e.g. methanol, ethanol, isopropanol, etc.), fatty acids (e.g. acetic acid, etc.), ethers (e.g. dioxane, tetrahydrofuran, diethyl ether, ethylene glycol monomethyl ether, etc.), aromatic hyrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylsulfoxide, hexamethylphosphoric triamide, etc.), or a mixture of these solvents. The hydroxylamine is usually used in an amount of at least 1 mole, preferably 1 to 5 moles, to 1 mole of the starting compound. The reaction is usually carried out at a temperature of from room temperature to about 200° C., preferably from room temperature to about 150° C., for about 1 to 15 hours.

In case of the compounds of the formula (1) wherein $R^{13}$ is a lower alkoxycarbonyl-substituted alkoxy, a lower alkanoyloxy-substituted lower alkoxy, a lower alkanoyloxy-substituted lower alkyl, a lower alkanoyloxy, a lower alkoxycarbonyl, a lower alkoxycarbonyl(lower)alkyl, $R^6$ or $R^7$ is a lower alkoxycarbonyl(lower)alkyl, $R^4$ or $R^5$ is a lower alkanoyloxy(lower)alkanoyl, a cycloalkylcarbonyl having at least one substituent of a lower alkanoyloxy on the cycloalkyl group, or a lower alkanoyloxy(lower)alkyl, or $R^1$ is a lower alkanoyloxy, these compounds can be converted by hydrolysis thereof into the corresponding compounds (1) wherein $R^{13}$ is a carboxy-substituted lower alkoxy, a hydroxy-substituted lower alkoxy, a hydroxy-substituted lower alkyl, hydroxy, carboxy, a carboxy-substituted lower alkyl, $R^6$ or $R^7$ is a carboxy-substituted lower alkyl, $R^4$ or $R^5$ is a hydroxy-substituted lower alkanoyl, a cycloalkylcarbonyl having at least one hydroxy substituent on the cycloalkyl group, or a hydroxy-substituted lower alkyl, or $R^1$ is hydroxy. The above hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described herebefore.

In the case of the compounds of the formula (1) wherein $R^1$ is a lower alkanoyl-substituted amino; $R^2$ is a an alkanoyl; $R^2$ is a group of the formula:

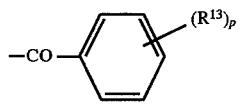

(wherein $R^{13}$ and p are as defined above), or a phenoxycarbonyl having at least one lower alkanoyl-substituted amino on the phenyl ring; $R^4$ or $R^5$ is a lower alkanoyl having optionally one to three substituents of a halogen atom, an amino-substituted lower alkanoyl having a lower alkanoyl substituent, an amino-substituted lower alkyl having a lower alkanoyl substituent, a piperidinylcarbonyl having a lower alkanoyl substituent on the nitrogen atom of the piperidine ring, or a phenylsulfonyl having at least one lower alkanoyl-substituted amino on the phenyl ring; $R^6$ or $R^7$ is a lower alkaonyl having one to three substituents of a halogen atom; or $R^4$ and $R^5$ or $R^{11}$ and $R^{12}$ form a heterocyclic group which has a lower alkanoyl substituent on the nitrogen atom of said heterocyclic group, these compounds can be converted by hydrolysis into the corresponding compounds of the formula (1) wherein $R^1$ is amino; $R^2$ is hydrogen atom; $R^2$ is a phenoxycarbonyl having at least one amino substituent on the phenyl ring; $R^4$ or $R^5$ is hydrogen atom, an amino-substituted lower alkanoyl, an amino-substituted lower alkyl, unsubstituted piperidinylcarbonyl, or a phenylsulfonyl having at least one amino substituent on the phenyl group; $R^6$ or $R^7$ is hydrogen atom; or $R^4$ and $R^5$ or $R^{11}$ and $R^{12}$ form a heterocyclic group which have no substituent on the nitrogen atom of said heterocyclic group. The hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinbefore.

In the case of the compounds of the formula (1) wherein $R^4$ or $R^5$ is a phenyl(lower)alkyl; $R^{11}$ or $R^{12}$ is a phenyl (lower)alkyl; or $R^4$ and $R^5$ or $R^{11}$ and $R^{12}$ form a heterocyclic group which has a phenyl(lower)alkyl substituent on the nitrogen atom of said heterocyclic group, these compounds can be subjected to a reduction reaction to obtain the corresponding compounds of the formula (1) wherein $R^4$ or $R^5$ is hydrogen atom; $R^{11}$ or $R^{12}$ is hydrogen atom; or $R^4$ and $R^5$ or $R^{11}$ and $R^{12}$ form a heterocyclic group which has no substituent on the nitrogen atom of said heterocyclic group. The reduction is carried out under the same conditions as in the above-mentioned reduction of converting a compound (1) wherein $R^6$ or $R^7$ is a phenyl(lower)alkoxycarbonyl into the compound (1) wherein $R^6$ or $R^7$ is hydrogen atom. Besides, the reduction reaction can also be carried out by using the same solvent and catalyst as in the catalytic hydrogenation reaction together with a hydrogen donor (e.g. formic acid, cyclohexene, hydrazine hydrate, ammonium formate, etc.), at a temperature of from room temperature to 150° C., preferably from room temperature to 100° C., for about 1 to 6 hours.

The compound of the formula (1) wherein $R^2$ is a benzoyl having at least one lower alkenyloxy substituent can be converted into the corresponding compound (1) wherein $R^2$ has at least two substituents of hydroxy and a lower alkenyl by subjecting it to Claisen rearrangement. The reaction is carried out by heating said compound in an appropriate solvent. The solvent includes solvents having a high boiling point, such as dimethylformamide, diphenyl ether, dimethylaniline, tetrahydronaphthalene, etc. The reaction is usually carried out at a temperature of 100° C. to 250° C., preferably from 150° C. to 250° C. for about 1 to 30 hours.

In the case of the compounds of the formula (1) wherein $R^{13}$ is a carboxy-substituted alkoxy, carboxy or a carboxy-substituted lower alkyl; $R^6$ or $R^7$ is a carboxy-substituted lower alkyl; $R^4$ and $R^5$ form a heterocyclic group which has at least one carboxyl substituent on the heterocyclic group, these compounds can be converted by esterification thereof into the corresponding compounds of the formula (1) wherein $R^{13}$ is a lower alkoxycarbonyl-substituted alkoxy, a lower alkoxycarbonyl, or a lower alkoxycarbonyl(lower) alkyl; $R^6$ or $R^7$ is a lower alkoxycarbonyl(lower)alkyl; or $R^4$ and $R^5$ form a heterocyclic group which has at least one lower alkoxycarbonyl substituent on the heterocyclic group. The esterification is usually carried out by reacting the compound with an alochol (e.g. methanol, ethanol, isopropanol, etc.) in the presence of a mineral acid (e.g. hydrochloric acid, sulfuric acid, etc.) and a halogenating agent (e.g. thionyl chloride, phosphorus oxychloride, phosphorus pentoxide, phosphorus trichloride, etc.), at a temperature of 0° C. to about 150° C., preferably from 50° C. to 100° C., for about 1 to 10 hours.

In the case of the compounds of the formula (1) wherein $R^4$ or $R^5$ is a lower alkoxycarbonyl or a lower alkoxycarbonyl(lower)alkyl; $R^6$ or $R^7$ is a lower alkoxycarbonyl(lower)alkyl or a carboxy(lower)alkyl; or $R^4$ and $R^5$ form a heterocyclic group which has at least one substituent of carboxy or a lower alkoxycabonyl on the heterocyclic group, these compounds can be reacted with an amine having optionally a lower alkyl-substituent or an amine having optionally a substituent selected from a lower alkyl and a lower alkanoyl under the same coniditons as in the reaction of the compound (1d) and the compound (7) in the above Reaction Scheme-5 to obtain the corresponding compounds (1) wherein $R^4$ or $R^5$ is an amido having optionally a lower alkyl substituent, or an amido-substituted lower alkyl which has optionally a substituent selected from a lower alkyl and a lower alkanoyl; $R^6$ or $R^7$ is an amido-substituted lower alkyl having optionally a lower alkyl substituent on the amido group; or $R^4$ and $R^5$ form a heterocyclic group being substituted by at least one amido group which has optionally a lower alkyl substituent. In this reaction, when the $R^6$ in the compound (1) is hydrogen atom and the $R^7$ is a carboxy(lower)alkyl, these groups may occasionally form an intermolecular amido bond to give the compound wherein $R^6$ and $R^7$ form a group of the formula:

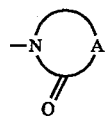

(wherein A is as defined above).

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding compounds (1) wherein $R^4$ or $R^5$ is a benzoyl which has at least one amino having one or two lower alkyl substituents; a phenylsulfonyl which phenyl ring is substituted by at least one amino having one or two lower alkyl substituents; an amino-substituted lower alkyl wherein the amino group has one or two lower alkyl substituents; or $R^{13}$ is a phenylsulfonyl-substituted lower alkoxy which phenyl ring is substituted by at least one amino having one or two lower alkyl substituents by treating them under the same conditions as in the reaction of the compound (1k) and the compound (14) in the above Reaction Scheme-9A.

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding compounds (1) wherein $R^4$ or $R^5$ is a benzoyl which has a substituent selected from a lower alkanoyl and a lower alkoxycarbonyl and further at least one amino having optionally one lower alkyl substituent; a phenylsulfonyl which phenyl ring is substituted by a lower alkanoyl and further by at least one amino having optionally one lower alkyl substituent; an amino-substituted lower alkyl wherein the amino group has a lower alkanoyl substituent and further at least one amino having optionally a lower alkyl substituent; or $R^{13}$ is a phenylsulfonyl-substituted lower alkoxy which phenyl ring is substituted by a lower alkanoyl and further by at least one amino having optionally one lower alkyl substituent by treating them under the same conditions as in the reaction of the compound (1k) and the compound (15) in the above Reaction Scheme-9A.

The compound of the formula (1d) can also be prepared by reducing the compound (1) wherein $R^2$ is a phenyl(lower) alkyl under the same conditions as in the above-mentioned reduction of the compound (1) wherein $R^2$ is a heterocyclic group-substituted carbonyl which has at least one phenyl (lower)alkoxycarbonyl on the nitrogen atom. The reduction reaction may be carried out in the presence of an acid (e.g. hydrochloric acid, etc.).

The compound (1) wherein $R^{13}$ is a tri(lower) alkylammonium can also be prepared by reacting a compound (1) wherein $R^{13}$ is a di(lower)alkylamino with a compound of the formula: $R^{50}X$ (wherein $R^{50}$ is a lower alkyl and X is a halogen atom) under the same conditions as in the reaction of the compound (1h) and the compound (11) in the above Reaction Scheme-8.

The compound (1) wherein $R^{13}$ is an ammonium(lower) alkoxy having three substituents selected from a lower alkyl, a lower alkenyl and oxo can also be prepared by reacting a compound (1) wherein $R^{13}$ is an amino-substituted lower alkoxy which has two substituents selected from a lower alkyl and/or a lower alkenyl on the amino group with a compound of the formula: $R^{51}X$ (wherein $R^{51}$ is a lower alkyl or a lower alkenyl, and X is as defined above) under the same conditions as in the reaction of the compound (1h) and the compound (11) of the above Reaction Scheme-8. Besides, said compound can be converted into a compound (1) wherein $R^{13}$ is an ammonium(lower)alkoxy having oxo substituent by oxidizing the compound under the same conditions as in the above-mentioned oxidization reaction for converting the compound (1) wherein $R^{13}$ is a lower alkylthio into the corresponding compound (1) wherein $R^{13}$ is a lower alkylsulfonyl.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, citric acid, succinic acid, benzoic acid, etc. Among the active compounds (1) of the invention, the compounds having an ammonium group can be converted into a salt thereof with a pharmaceutically acceptable halogen anion (e.g. chlorine anion, bromine anion, fluorine anion, or iodine anion). These salts are useful as an active ingredient as like as the compounds (1) in the free form.

In addition, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromtography, preparative thin layer chromatography, extraction with a solvent, and the like.

The compounds and their salts of this invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspendions are sterilized and are preferably made isotonic with the blood. In the preparation of these solutions, emulsions and suspensions, there are used conventional diluents, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Components | Amount |
| --- | --- |
| 1-[1-(4-Dimethylaminobenzoyl)-4-piperidinyl]-3,4-dihydrocarbostyril | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 1-[1-(2-Methoxy-4-ethoxybenzoyl)-4-piperidinyl]-3,4-dihydrocarbostyril | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 7-Fluoro-1-[1-(2,4-dimethoxybenzoyl)-4-piperidinyl]-3,4-dihydrocarbostyril | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

A mixture of aniline (28.0 g), 1-benzyl-4-piperidone (56.7 g), acetic acid (55 ml), platinum oxide (0.9 g) and ethanol (420 ml) is subjected to catalytic reduction at room temperature at normal pressure for 2 hours. The catalyst is removed by filtration and the filtrate is concentrated.

The resulting residue is made alkaline with a 10% aqueous sodium hydroxide solution and extracted with dichloromethane. After the extract is dried and concentrated, n-hexane is added to the residue and the formed crystals are separated by filtration and recrystallized from n-hexane to give N-(1-benzyl-4-piperidinyl)aniline (63.3 g) as colorless prisms, m.p. 73°–75° C.

Using appropriate starting materials, the same procedure as in Reference Example 1 is repeated to give the following compounds:

N-(1-Benzyl-4-piperidinyl)-4-methoxyaniline, m.p. 75°–76° C. (recrystallized from n-hexane), colorless prisms N-(1-Benzyl-4-piperidinyl)-4-methylaniline, m.p. 95°–96° C. (recrystallized from n-hexane), colorless prisms N-(1-Benzyl-4-piperidinyl)-4-fluoroaniline, m.p. 87°–88° C. (recrystallized from n-hexane), colorless prisms N-(1-Benzyl-4-piperidinyl)-3-methylaniline NMR (CDCl$_3$) δ: 1.38–1.64 (2H, m), 2.00–2.20 (4H, m), 2.26 (3H, s), 2.72–2.94 (2H, m), 3.20–3.40 (1H, m), 3.62 (2H, s), 3.55–3.70 (1H, m), 6.39 (2H, d, J=6.2 Hz), 6.49 (1H, d, J=7.4 Hz), 7.04 (1H, t, J=7.4 Hz), 7.20–7.45 (6H, m)

N-(1-Benzyl-4-piperidinyl)-3-fluoroaniline, m.p. 72°–74° C. (recrystallized from n-hexane), colorless prisms N-(1-Benzyl-4-piperidinyl)-2-methylaniline, m.p. 100°–102° C. (recrystallized from n-hexane), colorless prisms N-(1-Benzyl-4-piperidinyl)-3-acetaminoaniline NMR (CDCl$_3$) δ: 1.34–2.73 (2H, m), 1.82–2.25 (7H, m), 2.68–2.95 (2H, m), 3.28 (1H, brs), 3.51 (2H, s), 3.58–3.80 (1H, m), 6.30–6.60 (2H, m), 7.01–7.53 (7H, m)

N-(1-Benzoyl-4-piperidinyl)aniline, m.p. 161°–163° C. (recrystallized from ethanol), white powders N-(1-Benzyl-3-piperidinyl)aniline NMR (CDCl$_3$) δ: 1.4–1.8 (4H, m), 2.3–2.5 (3H, m), 2.7–2.8 (1H, m), 3.51 (2H, d, J=2.4 Hz), 3.4–3.7 (1H, m), 3.9–4.1 (1H, m), 6.6–6.8 (3H, m), 7.1–7.3 (7H, m)

N-(1-Benzyl-3-pyrrolidinyl)aniline

NMR (CDCl$_3$) δ: 1.6–1.8 (1H, m), 2.2–2.6 (3H, m), 2.7–2.9 (2H, m), 3.62 (2H, s), 3.8–4.2 (1H, m), 6.5–6.8 (3H, m), 7.1–7.4 (7H, m)

N-(1-Benzyl-3-methyl-4-piperidinyl)aniline

NMR (CDCl$_3$) δ: 0.9–1.1 (3H, m), 1.6–2.0 (2H, m), 2.0–2.7 (4H, m), 2.8–3.0 (1H, m), 3.3–3.7 (3H, m), 6.5–6.7 (3H, m), 7.1–7.4 (7H, m)

Reference Example 2

To a mixture of N-(1-benzyl-4-piperidinyl)aniline (0.9 g), diisopropyl ether (30 ml) and triethylamine (0.5 g) is added β-ethoxyacrylic acid chloride (0.7 g) in portions at 60° C. After refluxing for 1 hour, the reaction mixture is poured into ice-water and extracted with ethyl acetate. The extract is dried and concentrated and to the resulting residue is added n-hexane and the formed crystals are separated by filtration and recrystallized from n-hexane to give N-(β-ethoxyacryloyl)-N-(1-benzyl-4-piperidinyl)aniline (1.1 g) as white powders, m.p. 106°–108° C.

Reference Example 3

To a mixture of N-(1-benzyl-4-piperidinyl)aniline (1.8 g), diisopropyl ether (20 ml) and triethylamine (0.87 g) is added dropwise a solution of β-n-butoxyacrylic acid chloride (1.4 g) in diisopropyl ether (5 ml) with stirring and heating at 70° C. After completion of dropwise addition, the mixture is further stirred with heating at the same temperature for 0.5 hour. After cooling, water is added to the reaction mixture and the mixture is subjected to extraction with ethyl acetate. The extract is washed with water and dried over magnesium sulfate. The solvent is distilled off under reduced pressure and the resulting residue is purified by silica gel column chromatography give N-(β-n-butoxyacryloyl)-N-(1-benzyl-4-piperidinyl)aniline (2.6 g).

NMR (CDCl$_3$) δ: 0.86 (3H, t, J=7.1 Hz), 1.2–1.4 (1H, m), 1.4–1.6 (2H, m), 1.6–1.9 (2H, m), 2.1–2.3 (1H, m), 2.4–2.6 (3H, m), 2.7–2.9 (1H, m), 3.4–3.7 (4H, m), 4.86 (1H, d, J=12 Hz), 5.1–5.3 (1H, m), 7.1–7.5 (10H, m), 7.47 (1H, d, J=12 Hz)

Using appropriate starting materials, the procedure of above Reference Examples 2 and 3 is repeated to give the following compounds:

N-(β-n-Butoxyacryloyl)-N-(1-benzyl-3-piperidinyl)aniline

NMR (CDCl$_3$) δ: 0.85 (3H, t, J=7 Hz), 0.8–2.0 (10H, m), 2.6–2.8 (1H, m), 3.0–3.2 (1H, m), 3.40, 3.53 (2H, AB-q, J=13.2 Hz), 3.62 (2H, t, J=6.3 Hz), 4.7–5.0 (2H, m), 7.0–7.6 (10H, m)

N-(β-n-Butoxyacryloyl)-N-(4-nitrophenyl)aniline

NMR (CDCl$_3$) δ: 0.90 (3H, t, J=7.2 Hz), 1.3–1.6 (2H, m), 1.6–1.8 (2H, m), 3.76 (2H, t, J=6.4 Hz), 5.17 (1H, d, J=11.9 Hz), 7.1–7.6 (7H, m), 7.66 (1H, d, J=11.9 Hz), 8.14 (2H, d, J=9.2 Hz)

Reference Example 4

2-(2-Carbamoylethyl)aniline (37 g) and 1-benzoyl-4-oxopiperidine (67.6 g) are dissolved in ethanol (500 ml) and to the solution is added acetic acid to adjust the pH of the solution to about 5.5. To the solution is further added PtO$_2$ (1 g) and the mixture is stirred under 1 atm. at room temperature under H$_2$ atmosphere. When H$_2$ is absorbed up to 5 liters, the reaction is stopped and the catalyst is separated by filtration. The filtrate is concentrated to give N-(1-benzoyl-4-piperidinyl)-2-(2-carbamoylethyl)aniline.

Reference Example 5

To a concentrated sulfuric acid (15 ml) is added in portions N-(β-ethoxyacryloyl)-N-(1-benzyl-4-piperidinyl)aniline (1.1 g) at 60° C. After stirring the mixture at the same temperature for 15 minutes, the reaction mixture is poured into ice-water, made alkaline with a 10% aqueous sodium hydroxide solution and extracted with dichloromethane. After the extract is concentrated by distilling off the solvent, the resulting residue is purified by silica gel column chromatography (eluent; dichloromethane:methanol=50:1) and recrystallized from ethyl acetate to give 1-(1-benzyl-4-piperidinyl)carbostyril (0.8 g) as white powders, m.p. 97°–99° C.

Using appropriate starting materials, the procedure of Reference Example 5 is repeated to give the following compounds:

6-Methoxy-1-(1-benzyl-4-piperidinyl)carbostyril hydrochloride as white powders, m.p. 227°–230° C. (recrystallized from methanol)

6-Methyl-1-(1-benzyl-4-piperidinyl)carbostyril hydrochloride as white powders, m.p. 259°–261° C. (recrystallized from ethanol)

6-Fluoro-1-(1-benzyl-4-piperidinyl)carbostyril hydrochloride as white powders, m.p. 232°–236° C. (recrystallized from ethanol)

7-Methyl-1-(1-benzyl-4-piperidinyl)carbostyril

NMR (CDCl$_3$) δ: 1.62–1.85 (2H, m), 2.18–2.40 (2H, m), 2.52 (3H, s), 2.75–3.22 (4H, m), 3.61 (2H, s), 5.28 (1H, brs), 6.58 (1H, d, J=9.3 Hz), 7.01 (1H, d, J=7.9 Hz), 7.20–7.48 (6H, m), 7.55 (1H, d, J=9.3 Hz)

7-Fluoro-1-(1-benzyl-4-piperidinyl)carbostyril hydrochloride as white powders, m.p. 254°–257° C. (recrystallized from ethanol)

8-Methyl-1-(1-benzyl-4-piperidinyl)carbostyril hydrochloride as white powders, m.p. 253°–257° C. (recrystallized from ethanol)

7-Acetamido-1-(1-benzyl-4-piperidinyl)carbostyril

NMR (CDCl$_3$) δ: 1.60–1.82 (2H, m), 2.11–2.35 (2H, m), 2.24 (3H, s), 2.72–3.15 (4H, m), 3.55 (2H, s), 5.25 (1H, bs), 6.54 (1H, d, J=8.7 Hz), 7.14–7.60 (9H, m), 8.28 (1H, s), 8.63 (1H, s)

1-(1-Benzyl-3-pyrrolidinyl)carbostyril

NMR (CDCl$_3$) δ: 2.1–2.7 (4H, m), 3.1–3.2 (1H, m), 3.2–3.4 (1H, m), 3.59 (1H, d, J=12.9 Hz), 3.87 (1H, d, J=12.9 Hz), 6.4–6.5 (1H, m), 6.64 (1H, d, J=9.4 Hz), 7.1–7.7 (9H, m), 8.74 (1H, d, J=8.6 Hz)

1-(1-Benzyl-3-methyl-4-piperidinyl)carbostyril

NMR (CDCl$_3$) δ: 1.30 (3H, d, J=7.1 Hz), 1.7–1.8 (1H, m), 2.0–2.2 (1H, m), 2.3–2.5 (2H, m), 2.8–2.9 (1H, m), 3.0–3.2

(1H, m), 3.48 (1H, d, J=13.5 Hz), 3.62 (1H, d, J=13.5 Hz), 3.6–3.9 (1H, m), 4.4–4.6 (1H, m), 6.58 (2H, d, J=9.4 Hz), 7.56 (2H, d, J=9.4 Hz), 7.1–7.6 (9H, m)

1-(1-Benzyl-4-piperidinyl)-7-dimethylaminocarbostyril

NMR (CDCl$_3$) δ: 1.65–1.82 (2H, m), 2.18–2.40 (2H, m), 2.80–3.20 (4H, m), 3.12 (6H, s), 3.61 (2H, s), 5.28 (1H, brs), 6.35 (1H, d, J=9.2 Hz), 6.65 (1H, dd, J=8.8 Hz, 2.2 Hz), 6.80–7.10 (1H, m), 7.15–7.40 (6H, m), 7.48 (1H, d, J=9.2 Hz)

1-(4-Nitrophenyl)carbostyril

NMR (CDCl$_3$) δ: 6.60 (1H, d, J=8.3 Hz), 6.78 (1H, d, J=9.6 Hz), 7.2–7.4 (2H, m), 7.52 (2H, d, J=9.0 Hz), 7.64 (1H, dd, J=1.5 Hz, 6.1 Hz), 7.83 (1H, d, J=9.6 Hz), 8.48 (2H, d, J=9.0 Hz)

Reference Example 6

To N-(1-benzyl-4-piperidinyl)aniline (13.3 g) is added benzene (70 ml) and thereto is added dropwise a solution of diketene (5.0 g) in benzene (10 ml) at room temperature. After refluxing for 1 hour, the reaction mixture is concentrated by distilling off the solvent. To the resulting residue are added ethyl acetate and diethyl ether and the formed crystals are separated by filtration and recrystallized from ethyl acetate/n-hexane to give N-(1-benzyl-4-piperidinyl)-α-acetoacetoanilide (16.0 g) as white powders, m.p. 124°–126° C.

Reference Example 7

N-(1-Benzyl-4-piperidinyl)-α-acetoacetoanilide (13.2 g) is added in portions to concentrated sulfuric acid (80 ml) at 80° C. After stirring at 90° C. for 1 hour, the reaction mixture is poured into ice-water, made alkaline with potassium carbonate and then extracted with ethyl acetate. After the extract is concentrated by distilling off the solvent, the resulting residue is purified by silica gel column chromatography (eluent; ethyl acetate:methanol=100:1) to give 4-methyl-1-(1-benzyl-4-piperidinyl)carbostyril (1.5 g).

NMR (CDCl$_3$) δ: 1.60–1.85 (2H, m), 2.15–2.35 (2H, m), 2.42 (3H, s), 2.65–3.20 (4H, m), 3.59 (2H, s), 5.29 (1H, brs), 7.13–7.95 (9H, m)

Reference Example 8

To 1-(1-benzyl-4-piperidinyl)-7-acetylaminocarbostyril (3.0 g) are added ethanol (32 ml) and an aqueous 10% sodium hydroxide solution (32 ml) and the mixture is refluxed for 1 hour. After the reaction mixture is concentrated by distilling off the solvent, water is added to the residue and the resulting solution is extracted with dichloromethane. The extract is concentrated by distilling off the solvent and recrystallized from ethanol/chloroform to give 1-(1-benzyl-4-piperidinyl)-7-aminocarbostyril (2.4 g) as white powders, m.p. 238°–241° C.

Reference Example 9

To a mixture of 1-(1-benzyl-4-piperidinyl)-7-aminocarbostyril (0.7 g), methanol (10 ml) and 37% formalin (1.4 ml) is added NaBH$_3$CN (0.3 g) in portions. Thereafter, acetic acid (0.7 ml) is added thereto in portions at room temperature and the mixture is stirred at the same temperature for 1 hour. After completion of the reaction, water is added to the reaction mixture and the mixture is neutralized with an aqueous potassium carbonate and then extracted with ethyl acetate. The extract is concentrated by distilling off the solvent to give 1-(1-benzyl-4-piperidinyl)-7-dimethylaminocarbostyril (0.7 g).

NMR (CDCl$_3$) δ: 1.65–1.82 (2H, m), 2.18–2.40 (2H, m), 2.80–3.20 (4H, m), 3.12 (6H, s), 3.61 (2H, s), 5.28 (1H, brs), 6.35 (1H, d, J=9.2 Hz), 6.65 (1H, dd, J=8.8 Hz, 2.2 Hz), 6.80–7.10 (1H, m), 7.15–7.40 (6H, m), 7.48 (1H, d, J=9.2 Hz)

Reference Example 10

To 10% Pd—C (0.1 g) is added acetic acid (20 ml) and then 1-(4-nitrophenyl)carbostyril (0.9 g) and the mixture is subjected to catalytic reduction at 80° C. under normal pressure. After completion of the reaction, 10% Pd—C is removed by filtration and the resulting solution is concentrated under reduced pressure. To the concentrate is added water and the solution is made alkaline with an aqueous sodium hydroxide solution and then extracted with dichloromethane. The extract is washed with water and dried over magnesium sulfate. The solvent is distilled off under reduced pressure and the residue is purified by silica gel column chromatography and recrystallized from ethanol to give 1-(4-aminophenyl)carbostyril (0.66 g) as brown powders, m.p. 225°–230° C.

NMR (CDCl$_3$) δ: 2.7–2.9 (2H, m), 3.0–3.1 (2H, m), 3.8 (2H, brs), 6.50 (1H, dd, J=1.4 Hz, 7.8 Hz), 6.7–6.8 (2H, m), 6.8–7.1 (4H, m), 7.1–7.2 (1H, m)

Reference Example 11

To a solution of 3,4-dihydrocarbostyril (3 g) in N-methylpyrrolidone (30 ml) are added p-iodobenzoic acid (5.58 g), copper (0.3 g) and potassium carbonate (3.03 g) and the mixture is stirred at 150° C. for 4 hours. An aqueous sodium hydroxide solution is added to the reaction mixture and the mixture is washed with dichloromethane. The aqueous layer is made acidic with concentrated hydrochloric acid and then extracted with diethyl ether and the extract is dried over magnesium sulfate. After the solvent is distilled off under reduced pressure, methanol (50 ml) is added to the residue and thionyl chloride (10 ml) is slowly while to the solution while stirring with ice-cooling. After completion of dropwise addition, the mixture is refluxed for 0.5 hour. After methanol is distilled off under reduced pressure, water is added to the residue and the solution is extracted with dichloromethane and dried over magnesium sulfate. The solvent is distilled off under reduced pressure and the resulting residue is purified by silica gel column chromatography to give 1-(4-methoxycarbonylphenyl)-3,4-dihydrocarbostyril (1.44 g).

NMR (CDCl$_3$) δ: 2.7–2.9 (2H, m), 3.0–3.2 (2H, m), 3.93 (3H, s), 6.3–6.4 (1H, m), 6.9–7.1 (2H, m), 7.2–7.3 (1H, m), 7.34 (2H, d, J=8.6 Hz), 8.17 (2H, d, J=8.6 Hz)

Reference Example 12

To a solution of 1-(4-methoxycarbonylphenyl)-3,4-dihydrocarbostyril (1.84 g) in methanol (40 ml) is added a 5% aqueous sodium hydroxide solution (20 ml) and the mixture is stirred at room temperature overnight. Methanol is distilled off under reduced pressure and to the residue is added water. After the solution is washed with dichloromethane, the aqueous layer is made acidic with concentrated hydrochloric acid and extracted with diethyl ether and dried over magnesium sulfate. The solvent is distilled off under reduced pressure and the resulting residue is purified by silica gel column chromatography, followed by recrystallization from ethanol to give 1-(4-carboxyphenyl)-3,4-dihydrocarbostyril (0.87 g) as pale yellow powders, m.p. 265°–270° C.

NMR (DMSO-d$_6$) δ: 2.7–2.9 (2H, m), 2.9–3.2 (2H, m), 6.21 (1H, d, J=7.4 Hz), 6.9–7.2 (2H, m), 7.29 (1H, d, J=6.3 Hz), 7.38 (2H, d, J=8.3 Hz), 8.08 (2H, d, J=8.3 Hz)

Reference Example 13

Using appropriate starting materials, the procedure of Reference Example 1 is repeated to give the following compounds:

N-(1-Benzyl-4-piperidinyl)-3,4-difluoroaniline
  NMR (CDCl$_3$) δ: 1.30–1.65 (2H, m), 1.86–2.25 (4H, m), 2.72–2.97 (2H, m), 3.04–3.30 (1H, m), 3.36–3.60 (3H, m), 6.11–6.46 (2H, m), 6.80–7.00 (1H, m), 7.30 (5H, s)

N-(1-Benzyl-4-piperidinyl)-3,5-difluoroaniline
  NMR (CDCl$_3$) δ: 1.45–1.62 (2H, m), 1.95–2.25 (4H, m), 2.75–2.93 (2H, m), 3.10–3.30 (1H, m), 3.52 (2H, s), 3.70–3.87 (1H, m), 5.98–6.15 (3H, m), 7.20–7.48 (5H, m)

Reference Example 14

Using appropriate starting materials, the procedure of Reference Example 5 is repeated to give the following compounds:

6,7-Difluoro-1-(1-benzyl-4-piperidinyl)carbostyril as white powders (recrystallized from ethanol), m.p. 132°–134° C.

5,7-Difluoro-1-(1-benzyl-4-piperidinyl)carbostyril as colorless prisms (recrystallized from ethanol), m.p. 165°–166° C.

Reference Example 15

To a mixture of N-(1-benzyl-4-piperidinyl)aniline (6.4 g), diisopropyl ether (70 ml) and triethylamine (4.8 ml) is added at 70° C. a solution of α-methylcinnamoyl chloride (4.9 g) in diisopropyl ether (10 ml). After stirring at the same temperature for 30 minutes, water is added to the reaction solution and the mixture is extracted with ethyl acetate. The extract is concentrated by distilling off the solvent and to the resulting residue is added diethyl ether and the formed crystals are separated by filtration to give N-(α-methylcinnamoyl)-N-(1-benzyl-4-piperidinyl)aniline (8.9 g), m.p. 150°–152° C.

Reference Example 16

To grinded aluminum chloride (26 g) are added chlorobenzene (26 ml) and N-(α-methylcinnamoyl)-N-(1-benzyl-4-piperidinyl)aniline (8.7 g) and the mixture is heated at 110° C. for 1 hour. After cooling, the reaction mixture is poured into ice-water and made alkaline with an aqueous sodium hydroxide solution. After extraction with dichloromethane, the extract is concentrated and the resulting residue is purified by silica gel column chromatography (eluent; methylene chloride). The purified substance is converted into hydrochloride and then recrystallized from ethanol/water to give 1-(1-benzyl-4-piperidinyl)-3-methylcarbostyril hydrochloride (5.8 g) as colorless needles, m.p. 274°–276° C.

Reference Example 17

A mixture of o-aminobenzyl alcohol (20.4 g), ethanol (300 ml), 1-benzyl-4-piperidone (31.6 g) and acetic acid (40 ml) is refluxed for 30 minutes. After concentrating the reaction mixture, water is added to the resulting residue and the mixture is extracted with dichloromethane. After concentrating the extract to remove the solvent, n-hexane is added to the resulting residue and the formed crystals are separated by filtration to give 1-benzylspiro[piperidin-4,2'-(4H-1',2'-dihydro-3,1-benzoxadine)] (37.7 g), m.p. 114°–115° C.

Reference Example 18

To a mixture of 1-benzylspiro[piperidin-4,2'-(4H-1',2'-dihydro-3,1-benzoxadine)] (10.3 g), methanol (80 ml) and sodium cyanoborohydride (2.2 g) is added acetic acid (4.1 ml) in portions and the mixture is stirred at room temperature overnight. The reaction mixture is diluted with water and made alkaline with an aqueous potassium carbonate solution and the formed crystals are separated by filtration to give N-(1-benzyl-4-piperidinyl)-o-hydroxymethylaniline (9.4 g), m.p. 164°–168° C.

Reference Example 19

A mixture of N-(1-benzyl-4-piperidinyl)-o-hydroxymethylaniline (2.9 g), chloroform (100 ml) and manganese dioxide (12 g) is refluxed for 1 hour. After cooling, the mixture is filtered and the filtrate is concentrated. The resulting residue is purified by silica gel column chromatography (eluent; dichloromethane) to give N-(1-benzyl-4-piperidinyl)-o-formylaniline (2.4 g) as yellow powders, m.p. 87°–90° C.

Reference Example 20

A mixture of N-(1-benzyl-4-piperidinyl)-o-formylaniline (32.0 g), diethyl malonate (35.4 g), piperidine (5 ml), acetic acid (2.5 ml), anhydrous toluene (320 ml) and molecular sieves (32 g) is refluxed for 8 hours. After concentrating the reaction mixture, dichloromethane is added to the residue and the mixture is filtered. Water is added to the filtrate and the mixture is extracted with dichloromethane. After concentrating the extract, the resulting residue is purified by silica gel column chromatography (eluent; dichloromethane/methanol=50/1) to give 3-ethoxycarbonyl-1-(1-benzyl-4-piperidinyl)carbostyril (27.2 g).

NMR (CDCl$_3$) δ: 1.41 (3H, t, J=7.1 Hz), 1.65–1.86 (2H, m), 2.14–2.40 (2H, m), 2.68–3.25 (4H, m), 3.53 (2H, s), 4.41 (2H, q, J=7.1 Hz), 5.28 (1H, brs), 7.16–7.93 (9H, m), 8.30 (1H, s)

Reference Example 21

Using appropriate starting materials, the procedure of Reference Example 1 is repeated to give the following compounds:

N-(1-Benzoyl-4-piperidinyl)-3-fluoroaniline as white powders (recrystallized from ethanol), m.p. 114°–116° C.

N-(1-Benzoyl-4-piperidinyl)-3,5-difluoroaniline as white powders (recrystallized from ethanol), m.p. 175°–176° C.

Reference Example 22

Using appropriate starting materials, the procedure of Reference Examples 17 and 18 is repeated to give the following compound:

N-(1-Benzyl-4-piperidinyl)-2-hydroxymethyl-3-methylaniline as white powders, m.p. 182°–184° C.

Reference Example 23

Using appropriate starting materials, the procedure of Reference Example 19 is repeated to give the following compound:

N-(1-Benzyl-4-piperidinyl)-2-formyl-3-methylaniline as yellow powders, m.p. 114°–116° C.

Reference Example 24

To N-(1-benzyl-4-piperidinyl)-2-formyl-3-methylaniline (7.0 g) are added methanol (100 ml) and methyl (triphenylphosphoranylidene)acetate (15 g) and the mixture is refluxed for 1 hour. After cooling, the formed crystals are separated by filtration to give methyl 2-methyl-5-[(1-benzyl- 4-piperidinyl)amino]cinnamate (5.6 g) as pale yellow powders, m.p. 140°–142° C.

Example 1

To N-(1-benzoyl-4-piperidinyl)-2-(2-carbamoylethyl) aniline (85 g) prepared in Reference Example 4 is added 5% hydrochloric acid (500 ml) and the mixture is refluxed for 5 hours. After cooling, the reaction mixture is extracted with diethyl ether and the aqueous layer is made alkaline with a 50% aqueous sodium hydroxide solution and extracted with ethyl acetate. The extract is dried over sodium carbonate and concentrated. The concentrate is purified by silica gel column chromatography (eluent; n-hexane/ethyl acetate=1/0–10/1) and recrystallized from ethanol/n-hexane to give 1-(1-benzoyl-4-piperidinyl)-3,4-dihydrocarbostyril (35 g) as white powders, m.p. 108°–111° C.

Examples 2 to 383C

Using appropriate starting materials, the procedure of Example 1 is repeated to give the following compounds as shown in Table 1. Table 2 shows the NMR analysis of these compounds.

TABLE 1

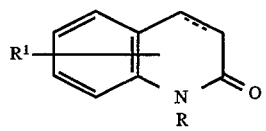

Example 2

Structure

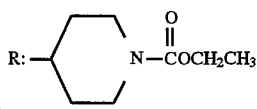

R¹: H
Bond between 3- and 4-positions in the carbostyril ring: single bond
Crystalline form: white powders
Recrystallization solvent: ethanol/n-hexane
Melting point: 82–83° C.
Form: Free Example 3

Structure

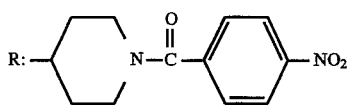

R¹: H
Bond between 3- and 4-positions in the carbostyril ring: single bond
Crystalline form: pale yellow powders
Recrystallization solvent: ethanol/n-hexane
Melting point: 142–145° C.
Form: Free Example 4

Structure

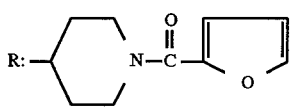

R¹: H
Bond between 3- and 4-positions in the carbostyril ring: single bond
Crystalline form: white powders
Recrystallization solvent: ethanol/n-hexane
Melting point: 108–111° C.
Form: Free TABLE 1-continued Example 5

Structure

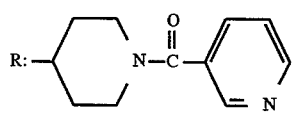

R¹: H
Bond between 3- and 4-positions in the
carbostyril ring: single bond
Crystalline form: white powders
Recrystallization solvent: ethanol/n-hexane
Melting point: 113–116° C.
Form: Free Example 6

Structure

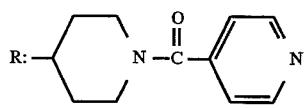

R¹: H
Bond between 3- and 4-positions in the
carbostyril ring: single bond
Crystalline form: white powders
Recrystallization solvent: ethanol/n-hexane
Melting point: 105–108° C.
Form: Free Example 7

Structure

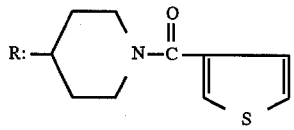

R¹: H
Bond between 3- and 4-positions in the
carbostyril ring: single bond
Crystalline form: white powders
Recrystallization solvent: ethanol/n-hexane
Melting point: 129–132° C.
Form: Free Example 8

Structure

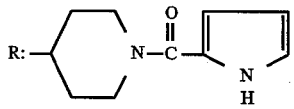

R¹: H
Bond between 3- and 4-positions in the
carbostyril ring: single bond
Crystalline form: white powders
Recrystallization solvent: ethanol/n-hexane
Melting point: 161–162° C. (decomposition)
Form: Free Example 9

Structure

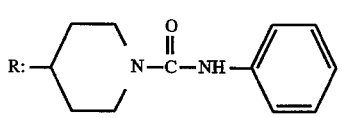

TABLE 1-continued

R¹: H
Bond between 3- and 4-positions in the
carbostyril ring: single bond
Crystalline form: white powders
Recrystallization solvent: ethanol/n-hexane
Melting point: 194–196° C.
Form: Free
Example 10

Structure

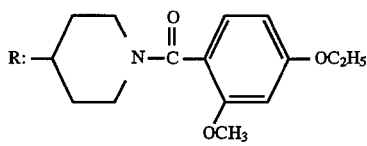

R¹: H
Bond between 3- and 4-positions in the
carbostyril ring: double bond
Crystalline form: white powders
Recrystallization solvent: ethanol/n-hexane
Melting point: 172–174° C.
Form: Free
Example 11

Structure

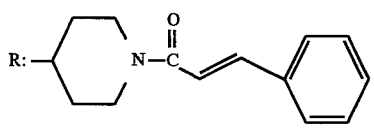

R¹: H
Bond between 3- and 4-positions in the
carbostyril ring: single bond
Crystalline form: white powders
Recrystallization solvent: ethanol/n-hexane
Melting point: 144–147° C.
Form: Free
Example 12

Structure

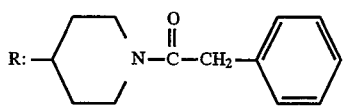

R¹: H
Bond between 3- and 4-positions in the
carbostyril ring: single bond
NMR analysis: 1)
Form: Free
Example 13

Structure

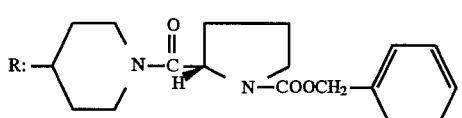

R¹: H
Bond between 3- and 4-positions in the
carbostyril ring: single bond
Crystalline form: white powders
Recrystallization solvent: ethanol/n-hexane
Melting point: 143–147° C.
Form: Free TABLE 1-continued Example 14

Structure

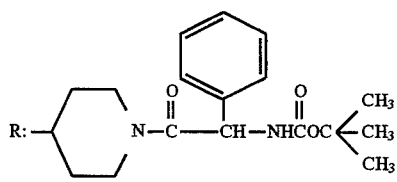

R¹: H
Bond between 3- and 4-positions in the
carbostyril ring: single bond
Crystalline form: white powders
Recrystallization solvent: ethanol/n-hexane
Melting point: 143–146° C.
Form: Free Example 15

Structure

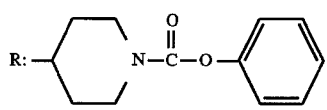

R¹: H
Bond between 3- and 4-positions in the
carbostyril ring: single bond
Crystalline form: white powders
Recrystallization solvent: diethyl ether/n-hexane
Melting point: 138–140° C.
Form: Free Example 16

Structure

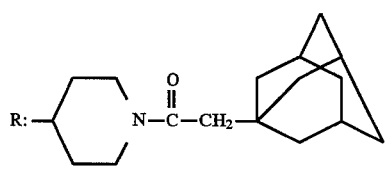

R¹: H
Bond between 3- and 4-positions in the
carbostyril ring: single bond
Crystalline form: white powders
Recrystallization solvent: n-hexane
Melting point: 143–145° C.
Form: Free Example 17

Structure

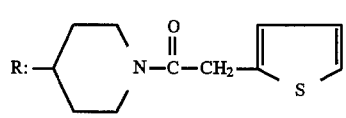

R¹: H
Bond between 3- and 4-positions in the
carbostyril ring: single bond
NMR analysis: 2)
Form: Free TABLE 1-continued Example 18

Structure

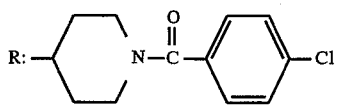

R¹: H
Bond between 3- and 4-positions in the
carbostyril ring: single bond
Crystalline form: white powders
Recrystallization solvent: n-hexane/ethanol
Melting point: 111–112° C.
Form: Free Example 19

Structure

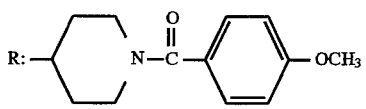

R¹: H
Bond between 3- and 4-positions in the
carbostyril ring: single bond
Crystalline form: white powders
Recrystallization solvent: n-hexane/ethanol
Melting point: 93–96° C.
Form: Free Example 20

Structure

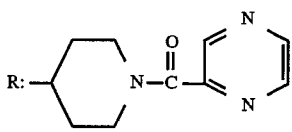

R¹: H
Bond between 3- and 4-positions in the
carbostyril ring: single bond
NMR analysis: 3)
Form: Free Example 21

Structure

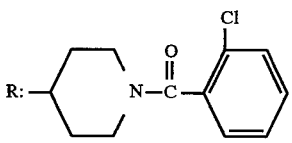

R¹: H
Bond between 3- and 4-positions in the
carbostyril ring: single bond
Crystalline form: white powders
Recrystallization solvent: n-hexane/ethanol
Melting point: 175–178° C.
Form: Free Example 22

Structure

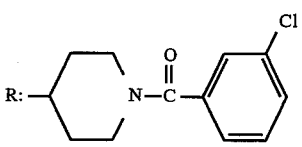

TABLE 1-continued

R¹: H
Bond between 3- and 4-positions in the
carbostyril ring: single bond
Crystalline form: white powders
Recrystallization solvent: n-hexane/ethanol
Melting point: 123–126° C.
Form: Free
Example 23

Structure

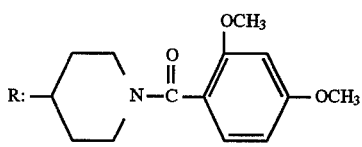

R¹: H
Bond between 3- and 4-positions in the
carbostyril ring: single bond
Crystalline form: white powders
Recrystallization solvent: n-hexane/ethanol
Melting point: 141–143° C.
Form: Free
Example 24

Structure

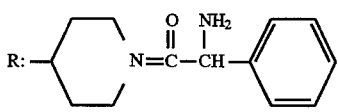

R¹: H
Bond between 3- and 4-positions in the
carbostyril ring: single bond
Crystalline form: white powders
Recrystallization solvent: diethyl ether
Melting point: 116–120° C.
Form: Free
Example 25

Structure

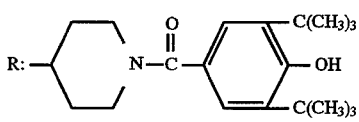

R¹: H
Bond between 3- and 4-positions in the
carbostyril ring: single bond
Crystalline form: white powders
Recrystallization solvent: n-hexane/ethanol
Melting point: 134–136° C.
Form: Free
Example 26

Structure

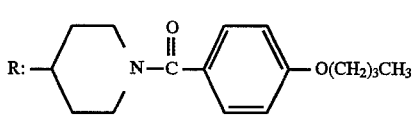

R¹: H
Bond between 3- and 4-positions in the
carbostyril ring: single bond
NMR analysis: 4)
Form: Free TABLE 1-continued Example 27

Structure

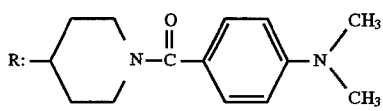

R¹: H
Bond between 3- and 4-positions in the
carbostyril ring: single bond
Crystalline form: white powders
Recrystallization solvent: n-hexane/ethanol
Melting point: 153–155° C.
Form: Free Example 28

Structure

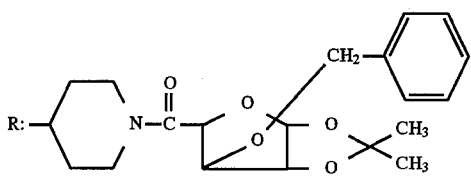

R¹: H
Bond between 3- and 4-positions in the
carbostyril ring: single bond
NMR analysis: 5)
Form: Free Example 29

Structure

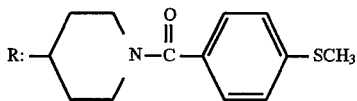

R¹: H
Bond between 3- and 4-positions in the
carbostyril ring: single bond
NMR analysis: 6)
Form: Free Example 30

Structure

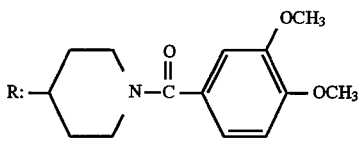

R¹: H
Bond between 3- and 4-positions in the
carbostyril ring: single bond
Crystalline form: white powders
Recrystallization solvent: n-hexane/ethanol
Melting point: 121–124° C.
Form: Free Example 31

Structure

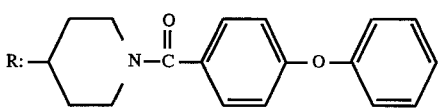

TABLE 1-continued

R[1]: H
Bond between 3- and 4-positions in the
carbostyril ring: single bond
Crystalline form: white powders
Recrystallization solvent: n-hexane/ethanol
Melting point: 205–208° C.
Form: Free Example 32

Structure

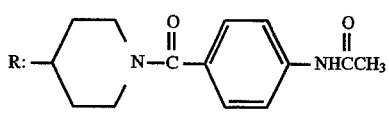

R[1]: H
Bond between 3- and 4-positions in the
carbostyril ring: single bond
Crystalline form: white amorphous
NMR analysis: 7)
Recrystallization solvent: n-hexane
Melting point: 85–90° C.
Form: Free Example 33

Structure

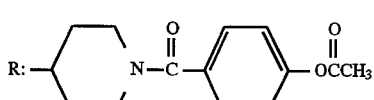

R[1]: H
Bond between 3- and 4-positions in the
carbostyril ring: single bond
Crystalline form: white powders
Recrystallization solvent: n-hexane/ethanol
Melting point: 170–171° C.
Form: Free Example 34

Structure

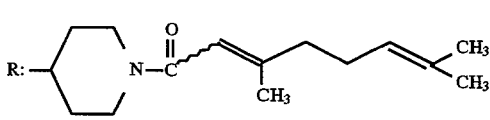

R[1]: H
Bond between 3- and 4-positions in the
carbostyril ring: single bond
NMR analysis: 8)
Form: Free Example 35

Structure

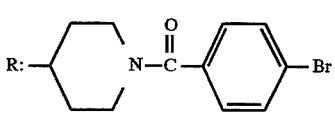

R[1]: H
Bond between 3- and 4-positions in the
carbostyril ring: single bond
Crystalline form: white powders
Recrystallization solvent: n-hexane/ethanol
Melting point: 124–126° C.
Form: Free TABLE 1-continued Example 36

Structure

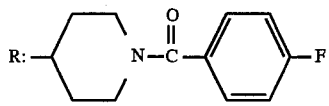

R¹: H
Bond between 3- and 4-positions in the
carbostyril ring: single bond
Crystalline form: white powders
Recrystallization solvent: n-hexane/ethanol
Melting point: 105–107° C.
Form: Free Example 37

Structure

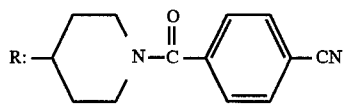

R¹: H
Bond between 3- and 4-positions in the
carbostyril ring: single bond
Crystalline form: pale yellow powders
Recrystallization solvent: n-hexane/ethanol
Melting point: 169–172° C.
Form: Free Example 38

Structure

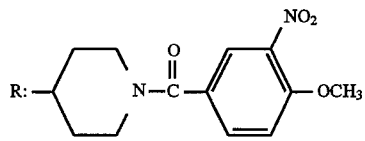

R¹: H
Bond between 3- and 4-positions in the
carbostyril ring: single bond
Crystalline form: white powders
Recrystallization solvent: n-hexane/ethanol
Melting point: 85–90° C.
Form: Free
NMR analysis: 9)

Example 39

Structure

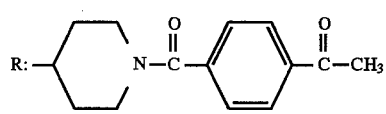

R¹: H
Bond between 3- and 4-positions in the
carbostyril ring: single bond
NMR analysis: 10)
Form: Free Example 40

Structure

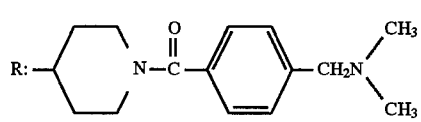

TABLE 1-continued

R[1]: H
Bond between 3- and 4-positions in the
carbostyril ring: single bond
Crystalline form: white powders
Recrystallization solvent: n-hexane/ethanol
Melting point: 83–86° C.
Form: Free

Example 41

Structure

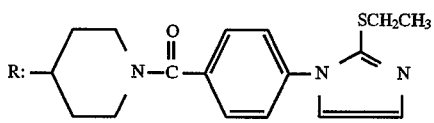

R[1]: H
Bond between 3- and 4-positions in the
carbostyril ring: single bond
NMR analysis: 11)
Form: Free

Example 42

Structure

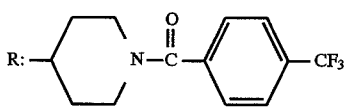

R[1]: H
Bond between 3- and 4-positions in the
carbostyril ring: single bond
Crystalline form: white powders
Recrystallization solvent: n-hexane/ethanol
Melting point: 161–163° C.
Form: Free

Example 43

Structure

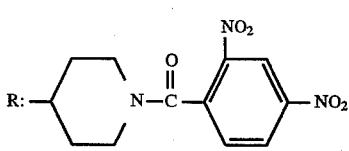

R[1]: H
Bond between 3- and 4-positions in the
carbostyril ring: single bond
Crystalline form: pale yellow powders
Recrystallization solvent: n-hexane/ethanol
Melting point: 108–111° C.
Form: Free

Example 44

Structure

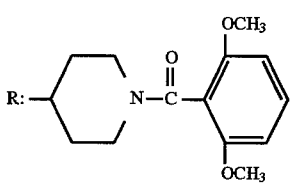

R[1]: H
Bond between 3- and 4-positions in the
carbostyril ring: single bond
Crystalline form: white powders
Recrystallization solvent: n-hexane/ethanol
Melting point: 202–204° C.
Form: Free

TABLE 1-continued

Example 45

Structure

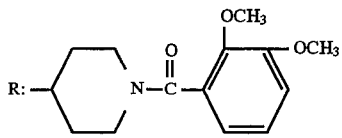

R¹: H
Bond between 3- and 4-positions in the
carbostyril ring: single bond
Crystalline form: white powders
Recrystallization solvent: n-hexane/ethanol
Melting point: 194–195° C.
Form: Free Example 46

Structure

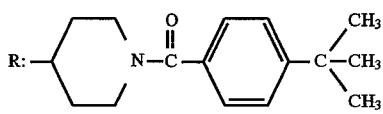

R¹: H
Bond between 3- and 4-positions in the
carbostyril ring: single bond
Crystalline form: white powders
Recrystallization solvent: n-hexane/ethanol
Melting point: 110–112° C.
Form: Free Example 47

Structure

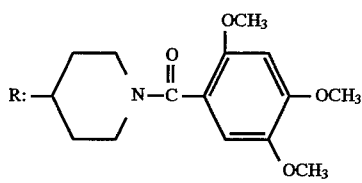

R¹: H
Bond between 3- and 4-positions in the
carbostyril ring: single bond
Crystalline form: white powders
Recrystallization solvent: n-hexane/ethanol
Melting point: 123–126° C.
Form: Free Example 48

Structure

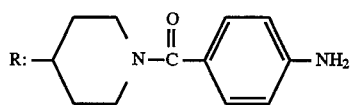

R¹: H
Bond between 3- and 4-positions in the
carbostyril ring: single bond
Crystalline form: white powders
Recrystallization solvent: n-hexane/ethanol
Melting point: 198–199° C.
Form: Free

TABLE 1-continued

Example 49

Structure

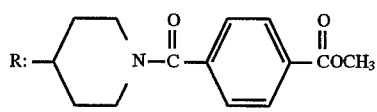

R[1]: H
Bond between 3- and 4-positions in the
carbostyril ring: single bond
Crystalline form: white powders
Recrystallization solvent: n-hexane/ethanol
Melting point: 160–162° C.
Form: Free Example 50

Structure

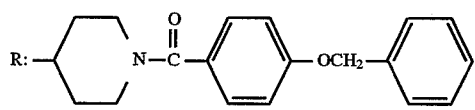

R[1]: H
Bond between 3- and 4-positions in the
carbostyril ring: single bond
NMR analysis: 12)
Form: Free Example 51

Structure

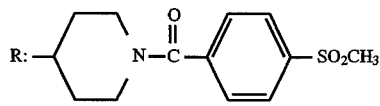

R[1]: H
Bond between 3- and 4-positions in the
carbostyril ring: single bond
Crystalline form: white powders
Recrystallization solvent: n-hexane/ethanol
Melting point: 194–196° C.
Form: Free Example 52

Structure

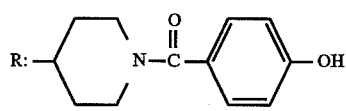

R[1]: H
Bond between 3- and 4-positions in the
carbostyril ring: single bond
Crystalline form: white powders
Recrystallization solvent: n-hexane/ethanol
Melting point: 182–183° C.
Form: Free Example 53

Structure

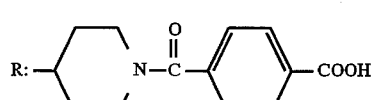

R[1]: H
Bond between 3- and 4-positions in the
carbostyril ring: single bond

TABLE 1-continued

Crystalline form: white powders
Recrystallization solvent: n-hexane/ethanol
Melting point: 232–235° C.
Form: Free
Example 54

Structure

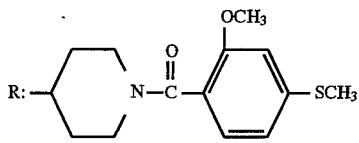

R[1]: H
Bond between 3- and 4-positions in the
carbostyril ring: single bond
NMR analysis: 13)
Form: Free
Example 55

Structure

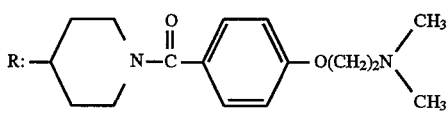

R[1]: H
Bond between 3- and 4-positions in the
carbostyril ring: single bond
NMR analysis: 14)
Form: Free
Example 56

Structure

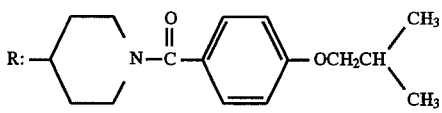

R[1]: H
Bond between 3- and 4-positions in the
carbostyril ring: single bond
NMR analysis: 15)
Form: Free
Example 57

Structure

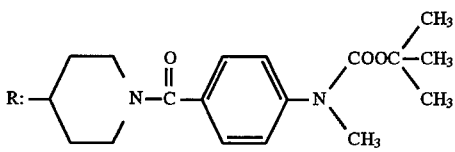

R[1]: H
Bond between 3- and 4-positions in the
carbostyril ring: single bond
NMR analysis: 16)
Form: Free
Example 58

Structure

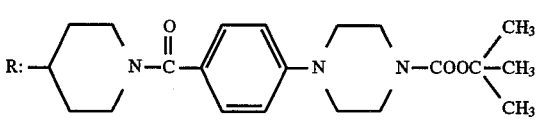

R[1]: H
Bond between 3- and 4-positions in the
carbostyril ring: single bond

TABLE 1-continued

Crystalline form: white powders  
Recrystallization solvent: n-hexane  
Melting point: 136–138° C.  
Form: Free  
Example 59

Structure

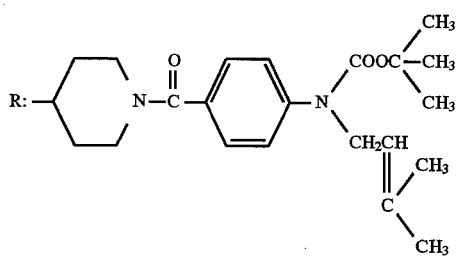

R¹: H  
Bond between 3- and 4-positions in the  
carbostyril ring: single bond  
NMR analysis: 17)  
Form: Free  
Example 60

Structure

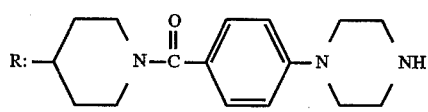

R¹: H  
Bond between 3- and 4-positions in the  
carbostyril ring: single bond  
NMR analysis: 18)  
Form: Free  
Example 61

Structure

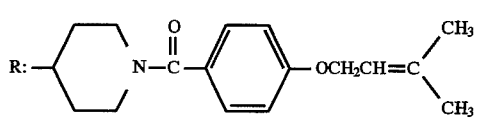

R¹: H  
Bond between 3- and 4-positions in the  
carbostyril ring: single bond  
NMR analysis: 19)  
Form: Free  
Example 62

Structure

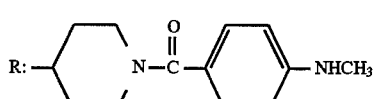

R¹: H  
Bond between 3- and 4-positions in the  
carbostyril ring: single bond  
Crystalline form: white powders  
Recrystallization solvent: n-hexane/ethanol  
Melting point: 184–186° C.  
Form: Free TABLE 1-continued Example 63

Structure

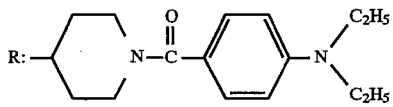

R¹: H
Bond between 3- and 4-positions in the
  carbostyril ring: single bond
Crystalline form: white powders
Recrystallization solvent: n-hexane/ethanol
Melting point: 139–140° C.
Form: Free Example 64

Structure

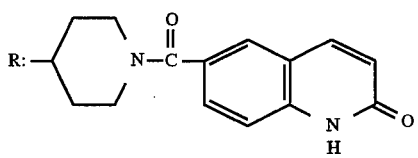

R¹: H
Bond between 3- and 4-positions in the
  carbostyril ring: single bond
Crystalline form: white powders
Recrystallization solvent: n-hexane/ethanol
Melting point: 238–240° C.
Form: Free Example 65

Structure

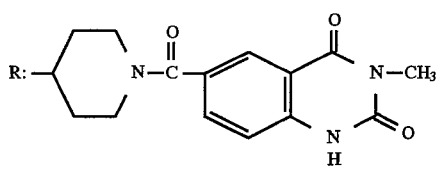

R¹: H
Bond between 3- and 4-positions in the
  carbostyril ring: single bond
Crystalline form: white powders
Recrystallization solvent: n-hexane/ethanol
Melting point: 224–226° C.
Form: Free Example 66

Structure

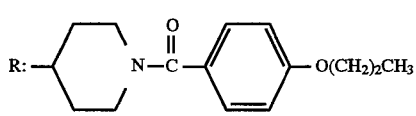

R¹: H
Bond between 3- and 4-positions in the
  carbostyril ring: single bond
Crystalline form: white powders
Recrystallization solvent: n-hexane/ethanol
Melting point: 110–111° C.
Form: Free TABLE 1-continued Example 67

Structure

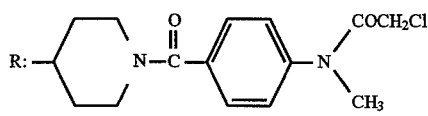

R¹: H
Bond between 3- and 4-positions in the
carbostyril ring: single bond
Crystalline form: white powders
Recrystallization solvent: n-hexane/ethanol
Melting point: 220–222° C. (decomposition)
Form: Free Example 68

Structure

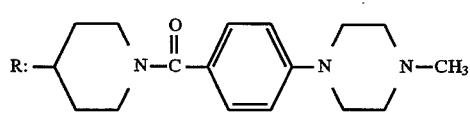

R¹: H
Bond between 3- and 4-positions in the
carbostyril ring: single bond
NMR analysis: 20)
Form: Free Example 69

Structure

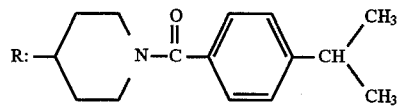

R¹: H
Bond between 3- and 4-positions in the
carbostyril ring: single bond
NMR analysis: 21)
Form: Free Example 70

Structure

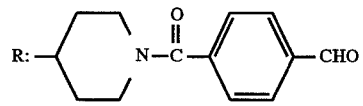

R¹: H
Bond between 3- and 4-positions in the
carbostyril ring: single bond
NMR analysis: 22)
Form: Free Example 71

Structure

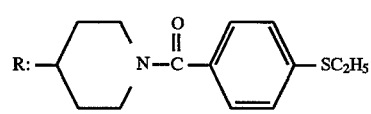

R¹: H
Bond between 3- and 4-positions in the
carbostyril ring: single bond
Crystalline form: white powders
Recrystallization solvent: n-hexane/ethanol
Melting point: 98–99° C.
Form: Free TABLE 1-continued Example 72

Structure

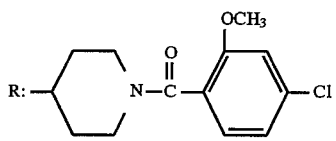

R¹: H
Bond between 3- and 4-positions in the
carbostyril ring: single bond
Crystalline form: white powders
Recrystallization solvent: n-hexane/ethanol
Melting point: 84–87° C.
Form: Free Example 73

Structure

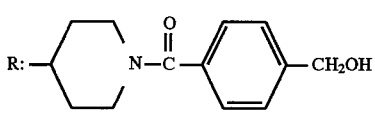

R¹: H
Bond between 3- and 4-positions in the
carbostyril ring: single bond
Crystalline form: white powders
Recrystallization solvent: n-hexane/ethanol
Melting point: 138–139° C.
Form: Free Example 74

Structure

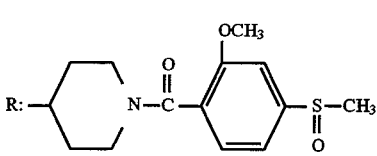

R¹: H
Bond between 3- and 4-positions in the
carbostyril ring: single bond
Crystalline form: white powders
Recrystallization solvent: n-hexane/ethanol
Melting point: 95–98° C.
Form: Free Example 75

Structure

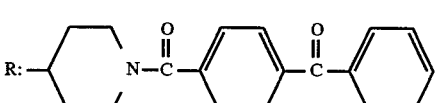

R¹: H
Bond between 3- and 4-positions in the
carbostyril ring: single bond
Crystalline form: white powders
Recrystallization solvent: n-hexane/ethanol
Melting point: 240–243° C. (decomposition)
Form: Free TABLE 1-continued Example 76

Structure

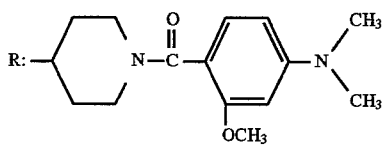

R$^1$: H
Bond between 3- and 4-positions in the
carbostyril ring: single bond
Crystalline form: white powders
Recrystallization solvent: n-hexane/ethanol
Melting point: 93–96° C. (decomposition)
Form: Free Example 77

Structure

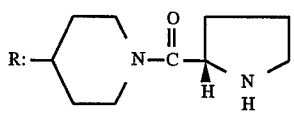

R$^1$: H
Bond between 3- and 4-positions in the
carbostyril ring: single bond
NMR analysis: 23)
Form: Free Example 78

Structure

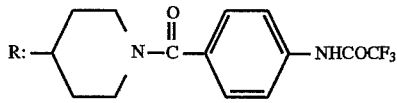

R$^1$: H
Bond between 3- and 4-positions in the
carbostyril ring: single bond
Crystalline form: pale red powders
Recrystallization solvent: n-hexane
Melting point: 104–107° C.
Form: Free Example 79

Structure

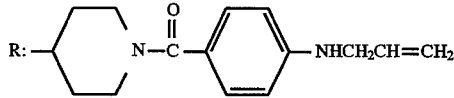

R$^1$: H
Bond between 3- and 4-positions in the
carbostyril ring: single bond
NMR analysis: 24)
Form: Free Example 80

Structure

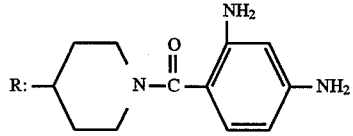

R$^1$: H
Bond between 3- and 4-positions in the
carbostyril ring: single bond

TABLE 1-continued

Crystalline form: white powders
Recrystallization solvent: n-hexane/ethanol
Melting point: 113–116° C.
Form: Free Example 81

Structure

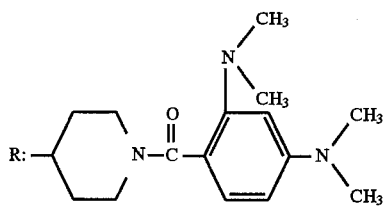

R[1]: H
Bond between 3- and 4-positions in the
carbostyril ring: single bond

Crystalline form: pale grey powders
Recrystallization solvent: n-hexane/ethanol
Melting point: 162–164° C.
Form: Free Example 82

Structure

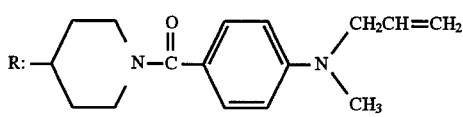

R[1]: H
Bond between 3- and 4-positions in the
carbostyril ring: single bond

NMR analysis: 25)
Form: Free

Example 83

Structure

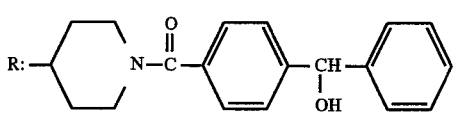

R[1]: H
Bond between 3- and 4-positions in the
carbostyril ring: single bond

Crystalline form: white powders
Recrystallization solvent: n-hexane/ethanol
Melting point: 93–96° C.
Form: Free Example 84

Structure

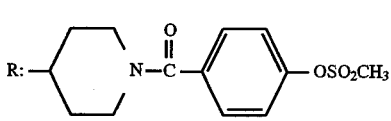

R[1]: H
Bond between 3- and 4-positions in the
carbostyril ring: single bond

NMR analysis: 26)
Form: Free

TABLE 1-continued

Example 85

Structure

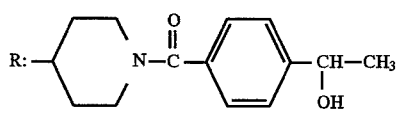

R¹: H
Bond between 3- and 4-positions in the
carbostyril ring: single bond
Crystalline form: white powders
Recrystallization solvent: n-hexane/ethanol
Melting point: 144–146° C.
Form: Free Example 86

Structure

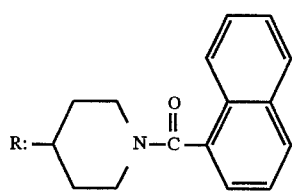

R¹: H
Bond between 3- and 4-positions in the
carbostyril ring: single bond
Crystalline form: white powders
Recrystallization solvent: n-hexane/ethanol
Melting point: 197–199° C.
Form: Free Example 87

Structure

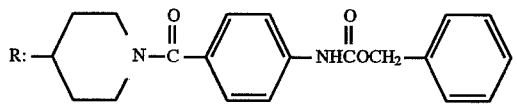

R¹: H
Bond between 3- and 4-positions in the
carbostyril ring: single bond
NMR analysis: 27)
Form: Free Example 88

Structure

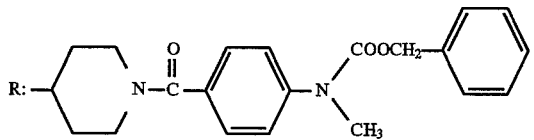

R¹: H
Bond between 3- and 4-positions in the
carbostyril ring: single bond
NMR analysis: 28)
Form: Free Example 89

Structure

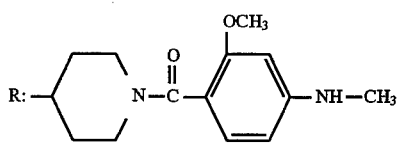

TABLE 1-continued

R¹: H
Bond between 3- and 4-positions in the
carbostyril ring: single bond

NMR analysis: 29)
Form: Free

Example 90

Structure

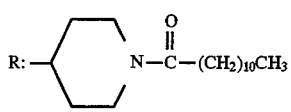

R¹: H
Bond between 3- and 4-positions in the
carbostyril ring: single bond

NMR analysis: 30)
Form: Free

Example 91

Structure

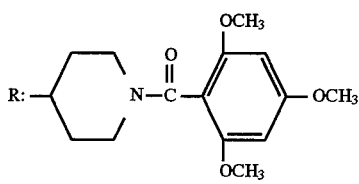

R¹: H
Bond between 3- and 4-positions in the
carbostyril ring: single bond

Crystalline form: white powders
Recrystallization solvent: n-hexane/ethanol
Melting point: 193–196° C.
Form: Free Example 92

Structure

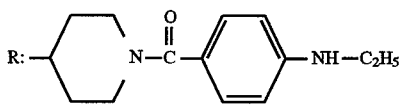

R¹: H
Bond between 3- and 4-positions in the
carbostyril ring: single bond

Crystalline form: white powders
Recrystallization solvent: n-hexane/ethanol
Melting point: 82–85° C.
Form: Free Example 93

Structure

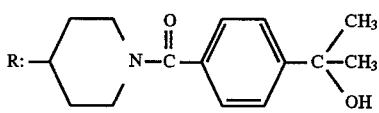

R¹: H
Bond between 3- and 4-positions in the
carbostyril ring: single bond

NMR analysis: 31)
Form: Free

TABLE 1-continued

Example 94

Structure

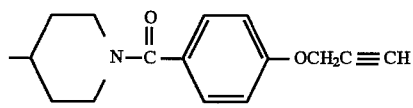

R¹: H
Bond between 3- and 4-positions in the
carbostyril ring: single bond
NMR analysis: 32)
Form: Free

Example 95

Structure

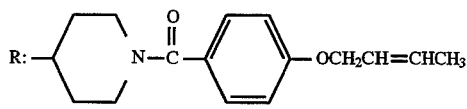

R¹: H
Bond between 3- and 4-positions in the
carbostyril ring: single bond
Crystalline form: white powders
Recrystallization solvent: n-hexane
Melting point: 122–125° C.
Form: Free

Example 96

Structure

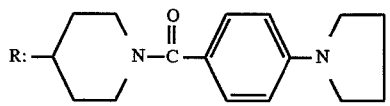

R¹: H
Bond between 3- and 4-positions in the
carbostyril ring: single bond
Crystalline form: pale yellow powders
Recrystallization solvent: n-hexane/ethanol
Melting point: 168–171° C.
Form: Free

Example 97

Structure

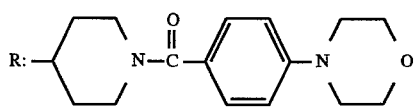

R¹: H
Bond between 3- and 4-positions in the
carbostyril ring: single bond
Crystalline form: pale yellow powders
Recrystallization solvent: n-hexane/ethanol
Melting point: 213–215° C.
Form: Free

Example 98

Structure

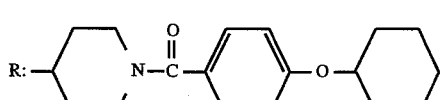

R¹: H
Bond between 3- and 4-positions in the
carbostyril ring: single bond

TABLE 1-continued

Crystalline form: white powders
Recrystallization solvent: n-hexane
Melting point: 111–114° C.
Form: Free
Example 99

Structure

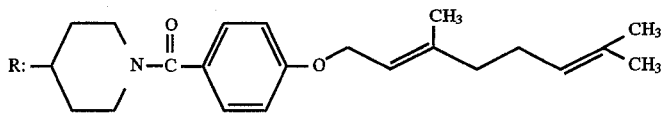

R¹: H
Bond between 3- and 4-positions in the
carbostyril ring: single bond
NMR analysis: 33)
Form: Free
Example 100

Structure

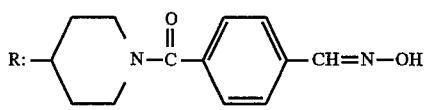

R¹: H
Bond between 3- and 4-positions in the
carbostyril ring: single bond
Crystalline form: white powders
Recrystallization solvent: n-hexane/ethanol
Melting point: 222–224° C.
Form: Free
Example 101

Structure

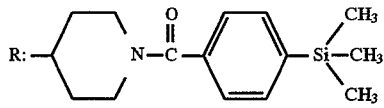

R¹: H
Bond between 3- and 4-positions in the
carbostyril ring: single bond
Crystalline form: white powders
Recrystallization solvent: n-hexane
Melting point: 149–151° C.
Form: Free
Example 102

Structure

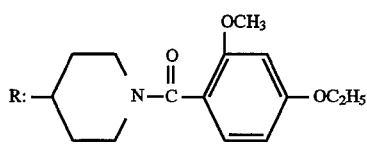

R¹: H
Bond between 3- and 4-positions in the
carbostyril ring: single bond
Crystalline form: colorless prisms
Recrystallization solvent: n-hexane/ethanol
Melting point: 174–175° C.
Form: Free

TABLE 1-continued

Example 103

Structure

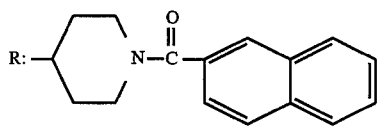

R$^1$: H
Bond between 3- and 4-positions in the
carbostyril ring: single bond
Crystalline form: white powders
Recrystallization solvent: n-hexane/ethanol
Melting point: 130–132° C.
Form: Free Example 104

Structure

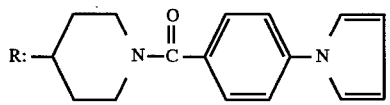

R$^1$: H
Bond between 3- and 4-positions in the
carbostyril ring: single bond
Crystalline form: pale grey powders
Recrystallization solvent: n-hexane
Melting point: 153–156° C.
Form: Free Example 105

Structure

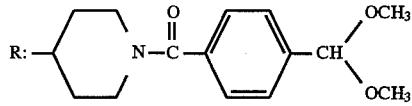

R$^1$: H
Bond between 3- and 4-positions in the
carbostyril ring: single bond
Crystalline form: white powders
Recrystallization solvent: n-hexane
Melting point: 134–136° C.
Form: Free Example 106

Structure

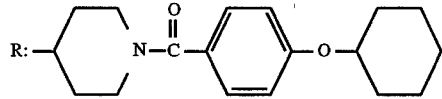

R$^1$: H
Bond between 3- and 4-positions in the
carbostyril ring: single bond
MR analysis: 34)
Form: Free Example 107

Structure

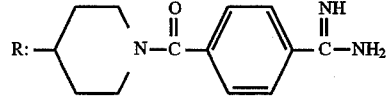

R$^1$: H
Bond between 3- and 4-positions in the
carbostyril ring: single bond

TABLE 1-continued

Crystalline form: white powders
Recrystallization solvent: water
Melting point: 92–97° C.
Form: Free
NMR analysis: 35)

Example 108

Structure

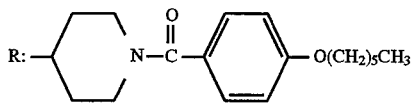

R¹: H
Bond between 3- and 4-positions in the
carbostyril ring: single bond
NMR analysis: 36)
Form: Free Example 109

Structure

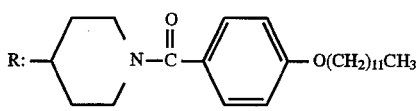

R¹: H
Bond between 3- and 4-positions in the
carbostyril ring: single bond
NMR analysis: 37)
Form: Free Example 110

Structure

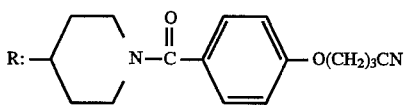

R¹: H
Bond between 3- and 4-positions in the
carbostyril ring: single bond
NMR analysis: 38)
Form: Free Example 111

Structure

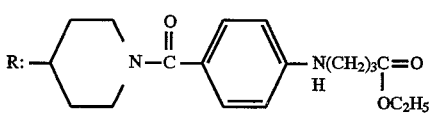

R¹: H
Bond between 3- and 4-positions in the
carbostyril ring: single bond
NMR analysis: 40)
Form: Free Example 112

Structure

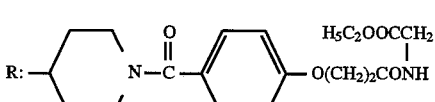

R¹: H
Bond between 3- and 4-positions in the
carbostyril ring: single bond
NMR analysis: 41)
Form: Free TABLE 1-continued Example 113

Structure

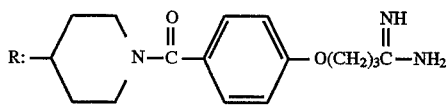

R¹: H
Bond between 3- and 4-positions in the
carbostyril ring: single bond
NMR analysis: 42)
Form: Free Example 114

Structure

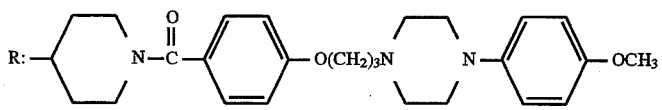

R¹: H
Bond between 3- and 4-positions in the
carbostyril ring: single bond
NMR analysis: 43)
Form: Free Example 115

Structure

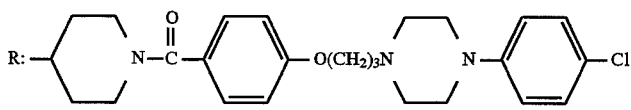

R¹: H
Bond between 3- and 4-positions in the
carbostyril ring: single bond
NMR analysis: 44)
Form: Free Example 116

Structure

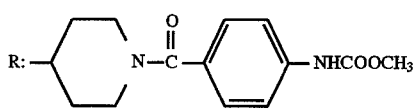

R¹: H
Bond between 3- and 4-positions in the
carbostyril ring: single bond
NMR analysis: 45)
Form: Free Example 117

Structure

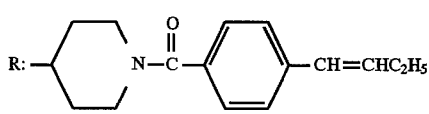

R¹: H
Bond between 3- and 4-positions in the
carbostyril ring: single bond
NMR analysis: 46)
Form: Free TABLE 1-continued Example 118

Structure

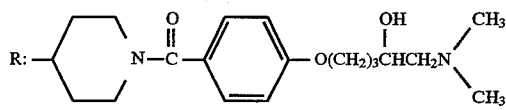

R[1]: H
Bond between 3- and 4-positions in the
carbostyril ring: single bond
NMR analysis: 47)
Form: Free Example 119

Structure

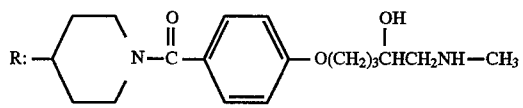

R[1]: H
Bond between 3- and 4-positions in the
carbostyril ring: single bond
NMR analysis: 48)
Form: Free Example 120

Structure

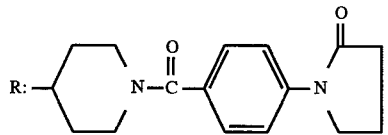

R[1]: H
Bond between 3- and 4-positions in the
carbostyril ring: single bond
NMR analysis: 49)
Form: Free Example 121

Structure

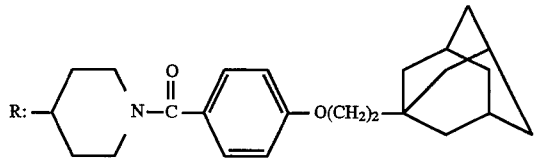

R[1]: H
Bond between 3- and 4-positions in the
carbostyril ring: single bond
NMR analysis: 50)
Form: Free Example 122

Structure

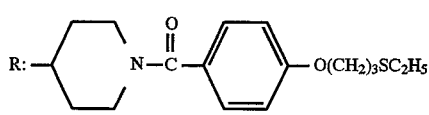

R[1]: H
Bond between 3- and 4-positions in the
carbostyril ring: single bond
NMR analysis: 51)
Form: Free

TABLE 1-continued

Example 123

Structure

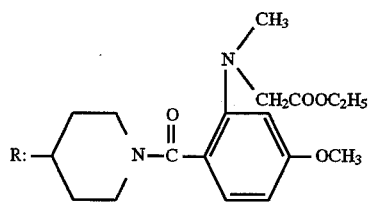

R[1]: H
Bond between 3- and 4-positions in the
carbostyril ring: single bond
NMR analysis: 52)
Form: Free Example 124

Structure

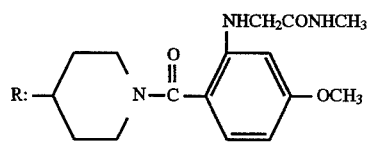

R[1]: H
Bond between 3- and 4-positions in the
carbostyril ring: single bond
NMR analysis: 53)
Form: Free Example 125

Structure

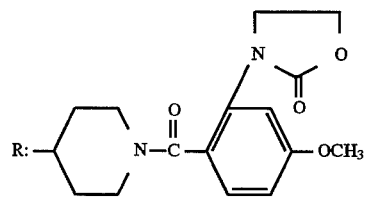

R[1]: H
Bond between 3- and 4-positions in the
carbostyril ring: single bond
NMR analysis: 54)
Form: Free Example 126

Structure

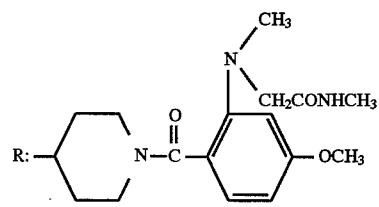

R[1]: H
Bond between 3- and 4-positions in the
carbostyril ring: single bond
NMR analysis: 55)
Form: Free TABLE 1-continued Example 127

Structure

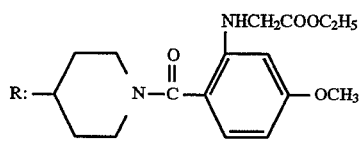

R¹: H
Bond between 3- and 4-positions in the
carbostyril ring: single bond
NMR analysis: 56)
Form: Free Example 128

Structure

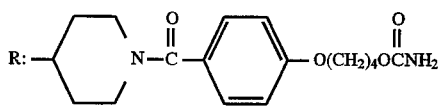

R¹: H
Bond between 3- and 4-positions in the
carbostyril ring: single bond
NMR analysis: 57)
Form: Free Example 129

Structure

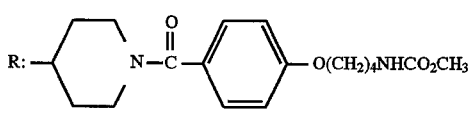

R¹: H
Bond between 3- and 4-positions in the
carbostyril ring: single bond
NMR analysis: 58)
Form: Free Example 130

Structure

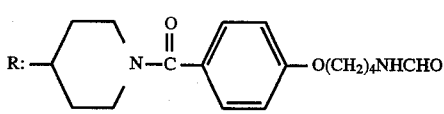

R¹: H
Bond between 3- and 4-positions in the
carbostyril ring: single bond
NMR analysis: 59)
Form: Free Example 131

Structure

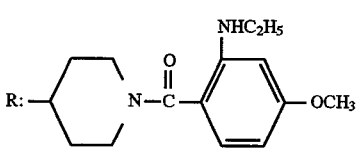

R¹: H
Bond between 3- and 4-positions in the
carbostyril ring: single bond
NMR analysis: 60)
Form: Free

TABLE 1-continued

Example 132

Structure

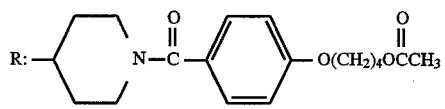

R[1]: H
Bond between 3- and 4-positions in the
carbostyril ring: single bond
Crystalline form: white powders
Recrystallization solvent: diethyl ether/n-hexane
Melting point: 67–69° C.
Form: Free Example 133

Structure

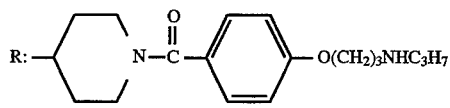

R[1]: H
Bond between 3- and 4-positions in the
carbostyril ring: single bond
NMR analysis: 61)
Form: Free Example 134

Structure

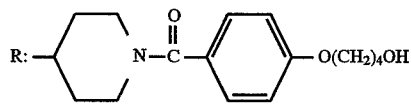

R[1]: H
Bond between 3- and 4-positions in the
carbostyril ring: single bond
Crystalline form: colorless needles
Recrystallization solvent: diethyl ether/n-hexane
Melting point: 136–138° C.
Form: Free Example 135

Structure

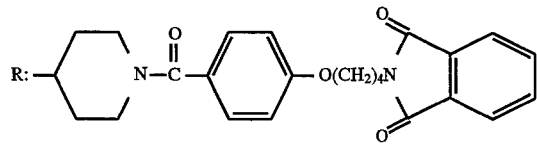

R[1]: H
Bond between 3- and 4-positions in the
carbostyril ring: single bond
Crystalline form: colorless needles
Recrystallization solvent: ethanol/diethyl ether
Melting point: 171–173° C.
Form: Free Example 136

Structure

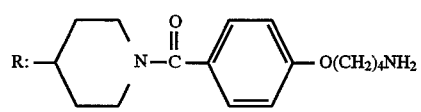

R[1]: H
Bond between 3- and 4-positions in the

TABLE 1-continued carbostyril ring: single bond
NMR analysis: 62)
Form: Free

Example 137

Structure

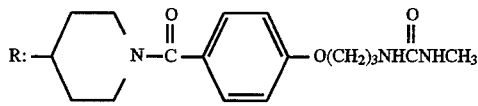

R¹: H
Bond between 3- and 4-positions in the
carbostyril ring: single bond
NMR analysis: 63)
Form: Free Example 138

Structure

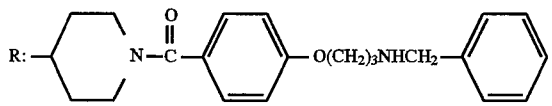

R¹: H
Bond between 3- and 4-positions in the
carbostyril ring: single bond
NMR analysis: 64)
Form: Free Example 139

Structure

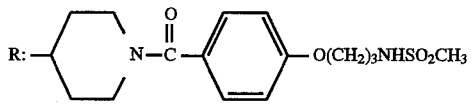

R¹: H
Bond between 3- and 4-positions in the
carbostyril ring: single bond
NMR analysis: 65)
Form: Free Example 140

Structure

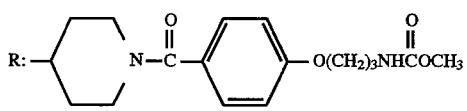

R¹: H
Bond between 3- and 4-positions in the
carbostyril ring: single bond
NMR analysis: 66)
Form: Free Example 141

Structure

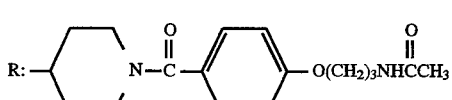

R¹: H
Bond between 3- and 4-positions in the
carbostyril ring: single bond
Crystalline form: colorless needles
Recrystallization solvent: ethanol/diethyl ether
Melting point: 147.5–149° C.

TABLE 1-continued

Form: Free
NMR analysis: 67)
Example 142

Structure

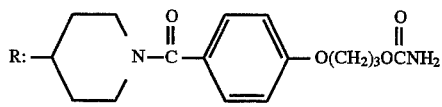

R¹: H
Bond between 3- and 4-positions in the
carbostyril ring: single bond
Crystalline form: colorless needles
Recrystallization solvent: ethanol
Melting point: 136–138° C.
Form: Free
NMR analysis: 68)
Example 143

Structure

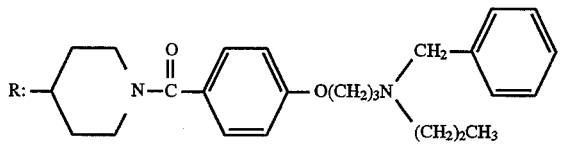

R¹: H
Bond between 3- and 4-positions in the
carbostyril ring: single bond
NMR analysis: 69)
Form: Free
Example 144

Structure

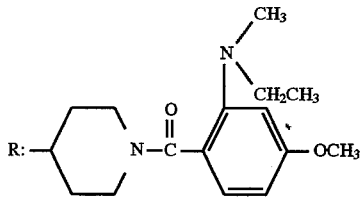

R¹: H
Bond between 3- and 4-positions in the
carbostyril ring: single bond
NMR analysis: 70)
Form: Free
Example 145

Structure

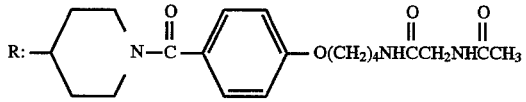

R¹: H
Bond between 3- and 4-positions in the
carbostyril ring: single bond
NMR analysis: 71)
Form: Free
Example 146

Structure

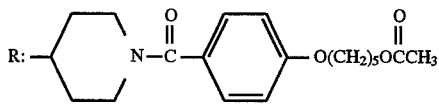

TABLE 1-continued

R¹: H
Bond between 3- and 4-positions in the
carbostyril ring: single bond

NMR analysis: 72)
Form: Free

Example 147

Structure

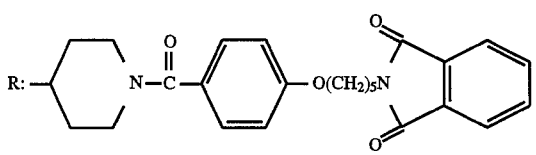

R¹: H
Bond between 3- and 4-positions in the
carbostyril ring: single bond

NMR analysis: 73)
Form: Free

Example 148

Structure

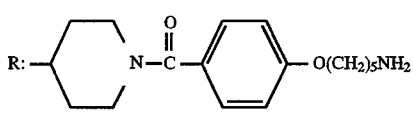

R¹: H
Bond between 3- and 4-positions in the
carbostyril ring: single bond

NMR analysis: 74)
Form: Free

Example 149

Structure

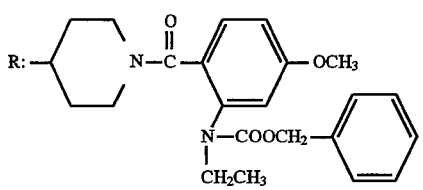

R¹: H
Bond between 3- and 4-positions in the
carbostyril ring: single bond

NMR analysis: 75)
Form: Free

Example 150

Structure

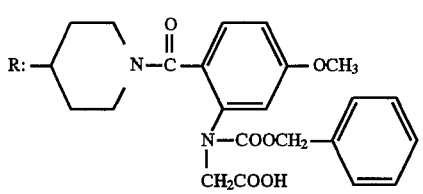

R¹: H
Bond between 3- and 4-positions in the
carbostyril ring: single bond

NMR analysis: 76)
Form: Free

TABLE 1-continued

Example 151

Structure

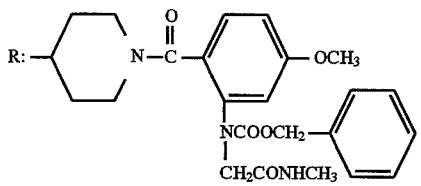

R[1]: H
Bond between 3- and 4-positions in the
carbostyril ring: single bond
NMR analysis: 77)
Form: Free Example 152

Structure

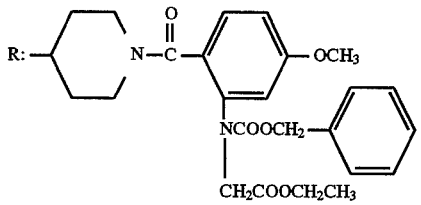

R[1]: H
Bond between 3- and 4-positions in the
carbostyril ring: single bond
NMR analysis: 78)
Form: Free Example 153

Structure

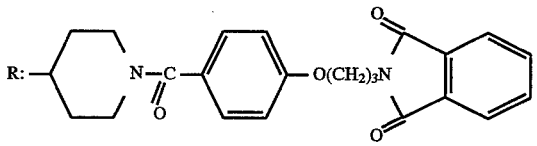

R[1]: 7-F
Bond between 3- and 4-positions in the
carbostyril ring: single bond
NMR analysis: 79)
Form: Free Example 154

Structure

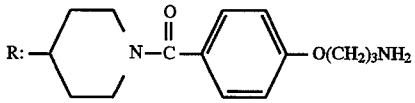

R[1]: 7-F
Bond between 3- and 4-positions in the
carbostyril ring: single bond
NMR analysis: 80)
Form: Free Example 155

Structure

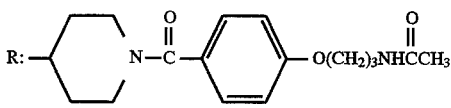

TABLE 1-continued

R¹: 7-F
Bond between 3- and 4-positions in the
carbostyril ring: single bond
NMR analysis: 81)
Form: Free Example 156

Structure

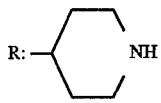

R¹: 7-C₂H₅
Bond between 3- and 4-positions in the
carbostyril ring: single bond
NMR analysis: 82)
Form: Free Example 157

Structure

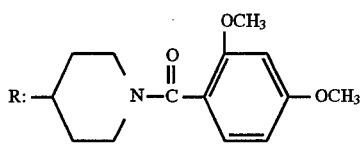

R¹: 7-C₂H₅
Bond between 3- and 4-positions in the
carbostyril ring: single bond
NMR analysis: 83)
Form: Free Example 158

Structure

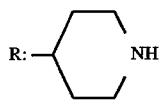

R¹: 7-OCH₃
Bond between 3- and 4-positions in the
carbostyril ring: single bond
NMR analysis: 84)
Form: Free Example 159

Structure

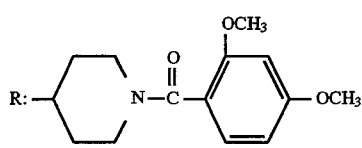

R¹: 7-OCH₃
Bond between 3- and 4-positions in the
carbostyril ring: single bond
NMR analysis: 85)
Form: Free Example 160

Structure

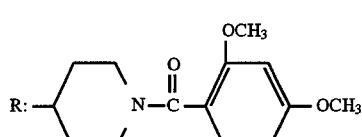

TABLE 1-continued

R¹: R¹: 6-NHCO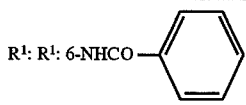

Bond between 3- and 4-positions in the
carbostyril ring: single bond
NMR analysis: 86)
Form: Free
Example 161

Structure

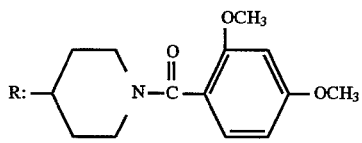

R¹: 6-NHCOCH₃
Bond between 3- and 4-positions in the
carbostyril ring: single bond
Crystalline form: white powders
Recrystallization solvent: ethanol
Melting point: 271–272° C.
Form: Free
Example 162

Structure

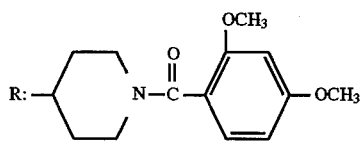

R¹: 6-NH₂
Bond between 3- and 4-positions in the
carbostyril ring: single bond
NMR analysis: 87)
Form: Free
Example 163

Structure

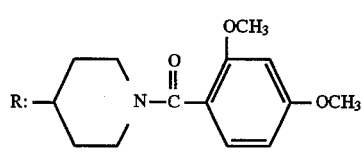

R¹: 6-NO₂
Bond between 3- and 4-positions in the
carbostyril ring: single bond
Crystalline form: pale yellow powders
Recrystallization solvent: ethanol
Melting point: 197–199° C.
Form: Free
Example 164

Structure

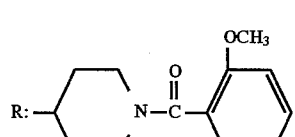

R¹: H
Bond between 3- and 4-positions in the
carbostyril ring: single bond
Crystalline form: white powders
Recrystallization solvent: dichloromethane/n-hexane

TABLE 1-continued

Melting point: 151.5–152.5° C.
Form: Free
Example 165

Structure

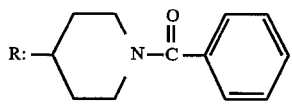

R¹: H
Bond between 3- and 4-positions in the
carbostyril ring: double bond
NMR analysis: 88)
Form: Free
Example 166

Structure

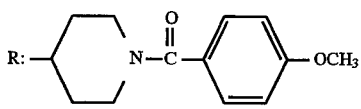

R¹: H
Bond between 3- and 4-positions in the
carbostyril ring: single bond
NMR analysis: 89)
Form: Free
Example 167

Structure

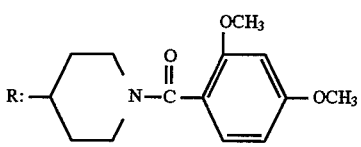

R¹: H
Bond between 3- and 4-positions in the
carbostyril ring: double bond
NMR analysis: 90)
Form: Free
Example 168

Structure

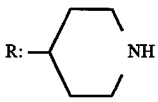

R¹: H
Bond between 3- and 4-positions in the
carbostyril ring: double bond
NMR analysis: 91)
Form: Free
Example 169

Structure

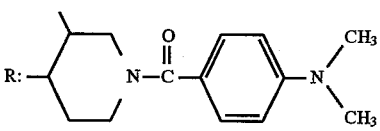

R¹: H
Bond between 3- and 4-positions in the
carbostyril ring: single bond
Crystalline form: white powders
Recrystallization solvent: ethanol/diethyl ether/n-hexane
Melting point: 181–183° C.
Form: Free TABLE 1-continued Example 170

Structure

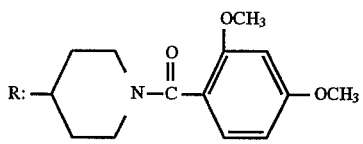

R¹: 6-F
Bond between 3- and 4-positions in the
carbostyril ring: single bond
NMR analysis: 92)
Form: Free Example 171

Structure

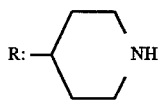

R¹: 6-F
Bond between 3- and 4-positions in the
carbostyril ring: single bond
NMR analysis: 93)
Form: Free Example 172

Structure

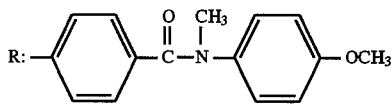

R¹: H
Bond between 3- and 4-positions in the
carbostyril ring: single bond
NMR analysis: 94)
Form: Free Example 173

Structure

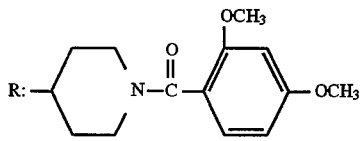

R¹: 7-F
Bond between 3- and 4-positions in the
carbostyril ring: single bond
NMR analysis: 95)
Form: Free Example 174

Structure

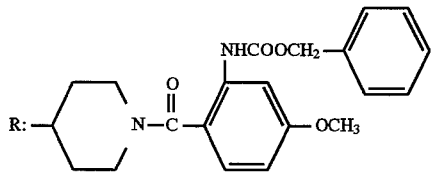

R¹: H
Bond between 3- and 4-positions in the
carbostyril ring: single bond
NMR analysis: 96)
Form: Free TABLE 1-continued Example 175

Structure

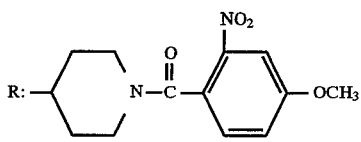

R¹: H
Bond between 3- and 4-positions in the
carbostyril ring: single bond
Crystalline form: colorless needles
Recrystallization solvent: ethanol/diethyl ether
Melting point: 151–154° C.
Form: Free Example 176

Structure

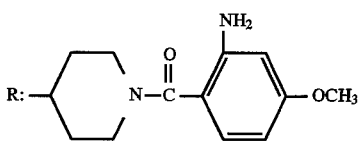

R¹: H
Bond between 3- and 4-positions in the
carbostyril ring: single bond
Crystalline form: colorless needles
Recrystallization solvent: ethanol
Melting point: 169–171° C.
Form: Free Example 177

Structure

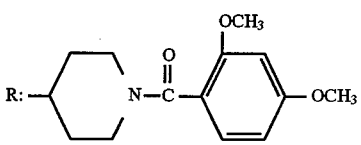

R¹: 7-F
Bond between 3- and 4-positions in the
carbostyril ring: single bond
NMR analysis: 97)
Form: Free Example 178

Structure

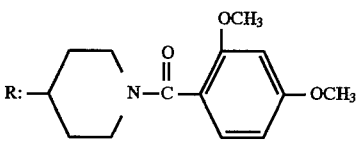

R¹: 6-CH₃
Bond between 3- and 4-positions in the
carbostyril ring: single bond
NMR analysis: 98)
Form: Free Example 179

Structure

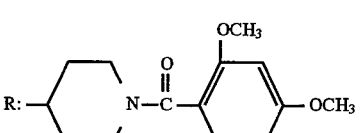

TABLE 1-continued

R$^1$: 8-CH$_3$
Bond between 3- and 4-positions in the
carbostyril ring: single bond
NMR analysis: 99)
Form: Free
Example 180

Structure

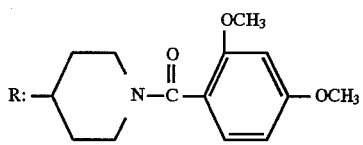

R$^1$: 7-CH$_3$
Bond between 3- and 4-positions in the
carbostyril ring: single bond
NMR analysis: 100)
Form: Free
Example 181

Structure

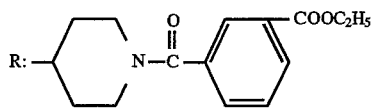

R$^1$: H
Bond between 3- and 4-positions in the
carbostyril ring: single bond
NMR analysis: 101)
Form: Free
Example 182

Structure

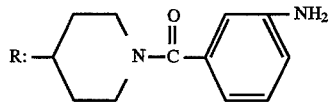

R$^1$: H
Bond between 3- and 4-positions in the
carbostyril ring: single bond
Crystalline form: white powders
Recrystallization solvent: ethanol/n-hexane
Melting point: 183–183.5° C.
Form: Free
Example 183

Structure

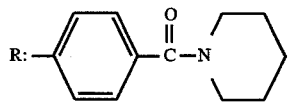

R$^1$: H
Bond between 3- and 4-positions in the
carbostyril ring: single bond
Crystalline form: white powders
Recrystallization solvent: ethanol/diethyl ether/n-hexane
Melting point: 175–176° C.
Form: Free
Example 184

Structure

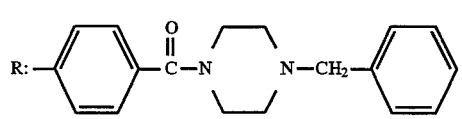

TABLE 1-continued

R¹: H
Bond between 3- and 4-positions in the
carbostyril ring: single bond
NMR analysis: 102)
Form: Free Example 185

Structure

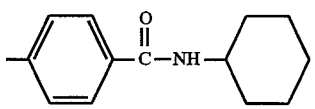

R¹: H
Bond between 3- and 4-positions in the
carbostyril ring: single bond
Crystalline form: white powders
Recrystallization solvent: ethanol/diethyl ether/n-hexane
Melting point: 291–292° C.
Form: Free Example 186

Structure

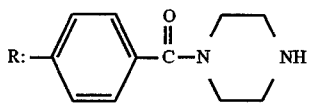

R¹: H
Bond between 3- and 4-positions in the
carbostyril ring: single bond
Crystalline form: white powders
Recrystallization solvent: ethanol/diethyl ether/n-hexane
Melting point: 215–216° C.
Form: Free Example 187

Structure

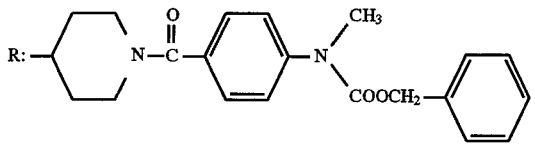

R¹: H
Bond between 3- and 4-positions in the
carbostyril ring: single bond
NMR analysis: 103)
Form: Free Example 188

Structure

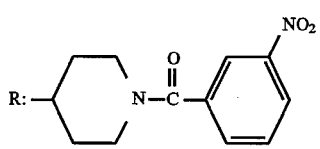

R¹: H
Bond between 3- and 4-positions in the
carbostyril ring: single bond
NMR analysis: 104)
Form: Free

TABLE 1-continued

Example 189

Structure

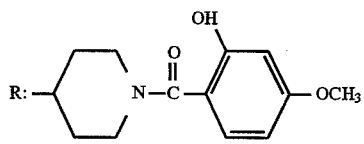

R¹: H
Bond between 3- and 4-positions in the
carbostyril ring: single bond
Crystalline form: white powders
Recrystallization solvent: dichloromethane/n-hexane
Melting point: 140.5–142° C.
Form: Free Example 190

Structure

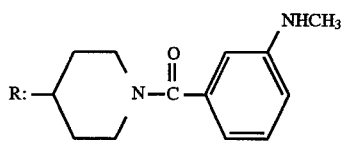

R¹: H
Bond between 3- and 4-positions in the
carbostyril ring: single bond
Crystalline form: white powders
Recrystallization solvent: ethanol/n-hexane
Melting point: 164–164.5° C.
Form: Free Example 191

Structure

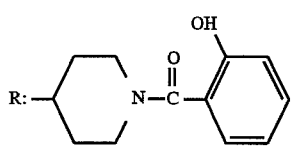

R¹: H
Bond between 3- and 4-positions in the
carbostyril ring: single bond
Crystalline form: colorless needles
Recrystallization solvent: ethanol/methanol/diethyl ether
Melting point: 156–158° C.
Form: Free Example 192

Structure

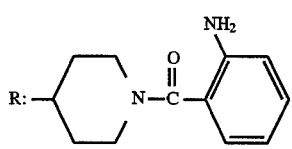

R¹: H
Bond between 3- and 4-positions in the
carbostyril ring: single bond
Crystalline form: colorless needles
Recrystallization solvent: ethanol/diethyl ether
Melting point: 158–166° C.
Form: Hydrochloride TABLE 1-continued Example 193

Structure

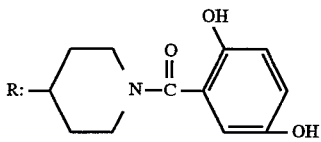

R[1]: H
Bond between 3- and 4-positions in the
carbostyril ring: single bond
Crystalline form: colorless prisms
Recrystallization solvent: ethanol/methanol
Melting point: 245–249° C.
Form: Free Example 194

Structure

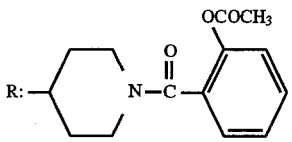

R[1]: H
Bond between 3- and 4-positions in the
carbostyril ring: single bond
Crystalline form: colorless prisms
Recrystallization solvent: ethanol/diethyl ether
Melting point: 159–161° C.
Form: Free Example 195

Structure

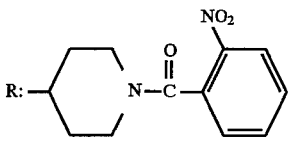

R[1]: H
Bond between 3- and 4-positions in the
carbostyril ring: single bond
Crystalline form: pale yellow needles
Recrystallization solvent: methanol/chloroform/diethyl ether
Melting point: 207–209° C.
Form: Free Example 196

Structure

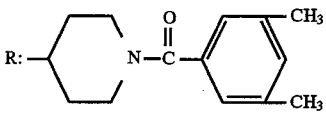

R[1]: H
Bond between 3- and 4-positions in the
carbostyril ring: single bond
Crystalline form: colorless needles
Recrystallization solvent: ethanol/diethyl ether/n-hexane
Melting point: 177–180° C.
Form: Free TABLE 1-continued Example 197

Structure

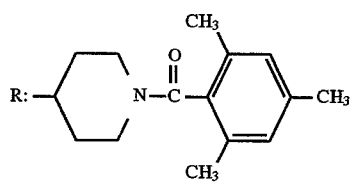

R¹: H
Bond between 3- and 4-positions in the
carbostyril ring: single bond
Crystalline form: colorless needles
Recrystallization solvent: ethyl acetate/diethyl ether/n-hexane
Melting point: 145–150° C.
Form: Free Example 198

Structure

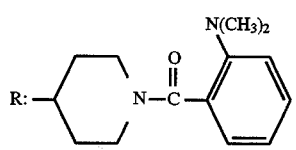

R¹: H
Bond between 3- and 4-positions in the
carbostyril ring: single bond
Crystalline form: colorless flakes
Recrystallization solvent: ethyl acetate/ethanol
Melting point: 209–211° C.
Form: Free Example 199

Structure

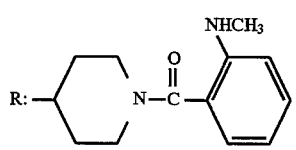

R¹: H
Bond between 3- and 4-positions in the
carbostyril ring: single bond
NMR analysis: 105)
Form: Free Example 200

Structure

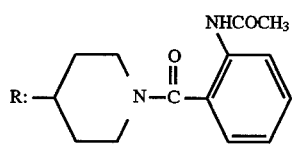

R¹: H
Bond between 3- and 4-positions in the
carbostyril ring: single bond
Crystalline form: colorless needles
Recrystallization solvent: ethyl acetate/diethyl ether
Melting point: 141–143° C.
Form: Free

TABLE 1-continued

Example 201

Structure

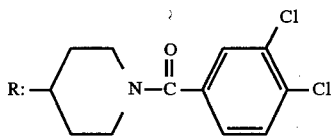

R[1]: H
Bond between 3- and 4-positions in the
carbostyril ring: single bond
NMR analysis: 106:
Form: Free Example 202

Structure

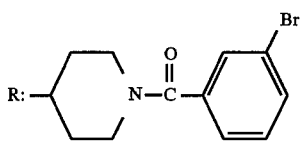

R[1]: H
Bond between 3- and 4-positions in the
carbostyril ring: single bond
Crystalline form: colorless prisms
Recrystallization solvent: ethyl acetate/diethyl ether/n-hexane
Melting point: 148–150° C.
Form: Free Example 203

Structure

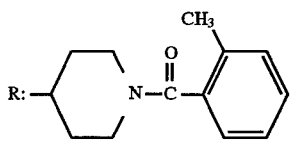

R[1]: H
Bond between 3- and 4-positions in the
carbostyril ring: single bond
Crystalline form: colorless prisms
Recrystallization solvent: ethanol/diethyl ether/n-hexane
Melting point: 169–172° C.
Form: Free Example 204

Structure

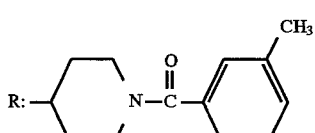

R[1]: H
Bond between 3- and 4-positions in the
carbostyril ring: single bond
Crystalline form: colorless prisms
Recrystallization solvent: ethyl acetate/diethyl ether/n-hexane
Melting point: 144–146° C.
Form: Free TABLE 1-continued Example 205

Structure

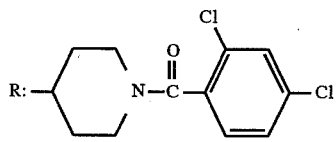

R¹: H
Bond between 3- and 4-positions in the
carbostyril ring: single bond
NMR analysis: 107)
Form: Free Example 206

Structure

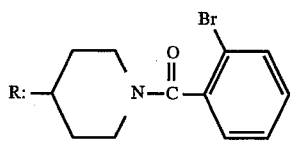

R¹: H
Bond between 3- and 4-positions in the
carbostyril ring: single bond
Crystalline form: colorless flakes
Recrystallization solvent: ethyl acetate/diethyl ether/n-hexane
Melting point: 181–183° C.
Form: Free Example 207

Structure

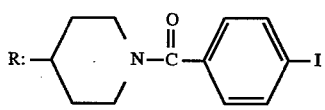

R¹: H
Bond between 3- and 4-positions in the
carbostyril ring: single bond
Crystalline form: colorless needles
Recrystallization solvent: ethyl acetate/diethyl ether/n-hexane
Melting point: 141–144° C.
Form: Free Example 208

Structure

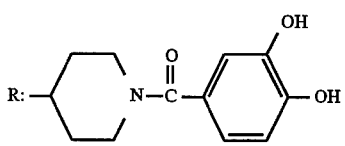

R¹: H
Bond between 3- and 4-positions in the
carbostyril ring: single bond
Crystalline form: colorless prisms
Recrystallization solvent: ethanol/diethyl ether
Melting point: 234–236° C.
Form: Free TABLE 1-continued Example 209

Structure

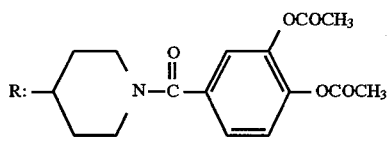

R¹: H
Bond between 3- and 4-positions in the
carbostyril ring: single bond
Crystalline form: colorless needles
Recrystallization solvent: ethyl acetate/diethyl ether
Melting point: 117–119° C.
Form: Free Example 210

Structure

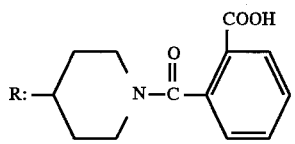

R¹: H
Bond between 3- and 4-positions in the
carbostyril ring: single bond
Crystalline form: white powders
Recrystallization solvent: ethanol/n-hexane
Melting point: 116–120° C.
Form: Free Example 211

Structure

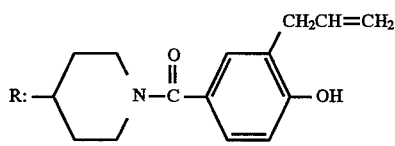

R¹: H
Bond between 3- and 4-positions in the
carbostyril ring: single bond
Crystalline form: white powders
Recrystallization solvent: dichloromethane/n-hexane
Melting point: 87–90° C.
Form: Free Example 212

Structure

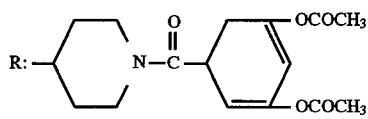

R¹: H
Bond between 3- and 4-positions in the
carbostyril ring: single bond
Crystalline form: white powders
Recrystallization solvent: dichloromethane/n-hexane
Melting point: 171.5–172.5° C.
Form: Free TABLE 1-continued Example 213

Structure

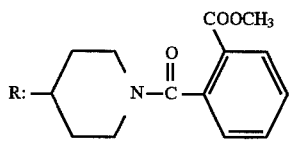

R¹: H
Bond between 3- and 4-positions in the
carbostyril ring: single bond
Crystalline form: white powders
Recrystallization solvent: dichloromethane/n-hexane
Melting point: 159.5–160° C.
Form: Free Example 214

Structure

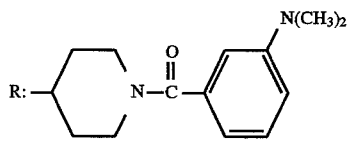

R¹: H
Bond between 3- and 4-positions in the
carbostyril ring: single bond
Crystalline form: white powders
Recrystallization solvent: dichloromethane/n-hexane
Melting point: 168–169° C.
Form: Free Example 215

Structure

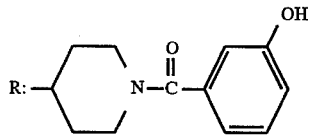

R¹: H
Bond between 3- and 4-positions in the
carbostyril ring: single bond
Crystalline form: white powders
Recrystallization solvent: dichloromethane/n-hexane
Melting point: 188–189° C.
Form: Free Example 216

Structure

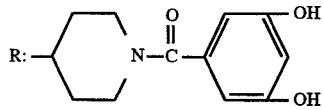

R¹: H
Bond between 3- and 4-positions in the
carbostyril ring: single bond
Crystalline form: white powders
Recrystallization solvent: dichloromethane/n-hexane
Melting point: 295° C. (decomposition)
Form: Free TABLE 1-continued Example 217

Structure

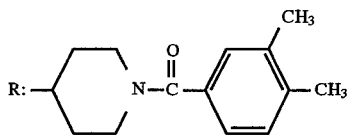

R¹: H
Bond between 3- and 4-positions in the
carbostyril ring: single bond
Crystalline form: white powders
Recrystallization solvent: ethanol/n-hexane
Melting point: 131.5–132.5° C.
Form: Free Example 218

Structure

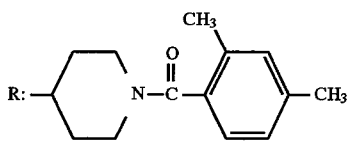

R¹: H
Bond between 3- and 4-positions in the
carbostyril ring: single bond
Crystalline form: white powders
Recrystallization solvent: dichloromethane/n-hexane
Melting point: 159–160° C.
Form: Free Example 219

Structure

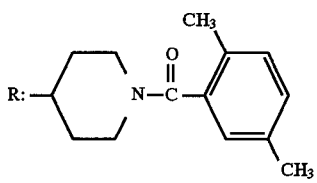

R¹: H
Bond between 3- and 4-positions in the
carbostyril ring: single bond
Crystalline form: white powders
Recrystallization solvent: dichloromethane/n-hexane
Melting point: 172–172.5° C.
Form: Free Example 220

Structure

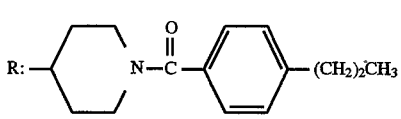

R¹: H
Bond between 3- and 4-positions in the
carbostyril ring: single bond
NMR analysis: 108)
Form: Free

TABLE 1-continued

Example 221

Structure

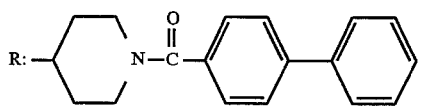

R¹: H
Bond between 3- and 4-positions in the
carbostyril ring: single bond
NMR analysis: 109)
Form: Free Example 222

Structure

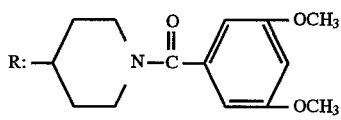

R¹: H
Bond between 3- and 4-positions in the
carbostyril ring: single bond
Crystalline form: white powders
Recrystallization solvent: dichloromethane/n-hexane
Melting point: 154–154.5° C.
Form: Free Example 223

Structure

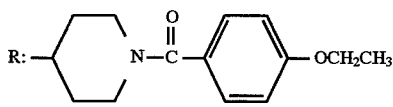

R¹: H
Bond between 3- and 4-positions in the
carbostyril ring: single bond
Crystalline form: white powders
Recrystallization solvent: dichloromethane/n-hexane
Melting point: 97–99° C.
Form: Free Example 224

Structure

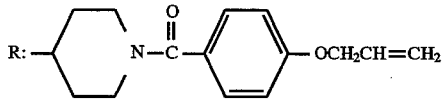

R¹: H
Bond between 3- and 4-positions in the
carbostyril ring: single bond
NMR analysis: 110)
Form: Free Example 225

Structure

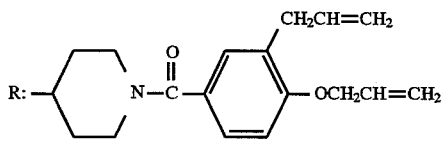

R¹: H
Bond between 3- and 4-positions in the
carbostyril ring: single bond

TABLE 1-continued

NMR analysis: 111)
Form: Free
Example 226

Structure

R: —[piperidine]—N—C(=O)—[C6H4]—CH3

R¹: H
Bond between 3- and 4-positions in the
carbostyril ring: single bond
Crystalline form: white powders
Recrystallization solvent: dichloromethane/n-hexane
Melting point: 112–113.5° C.
Form: Free
Example 227

Structure

R: —[piperidine]—N—C(=O)—[C6H3](OCH3)(OCH3)

R¹: H
Bond between 3- and 4-positions in the
carbostyril ring: single bond
NMR analysis: 112)
Form: Free
Example 228

Structure

R: —[piperidine]—N—C(=O)—[C6H3](OCOCH3)(OCOCH3)

R¹: H
Bond between 3- and 4-positions in the
carbostyril ring: single bond
Crystalline form: colorless needles
Recrystallization solvent: ethyl acetate/diethyl ether
Melting point: 134–137° C.
Form: Free
Example 229

Structure

R: —[piperidine]—N—C(=O)—[benzodioxole]

R¹: H
Bond between 3- and 4-positions in the
carbostyril ring: single bond
NMR analysis: 113)
Form: Free

TABLE 1-continued

Example 230

Structure

R: — [piperidine]—N—C(=O)—[phenyl with OCOCH₃ ortho and OCH₃ para]

R¹: H
Bond between 3- and 4-positions in the
carbostyril ring: single bond
NMR analysis: 114)
Form: Free

Example 231

Structure

R: — [piperidine]—N—C(=O)—[phenyl with NHCH₃ ortho and OCH₃ para]

R¹: H
Bond between 3- and 4-positions in the
carbostyril ring: single bond
NMR analysis: 115)
Form: Free

Example 232

Structure

R: — [piperidine]—N—C(=O)—[phenyl]—OCH₂CH₃

R¹: 7-F
Bond between 3- and 4-positions in the
carbostyril ring: single bond
NMR analysis: 116)
Form: Free

Example 233

Structure

R: — [phenyl]—C(=O)—N—[tetrahydroquinoline]

R¹: H
Bond between 3- and 4-positions in the
carbostyril ring: single bond
Crystalline form: white powders
Recrystallization ethanol/diethyl ether/n-hexane
Melting point: 162–163° C.
Form: Free

Example 234

Structure

R: — [piperidine]—N—C(=O)—[phenyl]—O(CH₂)₃NH₂

TABLE 1-continued

R¹: H
Bond between 3- and 4-positions in the
carbostyril ring: single bond
NMR analysis: 117)
Form: Free
Example 235

Structure

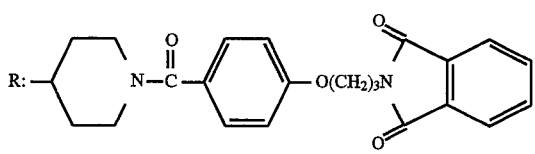

R¹: H
Bond between 3- and 4-positions in the
carbostyril ring: single bond
NMR analysis: 118)
Form: Free
Example 236

Structure

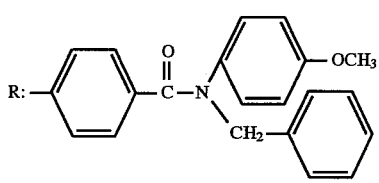

R¹: H
Bond between 3- and 4-positions in the
carbostyril ring: single bond
NMR analysis: 119)
Form: Free
Example 237

Structure

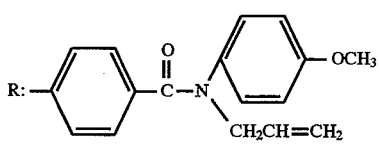

R¹: H
Bond between 3- and 4-positions in the
carbostyril ring: single bond
NMR analysis: 120)
Form: Free
Example 238

Structure

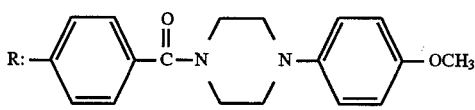

R¹: H
Bond between 3- and 4-positions in the
carbostyril ring: single bond
Crystalline form: white powders
Recrystallization solvent: ethanol/diethyl ether/n-hexane
Melting point: 179–180° C.
Form: Free TABLE 1-continued Example 239

Structure

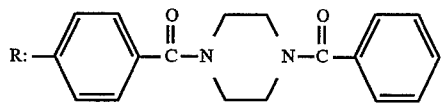

R¹: H
Bond between 3- and 4-positions in the
carbostyril ring: single bond
Crystalline form: white powders
Recrystallization solvent: ethanol/diethyl ether/n-hexane
Melting point: 188–189° C.
Form: Free Example 240

Structure

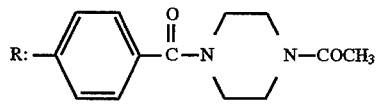

R¹: H
Bond between 3- and 4-positions in the
carbostyril ring: single bond
Crystalline form: white powders
Recrystallization solvent: ethanol/diethyl ether/n-hexane
Melting point: 217–218° C.
Form: Free Example 241

Structure

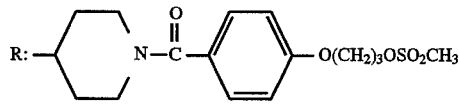

R¹: H
Bond between 3- and 4-positions in the
carbostyril ring: single bond
NMR analysis: 121)
Form: Free Example 242

Structure

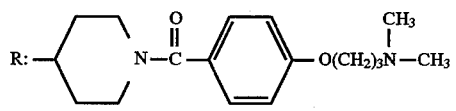

R¹: H
Bond between 3- and 4-positions in the
carbostyril ring: single bond
NMR analysis: 122)
Form: Hydrochloride Example 243

Structure

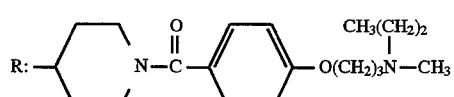

R¹: H
Bond between 3- and 4-positions in the
carbostyril ring: single bond
NMR analysis: 123)
Form: Free

TABLE 1-continued

Example 244

Structure

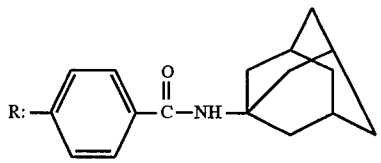

R¹: H
Bond between 3- and 4-positions in the
carbostyril ring: single bond
Crystalline form: white powders
Recrystallization solvent: ethanol/diethyl ether/n-hexane
Melting point: 279–280° C.
Form: Free Example 245

Structure

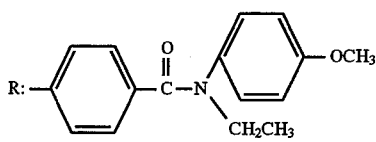

R¹: H
Bond between 3- and 4-positions in the
carbostyril ring: single bond
Crystalline form: white powders
Recrystallization solvent: ethanol/diethyl ether/n-hexane
Melting point: 155–156° C.
Form: Free Example 246

Structure

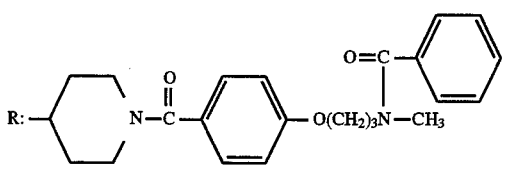

R¹: H
Bond between 3- and 4-positions in the
carbostyril ring: single bond
NMR analysis: 124)
Form: Free Example 247

Structure

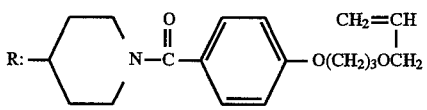

R¹: H
Bond between 3- and 4-positions in the
carbostyril ring: single bond
NMR analysis: 125)
Form: Free

TABLE 1-continued

Example 248

Structure

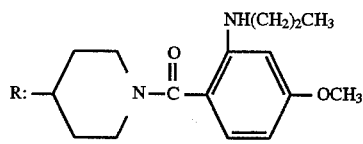

R¹: H
Bond between 3- and 4-positions in the
carbostyril ring: single bond
NMR analysis: 126)
Form: Free Example 249

Structure

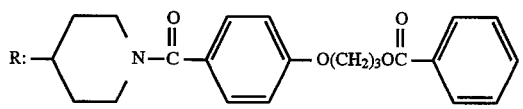

R¹: H
Bond between 3- and 4-positions in the
carbostyril ring: single bond
NMR analysis: 127)
Form: Free Example 250

Structure

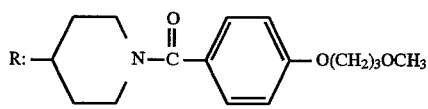

R¹: H
Bond between 3- and 4-positions in the
carbostyril ring: single bond
NMR analysis: 128)
Form: Free Example 251

Structure

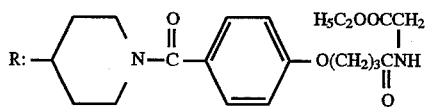

R¹: H
Bond between 3- and 4-positions in the
carbostyril ring: single bond
NMR analysis: 129)
Form: Free Example 252

Structure

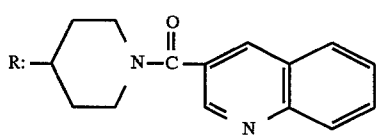

R¹: H
Bond between 3- and 4-positions in the
carbostyril ring: single bond
NMR analysis: 130)
Form: Free TABLE 1-continued Example 253

Structure

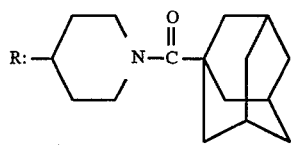

R[1]: H
Bond between 3- and 4-positions in the
carbostyril ring: single bond
NMR analysis: 131)
Form: Free Example 254

Structure

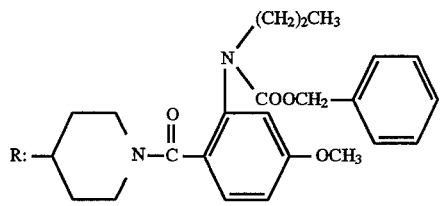

R[1]: H
Bond between 3- and 4-positions in the
carbostyril ring: single bond
Crystalline form: colorless needles
Recrystallization solvent: ethanol/diethyl ether/n-hexane
Melting point: 146–148° C.
Form: Free Example 255

Structure

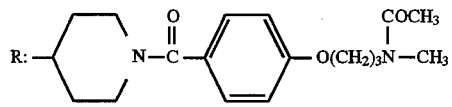

R[1]: H
Bond between 3- and 4-positions in the
carbostyril ring: single bond
NMR analysis: 132)
Form: Free Example 256

Structure

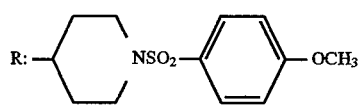

R[1]: H
Bond between 3- and 4-positions in the
carbostyril ring: single bond
NMR analysis: 133)
Form: Free Example 257

Structure

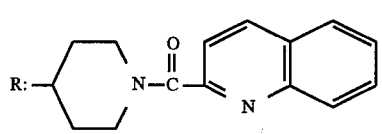

TABLE 1-continued

R$^1$: H
Bond between 3- and 4-positions in the
carbostyril ring: single bond
NMR analysis: 134)
Form: Free Example 258

Structure

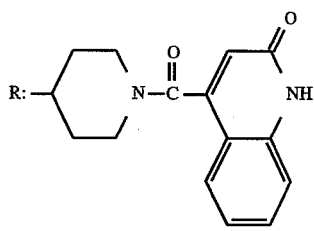

R$^1$: H
Bond between 3- and 4-positions in the
carbostyril ring: single bond
NMR analysis: 135)
Form: Free Example 259

Structure

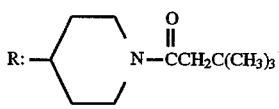

R$^1$: H
Bond between 3- and 4-positions in the
carbostyril ring: single bond
NMR analysis: 136)
Form: Free Example 260

Structure

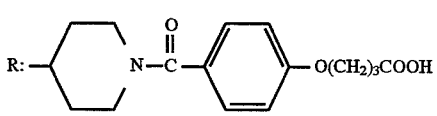

R$^1$: H
Bond between 3- and 4-positions in the
carbostyril ring: single bond
Crystalline form: white powders
Recrystallization solvent: ethanol/water
Melting point: 90–91° C.
Form: Free Example 261

Structure

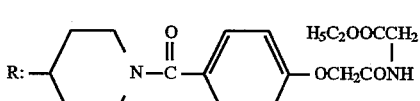

R$^1$: H
Bond between 3- and 4-positions in the
carbostyril ring: single bond
NMR analysis: 137)
Form: Free

TABLE 1-continued

Example 262

Structure

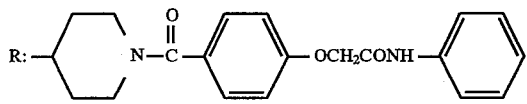

R[1]: H
Bond between 3- and 4-positions in the
carbostyril ring: single bond
NMR analysis: 138)
Form: Free Example 263

Structure

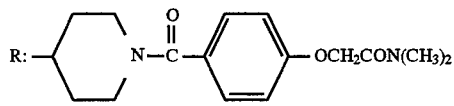

R[1]: H
Bond between 3- and 4-positions in the
carbostyril ring: single bond
NMR analysis: 139)
Form: Free Example 264

Structure

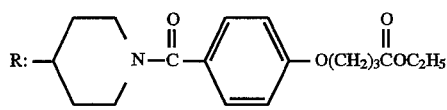

R[1]: H
Bond between 3- and 4-positions in the
carbostyril ring: single bond
NMR analysis: 140)
Form: Free Example 265

Structure

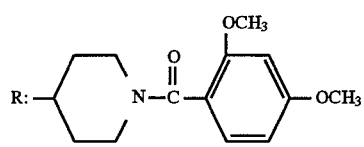

R[1]: 7-N(CH$_3$)$_2$
Bond between 3- and 4-positions in the
carbostyril ring: single bond
NMR analysis: 141)
Form: Free Example 266

Structure

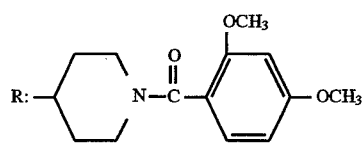

R[1]: 4-CH$_3$
Bond between 3- and 4-positions in the
carbostyril ring: single bond
NMR analysis: 142)
Form: Free

TABLE 1-continued

Example 267

Structure

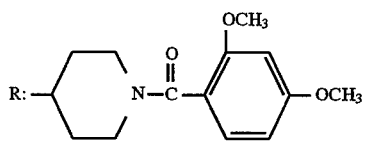

R¹: 7-NHCOCH₃
Bond between 3- and 4-positions in the
carbostyril ring: single bond
Crystalline form: white powders
Recrystallization solvent: ethanol
Melting point: 176–178° C.
Form: Free Example 268

Structure

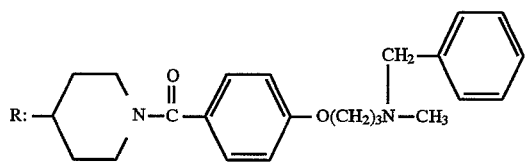

R¹: H
Bond between 3- and 4-positions in the
carbostyril ring: single bond
Crystalline form: colorless needles
Recrystallization solvent: ethanol/acetone/diethyl ether
Melting point: 222–226° C.
Form: Hydrochloride Example 269

Structure

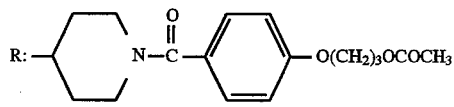

R¹: H
Bond between 3- and 4-positions in the
carbostyril ring: single bond
NMR analysis: 143)
Form: Free Example 270

Structure

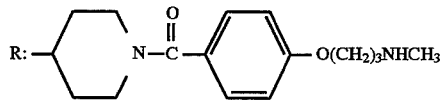

R¹: H
Bond between 3- and 4-positions in the
carbostyril ring: single bond
Crystalline form: colorless needles
Recrystallization solvent: ethanol/acetone/diethyl ether
Melting point: 89–93° C.
Form: Hydrochloride Example 271

Structure

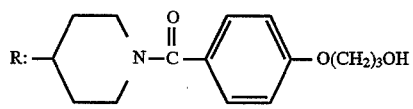

TABLE 1-continued

R¹: H
Bond between 3- and 4-positions in the
carbostyril ring: single bond
NMR analysis: 144)
Form: Free Example 272

Structure

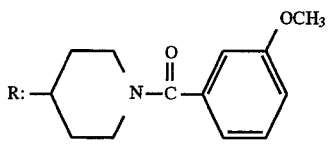

R¹: H
Bond between 3- and 4-positions in the
carbostyril ring: single bond
Crystalline form: white powders
Recrystallization solvent: dichloromethane/n-hexane
Melting point: 90–92° C.
Form: Free Example 273

Structure

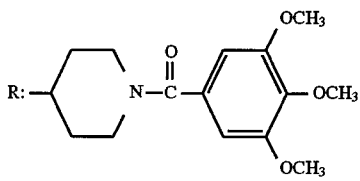

R¹: H
Bond between 3- and 4-positions in the
carbostyril ring: single bond
Crystalline form: white powders
Recrystallization solvent: dichloromethane/n-hexane
Melting point: 139–139.5° C.
Form: Free Example 274

Structure

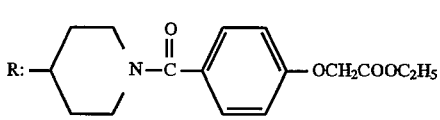

R¹: H
Bond between 3- and 4-positions in the
carbostyril ring: single bond
NMR analysis: 145)
Form: Free Example 275

Structure

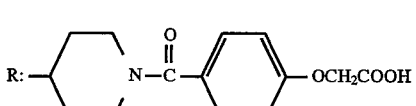

R¹: H
Bond between 3- and 4-positions in the
carbostyril ring: single bond
Crystalline form: white powders
Recrystallization solvent: ethanol
Melting point: 101.5–103.5° C.
Form: Free TABLE 1-continued Example 276

Structure

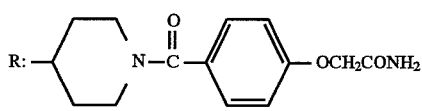

R¹: H
Bond between 3- and 4-positions in the
carbostyril ring: single bond
Crystalline form: white powders
Recrystallization solvent: ethanol
Melting point: 115–117° C.
Form: Free Example 277

Structure

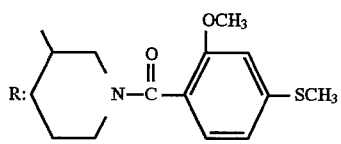

R¹: H
Bond between 3- and 4-positions in the
carbostyril ring: single bond
NMR analysis: 146)
Form: Free Example 278

Structure

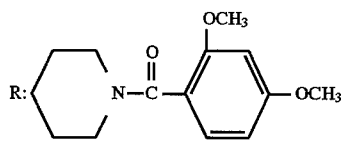

R¹: 6-OCH₃
Bond between 3- and 4-positions in the
carbostyril ring: single bond
NMR analysis: 147)
Form: Free Example 279

Structure

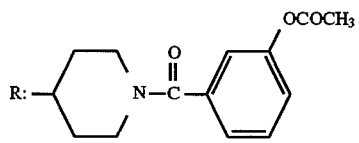

R¹: H
Bond between 3- and 4-positions in the
carbostyril ring: single bond
NMR analysis: 148)
Form: Free Example 280

Structure

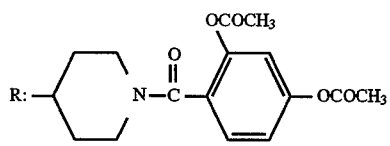

R¹: H
Bond between 3- and 4-positions in the

TABLE 1-continued carbostyril ring: single bond
NMR analysis: 149)
Form: Free
Example 281

Structure

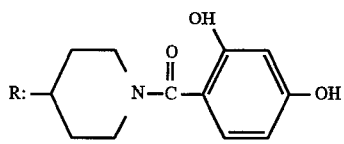

R¹: H
Bond between 3- and 4-positions in the
carbostyril ring: single bond
NMR analysis: 150)
Form: Free
Example 282

Structure

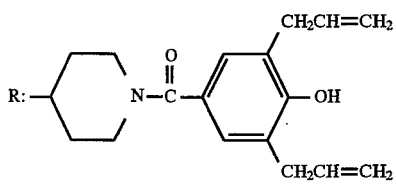

R¹: H
Bond between 3- and 4-positions in the
carbostyril ring: single bond
Crystalline form: white powders
Recrystallization solvent: dichloromethane/n-hexane
Melting point: 158–160° C.
Form: Free
Example 283

Structure

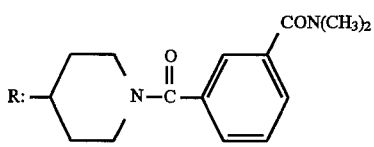

R¹: H
Bond between 3- and 4-positions in the
carbostyril ring: single bond
Crystalline form: colorless needles
Recrystallization solvent: ethyl acetate/diethyl ether
Melting point: 171–174° C.
Form: Free
Example 284

Structure

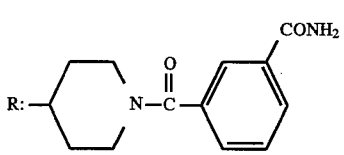

R¹: H
Bond between 3- and 4-positions in the
carbostyril ring: single bond
NMR analysis: 151)
Form: Free TABLE 1-continued Example 285

Structure

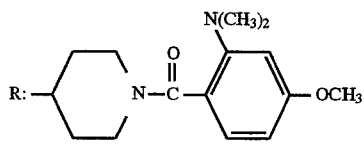

R¹: H
Bond between 3- and 4-positions in the
carbostyril ring: single bond
Crystalline form: colorless flakes
Recrystallization solvent: ethanol
Melting point: 138–140° C.
Form: Free Example 286

Structure

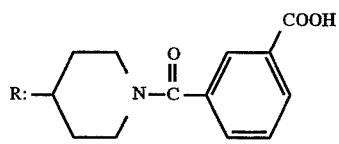

R¹: H
Bond between 3- and 4-positions in the
carbostyril ring: single bond
Crystalline form: colorless needles
Recrystallization solvent: dichloromethane/ethanol
Melting point: 237–240° C.
Form: Free Example 287

Structure

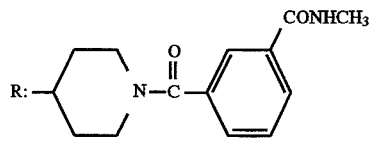

R¹: H
Bond between 3- and 4-positions in the
carbostyril ring: single bond
NMR analysis: 152)
Form: Free Example 288

Structure

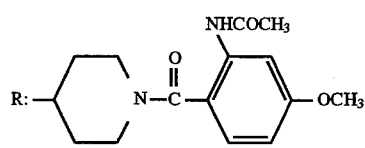

R¹: H
Bond between 3- and 4-positions in the
carbostyril ring: single bond
Crystalline form: colorless flakes
Recrystallization solvent: methanol/water
Melting point: 169–171° C.
Form: Free

TABLE 1-continued

Example 289

Structure

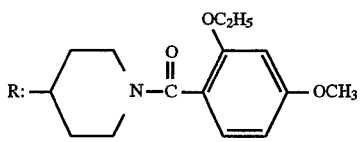

R[1]: H
Bond between 3- and 4-positions in the
carbostyril ring: single bond
NMR analysis: 153)
Form: Free Example 290

Structure

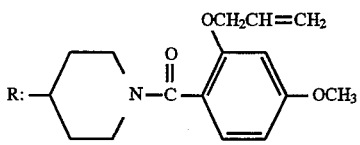

R[1]: H
Bond between 3- and 4-positions in the
carbostyril ring: single bond
NMR analysis: 154)
Form: Free Example 291

Structure

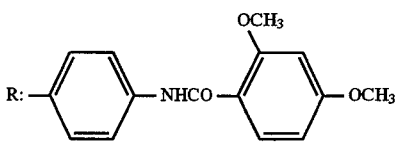

R[1]: H
Bond between 3- and 4-positions in the
carbostyril ring: single bond
Crystalline form: white powders
Recrystallization solvent: ethanol/diethyl ether/n-hexane
Melting point: 226–227° C.
Form: Free Example 292

Structure

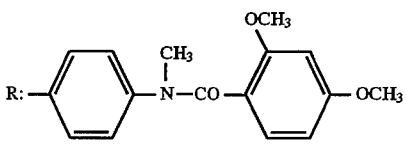

R[1]: H
Bond between 3- and 4-positions in the
carbostyril ring: single bond
NMR analysis: 155)
Form: Free Example 293

Structure

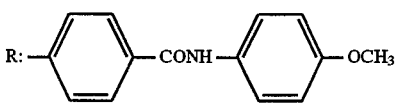

R[1]: H
Bond between 3- and 4-positions in the

TABLE 1-continued carbostyril ring: single bond
Crystalline form: white powders
Recrystallization solvent: ethanol/diethyl ether/n-hexane
Melting point: 254–255° C.
Form: Free Example 294

Structure

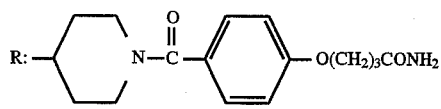

R¹: H
Bond between 3- and 4-positions in the
carbostyril ring: single bond
NMR analysis: 156)
Form: Free Example 295

Structure

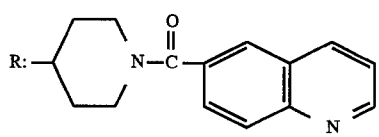

R¹: H
Bond between 3- and 4-positions in the
carbostyril ring: single bond
NMR analysis: 157)
Form: Free Example 296

Structure

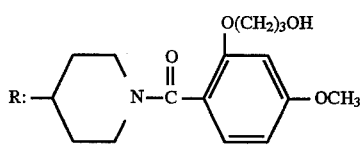

R¹: H
Bond between 3- and 4-positions in the
carbostyril ring: single bond
NMR analysis: 158)
Form: Free Example 297

Structure

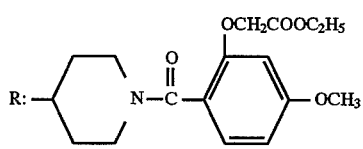

R¹: H
Bond between 3- and 4-positions in the
carbostyril ring: single bond
NMR analysis: 159)
Form: Free

TABLE 1-continued

Example 298

Structure

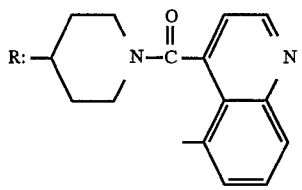

R[1]: H
Bond between 3- and 4-positions in the
carbostyril ring: single bond
NMR analysis: 160)
Form: Free Example 299

Structure

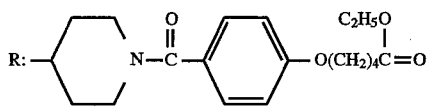

R[1]: H
Bond between 3- and 4-positions in the
carbostyril ring: single bond
NMR analysis: 161)
Form: Free Example 300

Structure

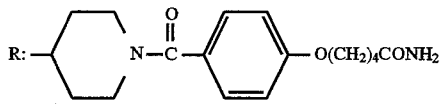

R[1]: H
Bond between 3- and 4-positions in the
carbostyril ring: single bond
Crystalline form: colorless prisms
Recrystallization solvent: ethanol/n-hexane
Melting point: 156–157° C.
Form: Free Example 301

Structure

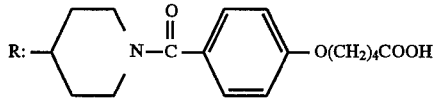

R[1]: H
Bond between 3- and 4-positions in the
carbostyril ring: single bond
Crystalline form: colorless needles
Recrystallization solvent: ethanol/water
Melting point: 175–176° C.
Form: Free Example 302

Structure

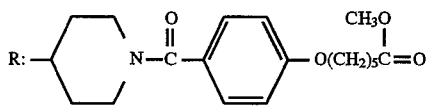

R[1]: H
Bond between 3- and 4-positions in the

TABLE 1-continued carbostyril ring: single bond
NMR analysis: 162)
Form: Free
Example 303

Structure

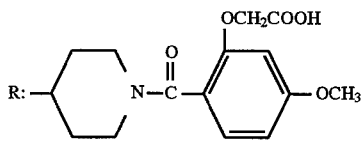

R¹: H
Bond between 3- and 4-positions in the
carbostyril ring: single bond
Crystalline form: white powders
Recrystallization solvent: ethanol/water
Melting point: 229.5–231° C.
Form: Free
Example 304

Structure

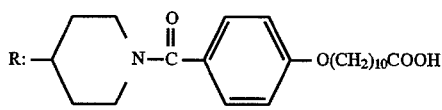

R¹: H
Bond between 3- and 4-positions in the
carbostyril ring: single bond
Crystalline form: white powders
Recrystallization solvent: ethanol/water
Melting point: 132–133° C.
Form: Free
Example 305

Structure

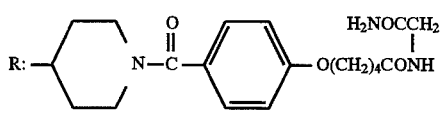

R¹: H
Bond between 3- and 4-positions in the
carbostyril ring: single bond
NMR analysis: 163)
Form: Free
Example 306

Structure

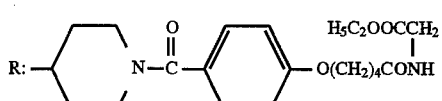

R¹: H
Bond between 3- and 4-positions in the
carbostyril ring: single bond
NMR analysis: 164)
Form: Free
Example 307

Structure

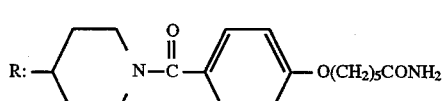

TABLE 1-continued

R¹: H
Bond between 3- and 4-positions in the
carbostyril ring: single bond
NMR analysis: 165)
Form: Free
Example 308

Structure

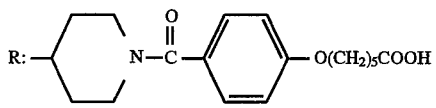

R¹: H
Bond between 3- and 4-positions in the
carbostyril ring: single bond
Crystalline form: colorless needles
Recrystallization solvent: ethanol/water
Melting point: 146–148° C.
Form: Free
Example 309

Structure

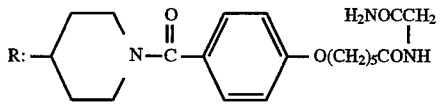

R¹: H
Bond between 3- and 4-positions in the
carbostyril ring: single bond
NMR analysis: 166)
Form: Free
Example 310

Structure

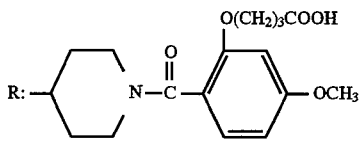

R¹: H
Bond between 3- and 4-positions in the
carbostyril ring: single bond
Crystalline form: white powders
Recrystallization solvent: ethanol/water
Melting point: 179.5–181.5° C.
Form: Free
Example 311

Structure

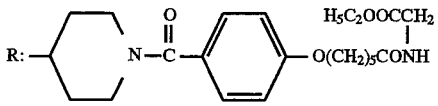

R¹: H
Bond between 3- and 4-positions in the
carbostyril ring: single bond
NMR analysis: 166A)
Form: Free
Example 312

Structure

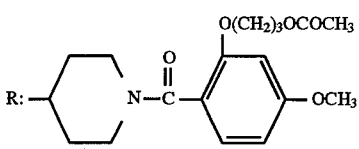

TABLE 1-continued

R¹: H
Bond between 3- and 4-positions in the
carbostyril ring: single bond
NMR analysis: 167)
Form: Free Example 313

Structure

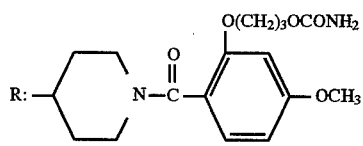

R¹: H
Bond between 3- and 4-positions in the
carbostyril ring: single bond
NMR analysis: 168)
Form: Free Example 314

Structure

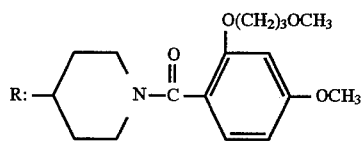

R¹: H
Bond between 3- and 4-positions in the
carbostyril ring: single bond
NMR analysis: 169)
Form: Free Example 315

Structure

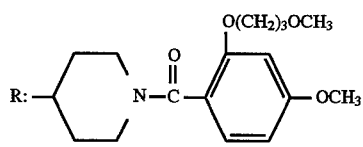

R¹: H
Bond between 3- and 4-positions in the
carbostyril ring: single bond
NMR analysis: 170)
Form: Free Example 316

Structure

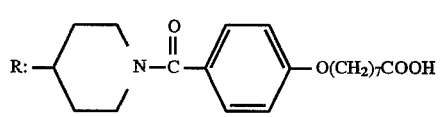

R¹: H
Bond between 3- and 4-positions in the
carbostyril ring: single bond
Crystalline form: colorless needles
Recrystallization solvent: ethanol/water
Melting point: 110–112° C.
Form: Free TABLE 1-continued Example 317

Structure

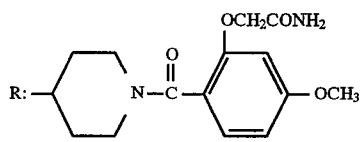

R¹: H
Bond between 3- and 4-positions in the
carbostyril ring: single bond
Crystalline form: white powders
Recrystallization solvent: ethanol/n-hexane
Melting point: 175.5–176.5° C.
Form: Free Example 318

Structure

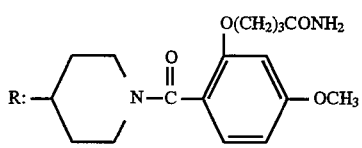

R¹: H
Bond between 3- and 4-positions in the
carbostyril ring: single bond
NMR analysis: 171)
Form: Free Example 319

Structure

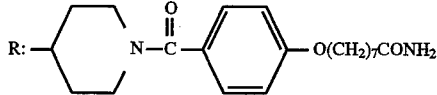

R¹: H
Bond between 3- and 4-positions in the
carbostyril ring: single bond
NMR analysis: 172)
Form: Free Example 320

Structure

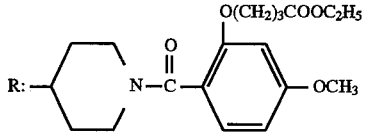

R¹: H
Bond between 3- and 4-positions in the
carbostyril ring: single bond
NMR analysis: 173)
Form: Free Example 321

Structure

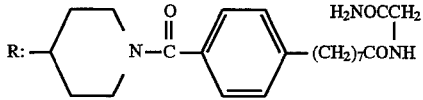

R¹: H
Bond between 3- and 4-positions in the
carbostyril ring: single bond

TABLE 1-continued

NMR analysis: 174)
Form: Free
Example 322

Structure

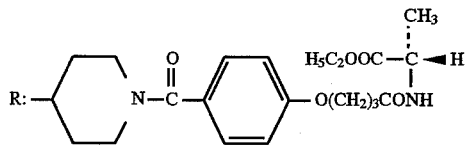

R¹: H
Bond between 3- and 4-positions in the
carbostyril ring: single bond
NMR analysis: 175)
Form: Free
Example 323

Structure

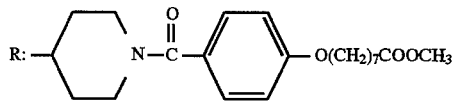

R¹: H
Bond between 3- and 4-positions in the
carbostyril ring: single bond
NMR analysis: 176)
Form: Free
Example 324

Structure

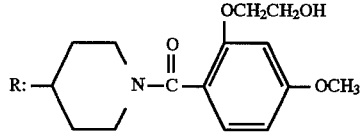

R¹: H
Bond between 3- and 4-positions in the
carbostyril ring: single bond
NMR analysis: 177)
Form: Free
Example 325

Structure

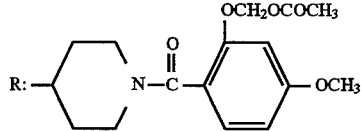

R¹: H
Bond between 3- and 4-positions in the
carbostyril ring: single bond
NMR analysis: 178)
Form: Free
Example 326

Structure

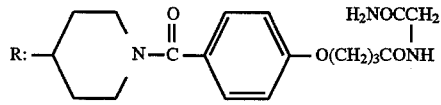

R¹: H
Bond between 3- and 4-positions in the
carbostyril ring: single bond

TABLE 1-continued

NMR analysis: 179)
Form: Free
Example 327

Structure

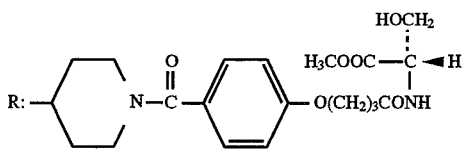

R¹: H
Bond between 3- and 4-positions in the
carbostyril ring: single bond
NMR analysis: 180)
Form: Free
Example 328

Structure

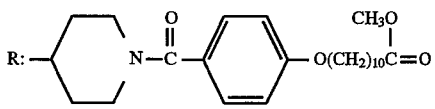

R¹: H
Bond between 3- and 4-positions in the
carbostyril ring: single bond
NMR analysis: 181)
Form: Free
Example 329

Structure

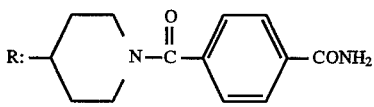

R¹: H
Bond between 3- and 4-positions in the
carbostyril ring: single bond
Crystalline form: white powders
Recrystallization solvent: diethyl ether/n-hexane
Melting point: 101–104° C.
Form: Free
Example 330

Structure

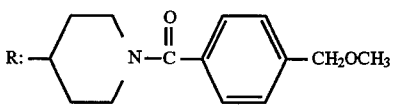

R¹: H
Bond between 3- and 4-positions in the
carbostyril ring: single bond
Crystalline form: white powders
Recrystallization solvent: n-hexane/ethanol
Melting point: 146–147° C.
Form: Free
Example 331

Structure

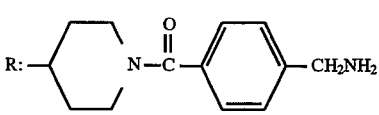

R¹: H
Bond between 3- and 4-positions in the
carbostyril ring: single bond

TABLE 1-continued

Crystalline form: pale yellow powders
Recrystallization solvent: ethanol/n-hexane
Melting point: 95–98° C.
Form: Free
Example 332

Structure

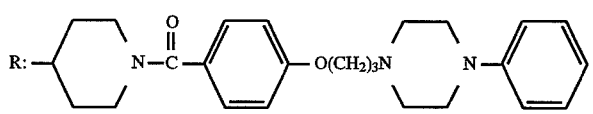

R$^1$: H
Bond between 3- and 4-positions in the
carbostyril ring: single bond
Crystalline form: white powders
Recrystallization solvent: diethyl ether/n-hexane
Melting point: 94–97° C.
Form: (COOH)$_2$
Example 333

Structure

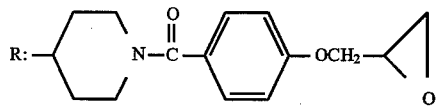

R$^1$: H
Bond between 3- and 4-positions in the
carbostyril ring: single bond
Crystalline form: white powders
Recrystallization solvent: ethanol/n-hexane
Melting point: 101–102° C.
Form: Free
Example 334

Structure

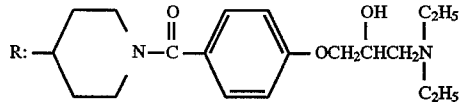

R$^1$: H
Bond between 3- and 4-positions in the
carbostyril ring: single bond
Crystalline form: white powders
Recrystallization solvent: diethyl ether
Melting point: 72–76° C.

Form: OH—C(CH$_2$COOH)(CH$_2$COOH)—COOH

Example 335

Structure

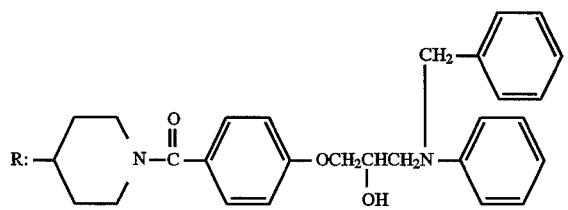

R$^1$: H
Bond between 3- and 4-positions in the
carbostyril ring: single bond
Crystalline form: white powders
Recrystallization solvent: ethanol/n-hexane

TABLE 1-continued

Melting point: 87–89° C.
Form: Free
Example 336

Structure

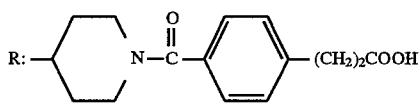

R¹: H
Bond between 3- and 4-positions in the
carbostyril ring: single bond
Crystalline form: white powders
Recrystallization solvent: diethyl ether/n-hexane
Melting point: 70–72° C.
Form: Free
Example 337

Structure

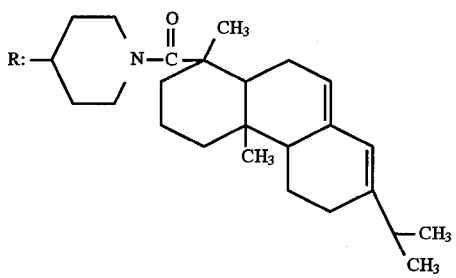

R¹: H
Bond between 3- and 4-positions in the
carbostyril ring: single bond
Crystalline form: white powders
Recrystallization solvent: ethanol/n-hexane
Melting point: 94–96° C.
Form: Free
Example 338

Structure

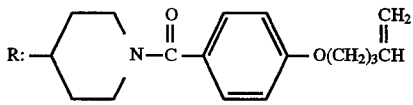

R¹: H
Bond between 3- and 4-positions in the
carbostyril ring: single bond
Crystalline form: white powders
Recrystallization solvent: ethanol/n-hexane
Melting point: 108–109° C.
Form: Free
Example 339

Structure

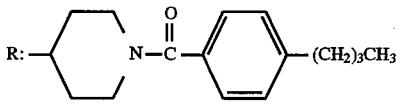

R¹: H
Bond between 3- and 4-positions in the
carbostyril ring: single bond
Crystalline form: white powders
Recrystallization solvent: n-hexane/ethanol
Melting point: 103–104° C.
Form: Free TABLE 1-continued Example 340

Structure

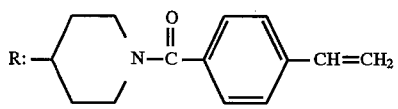

R¹: H
Bond between 3- and 4-positions in the
carbostyril ring: single bond
Crystalline form: white powders
Recrystallization solvent: ethanol/n-hexane
Melting point: 114–116° C.
Form: Free Example 341

Structure

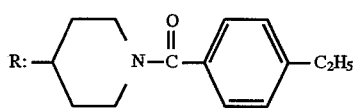

R¹: H
Bond between 3- and 4-positions in the
carbostyril ring: single bond
Crystalline form: white powders
Recrystallization solvent: ethanol/n-hexane
Melting point: 133–134° C.
Form: Free Example 342

Structure

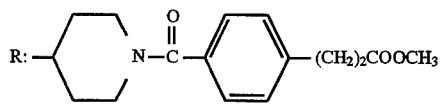

R¹: H
Bond between 3- and 4-positions in the
carbostyril ring: single bond
Crystalline form: white powders
Recrystallization solvent: n-hexane
Melting point: 85–86° C.
Form: Free Example 343

Structure

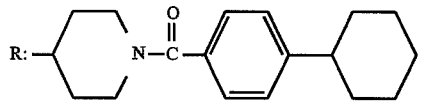

R¹: H
Bond between 3- and 4-positions in the
carbostyril ring: single bond
Crystalline form: white powders
Recrystallization solvent: n-hexane
Melting point: 121–122° C.
Form: Free Example 344

Structure

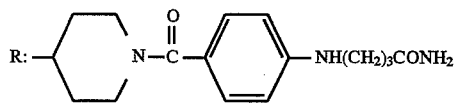

R¹: H
Bond between 3- and 4-positions in the

TABLE 1-continued carbostyril ring: single bond
Crystalline form: white powders
Recrystallization solvent: ethanol/n-hexane
Melting point: 71–73° C.
Form: Free
Example 345

Structure

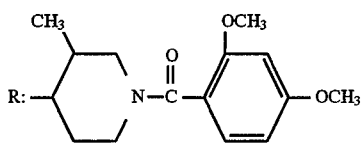

R[1]: H
Bond between 3- and 4-positions in the
carbostyril ring: single bond
NMR analysis: 182)
Form: Free
Example 346

Structure

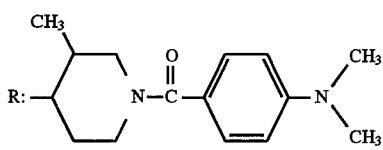

R[1]: H
Bond between 3- and 4-positions in the
carbostyril ring: single bond
NMR analysis: 183)
Form: Free
Example 347

Structure

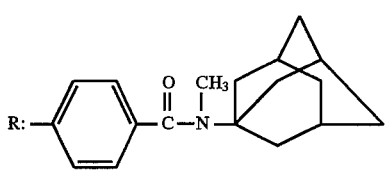

R[1]: H
Bond between 3- and 4-positions in the
carbostyril ring: single bond
NMR analysis: 184)
Form: Free
Example 348

Structure

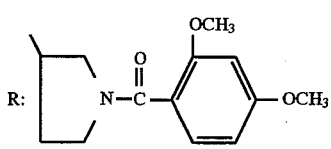

R[1]: H
Bond between 3- and 4-positions in the
carbostyril ring: single bond
NMR analysis: 185)
Form: Free TABLE 1-continued Example 349

Structure

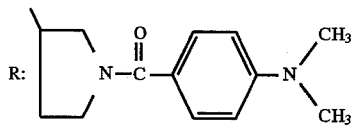

R¹: H
Bond between 3- and 4-positions in the
carbostyril ring: single bond
NMR analysis: 186)
Form: Free Example 350

Structure

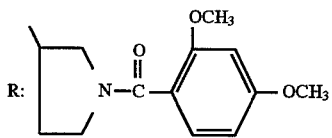

R¹: 6-CH₃
Bond between 3- and 4-positions in the
carbostyril ring: single bond
NMR analysis: 187)
Form: Free Example 351

Structure

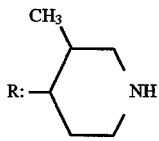

R¹: H
Bond between 3- and 4-positions in the
carbostyril ring: single bond
NMR analysis: 188)
Form: Free Example 352

Structure

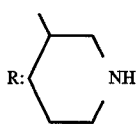

R¹: H
Bond between 3- and 4-positions in the
carbostyril ring: single bond
NMR analysis: 189)
Form: Free Example 353

Structure

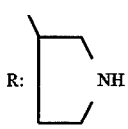

R¹: H
Bond between 3- and 4-positions in the
carbostyril ring: single bond

TABLE 1-continued

NMR analysis: 190)
Form: Free
Example 354

Structure

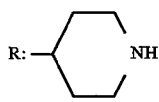

R¹: 6-OCH₃
Bond between 3- and 4-positions in the
carbostyril ring: single bond
NMR analysis: 191)
Form: Free
Example 355

Structure

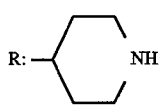

R¹: H
Bond between 3- and 4-positions in the
carbostyril ring: single bond
NMR analysis: 192)
Form: Free
Example 356

Structure

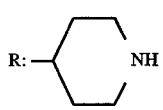

R¹: 7-CH₃
Bond between 3- and 4-positions in the
carbostyril ring: single bond
NMR analysis: 193)
Form: Free
Example 357

Structure

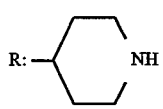

R¹: 7-F
Bond between 3- and 4-positions in the
carbostyril ring: single bond
NMR Analysis: 194)
Form: Free
Example 358

Structure

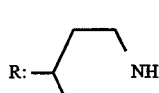

R¹: 8-CH₃
Bond between 3- and 4-positions in the
carbostyril ring: single bond
NMR analysis: 195)
Form: Free TABLE 1-continued Example 359

Structure

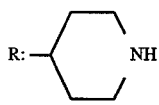

R[1]: 7-NHCOCH$_3$
Bond between 3- and 4-positions in the
carbostyril ring: single bond
NMR analysis: 196)
Form: Free Example 360

Structure

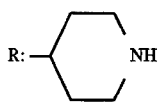

R[1]: 4-CH$_3$
Bond between 3- and 4-positions in the
carbostyril ring: single bond
NMR analysis: 197)
Form: Free Example 361

Structure

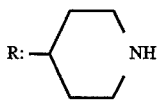

R[1]: 7-N(CH$_3$)$_2$
Bond between 3- and 4-positions in the
carbostyril ring: single bond
NMR analysis: 198)
Form: Free Example 362

Structure

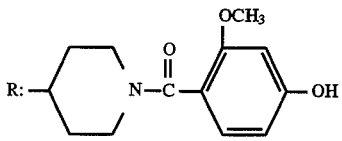

R[1]: H
Bond between 3- and 4-positions in the
carbostyril ring: single bond
NMR analysis: 199)
Form: Free Example 363

Structure

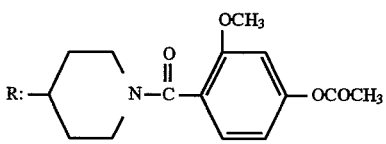

R[1]: H
Bond between 3- and 4-positions in the
carbostyril ring: single bond
NMR analysis: 200)
Form: Free

TABLE 1-continued

Example 364

Structure

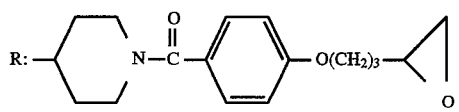

R[1]: H
Bond between 3- and 4-positions in the
carbostyril ring: single bond
NMR analysis: 201)
Form: Free Example 365

Structure

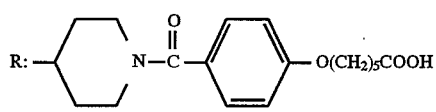

R[1]: H
Bond between 3- and 4-positions in the
carbostyril ring: single bond
Crystalline form: colorless needles
Recrystallization solvent: ethanol/water
Melting point: 146–148° C.
Form: Free Example 366

Structure

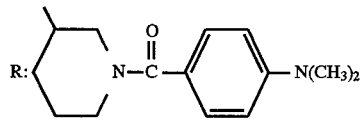

R[1]: H
Bond between 3- and 4-positions in the
carbostyril ring: single bond
Crystalline form: white powders
Recrystallization solvent: ethanol/diethyl ether/n-hexane
Melting point: 181–183° C.
Form: Free Example 367

Structure

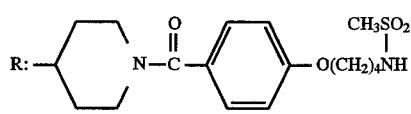

R[1]: H
Bond between 3- and 4-positions in the
carbostyril ring: single bond
Crystalline form: colorless prisms
Recrystallization solvent: ethanol
Melting point: 99–101° C.
Form: Free Example 368

Structure

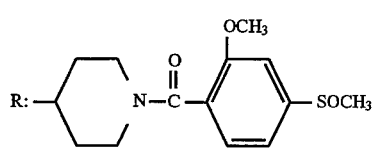

TABLE 1-continued

R¹: H
Bond between 3- and 4-positions in the
carbostyril ring: single bond
Crystalline form: white powders
Recrystallization solvent: ethanol/n-hexane
Melting point: 83–86° C.
Form: Free Example 369

Structure

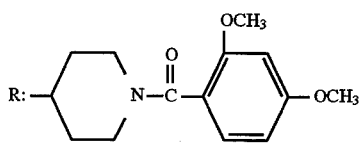

R¹: 7-C₂H₅
Bond between 3- and 4-positions in the
carbostyril ring: single bond
NMR analysis: 202)
Form: Free Example 370

Structure

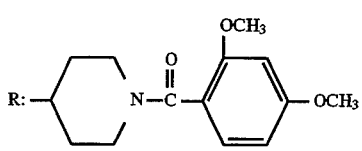

R¹: 7-OCH₃
Bond between 3- and 4-positions in the
carbostyril ring: single bond
NMR analysis: 203)
Form: Free Example 371

Structure

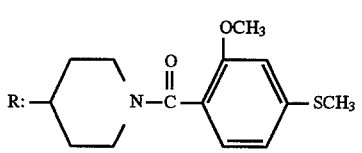

R¹: 7-F
Bond between 3- and 4-positions in the
carbostyril ring: single bond
NMR analysis: 204)
Form: Free Example 372

Structure

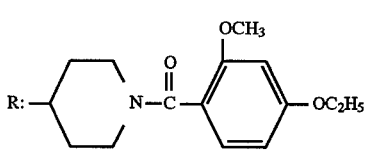

R¹: 7-F
Bond between 3- and 4-positions in the
carbostyril ring: single bond
Crystalline form: white powders
Recrystallization solvent: ethanol/water
Melting point: 159–161° C.
Form: Free TABLE 1-continued Example 373

Structure

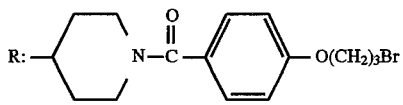

R¹: H
Bond between 3- and 4-positions in the
  carbostyril ring: single bond
NMR analysis: 205)
Form: Free Example 374

Structure

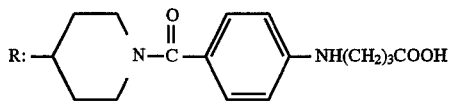

R¹: H
Bond between 3- and 4-positions in the
  carbostyril ring: single bond
NMR analysis: 206)
Form: Free Example 375

Structure

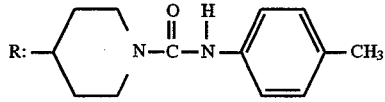

R¹: H
Bond between 3- and 4-positions in the
  carbostyril ring: single bond
Crystalline form: colorless flakes
Recrystallization solvent: diethyl ether
Melting point: 175–176° C.
Form: Free Example 376

Structure

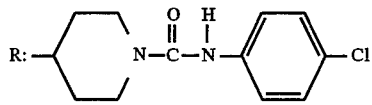

R¹: H
Bond between 3- and 4-positions in the
  carbostyril ring: single bond
Crystalline form: white powders
Recrystallization solvent: diethyl ether
Melting point: 199–200° C.
Form: Free Example 377

Structure

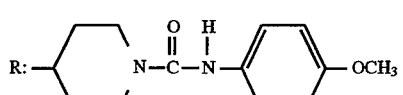

R¹: H
Bond between 3- and 4-positions in the
  carbostyril ring: single bond
Crystalline form: white powders
Recrystallization solvent: diethyl ether

TABLE 1-continued

Melting point: 167–168° C.
Form: Free

Example 378

Structure

R: —[piperidine ring]—N—C(=O)—N(H)—[phenyl with 2-OCH₃, 4-OCH₃]

R¹: H
Bond between 3- and 4-positions in the
carbostyril ring: single bond
Crystalline form: white powders
Recrystallization solvent: diethyl ether/n-hexane
Melting point: 136–137° C.
Form: Free

Example 379

Structure

R: —[piperidine ring]—N—CO₂—[phenyl]—NO₂

R¹: H
Bond between 3- and 4-positions in the
carbostyril ring: single bond
Crystalline form: white powders
Recrystallization solvent: diethyl ether/n-hexane
Melting point: 154–155° C.
Form: Free

Example 380

Structure

R: —[piperidine ring]—N—CO₂—[phenyl]—NH₂

R¹: H
Bond between 3- and 4-positions in the
carbostyril ring: single bond
Crystalline form: white powders
Recrystallization solvent: diethyl ether/n-hexane
Melting point: 167–168° C.
Form: Free

Example 381

Structure

R: —[piperidine ring]—N—CO₂—[phenyl]—N(CH₃)₂

R¹: H
Bond between 3- and 4-positions in the
carbostyril ring: single bond
Crystalline form: white powders
Recrystallization solvent: diethyl ether/n-hexane
Melting point: 189–191° C.
Form: Free

Example 382

Structure

R: —[piperidine ring]—N—CO₂—[phenyl]—NHCOCH₃

TABLE 1-continued

R¹: H
Bond between 3- and 4-positions in the
carbostyril ring: single bond
Crystalline form: white powders
Recrystallization solvent: diethyl ether/n-hexane
Melting point: 215–216° C.
Form: Free
Example 383

Structure

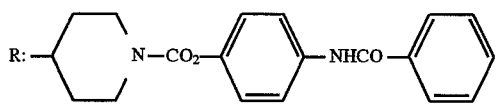

R¹: H
Bond between 3- and 4-positions in the
carbostyril ring: single bond
Crystalline form: white powders
Recrystallization solvent: diethyl ether/n-hexane
Melting point: 199–200° C.
Form: Free
Example 383A Structure

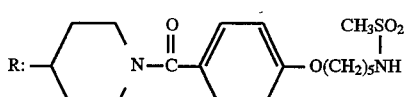

R¹: H
Bond between 3- and 4-positions in the
carbostyril ring: single bond
NMR analysis: 207)
Form: Free
Example 383B Structure

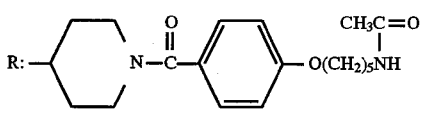

R¹: H
Bond between 3- and 4-positions in the
carbostyril ring: single bond
Crystalline form: colorless prisms
Recrystallization solvent: ethanol/ethyl acetate
Melting point: 141–142° C.
NMR analysis: 208)
Form: Free
Example 383C Structure

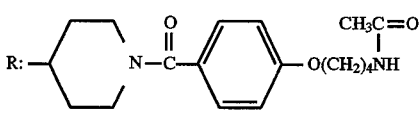

R¹: H
Bond between 3- and 4-positions in the
carbostyril ring: single bond
NMR analysis: 209)
Form: Free

TABLE 2

| No. | NMR (CDCl$_3$) δ value |
|---|---|
| 1 | 1.55–1.82(2H, m), 2.08–2.87(7H, m), 2.95–3.17(1H, m), 3.79(2H, s), 3.90–4.08(1H, m), 4.35–4.58(1H, m), 4.73–4.92(1H, m), 6.86–7.48(9H, m) |
| 2 | 1.65–1.84(2H, m), 2.25–2.88(7H, m), 3.05–3.24(1H, m), 3.97(2H, s), 4.00–4.13(1H, m), 4.38–4.58(1H, m), 4.73–4.92(1H, m), 6.92–7.28(7H, m) |
| 3 | 1.72–2.01(2H, m), 2.53–3.01(7H, m), 3.13–3.33(1H, m), 4.09–4.23(1H, m), 4.43–4.62(1H, m), 4.87–5.04(1H, m), 6.97–7.33(4H, m), 8.55(1H, dd, J=2.5, 1.4Hz), 8.64(1H, d, J=2.5Hz), 8.99(1H, d, J=1.4Hz) |
| 4 | 0.98(3H, t, J=7.3Hz), 1.40–1.93(6H, m), 2.50–3.15(8H, m), 3.99(2H, t, J=6.4Hz), 3.13–5.10(3H, m), 6.83–7.48(4H, m) |
| 5 | 1.46–1.86(8H, m), 2.33–3.04(8H, m), 3.95–5.10(8H, m), 6.02–6.20(1H, m), 6.96–7.40(9H, m) |
| 6 | 1.65–1.93(2H, m), 2.50(3H, s), 2.52–3.24(8H, m), 3.56–5.25(3H, m), 6.95–7.46(8H, m) |
| 7 | 1.65–1.96(2H, m), 2.18(3H, s), 2.46–3.18(8H, m), 3.72–5.13(3H, m), 6.95–7.32(4H, m), 7.32–7.56(4H, m), 7.95(1H, brs) |
| 8 | 1.20–3.33(20H, m), 3.85–5.85(8H, m), 6.96–7.29(4H, m) |
| 9 | 1.12–1.93(2H, m), 2.52–3.30(8H, m), 4.00(3H, s), 3.73–5.15(3H, m) 7.00–7.34(5H, m), 7.72(1H, dd, J=8.6, 2.1Hz), 7.99(1H, d, J=2.1Hz) |
| 10 | 1.63–2.04(2H, m), 2.52–3.24(8H, m), 2.63(3H, s), 3.71–3.89(1H, m), 4.26–4.44(1H, m), 4.80–5.04(1H, m), 7.00–7.33(4H, m), 7.56(2H, d, J=8.0Hz), 8.01(2H, d, J=8.0Hz) |
| 11 | 1.33(3H, t, J=7.3Hz), 1.68–2.06(2H, m), 2.50–3.30(8H, m), 3.13(2H, q, J=7.3Hz), 3.72–5.13(3H, m), 6.97–7.34(6H, m), 7.44(2H, d, J=8.5Hz), 7.58(2H, d, J=8.5Hz) |
| 12 | 1.72–1.98(2H, m), 2.54–3.20(8H, m), 3.84–5.08(3H, m), 5.13(2H, s), 6.98–7.52(13H, m) |
| 13 | 1.58–1.73(1H, m), 1.78–1.96(1H, m), 2.50(3H, s), 2.42–3.26(8H, m), 3.56–3.73(1H, m), 3.28–3.97(3H, m), 4.20–4.73(1H, m), 4.88–5.05(1H, m), 6.78–6.92(2H, m), 6.98–7.36(4H, m) |
| 14 | 1.72–1.94(2H, m), 2.48–3.26(10H, m), 2.66(6H, s), 3.77–5.28(5H, m), 6.94–7.45(6H, m) |
| 15 | 1.03(6H, d, J=6.7Hz), 1.70–1.90(2H, m), 1.95–2.22(1H, m), 2.47–3.18(8H, m), 3.74(2H, d, J=6.5Hz), 3.66–5.10(3H, m), 6.84–7.49(8H, m) |
| 16 | 1.47(9H, s), 1.68–1.97(2H, m), 2.50–3.22(8H, m), 3.28(3H, s), 3.66–5.10(3H, m), 6.96–7.52(8H, m) |
| 17 | 1.45(9H, s), 1.55(3H, s), 1.69(3H, s), 1.60–1.94(2H, m), 2.50–3.23(8H, m), 3.72–5.14(3H, m), 4.22(2H, d, J=6.4Hz), 5.20–5.33(1H, m), 6.98–7.44(8H, m) |
| 18 | 1.68–1.93(2H, m), 2.50–3.34(16H, m), 3.90–4.97(3H, m), 6.89(2H, d, J=8.8Hz), 6.98–7.31(4H, m), 7.41(2H, d, J=8.8Hz) |
| 19 | 1.56–1.79(2H, m), 1.75(3H, s), 1.80(3H, s), 2.47–3.14(8H, m), 3.93–5.05(3H, m), 4.53(2H, d, J=6.8Hz), 5.40–5.57(1H, m), 6.83–7.53(8H, m) |
| 20 | 1.70–1.90(2H, m), 2.36(3H, s), 2.43–3.12(12H, m), 3.22–3.35(4H, m), 3.92–4.86(3H, m), 6.89(2H, d, J=8.8Hz), 6.96–7.32(4H, m), 7.41(2H, d, J=8.8Hz) |
| 21 | 1.25(6H, d, J=6.9Hz), 1.63–2.00(2H, m), 2.49–3.27(9H, m), 3.70–5.20(3H, m), 6.97–7.47(8H, m) |
| 22 | 1.68–2.07(2H, m), 2.50–3.30(8H, m), 3.70–3.93(1H, m), 4.28–4.45(1H, m), 4.83–4.58(1H, m), 7.02–7.33(4H, m), 7.62–7.69(2H, m), 7.93–8.01(2H, m), 10.08(1H, s) |
| 23 | 1.72–2.29(6H, m), 2.39–2.92(7H, m), 3.10–3.32(1H, m), 3.35–3.65(2H, m), 3.82–4.25(2H, m), 4.52–4.90(2H, m), 6.30–7.35(5H, m) |
| 24 | 1.72–1.92(2H, m), 2.52–3.12(8H, m), 3.72–3.88(2H, m), 4.07(1H, brs), 4.15–4.76(3H, m), 5.14–5.35(2H, m), 5.83–6.04(1H, m), 6.56–6.62(2H, m), 6.98–7.37(4H, m) |
| 25 | 1.72–1.90(2H, m), 2.52–3.10(8H, m), 2.99(3H, s), 3.93–4.02(2H, m), 4.23–4.68(3H, m), 5.08–5.21(2H, m), 5.72–5.94(1H, m), 6.61–6.75(2H, m), 6.96–7.32(4H, m), 7.35–7.46(2H, m) |
| 26 | 1.63–2.05(2H, m), 2.52–3.23(8H, m), 3.18(3H, s), 3.59–5.18(3H, m), 6.98–7.42(6H, m), 7.52–7.62(2H, m) |
| 27 | 1.65–1.97(2H, m), 2.48–3.22(8H, m), 3.73–5.15(3H, m), 5.20(2H, s), 6.98–7.45(13H, m) |
| 28 | 1.61–1.95(2H, m), 2.44–3.22(8H, m), 3.33(3H, s), 3.59–3.74(1H, m), 3.75–3.92(3H, m), 4.29–4.72(1H, m), 4.89–5.08(1H, m), 5.18(2H, s), 6.80–7.42(12H, m) |
| 29 | 1.56–1.95(2H, m), 2.45–3.28(8H, m), 2.85(3H, s), 3.62–4.03(5H, m), 4.32–5.12(2H, m), 6.10(1H, d, J=2.0Hz), 6.20(1H, dd, J=8.2, 2.0Hz), 6.95–7.31(4H, m) |
| 30 | 0.77–1.98(23H, m), 2.28–3.22(10H, m), 3.90–4.08(1H, m), 4.32–4.53(1H, m), 4.73–4.94(1H, m), 6.93–7.33(4H, m) |
| 31 | 1.33(9H, s), 1.58–2.01(2H, m), 2.48–3.21(8H, m), 3.77–5.11(3H, m), 6.99–7.31(4H, m), 7.41(4H, s) |
| 32 | 1.68–1.96(2H, m), 2.48–3.22(8H, m), 2.54(1H, s), 3.82–5.32(3H, m), 4.72(2H, d, J=2.4Hz), 6.92–7.33(6H, m), 7.38–7.52(2H, m) |
| 33 | 1.60–1.92(2H, m), 1.61(3H, s), 1.68(3H, s), 1.75(3H, s), 1.95–2.22(4H, m), 2.51–3.15(8H, m), 3.88–4.93(3H, m), 4.56(2H, d, J=6.6Hz), 5.04–5.18(1H, m), 5.42–5.56(1H, m), 6.88–7.32(6H, m), 7.38–7.48(2H, m) |
| 34 | 1.20–2.10(12H, m), 2.44–3.13(8H, m), 3.78–5.08(4H, m), 6.90(2H, d, J=8.7Hz), 6.97–7.32(4H, m), 7.40(2H, d, J=8.7Hz) |

DMSO-d$_6$

| 35 | 1.55–1.92(2H, m), 2.32–3.05(7H, m), 3.12–3.62(2H, m), 4.22–4.72(2H, m), 6.92–7.38(4H, m), 7.63(2H, d, J=8.2Hz), 7.92(2H, d, J=8.2Hz), 9.48(3H, brs) |

MS(m/e) = 377(m$^+$)

CDCl$_3$

| 36 | 0.85–1.02(3H, m), 1.25–1.60(6H, m), 1.70–1.92(4H, m), 2.52–3.16(8H, m), 3.98(2H, t, J=6.5Hz), 3.86–5.06(3H, m), 6.84–6.96(2H, m), 6.98–7.33(4H, m), 7.38–7.50(2H, m) |
| 37 | 0.80–0.96(3H, m), 1.18–1.55(18H, m), 1.68–1.92(4H, m), 2.51–3.11(8H, m), 3.78–5.05(3H, m), 3.97(2H, t, J=6.5Hz), 6.84–6.98(2H, m), 7.00–7.32(4H, m), 7.38–7.50(2H, m) |
| 38 | 1.68–1.94(2H, m), 2.08–2.26(2H, m), 2.48–3.21(10H, m), 3.81–5.10(3H, m), 4.11(2H, t, J=5.7Hz), 6.91(2H, d, J=8.8Hz), 6.98–8.30(4H, m), 7.44(2H, d, J=8.8Hz) |
| 40 | 1.26(3H, t, J=7.1Hz), 1.70–2.10(4H, m), |

TABLE 2-continued

| No. | NMR (CDCl₃) δ value |
|---|---|
| | 2.42(2H, t, J=7.0Hz), 2.49–3.31(10H, m), 4.14(2H, q, J=7.1Hz), 3.93–4.28(4H, m), 6.57(2H, d, J=8.6Hz), 6.95–7.33(4H, m), 7.34(2H, d, J=8.6Hz) |
| 41 | 1.21(3H, t, J=7.1Hz), 1.55–1.95(2H, m), 2.42–3.05(10H, m), 2.94(2H, t, J=7.3Hz), 3.70–5.02(5H, m), 4.14(2H, q, J=7.1Hz), 5.28–5.95(1H, m), 6.90–7.25(6H, m), 7.32(2H, d, J=8.1Hz) |
| 42 | 1.43–1.70(2H, m), 1.71–1.96(2H, m), 2.09–2.35(2H, m), 2.45–3.18(8H, m), 3.76–5.04(5H, m), 6.84–7.43(8H, m), 8.42–9.13(3H, m) |
| 43 | 1.56–1.83(2H, m), 2.01–2.21(2H, m), 2.43–3.11(12H, m), 3.49–3.61(4H, m), 3.70(3H, s), 3.62–4.95(7H, m), 6.71–6.90(6H, m), 6.92–7.25(4H, m), 7.30–7.45(2H, m) |
| 44 | 1.63–1.86(2H, m), 2.02–2.22(2H, m), 2.44–3.21(12H, m), 3.42–3.70(4H, m), 3.68–4.97(7H, m), 6.72–7.43(12H, m) |
| 45 | 1.65–1.98(2H, m), 2.49–3.22(8H, m), 3.78(3H, m), 3.75–5.07(3H, m), 6.96–7.32(5H, m), 7.43(4H, s) |
| 46 | 1.05–1.33(3H, m), 1.66–2.02(2H, m), 2.30–3.26(10H, m), 3.83–5.13(3H, m), 5.69–5.83, 6.35–6.75(2H, m), 7.02–7.54(8H, m) |
| 47 | 1.42–2.16(6H, m), 2.18–2.45(8H, m), 2.52–3.18(8H, m), 3.28–5.12(7H, m), 6.90(2H, d, J=8.6Hz), 6.97–7.30(4H, m), 7.42(2H, d, J=8.6Hz) |
| 48 | 1.48–2.14(6H, m), 2.35–3.18(13H, m), 3.53–5.02(8H, m), 6.90(2H, d, J=8.7Hz), 6.98–7.29.(4H, m), 7.41(2H, d, J=8.7Hz) |
| 49 | 1.58–1.88(2H, m), 2.03–2.25(2H, m), 2.45–3.13(10H, m), 3.67–5.03(5H, m), 6.86–7.25(4H, m), 7.35–7.68(4H, m) |
| 50 | 1.49–1.89(16H, m), 1.90–2.07(3H, m), 2.48–3.12(8H, m), 3.79–4.99(3H, m), 4.05(2H, t, J=7.2Hz), 6.89(2H, d, J=8.7Hz), 6.97–7.31(4H, m), 7.41(2H, d, J=8.7Hz) |
| 51 | 1.27(3H, t, J=7.4Hz), 1.68–1.92(2H, m), 1.98–2.18(2H, m), 2.45–3.14(10H, m), 3.70–5.15(3H, m), 4.10(2H, t, J=6.1Hz), 6.91(2H, d, J=8.6Hz), 6.99–7.32(4H, m), 7.43(2H, d, J=8.6Hz) |
| 52 | 1.18–1.37(3H, m), 1.50–2.02(2H, m), 2.32–3.35(11H, m), 4.45–4.51(9H, m), 4.78–5.09(1H, m), 6.39–6.60(2H, m), 6.94–7.35(5H, m) |
| 53 | 1.65–1.97(2H, m), 2.49–3.10(11H, m), 3.78(3H, s), 3.85(2H, d, J=6.1Hz), 4.13–4.62(3H, m), 6.02(1H, t, J=6.1Hz), 6.14(1H, d, J=2.3Hz), 6.30(1H, dd, J=2.3, 8.5Hz), 6.84–7.35(6H, m) |
| 54 | 1.62–2.05(2H, m), 2.48–3.28(8H, m), 3.47(1H, d, J=5.1Hz), 3.75–4.94(6H, m), 3.83(3H, s), 6.75–7.47(7H, m) |
| 55 | 1.64–2.06(2H, m), 2.48–3.69(15H, m), 3.80(3H, m), 3.81–4.52(3H, m), 4.79–5.09(1H, m), 6.44–6.70(2H, m), 6.92–7.38(5H, m), 7.85–8.21(1H, m) |
| 56 | 1.30(3H, t, J=7.1Hz), 1.71–1.92(2H, m), 2.47–3.11(8H, m), 3.79(3H, s), 3.91(2H, d, J=5.4Hz), 4.25(2H, q, J=7.1Hz), 4.31–4.61(3H, m), 5.91(1H, t, J=5.3Hz), 6.07(1H, d, J=2.3Hz), 6.26(1H, dd, J=2.3, 8.4Hz), 6.94–7.36(5H, m) |
| 57 | 1.67–2.01(6H, m), 2.47–3.14(8H, m), 3.95–4.91(9H, m), 6.84–7.52(8H, m) |
| 58 | 1.54–2.00(6H, m), 2.45–3.36(10H, m), 3.67(3H, m), 3.84–5.08(4H, m), 4.00(2H, t, J=5.9Hz), 6.89(2H, d, J=8.7Hz), 6.94–7.48(4H, m), 7.42(2H, d, J=8.7Hz) |
| 59 | 1.55–2.00(6H, m), 2.45–3.48(10H, m), 3.76–5.10(3H, m), 3.99(2H, t, J=5.7Hz), 5.74–6.25(1H, m), 6.78–7.53(8H, m), |
| 60 | 8.15(1H, s) 1.30(3H, t, J=7.1Hz), 1.67–1.90(2H, m), 2.49–3.26(10H, m), 3.81,(3H, s), 4.27–4.56(3H, m), 5.33–5.49(1H, m), 6.09–6.27(2H, m), 6.91–7.31(5H, m) |
| 61 | 0.97(3H, t, J=7.5Hz), 1.55–2.01(4H, m), 2.09–2.35(2H, m), 2.41–5.13(18H, m), 6.90(2H, d, J=8.7Hz), 6.95–7.38(4H, m), 7.42(2H, d, J=8.7Hz) |
| 62 | 1.51–2.02(8H, m), 2.48–3.20(10H, m), 3.72–5.08(3H, m), 4.01(2H, t, J=6.2Hz), 6.80–7.55(8H, m) |
| 63 | 1.55–2.20(4H, m), 2.49–3.50(10H, m), 2.96(3H, m), 3.90–5.13(4H, m), 4.09(2H, t, J=5.7Hz), 6.90(2H, d, J=8.7Hz), 6.95–7.38(4H, m), 7.43(2H, d, J=8.7Hz) |
| 64 | 1.60–2.15(5H, m), 2.47–3.18(10H, m), 3.82(2H, s), 3.95–5.11(3H, m), 4.08(3H, t, J=6.2Hz), 6.89(2H, d, J=8.5Hz), 6.95–7.50(9H, m), 7.42(2H, d, J=8.5Hz) |
| 65 | 1.59–2.20(4H, m), 2.50–3.49(10H, m), 2.96(3H, s), 3.91–5.11(4H, m), 4.09(2H, t, J=5.7Hz), 6.90(2H, d, J=8.7Hz), 6.94–7.40(4H, m), 7.43(2H, d, J=8.7Hz) |
| 66 | 1.60–2.10(4H, m), 2.45–3.49(13H, m), 3.80–5.01(7H, m), 6.88(2H, d, J=8.6Hz), 6.95–7.45(4H, m), 7.40(2H, d, J=8.6Hz) |
| 67 | 1.63–2.15(4H, m), 1.99(3H, s), 2.49–3.20(8H, m), 3.35–3.60(2H, m), 3.90–5.10(3H, m), 4.06(2H, t, J=5.9Hz), 5.89(1H, brs), 6.89(2H, d, J=8.7Hz), 6.95–7.37(4H, m), 7.43(2H, d, J=8.7Hz) |
| 68 | 1.60–2.32(8H, m), 2 41–3.27(8H, m), 3.71–5.15(5H, m), 4.07(2H, t, J=6.2Hz), 4.26(2H, t, J=6.2Hz), 6.96(2H, d, J=8.6Hz), 6.99–7.40(4H, m), 7.43(2H, d, J=8.6Hz) |
| 69 | 0.86(3H, t, J=7.3Hz), 1.35–2.04(6H, m), 2.40(2H, t, J=7Hz), 2.50–3.17(10H, m), 3.57(2H, s), 3.90–5.05(3H, m), 4.00(2H, t, J=6.5Hz), 6.85(2H, d, J=8.8Hz), 6.94–7.38(9H, m), 7.42(2H, d, J=8.8Hz) |
| 70 | 0.99–1.23(3H, m), 1.54–2.00(2H, m), 2.35–3.40(13H, m), 3.52–3.77(1H, m), 3.80(3H, s), 4.15–4.52(1H, m), 4.83–5.04(1H, m), 6.49–6.57(2H, m), 6.90–7.35(4H, m) |
| 71 | 1.50–2.12(6H, m), 2.03(3H, m), 2.45–3.44(10H, m), 3.88(2H, d, J=5.1Hz), 3.98(2H, t, J=6.0Hz), 4.01–5.05(3H, m), 6.50–7.52(10H, m) |
| 72 | 1.45–2.01(8H, m), 2.06(3H, s), 2.48–3.25(8H, m), 3.70–5.12(3H, m), 3.99(2H, t, J=6.3Hz), 4.10(2H, t, J=6.3Hz), 6.89(2H, d, J=8.8Hz), 6.97–7.35(4H, m), 7.43(2H, d, J=8.8Hz) |
| 73 | 1.40–2.02(8H, m), 2.48–3.15(8H, m), 3.60–5.12(3H, m), 3.72(2H, t, J=7.0Hz), 3.97(2H, t, J=6.3Hz), 6.87(2H, d, J=8.7Hz), 6.92–7.32(4H, m), 7.41(2H, d, J=8.7Hz), 7.61–7.93(4H, m) |
| 74 | 1.35–2.02(10H, m), 2.47–3.25(10H, m), 3.71–5.16(3H, m), 3.99(2H, t, J=6.4Hz), 6.89(2H, d, J=8.7Hz), 6.93–7.35(4H, m), 7.42(2H, d, J=8.7Hz) |
| 75 | 1.01–5.60(20H, m), 3.82(3H, s), 6.55–7.60(12H, m) |
| 76 | 1.52–5.51(17H, m), 3.83(3H, s), 6.75–7.55(12H, m) |
| 77 | 1.50–5.52(20H, m), 3.82(3H, s), 6.69–7.55(12H, m), 9.20–9.75(1H, m) |
| 78 | 1.09–5.45(25H, m), 6.77–7.48(12H, m) |
| 79 | 1.65–1.97(2H, m), 2.10–2.30(2H, m), 2.48–3.01(8H, m), 3.82–4.78(7H, m), 6.62–6.93(4H, m), 7.11(1H, dd, J=6.2, 7.3Hz), 7.38(2H, d, J=8.5Hz), 7.66–7.86(4H, m) |
| 80 | 1.55–2.10(4H, m), 2.43–3.18(10H, m), 3.74–5.18(5H, m), 6.65–7.00(4H, m), |

TABLE 2-continued

| No. | NMR (CDCl$_3$) δ value |
|---|---|
|  | 7.10(1H, dd, J=6.4, 7.3Hz), 7.41(2H, d, J=8.7Hz) |
| 81 | 1.60–1.90(2H, m), 1.98(3H, s), 1.90–2.10(2H, m), 2.43–3.10(8H, m), 3.45(2H, q, J=6.4Hz), 4.05(2H, t, J=5.9Hz), 3.82–5.04(3H, m), 5.92(1H, brs), 6.65–6.97(4H, m), 7.11(1H, dd, J=6.4, 7.3Hz), 7.43(2H, d, J=8.7Hz) |
| 82 | 1.25(3H, t, J=7.5Hz), 1.64–1.82(2H, m), 1.91(1H, brs), 2.35–2.87(10H, m), 3.15–3.35(2H, m), 4.16–4.50(1H, m), 6.85(1H, d, J=7.7Hz), 7.00(1H, s), 7.10(1H, d, J=7.7Hz) |
| 83 | 1.26(3H, t, J=7.5Hz), 1.58–1.98(2H, m), 2.45–3.22(10H, m), 3.58–3.98(7H, m), 4.23–4.61(1H, m), 4.87–5.05(1H, m), 6.40–6.57(2H, m), 6.80–7.38(3H, m) |
| 84 | 1.62–1.95(1H, m), 2.50–2.93(9H, m), 3.15–3.50(2H, m), 3.84(3H, s), 4.15–4.48(1H, m), 6.50–6.60(1H, m), 6.70–6.82(1H, m), 7.06(1H, d, J=8.2Hz) |
| 85 | 1.55–1.98(2H, m), 2.44–3.25(8H, m), 3.60–4.10(10H, m), 4.20–4.75(1H, m), 4.86–5.05(1H, m), 6.44–6.85(4H, m), 7.07(1H, d, J=8.2Hz), 7.17–7.36(1H, m) |
| 86 | 1.54–1.92(2H, m), 2.32–3.22(8H, m), 3.50–3.90(7H, m), 4.23–4.71(1H, m), 4.82–5.00(1H, m), 6.34–6.60(2H, m), 6.95–7.72(5H, m), 7.90(2H, d, J=7.0Hz), 8.40–8.65(1H, m) |
| 87 | 1.50–1.93(2H, m), 2.34–3.20(8H, m), 3.30–4.15(9H, m), 4.22–4.75(1H, m), 4.85–5.03(1H, m), 6.42–6.63(4H, m), 6.82–7.33(2H, m) |
| 88 | 1.60–2.02(2H, m), 2.62–3.41(4H, m), 3.73–4.26(1H, m), 4.50–5.72(2H, m), 6.64(1H, d, J=9.4Hz), 7.15–7.70(10H, m) |
| 89 | 1.55–1.96(2H, m), 2.72–3.30(4H, m), 3.84(3H, s), 3.82–5.55(3H, m), 6.65(1H, d, J=9.4Hz), 6.93(1H, d, J=8.7Hz), 7.23(1H, t, J=7.6Hz), 7.48–7.75(6H, m) |
| 90 | 1.55–1.95(2H, m), 2.63–3.34(4H, m), 3.66–4.00(7H, m), 4.95–5.16(1H, m), 6.42–6.77(3H, m), 7.13–7.40(2H, m), 7.45–7.86(4H, m) |
| 91 | 1.62–2.03(3H, m), 2.55–3.03(4H, m), 3.14–3.50(2H, m), 4.68–5.85(1H, br), 6.65(1H, d, J=9.4Hz), 7.19(1H, t, J=7.4Hz) |
| 92 | 1.55–1.98(2H, m), 2.38–3.26(8H, m), 3.57–4.00(7H, m), 4.24–4.71(1H, m), 4.85–5.07(1H, m), 6.50–6.61(2H, m), 6.83–7.39(4H, m) |
| 93 | 1.60–2.05(3H, m), 2.31–3.00(8H, m), 3.10–3.48(2H, m), 4.21–4.52(1H, m), 6.76–7.38(3H, m) |
| 94 | 2.76(3H, t, J=8.1Hz), 3.0(3H, t, J=8Hz), 3.48(3H, s), 3.75(3H, s), 6.19(1H, dd, J=3.1, 6Hz), 6.78(2H, d, J=8.3Hz), 6.9–7.2(7H, m), 7.43(2H, d, J=8.4Hz) |
| 95 | 1.57–1.95(2H, m), 2.50(3H, s), 2.45–3.25(7H, m), 3.57–4.00(4H, m), 4.15–4.77(1H, m), 4.88–5.07(1H, m), 6.63–7.36(6H, m) |
| 96 | 1.73–1.95(2H, m), 2.49–3.11(8H, m), 3.84(3H, s), 4.24–4.58(3H, m), 5.21(2H, s), 6.57(1H, dd, J=2.5, 8.5Hz), 6.96–7.52(10H, m), 7.87(1H, d, J=2.5Hz), 8.81(1H, s) |
| 97 | 1.54–1.72(1H, m), 1.77–1.92(1H, m), 2.40–3.23(8H, m), 3.58–3.73(1H, m), 3.73–3.95 (6H, m), 4.20–4.77(1H, m), 4.88–5.07(1H, m), 6.43–6.60(2H, m), 6.65–7.00(1H, m), 7.05–7.37(2H, m) |
| 98 | 1.55–1.93(2H, m), 2.30(3H, s), 2.40–3.24(8H, m), 3.56–3.72(1H, m), 3.73–3.85(6H, m), 4.27–4.73(1H, m), 4.85–5.02(1H, m), 6.41–6.57(2H, m), |

TABLE 2-continued

| No. | NMR (CDCl$_3$) δ value |
|---|---|
|  | 6.90–7.37(4H, m) |
| 99 | 1.58–2.00(2H, m), 2.35(3H, s), 2.32–3.14(8H, m), 3.27–3.48(1H, m), 3.53–4.00(7H, m), 4.78–5.01(1H, m), 6.37–6.64(2H, m), 6.87–7.48(4H, m) |
| 100 | 1.57–1.97(2H, m), 2.37(3H, s), 2.43–3.26(8H, m), 3.48–3.98(7H, m), 4.21–4.63(1H, m), 4.84–5.07(1H, m), 6.42–6.60(2H, m), 6.78–7.47(4H, m) |
| 101 | 1.40(3H, t, J=7.1Hz), 1.55–2.09(2H, m), 2.43–3.34(8H, m), 3.66–4.07(1H, m), 4.25–4.58(1H, m), 4.39(2H, q, J=7.1Hz), 4.75–5.12(1H, m), 6.96–7.74(6H, m), 8.01–8.23(2H, m) |
| 102 | 2.3–2.7(4H, br), 2.8(2H, t, J=8Hz), 3.1(2H, t, J=8Hz), 3.4–3.9(4H, m), 3.55(2H, s), 6.36(1H, dd, J=2.2, 6.9Hz), 6.9–7.1(2H, m), 7.1–7.4(8H, m), 7.54(2H, d, J=8.4Hz) |
| 103 | 1.60–2.08(2H, m), 2.45–3.10(8H, m), 3.35(3H, s), 3.62–4.05(1H, br), 4.34(1H, m), 4.60–5.07(1H, br), 5.16(2H, s), 6.76–7.53(13H, m) |
| 104 | 1.82(2H, m), 2.54–3.32(8H, m), 3.77(1H, brs), 4.35(1H, m), 4.89(1H, brs), 7.00–7.30(4H, m), 7.59–7.67(1H, m), 7.80–7.84(1H, m), 8.27–8.33(2H, m) |
| 105 | 1.68–2.01(2H, m), 2.50–3.09(11H, m), 4.19–4.73(3H, m), 4.88–5.33(1H, m), 6.60–6.75(2H, m), 4.96–7.39(6H, m) |
| 106 | 1.60–2.03(2H, m), 2.45–3.32(8H, m), 3.67–4.07(1H, m), 4.15–4.44(1H, m), 4.61–5.04(1H, m), 6.96–7.68(7H, m) |
| 107 | 1.51–2.08(2H, m), 2.42–3.67(9H, m), 4.15–5.09(2H, m), 6.90–7.62(7H, m) |
| 108 | 0.94(3H, t, J=7.3Hz), 1.50–1.97(4H, m), 2.50–3.20(10H, m), 3.74–4.20(1H, br), 4.41(1H, m), 4.50–5.08(1H, br), 6.98–7.34(6H, m), 7.38(2H, d, J=8.1Hz) |
| 109 | 1.85(2H, m), 2.55–3.30(8H, m), 3.78–4.38(1H, br), 4.41(1H, m), 4.66–5.17(1H, br), 6.99–7.66(13H, m) |
| 110 | 1.84(2H, m), 2.55–3.10(8H, m), 4.00–5.00(2H, m), 4.40(1H, m), 4.57(2H, d, J=5.3Hz), 5.31(1H, d, J=10.5Hz), 5.42(1H, d, J=16.6Hz), 6.06(1H, ddt, J=16.6, 10.5, 5.3Hz), 6.93(2H, d, J=8.7Hz), 6.99–7.32(4H, m), 7.43(2H, d, J=8.7Hz) |
| 111 | 1.82(2H, m), 2.51–3.12(8H, m), 3.43(2H, d, J=6.8Hz), 4.12–4.70(2H, m), 4.43(1H, m), 4.58(2H, d, J=5.0Hz), 5.06(1H, d, J=10.0Hz), 5.08(1H, d, J=17.0Hz), 5.29(1H, d, J=9.0Hz), 5.43(1H, d, J=18.9Hz), 5.92–6.16(2H, m), 6.84(1H, d, J=8.5Hz), 7.00–7.37(6H, m) |
| 112 | 1.6–2.1(3H, m), 2.4–2.7(2H, m), 2.7–3.2(4H, m), 3.4–4.2(3H, m), 3.8(6H, s), 4.7–5.0(1H, br), 6.4–6.6(2H, m), 6.9–7.4(5H, m) |
| 113 | 1.66–1.97(2H, m), 2.44–3.10(8H, m), 3.90–5.00(2H, m), 4.39(1H, m), 6.00(2H, s), 6.83(1H, d, J=8.2Hz), 6.96–7.32(6H, m) |
| 114 | 1.83(2H, m), 2.31(3H, s), 2.48–3.17(8H, m), 3.82(3H, s), 4.13–4.63(2H, m), 4.70–5.02(1H, m), 6.67–6.88(2H, m), 6.97–7.49(5H, m) |
| 115 | 1.70–1.92(2H, m), 2.47–3.08(11H, m), 3.82(3H, s), 4.26–4.61(3H, m), 5.55(1H, brs), 6.12–6.29(2H, m), 6.95–7.36.(5H, m) |
| 116 | 1.42(3H, t, J=6.9Hz), 1.64–1.90(2H, m), 2.44–3.17(8H, m), 4.05(2H, q, J=6.9Hz), 3.90–5.00(3H, m), 6.65–6.98(4H, m), 7.03–7.17(1H, m), 7.41(2H, d, J=8.7Hz) |

TABLE 2-continued

| No. | NMR (CDCl₃) δ value |
|---|---|
| 117 | 1.64–2.10(4H, m), 2.97–3.18(8H, m), 2.92(2H, t, J=6.8Hz), 4.08(2H, t, J=6.1Hz), 4.10–5.15(3H, m), 6.82–7.58(8H, m) MS(m/e): 407(m⁺), 333, 260, 229, 121, 82 |
| 118 | 1.62–1.95(2H, m), 2.07–2.33(2H, m), 2.43–3.16(8H, m), 3.92(2H, t, J=6.8Hz), 4.06(2H, t, J=6.1Hz), 3.95–5.05(3H, m), 6.80(2H, d, J=8.7Hz), 6.95–7.39(4H, m), 7.38(2H, d, J=8.7Hz), 7.65–8.00(4H, m) |
| 119 | 2.76(2H, t, J=8.1Hz), 3.02(2H, t, J=7.8Hz), 3.72(3H, s), 5.10(2H, s), 6.17(1H, dd, J=2.6, 6.5Hz), 6.68(2H, d, J=9.0Hz), 6.85(2H, d, J=8.8Hz), 6.9–7.4(10H, m), 7.46(2H, d, J=8.5Hz) |
| 120 | 2.76(2H, t, J=8.1), 3.02(2H, t, J=7.9Hz), 3.75(3H, s), 4.50(2H, d, J=6Hz), 5.20(1H, d, J=1.62Hz), 5.19(1H, d, J=11.0Hz), 5.9–6.1(1H, m), 6.18(1H, dd, J=2.6, 6.5Hz), 6.76(2H, d, J=8.9Hz), 6.9–7.3(7H, m), 7.45(2H, d, J=8.3Hz) |
| 121 | 1.64–1.96(2H, m), 2.15–2.87(2H, m), 2.49–3.20(8H, m), 3.01(3H, s), 4.02–5.03(3H, m), 4.12(2H, t, J=5.9Hz), 4.53(2H, t, J=6.1Hz), 6.91(2H, d, J=8.7Hz), 6.95–7.46(4H, m), 7.44(2H, d, J=8.7Hz) |
| 122 | 1.55–3.26(14H, m), 2.72(6H, s), 3.90–5.18(3H, m), 4.05(2H, t, J=5.7Hz), 6.90(2H, d, J=8.7Hz), 6.93–7.38(4H, m), 7.43(2H, d, J=8.7Hz) |
| 123 | 0.91(3H, t, J=5.8Hz), 1.42–3.31(21H, m), 2.33(3H, s), 3.88–5.15(3H, m), 4.05(2H, t, J=5Hz), 6.91(2H, d, J=7Hz), 6.95–7.38(4H, m), 7.42(2H, d, J=7Hz) |
| 124 | 1.65–5.12(22H, m), 6.67–7.60(13H, m) |
| 125 | 1.65–1.99(2H, m), 2.07(2H, quint, J=6.2Hz), 2.49–3.24(8H, m), 3.62(2H, t, J=6.2Hz), 3.87–4.93(5H, m), 4.10(2H, t, J=6.2Hz), 5.11–5.38(2H, m), 5.80–6.07(1H, m), 6.80–7.53(8H, m) |
| 126 | 1.02(3H, t, J=7.3Hz), 1.60–2.07(4H, m), 2.47–3.18(10H, m), 3.80(3H, s), 4.30–4.58(1H, m), 5.53(1H, t, J=5.2Hz), 6.07–6.28(2H, m), 6.94–7.34(5H, m) |
| 127 | 1.64–1.92(2H, m), 2.28(2H, quint, J=6.1Hz), 2.45–3.27(8H, m), 4.02–5.22(3H, m), 4.16(2H, t, J=6.1Hz), 4.53(2H, t, J=6.1Hz), 6.83–7.69(11H, m), 7.98–8.18(2H, m) |
| 128 | 1.69–1.97(2H, m), 2.06(2H, quint, J=6.2Hz), 2.48–3.16(8H, m), 3.36(3H, s), 3.56(2H, t, J=6.2Hz), 4.09(2H, t, J=6.2Hz), 4.12–5.04(3H, m), 6.91(2H, t, J=8.7Hz), 6.94–7.35(4H, m), 7.43(2H, d, J=8.7Hz) |
| 129 | 1.28(3H, t, J=7.1Hz), 1.83(2H, m), 2.15(2H, quint, J=6.7Hz), 2.47(2H, t, J=6.7Hz), 2.50–3.20(8H, m), 3.60–5.10(2H, m), 4.02(2H, s), 4.05(2H, t, J=6.7Hz), 4.21(2H, q, J=7.1Hz), 4.39(1H, m), 6.12(1H, brs), 6.91(2H, d, J=8.6Hz), 6.99–7.29(4H, m), 7.42(2H, d, J=8.6Hz) |
| 130 | 1.87(2H, m), 2.50–3.43(8H, m), 3.94(1H, m), 4.38(1H, m), 4.96(1H, m), 6.99–7.30(4H, m), 7.58–7.65(1H, m), 7.75–7.98(2H, m), 8.12–8.16(1H, m), 8.31(1H, m), 9.01(1H, m) |
| 131 | 1.73(6H, m), 1.82(2H, m), 2.04(9H, m), 2.43–3.00(8H, m), 4.46(1H, m), 4.67(1H, m), 4.73(1H, m), 6.98–7.30(4H, m) |
| 132 | 1.65–2.28(7H, m), 2.44–3.20(11H, m), 3.42–5.11(7H, m), 6.83–7.60(8H, m) |
| 133 | 1.40–1.90(2H, m), 2.30–2.95(8H, m), 3.90(3H, s), 3.98(2H, m), 4.32(1H, m), 6.90–7.27(6H, m), 7.73(2H, m) |
| 134 | 1.55–2.05(2H, m), 2.54–3.33(8H, m), 4.05–4.24(1H, m), 4.47–4.65(1H, m), 4.93–5.10(1H, m), 6.98–7.31(4H, m), 7.64(1H, m), 7.71–7.80(2H, m), 7.86(1H, m), 8.11(1H, d, J=8.4Hz), 8.28(1H, d, J=8.4Hz) |
| 135 | 1.56–1.86(1H, m), 1.86–2.30(1H, m), 2.44–3.35(8H, m), 3.60–3.86(1H, m), 4.12–4.62(1H, m), 4.91–5.20(1H, m), 6.63–7.78(9H, m) |
| 136 | 1.08(9H, s), 1.80(2H, m), 2.32(2H, s), 2.45–2.76(5H, m), 2.76–2.92(2H, m), 3.05–3.18(1H, m), 4.03–4.18(1H, m), 4.40(1H, m), 4.78–4.98(1H, m), 6.97–7.28(4H, m) |
| 137 | 1.30(3H, t, J=7.1Hz), 1.84(2H, m), 2.50–3.22(8H, m), 3.90(1H, t, J=5.4Hz), 3.43–5.20(2H, m), 4.13(2H, d, J=5.4Hz), 4.24(2H, q, J=7.1Hz), 4.57(2H, s), 4.38(1H, m), 6.97(2H, d, J=8.7Hz), 7.03–7.32(4H, m), 7.47(2H, d, J=8.7Hz) |
| 138 | 1.75(2H, m), 2.51–3.31(8H, m), 3.80–5.28(2H, m), 4.37(1H, m), 4.64(2H, s), 6.90–7.67(13H, m) |
| 139 | 1.83(2H, m), 2.54–3.23(8H, m), 2.94(3H, s), 3.09(3H, s), 3.76–5.17(2H, m), 4.39(1H, m), 4.73(2H, s), 6.97(2H, d, J=8.6Hz), 7.02–7.27(4H, m), 7.43(2H, d, J=8.6Hz) |
| 140 | 1.26(3H, t, J=7.1Hz), 1.83(2H, m), 2.12(2H, quint, J=6.2Hz), 2.40–3.20(10H, m), 3.40–5.10(2H, m), 4.04(2H, t, J=6.2Hz), 4.15(2H, q, J=7.1Hz), 4.39(1H, m), 6.90(2H, d, J=8.6Hz), 6.98–7.28(4H, m), 7.43(2H, d, J=8.6Hz) |
| 141 | 1.54–1.98(2H, m), 2.40–3.22(9H, m), 2.95(6H, s), 3.58–3.90(7H, m), 4.85–5.06(1H, m), 6.33–6.62(4H, m), 6.70(1H, d, J=8.2Hz), 7.12–7.30(1H, m) |
| 142 | 1.27(3H, d, J=6.8Hz), 1.55–1.95(2H, m), 2.28–3.24(7H, m), 3.55–3.97(7H, m), 4.27–4.73(1H, m), 4.75–5.07(1H, m), 6.38–6.60(2H, m), 6.97–7.38(5H, m) |
| 143 | 1.67–3.23(12H, m), 2.06(3H, s), 3.94–5.15(3H, m), 4.08(2H, t, J=6.2Hz), 4.26(2H, t, J=6.2Hz), 6.77–7.75(8H, m) |
| 144 | 1.54–2.23(5H, m), 2.51–3.20(8H, m), 3.77–5.08(5H, m), 4.15(2H, t, J=6Hz), 6.83–7.59(8H, m) |
| 145 | 1.31(3H, t, J=7.1Hz), 1.83(2H, m), 2.54–3.26(8H, m), 3.70–5.20(2H, m), 4.30(2H, q, J=7.1Hz), 4.38(1H, m), 4.65(2H, s), 6.93(2H, d, J=8.7Hz), 6.99–7.36(4H, m), 7.44(2H, d, J=8.7Hz) |
| 146 | 1.6–2.1(3H, m), 2.4–2.6(2H, m), 2.5(3H, s), 2.6–3.2(4H, m), 3.4–4.1(6H, m), 4.8–5.0(1H, br), 6.6–7.4(7H, m) |
| 147 | 1.55–1.93(2H, m), 2.30–3.24(8H, m), 3.56–4.05(10H, m), 4.27–4.72(1H, m), 4.84–5.07(1H, m), 6.40–6.60(2H, m), 6.64–6.82(2H, m), 6.93–7.38(2H, m) |
| 148 | 1.80(2H, m), 2.31(3H, s), 2.52–3.25(8H, m), 3.68–4.20(1H, br), 4.34(1H, m), 4.65–5.13(1H, br), 6.88–7.52(8H, m) |
| 149 | 1.56–2.00(2H, m), 2.30(6H, s), 2.50–3.15(8H, m), 3.20–3.90(1H, m), 4.27(1H, m), 4.90(1H, m), 6.95–7.33(7H, m) |
| 150 | 1.70–2.00(2H, m), 2.55–3.15(8H, m), 4.33(1H, m), 4.47(1H, m), 4.54(1H, m), 6.36–6.49(2H, m), 7.02–7.35(5H, m) |
| 151 | 1.59–2.11(2H, m), 2.48–3.33(8H, m), 3.70–5.15(3H, m), 5.58–6.60(2H, m), 6.97–8.05(8H, m) |
| 152 | 1.56–3.35(13H, m), 3.60–5.08(3H, m), 6.75–7.98(8H, m) |
| 153 | 1.31–1.78(5H, m), 2.32–3.28(8H, m), 3.68(1H, m), 3.81(3H, s), 4.06(2H, m), 4.43(1H, m), 4.96(1H, m), 6.49–6.62(2H, m), 6.97–7.44(5H, m) |
| 154 | 1.53–1.90(2H, m), 2.35–3.27(8H, m), 3.60–3.77(1H, m), 3.81(3H, s), 4.29–4.60(1H, br), 4.58(2H, m), 4.88–5.06(1H, m), 5.18–5.51(2H, m), |

TABLE 2-continued

| No. | NMR (CDCl$_3$) δ value |
|---|---|
|  | 6.08(1H, m), 6.42–6.60(2H, m), 6.93–7.48(5H, m) |
| 155 | 2.78(3H, t, J=8Hz), 3.04(3H, t, J=8Hz), 3.50(3H, s), 3.59(3H, s), 3.76(3H, s), 6.0–6.1(1H, br), 6.2(1H, brs), 6.41(1H, dd, J=2.3, 8.4Hz), 6.9–7.1(4H, m), 7.1–7.3(4H, m) |
| 156 | 1.66–2.03(2H, m), 2.14(2H, m), 2.44(2H, t, J=7.2Hz), 2.51–3.32(8H, m), 3.70–5.30(2H, m), 4.04(2H, t, J=6.0Hz), 4.38(1H, m), 5.75(1H, brs), 5.90(1H, brs), 6.90(2H, d, J=8.6Hz), 6.99–7.29(4H, m), 7.42(2H, d, J=8.6Hz) |
| 157 | 1.55–2.10(2H, m), 2.22–3.36(8H, m), 3.78–4.20(1H, m), 4.23–4.56(1H, m), 4.70–5.18(1H, m), 6.95–7.34(4H, m), 7.46(1H, dd, J=8.3, 4.2Hz), 7.67(1H, dd, J=8.3, 1.3Hz), 7.90(1H, d, J=8.3Hz), 8.20(2H, m), 8.96(1H, dd, J=4.2, 1.3Hz) |
| 158 | 1.58–2.31(4H, m), 2.44–3.30(8H, m), 3.60–4.50(6H, m), 3.81(3H, s), 4.70–5.15(1H, m), 6.43–6.60(2H, m), 6.99–7.33(5H, m) |
| 159 | 1.29(3H, t, J=7.1Hz), 1.58–1.98(2H, m), 2.53–3.37(8H, m), 3.80(3H, s), 4.21(2H, q, J=7.1Hz), 4.22–4.47(1H, m), 4.62(2H, s), 4.63–4.80(1H, m), 4.87–5.07(1H, m), 6.28–6.37(1H, m), 6.52–6.66(1H, m), 6.95–7.46(5H, m) |
| 160 | 1.46–2.12(4H, m), 2.45–3.22(8H, m), 3.36–3.55(1H, m), 4.22–4.53(1H, m), 5.02–5.17(1H, m), 6.98–7.74(7H, m), 8.03–8.26(2H, m), 8.94–9.05(1H, m) |
| 161 | 1.26(3H, t, J=7.1Hz), 1.63–2.00(6H, m), 2.32–2.44(2H, m), 2.54–3.03(8H, m), 3.75–5.03(2H, m), 3.95–4.09(2H, m), 4.14(2H, q, J=7.1Hz), 4.40(1H, m), 6.90(2H, d, J=8.7Hz), 6.98–7.27(4H, m), 7.43(2H, d, J=8.7Hz) |
| 162 | 1.42–1.62(2H, m), 1.62–1.93(6H, m), 2.36(2H, t, J=7.1Hz), 2.45–3.12(8H, m), 3.67(3H, s), 3.74–5.03(2H, m), 3.98(2H, t, J=6.3Hz), 4.39(1H, m), 6.90(2H, d, J=8.7Hz), 6.99–7.28(4H, m), 7.43(2H, d, J=8.7Hz) |
| 163 | 1.63–2.10(6H, m), 2.33(2H, m), 2.46–3.18(8H, m), 3.50–5.00(2H, m), 3.89(2H, d, J=4.8Hz), 4.00(2H, m), 4.37(1H, m), 5.76(1H, brs), 6.50(1H, brs), 6.74(1H, brs), 6.89(2H, d, J=8.6Hz), 6.99–7.27(4H, m), 7.41(2H, d, J=8.6Hz) |
| 164 | 1.28(3H, t, J=7.1Hz), 1.83(6H, m), 2.17(2H, m), 2.43–3.18(8H, m), 3.55–5.00(2H, m), 3.98(2H, m), 3.99(2H, d, J=5.1 Hz), 4.20(2H, q, J=7.1Hz), 4.37(1H, m), 6.66(1H, brs), 6.89(2H, d, J=8.6Hz), 6.99–7.32(4H, m), 7.42(2H, d, J=8.6Hz) |
| 165 | 1.41–2.10(8H, m), 2.26(2H, t, J=7.3Hz), 2.54–3.24(8H, m), 3.80–5.10(2H, m), 3.99(2H, t, J=6.3Hz), 4.39(1H, m), 5.22–5.86(2H, m), 6.89(2H, d, J=8.7Hz), 6.99–7.29(4H, m), 7.42(2H, d, J=8.7Hz) |
| 166 | 1.48–1.62(2H, m), 1.62–2.17(6H, m), 2.27(2H, t, J=7.3Hz), 2.54–3.30(8H, m), 3.30–5.10(2H, m), 3.91(2H, d, J=5.0Hz), 3.98(2H, t, J=6.3Hz), 4.37(1H, m), 5.75(1H, brs), 6.51(1H, brs), 6.66(1H, brs), 6.89(2H, d, J=8.7Hz), 6.99–7.27(4H, m), 7.41(2H, d, J=8.7Hz) |
| 166A | 1.28(3H, t, J=7.1Hz), 1.46–1.63(2H, m), 1.63–1.96(6H, m), 2.28(2H, t, J=7.3Hz), 2.54–3.12(8H, m), 3.62–5.07(2H, m), 3.98(2H, t, J=6.4Hz), 4.01(2H, d, J=5.3Hz), 4.20(2H, q, J=7.1Hz), 4.48(1H, m), 6.45(1H, brs), 6.89(2H, d, J=8.7Hz), 6.99–7.31(4H, m), 7.42(2H, d, J=8.7Hz) |
| 167 | 1.57–1.94(2H, m), 2.02–2.35(2H, m), 2.06(3H, s), 2.45–3.24(8H, m), 3.64(1H, m), 3.82(3H, s), 3.98–4.50(5H, m), 4.85–5.06(1H, m), 6.38–6.63(2H, m), 6.97–7.33(5H, m) |
| 168 | 1.67(1H, m), 1.75–1.94(1H, m), 2.00–2.37(2H, m), 2.45–3.26(8H, m), 3.56–3.80(1H, m), 3.81(3H, s), 3.94–4.47(5H, m), 4.66–5.27(3H, m), 6.44–6.55(2H, m), 6.98–7.32(5H, m) |
| 169 | 1.55–1.77(1H, m), 1.77–1.94(1H, m), 1.94–2.33(2H, m), 2.33–3.24(8H, m), 3.35(3H, s), 3.42–3.77(3H, m), 3.81(3H, s), 3.95–4.27(2H, m), 4.40(1H, m), 4.87–5.07(1H, m), 6.42–6.62(2H, m), 6.98–7.32(5H, m) |
| 170 | 1.53–1.77(1H, m), 1.77–1.98(1H, m), 2.32–3.33(8H, m), 3.43(3H, s), 3.56–3.99(3H, m), 3.81(3H, s), 3.99–4.30(2H, m), 4.40(1H, m), 4.85–5.06(1H, m), 6.49–6.66(2H, m), 6.97–7.43(5H, m) |
| 171 | 1.62–1.82(1H, m), 1.82–2.02(1H, m), 2.03–2.40(2H, m), 2.40–3.26(10H, m), 3.68–3.90(1H, m), 3.81(3H, s), 3.97(1H, m), 4.02–4.26(2H, m), 4.36–5.10(1H, m), 6.43–6.57(2H, m), 7.00–7.29(5H, m) |
| 172 | 1.26–1.98(12H, m), 2.20(2H, t, J=7.5Hz), 2.53–3.27(8H, m), 3.77–5.05(2H, m), 3.97(2H, t, J=6.4Hz), 4.37(1H, m), 6.01(1H, brs), 6.05(1H, brs), 6.90(2H, d, J=8.6Hz), 6.99–7.29(4H, m), 7.42(2H, d, J=8.6Hz) |
| 173 | 1.26(3H, t, J=7.1Hz), 1.54–1.75(1H, m), 1.75–1.96(1H, m), 2.03–2.33(2H, m), 2.44–3.24(10H, m), 3.57–3.78(1H, m), 3.80(3H, s), 4.01(2H, t, J=6.3Hz), 4.14(2H, q, J=7.1Hz), 4.39(1H, m), 4.82–5.04(1H, m), 6.40–6.59(2H, m), 6.98–7.33(5H, m) |
| 174 | 1.10–2.06(12H, m), 2.23(2H, t, J=7.5Hz), 2.42–3.24(8H, m), 3.67–5.15(2H, m), 3.90(2H, d, J=5.2Hz), 3.97(2H, t, J=6.4Hz), 4.37(1H, m), 6.09(1H, brs), 6.90(2H, d, J=8.6Hz), 6.97–7.30(4H, m), 7.41(2H, d, J=8.6Hz) |
| 175 | 1.27(3H, t, J=7.1Hz), 1.39(3H, d, J=7.2Hz), 1.63–1.95(2H, m), 2.14(2H, quint, J=6.5Hz), 2.43(2H, t, J=6.5Hz), 2.54–3.10(8H, m), 3.80–5.15(2H, m), 4.04(2H, t, J=6.5Hz), 4.19(2H, q, J=7.1Hz), 4.39(1H, m), 4.57(1H, quint, J=7.2Hz), 6.29(1H, d, J=7.2Hz), 6.90(2H, d, J=8.7Hz), 6.99–7.29(4H, m), 7.42(2H, d, J=8.7Hz) |
| 176 | 1.18–1.54(6H, m), 1.54–1.93(6H, m), 2.32(2H, t, J=7.4Hz), 2.54–3.10(8H, m), 3.67(3H, s), 3.80–5.05(2H, m), 3.97(2H, t, J=6.5Hz), 4.40(1H, m), 6.70(2H, d, J=8.6Hz), 6.99–7.27(4H, m), 7.43(2H, d, J=8.6Hz) |
| 177 | 1.62–1.96(2H, m), 2.52–3.18(8H, m), 3.68–4.42(6H, m), 3.81(3H, s), 4.80–5.05(1H, m), 6.47–6.64(2H, m), 6.99–7.29(5H, m) |
| 178 | 1.54–1.93(2H, m), 2.04(3H, s), 2.27–3.28(8H, m), 3.56–3.80(1H, m), 3.81(3H, s), 4.00–4.73(5H, m), 4.83–5.05(1H, m), 6.49–6.65(2H, m), 6.98–7.36(4H, m) |
| 179 | 1.52–1.98(2H, m), 2.12(2H, quint, J=6.5Hz), 2.45(2H, t, J=6.5Hz), 2.54–3.24(8H, m), 3.65–5.18(2H, m), 3.89(2H, d, J=5.2Hz), 4.02(2H, t, J=6.5Hz), 4.36(1H, m), 6.00(1H, brs), 6.61(1H, brs), 6.89(2H, d, J=8.6Hz), 6.99–7.29(5H, m), 7.40(2H, d, J=8.6Hz) |
| 180 | 1.57–1.94(2H, m), 2.12(2H, quint, J=6.6Hz), |

TABLE 2-continued

| No. | NMR (CDCl₃) δ value |
|---|---|
|  | 2.43(2H, t, J=6.6Hz), 2.54–3.14(8H, m), 3.28(1H, m), 3.76(3H, s), 4.00(2H, d, J=3.8Hz), 4.01(2H, t, J=6.6Hz), 4.10–5.00(1H, m), 4.37(1H, m), 4.65(1H, dt, J=7.6, 3.8Hz), 6.74(1H, d, J=7.6Hz), 6.91(2H, d, J=8.7Hz), 6.99–7.29(4H, m), 7.42(2H, d, J=8.7Hz) |
| 181 | 1.22–1.94(18H, m), 2.31(2H, t, J=7.5Hz), 2.42–3.17(8H, m), 3.66(3H, s), 3.80–5.10(2H, m), 3.97(2H, t, J=6.5Hz), 4.40(1H, m), 6.90(2H, d, J=8.6Hz), 6.99–7.28(4H, m), 7.43(2H, d, J=8.6Hz) |
| 182 | 0.9–1.4(3H, s), 1.5–1.8(1H, m), 2.3–2.7(3H, m), 2.8–3.3(4H, m), 3.3–4.0(8H, m), 4.2–4.5(1H, m), 4.6–4.9(1H, br), 6.4–6.6(2H, m), 7.0–7.4(5H, m) |
| 183 | 1.12(3H, d, J=6.9Hz), 1.6–1.8(1H, m), 2.4–2.7(3H, m), 2.8–2.9(2H, m), 3.00(6H, s), 2.9–3.4(3H, m), 4.1–4.5(3H, m), 6.68(2H, d, J=8.8Hz), 7.0–7.3(4H, m), 7.40(2H, d, J=8.8Hz) |
| 184 | 1.6–1.8(6H, m), 2.1–2.3(3H, br), 2.3–2.4(6H, br), 2.7–2.9(2H, m), 2.92(3H, s), 3.0–3.2(2H, m), 6.3–6.5(1H, m), 6.9–7.1(2H, m), 7.2–7.3(1H, m), 7.25(2H, d, J=8.5Hz), 7.56(2H, d, J=8.5Hz) |
| 185 | 2.1–2.3(1H, m), 2.5–2.9(5H, m), 3.3–4.2(10H, m), 5.0–5.2(1H, m), 6.4–6.6(2H, m), 7.0–7.2(2H, m) |
| 186 | 2.1–2.3(1H, m), 2.5–2.9(5H, m), 2.99(6H, s), 3.6–4.3(4H, m), 4.8–5.0(1H, br), 6.6–6.7(2H, m) |
| 187 | 2.1–2.4(1H, m), 2.5–3.0(8H, m), 3.3–4.2(7H, m), 5.0–5.2(1H, m), 6.7–7.1(4H, m), 7.1–7.3(3H, m) |
| 188 | 1.22(3H, d, J=7.1Hz), 1.5–1.7(1H, m), 2.3–2.5(1H, m), 2.5–3.3(9H, m), 4.1–4.3(1H, m), 6.9–7.1(1H, m), 7.1–7.3(3H, m) |
| 189 | 1.6–2.0(3H, m), 2.5–2.6(8H, m), 3.6–3.9(2H, m), 4.0–4.3(1H, m), 6.9–7.1(1H, m), 7.1–7.3(3H, m) |
| 190 | 2.1–2.4(2H, m), 2.5–2.7(2H, m), 2.7–3.1(3H, m), 3.1–3.3(1H, m), 3.3–3.6(2H, m), 3.9(1H, s), 4.6–4.8(1H, m), 7.0–7.3(4H, m) |
| 191 | 1.65–1.97(2H, m), 2.40–2.92(9H, m), 3.15–3.34(2H, m), 3.78(3H, s), 4.25–4.49(1H, m), 6.67–6.72(2H, m), 7.16(1H, d, J=8.9Hz) |
| 192 | 1.55–1.85(3H, m), 2.30(3H, s), 2.36–2.90(8H, m), 3.15–3.32(2H, m), 4.23–4.48(1H, m), 6.90–7.06(2H, m), 7.11(1H, d, J=8.1Hz) |
| 193 | 1.63–1.95(3H, m), 2.36(3H, s), 2.43–2.90(8H, m), 3.13–3.31(2H, m), 4.18–4.40(1H, m), 6.81(1H, d, J=7.5Hz), 6.95–7.10(2H, m) |
| 194 | 1.65–1.86(2H, m), 1.98(2H, brs), 2.40–2.90(8H, m), 3.15–3.38(2H, m), 4.14–4.48(1H, m), 6.70(1H, dt, J=8.2, 2.3Hz), 6.94(1H, dd, J=11.0, 2.3Hz), 7.09(1H, t, J=8.1Hz) |
| 195 | 1.62–1.95(3H, m), 2.35(3H, s), 2.38–2.90(8H, m), 3.10–3.48(3H, m), 6.88–7.20(3H, m) |
| 196 | 1.64–1.83(2H, m), 2.19(3H, s), 2.40–2.86(8H, m), 4.42–4.62(1H, m), 7.08(2H, s), 7.67(1H, s), 7.81(1H, brs) |
| 197 | 1.27(3H, t, J=7.0Hz), 1.62–1.83(2H, m), 1.91(1H, brs), 2.30–3.32(9H, m), 4.23–4.45(1H, m), 6.96–7.30(4H, m) |
| 198 | 1.67–1.86(2H, m), 2.21(1H, brs), 2.43–2.83(8H, m), 2.95(6H, s), 3.15–3.32(2H, m), 4.16–4.40(1H, m), 6.41(1H, dd, J=8.3, 2.3Hz), |

TABLE 2-continued

| No. | NMR (CDCl₃) δ value |
|---|---|
|  | 6.57(1H, d, J=2.3Hz), 7.01(1H, d, J=8.3Hz) |
| 199 | 1.56–1.95(2H, m), 2.43–3.23(8H, m), 3.56–3.83(1H, m), 3.67(3H, d, J=9.3Hz), 4.23–4.67(1H, m), 4.86–5.05(1H, m), 6.26–6.42(2H, m), 6.96–7.35(5H, m), 8.57–8.73(1H, m) |
| 200 | 1.60–1.74(1H, m), 1.80–1.93(1H, m), 2.31(3H, s), 2.47–3.38(8H, m), 3.58–3.75(1H, m), 3.91(3H, d, J=8.9Hz), 4.27–4.69(1H, m), 4.88–5.03(1H, m), 6.67–6.91(2H, m), 6.96–7.30(5H, m) |
| 201 | 1.52–2.10(6H, m), 2.45–3.10(11H, m), 3.72–5.10(5H, m), 6.90(2H, d, J=8.7Hz), 6.97–7.32(4H, m), 7.43(2H, d, J=8.7Hz) |
| 202 | 1.26(3H, t, J=7.5Hz), 1.62–1.98(2H, m), 2.35–3.28(10H, m), 3.57–3.98(7H, m), 4.41(1H, brs), 4.85–5.05(1H, m), 6.40–6.60(2H, m), 6.82–7.00(2H, m), 7.08(1H, d, J=7.5Hz), 7.16–7.35(1H, m) |
| 203 | 1.58–2.00(2H, m), 2.42–3.25(8H, m), 3.60–4.02(10H, m), 4.20–4.70(1H, m), 4.86–5.05(1H, m), 6.42–6.80(4H, m), 7.07(1H, d, J=8.2Hz), 7.13–7.38(1H, m) |
| 204 | 1.58–2.02(2H, m), 2.50(3H, s), 2.40–3.28(8H, m), 3.57–4.00(4H, m), 4.15–4.78(1H, m), 4.87–5.08(1H, m), 6.65–7.38(6H, m) |
| 205 | 1.67–1.93(2H, m), 2.33(2H, quint, J=6.1Hz), 2.48–3.15(8H, m), 3.61(2H, t, J=6.4Hz), 3.78–5.28(3H, m), 4.14(2H, t, J=5.8Hz), 6.92(2H, d, J=8.7Hz), 6.98–7.32(4H, m), 7.44(2H, d, J=8.7Hz) |
| 206 | 1.72–2.13(4H, m), 2.45(2H, t, J=7.0Hz), 2.47–3.35(10H, m), 3.90–4.35(4H, m), 6.55(2H, d, J=8.6Hz), 6.93–7.30(6H, m), 7.33(2H, d, J=8.6Hz), 8.95(1H, brs) |
| 207 | 1.44–1.97(8H, m), 2.48–3.30(10H, m), 2.96(3H, s), 3.83–5.02(4H, m), 3.98(2H, t, J=6.1Hz), 6.89(2H, d, J=8.7Hz), 6.98–7.35(4H, m), 7.42(2H, d, J=8.7Hz) |
| 208 | 1.46–2.02(8H, m), 1.97(3H, s), 2.48–3.37(10H, m), 3.80–5.09(3H, m), 3.97(2H, t, J=6.2Hz), 5.87(1H, brs), 6.89(2H, d, J=8.8Hz), 6.95–7.39(4H, m), 7.42(2H, d, J=8.8Hz) |
| 209 | 1.52–2.03(6H, m), 1.97(3H, s), 2.47–3.40(10H, m), 3.81–4.96(3H, m), 3.99(2H, t, J=6.1Hz), 5.86(1H, brs), 6.88(2H, d, J=8.7Hz), 6.94–7.38(4H, m), 7.42(2H, d, J=8.7Hz) |

Example 384

Acetic acid (30 ml) and 1-(1-benzyl-3-methyl-4-piperidinyl)carbostyril (2.1 g) are added to 10% palladium-carbon (0.5 g) and the mixture is subjected to catalytic reduction at 80° C. under atmospheric pressure. After the catalytic reduction, 10% palladium-carbon is filtered off and the filtrate is concentrated under reduced pressure. Water is added to the residue and the mixture is basified with aqueous sodium hydroxide solution and then extracted with dichloromethane. After washed with water, the extract is dried with magnesium sulfate and the solvent is distilled off under reduced pressure to give 1-(3-methyl-4-piperidinyl)-3,4-dihydrocarbostyril (1.01 g).

NMR (CDCl₃) δ ppm: 1.22 (3H, d, J=7.1 Hz), 1.5–1.7 (1H, m), 2.3–2.5 (1H, m), 2.5–3.3 (9H, m), 4.1–4.3 (1H, m), 6.9–7.1 (1H, m), 7.1–7.3 (3H, m)

The compounds of the above Examples 1–9, 11–164, 169–350, 352–383C are obtained in the same manners as in Example 384.

Example 385

Conc. sulfuric acid (8 ml) is added to N-(β-ethoxyacryloyl)-N-(1-benzoyl-4-piperidinyl)aniline (0.8 g) and the mixture is reacted at 60° C. for 30 minutes. The reaction mixture is poured into ice-water and then extracted with dichloromethane. The solvent is concentrated and the resulting residue is purified by silica gel column chromatography (solvent; dichloromethane:methanol=50:1) to give 1-(1-benzoyl-4-piperidinyl)carbostyril (0.53 g).

NMR (CDCl$_3$) δ ppm: 1.60–2.02 (2H, m), 2.62–3.41 (4H, m), 3.73–4.26 (1H, m), 4.50–5.72 (2H, m), 6.64 (1H, d, J=9.4 Hz), 7.15–7.70 (10H, m)

The compounds of the above Examples 10 and 166–168 are obtained in the same manners as in Example 385.

Example 386

Ethanol (10 ml) and 10% aqueous sodium hydroxide solution (12 ml) are added to 1-(1-benzoyl-4-piperidinyl)carbostyril (1.0 g) and the mixture is refluxed with heating for 7 hours. After concentration, water is added thereto and the mixture is extracted with dichloromethane. The dichloromethane layer is collected by filtration and water is added thereto. The mixture is acidified with diluted hydrochloric acid. The aqueous layer is basified with diluted aqueous sodium hydroxide solution, extracted with dichloromethane and then concentrated to give 1-(4-piperidinyl)carbostyril (0.58 g).

NMR (CDCl$_3$) δ ppm: 1.62–2.03 (3H, m), 2.55–3.03 (4H, m), 3.14–3.50 (2H, m), 4.68–5.85 (1H, br), 6.65 (1H, d, J=9.4 Hz), 7.19 (1H, t, J=7.4 Hz), 7.35–8.00 (4H, m)

Using the suitable starting materials, the compounds of the above Examples 156, 158, 171, 186, 351–361 and the following Examples 580, 581 and 577A are obtained in the same manners as in Example 386.

Example 387

1-(4-Piperidinyl)-3,4-dihydrocarbostyril (0.2 g) is added to conc. sulfuric acid (5 ml) and thereto is added fuming nitric acid (0.1 ml) under ice cooling. The mixture is stirred at room temperature for 30 minutes, and then the reaction mixture is poured into ice-water. The mixture is basified and extracted with dichloromethane. The solvent is concentrated to give 6-nitro-1-(4-piperidinyl)-3,4-dihydrocarbostyril (0.2 g).

NMR (CDCl$_3$) δ ppm: 1.65–2.10 (3H, m), 2.44–3.45 (10H, m), 4.26–4.55 (1H, m), 7.34 (1H, d, J=8.9 Hz), 8.00–8.22 (2H, m)

Using the suitable starting materials, the compounds of the above Examples 3, 38, 43, 163, 175, 188, 195, 379 and the following Example 510 are obtained in the same manners as in Example 387.

Example 388

A mixture of 10% palladium-carbon (0.4 g) and acetic acid (50 ml) is added to 6-nitro-1-[1-(2,4-dimethoxybenzoyl)-4-piperidinyl]-3,4-dihydrocarbostyril (4.0 g) and the mixture is subjected to catalytic reduction at 70° C. for 1 hour. The catalyst is filtered off and the filtrate is concentrated. The resulting residue is basified with 10% aqueous sodium hydroxide solution and extracted with dichloromethane. The solvent is concentrated and the resulting residue is purified by silica gel column chromatography (solvent; dichloromethane:methanol=20:1) to give 6-amino-1-[1-(2,4-dimethoxybenzoyl)-4-piperidinyl]-3,4-dihydrocarbostyril (1.9 g).

NMR (CDCl$_3$) δ ppm: 1.50–1.93 (2H, m), 2.34–3.20 (8H, m), 3.30–4.15 (9H, m), 4.22–4.75 (1H, m), 4.85–5.03 (1H, m), 6.42–6.63 (4H, m), 6.82–7.33 (2H, m)

Using the suitable starting materials, the compounds of the above Examples 48, 80, 182, 176, 192, 380 and the following Examples 485, 511 are obtained in the same manners as in Example 388 and in following Example 401.

Example 389

Dichloromethane (10 ml) and triethylamine (0.15 ml) are added to 6-amino-1-[1-(2,4-dimethoxybenzoyl)-4-piperidinyl]-3,4-dihydrocarbostyril (0.3 g). Acetic anhydride (0.2 ml) is added thereto and the mixture is stirred at room temperature for 1 hour. Water is added to the reaction mixture and extracted with dichloromethane. After concentration, the residue is purified by silica gel column chromatography (solvent; chloroform:methanol=20:1) and further recrystallized from ethanol to give 6-acetylamino-1-[1-(2,4-dimethoxybenzoyl)-4-piperidinyl]-3,4-dihydrocarbostyril (0.25 g) as white powder, m.p. 271°–272° C.

The compounds of the above Examples 160, 267, 359 and the following Examples 484 and 486 are obtained in the same manners as in Example 389.

Example 390

7-Fluoro-1-(4-piperidinyl)-3,4-dihydrocarobstyril (2.37 g), 2-methoxy-4-ethoxybenzoic acid (2.43 g) and bis(2-oxo-oxazolydinyl)phosphinyl chloride (3.65 g) are dissolved in dichloromethane (50 ml) and thereto is added dropwise triethylamine (4 ml). The mixture is stirred at room temperature overnight and poured into water. The mixture is extracted with dichloromethane, dried with sodium carbonate and then purified by silica gel column chromatography (solvent; n-hexane:ethyl acetate=1:1). The resultant is recrystallized from ethanol/water to give 7-fluoro-1-[1-(2-methoxy-4-ethoxybenzoyl)-4-piperidinyl]-3,4-dihydrocarbostyril (2.5 g) as white powder, m.p. 159°–161° C.

Example 391

1-(4-Piperidinyl)-3,4-dihydrocarbostyril (500 mg) and triethylamine (0.6 ml) are dissolved in dichloromethane (10 ml) and thereto is added dropwise ethyl chlorocarbonate (0.31 ml) gradually. The mixture is stirred at room temperature for 2 hours and poured into water. The mixture is extracted with chloroform, dried with sodium carbonate and purified by silica gel column chromatography (solvent; n-hexane:ethyl acetate=3:1). The resultant is re-crystallized from ethanol/n-hexane to give 1-(1-ethoxycarbonyl-4-piperidinyl)-3,4-dihydrocarbostyril (0.1 g) as white powder, m.p. 82°–83° C.

Example 392

1-(4-Piperidinyl)-3,4-dihydrocarbostyril (500 mg), triethylamine (1.2 ml) and pyrrole-2-carboxylic acid (314 mg) are dissolved in dichloromethane (10 ml) and thereto is added dropwise diethyl cyanophosphate (0.82 ml) under ice cooling. The mixture is stirred with ice cooling for 1 hour and then stirred at room temperature for 2 hours. The mixture is poured into water, extracted with chlorform, dried with sodium carbonate and purified by silica gel column chromatography (solvent; dichloromethane:methanol=20:1). The resultant is recrystallized from n-hexane/diethyl ether to give 1-[1-(2-pyrrolylcarbonyl)-4-piperidinyl]-3,4- dihyrocarbostyril (0.2 g), as white powder, m.p. 161°–162° C. (decomposed).

Example 393

1-(4-Piperidinyl)-3,4-dihydrocarbostyril (0.8 g) is dissolved in dichloromethane (20 ml) and thereto is added phenylisocyanate (0.57 ml) and the mixture is stirred at room temperature for 4 hours. The solvent is concentrated and the residue is purified by silica gel column chromatography (solvent; n-hexane:ethyl acetate=5:1) and recrystallized from n-hexane/ethanol to give 1-(1-anilinocarbonyl-4-piperidinyl)-3,4-dihydrocarbostyril (0.8 g), as white powder, m.p. 194°–196° C.

The compounds of the above Examples 1–155, 157, 159–167, 169–170, 173–182, 187–232, 234–235, 241–243, 246–290, 294–346, 348–350, 362–383C and the following Examples 436, 438, 440, 442, 443–460, 465–475, 482–579 and 582–587 are obtained in the same manners as in Examples 390–393.

Example 394

1-[1-(4-α-t-Butoxycarbonylaminophenylacetyl)-4-piperidinyl]-3,4-dihydrocarbostyril (400 mg) is dissolved in formic acid (5 ml) and the mixture is stirred at room temperature overnight. The solvent is distilled off under reduced pressure and the resulting oily product is purified by silica gel column chromatography (solvent; dichloromethane:methanol=8:1). The resultant is recrystallized from diethyl ether to give 1-[1-(4-α-aminophenylacetyl)-4-piperidinyl]-3,4-dihydrocarbostyril (0.22 g), as white powder, m.p. 116°–120° C.

Example 395

A mixture (5 ml) of hydrobromic acid and acetic acid (35% solution) is added to 1-{1-[4-(N-t-butoxycarbonyl-N-methylamino)benzoyl]-4-piperidinyl}-3,4-dihyrocarbostyril (1.8 g) and the mixture is stirred at room temperature overnight. The reaction mixture is poured into water and the pH value thereof is adjusted to pH 12–14 by adding potassium carbonate. The mixture is extracted with chloroform, dried with sodium carbonate and then purified by silica gel column chromatography (solvent; n-hexane:ethyl acetate= 1:1). The resultant is recrystallized from n-hexane/ethanol to give 1-{1-[4-(N-methylamino)benzoyl]-4-piperidinyl}-3,4-dihydrocarbostyril (1.2 g), as white powder, m.p. 184°–186° C.

Example 396

1-[1-(1-Benzyloxycarbonyl-2-pyrrolidinylcarbonyl)-4-piperidinyl]-3,4-dihydrocarbostyril (0.87 g) is dissolved in ethanol (20 ml) and thereto is added 5% palladium-carbon (0.1 g). The mixture is stirred at room temperature under 1 atm. under hydrogen atmosphere. After the completion of the reaction, the catalyst is filtered off and the filtrate is concentrated. The resultant is purified by silica gel column chromatography (solvent; dichloromethane:methanol=8:1) to give 1-[1-(2-pyrrolidinylcarbonyl)-4-piperidinyl]-3,4-dihydrocarbostyril (205 mg).

NMR (CDCl$_3$) δ ppm: 1.72–2.29 (6H, m), 2.39–2.92 (7H, m), 3.10–3.32 (1H, m), 3.35–3.65 (2H, m), 3.82–4.25 (2H, m), 4.52–4.90 (2H, m), 6.30–7.35 (5H, m)

Example 397

1-[1-(4-Benzyloxybenzoyl)-4-piperidinyl]-3,4-dihyrocarbostyril (4.76 g) is dissolved in methanol (100 ml) and thereto is added 5% palladium-carbon (1 g). The mixture is stirred at room temperature under 1 atm. under hydrogen atmosphere. After the completion of the reaction, the catalyst is filetered off and the filtrate is concentrated. The resultant is purified by silica gel column chromatography (solvent; n-hexane:ethyl acetate=1:1) and further recrystallized from n-hexane/ethanol to give 1-[1-(4-hydroxybenzoyl)-4-piperidinyl]-3,4-dihydrocarbostyril (2.5 g) as white powder, m.p. 182°–183° C.

Example 398

60% Sodium hydride (0.34 g) is washed with n-hexane and thereto is added dimethylformamide (20 ml). Thereto are added 1-[1-(4-hydroxybenzoyl)-4-piperidinyl]-3,4-dihydrocarbostyril (1 g), 2-chloroethyldimethylamine hydrochloride (0.66 g) and sodium iodide (1.7 g) and the mixture is stirred at 50°–60° C. under argon atmosphere for 2 hours. Then, the mixture is further stirred at room temperature overnight. The reaction mixture is poured into water and extracted with ethyl acetate/toluene, dried with sodium carbonate. The resultant is purified by silica gel column chromatography (solvent; n-hexane:ethyl acetate= 1:1) to give 1-{1-[1-(2-dimethylaminoethoxy)benzoyl]-4-piperidinyl}-3,4-dihydrocarbostyril (0.362 g).

NMR (DMSO-d$_6$) δ ppm: 1.72–1.94 (2H, m), 2.48–3.26 (10H, m), 2.66 (6H, s), 3.77–5.28 (5H, m), 6.94–7.45 (6H, m)

Example 399

1-[1-(4-Hydroxybenzoyl)-4-piperidinyl]-3,4-dihydrocarbostyril (500 mg), prenyl bromide (0.5 ml) and 1,8-diazabicyclo[5.4.0]-undecene-7 (0.65 ml) are dissolved in isopropanol (10 ml) and the mixture is refluxed with heating for 4 hours. The solvent is distilled off under reduced pressure and the residue is purified by silica gel column chromatography (solvent; n-hexane:ethyl acetate=2:1) to give 1-{1-[4-(2-isopentenyloxy)benzoyl]-4-piperidinyl}-3, 4-dihydrocarbostyril (0.159 g).

NMR (CDCl$_3$) δ ppm: 1.56–1.79 (2H, m), 1.75 (3H, s), 1.80 (3H, s), 2.47–3.14 (8H, m), 3.93–5.05 (3H, m), 4.53 (2H, d, J=6.8 Hz), 5.40–5.57 (1H, m), 6.83–7.53 (8H, m)

The compounds of the above Examples 10, 19, 23, 26, 30, 31, 33, 38, 44, 45, 47, 50, 54, 55, 56, 61, 66, 72, 74, 76, 84, 89, 91, 94, 95, 98, 99, 102, 106, 108–110, 113–115, 118–119, 121–155, 157, 159–164, 166, 167, 170, 172–180, 189, 194, 209, 212, 222–225, 227, 228, 230–232, 234–235, 241–243, 246–251, 254–256, 260–280, 285, 288–294, 296, 297, 299–328, 332–335, 338, 345, 348, 350, 362–365, 367–373, 377–378, 383A–383C and the following Examples 436, 438, 440, 442, 445, 472, 475, 482–577, 582–587 are obtained in the same manners as in Examples 398 and 399.

Example 400

Trifluoroacetic acid (0.21 ml) is added dropwise with stirring to a mixture of 1-{1-[4-(3-hydroxypropoxy) benzoyl]-4-piperidinyl}-3,4-dihydrocarbostyril (0.51 g), NaOCN (0.16 g), toluene (5 ml) and chloroform (5 ml) at room temperature. After adding, the mixture is stirred at room temperature overnight. Ethyl acetate is added to the reaction mixture and the mixture is washed with saturated aqueous sodium hydrogen carbonate solution, water and saline solution successively and then dried with sodium sulfate. The solvent is distilled off and the resulting residue is purified by silica gel column chromatography (solvent;

dichloromethane:methanol=100:1) to give 1-{1-[4-(3-carbamoyloxypropoxy)benzoyl-4-piperidinyl}-3,4-dihydrocarbostyril (0.15 g).

NMR (CDCl₃) δ ppm: 1.60–2.32 (4H, m), 2.41–3.27 (8H, m), 3.71–5.15 (5H, m), 4.07 (2H, t, J=6.2 Hz), 4.26 (2H, t, J=6.2 Hz), 6.96 (2H, d, J=8.6 Hz), 6.99–7.40 (4H, m), 7.43 (2H, d, J=8.6 Hz)

The compounds of the above Examples 128, 313 and the following Examples 470, 569 are obtained in the same manners as in Example 400.

Example 401

1-[1-(4-Nitrobenzoyl)-4-piperidinyl-3,4-dihydrocarbostyril (4.21 g) is dissolved in ethanol (100 ml) and thereto is added 5% palladium-carbon (1 g) and the mixture is stirred at room temperature under 1 atm. under hydrogen atomsphere. After the reaction, the catalyst is removed by fileration. The filtrate is concentrated and the residue is purified by silica gel column chromatography (solvent: dichloromethane:methanol=20:1) and recrystallized from n-hexane/ethanol to give 1-[1-(4-aminobenzoyl)-4-piperidinyl]-3,4-dihydrocarbostyril (2.1 g) as white powder, m.p.: 198°–199° C.

Example 402

1-[1-(4-Methoxycarbonylbenzoyl)-4-piperidinyl]-3,4-dihydrocarbostyril (6.33 g) and sodium hydroxide (1.94 g) are dissolved in methanol (100 ml) and the mixture is stirred at room temperature overnight. After the solvent is concentrated, water is added to the residue and the mixture is extracted with diethyl ether. The aqueous layer is adjusted to pH 1 by adding conc. hydrochloric acid and extracted with ethyl acetate. The extract is dried with magnesium sulfate, concentrated and recrystallized from n-hexane/ethanol to give 1-[1-(4-carboxybenzoyl)-4-piperidinyl]-3,4-dihydrocarbostyril (4.5 g) as white powder, m.p.: 232°–235° C.

Using the suitable starting materials, the compounds of the above Examples 260, 275, 301, 303, 304, 308, 310, 316, 336, 365, 374 and the following Example 482 are obtained in the same manners as in Example 402.

Example 403

1-{1-[4-(N-methylamino)benzoyl]-4-piperidinyl}-3,4-dihydrocarbostyril (200 mg) is dissolved in dichloromethane (5 ml) and thereto is added α-chloroacetyl chloride (55 μl) under ice cooling. Continually thereto is added triethylamine (0.23 ml) and the mixture is stirred at room temperature overnight. After the solvent is concentrated, the residue is purified by silica gel column chromatography (solvent: n-hexane:ethyl acetate=1:1) and recrystallized from n-hexane/ethanol to give 1-{1-[4-(N-α-chloroacetyl-N-methylamino)benzoyl]-4-piperidinyl]-3,4-dihydrocarbostyril (0.18 g) as white powder, m.p.: 220°–222° C. (decomposed).

Example 404

1-[1-(4-Aminobenzoyl)-1-piperidinyl]-3,4-dihydrocarbostyril (4 g) is dissolved in dichloromethane (100 ml) and thereto is added trifluoroacetic anhydride (2.1 ml). Under ice cooling, thereto is added dropwise triethylamine (4.78 ml) and the mixture is stirred at the same temperature for 2 hours and then at room temperature overnight. The reaction mixture is poured into water and extracted with chloroform and dried with magnesium sulfate. The resulting residue is purified by silica gel column chromatography (solvent: n-hexane:ethyl acetate=1:1) and recrystallized from n-hexane to give 1-[1-(4-trifluoroacetylamino)-4-piperidinyl]-3,4-dihydrocarbostyril (3.8 g) as light red powder, m.p.: 104°–107° C.

Example 405

A mixture of 1-[1-(2-aminobenzoyl)-4-piperidinyl]-3,4-dihydrocarbostyril (0.96 g), acetic anhydride (10 ml) and conc. sulfuric acid (0.1 ml) is stirred at room temperature for 2 hours. The reaction mixture is basified with 1N aqueous sodium hydroxide solution and extracted with ethyl acetate. The extract is washed successively with saturated aqueous sodium hydrogen carbonate solution, 1N hydrochloric acid and saturated saline solution and dried with sodium sulfate. After the solvent is distilled off, the residue is recrystallized from ethyl acetate/diethyl ether to give 1-[1-(2-acetylaminobenzoly)-4-piperidinyl]-3,4-dihydrocarbostyril (0.55 g) as colorless needles, m.p.: 141°–143° C.

Using the suitable starting materials, the compounds of the above Examples 32, 57–59, 67, 78, 87, 88, 116, 129, 130, 137, 140–141, 145, 149–152, 155, 174, 187, 200, 246, 254, 255, 288, 291, 292, 382, 383, 383B, 383C and the following Examples 451, 452, 463, 467, 468, 469, 488, 500–503, 506–508, 510, 511, 513–515, 519–521, 523, 536, 537, 587 are obtained in the same manners as in Examples 403–405.

Example 406

1-[1-(3-Ethoxycarbonylbenzoyl)-4-piperidinyl]-3,4-dihydrocarbostyril (0.5 g), aqueous ammonia (10 ml) and ammonium chloride (the effective amount as a catalyst) are dissolved in ethanol (10 ml) and the mixture is stirred at 110°–130° C. for 10 hours in an autoclave. Ethanol is distilled off under reduced pressure and the residue is extracted with methylene chloride. The organic layer is washed with water and saturated saline solution, dried with sodium sulfate and concentrated. The solvent is distilled off and the resulting residue is purified by silica gel column chromatography (solvent: methylene chloride:methanol= 10:1) to give 1-[1-(3-carbamoylbenzoyl)-4-piperidinyl]-3,4-dihydrocarbostyril (0.15 g).

NMR (CDCl₃) δ ppm: 1.59–2.11 (2H, m), 2.48–3.33 (8H, m), 3.70–5.15 (3H, m), 5.58–6.60 (2H, m), 6.97–8.05 (8H, m)

Using the suitable starting materials, the compounds of the above Examples 276, 294, 300, 305, 307, 309, 313, 317–319, 321, 326, 329 and 344 are obtained in the same manners as in Example 406.

Example 407

A mixture of 1-{1-[4-3-methylaminopropoxy)benzoyl]-4-piperidinyl}-3,4-dihydrocarbostyril (0.5 g), propyl bromide (0.13 ml), sodium hydrogen carbonate (0.15 g) and acetonitrile (10 ml) is stirred at room temperature for 8 hours. Further thereto are added propyl bromide (0.13 ml) and sodium hydrogen carbonate (0.15 g) and the mixture is stirred with heating at 60° C. for 8 hours. The solvent is distilled off and the resulting residue is extracted with ethyl acetate. The extract is washed successively with saturated sodium hydrogen carbonate, water and saline solution and dried with sodium sulfate. The solvent is distilled off and the resulting residue is purified by silica gel column chromatography (solvent: dichloromethane:methanol=20:1) to give 1-[1-{4-[3-(N-methyl-N-propylamino)propoxy]benzoyl}-4-piperidinyl]-3,4-dihydrocarbostyril (0.15 g).

NMR (CDCl$_3$) δ ppm: 0.91 (3H, t, J=5.8 Hz), 1.42–3.31 (21H, m), 2.33 (3H, s), 3.88–5.15 (3H, m), 4.05 (2H, t, J=5 Hz), 6.91 (2H, d, J=7 Hz), 6.95–7.38 (4H, m), 7.42 (2H, d, J=7 Hz)

Example 408

A mixture of 1-{1-[4-(3-aminopropoxy)benzoyl]-4-piperidinyl}-3,4-dihydrocarbostyril (1.4 g), benzaldehyde (0.42 ml) and methanol (15 ml) is stirred at room temperature for 3 hours and cooled with ice. Thereto is added sodium boron hydride (0.21 g) and the mixture is stirred under ice cooling for 2 hours and then allowed to stand at room temperature overnight. The solvent is distilled off and water is added to the resulting residue and the mixture is extracted with ethyl acetate. The extract is washed successively with saturated sodium hydrogen carbonate, water and saline solution, dried with sodium sulfate and then the solvent is distilled off. The resulting residue is purified by silica gel column chromatography (solvent: methanol:dichloromethane=1:100) to give 1-{1-[4-benzylaminopropoxy)benzoyl]-4-piperidinyl}-3,4-dihydrocarbostyril (1.02 g).

NMR (CDCl$_3$) δ ppm: 1.60–2.15 (5H, m), 2.47–3.18 (10H, m), 3.82 (2H, s), 3.95–5.11 (3H, m), 4.08 (3H, t, J=6.2 Hz), 6.89 (2H, d, J=8.5 Hz), 6.95–7.50 (9H, m), 7.42 (2H, d, J=8.5 Hz)

Example 409

1-[1-(2-Methoxy-4-methylaminobenzoyl)-4-piperidinyl]-3,4-dihydrocarbostyril (500 mg) is dissolved in methanol (10 ml) and thereto is added formaldehyde (0.54 ml) and then thereto is added NaBH$_3$CN (86.4 mg) under ice cooling. The mixture is stirred under ice cooling for 2 hours and further stirred at room temperature. The reaction mixture is concentrated and to the residue is added saturated aqueous sodium hydrogen carbonate solution. The mixture is extracted with chloroform and dried with sodium sulfate. The solvent is distilled off and the resulting residue is purified by silica gel column chromatography (solvent: n-hexane:ethyl acetate=1:1) and recrystallized from n-hexane/ethanol to give 1-[1-(2-methoxy-4-dimethylaminobenzoyl)-4-piperazinyl]-3,4-dihydrocarbostyril (0.263 g) as white powder, m.p.: 93°–96° C.

Using the suitable starting materials, the compounds of the above Examples 27, 40, 55, 57, 59, 62, 63, 65, 67, 68, 76, 79, 81, 82, 88, 89, 92, 114, 115, 118, 119, 123, 124, 126, 127, 131, 133, 138, 139, 143, 144, 149, 150–152, 169, 184, 185, 187, 190, 198, 199, 214, 231, 236–238, 242–246, 248, 251, 254, 255, 261–263, 265, 268, 270, 283, 285, 287, 291–293, 305, 306, 309, 311, 321, 322, 326, 327, 332, 334, 335, 344, 346, 349, 361, 366, 367, 374, 381, 383A and the following Examples 448, 449, 454, 455, 456, 458, 459, 464, 466, 474A, 489–496, 498, 499, 504, 505, 509, 516–518, 522, 532, 539–546, 550–552, 554–556, 559, 562–565 and 567 are obtained in the same manners as in Examples 407–409.

Example 410

A mixture of 1-[1-{4-[3-(N-benzyl-N-methylamino)propoxy]benzoyl}-4-piperidinyl]-3,4-dihydrocarbostyril (5.3 g), 5% palladium-carbon (0.8 g), ammonium formate (2.6 g) and ethanol (300 ml) is refluxed with heating for 2 hours. The catalyst is filtered off and ethanol is distilled off under reduced pressure. To the residue is added chloroform and the mixture is washed successively with saturated sodium hydrogen carbonate, water and saline solution. Further the mixture is dried with sodium sulfate and the solvent is distilled off. The resulting residue is purified by silica gel column chromatography (solvent: dichloromethane:methanol=20:1→5:1) to give 1-[1-{4-[3-(N-methylamino)propoxy]benzoyl}-4-piperidinyl]-3,4-dihydrocarbostyril (4.37 g).

This product is dissolved in acetone and converted into hydrochloride salt thereof in hydrochloric acid/ethanol. The precipitated crystal is collected by filtration and recrystallized from ethanol/acetone/diethyl ether to give 1-[1-{4-[3-(N-methylamino)propoxy]benzoyl}-4-piperidinyl]-3,4-dihydrocarbostyril hydrochloride as colorless needles, m.p.: 89°–93° C.

Example 411

1-[1-{4-[3-(Phthalimido-1-yl)propoxy]benzoyl}-4-piperidinyl]-3,4-dihydrocarbostyril (9.5 g), hydrazine hydrate (1.03 ml) and ethanol (100 ml) are refluxed with heating for 2.5 hours. After cooling, the mixture is adjusted to pH 1 by adding conc. hydrochloric acid and the precipitated materials are filtered off. Most of ethanol is distilled off from the filtrate and water is added to the residue. The insoluble materials are filtered off and the mother liquid is basified with 5N sodium hydroxide, extracted with ethyl acetate. The organic layer is washed with saturated saline solution and dried with sodium sulfate, concentrated. The residue is purified by silica gel column chromatography (solvent: methylene chloride:methanol=15:1) to give 1-{1-[4-(3-aminopropoxy)benzoyl]-4-piperidinyl}-3,4-dihydrocarbostyril (5.18 g).

NMR (CDCl$_3$) δ ppm: 1.64–2.10 (4H, m), 2.97–3.18 (8H, m), 2.92 (2H, t, J=6.8 Hz), 4.08 (2H, t, J=6.1 Hz), 4.10–5.15 (3H, m), 6.82–7.58 (8H, m)

Using the suitable starting materials, the compounds of the above Examples 136, 148, 154 and the following. Examples 473 and 586 are obtained in the same manners as in Example 411.

Example 412

1-{1-[4-(3-Aminopropoxy)benzoyl]-4-piperidinyl}-3,4-dihydrocarbostyril (0.5 g), methylisocyanate (0.15 ml) and acetone (10 ml) are heated at 100° C. for 18 hours in an autoclave. Acetone is distilled off and the residue is purified by silica gel column chromatography (solvent: methylene chloride:methanol=100–50:1) to give 1-{1-[4-(3-(3-methylureido)propoxy)benzoyl]-4-piperidinyl}-3,4-dihydrocarbostyril (0.19 g).

NMR (CDCl$_3$) δ ppm: 1.55–2.20 (4H, m), 2.49–3.50 (10H, m), 2.96 (3H, m), 3.90–5.13 (4H, m), 4.09 (2H, t, J=5.7 Hz), 6.90 (2H, d, J=8.7 Hz), 6.95–7.38 (4H, m), 7.43 (2H, d, J=8.7 Hz)

Example 413

A mixture of formic acid (0.19 ml) and acetic anhydride (0.4 ml) is stirred with heating at 50°–60° C. for 1.5 hour. Thereto is added 1-{1-[4-(4-aminobutoxy)benzoyl]-4-piperidinyl}-3,4-dihydrocarbostyril (0.6 g) at room temperature and the mixture is stirred at room temperature for 13 hours. The reaction mixture is poured into ice-water and extracted with ethyl acetate. The extract is washed with aqueous sodium hydrogen carbonate, water and saline solution and dried with sodium sulfate. The solvent is distilled off and the resulting residue is purified by silica gel column chromatography (solvent: dichloromethane:methanol=

50:1→25:1) to give 1-{1-[4-(4-formylaminobutoxy) benzoyl]-4-piperidinyl}-3,4-dihydrocarbostyril (0.49 g).

NMR (CDCl$_3$) δ ppm: 1.55–2.00 (6H, m), 2.45–3.48 (10H, m), 3.76–5.10 (3H, m), 3.99 (2H, t, J=5.7 Hz), 5.74–6.25 (1H, m), 6.78–7.53 (8H, m), 8.15 (1H, s)

Using the suitable starting materials, the compounds of the above Example 130 and the following Examples 488 and 508 are obtained in the same manners as in Example 413.

Example 414

1-[1-(4-Formylbenzoyl)-4-piperidinyl]-3,4-dihydrocarbostyril (500 mg) is dissolved in methanol (10 ml) and thereto is added sodium boron hydride (63 mg) under ice cooling and the mixture is stirred for 2 hours. The solvent is concentrated and the resulting residue is purified by silica gel column chromatography (solvent: n-hexane:ethyl acetate=2:1) and recrystallized from n-hexane/ethanol to give 1-[1-(4-hydroxymethylbenzoyl)-4-piperidinyl]-3,4-dihydrocarbostyril (390 mg) as white powder, m.p.: 138°–139° C.

Using the suitable starting materials, the compounds of the above Examples 83, 85 and the following Examples 444 and 456 are obtained in the same manners as in Example 414.

Example 415

60% Sodium hydride (147 mg) is washed with n-hexane and thereto is added dimethylformamide (10 ml) under argon atmosphere. To the mixture is added 1-[1-(4-trifluoroacetylaminobenzoyl)-4-piperidinyl]-3,4-dihydrocarbostyril (1 g) under ice cooling, and the mixture is stirred for a while and then thereto is added dropwise allyl bromide (0.32 ml). The mixture is stirred under ice cooling for 1 hour and then at room temperature overnight to give 1-{1-[4-(N-trifluoroacetyl-N-allylamino)benzoyl]-4-piperidinyl}-3,4-dihydrocarbostyril. To this product are added water (20 ml) and sodium hydroxide (0.1 g) and the mixture is stirred for 4 hours. The reaction mixture is poured into water and extracted with ethyl acetate/toluene (1:1), dried with sodium carbonate. The solvent is distilled off and the resulting residue is purified by silica gel column chromatography (solvent: n-hexane:ethyl acetate=1:1) to give 1-[1-(4-allylaminobenzoyl)-4-piperidinyl]-3,4-dihydrocarbostyril (0.5 g).

NMR (CDCl$_3$) δ ppm: 1.72–1.92 (2H, m), 2.52–3.12 (8H, m), 3.72–3.88 (2H, m), 4.07 (1H, brs), 4.15–4.76 (3H, m), 5.14–5.35 (2H, m), 5.83–6.04 (1H, m), 6.56–6.62 (2H, m), 6.98–7.37 (6H, m)

Example 416

1-[1-(2-Methoxy-4-methylthiobenzoyl)-4-piperidinyl]-3,4-dihydrocarbostyril (500 mg) is dissolved in methanol (10 ml) and thereto is added a solution of NaIO$_4$ (391 mg) in water (4 ml) and the mixture is stirred at room temperature overnight. The solvent is distilled off under reduced pressure, and water is added to the resulting residue. The mixture is extracted with chloroform, dried with magnesium sulfate. The solvent is distilled off and the resulting residue is purified by silica gel column chromatography (solvent: n-hexane:ethyl acetate=2:1) and recrystallized from n-hexane/ethanol to give 1-[1-(2-methoxy-4-methylsulfinylbenzoyl)-4-piperidinyl]-3,4-dihydrocarbostyril (0.31 g) as white powder, m.p.: 95°–98° C.

Using the suitable starting meterials, the compounds of the above Examples 51, 368 and the following Example 570 are obtained in the same manners as in Example 416.

Example 417

1-[1-(2-Methoxy-4-acetyloxybenzoyl)-4-piperidinyl]-3,4-dihydrocarbostyril (0.4 g) and sodium hydroxide (0.5 g) are dissolved in methanol (20 ml) and the mixture is stirred at room temperature for 1 hour. The solvent is concentrated and water is added to the residue, then the mixture is extracted with chloroform, dried with magnesium sulfate. The solvent is ditilled off and the resulting residue is purified by silica gel column chromatography (solvent: n-hexane:ethyl acetate=1:1) to give 1-[1-(2-methoxy-4-hydroxybenzoyl)-4-piperidinyl]-3,4-dihydrocarbostyril (0.3 g).

NMR (CDCl$_3$) δ ppm: 1.56–1.95 (2H, m), 2.43–3.23 (8H, m), 3.56–3.83 (1H, m), 3.67 (3H, d, J=9.3 Hz), 4.23–4.67 (1H, m), 4.86–5.05 (1H, m), 6.26–6.42 (2H, m), 6.96–7.35 (5H, m), 8.57–8.73 (1H, m)

Example 418

1-{1-[4-(2-Cyclohexenyloxy)benzoyl]-4-piperidinyl}-3,4-dihydrocarbostyril (200 mg) is dissolved in ethanol (5 ml) and thereto is added 10% palladium-carbon (50 mg). The mixture is stirred at room temperature under atmospheric pressure under hydrogen atmosphere. After the completion of the reaction, the catalyst is removed by filtration. The resulting filtrate is concentrated and purified by silica gel column chromatography (solvent: n-hexane:ethyl acetate=1:1) to give 1-[1-(4-cyclohexyloxybenzoyl)-4-piperidinyl]-3,4-dihydrocarbostyril (174 mg).

NMR (CDCl$_3$) δ ppm: 1.20–2.10 (12H, m), 2.44–3.13 (8H, m), 3.78–5.08 (4H, m), 6.90 (2H, d, J=8.7 Hz), 6.97–7.32 (4H, m), 7.40 (2H, d, J=8.7 Hz)

Example 419

1-[1-(4-Formylbenzoyl)-4-piperidinyl]-3,4-dihydrocarbostyril (1 g), hydroxylamine hydrochloride (580 mg) and sodium acetate (1.6 g) are dissolved in ethanol (20 ml) and water (10 ml) and the mixture is stirred at room temperature overnight. The solvent is concentrated and water is added to the residue. The mixture is extracted with chloroform, dried with sodium carbonate. The solvent is distilled off and the resulting residue is purified by silica gel column chromatography (solvent: n-hexane:ethyl acetate=1:2) and recrystallized from n-hexane/ethanol to give 1-[1-(4-hydroxyiminomethylbenzoyl)-4-piperidinyl]-3,4-dihydrocarbostyril (1 g) as white powder, m.p.: 222°–224° C.

Example 420

1-[1-(4-Aminobenzoyl)-4-piperidinyl]-3,4-dihydrocarbostyril (500 mg) and 2,5-dimethoxytetrahydrofuran (0.19 ml) are refluxed-with heating for 2 hours in acetic acid. The solvent is concentrated and the residue is purified by silica gel column chromatography (solvent: n-hexane:ethyl acetate=1:1) and recrystallized from n-hexane to give 1-{1-[4-(1-pyrrolyl)benzoyl]-4-piperidinyl}-3,4-dihydrocarbostyril (228 mg) as light gray powder, m.p.: 153°–156° C.

Example 421

1-[1-(4-Glycidoxybenzoyl)-4-piperidinyl]-3,4-dihydrocarbostyril (200 mg) is dissolved in methanol (4 ml) and thereto is added diethylamine (0.26 ml) and the mixture is stirred at room temperature overnight, and then refluxed with heating for 3 hours. The solvent is concentrated and the residue is purified by silica gel column chromatography (solvent: n-hexane:ethyl acetate=1:1→dichloromethane:methanol=10:1) to give 1-{1-[4-(3-diethylamino-2-hydroxypropoxy)benzoyl]-4-piperidinyl}-3,4-dihydrocarbostyril (0.18 g).

This product is stirred with the equivalent amount of citric acid in diethyl ether to give citrate salt thereof as white powder, m.p.: 72°–76° C. (recrystallized from diethyl ether).

Using the suitable starting materials, the compounds of the above Examples 118, 119, 335 and the following Examples 448, 474A, 489, 532–535, 537, 538, 541–558, 562–567 are obtained in the same manners as in Example 421.

Example 422

1-[1-(4-Cyanobenzoyl)-4-piperidinyl]-3,4-dihydrocarbostyril (1 g) is dissolved in chloroform (10 ml) and thereto is added ethanol (0.18 ml). Under ice cooling, hydrochloric acid gas is passed through the mixture to saturate and further the mixture is stirred at 5°–7° C. for 4 days. After the reaction, the solvent is concentrated to give 1-{1-[4-(1-ethoxy-1-iminomethyl)benzoyl]-4-piperidinyl}-3,4-dihydrocarbostyril (1 g). This product is used for the subsequent reaction.

1-{1-[4-(1-Ethoxy-1-iminomethyl)benzoyl]-4-piperidinyl}-3,4-dihydrocarbostyril (1 g) is dissolved in methanol (10 ml) and thereto is added aqueous ammonia (10 ml) and the mixture is stirred at room temperature overnight. The solvent is concentrated and water is added to the residue. The mixture is extracted with chloroform, dried with sodium carbonate, concentrated and then purified by silica gel column chromatography (solvent: chloroform:methanol=10:1) and recrystallized from ethanol/n-hexane to give 1-[1-(4-carbamoyl-4-piperidinyl]-3,4-dihydrocarbostyril (0.2 g) as white powder, m.p.: 101°–104° C.

Further, the aqueous layer is concentrated and the resulting residue is recrystallized from water to give 1-[1-(4-amidinobenzoyl)-4-piperidinyl]-3,4-dihydrocarbostyril (0.4 g) as white powder, m.p.: 92°–97° C.

NMR (CDCl$_3$) δ ppm: 1.55–1.92 (2H, m), 2.32–3.05 (7H, m), 3.12–3.62 (2H, m), 4.22–4.72 (2H, m), 6.92–7.38 (4H, m), 7.63 (2H, d, J=8.2 Hz), 7.92 (2H, d, J=8.2 Hz), 9.48 (3H, brs)

Using the suitable starting materials, the compound of the above Example 113 is obtained in the same manners as in Example 422.

Example 423

1-{1-[4-(4-Pentenyloxy)benzoyl]-4-piperidinyl}-3,4-dihydrocarbostyril (2 g) is dissolved in dichloromethane (50 ml) and thereto is added gradually m-chloroperbenzoic acid (1.6 g) at room temperature. The mixture is stirred under the same conditions overnight and the reaction mixture is poured into aqueous sodium hydrogen carbonate solution and the mixture is extracted with chloroform and dried with magnesium sulfate. The solvent is distilled off and the resulting residue is purified by silica gel column chromatography (solvent: n-hexane:ethyl acetate=1:1) to give 1-{1-[4-(3-oxiranylpropoxy)benzoyl]-4-piperidinyl}-3,4-dihydrocarbostyril (1.5 g).

NMR (CDCl$_3$) δ ppm: 1.52–2.10 (6H, m), 2.45–3.10 (11H, m), 3.72–5.10 (5H, m), 6.90 (2H, d, J=8.7 Hz), 6.97–7.32 (4H, m), 7.43 (2H, d, J=8.7 Hz)

Using the suitable starting materials, the compounds of the above Example 333 and the following Example 572 are obtained in the same manners as in Example 423.

Example 424

1-[1-(4-Formylbenzoyl)-4-piperidinyl]-3,4-dihydrocarbostyril (4.77 g) is dissolved in methanol (100 ml) and thereto is added carbomethoxymethylenetriphenylphosphorane (5.3 g) and the mixture is stirred at room temperature for 1 hour. The solvent is concentrated and the residue is purified roughly by silica gel column chromatography (solvent: n-hexane:ethyl acetate=1:1) to give a mixture (8 g) of 1-{1-[4-(2-methoxycarbonylvinyl)benzoyl]-4-piperidinyl}-3,4-dihydrocarbostyril and triphenylphosphineoxide.

This mixture is dissolved in ethanol (100 ml) and thereto is added 10% palladium-carbon (1 g). The mixture is stirred at room temperature under 1 atm. under hydrogen atmosphere. After the reaction, the catalyst is removed by filtration and the resulting filtrate is concentrated. The resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl}-3,4-dihydrocarbostyril (3 g) as white powder, m.p.: 85°–86° C.

Using the suitable starting materials, the compounds of the above Examples 220, 336 and 339 are obtained in the same manners as in Example 424.

Example 425

To a mixture of propyltriphenylphosphonium bromide (2.34 g), potassium-t-butoxide (62 mg) and sodium amide powder (0.3 g) is added tetrahydrofuran (110 ml) under argon atmosphere and the mixture is stirred at room temperature for 3 hours. To the resulting yellowish red solution is added 1-[1-(4-formylbenzoyl)-4-piperidinyl]-3,4-dihydrocarbostyril (2 g) gradually under ice cooling and the mixture is stirred under the same conditions for 3 hours. The reaction mixture is poured into water and extracted with ethyl acetate/toluene and then dried over sodium carbonate. The resultant is purified by silica gel column chromatography (solvent: n-hexane:ethyl acetate=1:1) to give 1-{1-[4-(1-butenyl)benzoyl]-4-piperidinyl}-3,4-dihydrocarbostyril (2 g).

NMR (CDCl$_3$) δ ppm: 1.05–1.33 (3H, m), 1.66–2.02 (2H, m), 2.30–3.26 (10H, m), 3.85–5.13 (3H, m), 5.69–5.83, 6.35–6.75 (2H, m), 7.02–7.54 (8H, m)

Example 426

Ethanethiol (0.125 ml) is dissolved in methanol (10 ml) and thereto is added sodium methoxide (0.11 g). The mixture is stirred at room temperature for 30 minutes. Thereto is added a solution of 1-{1-[4-(3-bromopropoxy)benzoyl]-4-piperidinyl}-3,4-dihydrocarbostyril (0.59 g) in methanol (2 ml) and the mixture is stirred at room temperature overnight. The solvent is concentrated and water is added to the residue, extracted with chloroform, dried with sodium carbonate. The solvent is distilled off and the resulting residue is purified by silica gel column chromatography (solvent: n-hexane:ethyl acetate=1:1) to give 1-{1-[4-(3-ethylthiopropoxy)benzoyl]-4-piperidinyl}-3,4-dihydrocarbostyril (0.2 g).

NMR (CDCl$_3$) δ ppm: 1.27 (3H, t, J=7.4 Hz), 1.68–1.92 (2H, m), 1.98–2.18 (2H, m), 2.45–3.14 (10H, m), 3.70–5.15 (3H, m), 4.10 (2H, t, J=6.1 Hz), 6.91 (2H, d, J=8.6 Hz), 6.99–7.32 (4H, m), 7.43 (2H, d, J=8.6 Hz)

Using the suitable starting materials, the compounds of the above Example 40, 55, 56, 66, 114, 115, 129, 132, 133, 135, 136, 137–141, 143, 145, 146, 147, 148, 153–155, 234, 235, 241–243, 246, 249, 250, 251, 255, 261, 262, 268–270, 276, 294, 300, 305–307, 309, 311, 317–319, 321, 322, 325–327, 332, 367, 383A–383C and the following Examples 445, 449–459, 466–469, 471–473, 488–496, 498–531, 539–540, 559–560, 569, 585–587 are obtained in the same manners as in Example 426.

Example 427

1-[1-(4-Vinylbenzoyl)-4-piperidinyl]-3,4-dihydrocarbostyril (0.6 g) is dissolved in ethanol (10 ml) and thereto is added 10% palladium-carbon (0.1 g) and the mixture is stirred under hydrogen atmosphere. After the reaction, the catalyst is removed by filtration and the filtrate is concentrated. The resultant is purified by silica gel column chromatography (solvent: n-hexane:ethyl acetate=1:1) and recrystallized from n-hexane/ethanol to give 1-[1-(4-ethylbenzoyl)-4-piperidinyl]-3,4-dihydrocarbostyril (0.5 g) as white powder, m.p.: 133°–134° C.

Using the suitable starting materials, the compounds of the above Examples 69, 220 and 339 are obtained in the same manners as in Example 427.

Example 428

1-[1-(4-Allyloxybenzoyl)-4-piperidinyl]-3,4-dihydrocarbostyril (1.15 g) is dissolved in N,N-dimethylaniline (5 ml) and the mixture is heated at 180°–190° C. for 8 hours. After cooling, the reaction mixture is adjusted to around pH 4 by adding hydrochloric acid thereto. The mixture is extracted with dichloromethane and dried with magnesium sulfate. The solvent is distilled off and the residue is purified by silica gel column chromatography (solvent: n-hexane:ethyl acetate=3:1→1:3) and further purified by silica gel column chromatography (solvent: dichloromethane:methanol=100:1) and recrystallized from dichloromethane/n-hexane to give 1-[1-(4-hydroxy-3-allylbenzoyl)-4-piperidinyl]-3,4-dihydrocarbostyril (0.22 g) as white powder, m.p.: 87°–90° C.

Using the suitable starting materials, the compound of the above Example 282 is obtained in the same manners as in Example 428.

Example 429

To a solution of 1-(4-aminophenyl)-3,4-dihydrocarbostyril (0.45 g) in dichloromethane (15 ml) is added triethylamine (0.29 g). Thereto is added 2,4-dimethoxybenzoyl chloride (0.42 g) with stirring under ice cooling. The mixture is refluxed with heating for 0.5 hour. After cooling, water is added thereto and the mixture is extracted with dichloromethane, washed with water and then dried with magnesium sulfate. The solvent is distilled off under reduced pressure and the residue is purified by silica gel column chromatography and recrystallized from ethanol/diethyl ether/n-hexane to give 1-[4-(2,4-dimethoxybenzoylamino)phenyl]-3,4-dihydrocarbostyril (0.44 g) as white powder, m.p.: 226°–227° C.

Using the suitable starting materials, the compound of the above Example 292 is obtained in the same manners as in Example 429.

Example 430

To a solution of 1-[4-(4-methoxyanilinocarbonyl)phenyl]-3,4-dihydrocarbostyril (0.2 g) in dimethylformamide (15 ml) is added 60% sodium hydride (24 mg) with stirring under ice cooling and the mixture is stirred at room temperature for 0.5 hour. Then, thereto is added a solution of ethyl bromide (64 mg) in dimethylformamide (DMF, 1 ml) and the mixture is refluxed with heating for 1 hour. DMF is distilled off under reduced pressure and water is added to the residue and the mixture is extracted with dichloromethane. The extract is washed with water and dried with magnesium sulfate. The solvent is distilled off under reduced pressure and the resulting residue is purified by silica gel column chromatography to give 1-[4-(N-ethyl-4-methoxyanilinocarbonyl)phenyl]-3,4-dihydrocarbostyril (0.12 g).

NMR (CDCl$_3$) δ ppm: 2.76 (3H, t, J=8.1 Hz), 3.0 (3H, t, J=8 Hz), 3.48 (3H, s), 3.75 (3H, s), 6.19 (1H, dd, J=3.1 Hz, 6 Hz), 6.78 (2H, d, J=8.3 Hz), 6.9–7.2 (7H, m), 7.43 (2H, d, J=8.4 Hz)

Example 431

To a solution of 1-[4-(2,4-dimethoxybenzoylamino)phenyl]-3,4-dihydrocarbostyril (0.19 g) in dimethylformamide (8 ml) is added with stirring 60% sodium hydride (0.02 g) under ice cooling. The mixture is stirred at room temperature for 0.5 hour and thereto is added a solution of methyl iodide (0.08 g) in dimethylformamide (6 ml). The mixture is stirred at room temperature for 3 hours. The solvent is distilled off under reduced pressure and water is added to the residue. The mixture is extracted with dichloromethane, washed with water and dried with magnesium sulfate. The solvent is distilled off under reduced pressure and the resulting residue is purified by silica gel column chromatography to give 1-{4-[N-(2,4-dimethoxybenzoyl)-N-methylamino]phenyl}-3,4-dihydrocarbostyril (70 mg).

NMR (CDCl$_3$) δ ppm: 2.78 (3H, t, J=8 Hz), 3.04 (3H, t, J=8 Hz), 3.50 (3H, s), 3.59 (3H, s), 3.76 (3H, s), 6.0–6.1 (1H, m), 6.2 (1H, brs), 6.41 (1H, dd, J=2.3 Hz, 8.4 Hz), 6.9–7.1 (4H, m), 7.1–7.3 (4H, m)

Using the suitable starting materials, the compounds of the above Examples 245, 236, 237, 172, 292 and 347 are obtained in the same manners as in Examples 430 and 431.

Example 432

To a solution of 1-(4-carboxyphenyl)-3,4-dihydrocarbostyril (0.2 g) in chloroform (5 ml) is added thionyl chloride (0.8 ml) and the mixture is refluxed with heating for 1 hour. Then, chloroform and thionyl chloride are distilled off under reduced pressure to give 4-(3,4-dihydrocarbostyril-1-yl)benzoic acid chloride.

To a solution of p-anisidine (0.11 g) in chloroform (5 ml) is added triethylamine (0.15 g) and thereto is added with stirring a solution of 4-(3,4-dihydrocarbostyril-1-yl)benzoic acid chloride obtained above in chloroform (2 ml) under ice cooling. The mixture is stirred at room temperature overnight. Water is added to the reaction mixture and the mixture is extracted with dichloromethane, washed with water and dried with magnesium sulfate. The solvent is distilled off under reduced pressure and the resulting residue is crystallized from diethyl ether and further recrystallized from ethanol/diethyl ether/n-hexane to give 1-[4-(4-methoxyanilinocarbonyl)phenyl]-3,4-dihydrocarbostyril (240 mg) as white powder, m.p.: 254°–255° C.

Using the suitable starting materials, the compounds of the above Examples 172, 183–186, 233, 236–240, 244, 245 and 347 are obtained in the same manners as in Example 432.

Example 433

To a solution of 1-[4-(1-piperazinylcarbonyl)phenyl]-3,4-dihydrocarbostyril (0.15 g) in dichloromethane (20 ml) is added triethylamine (91 mg), and further thereto is added with stirring a solution of benzoyl chloride (69 mg) in dichloromethane (2 ml) under ice cooling and the mixture is stirred at room temperature for 1 hour. Water is added thereto and the mixture is extracted with dichloromethane, dried with magnesium sulfate. The solvent is distilled off under reduced pressure and the resulting residue is crystallized by adding diethyl ether and n-hexane. The precipitated crystal is recrystallized from ethanol/diethyl ether/n-hexane to give 1-[4-(4-benzoyl-1-piperazinyl)phenyl]-3,4-dihydrocarbostyril (0.16 g) as white powder, m.p.: 188°–189° C.

Using the suitable starting materials, the compound of the above Example 240 is obtained in the same manners as in Example 433.

Example 434

1-{1-[4-(2-Carboxyethyl)benzoyl]-4-piperidinyl}-3,4-dihydrocarbostyril (2 g) is dissolved in methanol (50 ml) and thereto is added dropwise thionyl chloride (1.1 ml) under ice cooling. After adding, the mixture is stirred at 0°–5° C. for 1 hour and further at room temperature overnight. The solvent is concentrated and the resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl}-3,4-dihyrocarbostyril (1.46 g) as white powder, m.p.: 85°–86° C.

Using the suitable starting materials, the compounds of the above Examples 49, 111, 112, 123, 127, 181, 213, 264, 274, 297, 299, 302, 306, 311, 320, 322, 323, 327, 328 and 342 are obtained in the same manners as in Example 434.

Using the suitable starting materials, the following compounds are obtained in the same manners as in Examples 1 and 384.

TABLE 3

(general structure with $(R^1)_q$, N-R, carbostyril)

Example 435

Structure

R: piperidine-NH $R^1$: F (6-, 7-positions), q: 2
Bond between 3- and 4-positions in the carbostyril ring: Single bond
NMR analysis: 210)
Form: Free Example 436

Structure

R: piperidine-N–C(=O)–phenyl(OCH₃)(OC₂H₅)

$R^1$: F (6-, 7-positions), q: 2
Bond between 3- and 4-positions in the carbostyril ring: Single bond
Crystalline form: White powders
Recrystallization solvent: Ethanol
Melting point: 135–136° C.
Form: Free Example 437

Structure

R: piperidine-NH $R^1$: F (5-, 7-positions), q: 2
Bond between 3- and 4-positions in the carbostyril ring: Single bond
Crystalline form: White powders
Recrystallization solvent: Ethanol
Melting point: 137–140° C.
Form: Free Example 438

Structure

R: piperidine-N–C(=O)–phenyl(OCH₃)(OC₂H₅)

$R^1$: F (5-, 7-positions, q: 2
Bond between 3- and 4-positions in the carbostyril ring: Single bond
Crystalline form: White powders
Recrystallization solvent: Ethanol
Melting point: 178–180° C.
Form: Free Example 439

Structure

R: piperidine-NH $R^1$: CH₃ (3-position), q: 1
Bond between 3- and 4-positions in the carbostyril ring: Single bond
NMR analysis: 211)
Form: Free Example 440

Structure

R: piperidine-N–C(=O)–phenyl(OCH₃)(OC₂H₅)

TABLE 3-continued

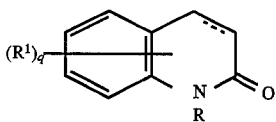

R¹: CH₃ (3-position), q: 1
Bond between 3- and 4-positions in the carbostyril ring: Single bond
NMR analysis: 212)
Form: Free Example 441

Structure

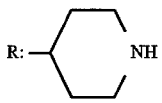

R¹: CO₂C₂H₅ (3-position), q: 1
Bond between 3- and 4-positions in the carbostyril ring: Single bond
NMR analysis: 213)
Form: Free Example 442

Structure

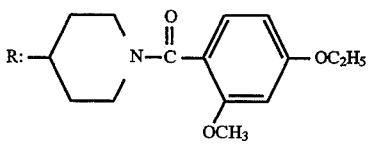

R¹: CO₂C₂H₅ (3-position), q: 1
Bond between 3- and 4-positions in the carbostyril ring: Single bond
NMR analysis: 214)
Form: Free Example 443

Structure

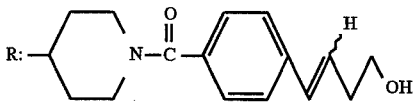

R¹: H, q: 1
Bond between 3- and 4-positions in the carbostyril ring: Double bond
NMR analysis: 215)
Form: Free Example 444

Structure

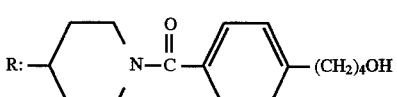

R¹: H, q: 1
Bond between 3- and 4-positions in the carbostyril ring: Single bond
Crystalline form: White powders
Recrystallization solvent: Ethanol/n-hexane
Melting point: 140–143° C.
Form: Free TABLE 3-continued

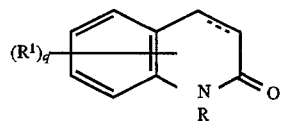

Example 445

Structure

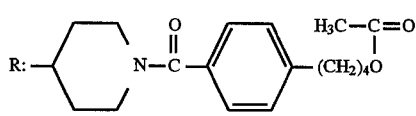

R¹: H, q: 1
Bond between 3- and 4-positions in the carbostyril ring: Single bond
NMR analysis: 216)
Form: Free Example 446

Structure

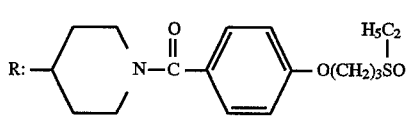

R¹: H, q: 1
Bond between 3- and 4-positions in the carbostyril ring: Single bond
NMR analysis: 217)
Form: Free Example 447

Structure

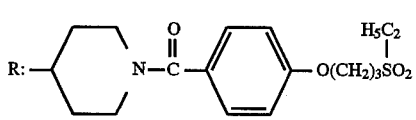

R¹: H, q: 1
Bond between 3- and 4-positions in the carbostyril ring: Single bond
NMR analysis: 218)
Form: Free Example 448

Structure

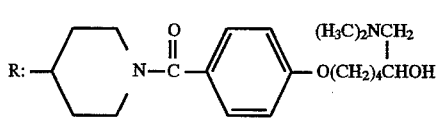

R¹: H, q: 1
Bond between 3- and 4-positions in the carbostyril ring: Single bond
NMR analysis: 219)
Form: Free

TABLE 3-continued

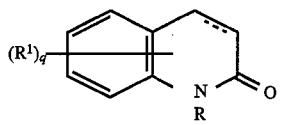

Example 449

Structure

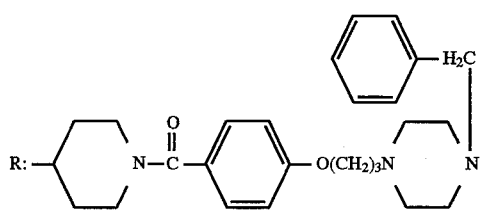

$R^1$: H, q: 1
Bond between 3- and 4-positions in the
carbostyril ring: Single bond
Crystalline form: White powders
Recrystallization solvent: Ethanol/water
Melting point: 208–210° C.
Form: Dioxalate

Example 450

Structure

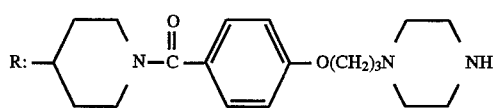

$R^1$: H, q: 1
Bond between 3- and 4-positions in the
carbostyril ring: Single bond
Crystalline form: Light yellow powders
Recrystallization solvent: n-Hexane/diethyl ether
Melting point: 64–68° C.
Form: Dihydrochloride.trihydrate

Example 451

Structure

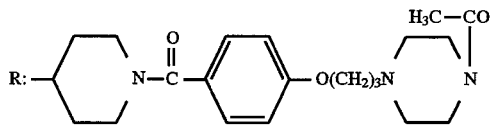

$R^1$: H, q: 1
Bond between 3- and 4-positions in the
carbostyril ring: Single bond
NMR analysis: 220)
Form: Free

Example 452

Structure

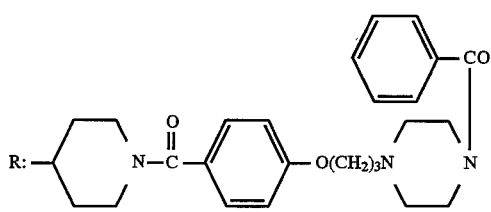

$R^1$H, q: 1
Bond between 3- and 4-positions in the
carbostyril ring: Single bond
NMR analysis: 221)
Form: Free

Example 453

Structure

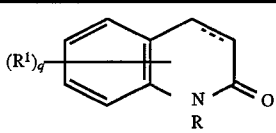

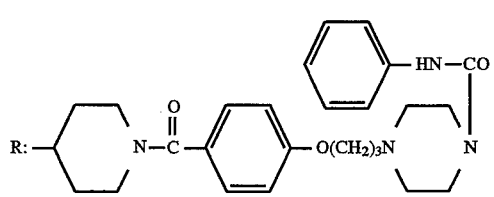

$R^1$: H, q: 1
Bond between 3- and 4-positions in the
carbostyril ring: Single bond
NMR analysis: 222)
Form: Free

Example 454

Structure

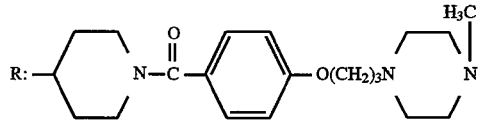

$R^1$: H, q: 1
Bond between 3- and 4-positions in the
carbostyril ring: Single bond
Crystalline form: White powders
Recrystallization solvent: Ethanol/water
Melting point: 214–217° C.
Form: Dioxalate

Example 455

Structure

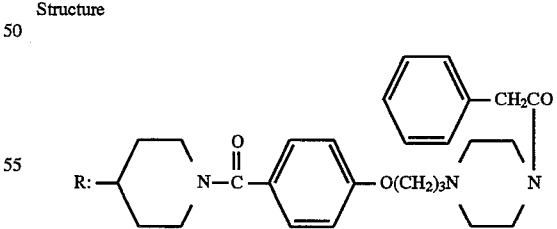

$R^1$: H, q: 1
Bond between 3- and 4-positions in the
carbostyril ring: Single bond
Crystalline form: White powders
Recrystallization solvent: Ethanol/water
Melting point: 208–211° C. (decomposed)
Form: Dioxalate TABLE 3-continued

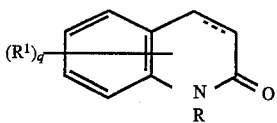

Example 456

Structure

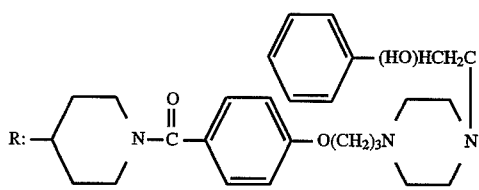

R[1]: H, q: 1
Bond between 3- and 4-positions in the
carbostyril ring: Single bond
Crystalline form: White powders
Recrystallization solvent: Ethanol/water
Melting point: 206–210° C.
Form: Dioxalate

Example 457

Structure

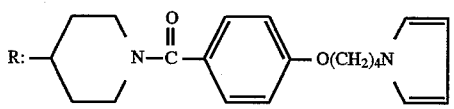

R[1]: H, q: 1
Bond between 3- and 4-positions in the
carbostyril ring: Single bond
NMR analysis: 223)
Form: Free

Example 458

Structure

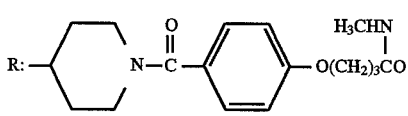

R[1]: H, q: 1
Bond between 3- and 4-positions in the
carbostyril ring: Single bond
NMR analysis: 224)
Form: Free

Example 459

Structure

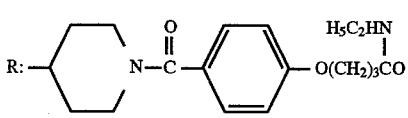

R[1]: H, q: 1
Bond between 3- and 4-positions in the
carbostyril ring: Single bond
NMR analysis: 225)
Form: Free TABLE 3-continued

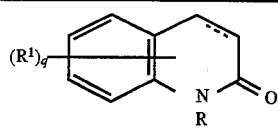

Example 460

Structure

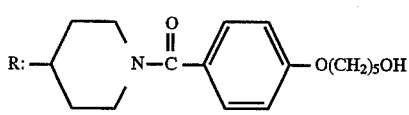

R[1]: H, q: 1
Bond between 3- and 4-positions in the
carbostyril ring: Single bond
Crystalline form: Colorless needles
Recrystallization solvent: Ethanol/diethyl ether
Melting point: 123–125° C.
Form: Free

Example 461

Structure

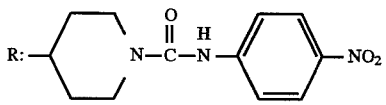

R[1]: H, q: 1
Bond between 3- and 4-positions in the
carbostyril ring: Single bond
Crystalline form: Light yellow needles
Recrystallization solvent: Ethanol/chloroform
Melting point: 194–196° C.
Form: Free

Example 462

Structure

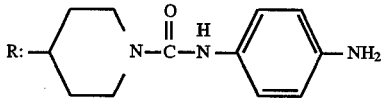

R[1]: H, q: 1
Bond between 3- and 4-positions in the
carbostyril ring: Single bond
NMR analysis: 226)
Form: Free

Example 463

Structure

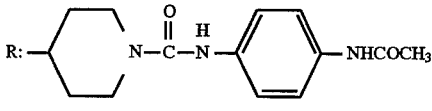

R[1]: H, q: 1
Bond between 3- and 4-positions in the
carbostyril ring: Single bond
Crystalline form: Colorless prisms
Recrystallization solvent: Ethanol
Melting point: 249–252° C.
Form: Free TABLE 3-continued

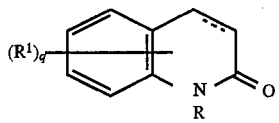

Example 464

Structure

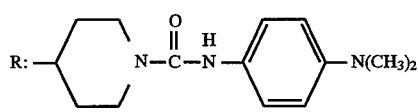

R¹: H, q: 1
Bond between 3- and 4-positions in the
carbostyril ring: Single bond
Crystalline form: Colorless prisms
Recrystallization solvent: Methanol
Melting point: 107–110° C.
Form: Free Example 465

Structure

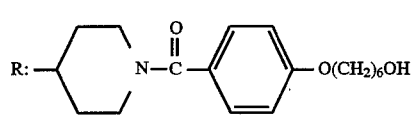

R¹: H, q: 1
Bond between 3- and 4-positions in the
carbostyril ring: Single bond
Crystalline form: Colorless needles
Recrystallization solvent: Ethanol/diethyl ether
Melting point: 120–122° C.
Form: Free Example 466

Structure

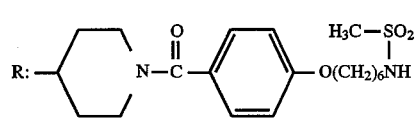

R¹: H, q: 1
Bond between 3- and 4-positions in the
carbostyril ring: Single bond
NMR analysis: 227)
Form: Free Example 467

Structure

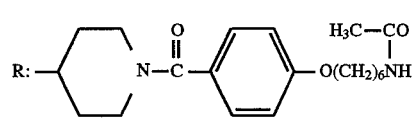

R¹: H, q: 1
Bond between 3- and 4-positions in the
carbostyril ring: Single bond
NMR analysis: 228)
Form: Free TABLE 3-continued

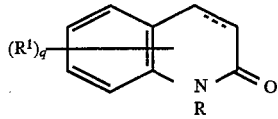

Example 468

Structure

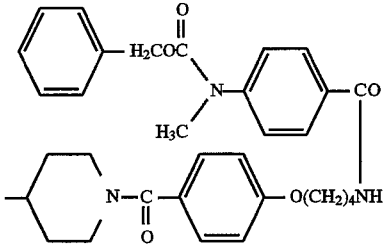

R¹: H, q: 1
Bond between 3- and 4-positions in the
carbostyril ring: Single bond
NMR analysis: 229)
Form: Free Example 469

Structure

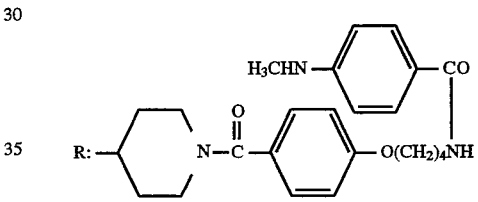

R¹: H, q: 1
Bond between 3- and 4-positions in the
carbostyril ring: Single bond
NMR analysis: 230)
Form: Free Example 470

Structure

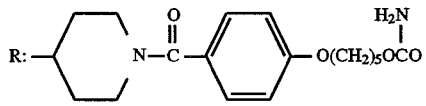

R¹: H, q: 1
Bond between 3- and 4-positions in the
carbostyril ring: Single bond
NMR analysis: 231)
Form: Free Example 471

Structure

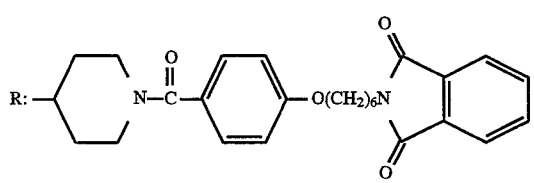

TABLE 3-continued

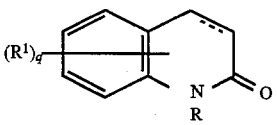

R¹: H, q: 1
Bond between 3- and 4-positions in the carbostyril ring: Single bond
NMR analysis: 232)
Form: Free Example 472

Structure

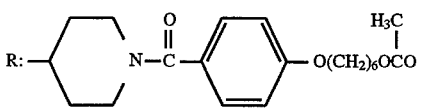

R¹: H, q: 1
Bond between 3- and 4-positions in the carbostyril ring: Single bond
NMR analysis: 233)
Form: Free Example 473

Structure

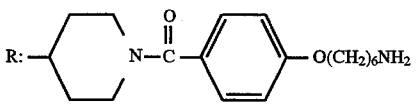

R¹: H, q: 1
Bond between 3- and 4-positions in the carbostyril ring: Single bond
NMR analysis: 234)
Form: Free Example 474

Structure

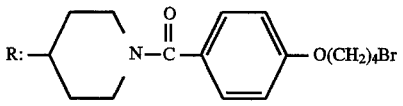

R¹: H, q: 1
Bond between 3- and 4-positions in the carbostyril ring: Single bond
NMR analysis: 235)
Form: Free Example 474A Structure

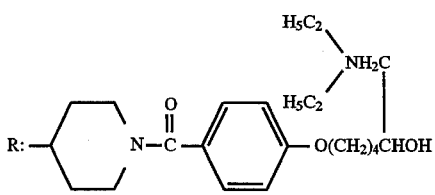

R¹: H, q: 1
Bond between 3- and 4-positions in the carbostyril ring: Single bond
NMR analysis: 236)
Form: Free

TABLE 4

| No. | NMR (CDCl$_3$) δ value |
|---|---|
| 210 | 1.60(1H, s), 1.68–1.85(2H, m), 2.35–2.92(8H, m) 3.15–3.32(2H, 4.18–4.40(1H, m), 6.86–7.18 (2H, m) |
| 211 | 1.21(3H, d, J=6.5Hz), 1.60–2.00(3H, m), 2.35–2.95(8H, m), 3.14–3.37(2H, m), 4.28–4.50(1H, m) 6.95–7.32(4H, m) |
| 212 | 1.21(3H, d, J=6.5Hz), 1.42(3H, t, J=7.0Hz), 1.62–2.04(2H, m), 2.30–3.28(7H, m), 3.55–3.95 (4H, m), 4.04(2H, q, J=7.0Hz), 4.25–5.10(2H, m) 6.38–6.60(2H, m), 6.98–7.40(5H, m) |
| 213 | 1.18(3H, t, J=7.1Hz), 1.50–1.88(3H, m), 2.50–3.46(9H, m), 3.60–3.62(2H, m), 4.03–4.28(2H, m), 4.47–4.60(1H, m), 6.95–7.30(4H, m) |
| 214 | 1.17(3H, t, J=7.1Hz), 1.42(3H, t, J=7.0Hz), 1.56–2.00(2H, m), 2.38–3.35(6H, m), 3.42–5.10 (11H, m), 6.37–6.60(2H, m), 6.95–7.40(5H, m) |
| 215 | 1.58–1.97(2H, m), 2.43–3.20(10H, m), 3.65–5.12 (5H, m), 5.68–5.84, 6.18–6.36(total: 1H, m), 6.51(1H, d, J=15.9Hz), 6.46–7.49(8H, m) |
| 216 | 1.56–1.98(6H, m), 2.05(3H, s), 2.52–3.21(10H, m) 3.76–5.08(5H, m), 6.98–7.43(8H, m) |
| 217 | 1.44(3H, t, J=7.5Hz), 1.68–1.97(2H, m), 2.28–3.17(10H, m), 3.05(2H, q, J=7.5Hz), 3.20(2H, t, J=7.4Hz), 3.78–5.13(3H, m), 4.15(2H, t, J=5.7 Hz), 6.86–7.49(8H, m) |
| 218 | 1.44(3H, t, J=7.5Hz), 1.68–1.97(2H, m), 2.28–3.17(10H, m), 3.05(2H, q, J=7.5Hz), 3.20(2H, t, J=7.4Hz), 3.78–5.13(3H, m), 4.15(2H, t, J=5.7 Hz), 6.86–7.49(8H, m) |
| 219 | 1.34–1.93(8H, m), 2.17–2.42(2H, m), 2.31(6H, s), 2.51–3.04(9H, m), 3.62–5.07(6H, m), 6.86–6.95 (2H, m), 6.97–7.32(4H, m), 7.36–7.48(2H, m) |
| 220 | 1.68–2.18(4H, m), 2.09(3H, s), 3.28–3.13(14H, m), 3.43–3.72(4H, m), 3.86–5.08(5H, m), 6.85–7.50 (8H, m) |
| 221 | 1.70–2.08(4H, m), 2.34–3.12(14H, m), 3.34–5.04 (9H, m), 6.88–7.52(8H, m), 7.40(5H, s) |
| 222 | 1.72–2.14(4H, m), 2.40–3.14(14H, m), 3.43–3.60 (4H, m), 3.73–5.13(5H, m), 6.47(1H, brs), 6.88–7.48(13H, m) |
| 223 | 1.71–2.15(6H, m), 2.46–3.20(8H, m), 3.80–5.15 (2H, m), 3.96(4H, t, J=6.8Hz), 4.39(1H, m), 6.15 (2H, t, J=2.1Hz), 6.67(2H, t, J=2.1Hz), 6.88 (2H, d, J=8.7Hz), 6.99–7.28(4H, m), 7.42(2H, d, J=8.7Hz) |
| 224 | 1.60–1.98(2H, m), 2.11(2H, quint, J=6.5Hz), 2.36 (2H, t, J=6.5Hz), 2.53–3.15(8H, m), 2.78(3H, d, J=4.8Hz), 3.60–5.10(2H, brs), 4.00(2H, t, J=6.5 Hz), 4.36(1H, m), 6.16(1H, brs), 6.88(2H, d, J= 8.7Hz), 6.99–7.29(4H, m), 7.41(2H, d, J=8.7Hz) |
| 225 | 1.33(3H, t, J=6.8Hz), 1.65–1.94(2H, m), 2.14 (2H, quint, J=6.6Hz), 2.37(2H, t, J=6.6Hz), 2.46–3.12(8H, m), 3.80–5.00(2H, m), 4.03(2H, t, J=6.6Hz), 4.05(2H, q, J=6.8Hz), 4.38(1H, m), 5.69(1H, brs), 6.90(2H, d, J=8.6Hz), 6.98–7.30 (4H, m), 7.42(2H, d, J=8.6Hz) |
| 226 | 1.63–1.92(2H, m), 2.40–3.80(10H, m), 4.08–4.55 (3H, m), 6.41(1H, brs), 6.52–6.75(2H, m), 6.92–7.35(6H, m), |
| 227 | 1.31–2.02(10H, m), 2.47–3.25(10H, m), 2.95(3H, s), 3.98(2H, t, J=6.3Hz), 4.04–5.05(4H, m), 6.89 (2H, d, J=8.8Hz), 6.95–7.37(4H, m), 7.42(2H, d, J=8.8Hz), |
| 228 | 1.25–2.18(13H, m), 2.45–3.40(10H, m), 3.97(2H, t, J=6.4Hz), 4.05–5.07(3H, m), 5.79(1H, brs), 6.89(2H, d, J=8.7Hz), 6.95–7.37(4H, m), 7.42 (2H, d, J=8.7Hz) |
| 229 | 1.60–2.05(6H, m), 2.43–3.15(8H, m), 3.34(3H, s), 3.49–3.63(2H, m), 3.82–5.05(5H, m), 5.17(2H, s), 6.50(1H, brs), 6.88(2H, d, J=8.6Hz), 6.94–7.49 (13H, m), 7.74(2H, d, J=8.6Hz) |
| 230 | 1.60–2.07(6H, m), 2.42–3.18(11H, m), 3.35–3.62 (2H, m), 3.80–5.09(6H, m), 6.20–6.45(1H, m), 6.54 (2H, d, J=8.7Hz), 6.88(2H, d, J=8.7Hz), 6.94–7.35(4H, m), 7.40(2H, d, J=8.7Hz), 7.63(2H, d, J=8.7Hz) |

TABLE 4-continued

| No. | NMR (CDCl₃) δ value |
|---|---|
| 231 | 1.45–1.99(8H, m), 2.48–3.18(8H, m), 3.99(2H, t, J=6.3Hz), 4.10(2H, t, J=6.3Hz), 4.17–5.08(5H, m), 6.82–7.54(8H, m) |
| 232 | 1.27–1.99(10H, m), 2.40–3.15(8H, m), 3.70(2H, t, J=7Hz), 3.97(2H, t, J=6.3Hz), 4.08–5.10(3H, m), 6.29–7.96(12H, m) |
| 233 | 1.26–1.95(10H, m), 2.05(3H, s), 2.45–3.18(8H, m), 3.87–5.08(7H, m), 6.82–7.52(8H, m) |
| 234 | 1.25–2.03(12H, m), 2.45–3.26(10H, m), 3.98(2H, t, J=6.4Hz), 4.08–5.11(3H, m), 6.90(2H, d, J=8.8 Hz), 6.90–7.39(4H, m), 7.42(2H, d, J=8.8Hz) |
| 235 | 1.63–2.22(6H, m), 2.47–3.18(8H, m), 3.63(2H, t, J=6.6Hz), 3.94–5.04(5H, m), 6.82–7.52(8H, m) |
| 236 | 1.11(6H, t, J=7.2Hz), 1.35–1.96(8H, m), 2.32–3.13(14H, m), 3.58–5.07(5H, m), 4.00(2H, t, J=6.3Hz), 6.83–6.95(2H, m), 6.98–7.32(4H, m), 7.35–7.48(2H, m), |

The following compound is obtained in the same manners as in Examples 1 and 385.

TABLE 5

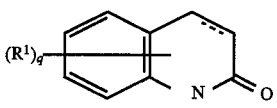

Example 475

Structure

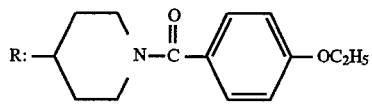

R¹: H, q: 1
Bond between 3- and 4-positions in the carbostyril ring: Double bond
Crystalline form: Colorless needles
Recrystallization solvent: Ethanol/diethyl ether
Melting point: 144–146° C.
Form: Free Example 476

To a solution of 1-{1-[4-(3-ethylthiopropoxy)benzoyl]-4-piperidinyl}-3,4-dihydrocarbostyril (0.44 g) in dichloromethane (10 ml) is added m-chloroperbenzoic acid (0.52 g) under ice cooling. The mixture is stirred at room temperature overnight, and the reaction mixture is poured into aqueous sodium carbonate solution. The mixture is extracted with chloroform and dried with sodium carbonate. The solvent is distilled off and the resulting residue is purified by silica gel column chromatography (solvent: n-hexane:ethyl acetate=1:2) to give 1-{1-[4-(3-ethylsulfonylpropoxy)benzoyl]-4-piperidinyl}-3,4-dihydrocarbostyril (0.19 g).

NMR (CDCl₃) δ ppm: 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

Example 478

A mixture of 1-{1-[4-(4-aminobutoxy)benzoyl]-4-piperidinyl}-3,4-dihydrocarbostyril (0.50 g), acetic acid (10 ml) and 2,5-dimethoxytetrahydrofuran (0.17 ml) is refluxed with stirring under heating for 1 hour. The reaction solution is concentrated under reduced pressure and the resulting residue is purified by silica gel column chromatography (solvent: dichloromethane:methanol=100:1) to give 1-[1-{4-[4-(1-pyrrolyl)butoxy]benzoyl}-4-piperidinyl]-3,4-dihydrocarbostyril (0.30 g).

NMR (CDCl₃) δ ppm: 1.71–2.15 (6H, m), 2.46–3.20 (8H, m), 3.80–5.15 (2H, m), 3.96 (4H, t, J=6.8 Hz), 4.39 (1H, m), 6.15 (2H, t, J=2.1 Hz), 6.67 (2H, t, J=2.1 Hz), 6.88 (2H, d, J=8.7 Hz), 6.99–7.28 (4H, m), 7.42 (2H, d, J=8.7 Hz)

Example 479

Sodium metaperiodate (0.28 g) is dissolved in water (4 ml) and thereto is added a solution of 1-{1-[4-(3-ethylthiopropoxy)benzoyl]-4-piperidinyl}-3,4-dihydrocarbostyril (0.4 g) in methanol (15 ml) and the mixture is stirred at room temperature overnight. The reaction mixture is concentrated and the residue is extracted with chloroform. The extract is dried with magnesium sulfate and the solvent is distilled off. The resulting residue is purified by silica gel column chromatography (solvent: n-hexane:ethyl acetate=1:2→ethyl acetate:methanol=20:1) to give 1-{1-[4-(3-ethylsulfinylpropoxy)benzoyl]-4-piperidinyl}-3,4-dihydrocarbostyril (0.12 g).

NMR (CDCl₃) δ ppm: 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

Example 480

4-Hydroxypropyltriphenylphosphonium bromide (2.4 g) is dispersed into tetrahydrofuran (50 ml) and thereto is added dropwise lithium diisopropylamide (a solution in 1.99N tetrahydrofuran) (6.1 ml) at 0°–5° C. After adding, the mixture is stirred at 0°–5° C. for 1 hour and thereto is added 1-[1-(4-formylbenzoyl)-4-piperidinyl]-3,4-dihydrocarbostyril (2 g). The mixture is stirred at room temperature overnight. The reaction mixture is poured into ice-water and adjusted to pH 4–5 by adding conc. hydrochloric acid. The mixture is extracted with ethyl acetate and dried with magnesium sulfate. The solvent is distilled off and the resulting residue is purified by silica gel column chromatography (solvent: n-hexane:ethyl acetate=1:1→ethyl acetate:methanol=20:1) to give 1-{1-[4-(4-hydroxy-1-butenyl)benzoyl]-4-piperidinyl}-3,4-dihydrocarbostyril (1 g).

NMR (CDCl₃) δ ppm: 1.58–1.97 (2H, m), 2.43–3.22 (10H, m), 3.65–5.12 (5H, m), 5.68–5.84, 6.18–6.36 (total; 1H, m), 6.51 (1H, d, J=15.9 Hz), 6.96–7.49 (8H, m)

Example 481

To crushed aluminum chloride (26 g) are added chlorobenzene (26 ml) and N-cinnamoyl-N-(1-benzoyl-4-piperidinyl)aniline (8.7 g) and the mixture is reacted at 110° C. for 1 hour. After cooling, the reaction mixture is poured into ice-water and the mixture is basified with aqueous sodium hydroxide solution. The mixture is extracted with dichloromethane and the solvent is concentrated. The residue is purified by silica gel column chromatography (solvent: methylene chloride) to give 1-(1-benzoyl-4-piperidinyl)carbostyril (5.9 g).

Using the suitable starting materials, the compounds of the above Examples 10, 166–168, 475 and the following Examples 578–587 are obtained in the same manners as in Example 481.

Using the suitable materials, the following compounds are obtained in the same manners as in Exampels 1 and 384.

TABLE 6

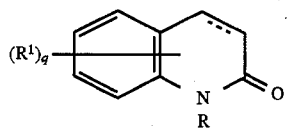

Example 482

Structure

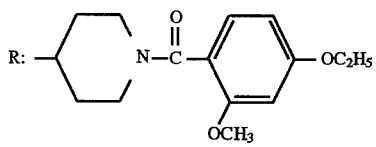

R¹: —COOH (3-position), q: 1
Bond between 3- and 4-positions in the carbostyril ring: Single bond
Crystalline form: White amorphous form
NMR analysis: 237)
Form: Free Example 483

Structure

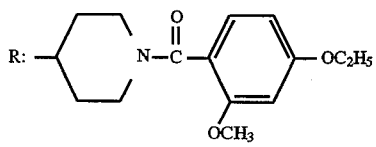

R¹: —CONHNH₂ (3-position), q: 1
Bond between 3- and 4-positions in the carbostyril ring: Single bond
Crystalline form: White amorphous form
NMR analysis: 238)
Form: Free Example 484

Structure

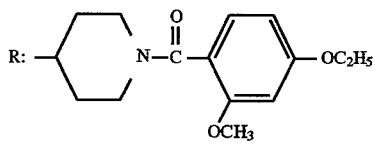

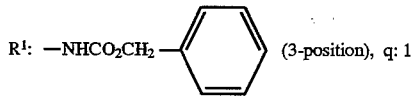  (3-position), q: 1

Bond between 3- and 4-positions in the carbostyril ring: Single bond
Crystalline form: White amorphous form
NMR analysis: 239)
Form: Free Example 485

Structure

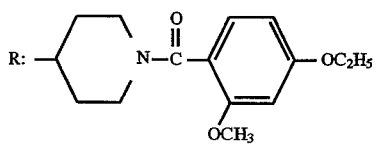

R¹: —NH₂ (3-position), q: 1
Bond between 3- and 4-positions in the carbostyril ring: Single bond
Crystalline form: White powders
Melting point: 257–260° C.
Form: Hydrochloride TABLE 6-continued

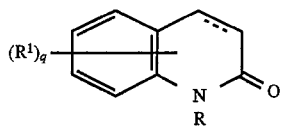

Example 486

Structure

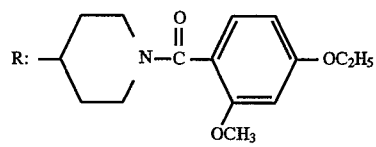

$R^1$: —NHCOCH$_3$ (3-position), q: 1
Bond between 3- and 4-positions in the carbostyril ring: Single bond
Crystalline form: White amorphous form
NMR analysis: 240)
Form: Free

Example 487

Structure

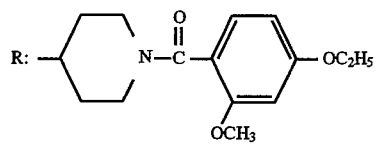

$R^1$: —N(CH$_3$)$_2$ (3-position), q: 1
Bond between 3- and 4-positions in the carbostyril ring: Single bond
Crystalline form: White amorphous form
NMR analysis: 241)
Form: Free

Example 488

Structure

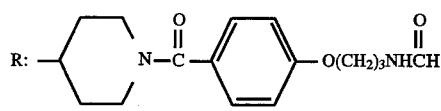

$R^1$: F (7-position), q: 1
Bond between 3- and 4-positions in the carbostyril ring: Single bond
Crystalline form: White amorphous form
NMR analysis: 242)
Form: Free

Example 489

Structure

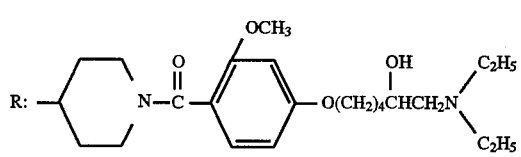

$R^1$: F (5-, 7-position), q: 2
Bond between 3- and 4-positions in the carbostyril ring: Single bond
Crystalline form: White amorphous form
NMR analysis: 245)
Form: Free TABLE 6-continued

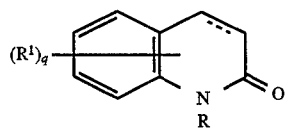

Example 490

Structure

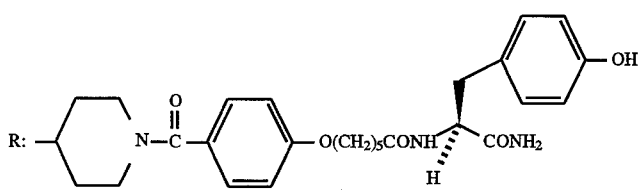

$R^1$: H, q: 1
Bond between 3- and 4-positions in the carbostyril ring: Single bond
Crystalline form: White amorphous form
NMR analysis: 246)
Form: Free Example 491

Structure

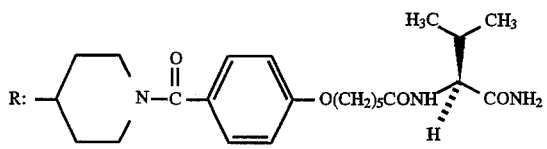

$R^1$: H, q: 1
Bond between 3- and 4-positions in the carbostyril ring: Single bond
Crystalline form: White amorphous form
NMR analysis: 247)
Form: Free Example 492

Structure

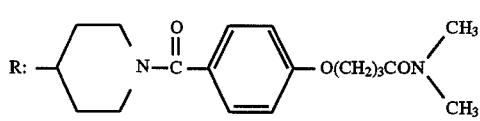

$R^1$: H, q: 1
Bond between 3- and 4-positions in the carbostyril ring: Single bond
Crystalline form: White amorphous form
NMR analysis: 248)
Form: Free Example 493

Structure

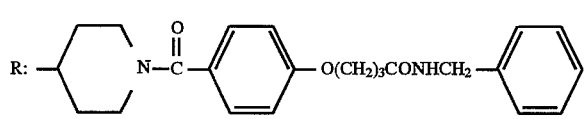

$R^1$: H, q: 1
Bond between 3- and 4-positions in the carbostyril ring: Single bond
Crystalline form: White amorphous form
NMR analysis: 249)
Form: Free

TABLE 6-continued

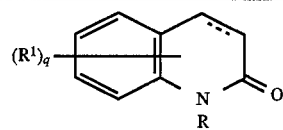

Example 494

Structure

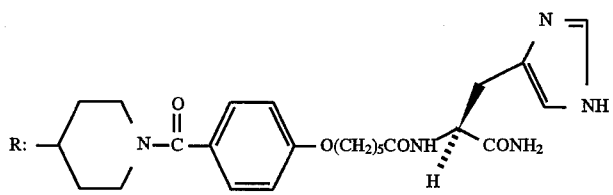

R¹: H, q: 1
  Bond between 3- and 4-positions in the carbostyril ring: Single bond
Crystalline form: White amorphous form
NMR analysis: 250)
Form: Free

Example 495

Structure

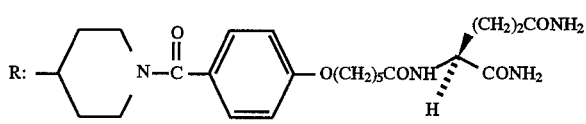

R¹: H, q: 1
  Bond between 3- and 4-positions in the carbostyril ring: Single bond
Crystalline form: White amorphous form
NMR analysis: 251)
Form: Free

Example 496

Structure

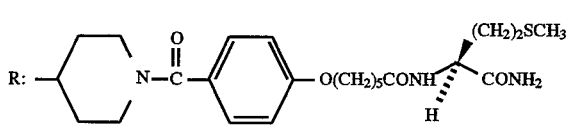

R¹: H, q: 1
  Bond between 3- and 4-positions in the carbostyril ring: Single bond
Crystalline form: White amorphous form
NMR analysis: 252)
Form: Free

Example 497

Structure

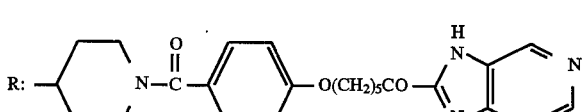

R¹: H, q: 1
  Bond between 3- and 4-positions in the carbostyril ring: Single bond
Crystalline form: White amorphous form
NMR analysis: 253)
Form: Free

TABLE 6-continued

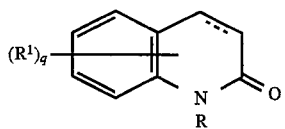

Example 498

Structure

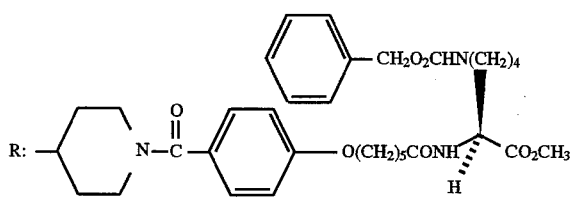

R¹: H, q: 1
Bond between 3- and 4-positions in the carbostyril ring: Single bond
Crystalline form: White amorphous form
NMR analysis: 254)
Form: Free

Example 499

Structure

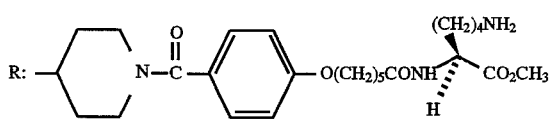

R¹: H, q: 1
Bond between 3- and 4-positions in the carbostyril ring: Single bond
Crystalline form: White amorphous form
NMR analysis: 255)
Form: Free

Example 500

Structure

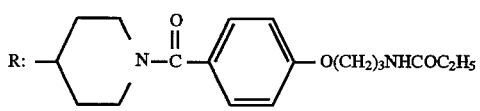

R¹: H, q: 1
Bond between 3- and 4-positions in the carbostyril ring: Single bond
Crystalline form: White amorphous form
NMR analysis: 256)
Form: Free

Example 501

Structure

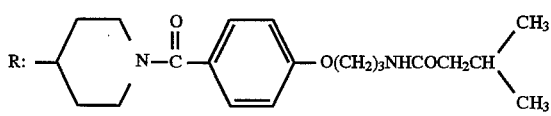

R¹: H, q: 1
Bond between 3- and 4-positions in the carbostyril ring: Single bond
Crystalline form: White amorphous form
NMR analysis: 257)
Form: Free TABLE 6-continued

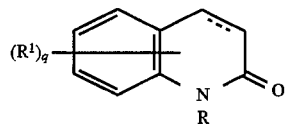

Example 502

Structure

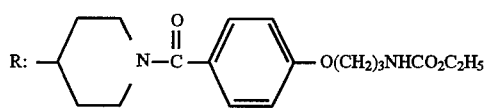

R¹: H, q: 1
Bond between 3- and 4-positions in the carbostyril ring: Single bond
Crystalline form: White amorphous form
NMR analysis: 258)
Form: Free Example 503

Structure

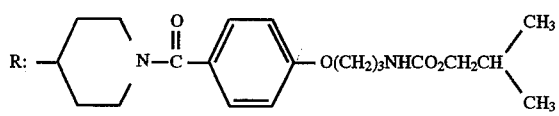

R¹: H, q: 1
Bond between 3- and 4-positions in the carbostyril ring: Single bond
Crystalline form: White amorphous form
NMR analysis: 259)
Form: Free Example 504

Structure

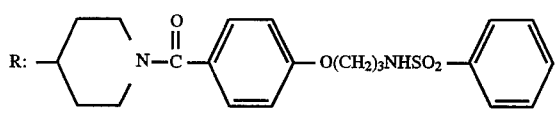

R¹: H, q: 1
Bond between 3- and 4-positions in the carbostyril ring: Single bond
Crystalline form: White amorphous form
NMR analysis: 260)
Form: Free Example 505

Structure

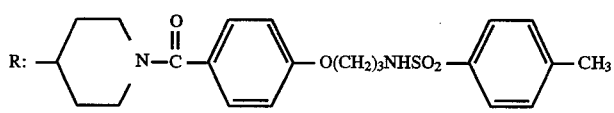

R¹: H, q: 1
Bond between 3- and 4-positions in the carbostyril ring: Single bond
Crystalline form: White amorphous form
NMR analysis: 261)
Form: Free Example 506

Structure

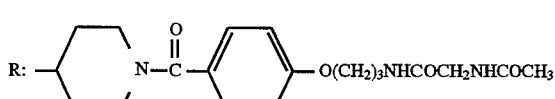

TABLE 6-continued

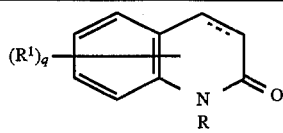

R¹: H, q: 1
Bond between 3- and 4-positions in the carbostyril ring: Single bond
Crystalline form: White amorphous form
NMR analysis: 262)
Form: Free Example 507

Structure

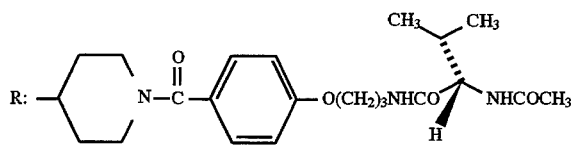

R¹: H, q: 1
Bond between 3- and 4-positions in the carbostyril ring: Single bond
Crystalline form: White amorphous form
NMR analysis: 263)
Form: Free Example 508

Structure

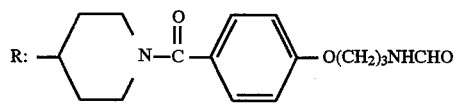

R¹: H, q: 1
Bond between 3- and 4-positions in the carbostyril ring: Single bond
Crystalline form: White amorphous form
NMR analysis: 264)
Form: Free Example 509

Structure

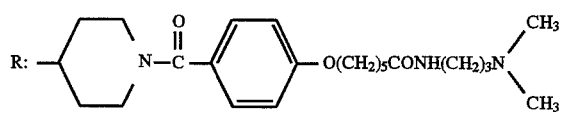

R¹: H, q: 1
Bond between 3- and 4-positions in the carbostyril ring: Single bond
Crystalline form: White amorphous form
NMR analysis: 265)
Form: Free Example 510

Structure

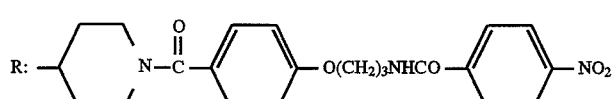

R¹: H, q: 1
Bond between 3- and 4-positions in the carbostyril ring: Single bond
Crystalline form: White amorphous form
NMR analysis: 266)
Form: Free TABLE 6-continued

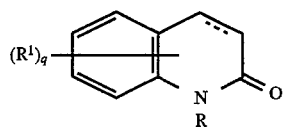

Example 511

Structure

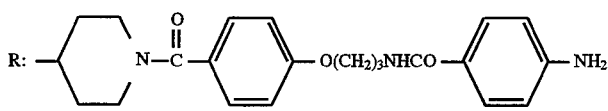

R¹: H, q: 1
Bond between 3- and 4-positions in the carbostyril ring: Single bond
Crystalline form: White amorphous form
NMR analysis: 267)
Form: Free Example 512

Structure

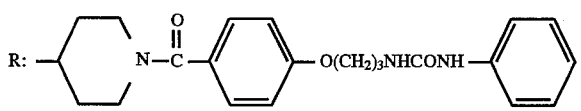

R¹: H, q: 1
Bond between 3- and 4-positions in the carbostyril ring: Single bond
Crystalline form: White powders
NMR analysis: 268)
Recrystallization solvent: Ethyl acetate/n-hexane
Melting point: 121–126° C.
Form: Free Example 513

Structure

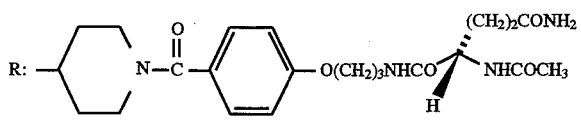

R¹: H, q: 1
Bond between 3- and 4-positions in the carbostyril ring: Single bond
Crystalline form: White amorphous form
NMR analysis: 269)
Form: Free Example 514

Structure

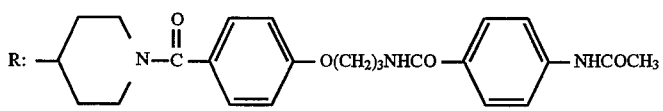

R¹: H, q: 1
Bond between 3- and 4-positions in the carbostyril ring: Single bond
Crystalline form: White amorphous form
NMR analysis: 270)
Form: Free TABLE 6-continued

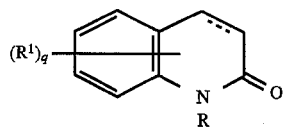

Example 515

Structure

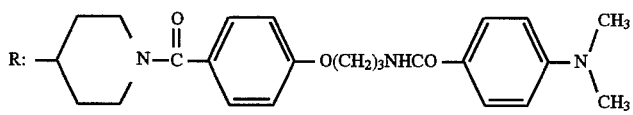

R$^1$: H, q: 1
Bond between 3- and 4-positions in the carbostyril ring: Single bond
Crystalline form: White powder
Recrystallization solvent: Ethyl acetate/n-hexane
Melting point: 175.5–177° C.
Form: Free

Example 516

Structure

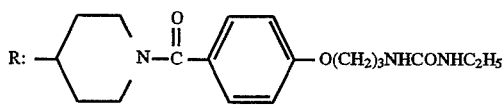

R$^1$: H, q: 1
Bond between 3- and 4-positions in the carbostyril ring: Single bond
Crystalline form: White amorphous form
NMR analysis: 271)
Form: Free

Example 517

Structure

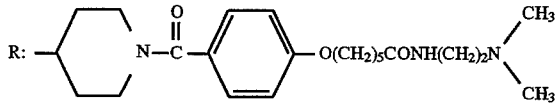

R$^1$: H, q: 1
Bond between 3- and 4-positions in the carbostyril ring: Single bond
NMR analysis: 272)
Form: Free

Example 518

Structure

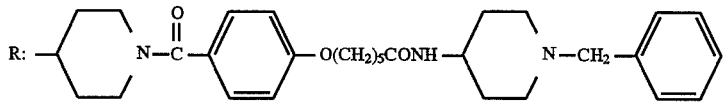

R$^1$: H, q: 1
Bond between 3- and 4-positions in the carbostyril ring: Single bond
Crystalline form: White amorphous form
NMR analysis: 273)
Form: Free

Example 519

Structure

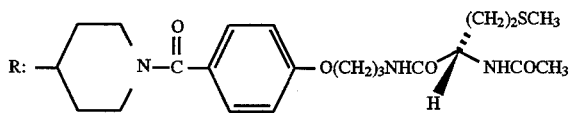

TABLE 6-continued

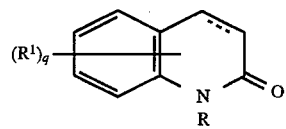

R¹: H, q: 1
Bond between 3- and 4-positions in the carbostyril ring: Single bond
Crystalline form: White amorphous form
NMR analysis: 274)
Form: Free Example 520

Structure

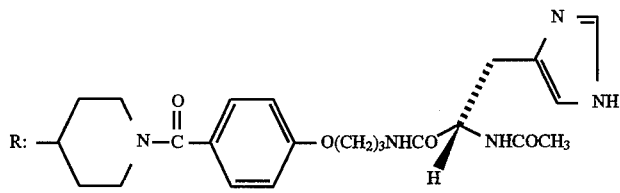

R¹: H, q: =1
Bond between 3- and 4-positions in the carbostyril ring: Single bond
Crystalline form: White amorphous form
NMR analysis: 275)
Form: Free Example 521

Structure

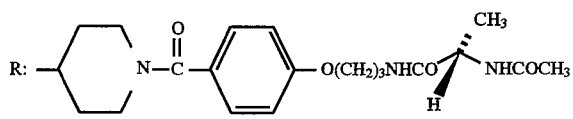

R¹: H, q: 1
Bond between 3- and 4-positions in the carbostyril ring: Single bond
Crystalline form: White amorphous form
NMR analysis: 276)
Form: Free Example 522

Structure

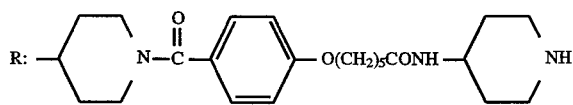

R¹: H, q: 1
Bond between 3- and 4-positions in the carbostyril ring: Single bond
Crystalline form: White amorphous form
NMR analysis: 277)
Form: Free Example 523

Structure

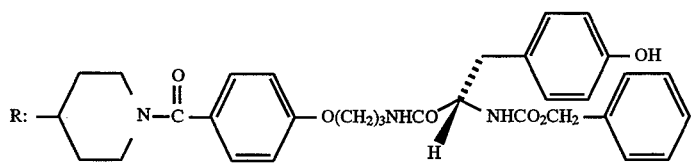

R¹: H, q: 1
Bond between 3- and 4-positions in the carbostyril ring: Single bond
Crystalline form: White amorphous form TABLE 6-continued

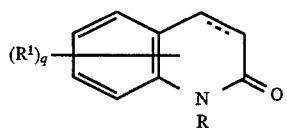

NMR analysis: 278)
Form: Free

Example 524

Structure

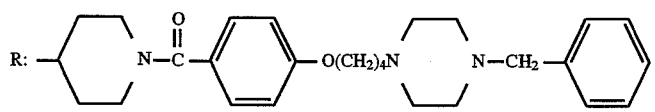

R¹: H, q: 1
Bond between 3- and 4-positions in the carbostyril ring: Single bond
NMR analysis: 279)
Form: Free Example 525

Structure

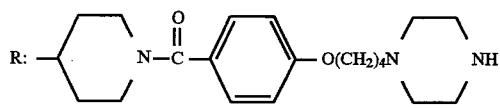

R¹: H, q: 1
Bond between 3- and 4-positions in the carbostyril ring: Single bond
Crystalline form: White powders
Recrystallization solvent: Ethanol/water
Melting point: 196–198° C.
Form: Dioxalate Example 526

Structure

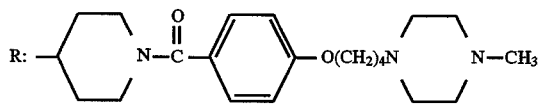

R¹: H, q: 1
Bond between 3- and 4-positions in the carbostyril ring: Single bond
Crystalline form: White powders
Recrystallization solvent: Ethanol/water
Melting point: 214–215° C.
Form: Dioxalate Example 527

Structure

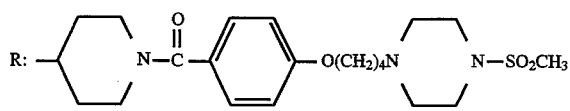

R¹: H, q: 1
Bond between 3- and 4-positions in the carbostyril ring: Single bond
NMR analysis: 280)
Form: Free

TABLE 6-continued

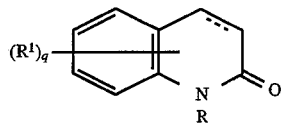

Example 528

Structure

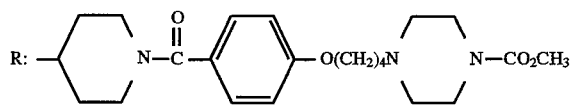

R¹: H, q: 1
Bond between 3- and 4-positions in the carbostyril ring: Single bond
NMR analysis: 281)
Form: Free

Example 529

Structure

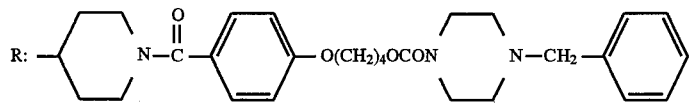

R¹: H, q: 1
Bond between 3- and 4-positions in the carbostyril ring: Single bond
NMR analysis: 282)
Form: Free

Example 530

Structure

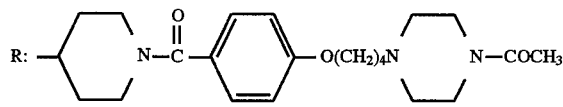

R¹: H, q: 1
Bond between 3- and 4-positions in the carbostyril ring: Single bond
NMR analysis: 283)
Form: Free

Example 531

Structure

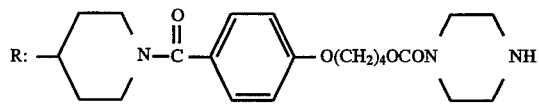

R¹: H, q: 1
Bond between 3- and 4-positions in the carbostyril ring: Single bond
NMR analysis: 284)
Form: Free

Example 532

Structure

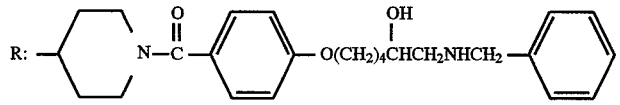

R¹: H, q: 1
Bond between 3- and 4-positions in the carbostyril ring: Single bond
NMR analysis: 285)
Form: Free TABLE 6-continued

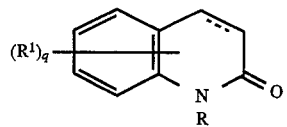

Example 533

Structure

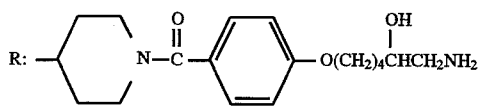

R¹: H, q: 1
Bond between 3- and 4-positions in the carbostyril ring: Single bond
NMR analysis: 286)
Form: Free Example 534

Structure

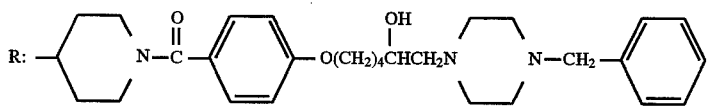

R¹: H, q: 1
Bond between 3- and 4-positions in the carbostyril ring: Single bond
Crystalline form: White powders
Recrystallization solvent: Ethanol/water
Melting point: 196–198° C.
Form: Dioxalate Example 535

Structure

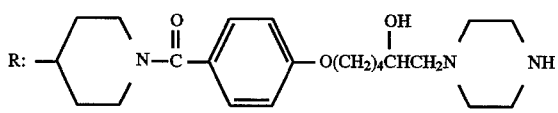

R¹: H, q: 1
Bond between 3- and 4-positions in the carbostyril ring: Single bond
Crystalline form: White powders
Recrystallization solvent: Ethanol/water
Melting point: 198–199° C.
Form: Dioxalate Example 536

Structure

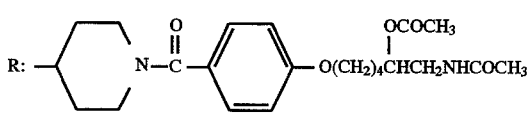

R¹: H, q: 1
Bond between 3- and 4-positions in the carbostyril ring: Single bond
NMR analysis: 287)
Form: Free Example 537

Structure

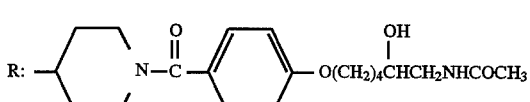

TABLE 6-continued

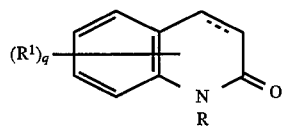

R¹: H, q: 1
Bond between 3- and 4-positions in the carbostyril ring: Single bond
NMR analysis: 288)
Form: Free Example 538

Structure

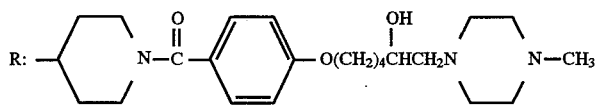

R¹: H, q: 1
Bond between 3- and 4-positions in the carbostyril ring: Single bond
NMR analysis: 289)
Form: Free Example 539

Structure

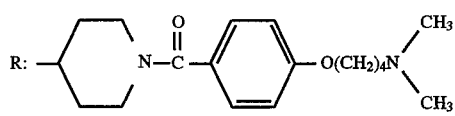

R¹: H, q: 1
Bond between 3- and 4-positions in the carbostyril ring: Single bond
NMR analysis: 290)
Form: Free Example 540

Structure

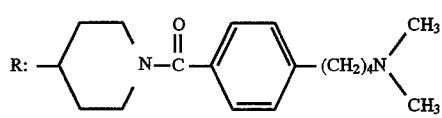

R¹: H, q: 1
Bond between 3- and 4-positions in the carbostyril ring: Single bond
NMR analysis: 291)
Form: Free Example 541

Structure

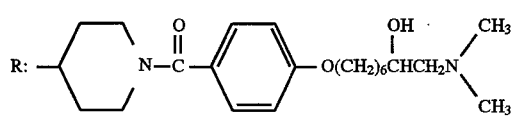

R¹: H, q: 1
Bond between 3- and 4-positions in the carbostyril ring: Single bond
NMR analysis: 292)
Form: Free TABLE 6-continued

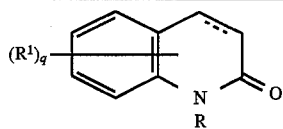

Example 542

Structure

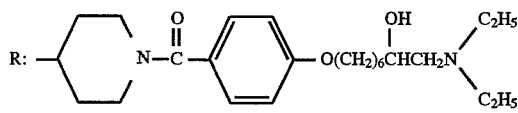

$R^1$: H, q: 1
Bond between 3- and 4-positions in the carbostyril ring: Single bond
NMR analysis: 293)
Form: Free Example 543

Structure

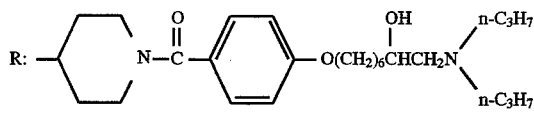

$R^1$: H, q: 1
Bond between 3- and 4-positions in the carbostyril ring: Single bond
NMR analysis: 294)
Form: Free Example 544

Structure

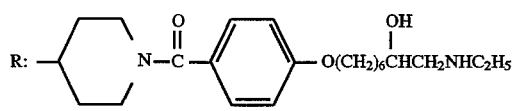

$R^1$: H, q: 1
Bond between 3- and 4-positions in the carbostyril ring: Single bond
NMR analysis: 295)
Form: Free Example 545

Structure

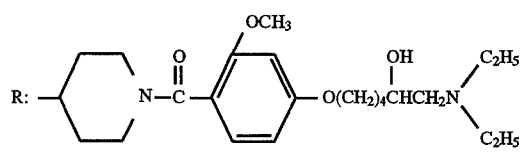

$R^1$: F (7-position), q: 1
Bond between 3- and 4-positions in the carbostyril ring: Single bond
NMR analysis: 296)
Form: Free Example 546

Structure

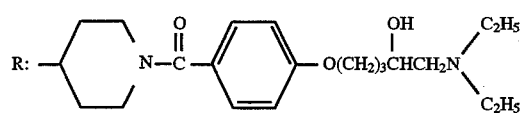

TABLE 6-continued

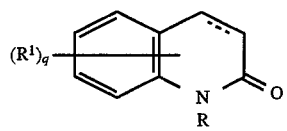

R¹: H, q: 1
Bond between 3- and 4-positions in the carbostyril ring: Single bond
NMR analysis: 297)
Form: Free Example 547

Structure

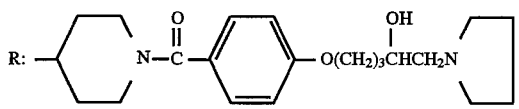

R¹: H, q: 1
Bond between 3- and 4-positions in the carbostyril ring: Single bond
NMR analysis: 298)
Form: Free Example 548

Structure

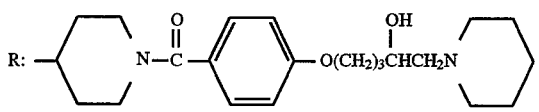

R¹: H, q: 1
Bond between 3- and 4-positions in the carbostyril ring: Single bond
NMR analysis: 299)
Form: Free Example 549

Structure

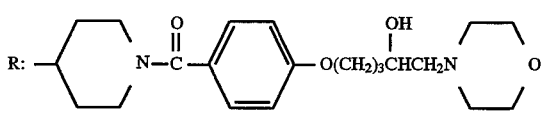

R¹: H, q: 1
Bond between 3- and 4-positions in the carbostyril ring: Single bond
NMR analysis: 300)
Form: Free Example 550

Structure

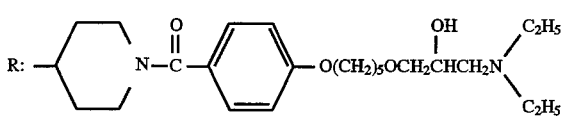

R¹: H, q: 1
Bond between 3- and 4-positions in the carbostyril ring: Single bond
NMR analysis: 301)
Form: Free TABLE 6-continued

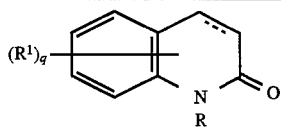

Example 551

Structure

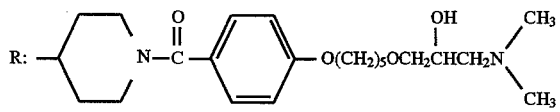

R¹: H, q: 1
Bond between 3- and 4-positions in the carbostyril ring: Single bond
NMR analysis: 302)
Form: Free Example 552

Structure

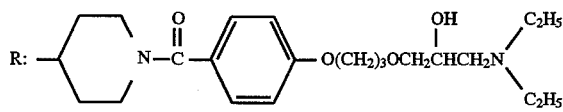

R¹: H, q: 1
Bond between 3- and 4-positions in the carbostyril ring: Single bond
NMR analysis: 303)
Form: Free Example 553

Structure

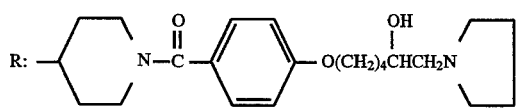

R¹: H, q: 1
Bond between 3- and 4-positions in the carbostyril ring: Single bond
NMR analysis: 304)
Form: Free Example 554

Structure

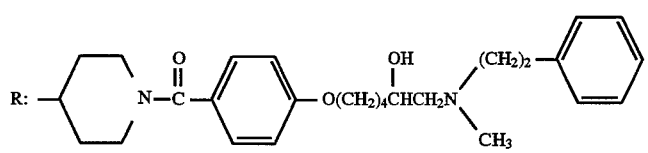

R¹: H, q: 1
Bond between 3- and 4-positions in the carbostyril ring: Single bond
NMR analysis: 305)
Form: Free Example 555

Structure

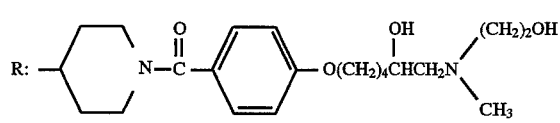

TABLE 6-continued

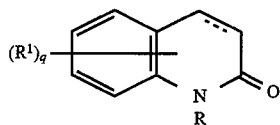

R$^1$: H, q: 1
Bond between 3- and 4-positions in the carbostyril ring: Single bond
NMR analysis: 306)
Form: Free Example 556

Structure

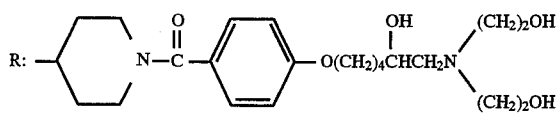

R$^1$: H, q: 1
Bond between 3- and 4-positions in the carbostyril ring: Single bond
NMR analysis: 307)
Form: Free Example 557

Structure

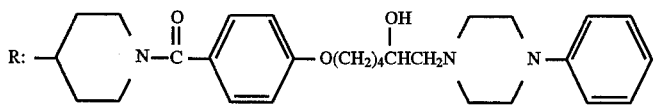

R$^1$: H, q: 1
Bond between 3- and 4-positions in the carbostyril ring: Single bond
NMR analysis: 308)
Form: Free Example 558

Structure

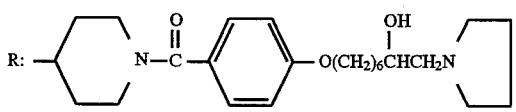

R$^1$: H, q: 1
Bond between 3- and 4-positions in the carbostyril ring: Single bond
NMR analysis: 309)
Form: Free Example 559

Structure

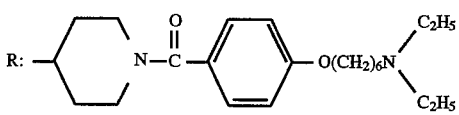

R$^1$: H, q: 1
Bond between 3- and 4-positions in the carbostyril ring: Single bond
NMR analysis: 310)
Form: Free TABLE 6-continued

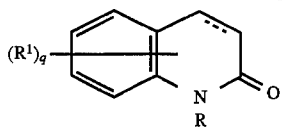

Example 560

Structure

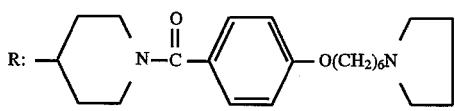

R[1]: H, q: 1
Bond between 3- and 4-positions in the carbostyril ring: Single bond
NMR analysis: 311)
Form: Free Example 561

Structure

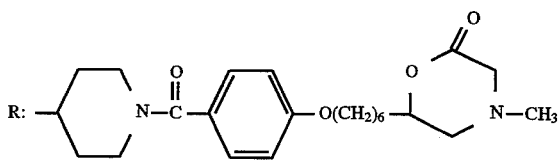

R[1]: H, q: 1
Bond between 3- and 4-positions in the carbostyril ring: Single bond
NMR analysis: 312)
Form: Free Example 562

Structure

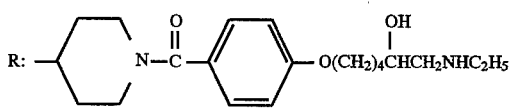

R[1]: H, q: 1
Bond between 3- and 4-positions in the carbostyril ring: Single bond
NMR analysis: 313)
Form: Free Example 563

Structure

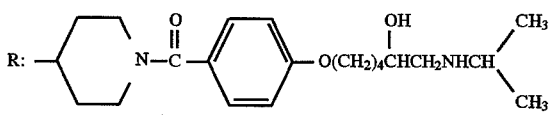

R[1]: H, q: 1
Bond between 3- and 4-positions in the carbostyril ring: Single bond
NMR analysis: 314)
Form: Free Example 564

Structure

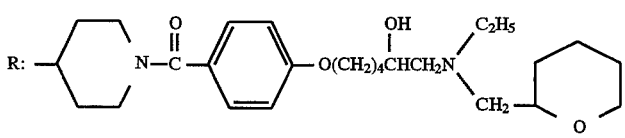

TABLE 6-continued

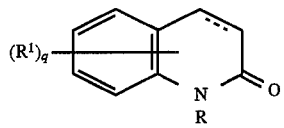

R¹: H, q: 1
Bond between 3- and 4-positions in the carbostyril ring: Single bond
NMR analysis: 315)
Form: Free Example 565

Structure

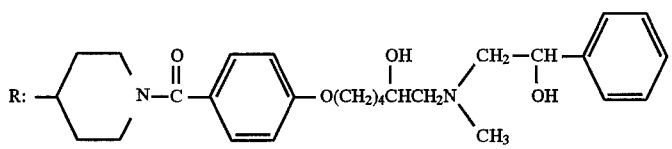

R¹: H, q: 1
Bond between 3- and 4-positions in the carbostyril ring: Single bond
NMR analysis: 316)
Form: Free Example 566

Structure

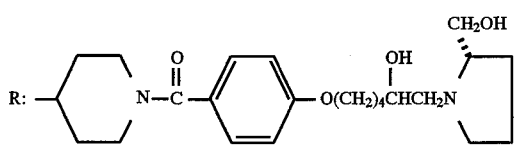

R¹: H, q: 1
Bond between 3- and 4-positions in the carbostyril ring: Single bond
NMR analysis: 317)
Form: Free Example 567

Structure

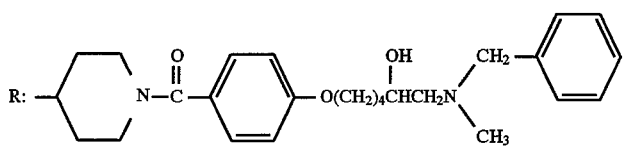

R¹: H, q: 1
Bond between 3- and 4-positions in the carbostyril ring: Single bond
NMR analysis: 318)
Form: Free Example 568

Structure

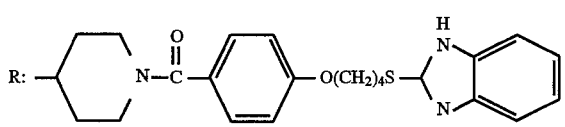

R¹: H, q: 1
Bond between 3- and 4-positions in the carbostyril ring: Single bond
Crystalline form: White amorphous form
NMR analysis: 319)
Form: Free TABLE 6-continued

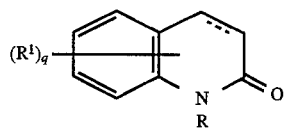

Example 569

Structure

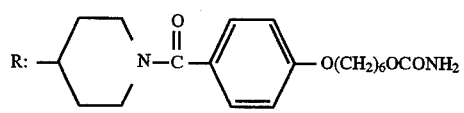

R$^1$: H, q: 1
Bond between 3- and 4-positions in the carbostyril ring: Single bond
Crystalline form: White amorphous form
NMR analysis: 320)
Form: Free Example 570

Structure

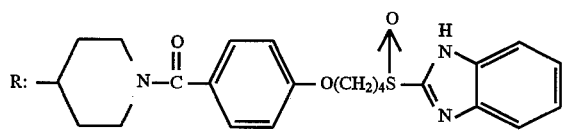

R$^1$: H, q: 1
Bond between 3- and 4-positions in the carbostyril ring: Single bond
Crystalline form: White amorphous form
NMR analysis: 321)
Form: Free Example 571

Structure

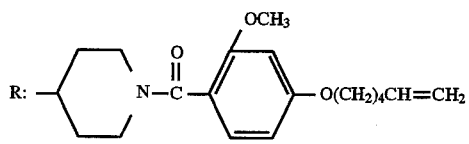

R$^1$: F (5-, 7-position), q: 2
Bond between 3- and 4-positions in the carbostyril ring: Single bond
Crystalline form: White amorphous form
NMR analysis: 325)
Form: Free Example 572

Structure

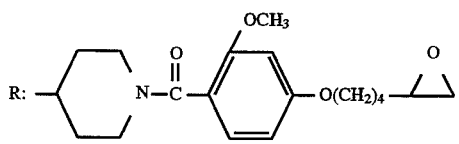

R$^1$: F (5-, 7-position), q: 2
Bond between 3- and 4-positions in the carbostyril ring: Single bond
Crystalline form: White amorphous form
NMR analysis: 326)
Form: Free TABLE 6-continued

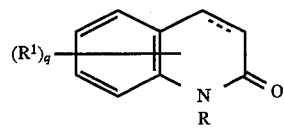

Example 573

Structure

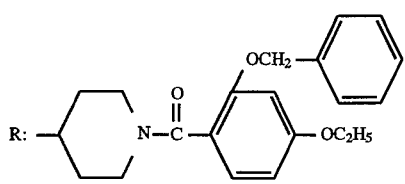

R$^1$: H, q: 1
Bond between 3- and 4-positions in the carbostyril ring: Single bond
Crystalline form: White powders
Recrystallization solvent: Ethanol
Melting point: 63–65° C.   Form: Free Example 574

Structure

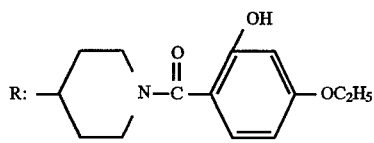

R$^1$: H, q: 1
Bond between 3- and 4-positions in the carbostyril ring: Single bond
Crystalline form: White powders
Recrystallization solvent: Ethanol
Melting point: 138–140° C.   Form: Free Example 575

Structure

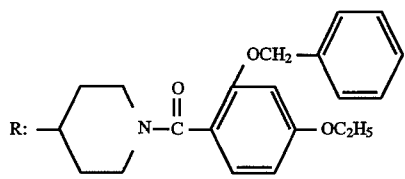

R$^1$: F (7-position), q: 1
Bond between 3- and 4-positions in the carbostyril ring: Single bond
Crystalline form: White powders
Recrystallization solvent: Ethanol
Melting point: 83–86° C.   Form: Free Example 576

Structure

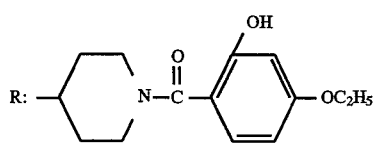

R$^1$: F (7-position), q: 1
Bond between 3- and 4-positions in the carbostyril ring: Single bond
Crystalline form: White powders
Recrystallization solvent: Ethanol
Melting point: 140–142° C.   Form: Free TABLE 6-continued

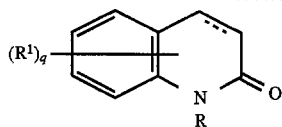

Example 577

Structure

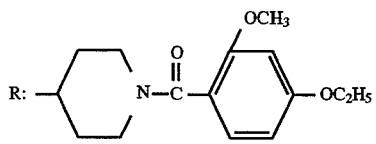

R[1]: CH$_3$ (5-position), q: 1
Bond between 3- and 4-positions in the carbostyril ring: Single bond
Crystalline form: White amorphous form
NMR analysis: 327)
Form: Free Example 577A Structure

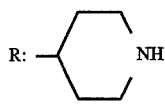

R[1]: CH$_3$ (5-position), q: 1
Bond between 3- and 4-positions in the carbostyril ring: Single bond
Crystalline form: White amorphous form
NMR analysis: 328)
Form: Free The following compounds are obtained in the same manners as in examples 1 and 385.

TABLE 7

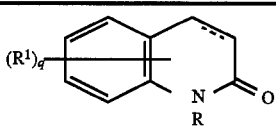

Example 578

Structure

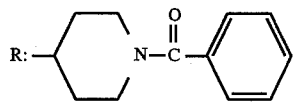

R[1]: F (7-position), q: 1
Bond between 3- and 4-positions in the carbostyryl ring: Double bond
Crystalline form: White powders
Recrystallization solvent: Ethanol
Melting point: 182–185° C.
Form: Free Example 579

Structure

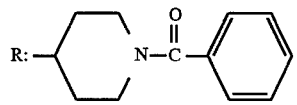

R[1]: F (5-, 7-positions), q: 2
Bond between 3- and 4-positions in the

TABLE 7-continued

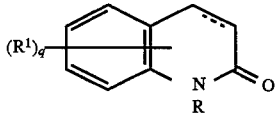

carbostyril ring: Double bond
Crystalline form: White powders
Recrystallization solvent: Ethanol
Melting point: 183–185° C.
Form: Free Example 580

Structure

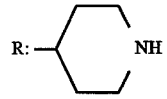

R[1]: F (7-position), q: 1
Bond between 3- and 4-positions in the carbostyril ring: Double bond
Crystalline form: White amorphous form
NMR analysis: 243)
Form: Free Example 581

Structure

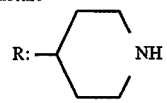

TABLE 7-continued

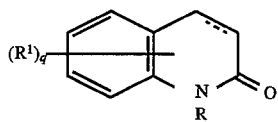

R¹: R (5-, 7-positions), q: 2
Bond between 3- and 4-positions in the
carbostyril ring: Double bond
Crystalline form: White powders
Recrystallization solvent: Ethanol/n-hexane
Melting point: 186–187° C.
Form: Free Example 582

Structure

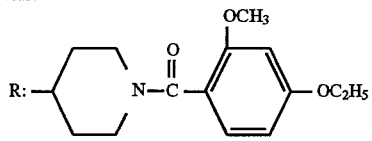

R¹: F (7-position), q: 1
Bond between 3- and 4-positions in the
carbostyril ring: Double bond
Crystalline form: White powders
Recrystallization solvent: Ethanol/diethyl ether
Melting pint: 187–188° C. Form: Free Example 583

Structure

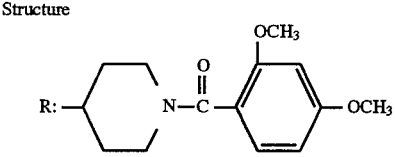

R¹: F (7-position), q: 1
Bond between 3- and 4-positions in the
carbostyril ring: Double bond
Crystalline form: White amorphous form
NMR analysis: 244)
Form: Free Example 584

Structure

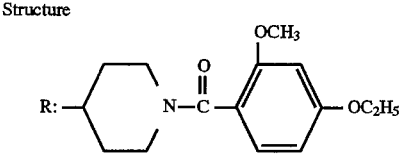

R¹: F( 5-, 7-positions), q: 2
Bond between 3- and 4-positions in the
carbostyril ring: Double bond
Crystalline form: White powders
Recrystallization solvent: Ethanol/diethyl ether
Melting point: 150–152° C.
Form: Free Example 585

Structure

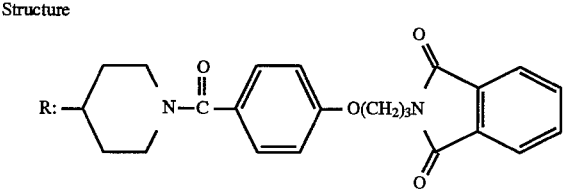

R¹: H, q: 1
Bond between 3- and 4-positions in the
carbostyril ring: Double bond
Crystalline form: White amorphous form TABLE 7-continued

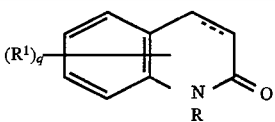

NMR analysis: 322)
Form: Free

Example 586

Structure

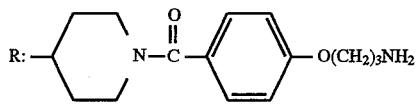

R¹: H, q: 1
Bond between 3- and 4-positions in the
carbostyril ring: Double bond
Crystalline form: White amorphous form
NMR analysis: 323)
Form: Free Example 587

Structure

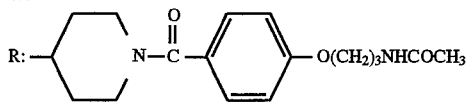

R¹: H, q: 1
Bond between 3- and 4-positions in the
carbostyril ring: Double bond
Crystalline form: White amorphous form
NMR analysis: 324)
Form: Free

TABLE 8

| No. | NMR (CDCl₃) δ value |
|---|---|
| 237 | 1.42(3H, t, J=7.0Hz), 1.58–2.05(2H, m), 2.35–3.47(7H, m), 3.55–3.95(4H, m), 4.04(2H, q, J=7 Hz), 4.38(1H, brs), 4.94(1H, brs), 6.37–6.56(2H, m), 7.00–7.40(5H, m) |
| 238 | 1.42(3H, t, J=7Hz), 1.52–1.95(2H, m), 2.30–3.93 (13H, m), 4.04(2H, q, J=7Hz), 4.15–5.06(3H, m), 6.40–6.62(2H, m), 6.97–7.50(5H, m) |
| 239 | 1.40(3H, t, J=7Hz), 1.55–2.00(2H, m), 2.30–5.05 (15H, m), 5.30(2H, s), 5.95(1H, brs), 6.50–6.60 (2H, m), 7.02–7.42(10H, m) |
| 240 | 1.42(3H, t, J=7Hz), 1.55–1.98(2H, m), 2.08(3H, s), 2.40–3.95(7H, m), 4.05(2H, q, J=7Hz), 4.20–4.65(2H, m), 4.90–5.11(1H, m), 6.42–6.73(3H, m), 7.02–7.40(5H, m) |
| 241 | 1.42(3H, t, J=7Hz), 1.50–1.96(2H, m), 2.43(6H, s), 2.51–3.28(7H, m), 3.57–3.95(4H, m), 4.04(2H, q, J=7Hz), 4.33–4.75(1H, m), 4.84–5.06(1H, m), 6.40–6.60(2H, m), 6.99–7.32(5H, m) |
| 242 | 1.68–2.15(4H, m), 2.45–3.20(8H, m), 3.40–3.62 (2H, m), 4.06(2H, t, J=5.9Hz), 4.10–5.10(3H, m), 6.26(1H, brs), 6.68–7.25(5H, m), 7.42(2H, d, J=8.7Hz), 8.15(1H, s) |
| 243 | 1.65–1.88(2H, m), 2.20(1H, brs), 2.60–3.05(4H, m), 3.18–3.42(2H, m), 5.15(1H, brs), 6.59(1H, d, J=9.4Hz), 6.94(1H, m), 7.35–7.65(3H, m) |
| 244 | 1.60–1.97(2H, m), 2.50–3.33(4H, m), 3.54–4.02 (7H, m), 4.95–5.12(1H, m), 6.40–6.65(3H, m), 6.90–7.13(1H, m), 7.15–7.67(4H, m) |
| 245 | 1.08(6H, t, J=7.1Hz), 1.32–1.90(8H, m), 2.25–3.20(15H, m), 3.60–5.10(9H, m), 6.40–6.85(4H, m), 7.15–7.30(1H, m) |
| 246 | 1.45–1.97(6H, m), 2.16(2H, m), 2.36–3.32(8H, m), 2.56(2H, m), 3.60–5.15(2H, m), 3.87(2H, m), 4.32 (2H, m), 4.68(2H, m), 6.19(1H, brs), 6.64(2H, d, |

TABLE 8-continued

| No. | NMR δ value |
|---|---|
| | J=8.0Hz), 6.83(2H, d, J=8.3Hz), 6.92–7.23(8H, m), 7.36(2H, d, J=8.3Hz) |
| 247 | 0.95(3H, d, J=6.0Hz), 0.98(3H, d, J=6.0Hz), 1.38–1.61(2H, m), 1.62–1.96(6H, m), 2.08(1H, m), 2.27(2H, t, J=7.3Hz), 2.53–3.15(8H, m), 3.77–4.85(2H, m), 3.97(2H, t, J=6.2Hz), 4.32(2H, m), 5.79(1H, brs), 6.50(2H, m), 6.89(2H, d, J=8.6 Hz), 6.99–7.27(4H, m), 7.42(2H, d, J=8.6Hz) |
| 248 | 1.67–1.96(2H, m), 2.14(2H, quint, J=6.3Hz), 2.40–3.10(8H, m), 2.52(2H, t, J=6.3Hz), 2.96 (3H, s), 3.02(3H, s), 3.85–5.10(2H, m), 4.07(2H, t, J=6.3Hz), 4.37(1H, m), 6.92(2H, d, J=8.6Hz), 6.98–7.33(4H, m), 7.43(2H, d, J=8.6Hz), |
| 249 | 1.65–1.95(2H, m), 2.12(2H, quint, J=6.4Hz), 2.41(2H, t, J=6.4Hz), 2.54–2.85(8H, m), 3.80–5.10(2H, m), 3.98(2H, t, J=6.4Hz), 4.35(1H, m), 4.40(2H, d, J=5.5Hz), 6.54–6.92(1H, brs), 6.83 (2H, d, J=8.6Hz), 6.99–7.31(9H, m), 7.37(2H, J=8.6Hz) |

| No. | NMR (DMSO-d$_6$) δ value |
|---|---|
| 250 | 1.21–1.82(8H, m), 2.08(2H, t, J=7.1Hz), 2.26–3.20(8H, m), 3.39(2H, m), 3.60–4.66(2H, brs), 3.93(2H, t, J=6.4Hz), 4.32(2H, m), 6.71(1H, m), 6.84–7.01(2H, brs), 6.94(2H, d, J=8.7Hz), 7.16–7.31(4H, m), 7.32(2H, d, J=8.7Hz), 7.47(1H, s), 7.88(1H, d, J=8.2Hz), |
| 251 | 1.10–1.97(10H, m), 2.07(2H, t, J=7.6Hz), 2.16 (2H, t, J=7.3Hz), 2.32–3.40(8H, m), 3.60–4.80 (2H, brs), 3.99(2H, t, J=6.4Hz), 4.15(1H, m), 4.28(1H, m), 6.74(1H, brs), 6.98(2H, d, J=8.6 Hz), 7.05(1H, brs), 7.20–7.29(4H, m), 7.36(2H, d, J=8.6Hz), 7.85(1H, d, J=7.7Hz) |

| No. | NMR (CDCl$_3$) δ value |
|---|---|
| 252 | 1.38–1.59(2H, m), 1.60–2.18(8H, m), 2.09(3H, s), 2.25(2H, t, J=7.2Hz), 2.44–3.17(8H, m), 2.57 (2H, t, J=6.1Hz), 3.55–5.10(2H, brs), 3.97(2H, t, J=6.1Hz), 4.38(1H, m), 4.64(1H, q, J=7.2Hz), 5.95(1H, brs), 6.78(1H, brs), 6.82(1H, brs), 6.89(2H, d, J=8.7Hz), 6.91–7.28(4H, m), 7.41 (2H, d, J=8.7Hz) |
| 253 | 1.42–1.64(2H, m), 1.64–2.06(6H, m), 2.57(2H, t, J=6.1Hz), 2.64–3.24(8H, m), 3.67–5.15(2H, m), 3.92(2H, t, J=6.1Hz), 4.34(1H, m), 6.84(2H, d, J=8.7Hz), 7.00–7.36(5H, m), 7.40(2H, d, J=8.7 Hz), 8.28(1H, d, J=5.6Hz), 8.80(1H, s) |
| 254 | 1.13–1.96(14H, m), 2.25(2H, t, J=7.3Hz), 2.46–3.08(8H, m), 3.16(2H, m), 3.72(3H, s), 3.96(2H, t, J=6.2Hz), 4.05–4.97(2H, m), 4.37(1H, m), 4.57 (1H, m), 5.07(1H, brs), 5.08(2H, s), 6.34(1H, d, J=7.5Hz), 6.88(2H, d, J=8.6Hz), 6.98–7.30(4H, m), 7.34(5H, s), 7.41(2H, d, J=8.6Hz) |
| 255 | 1.30–1.93(14H, m), 2.27(2H, t, J=7.3Hz), 2.53–3.11(10H, m), 3.73(3H, s), 3.98(2H, t, J=6.3 Hz), 4.13–5.06(2H, m), 4.38(1H, m), 4.59(1H, m), 6.46(1H, d, J=7.8Hz), 6.89(2H, d, J=8.6Hz), 6.98–7.30(4H, m), 7.42(2H, d, J=8.6Hz) |
| 256 | 1.14(3H, t, J=7.6Hz), 1.84(2H, m), 2.00(2H, quint, J=6.1Hz), 2.21(2H, q, J=7.6Hz), 2.43–3.23 (8H, m), 3.42(2H, q, J=6.1Hz), 3.65–5.14(2H, m), 4.03(2H, t, J=6.1Hz), 4.36(1H, m), 6.52(1H, brs), 6.89(2H, d, J=8.4Hz), 6.98–7.32(4H, m), 7.42(2H, d, J=8.4Hz) |
| 257 | 0.95(6H, t, J=6.3Hz), 1.84(2H, m), 1.94–2.22 (5H, m), 2.53–3.17(8H, m), 3.46(2H, q, J=6.1Hz), 3.66–5.05(2H, m), 4.05(2H, t, J=6.1Hz), 4.38 (1H, m), 6.00(1H, brs), 6.90(2H, d, J=8.7Hz), 6.99–7.29(4H, m), 7.43(2H, d, J=8.7Hz) |
| 258 | 1.24(3H, t, J=7.1Hz), 1.66–1.93(2H, m), 2.01 (2H, quint, J=6.2Hz), 2.53–3.15(8H, m), 3.39(2H, q, J=6.2Hz), 3.60–5.10(2H, m), 4.05(2H, t, J=6.2 Hz), 4.11(2H, q, J=7.1Hz), 4.39(1H, m), 4.94 (1H, brs), 6.91(2H, d, J=8.7Hz), 6.98–7.29(4H, m), 7.43(2H, d, J=8.7Hz) |
| 259 | 0.92(6H, d, J=6.7Hz), 1.60–1.94(3H, m), 2.02 (2H, quint, J=6.2Hz), 2.53–3.15(8H, m), 3.39(2H, q, J=6.2Hz), 3.60–5.20(2H, m), 3.84(2H, d, J=6.7 Hz), 4.06(2H, t, J=6.2Hz), 4.39(1H, m), 4.95 (1H, brs), 6.91(2H, d, J=8.7Hz), 6.98–7.29(4H, m), 7.43(2H, d, J=8.7Hz) |
| 260 | 1.55–1.87(2H, m), 1.95(2H, quint, J=6.0Hz), 2.52–3.10(8H, m), 3.12(2H, q, J=6.0Hz), 3.66–5.10(2H, m), 3.96(2H, t, J=6.0Hz), 4.37(1H, m), 5.51(1H, brs), 6.81(2H, d, J=8.6Hz), 6.98–7.30 (4H, m), 7.36–7.60(5H, m), 7.85(2H, d, J=8.6Hz) |
| 261 | 1.60–1.90(2H, m), 1.95(2H, quint, J=6.1Hz), 2.40 (3H, s), 2.50–3.10(8H, m), 3.15(2H, q, J=6.1Hz), 3.70–5.05(2H, m), 3.97(2H, t, J=6.1Hz), 4.38 (1H, m), 5.19(1H, t, J=6.1Hz), 6.82(2H, d, J=8.7 Hz), 6.98–7.28(4H, m), 7.27(2H, d, J=8.7Hz), 7.40(2H, d, J=8.7Hz), 7.74(2H, d, J=8.1Hz), |
| 262 | 1.68–1.93(2H, m), 1.93–2.14(2H, m), 2.02(3H, s), 2.53–3.25(8H, m), 3.46(2H, q, J=5.9Hz), 3.70–5.15(2H, m), 3.86(2H, d, J=4.6Hz), 4.04(2H, t, J=5.9Hz), 4.37(1H, m), 6.65(1H, brs), 6.77(1H, brs), 6.90(2H, d, J=8.6Hz), 6.98–7.33(4H, m), 7.42(2H, d, J=8.6Hz) |
| 263 | 0.93(6H, d, J=6.7Hz), 1.60–1.92(2H, m), 1.93–2.15(3H, m), 2.00(3H, s), 2.33–3.24(8H, m), 3.45 (2H, m), 3.70–5.10(2H, m), 4.03(2H, t, J=5.9Hz), 4.24(1H, t, J=8.5Hz), 4.38(1H, m), 6.63(1H, d, J=8.5Hz), 6.89(2H, d, J=8.6Hz), 6.98–7.29(5H, m), 7.42(2H, d, J=8.6Hz) |
| 264 | 1.67–1.94(2H, m), 2.04(2H, quint, J=6.2Hz), 2.53–3.20(8H, m), 3.51(2H, q, J=6.2Hz), 3.65–5.15(2H, m), 4.06(2H, t, J=6.2Hz), 4.37(1H, m), 6.29(1H, brs), 6.91(2H, d, J=8.7Hz), 6.98–7.29 (4H, m), 7.43(2H, d, J=8.7Hz), 8.14(1H, s) |
| 265 | 1.39–1.62(2H, m), 1.62–1.95(8H, m), 2.20(2H, t, J=7.4Hz), 2.33(6H, s), 2.50(2H, t, J=6.5Hz), 2.56–3.20(8H, m), 3.34(2H, q, J=5.9Hz), 3.66 (1H, brs), 3.86–5.20(1H, m), 3.98(2H, t, J=6.3 Hz), 4.39(1H, m), 6.89(2H, d, J=8.6Hz), 6.98–7.30(5H, m), 7.42(2H, d, J=8.6Hz) |
| 266 | 1.82(2H, m), 2.13(2H, quint, J=5.9Hz), 2.52–3.20 (8H, m), 3.66(2H, q, J=5.9Hz), 3.80–5.10(2H, m), 4.08(2H, t, J=5.9Hz), 4.31(1H, m), 6.86(2H, d, J=8.7Hz), 6.99–7.12(2H, m), 7.16–7.29(2H, m), 7.38(2H, d, J=8.7Hz), 7.59(1H, t, J=5.9Hz), 7.98(2H, dd, J=7.0, 1.9Hz), 8.20(2H, dd, J=7.0, 1.9Hz) |
| 267 | 1.67–1.94(2H, m), 2.09(2H, quint, J=6.0Hz), 2.53–3.20(8H, m), 3.46–5.00(4H, m), 3.60(2H, q, J=6.0Hz), 4.08(2H, t, J=6.0Hz), 4.34(1H, m), 6.63(2H, d, J=8.6Hz), 6.77(1H, t, J=6.0Hz), 6.88(2H, d, J=8.7Hz), 6.98–7.29(4H, m), 7.39 (2H, d, J=8.7Hz), 7.60(2H, d, J=8.6Hz) |
| 268 | 1.60–2.33(4H, m), 2.53–3.20(8H, m), 3.30(2H, m), 3.70–5.17(2H, m), 3.91(2H, t, J=5.9Hz), 4.33 (1H, m), 5.83(1H, brs), 6.82(2H, d, J=8.6Hz), 6.92–7.50(9H, m), 7.37(2H, d, J=8.6Hz), 7.67 (1H, s) |
| 269 | 1.70–2.12(4H, m), 2.00(3H, s), 2.14–2.50(4H, m), 2.53–3.20(8H, m), 3.44(2H, q, J=5.9Hz), 3.80–5.10(2H, brs), 4.03(2H, t, J=5.9Hz), 4.41(2H, m), 6.05(1H, brs), 6.70(1H, brs), 6.91(2H, d, J=8.6Hz), 6.98–7.32(5H, m), 7.41(2H, d, J=8.6 Hz), 7.51(1H, t, J=5.9Hz) |
| 270 | 1.66–1.97(2H, m), 2.04–2.30(2H, m), 2.15(3H, s), 2.44–3.20(8H, m), 3.60(2H, q, J=5.7Hz), 4.05 (2H, t, J=5.7Hz), 4.31(1H, m), 3.80–5.14(2H, m), 6.82(2H, d, J=8.7Hz), 6.99–7.42(5H, m), 7.31 (2H, d, J=8.7Hz), 7.54(2H, d, J=8.6Hz), 7.69 (2H, d, J=8.6Hz), 8.96(1H, brs) |
| 271 | 1.06(3H, t, J=6.8Hz), 1.84(2H, m), 1.92(2H, quint, J=5.9Hz), 2.25–3.20(8H, m), 3.15(2H, quint, J=6.8Hz), 3.30(2H, q, J=5.9Hz), 3.56–5.10 (2H, m), 4.00(2H, t, J=5.9Hz), 4.33(1H, m), 5.29 (1H, t, J=6.8Hz), 5.67(1H, t, J=5.9Hz), 6.89 (2H, d, J=8.4Hz), 6.98–7.32(4H, m), 7.39(2H, d, J=8.4Hz) |
| 272 | 1.40–1.62(2H, m), 1.62–1.94(6H, m), 2.23(2H, t, J=7.6Hz), 2.27(6H, s), 2.46(2H, t, J=5.8Hz), 2.52–3.10(8H, m), 3.34(2H, q, J=5.8Hz), 3.75–5.10(2H, m), 3.98(2H, t, J=6.3Hz), 4.38(1H, m), |

TABLE 8-continued

| | |
|---|---|
| | 6.33(1H, brs), 6.94(2H, d, J=8.7Hz), 6.98–7.30 (4H, m), 7.42(2H, d, J=8.7Hz), |
| 273 | 1.35–1.60(4H, m), 1.61–2.00(8H, m), 2.03–2.21 (4H, m), 2.53–3.14(10H, m), 3.50(2H, s), 3.60–5.20(2H, m), 3.83(1H, m), 3.97(2H, t, J=6.3Hz), 4.39(1H, m), 5.41(1H, d, J=8.0Hz), 6.88(2H, d, J=8.7Hz), 6.99–7.32(4H, m), 7.30(5H, m), 7.42 (2H, d, J=8.7Hz) |
| 274 | 1.70–2.20(6H, m), 1.99(3H, s), 2.08(3H, s), 2.35–3.20(10H, m), 3.45(2H, q, J=6.0Hz), 3.70–5.20(2H, m), 4.03(2H, t, J=6.0Hz), 4.38(1H, m), 4.57(1H, q, J=7.2Hz), 6.58(1H, d, J=6.0Hz), 6.80–6.98(1H, brs), 6.91(2H, d, J=8.6Hz), 6.99–7.29(4H, m), 7.43(2H, d, J=8.6Hz) |
| 275 | 1.70–2.03(4H, m), 2.05(3H, s), 2.58–3.22(8H, m), 2.99(2H, d, J=7.0Hz), 3.44(2H, d, J=5.9Hz), 3.55–5.30(2H, m), 3.96(2H, t, J=5.9Hz), 4.40 (1H, m), 4.72(1H, q, J=7.0Hz), 6.75(1H, s), 6.92 (2H, d, J=8.6Hz), 7.04–7.60(7H, m), 7.44(2H, d, J=8.6Hz) |
| 276 | 1.33(3H, d, J=7.0Hz), 1.65–1.93(2H, m), 1.93–2.12(2H, m), 1.97(3H, s), 2.53–3.20(8H, m), 3.43 (2H, q, J=6.1Hz), 3.80–5.20(2H, m), 4.02(2H, t, J=6.1Hz), 4.37(1H, m), 4.46(1H, quint, J=7.0 Hz), 6.64(1H, brs), 6.90(2H, d, J=8.7Hz), 6.98–7.29(5H, m), 7.42(2H, d, J=8.7Hz) |
| 277 | 1.38–1.64(4H, m), 1.65–2.10(8H, m), 2.20(2H, t, J=7.3Hz), 2.53–3.10(10H, m), 3.10–3.39(2H, m), 3.45–5.20(2H, m), 3.94(1H, m), 3.98(2H, t, J=6.3 Hz), 4.37(1H, m), 5.82(1H, d, J=7.8Hz), 6.90 (2H, d, J=8.7Hz), 6.98–7.28(4H, m), 7.41(2H, d, J=8.7Hz) |
| 278 | 1.85(4H, m), 2.54–3.24(10H, m), 3.35(2H, m), 3.63–5.00(2H, m), 3.85(2H, m), 4.31(2H, m), 5.11 (2H, s), 5.41(1H, brs), 6.15(1H, brs), 6.45(2H, d, J=8.3Hz), 6.77(2H, d, J=8.6Hz), 6.84(2H, d, J=8.3Hz), 7.00–7.30(4H, m), 7.34(5H, s), 7.37 (2H, d, J=8.6Hz), 8.12(1H, s) |
| 279 | 1.57–1.92(6H, m), 2.19–3.15(18H, m), 3.51–3.61 (2H, m), 3.84–5.22(3H, m), 3.99(2H, t, J=6.3Hz), 6.83–7.46(13H, m) |
| 280 | 1.57–2.05(6H, m), 2.40–3.56(21H, m), 3.73–5.12 (3H, m), 4.02(2H, t, J=5.9Hz), 6.83–7.52(8H, m) |
| 281 | 1.59–1.98(6H, m), 2.32–3.16(14H, m), 3.35–5.18 (7H, m), 3.70(3H, s), 4.01(2H, t, J=6.2Hz), 6.83–7.48(8H, m) |
| 282 | 1.66–2.12(6H, m), 2.32–3.13(12H, m), 3.33–5.10 (13H, m), 6.84–7.49(13H, m) |
| 283 | 1.57–1.95(6H, m), 2.09(3H, s), 2.28–3.28(14H, m), 3.48–5.07(7H, m), 4.01(2H, t, J=6.2Hz), 6.87–7.49(8H, m) |
| 284 | 1.71–1.98(6H, m), 2.15(1H, brs), 2.49–3.16(12H, m), 3.32–5.12(11H, m), 6.85–7.48(8H, m) |
| 285 | 1.34–2.01(8H, m), 2.41–3.23(12H, m), 3.56–5.18 (8H, m), 6.82–7.48(11H, m) |
| 286 | 1.39–1.96(8H, m), 2.03(2H, brs), 2.43–3.18(10H, m), 3.35–5.15(4H, m), 3.99(2H, t, J=6.3Hz), 6.84–7.47(8H, m) |
| 287 | 1.42–1.94(8H, m), 1.98(3H, s), 2.08(3H, s), 2.50–3.18(8H, m), 3.30–3.58(2H, m), 3.71–5.07 (4H, m), 3.97(2H, t, J=6.2Hz), 5.90–6.03(1H, m), 6.87–7.49(8H, m) |
| 288 | 1.38–2.08(8H, m), 1.99(3H, s), 2.39–3.56(11H, m), 3.58–5.11(6H, m), 6.17–6.42(1H, m), 6.82–7.48 (8H, m) |
| 289 | 1.37–1.94(8H, m), 2.14–3.15(19H, m), 2.32(3H, s), 3.58–5.07(4H, m), 3.99(2H, t, J=6.4Hz), 6.82–7.48(8H, m) |
| 290 | 1.65–1.98(6H, m), 2.33–3.13(10H, m), 2.39(6H, s), 3.88–4.99(3H, m), 4.02(2H, t, J=5.9Hz), 6.83–7.50(8H, m) |
| 291 | 1.44–2.03(6H, m), 2.21(6H, s), 2.28(2H, t, J=7.2 Hz), 2.52–3.28(10H, m), 3.76–5.13(3H, m), 6.98–7.42(8H, m) |
| 292 | 1.36–1.98(10H, m), 2.12–2.39(2H, m), 2.28(6H, s), 2.52–3.12(10H, m), 3.55–5.13(5H, m), 3.99 (2H, t, J=6.3Hz), 6.86–7.48(8H, m) |
| 293 | 1.04(6H, t, J=7.1Hz), 1.32–1.95(10H, m), 2.20–3.16(16H, m), 3.43–5.13(5H, m), 4.00(2H, t, J=6.4Hz), 6.86–7.49(8H, m) |
| 294 | 0.89(6H, t, J=7.4Hz), 1.32–1.94(16H, m), 2.26–3.12(14H, m), 3.45–4.98(5H, m), 3.99(2H, t, J=6.3Hz), 6.34–7.49(8H, m) |
| 295 | 1.12(3H, t, J=7.1Hz), 1.38–1.96(10H, m), 2.26–3.12(15H, m), 3.46–5.06(5H, m), 3.99(2H, t, J=6.0Hz), 6.89(2H, d, J=8.7Hz), 6.99–7.32(4H, m), 7.42(2H, d, J=8.7Hz) |
| 296 | 1.07(6H, t, J=7.2Hz), 1.28–1.94(8H, m), 2.25–3.17(15H, m), 3.55–5.08(7H, m), 3.96(2H, t, J=6.5Hz), 6.42–7.33(6H, m) |
| 297 | 1.04(6H, t, J=7.1Hz), 1.42–2.14(6H, m), 2.23–3.13(14H, m), 3.56–5.02(7H, m), 6.87–7.49(8H, m) |
| 298 | 1.51–2.13(10H, m), 2.52–3.40(15H, m), 3.78–5.03 (6H, m), 6.83–7.48(8H, m) |
| 299 | 1.35–2.10(12H, m), 2.13–3.12(15H, m), 3.57–4.83 (6H, m), 6.82–7.53(8H, m) |
| 300 | 1.44–2.12(6H, m), 2.20–3.13(15H, m), 3.15–4.86 (10H, m), 6.88–7.57(8H, m) |
| 301 | 1.08(6H, t, J=7.9Hz), 1.43–1.93(8H, m), 2.40–3.16(14H, m), 3.28–5.17(4H, m), 3.45(2H, t, J=5.1Hz), 3.51(2H, t, J=8.0Hz), 3.99(2H, t, J=6.4Hz), 6.84–7.48(4H, m) |
| 302 | 1.48–1.93(8H, m), 2.27–3.13(10H, m), 2.45(6H, s), 3.36–3.67(5H, m), 3.73–5.17(4H, m), 3.99(2H, t, J=6.3Hz), 6.86–7.50(8H, m) |
| 303 | 1.23(6H, t, J=7.2Hz), 1.67–1.94(2H, m) 2.06 (2H, quint, J=6.2Hz), 2.43–3.14(14H, m), 3.38–3.62(4H, m), 3.66(2H, t, J=6.1Hz), 3.87–5.22 (4H, m), 4.08(2H, t, J=6.1Hz), 6.85–7.48(8H, m) |
| 304 | 1.38–1.98(12H, m), 2.25–3.18(14H, m), 3.33–5.13 (7H, m), 6.80–7.50(8H, m) |
| 305 | 1.26–1.92(8H, m), 2.15–3.13(14H, m), 2.32(3H, s), 3.20–5.03(5H, m), 3.98(2H, t, J=6.4Hz), 6.82–7.47(13H, m) |
| 306 | 1.37–1.94(8H, m), 2.28–3.23(14H, m), 2.36(3H, s), 3.54–5.15(4H, m), 3.68(2H, t, J=4.8Hz), 4.00 (2H, t, J=6.3Hz), 6.83–7.52(8H, m) |
| 307 | 1.33–1.98(8H, m), 2.28–3.18(14H, m), 3.38–5.18 (11H, m), 3.98(2H, t, J=6.2Hz), 6.78–7.48(8H, m) |
| 308 | 1.35–1.98(8H, m), 2.25–3.32(18H, m), 3.38–5.10 (7H, m), 6.78–7.48(13H, m) |
| 309 | 1.38–1.98(16H, m), 2.23–3.15(14H, m), 3.32–5.05 (5H, m), 4.00.(2H, t, J=6.3Hz), 6.32–7.50(8H, m) |
| 310 | 1.43(6H, t, J=7.3Hz), 1.35–1.65(4H, m), 1.70–1.98(6H, m), 2.51–3.23(4H, m), 3.77–5.23(3H, m), 3.99(2H, t, J=6.2Hz), 6.85–7.51(8H, m) |
| 311 | 1.34–2.31(6H, m), 2.51–3.65(14H, m), 3.70–5.14 (3H, m), 3.98(2H, t, J=6.2Hz), 6.83–7.50(8H, m) |
| 312 | 1.46–2.06(12H, m), 2.16–3.13(14H, m), 3.33–5.07 (5H, m), 4.00(2H, t, J=6.0Hz), 6.83–7.48(8H, m) |
| 313 | 1.13(3H, t, J=7.2Hz), 1.38–2.02(9H, m), 2.37–3.13(12H, m), 3.53–5.12(3H, m), 3.99(2H, t, J=6.3Hz), 6.82–7.52(8H, m) |
| 314 | 1.11(6H, dd, J=6.3, 1.0Hz), 1.38–1.95(8H, m), 2.35–3.12(13H, m), 3.46–5.09(4H, m), 3.99(2H, t, J=6.3Hz), 6.32–7.49(8H, m) |
| 315 | 1.02(3H, t, J=7.1Hz), 1.28–2.03(14H, m), 2.21–3.12(14H, m), 3.28–5.12(8H, m), 3.99(2H, t, J=6.4Hz), 6.82–7.48(8H, m) |
| 316 | 1.38–1.96(8H, m), 2.28–3.13(17H, m), 3.62–5.08 (5H, m), 3.99(2H, t, J=6.3Hz), 6.82–7.48(13H, m) |
| 317 | 1.37–2.00(12H, m), 2.18–3.30(15H, m), 3.40–5.16 (4H, m), 3.47(1H, dd, J=11.1, 4.1Hz), 3.62(1H, dd, J=11.1, 4.1Hz), 3.99(2H, t, J=6.4Hz), 6.82–7.48(8H, m) |
| 318 | 1.35–1.95(8H, m), 2.18–3.13(10H, m), 2.24(3H, s), 3.46(1H, d, J=13.0Hz), 3.69(1H, d, J=13.0 Hz), 3.55–5.14(4H, m), 3.99(2H, t, J=6.3Hz), 6.82–7.48(13H, m) |
| 319 | 1.65–2.08(6H, m), 2.46–3.49(10H, m), 3.78–5.08 (5H, m), 6.81(2H, d, J=8.7Hz), 6.95–7.75(10H, m), 11.40(1H, brs) |
| 320 | 1.30–1.99(10H, m), 2.45–3.20(8H, m), 3.74–5.20 (5H, m), 3.98(2H, t, J=6.4Hz), 4.06(2H, t, J=6.6 Hz), 6.90(2H, d, J=8.7Hz), 6.93–7.57(6H, m) |
| 321 | 1.68–2.32(6H, m), 2.49–3.64(10H, m), 3.77–5.10 (5H, m), 6.80(2H, d, J=9.1Hz), 6.96–7.91(10H, m), 12.03(1H, s) |

TABLE 8-continued

| 322 | 1.55–1.97(2H, m), 2.07–2.32(2H, m), 2.55–5.17 (7H, m), 3.92(2H, t, J=6.8Hz), 4.06(2H, t, J=6 Hz), 6.65(1H, d, J=9.4Hz), 6.82(2H, d, J=8.7 Hz), 7.10–8.05(11H, m), |
|---|---|
| 323 | 1.61–2.08(6H, m), 2.65–3.34(4H, m), 2.93(2H, t, J=6.8Hz), 3.88–5.20(3H, m), 4.09(2H, t, J=6Hz), 6.65(1H, d, J=9.4Hz), 6.93(2H, d, J=8.8Hz), 7.11–7.77(7H, m) |
| 324 | 1.62–2.09(4H, m), 1.93(3H, s), 2.60–3.49(6H, m), 3.85–5.15(3H, m), 4.00(2H, t, J=5.9Hz), 6.00 (1H, brs), 6.59(1H, d, J=9.4Hz), 6.85(2H, d, J=8.7Hz), 7.08–7.66(7H, m) |
| 325 | 1.30–2.15(8H, m), 2.32–3.20(8H, m), 3.53–4.05 (6H, m), 4.20–4.78(1H, m), 4.80–5.15(3H, m), 5.70–5.93(1H, m), 6.38–6.88(4H, m), 7.10–7.35 (1H, m) |
| 326 | 1.28–1.96(8H, m), 2.30–3.21(11H, m), 3.56–4.10 (6H, m), 4.12–4.78(1H, m), 4.83–5.10(1H, m), 6.40–6.85(4H, m), 7.12–7.32(1H, m) |
| 327 | 1.41(3H, t, J=6.9Hz), 1.52–1.90(2H, m), 2.30 (3H, s), 2.38–3.27(8H, m), 3.55–3.93(4H, m), 4.04 (2H, q, J=6.9Hz), 4.20–4.68(1H, m), 4.80–5.08 (1H, m), 6.35–6.64(2H, m), 6.78–7.37(4H, m) |
| 328 | 1.64–1.86(3H, m), 2.30(3H, s), 2.40–2.90(8H, m), 3.12–3.31(2H, m), 4.20–4.40(1H, m), 6.82–7.20 (3H, m) |

Example 588

To 1-[1-(2-methoxy-4-ethoxybenzoyl)-4-piperidinyl]-3-ethoxycarbonyl-3,4-dihydrocarbostyril (0.48 g) are added sodium hydroxide (0.2 g), water (4 ml) and ethanol (10 ml) and the mixture is stirred at room temperature for 30 minutes. Water is added to the reaction mixture and the mixture is extracted with ethyl acetate. The aqueous layer is neutiralized with acetic acid and extracted with dichloromethane. The extract is concentrated to give 1-[1-(2-methoxy-4-ethoxybenzoyl)-4-piperidinyl]-3-carboxy-3,4-dihydrocarbostyril (0.38 g) as white amorphous form.

NMR (CDCl$_3$) δ ppm: 1.42 (3H, t, J=7.0 Hz), 1.58–2.05 (2H, m), 2.35–3.47 (7H, m), 3.55–3.95 (4H, m), 4.04 (2H, q, J=7 Hz), 4.38 (1H, brs), 4.94 (1H, brs), 6.37–6.56 (2H, m), 7.00–7.40 (5H, m)

Example 589

To 1-[1-(2-methoxy-4-ethoxybenzoyl)4-piperidinyl]-3-ethoxycarbonyl-3,4-dihydrocarbstyril (1.1 g) are added hydrazine monohydrate (1.1 g) and ethanol (15 ml) and the mixture is refluxed with heating for 7 hours. The reaction mixture is concentrated and the residue is purified by silica gel column chromatography (solvent: dichloromethane→dichloromethane:methanol=20:1) to give 1-[1-(2-methoxy-4-ethoxybenzoyl)4-piperidinyl]-3-hydrazinocarbonyl-3,4-dihydrocarbostyril (0.9 g) as white amorphous form.

NMR (CDCl$_3$) δ ppm: 1.42 (3H, t, J=7.0 Hz), 1.52–1.95 (2H, m), 2.30–3.93 (13H, m), 4.04 (2H, q, J=7 Hz), 4.15–5.06 (3H, m), 6.40–6.62 (2H, m), 6.97–7.50 (5H, m)

Example 590

To 1-[1-(2-methoxy-4-ethoxybenzoyl)-4-piperidinyl]-3-hydrazinocarbonyl-3,4-dihydrocarbostyril (1.4 g) are added dichloromethane (14 ml), 10% hydrochloric acid (5.5 ml) and water (14 ml). To the mixture is added dropwise a solution of sodium nitrite (0.25 g) in water (3 ml) at a temperature below 5° C. The mixture is stirred at 5° C. for 15 minutes. The dichloromethane layer is separated, dried and concentrated. To the resulting residue are added benzyl alcohol (0.5 g) and toluene (7 ml) and the mixture is refluxed with heating for 2 hours. After cocentration, the resulting residue is purified by silica gel column chromatography (solvent: dichloromethane) to give 1-[1-(2-methoxy-4-ethoxybenzoyl)-4-piperidinyl]-3-benzyloxycarbonylamino-3,4-dihydrocarbostyril (0.9 g) as white amorphous form.

NMR (CDCl$_3$) δ ppm: 1.40 (3H, t, J=7.0 Hz), 1.55–2.00 (2H, m), 2.30–5.05 (15H, m), 5.30 (2H, s), 5.95 (1H, brs), 6.50–6.60 (2H, m), 7.02–7.42 (10H, m)

Example 591

To 1-[1-(2-methoxy-4-ethoxybenzoyl)-4-piperidinyl]-3-benzyloxycarbonylamino-3,4-dihydrocarbostyril (0.8 g) are added ethanol (20 ml) and 10% palladium-carbon (0.15 g) and the mixture is subjected to catalytic reduction at room temperature for 4 hours. After the catalyst is removed by filtration, the resulting filtrate is concentrated. To the residue are added ethanol (5 ml) and conc. hydrochloric acid (0.2 ml) and the mixture is concentrated again. Diethyl ether is added to the residue and the precipitated crystal is collected by filtration and recrystallized from ethanol to give 1-[1-(2-methoxy-4-ethoxybenzoyl)-4-piperidinyl]-3-amino-3,4-dihydrocarbostyril.hydrochloride (0.52 g) as white powder, m.p.: 257°–260° C.

Example 592

To 1-{1-[4-(5-carboxypentyloxy)benzoyl]-4-piperidinyl}-3,4-dihydrocarbostyril (2.00 g) are added 3,4-diaminopyridine (0.47 g), phosphorus pentoxide (1.00 g) and methanesulfonic acid (7.0 ml) and the mixture is stirred with heating at 100°–120° C. for 3 hours. After cooling, the reaction solution is poured into ice-water (30 ml) and the mixture is adjusted to around pH 11 with aqueous sodium hydroxide solution and extracted with dichloromethane. The extract is dried with magnesium sulfate and the solvent is distilled off. The resulting residue is purified by silica gel column chromatography (solvent: dichloromethane:methanol=20:1→9:1) to give 1-{1-[4-(5-(imidazo[4,5-c]pyridine-2-yl)carboxypentyloxy)benzoyl]-4-piperidinyl}-3,4-dihydrocarbostyril (1.32 g) as white amorphous form.

NMR (CDCl$_3$) δ ppm: 1.42–1.64 (2H, m), 1.64–2.06 (6H, m), 2.57 (2H, t, J=6.1 Hz), 2.64–3.24 (8H, m), 3.67–5.15 (2H, m), 3.92 (2H, t, J=6.1 Hz), 4.34 (1H, m), 6.84 (2H, d, J=8.7 Hz), 7.00–7.36 (5H, m), 7.40 (2H, d, J=8.7 Hz), 8.28 (1H, d, J=5.6 Hz), 8.80 (1H, s)

Example 593

To methyl 2-methyl-5-[(1-benzyl-4-piperidinyl)amino] cinnamate (1.0 g) are added acetic acid (10 ml), conc. hydrochloric acid (3 ml), water (3 ml) and 10% palladium-carbon (0.2 g) and the mixture is subjected to catalytic reduction at 90° C. for 2 hours under atmospheric pressure. After cooling, the catalyst is removed by filtration and the filtrate is concentrated. Water is added to the resulting residue and the mixture is basified with potassium carbonate and then extracted with dichloromethane. The solvent is concentrated to give 5-methyl-1-(4-piperidinyl)-3,4-dihydrocarbostyril (0.6 g) as colorless amorphous form.

NMR (CDCl$_3$) δ ppm: 1.64–1.86 (3H, m), 2.30 (3H, s), 2.40–2.90 (8H, m), 3.12–3.31 (2H, m), 4.20–4.40 (1H, m), 6.82–7.20 (3H, m)

Using the suitable starting materials, the compounds of the above Examples 1–9, 11–164, 169–383C, 435–474A and 482–577A are obtained in the same manners as Example 593.

Using the suitable starting materials, the following compounds are obtained in the same manners as in Examples 1, 384 and 593.

TABLE 9

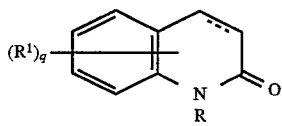

Example 594

Structure

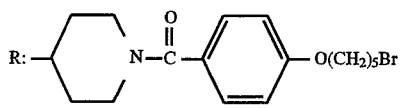

R¹: H,  q: 1
Bond between 3- and 4-positions in the carbostyril ring: Single bond
NMR analysis: 491)
Form: Free Example 595

Structure

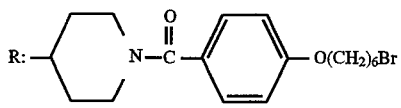

R¹: H,  q: 1
Bond between 3- and 4-positions in the carbostyril ring: Single bond
NMR analysis: 492)
Form: Free Example 596

Structure

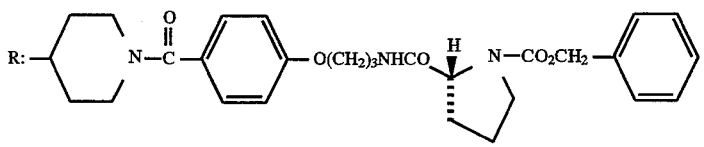

R¹: H,  q: 1
Bond between 3- and 4-positions in the carbostyril ring: Single bond
Crystalline form: Colorless amorphous form
NMR analysis: 329)
Form: Free Example 597

Structure

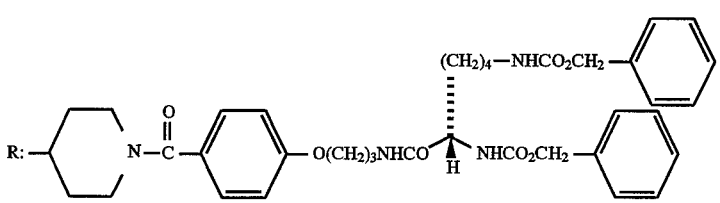

R¹: H,  q: 1
Bond between 3- and 4-positions in the carbostyril ring: Single bond
Crystalline form: Colorless amorphous form
NMR analysis: 330)
Form: Free TABLE 9-continued

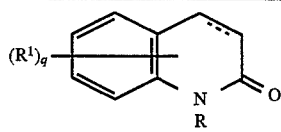

Example 598

Structure

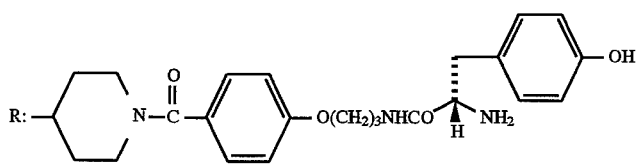

$R^1$: H,   q: 1
Bond between 3- and 4-positions in the
carbostyril ring: Single bond
Crystalline form: Colorless amorphous form
NMR analysis: 331)
Form: Free Example 599

Structure

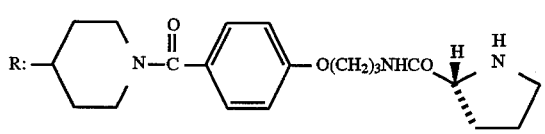

$R^1$: H,   q: 1
Bond between 3- and 4-positions in the
carbostyril ring: Single bond
Crystalline form: Colorless amorphous form
NMR analysis: 332)
Form: Free Example 600

Structure

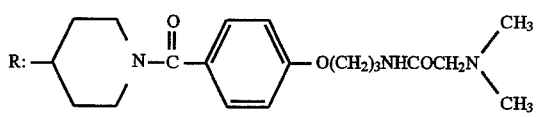

$R^1$: H,   q: 1
Bond between 3- and 4-positions in the
carbostyril ring: Single bond
NMR analysis: 333)
Form: Free Example 601

Structure

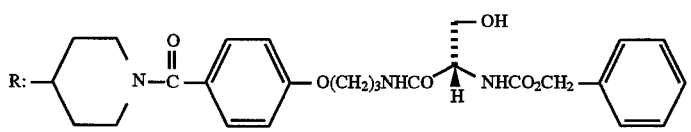

$R^1$: H,   q: 1
Bond between 3- and 4-positions in the
carbostyril ring: Single bond
Crystalline form: Colorless amorphous form
NMR analysis: 334)
Form: Free

TABLE 9-continued

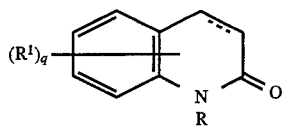

Example 602

Structure

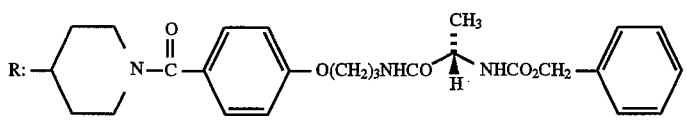

R[1]: H,  q: 1
Bond between 3- and 4-positions in the
carbostyril ring: Single bond
Crystalline form: Colorless amorphous form
NMR analysis: 335)
Form: Free Example 603

Structure

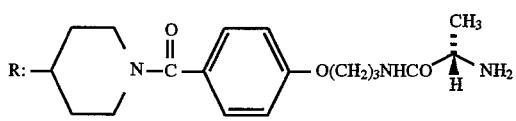

R[1]: H,  q: 1
Bond between 3- and 4-positions in the
carbostyril ring: Single bond
Crystalline form: Colorless amorphous form
NMR analysis: 336)
Form: Free Example 604

Structure

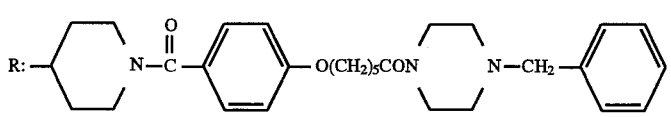

R[1]: H,  q: 1
Bond between 3- and 4-positions in the
carbostyril ring: Single bond
NMR analysis: 337)
Form: Free Example 605

Structure

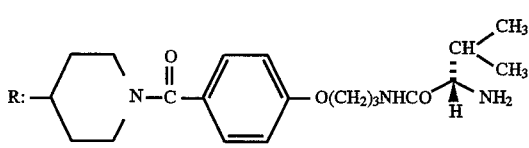

R[1]: H,  q: 1
Bond between 3- and 4-positions in the
carbostyril ring: Single bond
Crystalline form: Colorless amorphous form
NMR analysis: 338)
Form: Free TABLE 9-continued

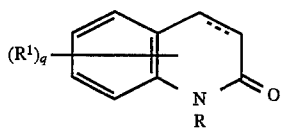

Example 606

Structure

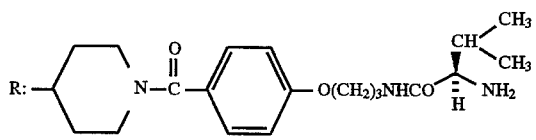

$R^1$: H,  q: 1
Bond between 3- and 4-positions in the
carbostyril ring: Single bond
Crystalline form: Colorless amorphous form
NMR analysis: 339)
Form: Free Example 607

Structure

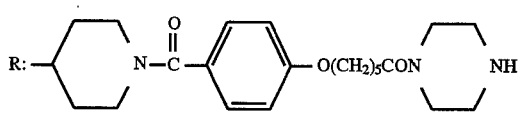

$R^1$: H,  q: 1
Bond between 3- and 4-positions in the
carbostyril ring: Single bond
Crystalline form: Colorless amorphous form
NMR analysis: 340)
Form: Free Example 608

Structure

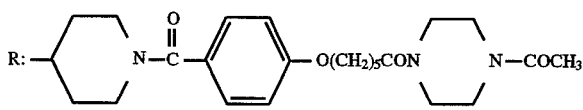

$R^1$: H,  q: 1
Bond between 3- and 4-positions in the
carbostyril ring: Single bond
Crystalline form: Colorless amorphous form
NMR analysis: 341)
Form: Free Example 609

Structure

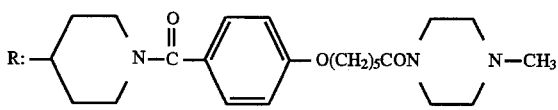

$R^1$: H,  q: 1
Bond between 3- and 4-positions in the
carbostyril ring: Single bond
Crystalline form: Colorless amorphous form
NMR analysis: 342)
Form: Free TABLE 9-continued

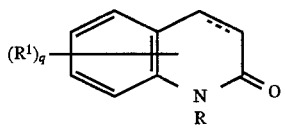

Example 610

Structure

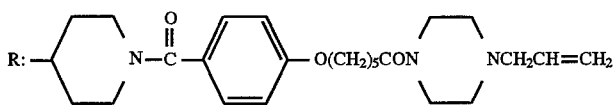

R¹: H,   q: 1
Bond between 3- and 4-positions in the
carbostyril ring: Single bond NMR analysis: 343)
Form: Free Example 611

Structure

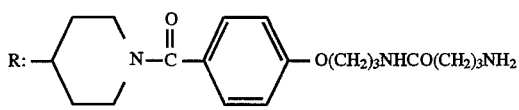

R¹: H,   q: 1
Bond between 3- and 4-positions in the
carbostyril ring: Single bond NMR analysis: 344)
Form: Free Example 612

Structure

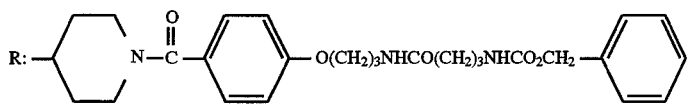

R¹: H,   q: 1
Bond between 3- and 4-positions in the
carbostyril ring: Single bond NMR analysis: 345)
Form: Free Example 613

Structure

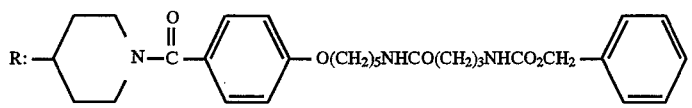

R¹: H,   q: 1
Bond between 3- and 4-positions in the
carbostyril ring: Single bond NMR analysis: 346)
Form: Free Example 614

Structure

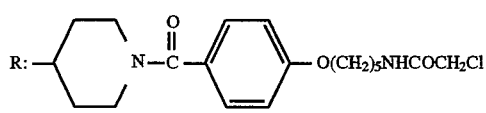

R¹: H,   q: 1
Bond between 3- and 4-positions in the
carbostyril ring: Single bond TABLE 9-continued

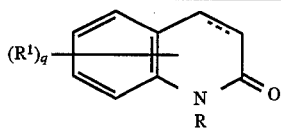

NMR analysis: 347)
Form: Free

Example 615

Structure

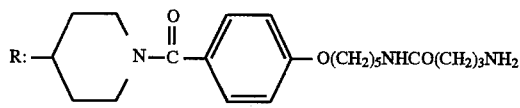

R¹: H,   q: 1
Bond between 3- and 4-positions in the
carbostyril ring: Single bond
NMR analysis: 348)
Form: Free Example 616

Structure

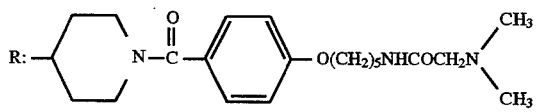

R¹: H,   q: 1
Bond between 3- and 4-positions in the
carbostyril ring: Single bond
NMR analysis: 349)
Form: Free Example 617

Structure

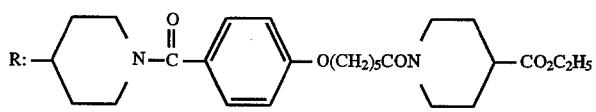

R¹: H,   q: 1
Bond between 3- and 4-positions in the
carbostyril ring: Single bond
NMR analysis: 350)
Form: Free Example 618

Structure

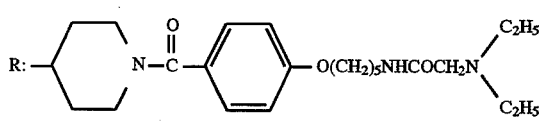

R¹: H,   q: 1
Bond between 3- and 4-positions in the
carbostyril ring: Single bond
NMR analysis: 351)
Form: Free Example 619

Structure

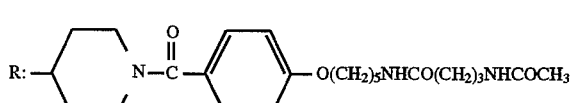

TABLE 9-continued

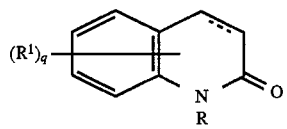

R[1]: H,   q: 1
Bond between 3- and 4-positions in the
carbostyril ring: Single bond
NMR analysis: 352)
Form: Free
Example 620

Structure

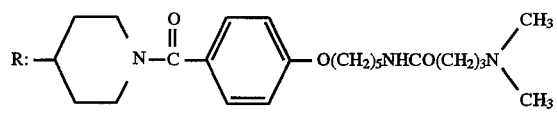

R[1]: H,   q: 1
Bond between 3- and 4-positions in the
carbostyril ring: Single bond
NMR analysis: 353)
Form: Free
Example 621

Structure

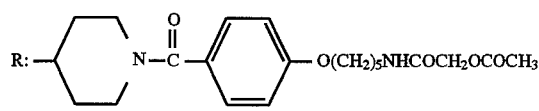

R[1]: H,   q: =1
Bond between 3- and 4-positions in the
carbostyril ring: Single bond
Crystalline form: Colorless amorphous form
NMR analysis: 354)
Form: Free
Example 622

Structure

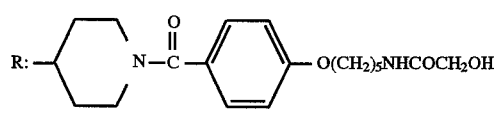

R[1]: H,   q: =1
Bond between 3- and 4-positions in the
carbostyril ring: Single bond
Crystalline form: Colorless amorphous form
NMR analysis: 355)
Form: Free
Example 623

Structure

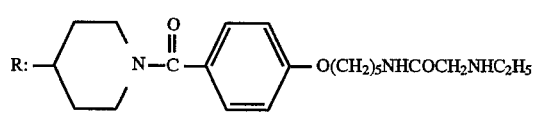

R[1]: H,   q: 1
Bond between 3- and 4-positions in the
carbostyril ring: Single bond
NMR analysis: 356)
Form: Free TABLE 9-continued

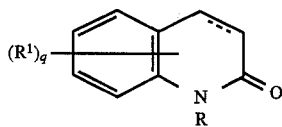

Example 624

Structure

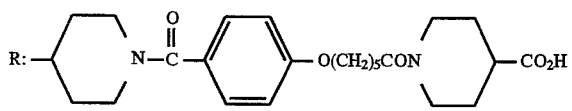

R[1]: H, q: =1
Bond between 3- and 4-positions in the
carbostyril ring: Single bond
Crystalline form: Colorless amorphous form
NMR analysis: 357)
Form: Free Example 625

Structure

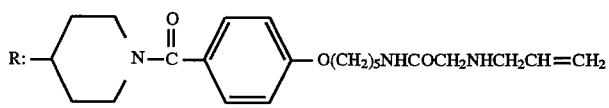

R[1]: H, q: 1
Bond between 3- and 4-positions in the
carbostyril ring: Single bond
NMR analysis: 358)
Form: Free Example 626

Structure

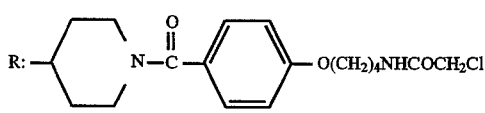

R[1]: H, q: 1
Bond between 3- and 4-positions in the
carbostyril ring: Single bond
NMR analysis: 359)
Form: Free Example 627

Structure

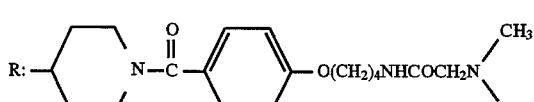

R[1]: H, q: 1
Bond between 3- and 4-positions in the
carbostyril ring: Single bond
NMR analysis: 360)
Form: Free Example 628

Structure

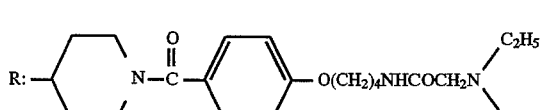

TABLE 9-continued

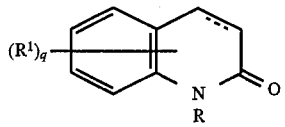

R$^1$: H,  q: 1
Bond between 3- and 4-positions in the
carbostyril ring: Single bond
NMR analysis: 361)
Form: Free
Example 629

Structure

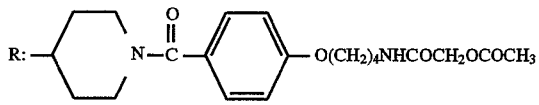

R$^1$: H,  q: =1
Bond between 3- and 4-positions in the
carbostyril ring: Single bond
Crystalline form: Colorless amorphous form
NMR analysis: 362)
Form: Free
Example 630

Structure

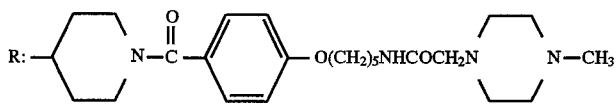

R$^1$: H,  q: 1
Bond between 3- and 4-positions in the
carbostyril ring: Single bond
NMR analysis: 363)
Form: Free
Example 631

Structure

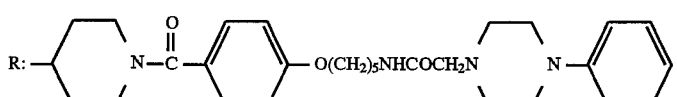

R$^1$: H,  q: =1
Bond between 3- and 4-positions in the
carbostyril ring: Single bond
Crystalline form: Colorless amorphous form
NMR analysis: 364)
Form: Free
Example 632

Structure

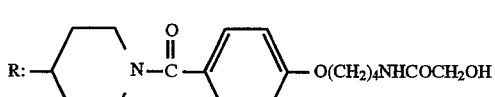

R$^1$: H,  q: =1
Bond between 3- and 4-positions in the
carbostyril ring: Single bond
Crystalline form: Colorless amorphous form
NMR analysis: 365)
Form: Free

TABLE 9-continued

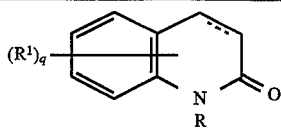

Example 633

Structure

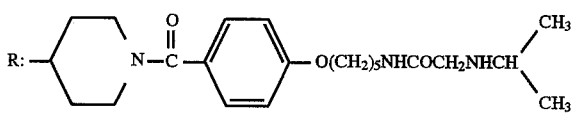

R¹: H,   q: 1
Bond between 3- and 4-positions in the
carbostyril ring: Single bond
NMR analysis: 366)
Form: Free

Example 634

Structure

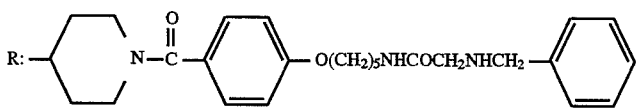

R¹: H,   q: 1
Bond between 3- and 4-positions in the
carbostyril ring: Single bond
NMR analysis: 367)
Form: Free

Example 635

Structure

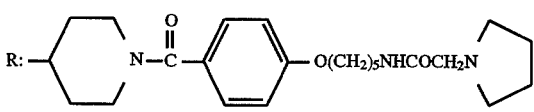

R¹: H,   q: 1
Bond between 3- and 4-positions in the
carbostyril ring: Single bond
NMR analysis: 368)
Form: Free

Example 636

Structure

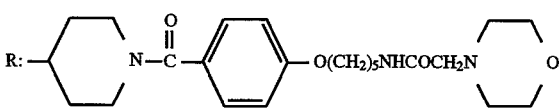

R¹: H,   q: 1
Bond between 3- and 4-positions in the
carbostyril ring: Single bond
NMR analysis: 369)
Form: Free

Example 637

Structure

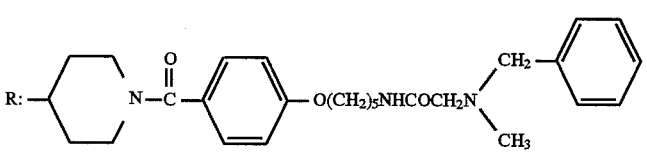

TABLE 9-continued

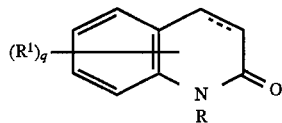

R¹: H,   q: 1
Bond between 3- and 4-positions in the
carbostyril ring: Single bond
NMR analysis: 370)
Form: Free
Example 638

Structure

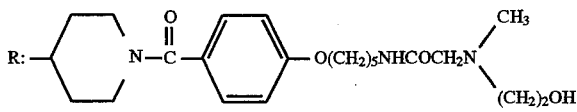

R¹: H,   q: 1
Bond between 3- and 4-positions in the
carbostyril ring: Single bond
NMR analysis: 371)
Form: Free
Example 639

Structure

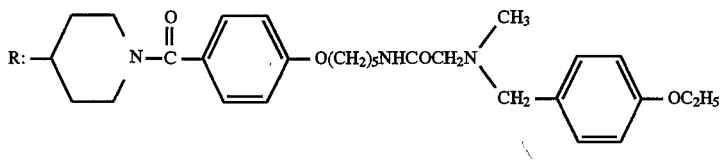

R¹: H,   q: 1
Bond between 3- and 4-positions in the
carbostyril ring: Single bond
NMR analysis: 372)
Form: Free
Example 640

Structure

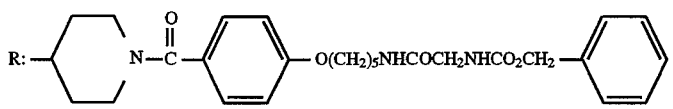

R¹: H,   q: 1
Bond between 3- and 4-positions in the
carbostyril ring: Single bond
Crystalline form: Colorless amorphous form
NMR analysis: 373)
Form: Free
Example 641

Structure

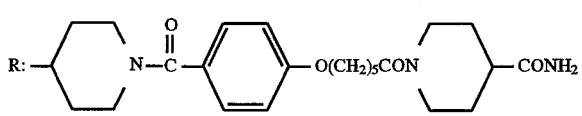

R¹: H,   q: 1
Bond between 3- and 4-positions-in the
carbostyril ring: Single bond
Crystalline form: Colorless amorphous form
NMR analysis: 374)
Form: Free TABLE 9-continued

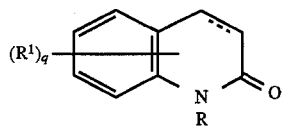

Example 642

Structure

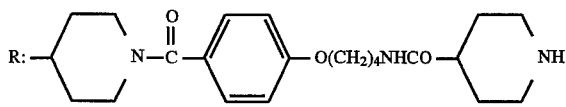

R[1]: H,  q: 1
Bond between 3- and 4-positions in the
carbostyril ring: Single bond
Crystalline form: Colorless amorphous form
NMR analysis: 375)
Form: Free Example 643

Structure

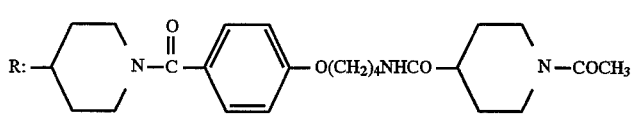

R[1]: H,  q: 1
Bond between 3- and 4-positions in the
carbostyril ring: Single bond
Crystalline form: Colorless amorphous form
NMR analysis: 376)
Form: Free Example 644

Structure

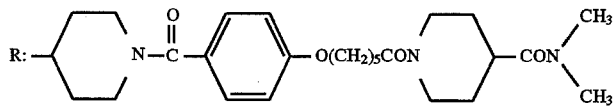

R[1]: H,  q: 1
Bond between 3- and 4-positions in the
carbostyril ring: Single bond
Crystalline form: Colorless amorphous form
NMR analysis: 377)
Form: Free Example 645

Structure

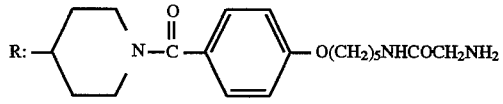

R[1]: H,  q: 1
Bond between 3- and 4-positions in the
carbostyril ring: Single bond
NMR analysis: 378)
Form: Free Example 646

Structure

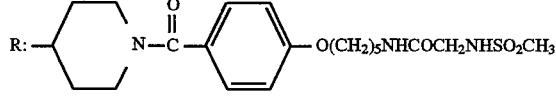

TABLE 9-continued

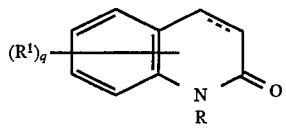

R¹: H,  q: 1
Bond between 3- and 4-positions in the
carbostyril ring: Single bond
Crystalline form: Colorless amorphous form
NMR analysis: 379)
Form: Free
Example 647

Structure

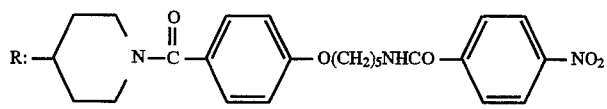

R¹: H,  q: 1
Bond between 3- and 4-positions in the
carbostyril ring: Single bond
Crystalline form: Colorless amorphous form
NMR analysis: 380)
Form: Free
Example 648

Structure

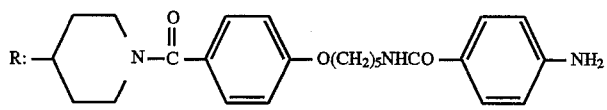

R¹: H,  q: 1
Bond between 3- and 4-positions in the
carbostyril ring: Single bond
Crystalline form: Colorless amorphous form
NMR analysis: 381)
Form: Free
Example 649

Structure

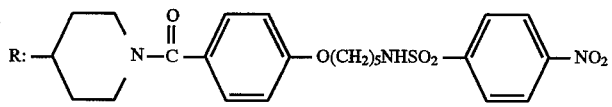

R¹: H,  q: 1
Bond between 3- and 4-positions in the
carbostyril ring: Single bond
Crystalline form: Colorless amorphous form
NMR analysis: 382)
Form: Free
Example 650

Structure

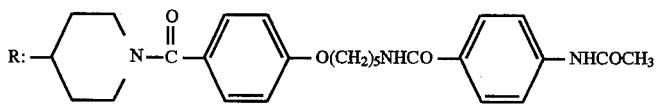

R¹: H,  q: 1
Bond between 3- and 4-positions in the
carbostyril ring: Single bond
Crystalline form: Colorless amorphous form
NMR analysis: 383)
Form: Free TABLE 9-continued

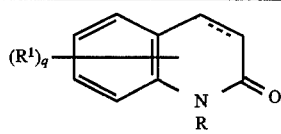

Example 651

Structure

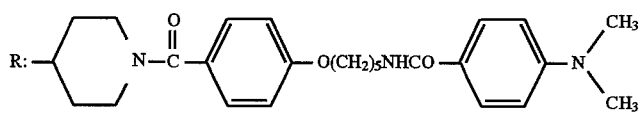

$R^1$: H, q: 1
Bond between 3- and 4-positions in the
carbostyril ring: Single bond
Crystalline form: Colorless amorphous form
NMR analysis: 384)
Form: Free Example 652

Structure

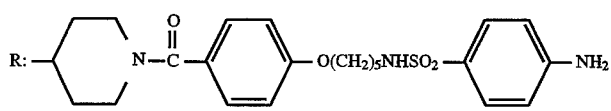

$R^1$: H, q: 1
Bond between 3- and 4-positions in the
carbostyril ring: Single bond
Crystalline form: Colorless amorphous form
NMR analysis: 385)
Form: Free Example 653

Structure

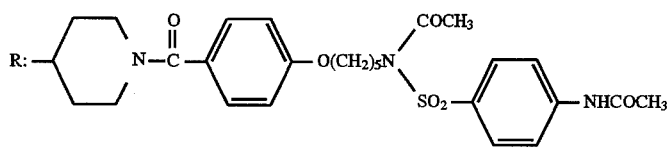

$R^1$: H, q: 1
Bond between 3- and 4-positions in the
carbostyril ring: Single bond
Crystalline form: Colorless amorphous form
NMR analysis: 386)
Form: Free Example 654

Structure

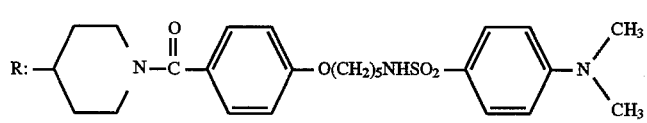

$R^1$: H, q: 1
Bond between 3- and 4-positions in the
carbostyril ring: Single bond
Crystalline form: Colorless amorphous form
NMR analysis: 387)
Form: Free TABLE 9-continued

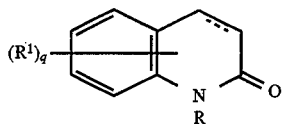

Example 655

Structure

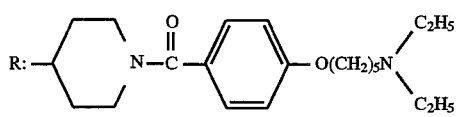

$R^1$: H, q: 1
Bond between 3- and 4-positions in the
carbostyril ring: Single bond
NMR analysis: 388)
Form: Free Example 656

Structure

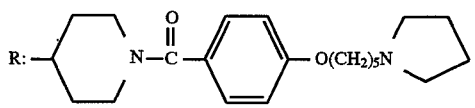

$R^1$: H, q: 1
Bond between 3- and 4-positions in the
carbostyril ring: Single bond
NMR analysis: 389)
Form: Free Example 657

Structure

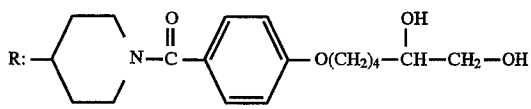

$R^1$: H, q: 1
Bond between 3- and 4-positions in the
carbostyril ring: Single bond
NMR analysis: 390)
Form: Free Example 658

Structure

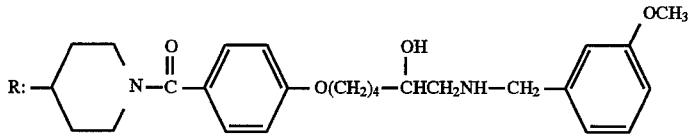

$R^1$: H, q: 1
Bond between 3- and 4-positions in the
carbostyril ring: Single bond
NMR analysis: 391)
Form: Free Example 659

Structure

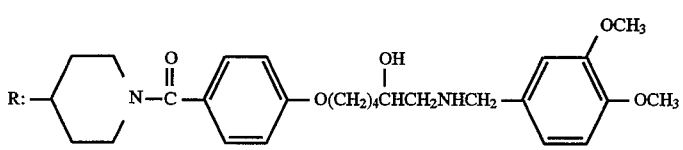

TABLE 9-continued

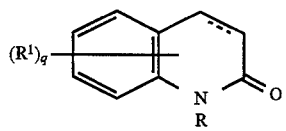

R¹: H,   q: 1
Bond between 3- and 4-positions in the
carbostyril ring: Single bond
Crystalline form: White powders
Recrystallization solvent: Ethanol/water
Melting point: 152–155° C.
Form: Oxalate Example 660

Structure

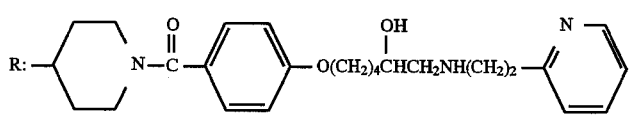

R¹: H,   q: 1
Bond between 3- and 4- positions in the
carbostyril ring: Single bond
NMR analysis: 392)
Form: Free Example 661

Structure

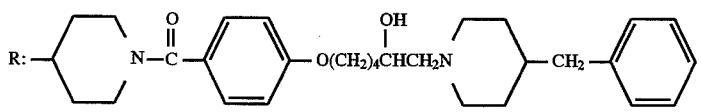

R¹: H,   q: 1
Bond between 3- and 4-positions in the
carbostyril ring: Single bond
NMR analysis: 393)
Form: Free Example 662

Structure

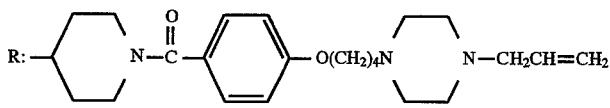

R¹: H,   q: 1
Bond between 3- and 4-positions in the
carbostyril ring: Single bond
NMR analysis: 394)
Form: Free Example 663

Structure

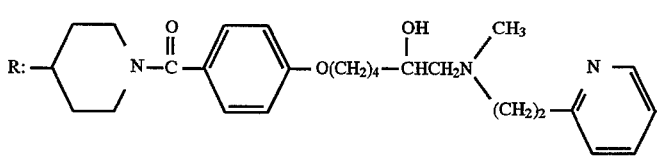

R¹: H,   q: 1
Bond between 3- and 4-positions in the
carbostyril ring: Single bond
NMR analysis: 395)
Form: Free

TABLE 9-continued

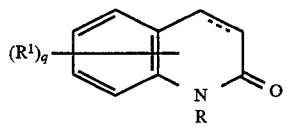

Example 664

Structure

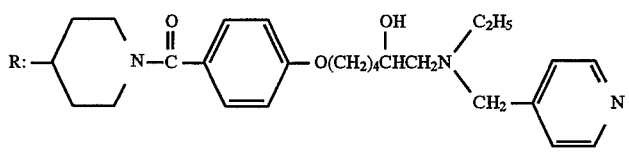

$R^1$: H, q: 1
Bond between 3- and 4-positions in the
carbostyril ring: Single bond
NMR analysis: 396)
Form: Free

Example 665

Structure

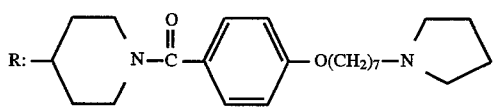

$R^1$: H, q: 1
Bond between 3- and 4-positions in the
carbostyril ring: Single bond
NMR analysis: 397)
Form: Free

Example 666

Structure

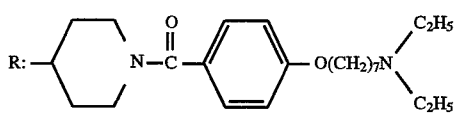

$R^1$: H, q: 1
Bond between 3- and 4-positions in the
carbostyril ring: Single bond
NMR analysis: 398)
Form: Free

Example 667

Structure

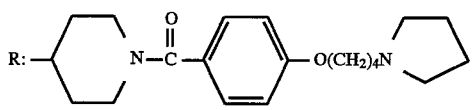

$R^1$: H, q: 1
Bond between 3- and 4-positions in the
carbostyril ring: Single bond
NMR analysis: 399)
Form: Free

Example 668

Structure

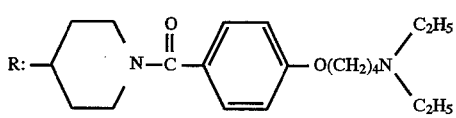

TABLE 9-continued

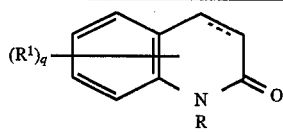

R[1]: H, q: 1
Bond between 3- and 4-positions in the
carbostyril ring: Single bond
NMR analysis: 400)
Form: Free Example 669

Structure

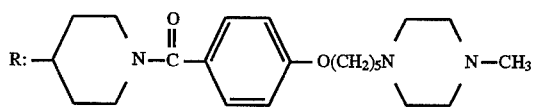

R[1]: H, q: 1
Bond between 3- and 4-positions in the
carbostyril ring: Single bond
Crystalline form: Colorless needles
Recrystallization solvent: Ethanol/water
Melting point: 216–217° C.    Form: Dioxalate Example 670

Structure

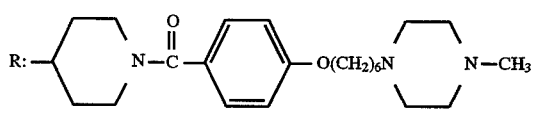

R[1]: H, q: 1
Bond between 3- and 4-positions in the
carbostyril ring: Single bond
Crystalline form: Colorless needles
Recrystallization solvent: Ethanol/water
Melting point: 216–217° C.    Form: Dioxalate Example 671

Structure

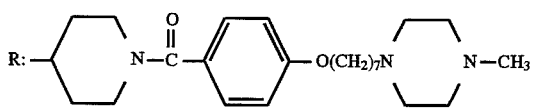

R[1]: H, q: 1
Bond between 3- and 4-positions in the
carbostyril ring: Single bond
Crystalline form: White powders
Recrystallization solvent: Ethanol/water
Melting point: 215–218° C.    Form: Dioxalate Example 672

Structure

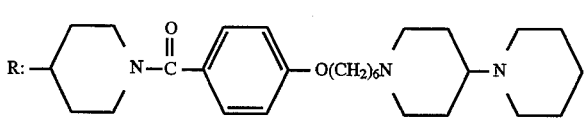

R[1]: H, q: 1
Bond between 3- and 4-positions in the
carbostyril ring: Single bond
Crystalline form: Colorles needles
Recrystallization solvent: Ethanol/water
Melting point: 195–196° C.    Form: Dioxalate TABLE 9-continued

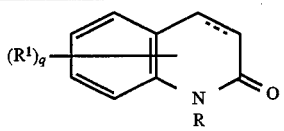

Example 673

Structure

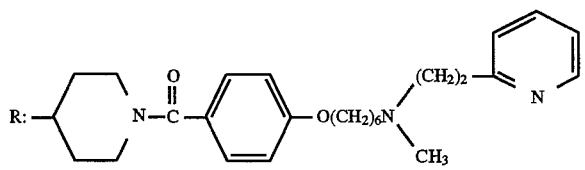

R[1]: H,   q: 1
Bond between 3- and 4-positions in the
carbostyril ring: Single bond
NMR analysis: 401)
Form: Free Example 674

Structure

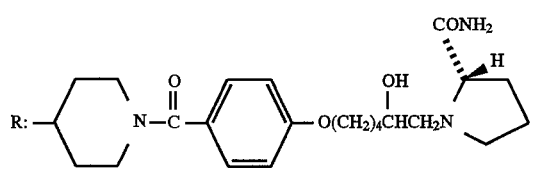

R[1]: H,   q: 1
Bond between 3- and 4-positions in the
carbostyril ring: Single bond
NMR analysis: 402)
Ms (m/z): 562    Form: Free Example 675

Structure

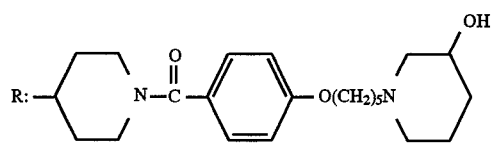

R[1]: H,   q: 1
Bond between 3- and 4-positions in the
carbostyril ring: Single bond
NMR analysis: 403)
Form: Free Example 676

Structure

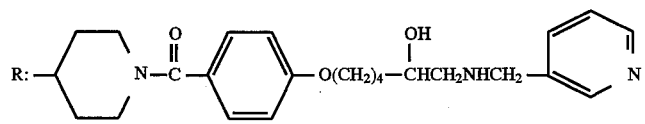

R[1]: H,   q: 1
Bond between 3- and 4-positions in the
carbostyril ring: Single bond
NMR analysis: 404)
Form: Free TABLE 9-continued

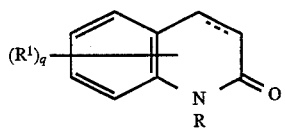

Example 677

Structure

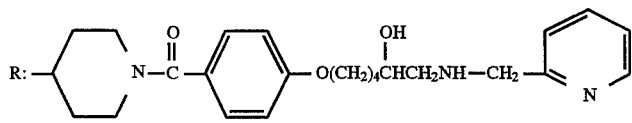

R¹: H, q: 1
Bond between 3- and 4-positions in the
carbostyril ring: Single bond
NMR analysis: 405)
Form: Free Example 678

Structure

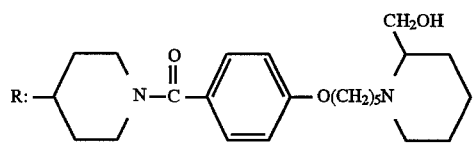

R¹: H, q: 1
Bond between 3- and 4-positions in the
carbostyril ring: Single bond
NMR analysis: 406)
Form: Free Example 679

Structure

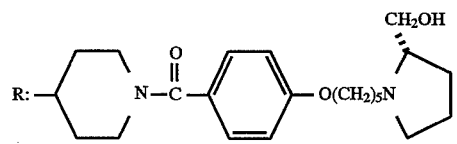

R¹: H, q: 1
Bond between 3- and 4-positions in the
carbostyril ring: Single bond
NMR analysis: 407)
Form: Free Example 680

Structure

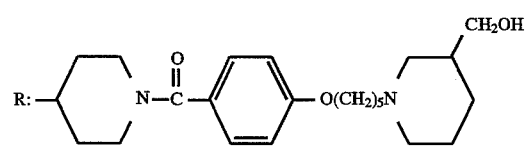

R¹: H, q: 1
Bond between 3- and 4-positions in the
carbostyril ring: Single bond
NMR analysis: 408)
Form: Free

TABLE 9-continued

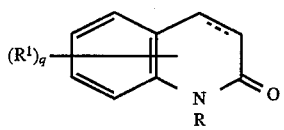

Example 681

Structure

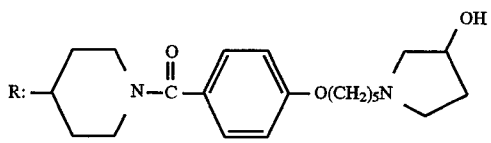

R¹: H,   q: 1
Bond between 3- and 4-positions in the
carbostyril ring: Single bond NMR analysis: 409)
Form: Free

Example 682

Structure

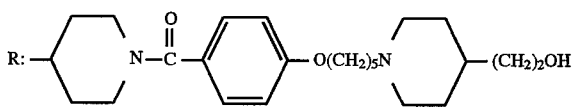

R¹: H,   q: 1
Bond between 3- and 4-positions in the
carbostyril ring: Single bond Crystalline form: Colorless amorphous form
NMR analysis: 410)
Form: Hydrochloride

Example 683

Structure

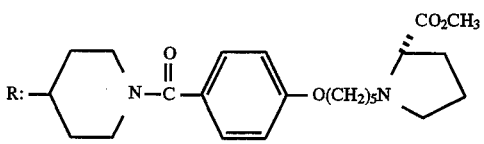

R¹: H,   q: 1
Bond between 3- and 4-positions in the
carbostyril ring: Single bond NMR analysis: 411)
Form: Free

Example 684

Structure

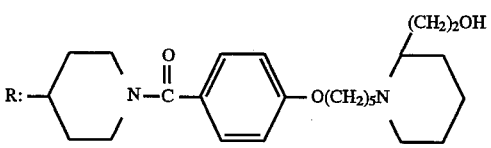

R¹: H,   q: =1
Bond between 3- and 4-positions in the
carbostyril ring: Single bond Crystalline form: Light yellow amorphous form
NMR analysis: 412)
Form: Hydrochloride

TABLE 9-continued

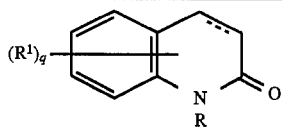

Example 685

Structure

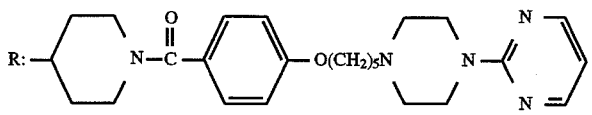

R[1]: H,   q: 1
Bond between 3- and 4-positions in the
carbostyril ring: Single bond NMR analysis: 413)
Form: Free Example 686

Structure

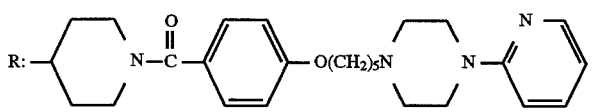

R[1]: H,   q: 1
Bond between 3- and 4-positions in the
carbostyril ring: Single bond NMR analysis: 414)
Form: Free Example 687

Structure

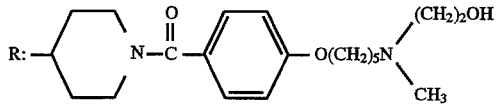

R[1]: H,   q: 1
Bond between 3- and 4-positions in the
carbostyril ring: Single bond NMR analysis: 415)
Form: Free Example 688

Structure

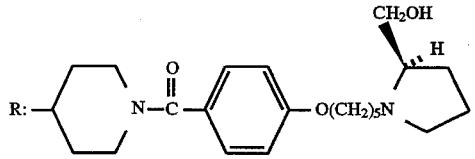

R[1]: H,   q: 1
Bond between 3- and 4-positions in the
carbostyril ring: Single bond NMR analysis: 416)
Form: Free Example 689

Structure

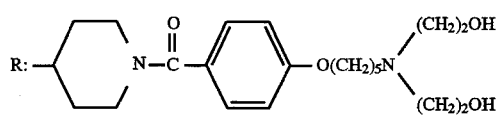

TABLE 9-continued

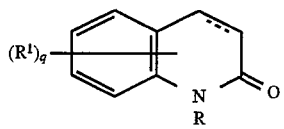

R¹: H,   q: 1
Bond between 3- and 4-positions in the
carbostyril ring: Single bond
NMR analysis: 417)
Form: Free
Example 690

Structure

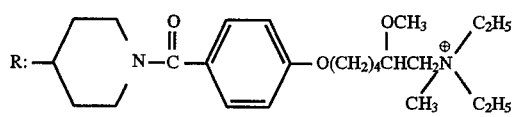

R¹: H,   q: 1
Bond between 3- and 4-positions in the
carbostyril ring: Single bond
Crystalline form: Colorless amorphous form
NMR analysis: 418)
FAB-MS (Pos.) (m/z): 551   Form: I⊖
Example 691

Structure

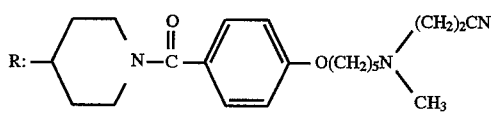

R¹: H,   q: 1
Bond between 3- and 4-positions in the
carbostyril ring: Single bond
NMR analysis: 419)
Form: Free
Example 692

Structure

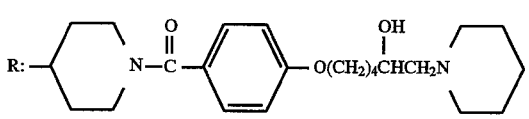

R¹: H,   q: 1
Bond between 3- and 4-positions in the
carbostyril ring: Single bond
NMR analysis: 420)
Form: Free
Example 693

Structure

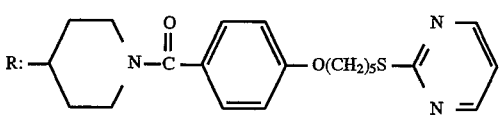

R¹: H,   q: 1
Bond between 3- and 4-positions in the
carbostyril ring: Single bond
NMR analysis: 421)
Form: Free TABLE 9-continued

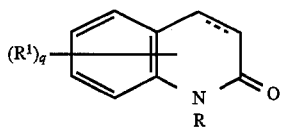

Example 694

Structure

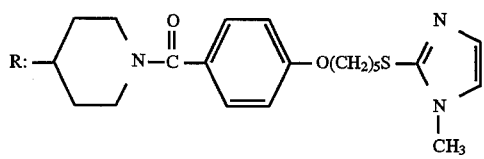

R¹: H, q: 1
Bond between 3- and 4-positions in the
carbostyril ring: Single bond
NMR analysis: 422)
Form: Free Example 695

Structure

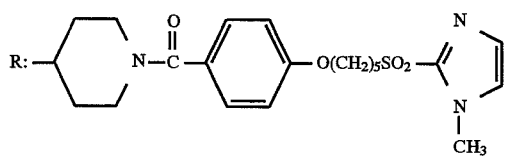

R¹: H, q: 1
Bond between 3- and 4-positions in the
carbostyril ring: Single bond
Crystalline form: Colorless amorphous form
NMR analysis: 423)
Form: Free Example 696

Structure

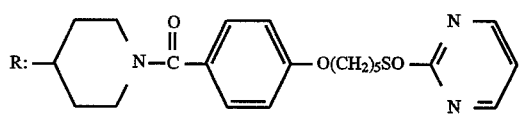

R¹: H, q: 1
Bond between 3- and 4-positions in the
carbostyril ring: Single bond
NMR analysis: 424)
Form: Free Example 697

Structure

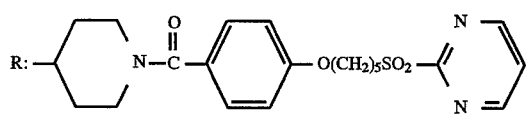

R¹: H, q: =1
Bond between 3- and 4-positions in the
carbostyril ring: Single bond
Crystalline form: Colorless amorphous form
NMR analysis: 425)
Form: Free TABLE 9-continued

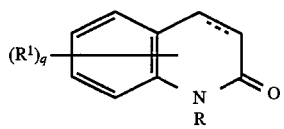

Example 698

Structure

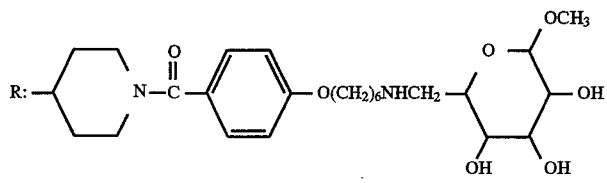

R¹: H, q: 1
Bond between 3- and 4-positions in the
carbostyril ring: Single bond NMR analysis: 426)
Form: Free Example 699

Structure

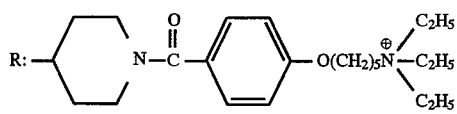

R¹: H, q: 1
Bond between 3- and 4-positions in the
carbostyril ring: Single bond NMR analysis: 427)
Form: Br⊖

Example 700

Structure

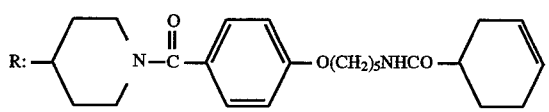

R¹: H, q: 1
Bond between 3- and 4-positions in the
carbostyril ring: Single bond NMR analysis: 428)
Form: Free Example 701

Structure

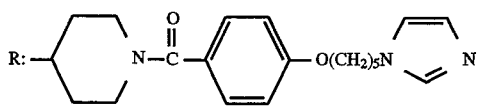

R¹: H, q: 1
Bond between 3- and 4-positions in the
carbostyril ring: Single bond Crystalline form: Colorless amorphous form
NMR analysis: 429)
Form: free

TABLE 9-continued

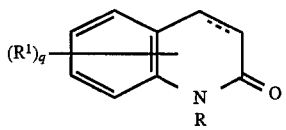

Example 702

Structure

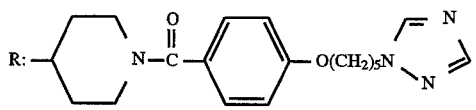

R¹: H, q: 1
Bond between 3- and 4-positions in the
carbostyril ring: Single bond
Crystalline form: Colorless amorphous form
NMR analysis: 430)
Form: Free

Example 703

Structure

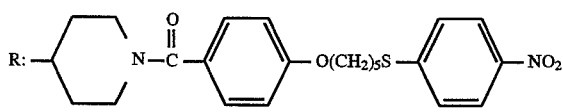

R¹: H, q: 1
Bond between 3- and 4-positions in the
carbostyril ring: Single bond
NMR analysis: 431)
Form: Free

Example 704

Structure

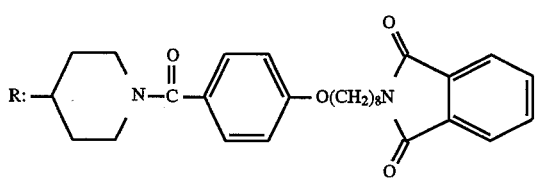

R¹: H, q: 1
Bond between 3- and 4-positions in the
carbostyril ring: Single bond
NMR analysis: 432)
Form: Free

Example 705

Structure

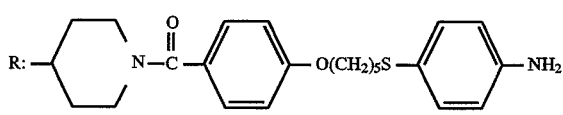

R¹: H, q: 1
Bond between 3- and 4-positions in the
carbostyril ring: Single bond
NMR analysis: 433)
Form: Free TABLE 9-continued

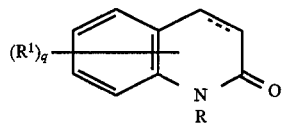

Example 706

Structure

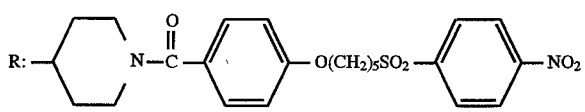

R[1]: H, q: 1
Bond between 3- and 4-positions in the
carbostyril ring: Single bond
NMR analysis: 434)
Form: Free Example 707

Structure

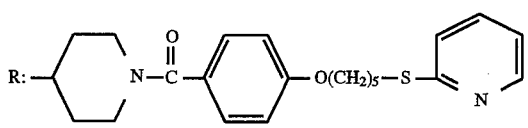

R[1]: H, q: 1
Bond between 3- and 4-positions in the
carbostyril ring: Single bond
NMR analysis: 435)
Form: Free Example 708

Structure

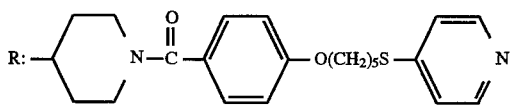

R[1]: H, q: 1
Bond between 3- and 4-positions in the
carbostyril ring: Single bond
NMR analysis: 436)
Form: Free Example 709

Structure

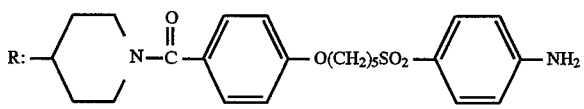

R[1]: H, q: 1
Bond between 3- and 4-positions in the
carbostyril ring: Single bond
Crystalline form: Colorless amorphous form
NMR analysis: 437)
Form: Free Example 710

Structure

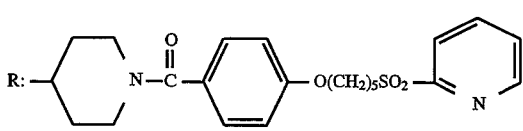

TABLE 9-continued

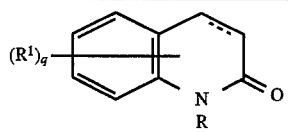

R$^1$: H,  q: 1
Bond between 3- and 4-positions in the
carbostyril ring: Single bond
NMR analysis: 438)
Form: Free Example 711

Structure

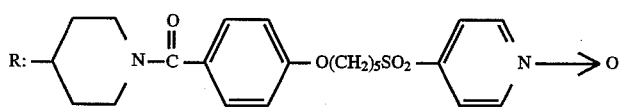

R$^1$: H,  q: 1
Bond between 3- and 4-positions in the
carbostyril ring: Single bond
Crystalline form: Colorless amorphous form
NMR analysis: 439)
Form: Free Example 712

Structure

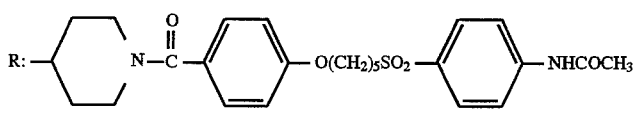

R$^1$: H,  q: 1
Bond between 3- and 4-positions in the
carbostyril ring: Single bond
Crystalline form: Colorless amorphous form
NMR analysis: 440)
Form: Free Example 713

Structure

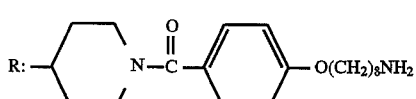

R$^1$: H,  q: 1
Bond between 3- and 4-positions in the
carbostyril ring: Single bond
NMR analysis: 441)
Form: Free Example 714

Structure

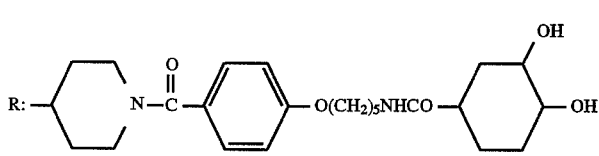

R$^1$: H,  q: 1
Bond between 3- and 4-positions in the
carbostyril ring: Single bond
NMR analysis: 442)
Form: Free

TABLE 9-continued

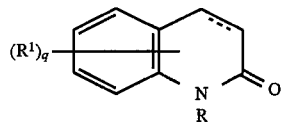

Example 715

Structure

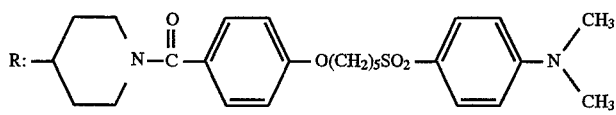

R[1]: H,   q: 1
Bond between 3- and 4-positions in the
carbostyril ring: Single bond
Crystalline form: Colorless amorphous form
NMR analysis: 443)
Form: Free

Example 716

Structure

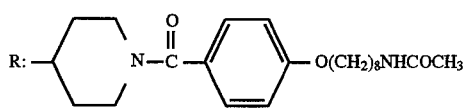

R[1]: H,   q: 1
Bond between 3- and 4-positions in the
carbostyril ring: Single bond
Crystalline form: Colorless amorphous form
NMR analysis: 444)    Form: Free

Example 717

Structure

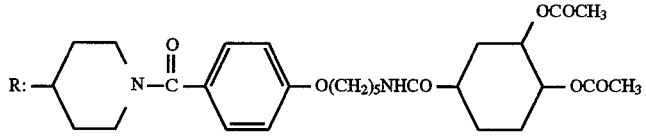

R[1]: H,   q: 1
Bond between 3- and 4-positions in the
carbostyril ring: Single bond
Crystalline form: Colorless amorphous form
NMR analysis: 445)    Form: Free

Example 718

Structure

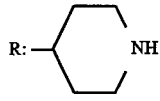

R[1]: —OH (5-position),   q: 1
Bond between 3- and 4-positions in the
carbostyril ring: Single bond
Crystalline form: White powders
Recrystallization solvent:. Methanol/diethyl ether
Melting point: 274° C. (decomposed)    Form: Hydrochloride

Example 719

Structure

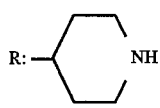

TABLE 9-continued

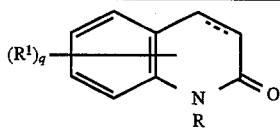

R[1]: —OC$_2$H$_5$ (5-position), q: 1
Bond between 3- and 4-positions in the
carbostyril ring: Single bond
Crystalline form: White powders
Recrystallization solvent: Methanol/diethyl ether
Melting point: 250° C. (decomposed)
Form: Hydrochloride Example 720

Structure

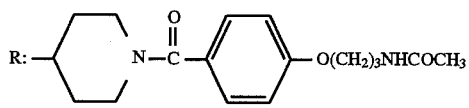

R[1]: —OH (5-position), q: 1
Bond between 3- and 4-positions in the
carbostyril ring: Single bond
Crystalline form: Colorless amorphous form
NMR analysis: 446) Form: Free Example 721

Structure

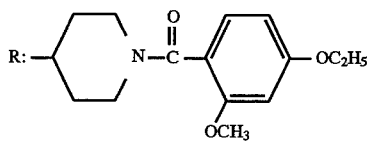

R[1]: —OH (5-position), q: 1
Bond between 3- and 4-positions in the
carbostyril ring: Single bond
Crystalline form: Colorless amorphous form
NMR analysis: 447) Form: Free Example 722

Structure

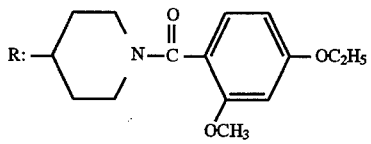

R[1]: —OCH$_3$ (5-position), q: 1
Bond between 3- and 4-positions in the
carbostyril ring: Single bond
Crystalline form: Colorless amorphous form
NMR analysis: 448) Form: Free Example 723

Structure

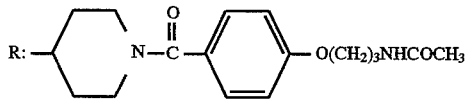

R[1]: —OC$_2$H$_5$ (5-position), q: 1
Bond between 3- and 4-positions in the
carbostyril ring: Single bond
Crystalline form: Colorless amorphous form
NMR analysis: 449) Form: Free TABLE 9-continued

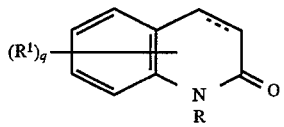

Example 724

Structure

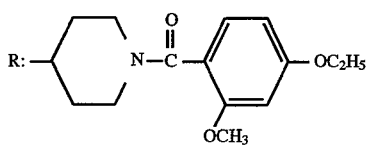

R¹: —OC₂H₅ (5-position), q: 1
Bond between 3- and 4-positions in the
carbostyril ring: Single bond
Crystalline form: Colorless amorphous form
NMR analysis: 450)   Form: Free Example 725

Structure

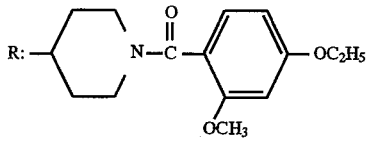

R¹: —OCOCH₃ (5-position), q: 1
Bond between 3- and 4-positions in the
carbostyril ring: Single bond
Crystalline form: Colorless amorphous form
NMR analysis: 451)   Form: Free Example 726

Structure

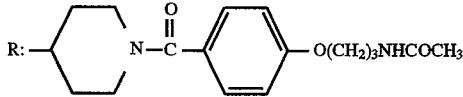

R¹: —OCH₃ (5-position), q: 1
Bond between 3- and 4-positions in the
carbostyril ring: Single bond
Crystalline form: Colorless amorphous form
NMR analysis: 452)   Form: Free Example 727

Structure

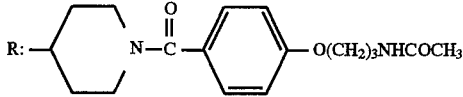

R¹: —OCOCH₃, q: 1
Bond between 3- and 4-positions in the
carbostyril ring: Single bond
Crystalline form: Colorless amorphous form
NMR analysis: 453)   Form: Free Example 728

Structure

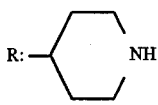

TABLE 9-continued

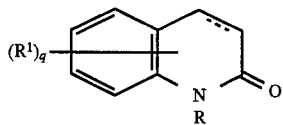

R[1]: —CH$_3$ (5-, 7-positions), q: 2
Bond between 3- and 4-positions in the
carbostyril ring: Single bond
Crystalline form: White powders
Melting point: 278–282° C.
Form: Hydrochloride
Example 729

Structure

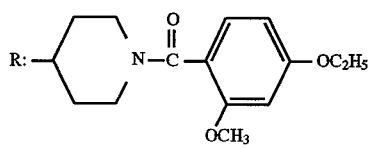

R[1]: —CH$_3$ (5-, 7-positions), q: 2
Bond between 3- and 4-positions in the
carbostyril ring: Single bond
Crystalline form: White powders
Melting point: 165–167° C.
Form: Free
Example 730

Structure

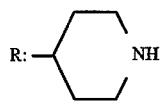

R[1]: F (5-position), q: 1
Bond between 3- and 4-positions in the
carbostyril ring: Single bond
NMR analysis: 454)
Form: Free
Example 731

Structure

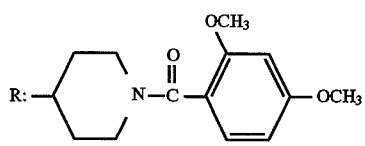

R[1]: F (5-position), q: 1
Bond between 3- and 4-positions in the
carbostyril ring: Single bond
Crystalline form: Colorless amorphous form
NMR analysis: 455)
Form: Free
Example 732

Structure

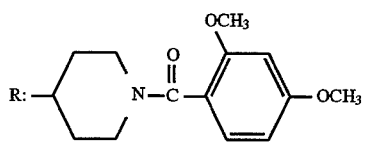

R[1]: F (5-position), q: 1
Bond between 3- and 4-positions in the
carbostyril ring: Single bond TABLE 9-continued

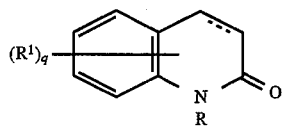

Crystalline form: Colorless amorphous form
NMR analysis: 456)
Form: Free
Example 733

Structure

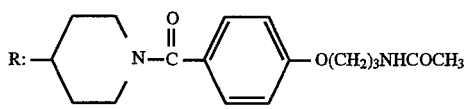

R$^1$: —CH$_3$ (5-position), q: 1
Bond between 3- and 4-positions in the
carbostyril ring: Single bond
Crystalline form: Colorless amorphous form
NMR analysis: 457)
Form: Free
Example 734

Structure

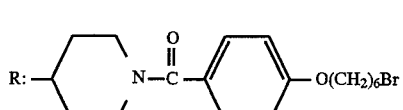

R$^1$: —CH$_3$ (5-position), q: 1
Bond between 3- and 4-positions in the
carbostyril ring: Single bond
Crystalline form: Colorless amorphous form
NMR analysis: 458)
Form: Free
Example 735

Structure

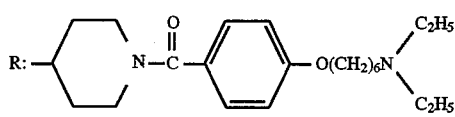

R$^1$: —CH$_3$ (5-position), q: 1
Bond between 3- and 4-positions in the
carbostyril ring: Single bond
Crystalline form: Colorless amorphous form
NMR analysis: 459)
Form: Free
Example 736

Structure

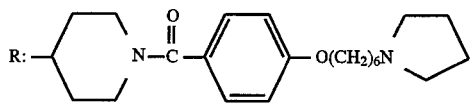

R$^1$: —CH$_3$ (5-position), q: 1
Bond between 3- and 4-positions in the
carbostyril ring: Single bond
Crystalline form: Colorless amorphous form
NMR analysis: 460)
Form: Free TABLE 9-continued

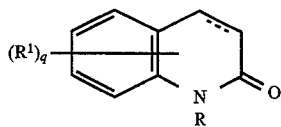

Example 737

Structure

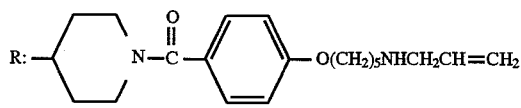

R¹: H,  q: 1
Bond between 3- and 4-positions in the
carbostyril ring: Single bond
NMR analysis:: 461)
Form: Free Example 738

Structure

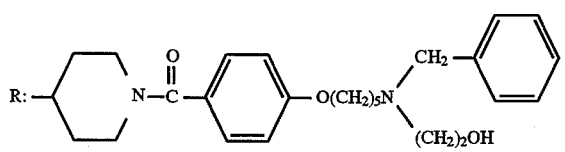

R¹: H,  q: 1
Bond between 3- and 4-positions in the
carbostyril ring: Single bond
NMR analysis: 462)
Form: Free Example 739

Structure

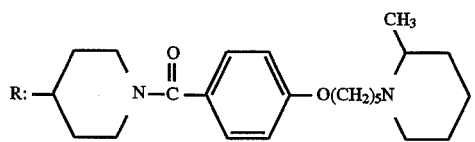

R¹: H,  q: 1
Bond between 3- and 4-positions in the
carbostyril ring: Single bond
NMR analysis: 463)
Form: Free Example 740

Structure

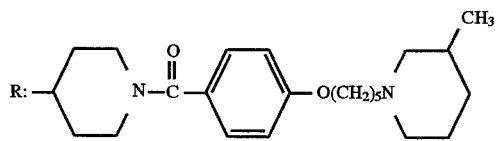

R¹: H,  q: 1
Bond between 3- and 4- positions in the
carbostyril ring: Single bond
NMR analysis: 464)
Form: Free

TABLE 9-continued

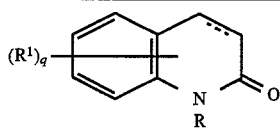

Example 741

Structure

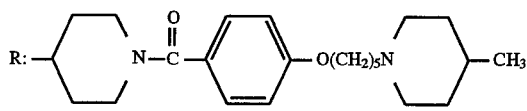

R[1]: H,  q: 1
Bond between 3- and 4-positions in the
carbostyril ring: Single bond
NMR analysis: 465)
Form: Free

Example 742

Structure

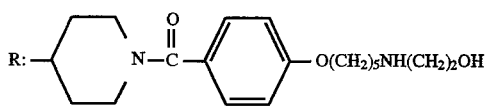

R[1]: H,  q: 1
Bond between 3- and 4-positions in the
carbostyril ring: Single bond
NMR analysis: 466)
Form: Free

Example 743

Structure

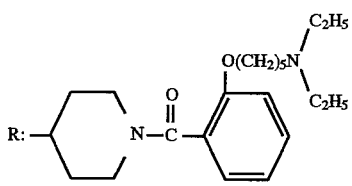

R[1]: H,  q: 1
Bond between 3- and 4-positions in the
carbostyril ring: Single bond
NMR analysis: 467)
Form: Free

Example 744

Structure

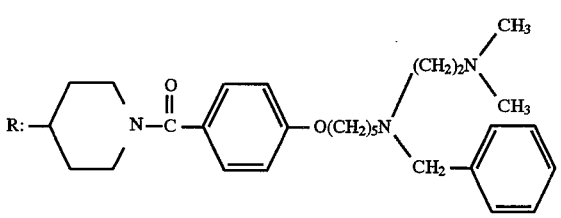

R[1]: H,  q: 1
Bond between 3- and 4-positions in the
carbostyril ring: Single bond
NMR analysis: 468)
Form: Free TABLE 9-continued

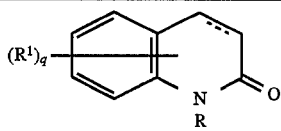

Example 745

Structure

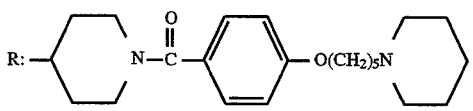

R¹: H,    q: 1
Bond between 3- and 4-positions in the
carbostyril ring: Single bond
NMR analysis: 469)
Form: Free Example 746

Structure

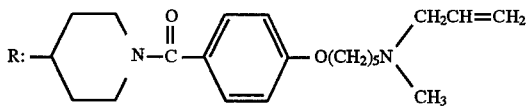

R¹: H,    q: 1
Bond between 3- and 4-positions in the
carbostyril ring: Single bond
NMR analysis: 470)
Form: Free Example 747

Structure

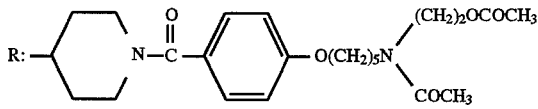

R¹: H,    q: 1
Bond between 3- and 4-positions in the
carbostyril ring: Single bond
NMR analysis: 471)
Form: Free Example 748

Structure

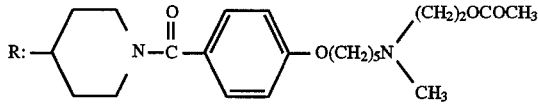

R¹: H,    q: 1
Bond between 3- and 4-positions in the
carbostyril ring: Single bond
NMR analysis: 472)
Form: Free Example 749

Structure

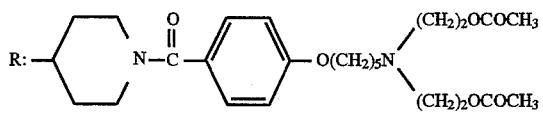

R¹: H,    q: 1
Bond between 3- and 4-positions in the
carbostyril ring: Single bond TABLE 9-continued

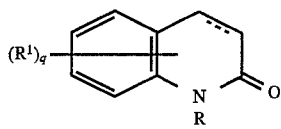

NMR analysis: 473)
Form: Free
Example 750

Structure

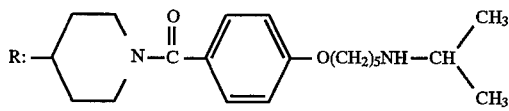

R¹: H, q: 1
Bond between 3- and 4-positions in the
carbostyril ring: Single bond NMR analysis: 474)
Form: Free
Example 751

Structure

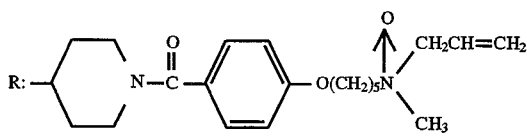

R¹: H, q: 1
Bond between 3- and 4-positions in the
carbostyril ring: Single bond NMR analysis: 475)
Form: Free
Example 752

Structure

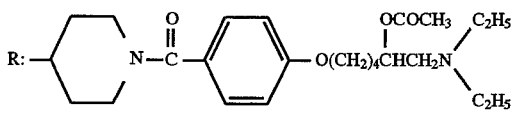

R¹: H, q: 1
Bond between 3- and 4-positions in the
carbostyril ring: Single bond NMR analysis: 476)
Form: Free
Example 753

Structure

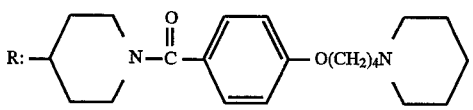

R¹: H, q: 1
Bond between 3- and 4-positions in the
carbostyril ring: Single bond NMR analysis: 477)
Form: Free
Example 754

Structure

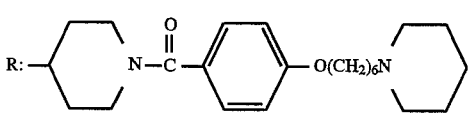

TABLE 9-continued

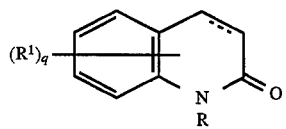

R[1]: H,  q: 1
Bond between 3- and 4-positions in the
carbostyril ring: Single bond
NMR analysis: 478)
Form: Free
Example 755

Structure

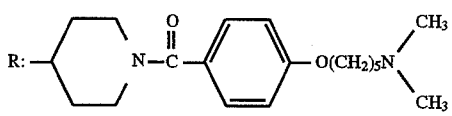

R[1]: H,  q: 1
Bond between 3- and 4-positions in the
carbostyril ring: Single bond
NMR analysis: 479)
Form: Free
Example 756

Structure

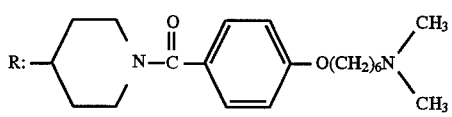

R[1]: H,  q: 1
Bond between 3- and 4-positions in the
carbostyril ring: Single bond
NMR analysis: 480)
Form: Free
Example 757

Structure

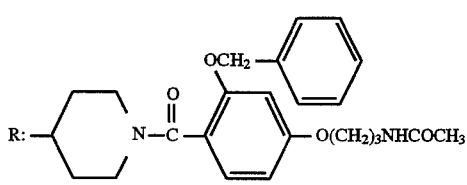

R[1]: H,  q: 1
Bond between 3- and 4-positions in the
carbostyril ring: Single bond
Crystalline form: Colorless amorphous form
NMR analysis: 481)
Form: Free
Example 758

Structure

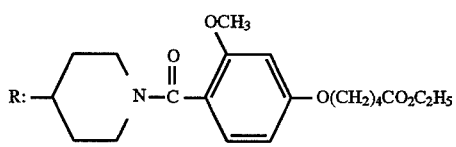

R[1]: H,  q: 1
Bond between 3- and 4-positions in the
carbostyril ring: Single bond
NMR analysis: 482)  Form: Free

TABLE 9-continued

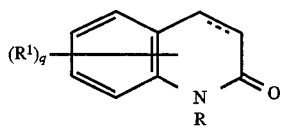

Example 759

Structure

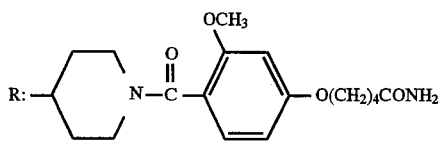

R[1]: H,   q: 1
Bond between 3- and 4-positions in the
carbostyril ring: Single bond
Crystalline form: Colorless amorphous form
NMR analysis: 483)   Form: Free Example 760

Structure

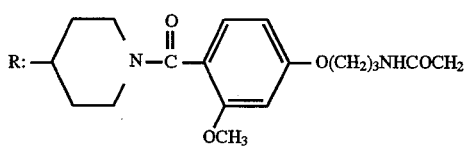

R[1]: H,   q: 1
Bond between 3- and 4-positions in the
carbostyril ring: Single bond
Crystalline form: Colorless needles
Recrystallization solvent: Ethanol/diethyl ether
Melting point: 155–157° C.   Form: Free Example 761

Structure

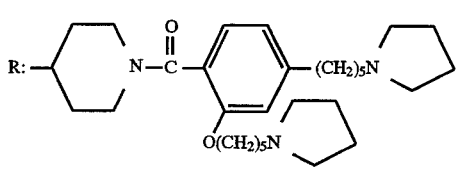

R[1]: H,   q: 1
Bond between 3- and 4-positions in the
carbostyril ring: Single bond
Crystalline form: Colorless amorphous form
NMR analysis: 484)   Form: Free Example 762

Structure

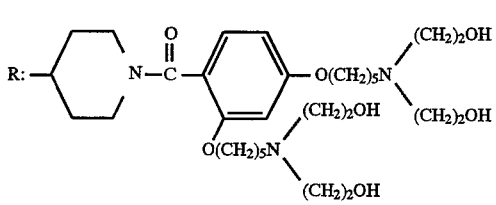

R[1]: H,   q: 1
Bond between 3- and 4-positions in the
carbostyril ring: Single bond
NMR analysis: 485)   Form: Free

TABLE 9-continued

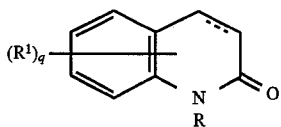

Example 763

Structure

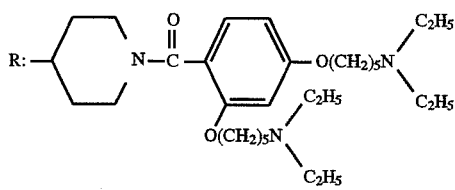

$R^1$: H,  q: 1
Bond between 3- and 4-positions in the
carbostyril ring: Single bond
NMR analysts: 486)   Form: Dihydrochloride Example 764

Structure

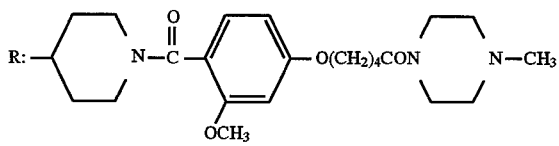

$R^1$: H,  q: 1
Bond between 3- and 4-positions in the
carbostyril ring: Single bond
Crystalline form: Colorless amorphous form
NMR analysis: 487)   Form: Free Example 765

Structure

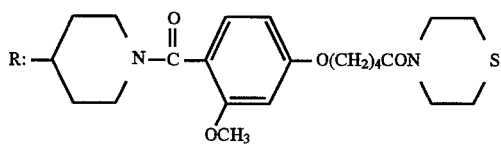

$R^1$: H,  q: 1
Bond between 3- and 4-positions in the
carbostyril ring: Single bond
Crystalline form: Colorless amorphous form
NMR analysis: 488)   Form: Free Example 766

Structure

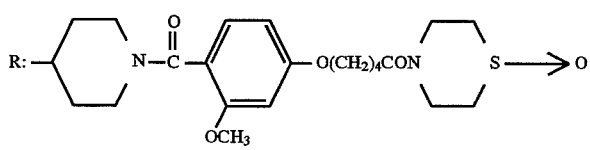

$R^1$: H,  q: 1
Bond between 3- and 4-positions in the
carbostyril ring: Single bond
Crystalline form: Colorless amorphous form
NMR analysis: 489)   Form: Free TABLE 9-continued

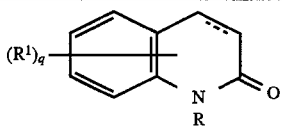

Example 767

Structure

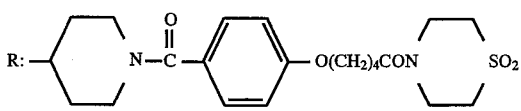

R¹: H,  q: 1
Bond between 3- and 4-positions in the
carbostyril ring: Single bond
Crystalline form: Colorless amorphous form
NMR analysis: 490)
Form: Free Example 768

Structure

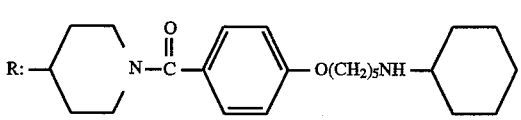

R¹: H,  q: 1
Bond between 3- and 4-positions in the
carbostyril ring: Single bond
NMR analysis: 493)
Form: Free Example 769

Structure

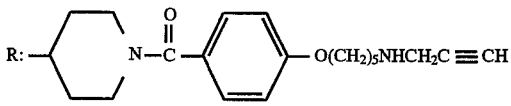

R¹: H,  q: 1
Bond between 3- and 4-positions in the
carbostyril ring: Single bond
NMR analysis: 494)
Form: Free Example 770

1-{1-[4-(4-Oxiranylbutoxy)benzoyl]-4-piperidinyl}-3,4-dihydrocarbostyril (1.6 g) is dissolved in a mixture of dioxane (30 ml) and water (10 ml). Thereto is added conc. sulfuric acid (0.1 ml) and the mixture is stirred at room temperature overnight. The mixture is neutralized with sodium hydrogen carbonate and then extracted with chloroform. The extract is dried with magnesium sulfate and the solvent is evaporated off. The resulting residue is purified by silica gel column chromatography (solvent: dichloromethane:methanol=50:1) to give 1-{1-[4-(5,6-dihydroxyhexyloxy)benzoyl]-4-piperidinyl}-3,4-dihydrocarbostyril (0.6 g).

NMR (CDCl$_3$) δ ppm: 1.35–1.93 (8H, m), 2.15–3.15 (10H, m), 3.32–3.78 (3H, m), 3.83–5.22 (3H, m), 3.97 (2H, t, J=6.3 Hz), 6.79–7.48 (8H, m)

Example 771

Using the suitable starting materials, the compounds of the above Examples 718, 719, 728 and 730 are obtained in the same manners as Example 386.

Example 772

Using the suitable starting materials, the compounds of the above Examples 594–717, 720–727, 729, 731–769 are obtained in the same manners as in Examples 390–393.

Example 773

Using the suitable starting materials, the compounds of the above Examples 594–717, 720–727, 729, 731–769 are obtained in the same manners as in Examples 398 and 399.

Example 774

Using the suitable starting materials, the compounds of the above Examples 596–648, 650–651, 653, 700, 712, 714, 716, 717, 720, 723, 726, 727, 733, 747, 757, and 760 are obtained in the same manners as in Examples 403–405.

Example 775

Using the suitable starting materials, the compounds of the above Examples 600, 604, 609, 610, 616, 618, 620, 623, 625, 627, 628, 630, 631, 633, 634, 637–639, 646, 649, 651, 652–655, 658–660, 662, 663, 666, 668–671, 673, 677, 685–687, 689–691, 698, 699, 715, 735–738, 742–744, 746–752, 755, 756, 762–764, 768–769 are obtained in the same manners as in Examples 407–409.

Example 776

Using the suitable starting materials, the compounds of the above Examples 695, 696, 697, 706, 709–712, 715, 751, 766 and 767 are obtained in the same manners as in Example 416.

Example 777

Using the suitable starting materials, the compounds of the above Examples 657–661, 663, 664, 674, 676, 677 and 692 are obtained in the same manners as in Example 421.

Example 778

Using the suitable starting materials, the compounds of the above Examples 596–603, 605, 606, 611–616, 618–623, 625–640, 642, 643, 645–656, 662, 665–673, 675, 678–689, 691, 693, 694, 698, 700–705, 707, 708, 713, 714, 716, 717, 720, 723, 726, 727, 733, 735–750, 753–757, 760–763, 768 and 769 are obtained in the same manners as in Example 426.

TABLE 10

| No. | NMR (CDCl$_3$) δ value |
|---|---|
| 329 | 1.64–2.44(8H, m), 2.50–3.20(8H, m), 3.25–3.70 (4H, m), 3.80–5.00(2H, brs), 3.99(2H, m), 4.33 (2H, m), 5.07(1H, d, J=12.5Hz), 5.19(1H, d, J=12.5Hz), 6.38(1H, brs), 6.89(2H, d, J=8.4Hz), 6.99–7.28(4H, m), 7.33(5H, m), 7.42(2H, d, J=8.4Hz) |
| 330 | 1.25–2.20(6H, m), 1.80(2H, m), 1.95(2H, m), 2.52–3.04(8H, m), 3.12(2H, m), 3.41(2H, q, J=5.4 Hz), 3.80–4.90(2H, brs), 3.98(2H, t, J=5.4Hz), 4.10(1H, m), 4.35(1H, m), 5.29(4H, s), 5.31(1H, brs), 5.70(1H, brs), 6.72(1H, brs), 6.87(2H, d, J=8.6Hz), 6.98–7.27(4H, m), 7.30(10H, s), 7.39 (2H, d, J=8.6Hz) |
| 331 | 1.84(2H, m), 2.40–3.15(10H, m), 3.23–3.50(2H, m), 3.56(2H, t, J=6.1Hz), 3.70–5.15(2H, brs), 3.94(2H, t, J=5.6Hz), 4.35(2H, m), 6.61(2H, d, J=8.0Hz), 6.84(2H, d, J=8.6Hz), 6.92(2H, d, J=8.0Hz), 6.99–7.29(4H, m), 7.40(2H, d, J=8.6 Hz), 7.50(1H, brs) |
| 332 | 1.65–2.50(8H, m), 2.50–3.10(10H, m), 3.45(2H, q, J=6.4Hz), 3.60–5.10(2H, brs), 3.81(1H, dd, J=9.0, 5.3Hz), 4.06(2H, t, J=5.9Hz), 4.38(1H, m), 6.92(2H, d, J=8.7Hz), 6.99–7.29(4H, m), 7.43 (2H, d, J=8.7Hz), 8.00(1H, brs) |
| 333 | 1.70–1.93(2H, m), 2.04(2H, quint, J=6.2Hz), 2.30 (6H, s), 2.53–3.20(8H, m), 2.96(2H, s), 3.50(2H, q, J=6.2Hz), 3.80–5.10(2H, brs), 4.08(2H, t, J=6.2Hz), 4.37(1H, m), 6.92(2H, d, J=8.7Hz), 6.99–7.29(4H, m), 7.44(2H, d, J=8.7Hz), 7.53 (1H, brs) |
| 334 | 1.60–1.89(2H, m), 1.97(2H, quint, J=6.0Hz), 2.53–3.20(8H, m), 3.44(2H, q, J=6.0Hz), 3.64 (1H, dd, J=11.2, 5.2Hz), 3.80–5.10(2H, brs), 4.00 (2H, t, J=6.0Hz), 4.12(1H, dd, J=11.2, 5.2Hz), 4.17(1H, m), 4.35(1H, m), 5.10(2H, s), 5.97(1H, d, J=6.0Hz), 6.89(2H, d, J=8.7Hz), 6.99–7.30 (4H, m), 7.33(5H, s), 7.39(2H, d, J=8.7Hz) |
| 335 | 1.37(3H, d, J=7.0Hz), 1.64–1.90(2H, m), 1.97 (2H, m), 2.53–3.20(8H, m), 3.43(2H, q, J=6.2Hz), 3.65–5.00(2H, brs), 4.00(2H, t, J=5.8Hz), 4.21 (1H, quint, J=7.0Hz), 4.37(1H, m), 5.05(1H, d, J=12.1Hz), 5.18(1H, d, J=12.1Hz), 5.55(1H, d, J=7.0Hz), 6.70(1H, brs), 6.88(2H, d, J=8.7Hz), 6.99–7.36(4H, m), 7.33(5H, s), 7.40(2H, d, J=8.7Hz) |

TABLE 10-continued

| | |
|---|---|
| 336 | 1.33(3H, d, J=6.9Hz), 1.63–1.95(2H, m), 2.03 (2H, quint, J=6.0Hz), 2.53–3.20(8H, m), 3.41–3.55 (3H, m), 3.80–5.20(2H, brs), 4.06(2H, t, J=6.0 Hz), 4.37(1H, m), 6.93(2H, d, J=8.6Hz), 6.99–7.89(4H, m), 7.43(2H, d, J=8.6Hz), 7.68(1H, t, J=6.0Hz) |
| 337 | 1.42–1.62(2H, m), 1.62–1.90(6H, m), 2.31–2.44 (6H, m), 2.54–3.10(8H, m), 3.46(2H, m), 3.51(2H, s), 3.63(2H, m), 3.83–5.15(2H, brs), 3.98(2H, t, J=6.4Hz), 4.39(1H, m), 6.89(2H, d, J=8.7Hz), 6.99–7.33(4H, m), 7.31(5H, s), 7.42(2H, d, J=8.7Hz) |
| 338 | 0.82(3H, d, J=6.9Hz), 0.99(3H, d, J=6.9Hz), 1.64–1.90(2H, m), 2.04(2H, m), 2.10–2.41(1H, m), 2.54–3.08(8H, m), 3.24(1H, d, J=3.8Hz), 3.48 (2H, q, J=6.5Hz), 3.67–5.50(2H, brs), 4.06(2H, t, J=5.9Hz), 4.38(1H, m), 6.92(2H, d, J=8.7Hz), 6.99–7.28(4H, m), 7.43(2H, d, J=8.7Hz), 7.67 (1H, brs) |
| 339 | 0.82(3H, d, J=6.9Hz), 0.99(3H, d, J=6.9Hz), 1.68–1.93(2H, m), 2.03(2H, quint, J=6.1Hz), 2.33 (1H, m), 2.54–3.17(8H, m), 3.25(1H, d, J=3.7Hz), 3.49(2H, q, J=6.1Hz), 3.80–5.20(2H, brs), 4.07 (2H, t, J=6.1Hz), 4.39(1H, m), 6.92(2H, d, J=8.7 Hz), 7.03–7.30(4H, m), 7.43(2H, d, J=8.7Hz), 7.64(1H, brs) |
| 340 | 1.41–1.60(2H, m), 1.61–1.98(6H, m), 2.35(2H, t, J=7.4Hz), 2.54–3.10(12H, m), 3.44(2H, t, J=4.9 Hz), 3.59(2H, t, J=4.9Hz), 3.80–5.20(2H, brs), 3.99(2H, t, J=6.3Hz), 4.39(1H, m), 6.89(2H, d, J=8.6Hz), 6.99–7.28(4H, m), 7.42(2H, d, J=8.6Hz) |
| 341 | 1.40–1.65(2H, m), 1.65–2.00(6H, m), 1.76(3H, s), 2.39(2H, t, J=7.4Hz), 2.54–3.20(8H, m), 3.49 (4H, m), 3.61(4H, m), 3.85–5.20(2H, brs), 4.00 (2H, t, J=6.3Hz), 4.39(1H, m), 6.89(2H, d, J=8.7 Hz), 6.99–7.25(4H, m), 7.42(2H, d, J=8.7Hz) |
| 342 | 1.40–1.65(2H, m), 1.65–2.02(6H, m), 2.37(2H, t, J=7.3Hz), 2.54–3.30(12H, m), 2.81(3H, s), 3.46–4.10(4H, m), 4.00(2H, t, J=6.2Hz), 4.10–5.20 (2H, brs), 4.37(1H, m), 6.90(2H, d, J=8.7Hz), 7.00–7.26(4H, m), 7.42(2H, d, J=8.7Hz) |
| 343 | 1.42–1.63(2H, m), 1.64–2.00(6H, m), 2.32–2.52 (6H, m), 2.54–3.10(8H, m), 3.01(2H, d, J=6.6Hz), 3.48(2H, m), 3.64(2H, m), 3.80–5.10(2H, brs), 3.99(2H, t, J=6.3Hz), 4.40(1H, m), 5.18(1H, d, J=10.3Hz), 5.20(1H, d, J=16.8Hz), 5.85(1H, ddt, J=16.8, 10.3, 6.6Hz), 6.89(2H, d, J=8.7Hz), 6.99–7.26(4H, m), 7.42(2H, d, J=8.7Hz) |
| 344 | 1.60–1.90(2H, m), 1.81(2H, quint, J=7.0Hz), 1.98 (2H, quint, J=6.2Hz), 2.25(2H, t, J=7.0Hz), 2.52–3.17(10H, m), 3.39(2H, q, J=6.2Hz), 3.65–5.15(2H, br), 3.90(2H, brs), 4.03(2H, t, J=6.2 Hz), 4.33(1H, m), 6.91(2H, d, J=8.5Hz), 6.98–7.28(5H, m), 7.40(2H, d, J=8.5Hz) |
| 345 | 1.70–1.93(2H, m), 1.81(2H, quint, J=6.6Hz), 1.98 (2H, quint, J=6.6Hz), 2.22(2H, t, J=6.6Hz), 2.46–3.10(8H, m), 3.21(2H, q, J=6.6Hz), 3.40 (2H, q, J=6.1Hz), 3.80–5.10(2H, brs), 4.01(2H, t, J=6.1Hz), 4.34(1H, m), 5.07(2H, s), 5.73(1H, brs), 6.89(2H, d, J=8.7Hz), 6.91(1H, brs), 6.99–7.25(4H, m), 7.32(5H, s), 7.40(2H, d, J=8.7Hz) |
| 346 | 1.52(4H, m), 1.66–1.97(6H, m), 2.20(2H, t, J=6.8 Hz), 2.53–3.05(8H, m), 3.10–3.32(4H, m), 3.70–5.10(2H, br), 3.96(2H, t, J=6.3Hz), 4.37(1H, m), 5.08(2H, s), 5.31(1H, brs), 6.30(1H, brs), 6.88(2H, d, J=8.7Hz), 6.99–7.27(4H, m), 7.33 (5H, s), 7.41(2H, d, J=8.7Hz) |
| 347 | 1.41–1.71(4H, m), 1.71–1.90(4H, m), 2.54–3.20 (8H, m), 3.34(2H, q, J=6.5Hz), 3.60–5.15(2H, brs), 3.99(2H, t, J=6.2Hz), 4.04(2H, s) 4.38 (1H, m), 6.72(1H, brs), 6.90(2H, d, J=8.5Hz), 6.99–7.28(4H, m), 7.43(2H, d, J=8.7Hz) |
| 348 | 1.32–1.67(4H, m), 1.67–2.00(6H, m), 2.25(2H, t, J=7.3Hz), 2.53–3.10(10H, m), 3.24(2H, q, J=6.2 Hz), 3.70–5.20(2H, brs), 3.97(2H, t, J=6.2Hz), 4.36(1H, m), 6.54(1H, m), 6.89(2H, d, J=8.7Hz), 6.99–7.23(4H, m), 7.41(2H, d, J=8.7Hz) |
| 349 | 1.25–1.72(4H, m), 1.73–1.94(4H, m), 2.29(6H, s), 2.54–3.10(8H, m), 2.94(2H, s), 3.31(2H, q, J=6.3 Hz), 3.74–5.10(2H, br), 3.99(2H, t, J=6.3Hz), |

TABLE 10-continued

| | |
|---|---|
| | 4.39(1H, m), 6.89(2H, d, J=8.7Hz), 6.99–7.28 (5H, m), 7.43(2H, d, J=8.7Hz) |
| 350 | 1.26(3H, t, J=7.1Hz), 1.42–2.05(12H, m), 2.37 (2H, t, J=7.4Hz), 2.44–3.25(11H, m), 3.50–5.10 (2H, brs), 3.73–3.94(1H, m), 3.99(2H, t, J=6.3 Hz), 4.15(2H, q, J=7.1Hz), 4.23–4.53(2H, m), 6.90(2H, d, J=8.7Hz), 6.99–7.29(4H, m), 7.42 (2H, d, J=8.7Hz) |
| 351 | 1.02(6H, t, J=7.1Hz), 1.39–1.71(4H, m), 1.71– 2.05(4H, m), 2.38–3.14(8H, m), 2.55(4H, q, J=7.1 Hz), 3.01(2H, s), 3.30(2H, q, J=6.3Hz), 3.70– 5.15(2H, brs), 3.98(2H, t, J=6.3Hz), 4.39(1H, m), 6.89(2H, d, J=8.7Hz), 6.99–7.27(4H, m), 7.43 7.45(1H, m) |
| 352 | 1.37–1.68(4H, m), 1.68–1.90(6H, m), 1.96(3H, s), 2.16(2H, t, J=6.7Hz), 2.54–3.15(8H, m), 3.15– 3.33(4H, m), 3.75–5.20(2H, brs), 3.98(2H, t, J=6.2Hz), 4.36(1H, m), 6.90(2H, d, J=8.5Hz), 6.92(1H, brs), 6.99–7.31(4H, m), 7.41(2H, d, J=8.5Hz) |
| 353 | 1.48–1.64(4H, m), 1.69–1.91(4H, m), 1.91–2.13 (2H, m), 2.21(2H, t, J=6.7Hz), 2.54–3.11(10H, m), 2.66(6H, m), 3.25(2H, q, J=6.2Hz), 3.70–5.10 (2H, brs), 3.98(2H, t, J=6.2Hz), 4.35(1H, m), 6.15(1H, brs), 6.90(2H, d, J=8.7Hz), 6.99–7.28 (4H, m), 7.41(2H, d, J=8.7Hz) |
| 354 | 1.37–1.69(4H, m), 1.69–1.94(4H, m), 2.16(3H, s), 2.53–3.20(8H, m), 3.32(2H, q, J=6.5Hz), 3.65– 5.15(2H, br), 3.98(2H, t, J=6.2Hz), 4.54(1H, m), 4.65(2H, s), 6.51(1H, brs), 6.90(2H, d, J=8.7Hz), 6.99–7.30(4H, m), 7.42(2H, d, J=8.7Hz) |
| 355 | 1.49–1.69(4H, m), 1.69–1.98(4H, m), 2.54–3.18 (8H, m), 3.31(2H, q, J=6.3Hz), 3.67(1H, t, J=5.1 Hz), 3.80–5.15(2H, brs), 4.00(2H, t, J=6.2Hz), 4.03(2H, d, J=5.1Hz), 4.37(1H, m), 6.64(1H, brs), 6.90(2H, d, J=8.7Hz), 6.99–7.28(4H, m), 7.41(2H, d, J=8.7Hz) |
| 356 | 1.10(3H, t, J=7.1Hz), 1.42–1.70(4H, m), 1.70– 1.95(4H, m), 2.54–3.17(8H, m), 2.61(2H, q, J=7.1 Hz), 3.24(2H, q), 3.30(2H, q, J=6.5Hz), 3.60– 5.20(2H, brs), 3.99(2H, t, J=6.3Hz), 4.37(1H, m), 6.90(2H, d, J=8.6Hz), 6.99–7.30(4H, m), 7.42 (2H, d, J=8.6Hz), 7.45(1H, brs) |
| 357 | 1.30–2.00(12H, m), 2.36(2H, m) 2.52–3.20(11H, m), 3.50–5.15(2H, brs) 3.60–3.84(1H, m), 3.98 (2H, t, J=6.1Hz), 4.22–4.60(2H, m), 6.88(2H, d, J=8.6Hz), 6.99–7.25(4H, m), 7.40(2H, d, J=8.6Hz) |
| 358 | 1.49–1.68(4H, m), 1.68–1.95(4H, m), 2.54–3.10 (8H, m), 3.23(2H, d, J=5.1Hz), 3.27(2H, s), 3.31 (2H, q, J=6.3Hz), 3.70–5.10(2H, brs), 3.98(2H, t, J=6.3Hz), 4.39(1H, m), 5.12(1H, d, J=10.2 Hz), 5.19(1H, d, J=17.2Hz), 5.85(1H, ddt, J=17.2, 10.2, 5.1Hz), 6.89(2H, d, J=8.7Hz), 6.99–7.38(5H, m), 7.42(2H, d, J=8.7Hz) |
| 359 | 1.63–1.96(6H, m), 2.54–3.20(8H, m), 3.39(2H, q, J=6.4Hz), 3.65–5.20(2H, brs) 4.01(2H, t, J=5.8 Hz), 4.05(2H, s), 4.38(1H, m), 6.80(1H, brs), 6.90(2H, d, J=8.7Hz), 6.99–7.25(4H, m), 7.43 (2H, d, J=8.7Hz) |
| 360 | 1.62–1.98(6H, m), 2.28(6H, s), 2.54–3.14(8H, m), 2.94(2H, s), 3.36(2H, q, J=6.5Hz), 3.70–5.10 (2H, brs), 4.01(2H, t, J=5.9Hz), 4.39(1H, m), 6.90(2H, d, J=8.7Hz), 6.99–7.25(4H, m), 7.27 (1H, brs), 7.43(2H, d, J=8.7Hz) |
| 361 | 1.03(6H, t, J=7.2Hz), 1.59–1.98(6H, m), 2.43– 3.20(8H, m), 2.55(4H, q, J=7.2Hz), 3.02(2H, s), 3.35(2H, q, J=6.5Hz), 3.70–5.10(2H, brs), 4.02 (2H, t, J=5.9Hz), 4.39(1H, m), 6.90(2H, d, J=8.7 Hz), 6.99–7.29(4H, m), 7.43(2H, d, J=8.7Hz), 7.51(1H, brs) |
| 362 | 1.60–1.94(6H, m), 2.15(3H, s), 2.54–3.20(8H, m), 3.37(2H, q, J=6.5Hz), 3.80–5.20(2H, brs), 4.00 (2H, t, J=5.8Hz), 4.37(1H, m), 4.55(2H, s), 6.60 (1H, bs), 6.90(2H, d, J=8.5Hz), 7.00–7.28(4H, m), 7.42(2H, d, J=8.5Hz) |
| 363 | 1.38–1.72(4H, m), 1.72–1.97(4H, m), 2.30(3H, s), 2.36–3.20(16H, m), 3.01(2H, s), 3.31(2H, q, J=6.4Hz), 3.70–5.15(2H, brs), 3.99(2H, t, J=6.2 Hz), 4.36(1H, m), 6.90(2H, d, J=8.7Hz), 6.99– |
| 364 | 7.30(5H, m), 7.43(2H, d, J=8.7Hz) 1.36–1.70(4H, m), 1.70–1.97(4H, m), 2.52–3.15 (8H, m), 2.66(4H, m), 3.06(2H, s), 3.20(4H, m), 3.33(2H, q, J=6.4Hz), 3.75–5.10(2H, brs), 3.98 (2H, t, J=6.1Hz), 4.34(1H, m), 6.60–7.36(11H, m), 7.40(2H, d, J=8.5Hz) |
| 365 | 1.56–1.97(6H, m), 2.54–3.22(8H, m), 3.34(2H, q, J=6.4Hz), 3.70–5.10(2H, brs), 3.98(2H, d, J=5.2 Hz), 4.00(2H, t, J=5.9Hz), 4.35(1H, m), 4.51 (1H, t, J=5.2Hz), 6.89(1H, brs), 6.90(2H, d, J=8.7Hz), 7.00–7.29(4H, m), 7.40(2H, d, J=8.7Hz) |
| 366 | 1.05(6H, d, J=6.2Hz), 1.38–1.72(4H, m), 1.72– 1.95(4H, m), 2.54–3.16(9H, m), 3.24(2H, s), 3.30 (2H, q, J=6.3Hz), 3.70–5.20(2H, brs), 3.98(2H, t, J=6.3Hz), 4.38(1H, m), 6.90(2H, d, J=8.6Hz), 6.99–7.32 94H, m), 7.42(2H, d, J=8.6Hz), 7.49 (1H, brs) |
| 367 | 1.40–1.69(4H, m), 1.69–1.96(4H, m), 2.54–3.16 (8H, m), 3.29(2H, s), 3.29(2H, q, J=6.3Hz), 3.67–5.20(2H, brs), 3.76(2H, s), 3.97(2H, t, J=6.3Hz), 4.38(1H, m), 6.88(2H, d, J=8.7Hz), 7.00–7.39(10H, m), 7.41(2H, d, J=8.7Hz) |
| 368 | 1.37–1.68(4H, m), 1.68–1.98(4H, m), 1.79(4H, m), 2.40–3.15(8H, m), 2.59(4H, m), 3.14(2H, s), 3.31 (2H, q, J=6.4Hz), 3.66–5.20(2H, brs), 3.99(2H, t, J=6.2Hz), 4.37(1H, m), 6.89(2H, d, J=8.6Hz), 6.98–7.29(5H, m), 7.42(2H, d, J=8.6Hz) |
| 369 | 1.37–1.71(4H, m), 1.71–1.94(4H, m), 2.35–3.15 (8H, m), 2.52(4H, m), 3.00(2H, s), 3.31(2H, q, J=6.4Hz), 3.69(4H, m), 3.80–5.20(2H, brs), 3.99 (2H, t, J=6.1Hz), 4.36(1H, m), 6.89(2H, d, J=8.6 Hz), 6.98–7.29(5H, m), 7.42(2H, d, J=8.6Hz) |
| 370 | 1.36–1.69(4H, m), 169–1.95(4H, m), 2.28(3H, s), 2.52–3.13(8H, m), 3.02(2H, s), 3.30(2H, q, J=6.4 Hz), 3.56(2H, s), 3.80–5.20(2H, brs), 3.96(2H, t, J=6.2Hz), 4.36(1H, m), 6.88(2H, d, J=8.7Hz), 6.98–7.35(5H, m), 7.29(5H, s), 7.42(2H, d, J=8.7Hz) |
| 371 | 1.38–1.69(4H, m), 1.69–1.94(4H, m), 2.33(3H, s), 2.54–3.17(8H, m), 2.58(2H, t, J=5.2Hz), 3.07 2H, s), 3.29(2H, q, J=6.4Hz), 3.65(2H, t, J=5.2 Hz), 3.80–5.20(2H, br), 3.98(2H, t, J=6.2Hz), 4.38(1H, m), 6.89(2H, d, J=8.7Hz), 6.99–7.28 (4H, m), 7.39(1H, bs), 7.42(2H, d, J=8.7Hz) |
| 372 | 1.40(3H, t, J=7.0Hz), 1.43–1.68(4H, m), 1.68– 1.93(4H, m), 2.26(3H, s), 2.54–3.10(8H, m), 3.01 (2H, s), 3.30(2H, q, J=6.4Hz), 3.49(2H, s), 3.75–5.10(2H, br), 3.97(2H, t, J=6.2Hz), 4.00 (2H, q, J=7.0Hz), 4.39(1H, m), 6.84(2H, d, J=8.5 Hz), 6.89(2H, d, J=8.6Hz), 6.99–7.28(5H, m), 7.18(2H, d, J=8.5Hz), 7.42(2H, d, J=8.6Hz) |
| 373 | 1.32–1.65(4H, m), 1.65–1.93(4H, m), 2.53–3.14 (8H, m), 3.24(2H, q, J=6.2Hz), 3.60–5.10(2H, brs), 3.82(6H, d, J=5.7Hz), 3.94(2H, t, J=6.2 Hz), 4.37(1H, m), 5.11(2H, s), 5.79(1H, brs), 6.48(1H, brs), 6.88(2H, d, J=8.7Hz), 6.99–7.36 (4H, m), 7.33(5H, s), 7.41(2H, d, J=8.7Hz) |
| 374 | 1.42–2.02(12H, m), 2.36(2H, t, J=7.4Hz), 2.38 (1H, m), 2.54–3.16(10H, m), 3.53–5.15(2H, brs), 3.76–3.97(1H, m), 4.00(2H, t, J=6.3Hz), 4.38 (1H, m), 4.48–4.67(1H, m), 5.58(1H, brs), 5.81 (1H, brs), 6.90(2H, d, J=8.7Hz), 6.99–7.29(4H, m), 7.42(2H, d, J=8.7Hz) |
| 375 | 1.45–1.98(10H, m), 2.23(1H, m), 2.54–3.10(10H, m), 3.12(1H, m), 3.18,(1H, m), 3.32(2H, q, J=6.4 Hz), 3.70–5.20(2H, brs), 4.00(2H, t, J=5.8Hz), 4.37(1H, m), 5.95(1H, brs), 6.90(2H, d, J=8.7 Hz), 6.99–7.28(4H, m), 7.42(2H, d, J=8.7Hz) |
| 376 | 1.44–2.02(10H, m), 2.09(3H, s), 2.29(1H, m), 2.54–3.20(10H, m), 3.32(2H, q, J=6.4Hz), 3.70– 5.20(2H, brs), 3.78–3.94(1H, m), 4.00(2H, t, J=5.8Hz), 4.36(1H, m), 4.52–4.69(1H, m), 5.87 (1H, brs), 6.89(2H, d, J=8.7Hz), 6.99–7.28(4H, m), 7.42(2H, d, J=8.7Hz) |
| 377 | 1.42–2.01(12H, m), 2.38(2H, t, J=7.3Hz), 2.52– 3.26(11H, m), 2.94(3H, s), 3.09(3H, s), 3.65– 5.20(2H, brs), 3.82–4.14(1H, m), 4.00(2H, t, J=6.2Hz), 4.36(1H, m), 4.53–4.74(1H, m), 6.91 (2H, d, J=8.6Hz), 6.98–7.29(4H, m), 7.42(2H, d, J=8.6Hz) |

TABLE 10-continued

| | |
|---|---|
| 378 | 1.37–1.71(4H, m), 1.71–1.90(4H, m), 2.53–3.16 (8H, m), 3.30(2H, q, J=6.3Hz), 3.32(2H, s), 3.70–5.20(2H, brs), 3.98(2H, t, J=6.1Hz), 4.35 (1H, m), 6.90(2H, d, J=8.5Hz), 6.99–7.29(4H, m), 7.42(2H, d, J=8.5Hz), 7.44(1H, bs) |
| 379 | 1.33–1.67(4H, m), 1.67–2.00(4H, m), 2.53–3.15 (8H, m), 2.96(3H, s), 3.24(2H, q, J=6.2Hz), 3.50–5.30(2H, brs), 3.71(2H, d, J=5.8Hz), 3.97 (2H, t, J=6.2Hz), 4.36(1H, m), 6.11(1H, t, J=5.8 Hz), 6.88(1H, brs), 6.90(2H, d, J=8.7Hz), 6.99–7.29(4H, m), 7.41(2H, d, J=8.7Hz) |
| 380 | 1.41–2.10(8H, m), 2.53–3.30(8H, m), 3.47(2H, q, J=6.2Hz), 3.70–5.20(2H, brs), 3.97(2H, t, J=6.2 Hz), 4.34(1H, m), 6.87(2H, d, J=8.7Hz), 6.99–7.29(5H, m), 7.39(2H, d, J=8.7Hz), 7.96(2H, dd, J=6.9, 2.0Hz), 8.22(2H, dd, J=6.9, 2.0Hz) |
| 381 | 1.41–1.73(4H, m), 1.73–2.02(4H, m), 2.53–3.20 (8H, m), 3.43(2H, q, J=6.4Hz), 3.70–5.20(2H, br), 3.97(2H, t, J=6.2Hz), 4.36(1H, m), 6.40 (1H, brs), 6.62(2H, d, J=8.5Hz), 6.87(2H, d, J=8.5Hz), 6.99–7.28(4H, m), 7.40(2H, d, J=8.5 Hz), 7.60(2H, d, J=8.5Hz) |
| 382 | 1.30–1.63(4H, m), 1.63–2.05(4H, m), 2.55–3.30 (8H, m), 3.00(2H, q, J=6.2Hz), 3.70–5.20(2H, brs), 3.90(2H, t, J=6.2Hz), 4.37(1H, m), 5.50 (1H, t, J=6.2Hz), 6.86(2H, d, J=8.7Hz), 7.00–7.29(4H, m), 7.41(2H, d, J=8.7Hz), 8.04(2H, dd, J=6.9, 2.0Hz), 8.33(2H, dd, J=6.9, 2.0Hz), |
| 383 | 1.40–1.95(8H, m), 2.15(3H, s), 2.54–3.20(8H, m), 3.44(2H, q, J=6.1Hz), 3.70–5.20(2H, brs), 3.95 (2H, t, J=6.1Hz), 4.33(1H, m), 6.76(1H, brs), 6.83(2H, d, J=8.7Hz), 7.00–7.30(4H, m), 7.34 (2H, d, J=8.7Hz), 7.53(2H, d, J=8.7Hz), 7.68 (2H, d, J=8.7Hz), 8.73(1H, brs) |
| 384 | 1.40–1.95(8H, 2.54–3.11(8H, m), 3.01(6H, s), 3.46(2H, q, J=6.5Hz), 3.80–5.30(2H, brs), 3.98(2H, t, J=6.3Hz), 4.39(1H, m), 6.14(1H, brs), 6.65(2H, dd, J=6.9, 2.1Hz), 6.89(2H, d, J=8.8Hz), 6.99–7.28(4H, m), 7.42(2H, d, J=8.8 Hz), 7.67(2H, dd, J=6.9, 2.1Hz) |
| 385 | 1.26–1.61(4H, m), 1.61–2.00(4H, m), 2.54–3.30 (8H, m), 2.91(2H, q, J=6.0Hz), 3.70–5.20(2H, brs), 3.90(2H, t, J=6.2Hz), 4.34(1H, m), 4.91 (1H, brs), 6.60(2H, d, J=8.6Hz), 6.85(2H, d, J=8.6Hz), 6.99–7.29(4H, m), 7.40(2H, d, J=8.6 Hz), 7.58(2H, d, J=8.6Hz) |
| 386 | 1.48–1.74(4H, m), 1.74–2.02(4H, m), 2.23(3H, s), 2.28(3H, s), 2.54–3.30(8H, m), 3.65–5.20(2H, brs), 3.79(2H, t, J=7.4Hz), 4.00(2H, t, J=5.9 Hz), 4.35(1H, m), 6.91(2H, d, J=8.7Hz), 7.00–7.30(4H, m), 7.41(2H, d, J=8.7Hz), 7.46(2H, d, J=8.4Hz), 7.65(2H, d, J=8.4Hz), 9.23(1H, s) |
| 387 | 1.33–1.64(4H, m), 1.64–1.93(4H, m), 2.54–3.15 (8H, m), 2.92(2H, q, J=6.5Hz), 3.02(6H, s), 3.70–5.20(2H, brs), 3.90(2H, t, J=6.3Hz), 4.38 (1H, m), 4.81(1H, J=6.5Hz), 6.66(2H, d, J=9.1 Hz), 6.86(2H, d, J=8.7Hz), 6.99–7.28(4H, m), 7.41(2H, d, J=8.7Hz), 7.69(2H, d, J=9.1Hz) |
| 388 | 1.02(6H, J=7.1Hz), 1.34–1.93(8H, m), 2.37–3.12(10H, m), 2.52(4H, q, J=7.1Hz), 3.86–5.08 (3H, m), 3.98(2H, t, J=6.5Hz), 7.83–7.49(8H, m) |
| 389 | 1.42–1.96(12H, m), 2.35–3.15(14H, m), 3.78–5.13 (3H, m), 3.98(2H, t, J=6.4Hz), 6.82–7.50(8H, m) |
| 390 | 1.35–1.93(8H, m), 2.15–3.15(10H, m), 3.32–3.78 (3H, m), 3.83–5.22(3H, m), 3.97(2H, t, J=6.3Hz), 6.79–7.48(8H, m) |
| 391 | 1.38–1.93(8H, m), 2.43–3.40(12H, m), 3.65–5.15 (4H, m), 3.81(3H, s), 3.84(2H, s), 3.97(2H, t, J=6.2Hz), 6.75–7.48(12H, m) |
| 392 | 1.30–1.96(6H, m), 2.49–3.62(16H, m), 3.68–5.05 (4H, m), 3.98(2H, t, J=6.2Hz), 6.78–7.52(8H, m), 7.62(1H, dt, J=7.7, 1.8Hz), 8.43–8.59(1H, m) |
| 393 | 1.18–1.95(14H, m), 2.13–3.10(16H, m), 3.56–5.14 (4H, m), 3.99(2H, t, J=6.3Hz), 6.83–7.48(13H, m), |
| 394 | 1.60–1.93(6H, m), 2.27–3.14(18H, m), 3.02(2H, d, J=6.2 Hz), 3.75–5.05(3H, m), 4.00(2H, t, J=6.2 Hz), 5.12–5.26(2H, m), 5.78–5.98(1H, m), 6.81–7.47(8H, m) |
| 395 | 1.32–2.03(8H, m), 2.33(3H, s), 2.28–3.13(15H, m), 3.52–5.15(4H, m), 3.98(2H, t, J=6.3Hz), 6.83–7.48(10H, m), 7.60(1H, dt, J=7.6, 1.8Hz), 8.50–8.57(1H, m) |
| 396 | 1.06(3H, t, J=6.7Hz), 1.20–1.96(8H, m), 2.28–3.15(12H, m), 3.22–5.08(5H, m), 3.46(1H, d, J=14.4Hz), 3.83(1H, d, J=14.4Hz), 3.99(2H, t, J=6.7Hz), 6.83–7.52(10H, m), 8.52–8.62(1H, m) |
| 397 | 1.25–1.62(8H, m), 1.65–1.93(8H, m), 2.36–3.13 (14H, m), 3.80–5.05(3H, m), 3.97(2H, t, J=6.5 Hz), 6.83–7.49(8H, m) |
| 398 | 1.09(6H, t, J=7.2Hz), 1.22–1.93(12H, m), 2.4–3.12(10H, m), 2.63(4H, q, J=7.2Hz), 3.12–5.11 (3H, m), 3.98(2H, t, J=6.6Hz), 6.84–7.48(8H, m) |
| 399 | 1.63–2.03(10H, m), 2.48–3.13(14H, m), 3.82–5.03 (3H, m), 4.01(2H, t, J=5.9Hz), 6.81–7.49(8H, m) |
| 400 | 1.05(6H, t, J=7.2Hz), 1.57–1.90(6H, m), 2.42–3.15(14H, m), 3.83–5.04(3H, m), 4.01(2H, t, J=6.4Hz), 6.83–7.48(8H, m) |
| 401 | 1.25–1.93(10H, m), 2.36(3H, s), 2.43–3.12(17H, m), 3.82–5.16(3H, m), 3.97(2H, t, J=6.4Hz), 6.85–7.48(10H, m), 7.60(1H, dt, J=7.6, 1.9Hz), 8.49–8.55(1H, m) |
| 402 | 1.35–3.35(26H, m), 3.62–4.42(5H, m), 3.99(2H, t, J=6.6Hz), 5.57(1H, brs), 6.83–7.47(8H, m), |
| 403 | 1.42–2.08(12H, m), 2.43–3.44(15H, m), 3.82–5.04 (4H, m), 3.99(2H, t, J=6.2Hz), 6.83–7.49(8H, m) |
| 404 | 1.32–1.93(8H, m), 2.25(2H, brs), 2.50–3.13(10H, m), 3.80–5.00(4H, m), 3.92(2H, s), 3.97(2H, t, J=6.5Hz), 6.82–7.48(10H, m), 7.65(1H, dt, J=7.6, 1.8Hz), 8.51–8.59(1H, m) |
| 405 | 1.32–1.92(10H, m), 2.48–3.17(10H, m), 3.72–5.18 (4H, m), 3.82(2H, s), 3.97(2H, t, J=6.4Hz), 6.83–7.49(9H, m), 7.65–7.75(1H, m), 8.50(1H, dd, J=4.8, 1.6Hz), 8.56(1H, d, J=1.8Hz) |
| 406 | 1.13–1.92(14H, m), 2.18–3.12(14H, m), 3.47(1H, dd, J=10.7, 4.1Hz), 3.75(1H, dd, J=10.7, 3.8Hz), 3.81–5.08(3H, m), 3.98(2H, t, J=6.4Hz), 6.83–7.48(8H, m) |
| 407 | 1.40–2.03(12H, m), 2.25–3.15(13H, m), 3.20–3.31 (1H, m), 3.45(1H, dd, J=11.0, 3.0Hz), 3.67(1H, dd, J=11.0, 3.6Hz), 3.75–5.13(3H, m), 3.99(2H, t, J=6.3Hz), 6.83–7.50(8H, m) |
| 408 | 1.07–1.93(13H, m), 1.96–3.13(15H, m), 3.53(1H, dd, J=10.5, 5.8Hz), 3.66(1H, dd, J=10.5, 5.0Hz), 3.74–5.13(3H, m), 3.98(2H, t, J=6.4Hz), 6.83–7.47(8H, m) |
| 409 | 1.42–1.93(8H, m), 2.12–3.14(17H, m), 3.83–5.14 (4H, m), 3.99(2H, t, J=6.4Hz), 6.83–6.96(2H, m), 6.96–7.32(4H, m), 7.33–7.48(2H, m) |

| No. | NMR (DMSO-d$_6$) δ value |
|---|---|
| 410 | 1.33–1.97(15H, m), 2.38–3.28(14H, m), 3.48(2H, t, J=6.3Hz), 3.90–4.83(3H, m), 4.07(2H, t, J=6.2 Hz), 6.95–7.49(8H, m), 10.30(1H, brs) |

| No. | NMR (CDCl$_3$) δ value |
|---|---|
| 411 | 1.40–1.66(4H, m), 1.68–2.22(8H, m), 2.26–3.28 (13H, m), 3.72(3H, s), 3.78–5.10(3H, m), 3.97 (2H, t, J=6.4Hz), 6.83–7.48(8H, m) |

| No. | NMR (DMSO-d$_6$) δ value |
|---|---|
| 412 | 1.30–2.13(16H, m), 2.33–3.60(16H, m), 3.62–4.93 (3H, m), 4.02(2H, t, J=6.2Hz), 6.87–7.05(3H, m), 7.18–7.42(5H, m), 10.03(1H, brs) |

| No. | NMR (CDCl$_3$) δ value |
|---|---|
| 413 | 1.43–1.93(8H, m), 2.35–3.12(14H, m), 3.67–5.24 (3H, m), 3.84(4H, t, J=5.3Hz), 4.00(2H, t, J=6.4 Hz), 6.47(1H, t, J=4.7Hz), 6.84–7.50(8H, m), 8.30(2H, d, J=4.7Hz) |
| 414 | 1.40–1.96(8H, m), 2.34–3.13(14H, m), 3.55(4H, t, J=4.8Hz), 3.75–5.21(3H, m), 4.00(2H, t, J=6.4 Hz), 6.55–6.67(2H, m), 6.85–7.53(9H, m), 8.12–8.22(1H, m) |
| 415 | 1.40–1.93(8H, m), 2.28(3H, s), 2.41–3.12(13H, |

| | |
|---|---|
| | m), 3.61(2H, t, J=5.5Hz), 3.75–5.25(3H, m), 3.99 (2H, t, J=6.4Hz), 6.85–7.49(8H, m) |
| 416 | 1.37–2.04(12H, m), 2.22–3.16(13H, m), 3.18–3.34 (1H, m), 3.45(1H, dd, J=11.0, 2.8Hz), 3.67(1H, dd, J=11.0, 3.5Hz), 3.85–5.23(3H, m), 3.99(2H, t, J=6.3Hz), 6.83–7.50(8H, m) |
| 417 | 1.38–1.93(8H, m), 2.28–3.13(16H, m), 3.63(4H, t, J=5.4Hz), 3.77–5.08(3H, m), 3.99(2H, t, J=6.3 Hz), 6.85–7.50(8H, m) |
| 418 | 1.38(6H, dt, J=7.1, 2.5Hz), 1.42–1.98(8H, m), 2.49–3.14(8H, m), 3.22–3.41(1H, m), 3.27(3H, s), 3.39(3H, s), 3.48–5.13(9H, m), 4.04(2H, t, J=6.2 Hz), 6.83–7.47(8H, m) |
| 419 | 1.38–1.95(8H, m), 2.27(3H, s), 2.36–3.19(14H, m), 3.78–5.06(3H, m), 3.99(2H, t, J=6.4Hz), 6.85–6.95(2H, m), 6.97–7.32(4H, m), 7.37–7.48 (2H, m) |
| 420 | 1.32–1.97(14H, m), 1.12–3.21(15H, m), 3.58–5.06 (4H, m), 3.99(2H, t, J=6.4Hz), 6.83–7.54(8H, m) |
| 421 | 1.51–2.00(8H, m), 2.47–3.28(8H, m), 3.18(2H, t, J=6.8Hz), 3.79–5.15(3H, m), 4.00(2H, t, J=6.1 Hz), 6.78–3.37(7H, m), 7.42(2H, d, J=8.7Hz), 8.50(2H, d, J=4.8Hz) |
| 422 | 1.45–2.17(8H, m), 2.44–3.24(10H, m), 3.61(3H, s), 3.80–5.12(3H, m), 3.97(2H, t, J=6.3Hz), 6.80–7.38(8H, m), 7.42(2H, d, J=8.7Hz) |
| 423 | 1.52–2.04(8H, m), 2.49–3.15(8H, m), 3.38–3.57 (2H, m), 3.75–5.12(8H, m), 6.88(2H, d, J=8.7Hz), 6.93–7.36(6H, m), 7.42(2H, d, J=8.7Hz) |
| 424 | 1.47–2.20(8H, m), 2.48–3.33(10H, m), 3.75–5.14 (5H, m), 6.87(2H, d, J=8.7Hz), 6.93–7.54(7H, m), 8.88(2H, d, J=4.9Hz) |
| 425 | 1.52–2.13(8H, m), 2.49–3.14(8H, m), 3.47–3.68 (2H, m), 3.85–5.11(3H, m), 3.99(2H, t, J=6.1Hz), 6.87(2H, d, J=8.8Hz), 6.93–7.38(4H, m), 7.42 (2H, d, J=8.8Hz), 7.57(1H, d, J=4.9Hz), 8.95 (1H, d, J=4.9Hz) |
| 426 | 1.09–2.02(10H, m), 2.42–5.21(29H, m), 6.89(2H, d, J=8.7Hz), 6.94–7.36(4H, m), 7.40(2H, d, J=8.7Hz) |
| 427 | 1.38(9H, t, J=7.1Hz), 1.48–2.19(8H, m), 2.49–3.16(8H, m), 3.27–3.45(2H, m), 3.50(6H, q, J=7.1 Hz), 3.80–5.11(3H, m), 4.03(2H, t, J=4.7Hz), 6.90(2H, d, J=8.6Hz), 6.97–3.38(4H, m), 7.41 (2H, d, J=8.6Hz) |
| 428 | 1.34–3.39(25H, m), 3.77–5.12(3H, m), 3.97(2H, t, J=6.3Hz), 5.57–5.92(3H, m), 6.88(2H, d, J=8.8 Hz), 6.94–7.36(4H, m), 7.42(2H, d, J=8.8Hz) |
| 429 | 1.35–1.99(8H, m), 2.42–3.20(8H, m), 3.72–5.15 (3H, m), 3.97(4H, t like, J=6.9Hz), 6.81–7.62 (11H, m) |
| 430 | 1.37–2.14(8H, m), 2.45–3.16(8H, m), 3.71–5.15 (3H, m), 3.98(2H, t, J=6.2Hz), 4.21(2H, t, J=7.0 Hz), 6.78–7.52(8H, m), 7.94(1H, s), 8.07(1H, s) |
| 431 | 1.53–2.01(8H, m), 2.48–3.17(10H, m), 3.80–5.12 (3H, m), 4.00(2H, t, J=6Hz), 6.89(2H, d, J=8.8 Hz), 6.92–7.55(8H, m), 6.05–8.22(2H, m) |
| 432 | 1.22–1.96(14H, m), 2.46–3.16(8H, m), 3.75–5.18 (3H, m), 3.68(2H, t, J=7.2Hz), 3.96(2H, t, J=6.5 Hz), 6.89(2H, d, J=8.7Hz), 6.94–7.36(4H, m), 7.42(2H, d, J=8.7Hz), 7.63–7.92(4H, m) |
| 433 | 1.40–2.02(8H, m), 2.41–3.22(10H, m), 3.50–5.15, (3H, m), 3.76(2H, brs), 3.95(2H, t, J=6 2.Hz), 6.48–6.68(2H, m), 6.87(2H, d, J=8.8Hz); 6.94–7.37(6H, m), 7.42(2H, d, J=8.8Hz) |
| 434 | 1.44–2.11(8H, m), 2.50–3.32(10H, m), 3.83–5.10 (3H, m), 3.96(2H, t, J=5.8Hz), 6.85(2H, d, J=8.7 Hz), 6.90–7.38(4H, m), 7.41(2H, d, J=8.7Hz), 8.05–8.21(2H, m), 8.36–8.52(2H, m) |
| 435 | 1.41–2.12(8H, m), 2.45–3.41(8H, m), 3.20(2H, t, J=6.9Hz), 3.70–5.11(3H, m), 3.99(3H, t, J=6.3 Hz), 6.75–7.17(11H, m), 8.37–8.52(2H, m) |
| 436 | 1.51–2.05(8H, m), 2.37–3.22(10H, m), 3.76–5.14 (3H, m), 4.00(2H, t, J=6.1Hz), 6.89(2H, d, J=8.7 Hz), 6.95–7.38(6H, m), 7.43(2H, d, J=8.7Hz), 8.30–8.49(2H, m) |
| 437 | 1.41–1.92(8H, m), 2.47–3.19(10H, m), 3.70–5.10 (5H, m), 3.93(2H, t, J=6Hz), 6.56–7.70(12H, m) |
| 438 | 1.46–2.02(8H, m), 2.43–3.19(8H, m), 3.31–3.56 (2H, m), 3.70–5.11(3H, m), 3.96(2H, t, J=5.9Hz), 6.75–7.51(8H, m), 7.56(1H, ddd, J=1.3, 4.7, 7.6 Hz), 7.89–8.18(2H, m), 8.68–8.81(1H, m) |
| 439 | 1.48–1.97(8H, m), 2.47–3.30(10H, m), 3.78–5.12 (5H, m), 6.87(2H, d, J=8.7Hz), 6.94–7.36(4H, m), 7.43(2H, d, J=8.7Hz), 7.68–7.88(2H, m), 8.23–8.39(2H, m) |
| 440 | 1.41–2.01(8H, m), 2.25(3H, s,), 2.48–3.16(10H, m), 3.71–5.18(3H, m), 3.90(2H, d, J=5.5Hz), 6.78 (2H, d, J=8.7Hz), 6.98–7.54(8H, m), 7.63(2H, d, J=8.7Hz), 9.03(1H, brs) |
| 441 | 1.15–2.16(16H, m), 2.44–3.13(10H, m), 3.75–5.20 (3H, m), 3.98(2H, t, J=6.5Hz), 6.90(2H, d, J=8.7 Hz), 6.94–7.37(4H, m), 7.42(2H, d, J=8.7Hz) |
| 442 | 1.22–5.20(34H, m), 5.92–6.19(1H, m), 6.90(2H, d, J=8.5Hz), 6.95–7.34(4H, m), 7.42(2H, d, J=8.5Hz), |
| 443 | 1.42–1.96(8H, m), 2.50–3.19(10H, m), 3.06(6H, s), 3.74–5.11(3H, m), 3.94(2H, t, J=6.2Hz), 6.69 (2H, d, J=9.1Hz), 6.85(2H, d, J=8.8Hz), 6.92–7.34(4H, m), 7.40(2H, d, J=8.8Hz), 7.69(2H, d, J=9.1Hz) |
| 444 | 1.20–2.02(14H, m), 1.97(3H, m), 2.48–3.32(10H, m), 3.77–5.15(3H, m), 3.98(2H, t, J=6.4Hz), 5.61 (1H, brs), 6.90(2H, d, J=8.7Hz), 6.98–7.38(4H, m), 7.42(2H, d, J=8.7Hz) |
| 445 | 1.29–3.40(25H, m), 2.03(3H, s), 2.07(3H, s), 3.81–5.15(7H, m), 5.76(brs), 6.89(2H, d, J=8.4 Hz), 6.96–7.51(6H, m) |
| 446 | 1.62–1.94(2H, m), 1.99(3H, s), 2.01(2H, m), 2.46–3.20(8H, m), 3.45(2H, q, J=6.3Hz), 3.70–5.20(2H, brs), 4.05(2H, t, J=5.9Hz), 4.34(1H, m), 6.00(1H, brs), 6.60(1H, d, J=8.1Hz), 6.67 (1H, d, J=8.1Hz), 6.89(2H, d, J=8.7Hz), 7.10 (1H, t, J=8.1Hz), 7.42(2H, d, J=8.7Hz) |
| 447 | 1.42(3H, t, J=7.0Hz), 1.57–1.75(1H, m), 1.75–1.93(1H, m), 2.40–3.24(8H, m), 3.56–3.92(4H, m), 4.04(2H, q, J=7.0Hz), 4.19–4.66(1H, m), 4.80–5.04(1H, m), 6.37–6.67(1H, m), 6.48(1H, d, J=8.1 Hz), 6.60–6.78(1H, m), 6.61(1H, d, J=8.1Hz), 7.01(1H, t, J=8.1Hz), 7.10–7.46(1H, m), 8.36 (1H, brs) |
| 448 | 1.42(3H, t, J=7.0Hz), 1.57–1.75(1H, m), 1.75–1.94(1H, m), 2.35–3.20(8H, m), 3.57–3.73(1H, m), 3.73–3.92(3H, m), 3.84(3H, s), 4.04(2H, q, J=7.0 Hz), 4.25–4.75(1H, m), 4.86–5.04(1H, m), 6.43–6.57(1H, m), 6.50(1H, d, J=8.2Hz), 6.64(1H, d, J=8.2Hz), 6.68–6.91(1H, m), 7.12–7.33(1H, m), 7.18(1H, t, J=8.2Hz) |
| 449 | 1.42(3H, t, J=6.9Hz), 1.66–1.91(2H, m), 1.91–2.13(2H, m), 1.97(3H, s), 2.47–3.20(8H, m), 3.42 (2H, q, J=6.3Hz), 3.80–5.20(2H, brs), 4.03(2H, t, J=6.9Hz), 4.05(2H, q, J=6.9Hz), 4.35(1H, m), 6.37(1H, brs), 6.64(1H, d, J=8.2Hz), 6.74(1H, d, J=8.2Hz), 6.89(2H, d, J=8.7Hz), 7.17(1H, t, J=8.2Hz), 7.42(2H, d, J=8.7Hz) |
| 450 | 1.42(6H, t, J=7.0Hz), 1.55–1.76(1H, m), 1.76–1.93(1H, m), 2.35–3.22(8H, m), 3.50–3.75(1H, m), 3.75–3.94(3H, m), 4.04(4H, q, J=7.0Hz), 4.26–4.72(1H, m), 4.82–5.05(1H, m), 6.49–6.58(1H, m), 6.51(1H, d, J=8.2Hz), 6.63(1H, d, J=8.2Hz), 6.68–6.92(1H, m), 7.15(1H, t, J=8.2Hz), 7.20–7.35(1H, m) |
| 451 | 1.42(3H, t, J=7.0Hz), 1.55–1.75(1H, m), 1.75–1.98(1H, m), 2.33(3H, s), 2.41–3.23(8H, m), 3.53–3.96(4H, m), 4.05(2H, q, J=7.0Hz), 4.18–4.68(1H, m), 4.86–5.08(1H, m), 6.46–6.60(1H, m), 6.49(1H, d, J=8.0Hz), 6.81(1H, d, J=8.0Hz), 6.94–7.32(2H, m), 7.24(1H, t, J=8.0Hz) |
| 452 | 1.55–1.88(2H, m), 1.88–2.10(2H, m), 1.97(3H, s), 2.47–3.20(8H, m), 3.42(2H, q, J=6.3Hz), 3.60–5.20(2H, brs), 3.84(3H, s), 4.03(2H, t, J=6.0 Hz), 4.34(1H, m), 6.30(1H, brs), 6.65(1H, d, J=8.3Hz), 6.75(1H, d, J=8.3Hz), 6.89(2H, d, J=8.7Hz), 7.20(1H, t, J=8.3Hz), 7.41(2H, d, J=8.7Hz) |
| 453 | 1.67–1.93(2H, m), 1.93–2.11(2H, m), 1.98(3H, s), 2.33(3H, s), 2.50–3.15(8H, m), 3.43(2H, q, J=6.4 Hz), 3.80–5.20(2H, br), 4.04(2H, t, J=5.9Hz), 4.33(1H, m), 6.13(1H, brs), 6.82(1H, d, J=8.1 Hz), 6.90(2H, d, J=8.7Hz), 7.01(1H, d, J=8.1 |

TABLE 10-continued

| | |
|---|---|
| | Hz), 7.26(1H, t, J=8.1Hz), 7.42(2H, d, J=8.7Hz) |
| 454 | 1.60–1.90(3H, m), 2.40–2.95(8H, m), 3.10–3.36 (2H, m), 4.23–4.48(8H, m), 6.70–7.22(3H, m) |
| 455 | 1.55–1.93(2H, m), 2.35–3.27(8H, m), 3.58–4.00 (7H, m), 4.25–4.74(1H, m), 4.86–5.07(1H, m), 6.44–6.60(2H, m), 6.73–7.37(4H, m) |
| 456 | 1.42(3H, t, J=7.0Hz), 1.55–1.90(2H, m), 2.35–3.20(8H, m), 3.60–3.93(4H, m), 4.01.(2H, q, J=7.0 Hz), 4.25–4.70(1H, m), 4.85–5.05(1H, m), 6.40–6.59(2H, m), 6.72–7.35(4H, m) |
| 457 | 1.70–2.12(4H, m), 1.95(3H, s), 2.31(3H, s), 2.42–3.15(8H, m), 3.35–3.50(2H, m), 3.80–5.10 (5H, m), 6.17(1H, brs), 6.80–7.20(5H, m), 7.42 (2H, d, J=8.5Hz) |
| 458 | 1.40–2.05(10H, m), 2.31(3H, s), 2.42–3.20(8H, m), 3.43(2H, t, J=6.7Hz), 3.70–5.05(5H, m), 6.80–7.22(5H, m), 7.42(2H, d, J=8.7Hz) |
| 459 | 1.03(6H, t, J=7.1Hz), 1.22–2.00(10H, m), 2.31 (3H, s), 2.40–3.23(14H, m), 3.80–5.21(5H, m), 6.85–7.20(5H, m), 7.42(2H, d, J=8.7Hz) |
| 460 | 1.30–2.15(14H, m), 2.31(3H, s), 2.38–3.20(14H, m), 3.80–5.05(5H, m), 6.80–7.22(5H, m), 7.42(2H, d, J=8.7Hz) |
| 461 | 1.42–1.96(8H, m), 2.42–3.13(12H, m), 3.30(2H, d, J=6.1Hz), 3.98(2H, t, J=6.3Hz), 3.80–4.97(3H, m), 4.98–5.28(2H, m), 5.83–6.04(1H, m), 6.82–7.48 (8H, m) |
| 462 | 1.34–1.95(9H, m), 2.45–3.15(12H, m), 3.57(2H, t J=5.4Hz), 3.63(2H, s), 3.95(2H, t, J=6.3Hz), 3.78–5.14(3H, m), 6.84–7.50(13H, m) |
| 463 | 1.07(3H, d, J=6.3Hz), 1.24–1.93(14H, m), 2.07–2.48(3H, m), 2.53–3.13(10H, m), 3.98(2H, t, J=6.4Hz), 3.82–5.10(3H, m), 6.84–7.50(8H, m) |
| 464 | 0.76–0.95(1H, m), 0.87(3H, d, J=6.1Hz), 1.38–1.93(14H, m), 2.27–2.41(2H, m), 2.52–3.12(10H, m), 3.98(2H, t, J=6.4Hz), 3.83–5.07(3H, m), 6.83–7.49(8H, m) |
| 465 | 0.92(3H, d, J=5.8Hz), 1.14–2.02(15H, m), 2.26–2.42(2H, m), 2.52–3.13(10H, m), 3.98(2H, t, J=6.4Hz), 3.86–5.06(3H, m), 6.83–7.52(8H, m) |
| 466 | 1.43–1.93(8H, m), 2.52–3.13(14H, m), 3.69(2H, t, J=5.3Hz), 3.99(2H, t, J=6.3Hz), 3.80–5.05(3H, m), 6.83–7.49(8H, m) |
| 467 | 1.04(6H, t, J=7.2Hz), 1.33–2.05(8H, m), 2.30–3.22(14H, m), 3.54–3.75(1H, m), 3.93–4.20(2H, m), 4.30–4.42(1H, m), 4.93–5.07(1H, m), 6.83–7.42 (8H, m) |
| 468 | 1.36–1.92(8H, m), 2.28(6H, s), 2.42–3.13(14H, m), 3.60(2H, s), 3.72–5.07(3H, m), 3.96(2H, t, J=6.4Hz), 6.85–7.48(13H, m) |
| 469 | 1.45–1.98(14H, m), 2.49–3.14(14H, m), 3.82–5.13 (3H, m), 3.99(2H, t, J=6.2Hz), 6.82–7.49(8H, m) |
| 470 | 1.38–1.94(8H, m), 2.22(3H, s), 2.28–2.44(2H, m), 2.49–3.10(8H, m), 3.00(2H, d, J=6.5Hz), 3.88–4.96(3H, m), 3.98(2H, t, J=6.4Hz), 5.08–5.24 (2H, m), 5.87(1H, ddt, J=17.1, 10.2, 6.5Hz), 6.83–7.49(8H, m) |
| 471 | 1.40–1.92(8H, m), 2.05, 2.07, 2.12, 2.14(total: 6H, s), 2.52–3.14(8H, m), 3.28–3.43(2H, m), 3.55 (2H, dt, J=8.5, 5.9Hz), 3.99(2H, dt, J=6.1, 6.1 Hz), 4.20(2H, dt, J=6.0, 6.0Hz). 3.84–4.98(3H, m), 6.85–7.50(8H, m) |
| 472 | 1.38–1.93(8H, m), 2.07(3H, s), 2.31(3H, s), 2.37–3.13(12H, m), 3.87–5.04(3H, m), 3.98(2H, t, J=6.4Hz), 4.18(2H, t, J=5.9Hz), 6.84–7.49(8H, m) |
| 473 | 1.37–1.94(8H, m), 2.05(6H, s), 2.49–3.12(10H, m), 2.77(4H, t, J=6.2Hz), 3.83–5.05(3H, m), 3.98 (2H, t, J=6.3Hz), 4.12(4H, t, J=6.1Hz), 6.85–7.48(8H, m) |
| 474 | 1.13(6H, d, J=6.3Hz), 1.40–1.93(8H, m), 2.49–3.13(12H, m), 3.84–5.03(3H, m), 3.98(2H, t, J=6.4Hz), 6.84–7.48(8H, m) |
| 475 | 1.44–2.08(8H, m), 2.02–3.30(10H, m), 3.09(3H, s), 3.77–5.02(3H, m), 3.87(2H, d, J=7.1Hz), 4.00 (2H, d, J=6.1Hz), 5.41–5.08(2H, m), 6.03–6.27 (1H, m), 6.83–7.48(8H, m) |
| 476 | 1.00(6H, t, J=7.1Hz), 1.41–1.93(8H, m), 2.05 (3H, s), 2.32–3.13(14H, m), 3.86–5.05(3H, m), 3.98(2H, t, J=6.3Hz), 4.90–5.03(1H, m), 6.85– |

TABLE 10-continued

| | |
|---|---|
| | 7.48(8H, m) |
| 477 | 1.38–1.93(12H, m), 2.37–3.13(14H, m), 3.87–5.05 (3H, m), 4.01(2H, t, J=6.4Hz), 6.83–7.49(8H, m) |
| 478 | 1.28–1.93(16H, m), 2.32–3.11(14H, m), 3.83–5.07 (3H, m), 3.97(2H, t, J=6.4Hz), 6.85–7.51(8H, m) |
| 479 | 1.43–1.96(8H, m), 2.26(6H, s), 2.26–2.42(2H, m), 2.53–3.07(8H, m), 3.91–5.04(3H, m), 3.99(2H, t, J=6.4Hz), 6.86–7.47(8H, m) |
| 480 | 1.30–1.92(10H, m), 2.30(6H, s), 2.27–2.43(2H, m), 2.53–3.12(8H, m), 3.87–4.87(3H, m), 3.98(2H, t, J=6.4Hz), 6.85–7.48(8H, m) |
| 481 | 1.55–2.16(7H, m), 2.37–5.37(17H, m), 6.38–7.59 (13H, m) |
| 482 | 1.26(3H, t, J=7.2Hz), 1.52–2.01(6H, m), 2.32–3.33(10H, m), 3.53–5.10(8H, m), 4.14(2H, q, J=7.2Hz), 6.40–6.58(2H, m), 6.96–7.33(5H, m) |
| 483 | 1.58–3.32(16H, m), 3.56–5.12(8H, m), 5.52–6.00 (2H, m), 6.48–6.60(2H, m), 6.95–7.48(5H, m) |
| 484 | 1.35–5.15(49H, m), 6.36–6.60(2H, m), 6.92–7.38 (5H, m) |
| 485 | 1.27–4.61(52H, m), 4.78–5.06(1H, m), 6.34–6.60 (2H, m), 6.93–7.40(5H, m) |

| No. | NMR (DMSO$_6$) δ value |
|---|---|
| 486 | 1.24(12H, t, J=7.2Hz), 1.31–2.12(14H, m), 2.25–4.43(26H, m), 4.55–4.79(1H, m), 6.48–6.72(2H, m), 6.94–7.43(5H, m), 10.49–10.97(2H, m) |

| No. | NMR (CDCl$_3$) δ value |
|---|---|
| 487 | 1.51–2.02(6H, m), 2.18–4.13(27H, m), 4.28–4.72 (1H, m), 4.88–5.08(1H, m), 6.37–6.59(2H, m), 6.92–7.38(5H, m) |
| 488 | 1.53–1.99(6H, m), 2.30–3.24(14H, m), 3.55–4.12 (10H, m), 4.22–4.75(1H, m), 4.86–5.08(1H, m), 6.39–6.58(2H, m), 6.92–7.38(5H, m) |
| 489 | 1.51–2.10(6H, m), 2.12–3.29(14H, m), 3.52–4.68 (11H, m), 4.77–5.07(1H, m), 6.35–6.62(2H, m), 6.92–7.48(5H, m) |
| 490 | 1.55–2.00(6H, m), 2.34–3.25(14H, m), 3.53–4.72 (11H, m), 4.81–5.07(1H, m), 6.39–6.58(2H, m), 6.92–7.37(5H, m) |
| 491 | 1.49–2.08(8H, m), 2.48–3.13(8H, m), 3.44(2H, t, J=6.7Hz), 3.76–5.08(3H, m), 4.00(2H, t, J=6.3 Hz), 6.83–7.48(8H, m) |
| 492 | 1.42–1.63(4H, m), 1.68–2.02(6H, m), 2.48–3.18 (8H, m), 3.43(2H, t, J=6.7Hz), 3.86–5.13(3H, m), 3.99(2H, t, J=6.3Hz), 6.84–7.52(8H, m) |
| 493 | 0.98–2.02(18H, m), 2.23–3.13(12H, m), 3.85–497 (3H, m), 3.98(2H, t, J=6.4Hz), 6.83–7.47(8H, m) |
| 494 | 1.42–1.95(9H, m), 2.22(1H, t, J=2.4Hz), 2.48–3.13(10H, m), 3.43(2H, d, J=2.4Hz), 3.84–5.13 (3H, m), 3.99(2H, t, J=6.4Hz), 6.84–7.51(8H, m) |

Using the suitable starting materials, the following compounds are obtained in the same manners as in Examples 1, 384, 390–393, 398, 399, 407–409, 426 and 593.

TABLE 11

(R$^1$)$_q$ — [phenyl] — N(R) — C(=O) structure

Example 779

Structure

R: [piperidinyl]—N—C(=O)—[phenyl]—O(CH$_2$)$_5$NHC(CH$_3$)$_3$

TABLE 11-continued

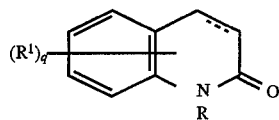

R[1]: H, q: 1
Bond between 3- and 4-positions in the carbostyril ring: Single bond
NMR analysis: 495)
Form: Free

Example 780

Structure

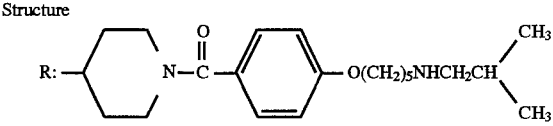

R[1]: H, q: 1
Bond between 3- and 4-positions in the carbostyril ring: Single bond
NMR analysis: 496)
Form: Free

Example 781

Structure

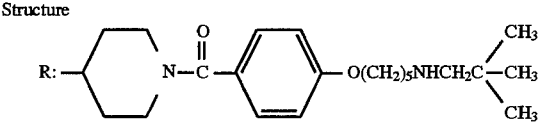

R[1]: H, q: 1
Bond between 3- and 4-positions in the carbostyril ring: Single bond
NMR analysis: 497)
Form: Free

Example 782

Structure

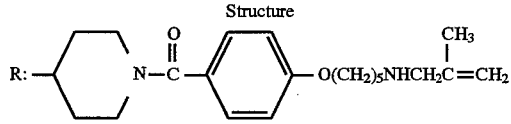

R[1]: H, q: 1
Bond between 3- and 4-positions in the carbostyril ring: Single bond
NMR analysis: 498)
Form: Free

Example 783

Structure

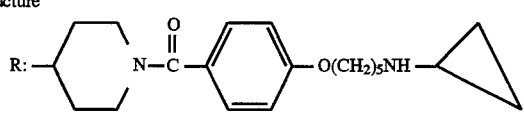

R[1]: H, q: 1
Bond between 3- and 4-positions in the carbostyril ring: Single bond
NMR analysis: 499)
Form: Free

Example 784

Structure

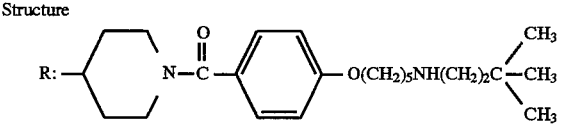

R[1]: H, q: 1
Bond between 3- and 4-positions in the carbostyril ring: Single bond

TABLE 11-continued

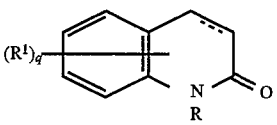

NMR analysis: 500)
Form: Free

Example 785

Structure

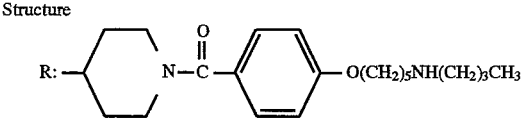

R[1]: H, q: 1
Bond between 3- and 4-positions in the carbostyril ring: Single bond
NMR analysis: 501)
Form: Free

Example 786

Structure

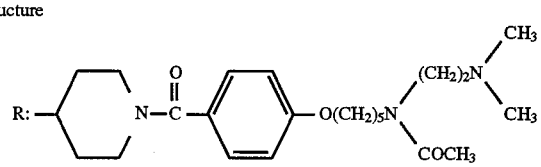

R[1]: H, q: 1
Bond between 3- and 4-positions in the carbostyril ring: Single bond
NMR analysis: 502)
Form: Free

Example 787

Structure

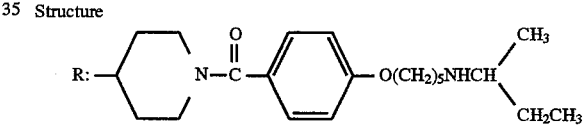

R[1]: H, q: 1
Bond between 3- and 4-positions in the carbostyril ring: Single bond
NMR analysis: 503)
Form: Free Using the suitable starting materials, the following compound is obtained in the same manners as in Examples 1, 384, 390–393, 398, 399, 407–409, 421 and 593.

TABLE 12

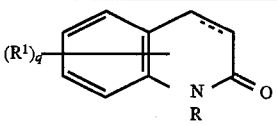

Example 788

Structure

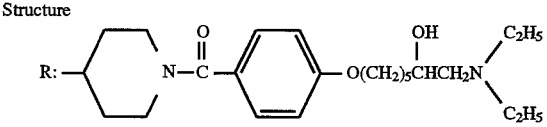

TABLE 12-continued

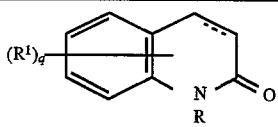

R[1]: H, q: 1
Bond between 3- and 4-positions in the
carbostyril ring: Single bond
NMR analysis: 504)
Form: Free

TABLE 13

| No. | NMR (CDCl$_3$) δ value |
|---|---|
| 495 | 1.66(9H, s), 1.42–1.93(8H, m), 2.51–3.22(11H, m), 3.83–5.15(3H, m), 3.98(2H, t, J=6.4Hz), 6.83–7.48(8H, m) |
| 496 | 0.93(6H, d, J=6.6Hz), 1.42–1.94(9H, m), 2.33–3.14(11H, m), 2.46(2H, d, J=6.9Hz), 3.83–5.18 (3H, m), 3.98(2H, t, J=6.4Hz), 6.85–7.48(8H, m) |
| 497 | 0.93(9H, s), 1.43–2.01(9H, m), 2.37(2H, s), 2.50–3.13(10H, m), 3.82–5.03(3H, m), 3.99(2H, t, J=6.4Hz), 6.86–6.94(2H, m), 6.98–7.30(4H, m), 7.38–7.47(2H, m) |
| 498 | 1.43–1.96(9H, m), 1.75(3H, s), 2.52–3.13(10H, m), 3.19(2H, s), 3.88–5.05(3H, m), 3.99(2H, t, J=6.4Hz), 4.85(2H, d, J=6.5Hz), 6.85–7.52(8H, m) |
| 499 | 0.28–0.51(4H, m), 1.41–1.94(9H, m), 2.06–2.21 (1H, m), 2.51–3.17(10H, m), 3.82–5.08(3H, m), 3.98(2H, t, J=6.4Hz), 6.86–7.51(8H, m) |
| 500 | 0.91(9H, s), 1.34–1.94(10H, m), 2.11(1H, brs), 2.49–3.12(12H, m), 3.84–5.03(3H, m), 3.98(2H, t, J=3.4Hz), 6.83–7.48(8H, m) |
| 501 | 0.91(3H, t, J=7.2Hz), 1.24–1.93(12H, m), 2.13 (1H, brs), 2.44–3.15(12H, m), 3.78–5.14(3H, m), 3.98(2H, t, J=6.4Hz), 6.84–7.48(8H, m) |
| 502 | 1.39–1.95(8H, m), 2.11(3H, d, J=1.5Hz), 2.27 (3H, s), 2.33(3H, s), 2.48–3.13(16H, m), 3.26–3.67(4H, m), 3.87–5.10(5H, m), 6.85–7.53(8H, m) |
| 503 | 0.90(3H, t, J=7.4Hz), 1.07(3H, d, J=6.3Hz), 1.20–1.92(10H, m), 2.22(1H, brs), 2.49–3.12(11H, m), 3.85–5.04(3H, m), 3.98(2H, t, J=6.4Hz), 6.83–7.48(8H, m) |
| 504 | 1.02(6H, t, J=7.1Hz), 1.31–1.93(10H, m), 2.16–3.13(15H, m), 3.49–3.67(1H, m), 3.85–4.93(3H, m), 3.98(2H, t, J=6.4Hz), 6.83–7.48(8H, m) |

Reference Example 25

1,3-Cyclohexanedione (10.0 g) is dissolved in toluene (100 ml) with heating and thereto is added 4-amino-1-benzylpiperidine (18.6 ml). The mixture is refluxed for 2 hours by using Dean-Stark apparatus. After cooling, the precipitated crystal is washed with diethyl ether, and recrystallized from toluene to give 1-(1-benzyl-4-piperidinylamino)-1-cyclohexen-3-on (24.2 g) as light yellow prisms, m.p.: 171°–172° C.

Reference Example 26

Acrylic acid (28.9 ml) is added to 1-(1-benzyl-4-piperidinylamino)-1-cyclohexen-3-on (100 g) and the mixture is refluxed with stirring for 6 hours. After cooling, the reaction mixture is dissolved in chloroform containing 10% methanol and purified by silica gel column chromatography (solvent; dichloromethane:methanol=40:1). The resultant is recrystallized from ethanol/water to give 1-(1-benzyl-4-piperidinyl)-5-oxo-3,4,5,6,7,8-hexahydrocarbostyril (23.98 g) as colorless needles, m.p.: 102°–103° C.

Reference Example 27

1-(1-Benzyl-4-piperidinyl)-5-oxo-3,4,5,6,7,8-hexahydrocarbostyril (10.0 g) is dissolved in chloroform (500 ml) and thereto is added N-bromosuccinimide (5.78 g). The mixture is refluxed with stirring for 2 hours. Thereto are added N-bromosuccinimide (5.00 g) and triethylamine (50 ml) and the mixture is refluxed with stirring for 3 hours. After cooling, the reaction mixture is washed twice with 30% aqueous sodium thiosulfate solution (200 ml) and once with saline solution (500 ml) and then dried with magnesium sulfate. The solvent is evaporated off and the resulting residue is purified by silica gel column chromatography (solvent: dichloromethane:methanol=40:1) and recrystallized from ethanol/water to give 1-(1-benzyl-4-piperidinyl)-5-hydroxy-3,4-dihydrocarbostyril (2.13 g) as colorless needles, m.p.: 183°–184° C.

Reference Example 28

1-(1-Benzyl-4-piperidinyl)-5-hydroxy-3,4-dihydrocarbostyril (500 mg) is dissolved in acetone (20 ml) and thereto are added potassium carbonate (246 mg) and ethyl iodide (0.18 ml). The mixture is refluxed with stirring for 6.5 hours. After the reaction, the insoluble materials are removed by filtration, and the filtrate is concentrated under reduced pressure. Dichloromethane is added to the resulting residue and the mixture is washed with 5% aqueous sodium hydroxide solution and then dried with magnesium sulfate. The solvent is evaporated and the resulting residue is purified by silica gel column chromatography (solvent; dichloromethane:methanol=50:1) to give 1-(1-benzyl-4-piperidinyl)-5-ethoxy-3,4-dihydrocarbostyril (0.27 g).

NMR (CDCl$_3$) δ ppm: 1.41 (3H, t, J=7.0 Hz), 1.58–1.82 (2H, m), 2.03–2.24 (2H, m), 2.47–3.10 (8H, m), 3.54 (2H, s), 4.03 (2H, q, J=7.0 Hz), 4.19–4.36 (1H, m), 6.60 (1H, d, J=8.2 Hz), 6.85 (1H, d, J=8.2 Hz), 7.14 (1H, t, J=8.2 Hz), 7.22–7.37 (5H, m)

Reference Example 29

Using the suitable starting materials, N-(1-benzyl-4-piperidinyl)-3,5-dimethylaniline is obtained in the same manner as in the above Reference Example 1.

NMR (CDCl$_3$) δ ppm: 1.35–1.60 (2H, m), 1.95–2.20 (4H, m), 2.22 (6H, s), 2.70–2.94 (2H, m), 3.15–3.40 (1H, m), 3.52 (2H, s), 6.22 (2H, s), 6.33 (1H, s), 7.20–7.40 (5H, m)

Reference Example 30

Using the suitable starting materials, N-cinnamoyl-N-(1-benzyl-4-piperidinyl)-3,5-dimethylaniline is obtained in the same manners as in the above Reference Example 15 as white powders, m.p.: 151°–154° C.

Reference Example 31

Using the suitable starting materials; 1-(1-benzyl-4-piperidinyl)-5,7-dimethylcarbostyril hydrochloride is obtained in the same manner as in the above Reference Example 16 as white powders, m.p.: 241°–244° C.

Reference Example 32

Using the suitable starting materials, N-(1-benzyl-4-piperidinyl)-2-formyl-3-fluoroaniline is obtained in the same manner as in the above Reference Example 19 as yellow powders, m.p.: 108°–109° C.

Reference Example 33

Using the suitable starting materials, methyl 2-fluoro-5-[(1-benzyl-4-piperidinyl)amino]cinnamate is obtained in the same manner as in the above Reference Example 24 as white powders, m.p.: 130°–133° C.

Reference Example 34

Potassium carbonate (8.9 g), 4-amino-1-benzyl-piperidine (18.5 g), cupric oxide (0.6 g) and dimethylformamide (25 ml) are added to 2-chloro-6-fluorobenzoic acid (11.3 g) and the mixture is reacted with heating at 140° C. for 6 hours. After the reaction, the solvent is concentrated and to the resulting residue are added water (200 ml) and active carbon (1 g). The mixture is refluxed for 30 minutes. After filtration, the filtrate is cooled and then adjusted to pH 8.0 with diluted hydrochloric acid. The precipitated crystal is collected by filtration and washed successively with water and methanol to give 2-(1-benzyl-4-piperidinylamino)-6-fluorobenzoic acid (7.6 g) as white powders, m.p.: 233°–236° C.

Reference Example 35

To a solution of lithium aluminium hydride (0.9 g) in anhydrous tetrahydrofuran (160 ml) is added 2-(1-benzyl-4-piperidinylamino)-6-fluorobenzoic acid (8.0 g) and the mixture is refluxed for 1 hour. After cooling, the reaction solution is poured into ice-water and then extracted with dichloromethane. The solvent is concentrated and to the resulting residue is added diethyl ether/n-hexane. The precipitated crystal is collected by filtration to give N-(1-benzyl-4-piperidinyl)-2-hydroxymethyl-3-fluoroaniline (4.6 g) as light yellow powders, m.p.: 167°–170° C.

Pharmacological Test

Experiment 1: $V_1$ receptor binding assay

Using rat liver plasma membrane preparations prepared according to Ichihara's method [cf: Akira Ichihara, J. Bio. Chem., 258 9283 (1983)], the plasma membrane (50000 dpm, $2\times10^{-10}$M) of [H]$^3$-Arg-vasopressin and a test compound (100 ng, $10^{-7}$–$10^{-4}$M) are incubated at 37° C. for 10 minutes in 100 mM Tris-HCl buffer pH: 8.0 (250 μl) containing 5 mM MgCl$_2$, 1 mM EDTA and 0.1% BSA. After incubation, the mixture is filtered three times using the glass filter (GF/F) so as to separate the membrane preparation combining with vasopressin and then washed with the buffer (5 ml). This glass filter is taken out and mixed with liquid scintillation cocktail. The amount of [H]$^3$-vasopressin combining with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_0} \times 100$$

$C^1$: The amount of [H]$^3$-vasopressin combining with the membrane in the presence of the test compound (known amount).

$C^0$: The amount of [H]$^3$-vasopressin combining with the membrane in the absence of the test compound.

$B^1$: The amount of [H]$^3$-vasopressin combining with the membrane in the presence of the excess amount of vasopressin ($10^{-6}$M).

The results are expressed as IC$_{50}$ values, which is the concentration of the test compound required to achieve the inhibitory effect in the rate of 50%.

The results are shown in the following Table 14.

Test Compounds 1. 1-[1-(4-Methylaminobenzoyl)-4-piperidinyl]-3,4-dihydrocarbostyril
2. 1-[1-(4-Dimethylaminobenzoyl)-4-piperidinyl]-3,4-dihydrocarbostyril
3. 1-{1-[4-(4-Carbamoylbutoxy)benzoyl]-4-piperidinyl}-3,4-dihydrocarbostyril
4. 1-{1-[4-(4-Carbamoylmethylaminocarbonylbutoxy)benzoyl]-4-piperidinyl}-3,4-dihydrocarbostyril
5. 1-{1-[4-(3-Cyanopropoxy)benzoyl]-4-piperidinyl}-3,4-dihydrocarbostyril
6. 1-{1-[4-(3-Amidinopropoxy)benzoyl]-4-piperidinyl}-3,4-dihydrocarbostyril
7. 1-{1-[4-(3-Carbamoylpropoxy)benzoyl]-4-piperidinyl}-3,4-dihydrocarbostyril
8. 1-{1-[4-(3-Ethoxycarbonylmethylaminocarbonylpropoxy)benzoyl]-4-piperidinyl}-3,4-dihydrocarbostyril
9. 1-{1-[4-(3-Carbamoylmethylaminocarbonylpropoxy)benzoyl]-4-piperidinyl}-3,4-dihydrocarbostyril
10. Methyl N-[4-{4-[4-(1,2,3,4-tetrahydro-2-oxo-1-quinolyl)-1-piperidinylcarbonyl]phenoxy}]butanoyl-L-serinate
11. Methyl N-[4-{4-[4-(1,2,3,4-tetrahydro-2-oxo-1-quinolyl)-1-piperidinylcarbonyl]phenoxy}]butanoyl-L-alanate
12. 1-{1-[4-(5-Carbamoylpentyloxy)benzoyl]-4-piperidinyl}-3,4-dihydrocarbostyril
13. 1-{1-[4-(5-Ethoxycarbonylmethylaminocarbonylpentyloxy)benzoyl]-4-piperidinyl}-3,4-dihydrocarbostyril
14. 1-{1-[4-(5-Carbamoylmethylaminocarbonylpentyloxy)benzoyl]-4-piperidinyl}-3,4-dihydrocarbostyril
15. 1-{1-[4-(7-Carbamoylheptyloxy)benzoyl]-4-piperidinyl}-3,4-dihydrocarbostyril
16. 1-{1-[4-(7-Carbamoylmethylaminocarbonylheptyloxy)benzoyl]-4-piperidinyl}-3,4-dihydrocarbostyril
17. 1-{1-[4-(3-Dimethylaminopropoxy)benzoyl]-4-piperidinyl}-3,4-dihydrocarbostyril
18. 1-{1-[4-(3-Benzylaminopropoxy)benzoyl]-4-piperidinyl}-3,4-dihydrocarbostyril
19. 1-{1-[4-[3-(Phthalimido-1-yl)propoxy]benzoyl]-4-piperidinyl}-3,4-dihydrocarbostyril
20. 1-{1-[4-(3-Acetylaminopropoxy)benzoyl]-4-piperidinyl}-3,4-dihydrocarbostyril
21. 1-{1-[4-(3-Methoxycarbonylaminopropoxy)benzoyl]-4-piperidinyl}-3,4-dihydrocarbostyril
22. 1-{1-[4-(3-Methylsulfonylaminopropoxy)benzoyl]-4-piperidinyl}-3,4-dihydrocarbostyril
23. 1-[1-{4-[3-(3-Methylureido)propoxy]benzoyl}-4-piperidinyl]-3,4-dihydrocarbostyril
24. 1-{1-[4-(4-Aminobutoxy)benzoyl]-4-piperidinyl}-3,4-dihydrocarbostyril
25. 1-{1-[4-(4-(N-Acetylglycylaminobutoxy)benzoyl]-4-piperidinyl}-3,4-dihydrocarbostyril
26. 1-{1-[4-(4-Formylaminobutoxy)benzoyl]-4-piperidinyl}-3,4-dihydrocarbostyril
27. 1-{1-[4-(4-Methoxycarbonylaminobutoxy)benzoyl]-4-piperidinyl}-3,4-dihydrocarbostyril
28. 1-{1-[4-(4-Methylsulfonylaminobutoxy)benzoyl]-4-piperidinyl}-3,4-dihydrocarbostyril
29. 1-{1-[4-(5-Aminopentyloxy)benzoyl]-4-piperidinyl}-3,4-dihydrocarbostyril
30. 1-{1-[4-(5-Methylamino-4-hydroxypentyloxy)benzoyl]-4-piperidinyl}-3,4-dihydrocarbostyril
31. 1-{1-[4-(5-Dimethylamino-4-hydroxypentyloxy)benzoyl]-4-piperidinyl}-3,4-dihydrocarbostyril
32. 1-{1-[4-(3-Hydroxypropoxy)benzoyl]-4-piperidinyl}-3,4-dihydrocarbostyril
33. 1-{1-[4-(3-Acetoxypropoxy)benzoyl]-4-piperidinyl}-3,4-dihydrocarbostyril
34. 1-{1-[4-(3-Methylsulfonyloxypropoxy)benzoyl]-4-piperidinyl}-3,4-dihydrocarbostyril
35. 1-{1-[4-(3-Carbamoyloxypropoxy)benzoyl]-4-piperidinyl}-3,4-dihydrocarbostyril
36. 1-{1-[4-(4-Hydroxybutoxy)benzoyl]-4-piperidinyl}-3,4-dihydrocarbostyril 37. 1-{1-[4-(4-Acetoxybutoxy)benzoyl]-4-piperidinyl}-3,4-dihydrocarbostyril
38. 1-{1-[4-(4-Carbamoyloxybutoxy)benzoyl]-4-piperidinyl}-3,4-dihydrocarbostyril
39. 1-{1-[4-(5-Acetoxypentyloxy)benzoyl]-4-piperidinyl}-3,4-dihydrocarbostyril
40. 1-[1-(4-Methoxybenzoyl)-4-piperidinyl]-3,4-dihydrocarbostyril
41. 1-[1-(4-Ethoxybenzoyl)-4-piperidinyl]-3,4-dihydrocarbostyril
42. 1-[1-(4-Propoxybenzoyl)-4-piperidinyl]-3,4-dihydrocarbostyril
43. 1-[1-(4-Butoxybenzoyl)-4-piperidinyl]-3,4-dihydrocarbostyril
44. 1-[1-(4-Allyloxybenzoyl)-4-piperidinyl]-3,4-dihydrocarbostyril
45. 1-[1-(4-Phenyloxybenzoyl)-4-piperidinyl]-3,4-dihydrocarbostyril
46. 1-[1-(4-Acetoxybenzoyl)-4-piperidinyl]-3,4-dihydrocarbostyril
47. 1-[1-(2,4-Dimethoxybenzoyl)-4-piperidinyl]-3,4-dihydrocarbostyril
48. 1-[1-(2-Methoxy-4-methylaminobenzoyl)-4-piperidinyl]-3,4-dihydrocarbostyril
49. 1-[1-(2-Methoxy-4-dimethylaminobenzoyl)-4-piperidinyl]-3,4-dihydrocarbostyril
50. 1-{1-[2,4-Bis(N,N-dimethylamino)benzoyl]-4-piperidinyl}-3,4-dihydrocarbostyril
51. 1-{1-[2-(2-Oxooxazolydine-3-yl)-4-methoxybenzoyl]-4-piperidinyl}-3,4-dihydrocarbostyril
52. 1-[1-(2-Methoxy-4-ethoxybenzoyl)-4-piperidinyl]-3,4-dihydrocarbostyril
53. 1-[1-(2-Methoxy-4-methylthiobenzoyl)-4-piperidinyl]-3,4-dihydrocarbostyril
54. 1-[1-(2-Methoxy-4-chlorobenzoyl)-4-piperidinyl]-3,4-dihydrocarbostyril
55. 1-[1-(2-Dimethylamino-4-methoxybenzoyl)-4-piperidinyl]-3,4-dihydrocarbostyril
56. 1-[1-(2-Ethylamino-4-methoxybenzoyl)-4-piperidinyl]-3,4-dihydrocarbostyril
57. 1-[1-(2-Propylamino-4-methoxybenzoyl)-4-piperidinyl]-3,4-dihydrocarbostyril
58. 1-{1-[2-(N-Methyl-N-ethylamino)-4-methoxybenzoyl]-4-piperidinyl}-3,4-dihydrocarbostyril
59. 1-[1-(2-Ethoxy-4-methoxybenzoyl)-4-piperidinyl]-3,4-dihydrocarbostyril
60. 1-[1-(2-Hydroxy-4-methoxybenzoyl)-4-piperidinyl]-3,4-dihydrocarbostyril
61. 1-[1-(2-Acetoxy-4-methoxybenzoyl)-4-piperidinyl]-3,4-dihydrocarbostyril
62. 1-[1-(2-Allyloxy-4-methoxybenzoyl)-4-piperidinyl]-3,4-dihydrocarbostyril
63. 1-{1-[2-(3-Hydroxypropoxy)-4-methoxybenzoyl]-4-piperidinyl}-3,4-dihydrocarbostyril
64. 1-{1-[2-(3-Acetoxypropoxy)-4-methoxybenzoyl]-4-piperidinyl}-3,4-dihydrocarbostyril
65. 1-{1-[2-(3-Carbamoyloxypropoxy)-4-methoxybenzoyl]-4-piperidinyl}-3,4-dihydrocarbostyril
66. 1-{1-[2-(3-Methoxypropoxy)-4-methoxybenzoyl]-4-piperidinyl}-3,4-dihydrocarbostyril
67. 1-{1-[2-(3-Carbamoylpropoxy)-4-methoxybenzoyl]-4-piperidinyl}-3,4-dihydrocarbostyril
68. 1-{1-[2-(2-Hydroxyethoxy)-4-methoxybenzoyl]-4-piperidinyl}-3,4-dihydrocarbostyril
69. 1-{1-[2-(2-Acetoxyethoxy)-4-methoxybenzoyl]-4-piperidinyl}-3,4-dihydrocarbostyril
70. 1-{1-[2-(2-Methoxyethoxy)-4-methoxybenzoyl]-4-piperidinyl}-3,4-dihydrocarbostyril
71. 1-[1-(4-Bromobenzoyl)-4-piperidinyl]-3,4-dihydrocarbostyril
72. 1-[1-(4-Benzoylbenzoyl)-4-piperidinyl]-3,4-dihydrocarbostyril
73. 1-[1-(4-Methylthiobenzoyl)-4-piperidinyl]-3,4-dihydrocarbostyril
74. 1-[1-(4-Ethylthiobenzoyl)-4-piperidinyl]-3,4-dihydrocarbostyril
75. 1-[1-(4-Methylbenzoyl)-4-piperidinyl]-3,4-dihydrocarbostyril
76. 1-[1-(4-Propylbenzoyl)-4-piperidinyl]-3,4-dihydrocarbostyril
77. 1-[1-(4-Butylbenzoyl)-4-piperidinyl]-3,4-dihydrocarbostyril
78. 1-[1-(3,4-Dimethylbenzoyl)-4-piperidinyl]-3,4-dihydrocarbostyril
79. 6-Fluoro-1-[1-(2,4-dimethoxybenzoyl)-4-piperidinyl]-3,4-dihydrocarbostyril
80. 7-Fluoro-1-[1-(2-methoxy-4-methylthiobenzoyl)-4-piperidinyl]-3,4-dihydrocarbostyril
81. 7-Methyl-1-[1-(2,4-dimethoxybenzoyl)-4-piperidinyl]-3,4-dihydrocarbostyril
82. 1-[1-(2-Methoxy-4-ethoxybenzoyl)-4-piperidinyl]carbostyril
83. 1-(1-Tricyclo[3.3.1.1$^{3,7}$]decanylcarbonyl-4-piperidinyl)-3,4-dihydrocarbostyril
84. 1-[1-(2-Methoxy-4-methylthiobenzoyl)-3-pyrrolidinyl]-3,4-dihydrocarbostyril
85. 1-{4-[N-(4-Methoxyphenyl)-N-benzylamidophenyl]-3,4-dihydrocarbostyril
86. 1-{1-[4-(3-[4-(4-Methoxyphenyl)-1-piperazinyl]propoxy)benzoyl]-4-piperidinyl}-3,4-dihydrocarbostyril
87. 1-{1-[4-(3-Allyloxypropoxy)benzoyl]-4-piperidinyl}-3,4-dihydrocarbostyril
88. 1-{1-[4-(3-Carbamoylpropylamino)benzoyl]-4-piperidinyl}-3,4-dihydrocarbostyril
89. 1-{1-[4-(2-Ethylthioimidazol-1-yl)benzoyl]-4-piperidinyl}-3,4-dihydrocarbostyril
90. 1-{1-[4-(N-Allyl-N-methylamino)benzoyl]-4-piperidinyl}-3,4-dihydrocarbostyril
91. 1-{1-[4-(1-Pyrrolidinyl)benzoyl]-4-piperidinyl}-3,4-dihydrocarbostyril
92. 1-[1-{4-[3-(N-Methyl-N-benzoylamino)propoxy]benzoyl}-4-piperidinyl}-3,4-dihydrocarbostyril
93. 1-[1-{4-[3-(4-Phenyl-1-piperazinyl)propoxy]-benzoyl}-4-piperidinyl]-3,4-dihydrocarbostyril
94. 1-{1-[4-(3-Benzoyloxypropoxy)benzoyl]-4-piperidinyl}-3,4-dihydrocarbostyril
95. 1-{1-[4-(3-Ethylthiopropoxy)benzoyl]-4-piperidinyl}-3,4-dihydrocarbostyril
96. 1-[1-(4-Propargylbenzoyl)-4-piperidinyl]-3,4-dihydrocarbostyril
97. 1-[1-(4-Benzyloxybenzoyl)-4-piperidinyl]-3,4-dihydrocarbostyril
98. 1-{1-[4-(2-Cyclohexenyloxy)benzoyl]-4-piperidinyl}-3,4-dihydrocarbostyril
99. 1-[1-(4-Cyclohexyloxybenzoyl)-4-piperidinyl]-3,4-dihydrocarbostyril
100. 1-[1-(4-Methylsulfonyloxybenzoyl)-4-piperidinyl]-3,4-dihydrocarbostyril
101. 1-[1-(4-Glycidoxybenzoyl)-4-piperidinyl]-3,4-dihydrocarbostyril
102. 1-{1-[4-Methoxy-2-(N-methyl-N-ethoxycarbonylmethylamino)benzoyl]-4-piperidinyl}-3,4-dihydrocarbostyril
103. 1-[1-(4-Methoxy-2-benzyloxycarbonylaminobenzoyl)-4-piperidinyl]-3,4-dihydrocarbostyril 104. 1-[1-(4-Methoxy-2-acetylaminobenzoyl)-4-piperidinyl]-3,4-dihydrocarbostyril
105. 1-[1-(4-Methoxy-2-methylaminocarbonylmethylamino)-4-piperidinyl]-3,4-dihydrocarbostyril
106. 1-[1-(4-Trifluoromethylbenzoyl)-4-piperidinyl]-3,4-dihydrocarbostyril
107. 1-[1-(4-Acetylbenzoyl)-4-piperidinyl]-3,4-dihydrocarbostyril
108. 1-[1-(4-Hydroxyiminomethylbenzoyl)-4-piperidinyl]-3,4-dihydrocarbostyril
109. 1-[1-(4-Methoxymethylbenzoyl)-4-piperidinyl]-3,4-dihydrocarbostyril
110. 1-[1-(4-Trimethylsilylbenzoyl)-4-piperidinyl]-3,4-dihydrocarbostyril
111. 1-[1-(4-Allylbenzoyl)-4-piperidinyl]-3,4-dihydrocarbostyril
112. 1-[1-(4-Cyclohexylbenzoyl)-4-piperidinyl]-3,4-dihydrocarbostyril
113. 1-[1-(3,4-Methylenedioxybenzoyl)-4-piperidinyl]-3,4-dihydrocarbostyril
114. 1-[1-(2,6-Dimethyl-1,5-heptadiene-1-carbonyl)-4-piperidinyl]-3,4-dihydrocarbostyril
115. 1-(1-(Tricyclo[3.3.1.1$^{3,7}$]decanylacetyl-4-piperidinyl]-3,4-dihydrocarbostyril
116. 1-[1-(2-Naphthylcarbonyl)-4-piperidinyl]-3,4-dihydrocarbostyril
117. 1-[1-(3-quinolylcarbonyl)-4-piperidinyl]-3,4-dihydrocarbostyril
118. 1-[3-Methyl-1-(2,4-dimethoxycarbonyl)-4-piperidinyl]-3,4-dihydrocarbostyril
119. 1-[1-(3-Nitro-4-methoxybenzoyl)-4-piperidinyl]-3,4-dihydrocarbostyril
120. 6,7-Difluoro-1-[1-(2-methoxy-4-ethoxybenzoyl)-4-piperidinyl]-3,4-dihydrocarbostyril
121. 1-{1-[4-(3-Methylaminocarbonylpropoxy)benzoyl]-4-piperidinyl}-3,4-dihydrocarbostyril
122. 1-{1-[4-(4-Hydroxy-1-butenyl)benzoyl]-4-piperidinyl}-3,4-dihydrocarbostyril
123. 1-{1-[4-(4-Hydroxybutyl)benzoyl]-4-piperidinyl}-3,4-dihydrocarbostyril
124. 1-{1-[4-(4-Acetoxybutyl)benzoyl]-4-piperidinyl}-3,4-dihydrocarbostyril
125. 1-[1-{4-[4-(1-pyrrolyl)butoxy]benzoyl}-4-piperidinyl]-3,4-dihydrocarbostyril
126. 1-[1-{4-[(4-Methylaminobenzoyl)aminobutoxy]benzoyl}-4-piperidinyl]-3,4-dihydrocarbostyril
127. 1-{1-[4-(Ethylsulfinylpropoxy)benzoyl]-4-piperidinyl}-3,4-dihydrocarbostyril
128. 1-{1-[4-(6-Hydroxyhexyloxy)benzoyl]-4-piperidinyl}-3,4-dihydrocarbostyril
129. 1-{1-[4-(5-Carbamoyloxypentyloxy)benzoyl]-4-piperidinyl}-3,4-dihydrocarbostyril
130. 1-{1-[4-(6-Acetoxyhexyloxy)benzoyl]-4-piperidinyl}-3,4-dihydrocarbostyril
131. 1-{1-[4-(6-Dimethylamino-5-hydroxyhexyloxy)benzoyl]-4-piperidinyl}-3,4-dihydrocarbostyril
132. 1-[1-{4-[3-(1-piperazinyl)propoxy]benzoyl}-4-piperidinyl]-3,4-dihyrocarbostyril.dihydrochloride.trihydrate
133. 1-[1-{4-[3-(4-Benzyl-1-piperazinyl)propoxy]benzoyl}-4-piperidinyl]-3,4-dihydrocarbostyril.dioxalate
134. 1-[1-{4-[3-(4-Acetyl-1-piperazinyl)propoxy]benzoyl}-4-piperidinyl]-3,4-dihydrocarbostyril
135. 1-[1-{4-[3-(4-Anilinocarbonyl-1-piperazinyl)propoxy]benzoyl}-4-piperidinyl]-3,4-dihydrocarbostyril
136. 1-[1-{4-[3-(4-Methyl-1-piperazinyl)propoxy]benzoyl}-4-piperidinyl]-3,4-dihydrocarbostyril.dioxalate
137. 1-[1-{4-[3-(4-Benzoylmethyl-1-piperazinyl)propoxy]benzoyl}-4-piperidinyl]-3,4-dihydrocarbostyril.dioxalate
138. 1-{1-[4-(3-[4-(2-Phenyl-2-hydroxyethyl)-1-piperazinyl]propoxy}benzoyl]-4-piperidinyl}-3,4-dihydrocarbostyril.dioxalate
139. 5,7-Difluoro-1-[1-(2-methoxy-4-ethoxybenzoyl)-4-piperidinyl]-3,4-dihydrocarbostyril
140. 1-{1-[4-(6-Aminohexyloxy)benzoyl]-4-piperidinyl}-3,4-dihydrocarbostyril
141. 1-{1-[4-(6-Acetylaminohexyloxy)benzoyl]-4-piperidinyl}-3,4-dihydrocarbostyril
142. 1-{1-[4-(6-Methylsulfonylaminohexyloxy)benzoyl]-4-piperidinyl}-3,4-dihydrocarbostyril
143. 1-{1-[4-(3-Ethylsulfonylpropoxy)benzoyl]-4-piperidinyl}-3,4-dihydrocarbostyril
144. 1-{1-[4-(6-Diethylamino-5-hydroxyhexyloxy)benzoyl]-4-piperidinyl}-3,4-dihydrocarbostyril
145. 1-{1-[4-(3-Formylaminopropoxy)benzoyl]-4-piperidinyl}-7-fluoro-3,4-dihydrocarbostyril
146. 1-{1-[4-{5-[1-(S)-Carbamoyl-2-(4-hydroxyphenyl)]ethylaminocarbonylpentyloxy}benzoyl]-4-piperidinyl}-3,4-dihydrocarbostyril
147. 1-{1-[4-{5-[1-(S)-Carbamoyl-2-methyl]propylaminocarbonylpentyloxy}benzoyl]-4-piperidinyl}-3,4-dihydrocarbostyril
148. 1-{1-[4-(3-Dimethylaminocarbonylpropoxy)benzoyl]-4-piperidinyl}-3,4-dihydrocarbostyril
149. 1-{1-[4-{5-[1-(S)-Carbamoyl-2}4(1H)imidazoyl}]ethylaminocarbonylpentyloxy}benzoyl]-4-piperidinyl}-3,4-dihydrocarbostyril
150. 1-{1-[4-(5-[1-(S),3-Dicarbamoyl]propylaminocarbonylpentyloxy)benzoyl]-4-piperidinyl}-3,4-dihydrocarbostyril
151. 1-[1-(2-Methoxy-4-ethoxybenzoyl)-4-piperidinyl]-7-fluorocarbostyril
152. 1-[1-(2-Methoxy-4-ethoxybenzoyl)-4-piperidinyl]-3-carboxy-3,4-dihydrocarbostyril
153. 1-{1-[4-(5-[1-(S)-Carbamoyl-3-(methylthio)]propylaminocarbonylpentyloxy)benzoyl]-4-piperidinyl}-3,4-dihydrocarbostyril
154. 1-{1-[4-(5-(Imidazo[4,5-c]pyridine-2-yl)carbonylpentyloxy)benzoyl]-4-piperidinyl}-3,4-dihydrocarbostyril
155. 1-[1-(2-Hydroxy-4-ethoxybenzoyl)-4-piperidinyl]-7-fluoro-3,4-dihydrocarbostyril
156. 1-{1-[4-[(4-Benzyl-1-piperazinyl)butoxy]benzoyl]-4-piperidinyl}-3,4-dihydrocarbostyril
157. 1-{1-[4-[4-(1-Piperazinyl)butoxy]benzoyl]-4-piperidinyl}-3,4-dihydrocarbostyril.dioxalate
158. 1-{1-[4-[4-(4-Methyl-1-piperazinyl)butoxy]benzoyl]-4-piperidinyl}-3,4-dihydrocarbostyril.dioxalate
159. 1-{1-[4-[4-(4-Methylsulfonyl-1-piperazinyl)butoxy]benzoyl]-4-piperidinyl}-3,4-dihydrocarbostyril
160. 1-{1-[4-[4-(4-Methoxycarbonyl-1-piperazinyl)butoxy]benzoyl]-4-piperidinyl}-3,4-dihydrocarbostyril
161. 1-{1-[4-[4-(4-Benzyl-1-piperazinyl)carbonyloxybutoxy]benzoyl]-4-piperidinyl}-3,4-dihydrocarbostyril
162. 1-{1-[4-[4-(4-Acetyl-1-piperazinyl)butoxy]benzoyl]-4-piperidinyl}-3,4-dihydrocarbostyril
163. 1-{1-[4-[4-(1-Piperazinyl)carbonyloxybutoxy]benzoyl]-4-piperidinyl}-3,4-dihydrocarbostyril
164. 1-{1-[4-[4-(Benzimidazol-1-yl)thiobutoxy]benzoyl]-4-piperidinyl}-3,4-dihydrocarbostyril
165. 1-{1-[4-{5-[(5-Benzyloxycarbonylamino)-1-(S)-methoxycarbonyl]pentylaminocarbonylpentyloxy}benzoyl]-4-piperidinyl}-3,4-dihydrocarbostyril 166. 1-{1-[4-{5-[5-Amino-1-(S)-methoxycarbonyl]pentylaminocarbonylpentyloxy}benzoyl]-4-piperidinyl}-3,4-dihydrocarbostyril
167. 1-{1-[4-(3-Isopentylaminopropoxy)benzoyl]-4-piperidinyl}-3,4-dihydrocarbostyril
168. 1-{1-[4-(3-Ethoxycarbonylaminopropoxy)benzoyl]-4-piperidinyl}-3,4-dihydrocarbostyril
169. 1-{1-[4-(3-Phenylsulfonylaminopropoxy)benzoyl]-4-piperidinyl}-3,4-dihydrocarbostyril
170. 1-{1-[4-(5-Hydroxy-6-benzylaminohexyloxy)benzoyl]-4-piperidinyl}-3,4-dihydrocarbostyril
171. 1-{1-[4-(5-Hydroxy-6-aminohexyloxy)benzoyl]-4-piperidinyl}-3,4-dihydrocarbostyril
172. 1-{1-[4-(5-Hydroxy-6-(4-benzyl-1-piperazinyl)hexyloxy]benzoyl]-4-piperidinyl}-3,4-dihydrocarbostyril.dioxalate
173. 1-{1-[4-(5-Hydroxy-6-(1-piperazinyl)hexyloxy]benzoyl]-4-piperidinyl}-3,4-dihydrocarbostyril.dioxalate
174. 1-{1-[4-(3-p-Toluenesulfonylaminopropoxy)benzoyl]-4-piperidinyl}-3,4-dihydrocarbostyril
175. 5,7-Difluoro-1-[1-(2-Methoxy-4-ethoxybenzoyl)-4-piperidinyl]carbostyril
176. 1-{1-[4-(5-Acetoxy-6-acetylaminohexyloxy)benzoyl]-4-piperidinyl}-3,4-dihydrocarbostyril
177. 1-{1-[4-(5-Hydroxy-6-acetylaminohexyloxy)benzoyl]-4-piperidinyl}-3,4-dihydrocarbostyril
178. 1-{1-[4-(5-Hydroxy-6-(4-methyl-1-piperazinyl)hexyloxy]benzoyl]-4-piperidinyl}-3,4-dihydrocarbostyril
179. 1-{1-[4-(4-Dimethylaminobutoxy)benzoyl]-4-piperidinyl}-3,4-dihydrocarbostyril
180. 1-{1-[4-(4-Dimethylaminobutyl)benzoyl]-4-piperidinyl}-3,4-dihydrocarbostyril
181. 1-{1-[4-(3-Acetylaminoacetylaminopropoxy)benzoyl]-4-piperidinyl}-3,4-dihydrocarbostyril
182. 1-{1-[4-(3-[2-(Acetylamino)valerylamino]propoxy)benzoyl]-4-piperidinyl}-3,4-dihydrocarbostyril
183. 1-{1-[4-(3-Formylaminopropoxy)benzoyl]-4-piperidinyl}-3,4-dihydrocarbostyril
184. 1-{1-[4-(7-Hydroxy-8-diethylaminooctyloxy)benzoyl]-4-piperidinyl}-3,4-dihydrocarbostyril
185. 7-Fluoro-1-{1-[4-(5-Hydroxy-6-diethylaminohexyloxy)-2-methoxybenzoyl]-4-piperidinyl}-3,4-dihydrocarbostyril
186. 1-{1-[4-(4-Hydroxy-5-(1-pyrrolidinyl)pentyloxy)benzoyl]-4-piperidinyl}-3,4-dihydrocarbostyril
187. 1-{1-[4-(7-Hydroxy-8-dimethylaminooctyloxy)benzoyl]-4-piperidinyl}-3,4-dihydrocarbostyril
188. 1-{1-[4-(4-(Hydroxy-5-(1-piperidinyl)pentyloxy)benzoyl]-4-piperidinyl}-3,4-dihydrocarbostyril
189. 1-{1-[4-(4-Hydroxy-5-morpholinopentyloxy)benzoyl]-4-piperidinyl}-3,4-dihydrocarbostyril
190. 1-{1-[4-(5-(2-Hydroxy-3-diethylaminopropoxy)pentyloxy)benzoyl]-4-piperidinyl}-3,4-dihydrocarbostyril
191. 1-{1-[4-(5-(2-Hydroxy-3-dimethylaminopropoxy)pentyloxy)benzoyl]-4-piperidinyl}-3,4-dihydrocarbostyril
192. 1-{1-[4-(3-(2-Hydroxy-3-diethylaminopropoxy)propoxy)benzoyl]-4-piperidinyl}-3,4-dihydrocarbostyril
193. 1-{1-[4-(3-(4-Aminobenzoylamino)propoxy)benzoyl]-4-piperidinyl}-3,4-dihydrocarbostyril
194. 1-{1-[4-(4-(Benzimidazol-2-yl)sulfinylbutoxy)benzoyl]-4-piperidinyl}-3,4-dihydrocarbostyril
195. 1-{1-[4-(3-(α-N-Acetyl-(L)-glutaminyl)aminopropoxy)benzoyl]-4-piperidinyl}-3,4-dihydrocarbostyril
196. 1-{1-[4-(3-(4-Acetylaminobenzoyl)aminopropoxy)benzoyl]-4-piperidinyl}-3,4-dihydrocarbostyril
197. 1-{1-[4-(5-(3-Dimethylaminopropyl)aminocarbonylpentyloxy)benzoyl]-4-piperidinyl}-3,4-dihydrocarbostyril
198. 1-{1-[4-(3-Ethylaminocarbonylaminopropoxy)benzoyl]-4-piperidinyl}-3,4-dihydrocarbostyril
199. 1-{1-[4-(5-(2-Dimethylaminoethyl)aminocarbonylpentyloxy)benzoyl]-4-piperidinyl}-3,4-dihydrocarbostyril
200. 1-{1-[4-(5-(1-Benzyl-4-piperidinyl)aminocarbonylpentyloxy)benzoyl]-4-piperidinyl}-3,4-dihydrocarbostyril
201. 5,7-Difluoro-1-{1-[2-methoxy-4-(5-hydroxy-6-diethylaminohexyloxy)benzoyl]-4-piperidinyl}-3,4-dihydrocarbostyril
202. 1-{1-[4-(5-Hydroxy-6-(1-pyrrolidinyl)hexyloxy)benzoyl]-4-piperidinyl}-3,4-dihydrocarbostyril
203. 1-{1-[4-(5-Hydroxy-6-[N-(2-phenylethyl)-N-methylamino]hexyloxy)benzoyl]-4-piperidinyl}-3,4-dihydrocarbostyril
204. 1-{1-[4-(5-Hydroxy-6-[N-(2-hydroxyethyl)-N-methylamino]hexyloxy)benzoyl]-4-piperidinyl}-3,4-dihydrocarbostyril
205. 1-{1-[4-(5-Hydroxy-6-(4-phenyl-1-piperazinyl)hexyloxy)benzoyl]-4-piperidinyl}-3,4-dihydrocarbostyril
206. 1-{1-[4-(7-Hydroxy-8-(1-pyrrolidinyl)octyloxy)benzoyl]-4-piperidinyl}-3,4-dihydrocarbostyril
207. 1-{1-[4-(3-(2-Acetylamino-4-methylthiobutyrylamino)propoxy)benzoyl]-4-piperidinyl}-3,4-dihydrocarbostyril
208. 1-{1-[4-(3-[2-(R)-Acetylamino-2-(4(1H)imidazolyl)methylacetylamino]propoxy)benzoyl]-4-piperidinyl}-3,4-dihydrocarbostyril
209. 1-{1-[4-(3-(2-Acetylaminopropanoylamino)propoxy)benzoyl]-4-piperidinyl}-3,4-dihydrocarbostyril
210. 1-{1-[4-(5-(4-Piperidinyl)aminocarbonylpentyloxy)benzoyl]-4-piperidinyl}-3,4-dihydrocarbostyril
211. 1-{1-[4-(3-[2-Benzyloxycarbonylamino-2α-(4-hydroxybenzyl)acetylamino]propoxy)benzoyl]-4-piperidinyl}-3,4-dihydrocarbostyril
212. 1-{1-[4-(6-Carbamoyloxyhexyloxy)benzoyl]-4-piperidinyl}-3,4-dihydrocarbostyril
213. 1-{1-[4-(6-Diethylaminohexyloxy)benzoyl]-4-piperidinyl}-3,4-dihydrocarbostyril
214. 1-{1-[4-(6-(1-Pyrrolidinyl)hexyloxy)benzoyl]-4-piperidinyl}-3,4-dihydrocarbostyril
215. 1-{1-[4-(6-(1-Methyl-5-oxo-3-morpholino)hexyloxy)benzoyl]-4-piperidinyl}-3,4-dihydrocarbostyril
216. 5-Methyl-1-[1-(2-methoxy-4-ethoxybenzoyl)-4-piperidinyl]-3,4-dihydrocarbostyril
217. 1-{1-[4-(5-Hydroxy-6-isopropylaminohexyloxy)benzoyl]-4-piperidinyl}-3,4-dihydrocarbostyril
218. 1-{1-[4-(5-Hydroxy-6-[N-ethyl-N-(2-tetrahydropyranylmethyl)amino]hexyloxy)benzoyl]-4-piperidinyl}-3,4-dihydrocarbostyril
219. 1-{1-[4-(5-Hydroxy-6-[N-methyl-N-(2-hydroxy-2-phenylethyl)amino]hexyloxy)benzoyl]-4-piperidinyl}-3,4-dihydrocarbostyril
220. 1-{1-[4-(6-[2(S)-Hydroxymethyl-1-pyrrolidinyl]-5-hydroxy)hexyloxy)benzoyl]-4-piperidinyl}-3,4-dihydrocarbostyril
221. 1-{1-[4-(3-(S)-{N-(Bezyloxycarbonyl)prolyl}aminopropoxy)benzoyl]-4-piperidinyl}-3,4-dihydrocarbostyril
222. 1-[1-{4-[3-(S)-{N,N'-Di(benzyloxycarbonyl)lysyl}aminopropoxy]benzoyl}-4-piperidinyl]-3,4-dihydrocarbostyril
223. 1-[1-{4-[3-(S)-Tyrosylaminopropoxy]benzoyl}-4-piperidinyl]-3,4-dihydrocarbostyril 224. 1-{1-[4-(3-(S)-Prolylaminopropoxy)benzoyl]-4-piperidinyl}-3,4-dihydrocarbostyril
225. 1-[1-{4-(3-(R)-Valylaminopropoxy]benzoyl}-4-piperidinyl]-3,4-dihydrocarbostyril
226. 1-[1-{4-(3-(S)-{N-(Benzyloxycarbonyl)seryl}aminopropoxy]benzoyl}-4-piperidinyl]-3,4-dihydrocarbostyril
227. 1-{1-(4-[4-(4-Allyl-1-piperazinyl)butoxy]benzoyl)-4-piperidinyl}-3,4-dihydrocarbostyril
228. 1-{1-(4-[4-(2-Chloroacetylamino)butoxy]benzoyl)-4-piperidinyl}-3,4-dihydrocarbostyril
229. 1-{1-(4-[5-(2-Acetoxyacetylamino)pentyloxy]benzoyl)-4-piperidinyl}-3,4-dihydrocarbostyril
230. 1-{1-(4-[5-(2-Hydroxyacetylamino)pentyloxy]benzoyl)-4-piperidinyl}-3,4-dihydrocarbostyril
231. 1-{1-(4-[4-(4-Piperidinylcarbonylamino)butoxy]benzoyl)-4-piperidinyl}-3,4-dihydrocarbostyril
232. 1-{1-(4-[4-(1-Acetyl-4-piperidinylcarbonylamino)butoxy]benzoyl)-4-piperidinyl}-3,4-dihydrocarbostyril
233. 1-{1-(4-[5-(4-[2-Pyrimidyl]-1-piperazinyl)pentyloxy]benzoyl)-4-piperidinyl}-3,4-dihydrocarbostyril
234. 1-{1-(4-[5-(4-[2-Pyridyl]-1-piperazinyl)pentyloxy]benzoyl)-4-piperidinyl}-3,4-dihydrocarbostyril
235. 1-{1-[4-(5-Triethylammouniumpentyloxy)benzoyl]-4-piperidinyl}-3,4-dihydrocarbostyril bromide
236. 1-{1-(4-[5-(4-(1-Imidazolyl)pentyloxy]benzoyl)-4-piperidinyl}-3,4-dihydrocarbostyril
237. 1-{1-(4-[5-(4-(1,2,4-Triazol-1-yl)pentyloxy]benzoyl)-4-piperidinyl}-3,4-dihydrocarbostyril
238. 1-{1-(4-[5-(2-(S)-Hydroxymethyl-1-pyrrolidinyl)pentyloxy]benzoyl)-4-piperidinyl}-3,4-dihydrocarbostyril
239. 1-{1-(4-[5-(2-(S)-Methoxycarbonyl-1-pyrrolidinyl)pentyloxy]benzoyl)-4-piperidinyl}-3,4-dihydrocarbostyril
240. 1-{1-(4-[5-(3-Hydroxy-1-piperidinyl)-pentyloxy]benzoyl)-4-piperidinyl}-3,4-dihydrocarbostyril
241. 1-{1-(4-[5-(2-Hydroxymethyl-1-piperidinyl)pentyloxy]benzoyl)-4-piperidinyl}-3,4-dihydrocarbostyril
242. 1-{1-(4-[5-(4-Methyl-1-piperidinyl)pentyloxy]benzoyl)-4-piperidinyl}-3,4-dihydrocarbostyril
243. 1-{1-(4-[6-(1-Piperidinyl)hexyloxy]benzoyl)-4-piperidinyl}-3,4-dihydrocarbostyril
244. 1-{1-(4-[5-(N-(2-Hydroxyethyl)-N-methylamino)pentyloxy]benzoyl)-4-piperidinyl}-3,4-dihydrocarbostyril
245. 1-{1-(4-[5-(N-Allyl-N-methylamino)pentyloxy]benzoyl)-4-piperidinyl}-3,4-dihydrocarbostyril
246. N-{5-[4-(4-(3,4-Dihydrocarbostyril-1-yl)-1-piperidinylcarbonyl)phenoxy]pentyl{, N-methyl, N-allylamine oxide
247. 1-{1-(4-[5-(N-(2-Cyanoethyl)-N-methylamino)pentyloxy]benzoyl)-4-piperidinyl}-3,4-dihydrocarbostyril
248. 1-{1-(4-[5-(N-(2-Dimethylaminoethyl)-N-benzylamino)pentyloxy]benzoyl)-4-piperidinyl}-3,4-dihydrocarbostyril
249. 1-{1-(4-[5-(N,N-Di(2-acetoxyethyl)amino)pentyloxy]benzoyl)-4-piperidinyl}-3,4-dihydrocarbostyril
250. 1-{1-(4-[5-(4-Benzyloxycarbonylaminobutyrylamino)pentyloxy]benzoyl)-4-piperidinyl}-3,4-dihydrocarbostyril
251. 1-{1-(4-[5-(2-Allylaminoacetylamino)pentyloxy]benzoyl)-4-piperidinyl}-3,4-dihydrocarbostyril
252. 1-{1-(4-[5-(2-(1-Pyrrolidinyl)acetylamino)pentyloxy]benzoyl)-4-piperidinyl}-3,4-dihydrocarbostyril
253. 1-{1-(4-[5-(2-Morpholinoacetylamino)pentyloxy]benzoyl)-4-piperidinyl}-3,4-dihydrocarbostyril
254. 1-{1-(4-[5-(2-(4-Methyl-1-piperazinyl)acetylamino)pentyloxy]benzoyl)-4-piperidinyl}-3,4-dihydrocarbostyril
255. 1-{1-(4-[5-(2-(4-Phenyl-1-piperazinyl)acetylamino)pentyloxy]benzoyl)-4-piperidinyl}-3,4-dihydrocarbostyril
256. 1-{1-(4-[5-(2-Benzylaminoacetylamino)pentyloxy]benzoyl)-4-piperidinyl}-3,4-dihydrocarbostyril
257. 1-{1-(4-[5-(2-(N-(2-Hydroxyethyl)-N-methylamino)acetylamino)pentyloxy]benzoyl)-4-piperidinyl}-3,4-dihydrocarbostyril
258. 1-{1-(4-[5-(4-Dimethylaminophenylsulfonylamino)pentyloxy]benzoyl)-4-piperidinyl]-3,4-dihydrocarbostyril
259. 1-{1-(4-[5-(4-Acetylaminobenzoyl)aminopentyloxy]benzoyl)-4-piperidinyl}-3,4-dihydrocarbostyril
260. 1-{1-(4-[5-(3,4-Dihydroxycyclohexylcarbonylaminopentyloxy]benzoyl)-4-piperidinyl}-3,4-dihydrocarbostyril
261. 1-{1-(4-[5-(3,4-Diacetoxycyclohexylcarbonyl)aminopentyloxy]benzoyl)-4-piperidinyl}-3,4-dihydrocarbostyril
262. 1-{1-(4-[5-(4-Aminobenzoyl)aminopentyloxy]benzoyl)-4-piperidinyl}-3,4-dihydrocarbostyril
263. 1-{1-(4-[5-(4-Nitrophenylsulfonyl)aminopentyloxy]benzoyl)-4-piperidinyl}-3,4-dihydrocarbostyril
264. 1-{1-(4-[5-(4-Aminophenylsulfonyl)aminopentyloxy]benzoyl)-4-piperidinyl}-3,4-dihydrocarbostyril
265. 1-{1-(4-[6-(4-(1-Piperidinyl)-1-piperidinyl)hexyloxy]benzoyl)-4-piperidinyl}-3,4-dihydrocarbostyril.dioxalate
266. 1-{1-(4-[6-(N-(2-(2-Pyridyl)ethyl)-N-methylamino)hexyloxy]benzoyl)-4-piperidinyl}-3,4-dihydrocarbostyril
267. 1-{1-(4-[6-(N-(2-Methoxy-3,4,5-trihydroxytetrahydropyran-2-yl)methylamino)hexyloxy]benzoyl)-4-piperidinyl}-3,4-dihydrocarbostyril
268. 1-{1-(4-[7-(Diethylamino)heptyloxy]benzoyl)-4-piperidinyl}-3,4-dihydrocarbostyril
269. 1-{1-(4-[5-(4-Benzyl-1-piperazinylcarbonyl)pentyloxy]benzoyl)-4-piperidinyl}-3,4-dihydrocarbostyril
270. 1-{1-(4-[5-(1-Piperazinylcarbonyl)pentyloxy]benzoyl)-4-piperidinyl}-3,4-dihydrocarbostyril
271. 1-{1-(4-[5-(4-Acetyl-1-piperazinylcarbonyl)pentyloxy]benzoyl)-4-piperidinyl}-3,4-dihydrocarbostyril
272. 1-{1-(4-[5-(4-Methyl-1-piperazinylcarbonyl)pentyloxy]benzoyl)-4-piperidinyl}-3,4-dihydrocarbostyril
273. 1-{1-(4-[5-(4-Allyl-1-piperazinylcarbonyl)pentyloxy]benzoyl)-4-piperidinyl}-3,4-dihydrocarbostyril
274. 1-{1-(4-[5-(4-Carboxy-1-piperidinylcabonyl)pentyloxy]benzoyl)-4-piperidinyl}-3,4-dihydrocarbostyril
275. 1-{1-(4-[5-(4-Carbamoyl-1-piperidinylcarbonyl)pentyloxy]benzoyl)-4-piperidinyl}-3,4-dihydrocarbostyril
276. 1-{1-(4-[5-(4-Dimethylaminocarbonyl-1-piperidinylcarbonyl)pentyloxy]benzoyl)-4-piperidinyl}-3,4-dihydrocarbostyril
277. 1-{1-[4-(8-Acetylaminooctyloxy)benzoyl]-4-piperidinyl}-3,4-dihydrocarbostyril
278. 1-{1-(4-[5-(1-Methyl-2-imidazolylthio)pentyloxy]benzoyl)-4-piperidinyl}-3,4-dihydrocarbostyril
279. 1-{1-(4-[5-(2-Pyrimidylthio)pentyloxy]benzoyl)-4-piperidinyl}-3,4-dihydrocarbostyril 280. 1-{1-(4-[5-(2-Pyrimidylsufinyl)pentyloxy]benzoyl)-4-piperidinyl}-3,4-dihydrocarbostyril
281. 1-{1-(4-[5-(2-Pyrimidylsulfonyl)pentyloxy]benzoyl)-4-piperidinyl}-3,4-dihydrocarbostyril
282. 1-{1-(4-[5-(1-Methyl-2-imidazolylsulfonyl)pentyloxy)benzoyl)-4-piperidinyl}-3,4-dihydrocarbostyril
283. 1-{1-(4-[5-(4-Pyridylthio)pentyloxy]benzoyl)-4-piperidinyl}-3,4-dihydrocarbostyril
284. 1-{1-(4-[5-(4-Aminophenylthio)pentyloxy]benzoyl)-4-piperidinyl}-3,4-dihydrocarbostyril
285. 1-{1-(4-[5-(4-Nitrophenylsulfonyl)pentyloxy]benzoyl)-4-piperidinyl}-3,4-dihydrocarbostyril
286. 1-{1-(4-[5-(4-Aminophenylsulfonyl)pentyloxy]benzoyl)-4-piperidinyl}-3,4-dihydrocarbostyril
287. 1-{1-(4-[5-(2-Pyridylsulfonyl)pentyloxy]benzoyl)-4-piperidinyl}-3,4-dihydrocarbostyril
288. 1-{1-(4-[5-(Pyridine-N-oxide-4-ylsulfonyl)pentyloxy]benzoyl)-4-piperidinyl}-3,4-dihydrocarbostyril
289. 1-{1-(4-[5-(4-Acetylaminophenylsulfonyl)pentyloxy]benzoyl)-4-piperidinyl}-3,4-dihydrocarbostyril
290. 1-{1-(4-[5-(4-Dimethylaminophenylsulfonyl)pentyloxy]benzoyl)-4-piperidinyl}-3,4-dihydrocarbostyril
291. 1-{1-(4-[2,4-Di(5-(1-pyrrolidinyl)pentyloxy]benzoyl)-4-piperidinyl}-3,4-dihydrocarbostyril
292. 1-{1-[2,4-Di(5-diethylaminopentyloxy]benzoyl)-4-piperidinyl}-3,4-dihydrocarbostyril
293. 1-{1-[2-Methoxy-4-(4-thiomorpholinocarbonylbutyloxy)benzoyl]-4-piperidinyl}-3,4-dihydrocarbostyril
294. 1-{1-[2-Methoxy-4-(4-carbamoylbutoxy)benzoyl]-4-piperidinyl}-3,4-dihydrocarbostyril
295. 1-{1-(2-Methoxy-4-[4-(4-oxothiomorpholino)carbonylbutyloxy)benzoyl]-4-piperidinyl}-3,4-dihydrocarbostyril
296. 1-{1-(2-Methoxy-4-[4-(4,4-dioxothiomorpholino)carbonylbutyloxy]benzoyl]-4-piperidinyl}-3,4-dihydrocarbostyril
297. 1-{1-[4-(5,6-Dihydroxyhexyloxy)benzoyl]piperidinyl}-3,4-dihydrocarbostyril
298. 1-{1-(4-[5-Hydroxy-6-(3-methoxybenzylamino)hexyloxy]benzoyl)-4-piperidinyl}-3,4-dihydrocarbostyril
299. 1-{1-(4-[5-Hydroxy-6-(3,4-dimethoxybenzylamino)hexyloxy]benzoyl)-4-piperidinyl}-3,4-dihydrocarbostyril.oxalate
300. 1-{1-(4-[5-Hydroxy-6-(N-methyl-N-(2-(2-pyridyl)ethyl)amino)hexyloxy]benzoyl)-4-piperidinyl}-3,4-dihydrocarbostyril
301. 1-{1-[4-(5-Methoxy-6-diethylmethylammoniumhexyloxy)benzoyl]-4-piperidinyl}-3,4-dihydrocarbostyril.iodine
302. 1-{1-[4-(5-Hydroxy-6-(2-(S)-carbamoyl-1-pyrrolidinylhexyloxy)benzoyl]-4-piperidinyl}-3,4-dihydrocarbostyril
303. 1-{1-[4-(5-Hydroxy-6-(1-piperidinyl)hexyloxy)benzoyl]-4-piperidinyl}-3,4-dihydrocarbostyril
304. 1-{1-(4-[5-Hydroxy-6-(4-benzyl-1-piperidinyl)hexyloxy]benzoyl)-piperidinyl}-3,4-dihydrocarbostyril
305. 1-{1-[4-(5-Acetoxy-6-diethylaminohexyloxy)benzoyl]-4-piperidinyl}-3,4-dihydrocarbostyril
306. 5-Fluoro-1-[1-(2-methoxy-4-ethoxybenzoyl)-4-piperidinyl]-3,4-dihydrocarbostyril
307. 5-Methyl-1-{1-[4-(6-diethylaminohexyloxy)benzoyl]-4-piperidinyl}-3,4-dihydrocarbostyril
308. 5-Hydroxy-1-[1-(2-methoxy-4-ethoxybenzoyl)-4-piperidinyl]-3,4-dihydrocarbostyril
309. 5-Acetoxy-1-[1-(2-Methoxy-4-ethoxybenzoyl)-4-piperidinyl]-3,4-dihydrocarbostyril
310. 1-{1-(4-[5-(2-Methanesulfonylaminoacetylamino)pentyloxy]benzoyl)-4-piperidinyl}-3,4-dihydrocarbostyril
311. 7-Fluoro-1-[1-(2,4-dimethoxybenzoyl)-4-piperidinyl}-3,4-dihydrocarbostyril
312. 1-{1-[4-(5-Acetylaminopentyloxy)benzoyl]-4-piperidinyl}-3,4-dihydrocarbostyril
313. 1-{1-[4-(4-Acetylaminobutoxy)benzoyl]-4-piperidinyl}-3,4-dihydrocarbostyril

TABLE 14

| Test Comp. No. | $IC_{50}$ (µM) |
| --- | --- |
| 1 | 0.4 |
| 2 | 0.5 |
| 3 | 0.33 |
| 4 | 0.24 |
| 5 | 0.49 |
| 6 | 0.47 |
| 7 | 0.31 |
| 8 | 0.3 |
| 9 | 0.35 |
| 10 | 0.32 |
| 11 | 0.30 |
| 12 | 0.23 |
| 13 | 0.28 |
| 14 | 0.16 |
| 15 | 0.26 |
| 16 | 0.15 |
| 17 | 0.43 |
| 18 | 0.27 |
| 19 | 0.5 |
| 20 | 0.44 |
| 21 | 0.36 |
| 22 | 0.34 |
| 23 | 0.24 |
| 24 | 0.33 |
| 25 | 0.24 |
| 26 | 0.25 |
| 27 | 0.27 |
| 28 | 0.16 |
| 29 | 0.28 |
| 30 | 0.33 |
| 31 | 0.25 |
| 32 | 0.46 |
| 33 | 0.45 |
| 34 | 0.25 |
| 35 | 0.15 |
| 36 | 0.37 |
| 37 | 0.36 |
| 38 | 0.27 |
| 39 | 0.15 |
| 40 | 0.5 |
| 41 | 0.2 |
| 42 | 0.3 |
| 43 | 0.4 |
| 44 | 0.3 |
| 45 | 0.2 |
| 46 | 0.5 |
| 47 | 0.1 |
| 48 | 0.4 |
| 49 | 0.2 |
| 50 | 0.4 |
| 51 | 0.49 |
| 52 | 0.08 |
| 53 | 0.08 |
| 54 | 0.27 |
| 55 | 0.2 |
| 56 | 0.33 |
| 57 | 0.27 |
| 58 | 0.45 |
| 59 | 0.2 |
| 60 | 0.2 |
| 61 | 0.3 |
| 62 | 0.15 |
| 63 | 0.27 |

TABLE 14-continued

| Test Comp. No. | IC$_{50}$ (μM) |
|---|---|
| 64 | 0.46 |
| 65 | 0.27 |
| 66 | 0.41 |
| 67 | 0.47 |
| 68 | 0.36 |
| 69 | 0.42 |
| 70 | 0.32 |
| 71 | 0.5 |
| 72 | 0.48 |
| 73 | 0.2 |
| 74 | 0.18 |
| 75 | 0.5 |
| 76 | 0.3 |
| 77 | 0.35 |
| 78 | 0.4 |
| 79 | 0.5 |
| 80 | 0.08 |
| 81 | 0.21 |
| 82 | 0.33 |
| 83 | 0.5 |
| 84 | 7.1 |
| 85 | 3 |
| 86 | 0.57 |
| 87 | 0.53 |
| 88 | 1.0 |
| 89 | 1.6 |
| 90 | 1.1 |
| 91 | 0.72 |
| 92 | 1.2 |
| 93 | 0.64 |
| 94 | 0.63 |
| 95 | 0.96 |
| 96 | 0.6 |
| 97 | 1.1 |
| 98 | 0.77 |
| 99 | 0.96 |
| 100 | 0.9 |
| 101 | 1.6 |
| 102 | 1.1 |
| 103 | 0.7 |
| 104 | 1.0 |
| 105 | 1.2 |
| 106 | 0.7 |
| 107 | 0.75 |
| 108 | 1.4 |
| 109 | 0.75 |
| 110 | 1.3 |
| 111 | 0.73 |
| 112 | 0.97 |
| 113 | 0.98 |
| 114 | 1.5 |
| 115 | 0.7 |
| 116 | 0.76 |
| 117 | 1.5 |
| 118 | 0.26 |
| 119 | 1.4 |
| 120 | 0.2 |
| 121 | 0.46 |
| 122 | 0.71 |
| 123 | 0.35 |
| 124 | 0.32 |
| 125 | 0.59 |
| 126 | 0.36 |
| 127 | 0.61 |
| 128 | 0.23 |
| 129 | 0.18 |
| 130 | 0.39 |
| 131 | 0.066 |
| 132 | 0.16 |
| 133 | 0.33 |
| 134 | 0.16 |
| 135 | 0.2 |
| 136 | 0.18 |
| 137 | 0.12 |
| 138 | 0.24 |
| 139 | 0.051 |
| 140 | 0.1 |
| 141 | 0.12 |
| 142 | 0.1 |
| 143 | 0.55 |
| 144 | 0.022 |
| 145 | 0.17 |
| 146 | 0.073 |
| 147 | 0.098 |
| 148 | 0.36 |
| 149 | 0.15 |
| 150 | 0.096 |
| 151 | 0.16 |
| 152 | 1.6 |
| 153 | 0.084 |
| 154 | 0.2 |
| 155 | 0.057 |
| 156 | 0.18 |
| 157 | 0.09 |
| 158 | 0.10 |
| 159 | 0.098 |
| 160 | 0.22 |
| 161 | 0.45 |
| 162 | 0.11 |
| 163 | 0.075 |
| 164 | 0.78 |
| 165 | 0.54 |
| 166 | 0.044 |
| 167 | 0.28 |
| 168 | 0.19 |
| 169 | 0.17 |
| 170 | 0.039 |
| 171 | 0.24 |
| 172 | 0.043 |
| 173 | 0.039 |
| 174 | 0.49 |
| 175 | 0.32 |
| 176 | 0.13 |
| 177 | 0.13 |
| 178 | 0.045 |
| 179 | 0.25 |
| 180 | 0.40 |
| 181 | 0.23 |
| 182 | 0.12 |
| 183 | 0.24 |
| 184 | 0.039 |
| 185 | 0.01 |
| 186 | 0.063 |
| 187 | 0.040 |
| 188 | 0.068 |
| 189 | 0.13 |
| 190 | 0.033 |
| 191 | 0.034 |
| 192 | 0.061 |
| 193 | 0.12 |
| 194 | 0.35 |
| 195 | 0.19 |
| 196 | 0.17 |
| 197 | 0.035 |
| 198 | 0.32 |
| 199 | 0.055 |
| 200 | 0.034 |
| 201 | 0.008 |
| 202 | 0.027 |
| 203 | 0.049 |
| 204 | 0.059 |
| 205 | 0.12 |
| 206 | 0.03 |
| 207 | 0.07 |
| 208 | 0.10 |
| 209 | 0.25 |
| 210 | 0.023 |
| 211 | 0.25 |
| 212 | 0.16 |
| 213 | 0.059 |

TABLE 14-continued

| Test Comp. No. | IC$_{50}$ (μM) |
|---|---|
| 214 | 0.058 |
| 215 | 0.17 |
| 216 | 0.041 |
| 217 | 0.053 |
| 218 | 0.044 |
| 219 | 0.060 |
| 220 | 0.020 |
| 221 | 0.25 |
| 222 | 0.65 |
| 223 | 0.072 |
| 224 | 0.094 |
| 225 | 0.099 |
| 226 | 0.48 |
| 227 | 0.13 |
| 228 | 0.20 |
| 229 | 0.20 |
| 230 | 0.18 |
| 231 | 0.041 |
| 232 | 0.12 |
| 233 | 0.21 |
| 234 | 0.18 |
| 235 | 0.066 |
| 236 | 0.26 |
| 237 | 0.075 |
| 238 | 0.033 |
| 239 | 0.15 |
| 240 | 0.048 |
| 241 | 0.021 |
| 242 | 0.059 |
| 243 | 0.039 |
| 244 | 0.034 |
| 245 | 0.054 |
| 246 | 0.29 |
| 247 | 0.17 |
| 248 | 0.034 |
| 249 | 0.045 |
| 250 | 0.32 |
| 251 | 0.098 |
| 252 | 0.086 |
| 253 | 0.18 |
| 254 | 0.060 |
| 255 | 0.38 |
| 256 | 0.19 |
| 257 | 0.20 |
| 258 | 0.47 |
| 259 | 0.11 |
| 260 | 0.15 |
| 261 | 0.12 |
| 262 | 0.093 |
| 263 | 0.36 |
| 264 | 0.16 |
| 265 | 0.019 |
| 266 | 0.035 |
| 267 | 0.082 |
| 268 | 0.027 |
| 269 | 0.16 |
| 270 | 0.044 |
| 271 | 0.042 |
| 272 | 0.038 |
| 273 | 0.057 |
| 274 | 0.49 |
| 275 | 0.046 |
| 276 | 0.11 |
| 277 | 0.30 |
| 278 | 0.11 |
| 279 | 0.18 |
| 280 | 0.087 |
| 281 | 0.054 |
| 282 | 0.075 |
| 283 | 0.61 |
| 284 | 0.40 |
| 285 | 0.23 |
| 286 | 0.15 |
| 287 | 0.10 |
| 288 | 0.048 |
| 289 | 0.10 |
| 290 | 0.30 |
| 291 | 0.098 |
| 292 | 0.077 |
| 293 | 0.22 |
| 294 | 0.17 |
| 295 | 0.077 |
| 296 | 0.073 |
| 297 | 0.52 |
| 298 | 0.065 |
| 299 | 0.065 |
| 300 | 0.034 |
| 301 | 0.047 |
| 302 | 0.088 |
| 303 | 0.038 |
| 304 | 0.037 |
| 305 | 0.065 |
| 306 | 0.084 |
| 307 | 0.023 |
| 308 | 0.095 |
| 309 | 0.073 |
| 310 | 0.16 |

Experiment 2: Anti-vasopressor activity in vivo

The spinal cord of male SD rat (weighing 300–400 g) is broken to give a pith rat. The blood pressure of the pith rat is measured through the cannula inserted into the femoral artery thereof by using a pressure transducer. The test compound and Arg-vasopressin are administered to the pith rat through the cannula inserted into the femoral vein. Anti-vasopressor activity of the test compound in vivo is determined according to the following equation.

$$\text{Anti-vasopressor activity (\%)} = \frac{P}{P_0} \times 100$$

$P_0$: The increase of diastolic pressure when Arg-vasopressin (30 mU/kg) is administered intravenously.

P: The increase of diastolic pressure when Arg-vasopressin (30 mU/kg) is administered intravenouly 3 minutes after the intravenous administration of the test compound.

The results are expressed as ED$_{50}$ value, which is the dose of the test compound required to reduce the increase of diastolic pressure caused by the intravenous administration of Arg-vasopressin (30 mU/kg) to 50% of its control value: P$^0$.

The results are shown in the following Table 15.

TABLE 15

| Test Comp. No. | ED$_{50}$ (mg/kg) | Test Comp. No. | ED$_{50}$ (mg/kg) |
|---|---|---|---|
| 2 | 1.0 | 47 | 0.4 |
| 20 | 0.2 | 311 | 0.3 |
| 40 | 0.8 | 312 | 0.8 |
| 41 | 0.5 | 313 | 0.3 |

What is claimed is:

1. A carbostyril derivative of the following formula:

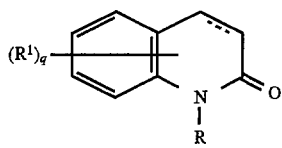
(1)

wherein $R^1$ is hydrogen; nitro; a lower alkoxy; a lower alkoxycarbonyl; a lower alkyl; a halogen; an amino having optionally one or two substituents selected from a lower alkanoyl, a lower alkyl, benzoyl and a phenyl(lower) alkoxycarbonyl; hydroxy; cyano; carboxy; a lower alkanoyloxy; or a hydrazinocarbonyl, q is an integer of 1 to 3 and q is 1 when $R^1$ is hydrogen and R is a group of the formula:

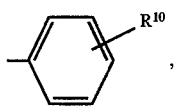

$R^{10}$ is a group of the formula:

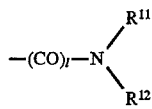

wherein l is 1 and $R^{11}$ and $R^{12}$ are the same or different and are each hydrogen, a lower alkyl, a phenyl(lower)alkyl, a lower alkenyl, a benzoyl which may optionally have a lower alkoxy as a substituent, tricyclo(3.3.1.1)decanyl, a phenyl which may optionally have a lower alkoxy as a substituent, or a cycloalkyl, or $R^{11}$ and $R^{12}$ may bind together with the nitrogen atom to which they bond to form a saturated or unsaturated heterocyclic group selected from the group consisting of pyrrolidinyl, piperidinyl, piperazinyl, morpholino, thiomorpholino, pyrrolyl, imidazolyl, pyrazolyl, imidazolidinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, 1,2,3,4-tetrahydroquinolyl, 1,2-dihydroquinolyl, indolyl, isoindolyl, 1,2-dihydroisoquinolyl, 1,2,3,4-tetrahydroisoquinolyl, 1H-indazolyl, 1,2-dihydroquinazolyl, 1,2-dihydrocinnolyl, 1,2-dihydroquinoxalyl, 1,2,3,4-tetrahydroquinazolyl, 1,2,3,4-tetrahydrocinnolyl and 1,2,3,4-tetrahydroquinoxalyl, wherein the heterocyclic group may optionally have a substituent selected from benzoyl, a lower alkanoyl, a phenyl(lower)alkyl and a phenyl which may optionally be substituted with a lower alkoxy and a lower alkanoyl, and the bond between the 3-position and the 4-position of the carbostyril ring is a single bond or double bond, or a salt thereof.

2. The compound according to claim 1, wherein the bond between the 3- and 4-positions of the carbostyril nucleus is a single bond, and a salt thereof.

3. The compound according to claim 1, wherein the bond between the 3- and 4-positions of the carbostyril nucleus is a double bond, and a salt thereof.

4. The compound according to claim 1, wherein $R^1$ is hydrogen or a halogen, and a salt thereof.

5. A vasopressin antagonistic composition which comprises as an active ingredient a compound of the formula (1) as set forth in claim 1, or a pharmaceutically acceptable salt thereof in admixture with a pharmaceutically acceptable carrier or diluent.

6. The compound according to claim 1, wherein l is 1, and $R^{11}$ and $R^{12}$ are the same or different and are each hydrogen, a lower alkyl, a phenyl(lower)alkyl, a lower alkenyl, a benzoyl which may optionally have a lower alkoxy as a substituent, tricyclo[3.3.1.1]decanyl, a phenyl which may optionally have a lower alkoxy as a substituent, or a cycloalkyl, or a salt thereof.

7. The compound according to claim 1, wherein l is 1 and $R^{11}$ and $R^{12}$ may bind together with the nitrogen atom to which they bond to form a saturated or unsaturated heterocyclic group selected from the group consisting of pyrrolidinyl, piperidinyl, piperazinyl, morpholino, thiomorpholino, pyrrolyl, imidazolyl, pyrazolyl, imidazolidinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, 1,2,3,4-tetrahydroquinolyl, 1,2-dihydroquinolyl, indolyl, isoindolyl, 1,2-dihydroisoquinolyl, 1,2,3,4-tetrahydroisoquinolyl, 1H-indazolyl, 1,2-dihydroquinazolyl, 1,2-dihydrocinnolyl, 1,2-dihydroquinoxalyl, 1,2,3,4-tetrahydroquinazolyl, 1,2,3,4-tetrahydrocinnolyl and 1,2,3,4-tetrahydroquinoxalyl, wherein the heterocyclic group may optionally have a substituent selected from benzoyl, a lower alkanoyl, a phenyl (lower)alkyl and a phenyl which may optionally be substituted with a lower alkoxy and a lower alkanoyl, or a salt thereof.

8. The compound according to claim 7, wherein $R^{11}$ and $R^{12}$ may bind together with the nitrogen atom to which they bond to form piperazinyl, piperidinyl and 1,2,3,4-tetrahydroquinolyl, or a salt thereof.

9. The compound according to claim 6, wherein $R^{11}$ and $R^{12}$ are the same or different and are each hydrogen, a lower alkyl, a phenyl(lower)alkyl, a lower alkenyl, or a phenyl which may optionally have a lower alkoxy as a substituent, or a salt thereof.

10. The compound according to claim 1, wherein $R^1$ is a hydrogen atom, or a hydrochloride salt thereof.

* * * * *